United States Patent
Burch et al.

(10) Patent No.: US 9,328,106 B2
(45) Date of Patent: May 3, 2016

(54) CYCLIC ETHER PYRAZOL-4-YL-HETEROCYCLYL-CARBOXAMIDE COMPOUNDS AND METHODS OF USE

(71) Applicant: Genentech, Inc., South San Francisco, CA (US)

(72) Inventors: Jason Burch, Redwood City, CA (US); Minghua Sun, Burlingame, CA (US); Xiaojing Wang, Foster City, CA (US); Wesley Blackaby, Saffron Walden (GB); Alastair James Hodges, Saffron Walden (GB); Andrew Sharpe, Saffron Walden (GB)

(73) Assignee: GENENTECH, INC., South San Francisco, CA (US)

( * ) Notice: Subject to any disclaimer, the term of this patent is extended or adjusted under 35 U.S.C. 154(b) by 143 days.

(21) Appl. No.: 14/036,160

(22) Filed: Sep. 25, 2013

(65) Prior Publication Data
US 2014/0088117 A1    Mar. 27, 2014

Related U.S. Application Data

(60) Provisional application No. 61/705,791, filed on Sep. 26, 2012, provisional application No. 61/864,882, filed on Aug. 12, 2013.

(51) Int. Cl.

| | | |
|---|---|---|
| C07D 417/12 | (2006.01) |
| C07D 405/14 | (2006.01) |
| A61K 45/06 | (2006.01) |
| A61K 31/427 | (2006.01) |
| A61K 31/497 | (2006.01) |
| A61K 31/4439 | (2006.01) |
| A61K 31/506 | (2006.01) |
| C07D 417/14 | (2006.01) |
| C07D 471/04 | (2006.01) |
| C07D 493/08 | (2006.01) |

(52) U.S. Cl.
CPC .......... *C07D 417/12* (2013.01); *A61K 31/427* (2013.01); *A61K 31/4439* (2013.01); *A61K 31/497* (2013.01); *A61K 31/506* (2013.01); *A61K 45/06* (2013.01); *C07D 405/14* (2013.01); *C07D 417/14* (2013.01); *C07D 471/04* (2013.01); *C07D 493/08* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 6,111,121 A | 8/2000 | Grubbs et al. |
| 6,307,087 B1 | 10/2001 | Buchwald et al. |
| 6,395,916 B1 | 5/2002 | Buchwald et al. |
| 6,946,560 B2 | 9/2005 | Buchwald et al. |
| 7,026,498 B2 | 4/2006 | Buchwald et al. |
| 7,223,879 B2 | 5/2007 | Buchwald et al. |
| 7,247,731 B2 | 7/2007 | Buchwald et al. |
| 7,560,582 B2 | 7/2009 | Buchwald et al. |
| 7,858,784 B2 | 12/2010 | Buchwald et al. |
| 8,436,001 B2 * | 5/2013 | Wang ........................ 514/255.05 |
| 2004/0254066 A1 | 12/2004 | Ramarao et al. |
| 2010/0056576 A1 | 3/2010 | Burger et al. |
| 2011/0076291 A1 | 3/2011 | Blaquiere et al. |
| 2012/0225062 A1 | 9/2012 | Burger et al. |
| 2013/0079321 A1 | 3/2013 | Hodges et al. |

FOREIGN PATENT DOCUMENTS

| | | |
|---|---|---|
| WO | 96/15111 A1 | 5/1996 |
| WO | 2007/044515 A1 | 4/2007 |
| WO | 2007/099326 A1 | 9/2007 |

OTHER PUBLICATIONS

Adam et al., "Targeting PIM Kinases Impairs Survival of Hematopoietic Cells Transformed by Kinase Inhibitor-Sensitive and Kinase Inhibitor-Resistant Forms of Fms-Like Tyrosine Kinase 3 and BCR/ABL" Cancer Research 66(7) ( 2006).

Aho et al., "Expression of Human pim Family Genes is Selectively up-regulated by Cytokines Promoting T Helper Type 1, but not T Helper Type 2, Cell Differentiation" Immunology 116:82-88 ( 2005).

Aho et al., "Pim-1 Kinase Promotes Inactivation of the Pro-Apoptotic Bad Protein by Phosphorylating it on the Ser112 Gatekeeper Site" FEBS Letter 571:43-49 ( 2004).

(Continued)

*Primary Examiner* — Kamal Saeed
(74) *Attorney, Agent, or Firm* — Alston & Bird LLP

(57) ABSTRACT

Cyclic ether pyrazol-4-yl-heterocyclyl-carboxamide compounds of Formula I, including stereoisomers, geometric isomers, tautomers, and pharmaceutically acceptable salts thereof, wherein $R^2$ is a cyclic ether and X is thiazolyl, pyrazinyl, pyridinyl, or pyrimidinyl, are useful for inhibiting Pim kinase, and for treating disorders such as cancer mediated by Pim kinase. Methods of using compounds of Formula I for in vitro, in situ, and in vivo diagnosis, prevention or treatment of such disorders in mammalian cells, or associated pathological conditions, are disclosed.

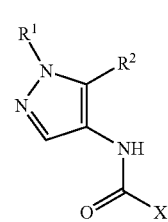

23 Claims, 8 Drawing Sheets

(56) References Cited

OTHER PUBLICATIONS

Aksoy et al., "Self-Renewal of Murine Embryonic Stem Cells is Supported by the Serine/Threonine Kinases Pim-1 and Pim-3" Stem Cells 25:2996-3004 ( 2007).
Allen et al., "Pim-2 Transgene Induces Lymphoid Tumors, Exhibiting Potent Synergy with c-myc" Oncogene 15:1133-1141 ( 1997).
Amson et al., "The Human Protooncogene Product p33pim is Expressed During Fetal Hematopoiesis and in Diverse Leukemias" Proc. Natl. Acad. Sci. USA 86:8857-8861 ( 1989).
Bachmann et al., "The Oncogenic Serine/Threonine Kinase Pim-1 Directly Phosphorylates and Activates the G2/M Specific Phosphatase Cdc25C" The International Journal of Biochemistry & Cell Biology 38:430-443 ( 2006).
Billingsley et al., "Pallaium-Catalyzed Borylation of Aryl Chlorides: Scope, Applications, and Computational Studies" Angewandte Chemie Int. Ed. 46:5359-5363 ( 2007).
Biscoe et al., "A New Class of Easily Activated Palladium Precatalysts for Facile C-N Cross-Coupling Reactions and the Low Temperature Oxidative Addition of Aryl Chlorides" Journal of American Chemical Society 130:6686-6687 ( 2008).
Cheng et al., "Relationship Between the Inhibition Constant (KI) and the Concentration of Inhibitor Which Causes 50 Per Cent Inhibition (I50) of an Enzymatic Reaction" Biochemical Pharmacology 22:3099-3108 ( 1973).
Chiesa et al., "A novel Role for HERG K+ Channels: Spike-Frequency Adaptation" Journal of Physiology 501(2):313-318 ( 1997).
Cibull et al., "Overexpression of Pim-1 During Progression of Prostatic Adenocarcinoma" Journal of Clinical Pathol. 59:285-288 ( 2006).
Claudio et al., "A Molecular Compendium of Genes Expressed in Multiple Myeloma" Blood 100(6):2175 ( 2002).
Cohen et al., "Increased Expression of the hPim-2 Gene in Human Chronic Lymphocytic Leukemia and Non-Hodgkin Lymphoma" Leukemia & Lymphoma 45(5):951-955.
Cuypers et al., "Murine Leukemia Virus-Induced T-Cell Lymphomagenesis: Integration of Proviruses in a Distinct Chromosomal Region" Cell 37:141-150 ( 1984).
DeBruin et al., "Anti-HERG Activity and the Risk of Drug-Induced Arrhythmias and Sudden Death" European Heart Journal 26:590-597 ( 2005).
Dhanasekaran et al., "Delineation of Prognostic Biomarkers in Prostate Cancer" Nature 412:822- ( 2001).
Eliel and Wilen Stereochemistry of Organic Compounds ( 1994).
Ellwood-Yen et al., "Myc-Driven Murine Prostate Cancer Shares Molecular Features with Human Prostate Tumors" Cancer Cell 4:223- ( 2003).
Ferroni et al., "Cyclic Guanidines: Synthesis and Antiplatelet Activity of 4,6,7,8-Tetrahydri-1H-Imidazo [1,2-a] Pyrazolo [3,4-d] Pyrimidin-7-Ones" Drug Research 40(12):1328- ( 1990).
Fox et al., "The Serine/Threonine Kinase Pim-2 is a Transcriptionally Regulated Apoptotic Inhibitor" Genes & Development 17:1841-1854 ( 2003).
Fujii et al., "Aberrant Expression of Serine/Threonine Kinase Pim-3 in Hepatocellular Carcinoma Development and its Role in the Proliferation of Human Hepatoma Cell Lines" International Journal of Cancer 114:209-218 ( 2005).
Greenstein et al., "Characterization of the MM.1 Human Multiple Myeloma (MM) Cell Liness: A Model System to Elucidate the Characteristics, Behavior, and Signaling of Steroid-Sensitive and Resistant Cells" Experimental Hematology 31:271-282 ( 2003).
Hammerman et al., "Pim and Akt Oncogenes are Independent Regulators of Hematopoietic Cell Growth and Survival" Blood 105(11):4477- ( 2005).
Hedley et al., "The Genetic Basis of Long QT and Short QT Syndromes: A Mutation Update" Human Mutation 30(11):1486-1511 ( 2009).
Hirano et al., "Roles of STAT3 in Mediating the Cell Growth, Differentiation and Survival Signals Relayed Through the IL-6 Family of Cytokine Receptors" Oncogene 19:2548-2556 ( 2000).
Huttmann et al., "Gene Expression Signatures Separate B-Cell Chronic Lymphocytic Leukaemia Prognostic Subgroups Defined by ZAP-70 and CD38 Expression Status" Leukemia 20:1774-1782 ( 2006).
"International Union of Pure and Applied Chemistry" Journal of American Chemical 82:5566 ( 1960).
Jacob III, "Resolution of (=)-5-Bromonornicotine. Synthesis of (R)- and (S)-Nornicotine of High Enantiomeric Purity" Journal of Org. Chem. 47:4165-4167 ( 1982).
Kim et al., "Cooperativity of Nkx3.1 and Pten Los of Function in a Mouse Model of Prostate Carcinogenesis" Pro. Natl. Acad. Sci. USA 99(5):2884-2889 ( 2002).
Kinzel et al., "A New Palladium Precatalyst Allows for the Fast Suzuki-Miyaura Coupling Reactions of Unstable Polyfluorophenyl and 2-Heteroaryl Boronic Acids" Journal of American Chemical Society 132:14073-14075 ( 2010).
Li et al., "Pim-3, a Proto-Oncogene with Serine/Threonine Kinase Activity, is Aberrantly Expressed in Human Pancreatic Cancer and Phosphorylates Bad to Block Bad-Mediated Apoptosis in Human Pancreatic Cancer Cell Lines" Cancer Research 66(13):6741- ( 2006).
Lochmuller, "Chromatographic Resolution of Enantiomers Selective Review" Journal of Chromatography 113:283-302 ( 1975).
Macdonald et al., "Pim Kinases Phosphorylate Multiple Sites on Bad and Promote I 4-3-3 Binding and Dissociation from Bcl-XL" BMC Cell Biology 76:1-14 ( 2006).
Mikkers et al., "High-Throughput Retroviral Tagging to Identify Components of Specific Signaling Pathways in Cancer" Nature Genetics 32:153- ( 2002)
Mikkers et al., "Mice Deficient for All PIM Kinases Display Reduced Body Size and ImpairedResponses to Hematopoietic Growth Factors" Molecular and Cellular Biology 24(13):6104-6115 ( 2004).
Mochizuki et al., "Physical and Functional Interactions Between Pim-1 Kinase and Cdc25A Phosphatase" The Journal of Biological Chemistry 274(26):18659-18666 ( 1999).
Molander et al., "Scope of Palladium-Catalyzed Aryl Borylation Utilizing Bis-Boronic Acid" Journal of American Chemical Society 134:11667-11673 ( 2012).
Nicolaou et al., "A Rationally Designed Molecule with Extremely Potent and Selective DNA Cleaving Properties and Apoptosis Inducing Activity" Angew. Chem. Int. Ed. Engl. 33(2):183- ( 1994).
Okamoto et al., "Optical Resolution of Dihydropyridine Enantiomers by High-Performance Liquid Chromatography Using Phenylcarbamates of Polysaccharides as a Chiral Stationary Phase" Journal of Chromatography 513:375-378 ( 1990).
Osol, A. Remington's Pharmaceutical Sciences 16 edition, ( 1980).
Overholt et al., "Chemosensing at the Carotid Body: Involvement of a HERG-like Potassium Current in Glomus Cells" Adv. Exp. Med. Biol. 475:241-248 ( 2000).
Qian et al., "Structural Basis of Constitutive Activity and a Unique Nucleotide Binding Mode of Human Pim-1 Kinase" The Journal of Biological Chemistry 280(7):6130-6137 ( 2005).
Redfern et al., "Relationships Between Preclinical Cardiac Electrophysiology, Clinical QT Interval Prolongation and Torsade de Pointes for a Broad Range of Drugs: Evidence for a Provisional Safety Margin in Drug Development" Cardiovascular Research 58:32-45 ( 2003).
Sanguinetti et al., "hERG Potassium Channels and Cardiac Arrhythmia" Nature 440(7083):463-469 ( 2006).
Schmidt et al., "Pyrazolo[3,4-d]Pyrimidine Mit Koffein-Ahnlicher Struktur Und Wirkung" Helvetica Chimica Acta 41:1052-1060 ( 1958).
Selten et al., "Proviral Activation of the Putative Oncogene Pim-1 in MuLV Induced T-Cell Lymphomas" The EMBO Journal 4(7):1793-1798 ( 1985).
Shirogane et al., "Synergistic Roles for Pim-1 and c-Myc in STAT3-Mediated Cell Cycle Progression and Antiapoptosis" Immunity 11:709-719 ( 1999).
Sun et al., "Application of Immobilized Metal Affinity Chromatography in Proteomics" Expert Rev. Proteomics 2(5):649-657 ( 2005).
Tamburini et al., "Protein Synthesis is Resistant to Rapamycin and Constitutes a Promising Therapeutic Target in Acute Myeloid Leukemia" Blood 114(8):1618- ( 2009).

(56) References Cited

OTHER PUBLICATIONS

Van Der Lugt et al., "Proviral Tagging in Eu-myc Transgenic Mice Lacking the Pim-1 Proto-Oncogene Leads to Compensatory Activation of Pim-2" The EMBO Journal 14(11):2536-2544 (1995).

Verbeek et al., "Mice Bearing the Eu-myc and Eu-pim-1 Transgenes Develop Pre-B-Cell Leukemia Prenatally" Molecular and Cellular Biology 11(2):1176-1179 (1991).

Walker et al., "A Rationally Designed Universal Catalyst for Suzuki Miyaura Coupling Processes" Agnew. Chem. Int. Ed. Engl. 43:1871-1876 (2004).

Wamhoff et al., "Heterocyclic B-Enamino Esters, 39.-Synthesis of 1H-Pyrasolo[3,4-d]Pyrimidines" Liebigs Annalen der Chemie 9:1910-1916 (1985).

Wang et al., "Phosphorylation of the Cell Cycle Inhibitor p21 by Pim-1 Kinase" Biochimica et Biophysica Acta 1593:45-55 (2002).

Warmuth et al., "Ba/F3 Cells and Their Use in Kinase Drug Discovery" Current Opinion in Oncology 19:55-60 (2007).

White et al., "Integration of Supercritical Fluid Chromatography into Drug Discovery as a Routine Support Tool: II. Investigation and Evaluation of Supercritical Fluid Chromatography for Achiral Batch Purification" Journal of Chromatography A 1074:175-785 (2005).

* cited by examiner

US 9,328,106 B2

CYCLIC ETHER PYRAZOL-4-YL-HETEROCYCLYL-CARBOXAMIDE COMPOUNDS AND METHODS OF USE

CROSS-REFERENCE TO RELATED APPLICATIONS

This non-provisional application filed under 37 CFR §1.53 (b), claims the benefit under 35 USC §119(e) of U.S. Provisional Application Ser. No. 61/705,791 filed on 26 Sep. 2012 and U.S. Provisional Application Ser. No. 61/864,882 filed on 12 Aug. 2013, which are incorporated by reference in entirety.

FIELD OF THE INVENTION

The invention relates generally to cyclic ether pyrazol-4-yl-heterocyclyl-carboxamide compounds for treating disorders mediated by Pim kinase (Pim-1, Pim-2, and/or Pim-3) inhibitors, thus useful as cancer therapeutics. The invention also relates to compositions, more specifically pharmaceutical compositions comprising these compounds and methods of using the same, either alone or in combination, to treat various forms of cancer and hyperproliferative disorders, as well as methods of using the compounds for in vitro, in situ and in vivo diagnosis or treatment of mammalian cells, or associated pathological conditions.

BACKGROUND OF THE INVENTION

Pim kinases are family of three highly-related serine and threonine protein kinases encoded by the genes Pim-1, Pim-2, and Pim-3. The gene names are derived from the phrase Proviral Insertion, Moloney, frequent integration sites for murine moloney virus wherein the insertions lead to overexpression of Pim kinases and either de novo T-cell lymphomas, or dramatic acceleration of tumorigenesis in a transgenic Myc-driven lymphoma model (Cuypers et al. (1984) Cell, vol. 37 (1) pp. 141-50; Selten et al. (1985) EMBO J. vol. 4 (7) pp. 1793-8; van der Lugt et al. (1995) EMBO J. vol. 14 (11) pp. 2536-44; Mikkers et al. (2002) Nature Genetics, vol. 32 (1) pp. 153-9; van Lohuizen et al. (1991) Cell, vol. 65 (5) pp. 737-52). These experiments reveal synergy with the oncogene c-Myc, and suggest that inhibition of the Pim kinases may have therapeutic benefit.

Mouse genetics suggests that antagonizing Pim kinases may have an acceptable safety profile; a Pim 1−/−; Pim-2−/−, Pim-3−/− mouse knockout is viable although slightly smaller than wild type littermates (Mikkers et al. (2004) Mol Cell Biol vol. 24 (13) pp. 6104-154). The three genes give rise to six protein isoforms including a protein kinase domain, and apparently without recognizable regulatory domains. All six isoforms are constitutively active protein kinases that do not require post-translational modification for activity, thus Pim kinases are regulated primarily at the transcriptional level (Qian et al. (2005) J Biol Chem, vol. 280 (7) pp. 6130-7). Pim kinase expression is highly inducible by cytokines and growth factors receptors and Pims are direct transcriptional targets of the Stat proteins, including Stat3 and Stat5. Pim-1, for example, is required for the gp130-mediated Stat3 proliferation signal (Aksoy et al. (2007) Stem Cells, vol. 25 (12) pp. 2996-3004; Hirano et al. (2000) Oncogene vol. 19 (21) pp. 2548-56; Shirogane et al. (1999) Immunity vol. 11 (6) pp. 709-19).

Pim kinases function in cellular proliferation and survival pathways parallel to the PI3k/Akt/mTOR signaling axis (Hammerman et al. (2005) Blood vol. 105 (11) pp. 4477-83). Indeed, several of the phosphorylation targets of the PI3k axis including Bad and eIF4E-BP1 are cell growth and apoptosis regulators and are also phosphorylation targets of the Pim kinases (Fox et al. (2003) Genes Dev vol. 17 (15) pp. 1841-54; Macdonald et al. (2006) Cell Biol vol. 7 pp. 1; Aho et al. (2004) FEBS Letters vol. 571 (1-3) pp. 43-9; Tamburini et al. (2009) Blood vol. 114 (8) pp. 1618-27). Pim kinase may affect cell survival since phosphorylation of Bad increases Bcl-2 activity and therefore promotes cell survival. Likewise, phosphorylation of eIF4E-BP1 by mTOR or Pim kinases causes depression of eIF4E, promoting mRNA translation and cellular growth. In addition, Pim-1 has been recognized to promote cell cycle progression through phosphorylation of CDC25A, p21, and Cdc25C (Mochizuki et al. (1999) J Biol Chem vol. 274 (26) pp. 18659-66; Bachmann et al. (2006) Int J Biochem Cell Biol vol. 38 (3) pp. 430-43; Wang et al. (2002) Biochim Biophys Acta vol. 1593 (1) pp. 45-55.

Pim kinases show synergy in transgenic mouse models with c-Myc-driven and Akt-driven tumors (Verbeek et al. (1991) Mol Cell Biol vol. 11 (2) pp. 1176-9; Allen et al. Oncogene (1997) vol. 15 (10) pp. 1133-41; Hammerman et al. (2005) Blood vol. 105 (11) pp. 4477-83). Pim Kinases are involved in transforming activity of oncogenes identified in acute myeloid leukemia (AML) including Flt3-ITD, BCR-abl, and Tel-Jak2. Expression of these oncogenes in BaF3 cells results in upregulation of Pim-1 and Pim-2 expression, resulting in IL-3 independent growth, and subsequent Pim inhibition results in apoptosis and cell growth arrest (Adam et al. (2006) Cancer Research 66 (7):3828-35). Pim overexpression and dysregulation has also been noted as a frequent event in many hematopoietic cancers, including leukemias and lymphoma (Amson et al. (1989) Proc Natl Acad Sci USA 86 (22):8857-61); Cohen et al. (2004) Leuk Lymphoma 45 (5): 951-5; Hüttmann et al. (2006) Leukemia 20 (10):1774-82) as well as multiple myeloma (Claudio et al. (2002) Blood 100 (6):2175-86. Multiple myeloma (MM) is a clonal B-lymphocyte malignancy, which is characterized by the accumulation of terminally differentiated antibody-producing cells in the bone marrow.

Pim 1 has been shown to be overexpressed and correlated to prostate cancer progression (Cibull et al. (2006) J Clin Pathol 59 (3):285-8; Dhanasekaran et al. (2001) Nature vol. 412 (6849):822-6). Pim 1 expression increases in mouse models with disease progression (Kim et al. (2002) Proc Natl Acad Sci USA 99 (5):2884-9). Pim-1 has been reported to be the most highly overexpressed mRNA in the subset of human prostate tumor samples which have a c-Myc-driven gene signature (Ellwood-Yen et al. (2003) Cancer Cell 4(3):223-38). Pim-3 has been also been shown to be overexpressed and to have a functional role in pancreatic cancer and hepatocellular carcinoma (Li et al. (2006) Cancer Research 66 (13): 6741-7; Fujii et al. (2005) Int J Cancer 114 (2):209-18.

Beyond oncology therapeutic and diagnostic applications, Pim kinases could play an important role in normal immune system function and Pim inhibition could be therapeutic for a number of different immunologic pathologies including tumorigensis (Nawijn et al (2011) Nature Rev. 11:23-34), inflammation, autoimmune conditions, allergy, and immune suppression for organ transplantation (Aho et al. (2005) Immunology 116 (1):82-8).

SUMMARY OF THE INVENTION

The invention relates to cyclic ether pyrazol-4-yl-heterocyclyl-carboxamide compounds for treating disorders mediated by Pim kinase (Pim-1, Pim-2, and/or Pim-3) inhibitors Formula I compounds.

Formula I compounds have the structure:

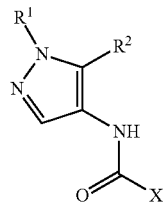

where R² is selected from the structures:

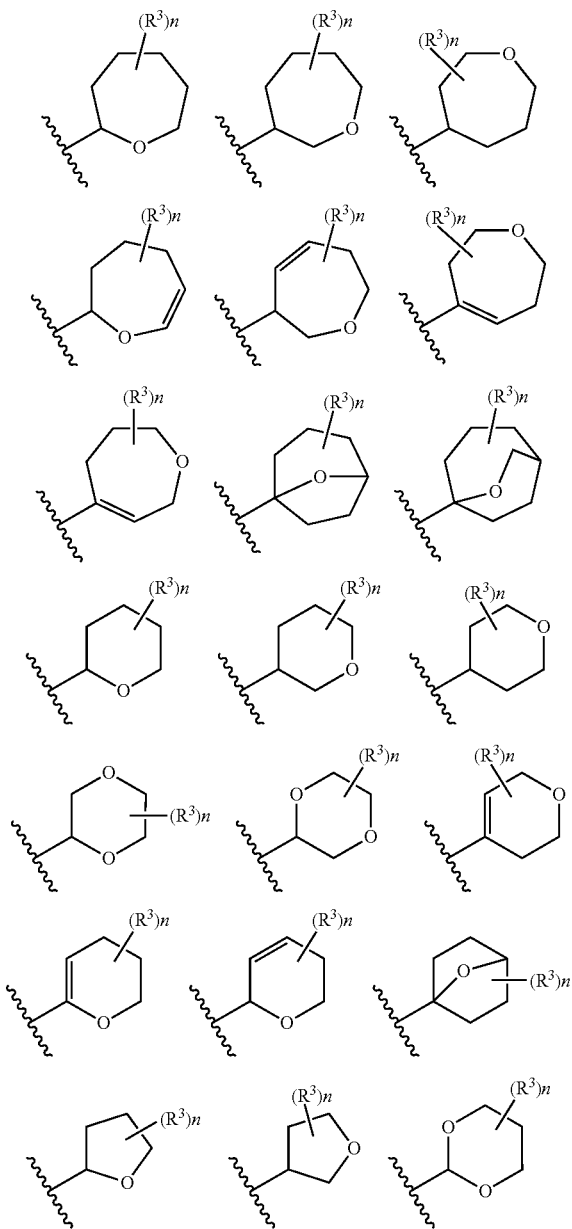

where the wavy line indicates the site of attachment and the dashed line indicates an optional double bond;

X is selected from the structures:

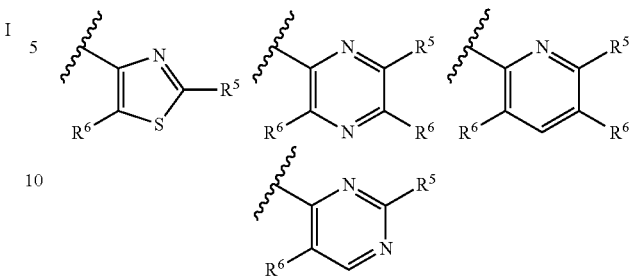

and stereoisomers, geometric isomers, tautomers, and pharmaceutically acceptable salts thereof. The various substituents, including $R^1$, $R^2$, $R^3$, $R^4$, $R^5$, $R^6$, $R^7$, and X are as defined herein.

One aspect of the invention is a pharmaceutical composition comprised of a Formula I compound and a pharmaceutically acceptable carrier, glidant, diluent, or excipient. The pharmaceutical composition may further comprise a chemotherapeutic agent.

The invention includes a method of treating a disease or disorder which method comprises administering a therapeutically effective amount of a Formula I compound to a patient with a disease or disorder selected from cancer, immune disorders, cardiovascular disease, viral infection, inflammation, metabolism/endocrine function disorders and neurological disorders, and mediated by Pim kinase. The method includes further administering an additional therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

The invention includes use of a Formula I compound in the manufacture of a medicament for the treatment of cancer, immune disorders, cardiovascular disease, viral infection, inflammation, metabolism/endocrine function disorders and neurological disorders, wherein the medicament mediates Pim kinase.

The invention includes a kit for treating a condition mediated by Pim kinase, comprising: a) a first pharmaceutical composition comprising a Formula I compound; and b) instructions for use.

The invention includes a Formula I compound for use as a medicament, and for use in treating a disease or disorder selected from cancer, immune disorders, cardiovascular disease, viral infection, inflammation, metabolism/endocrine function disorders and neurological disorders, and mediated by Pim kinase.

The invention includes methods of making a Formula I compound.

DETAILED DESCRIPTION OF EXEMPLARY EMBODIMENTS

Figure 1:
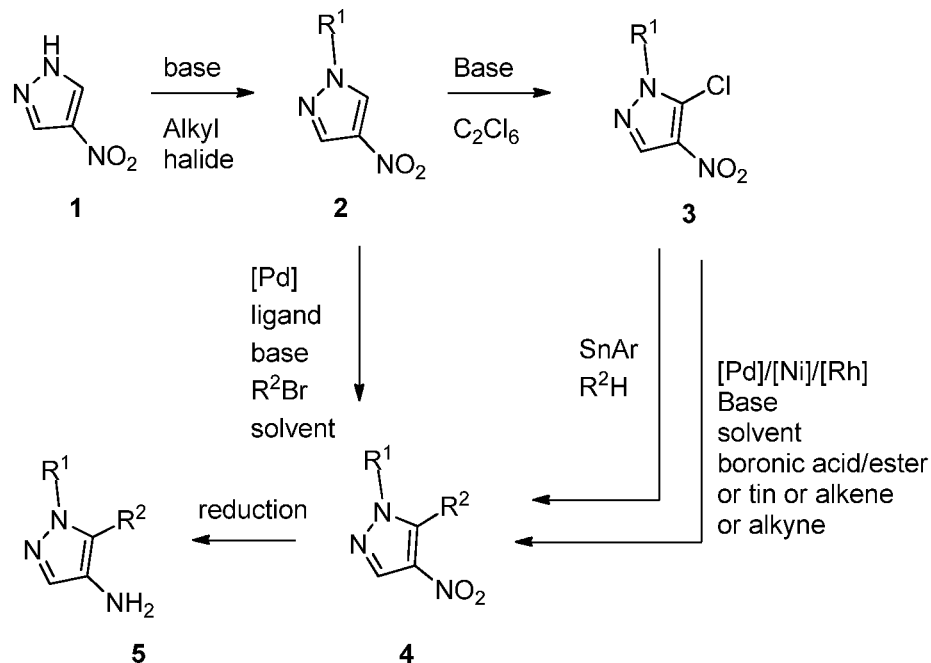
FIG. 1 shows an exemplary synthesis of 4-aminopyrazole compounds 5 from nitro-1H-pyrazole 1.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

DEFINITIONS

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally substituted substituted independently with one or more substituents described herein, and includes radicals having "cis" and "trans" orientations, or alternatively, "E" and "Z" orientations. Examples include, but are not limited to, ethylenylene or vinylene (—CH=CH—), allyl (—CH$_2$CH=CH—), and the like.

The term "alkynyl" refers to a linear or branched monovalent hydrocarbon radical of two to eight carbon atoms (C$_2$-C$_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The term "alkynylene" refers to a linear or branched divalent hydrocarbon radical of two to eight carbon atoms (C$_2$-C$_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —CH$_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms (C$_3$-C$_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms (C$_6$-C$_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms (C$_6$-C$_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (MEK inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis, PTK787/ZK 222584 (Novartis), fulvestrant (FASLODEX®, AstraZeneca), leucovorin (folinic acid), rapamycin (sirolimus, RAPAMUNE®, Wyeth), a rapamycin analog, mTOR inhibitor such as everolimus, a MEK inhibitor (GDC-0973), a Bcl-2 inhibitor such as navitoclax, (ABT-263) or ABT-199), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1);

eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (CAMPATH®), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), and tositumomab (BEXXAR®, Corixa, GlaxoSmithKline).

Humanized monoclonal antibodies with therapeutic potential as chemotherapeutic agents in combination with the Formula I compounds of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lebrikizumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Table 1 structures for illustrative purposes, while stereochemical determination awaits, such as x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099).

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

CYCLIC ETHER PYRAZOL-4-YL-HETEROCYCLYL-CARBOXAMIDE COMPOUNDS

The present invention provides cyclic ether pyrazol-4-yl-heterocyclyl-carboxamide compounds of Formula I, including Formulas Ia-i, and pharmaceutical formulations thereof, which are potentially useful in the treatment of diseases, conditions and/or disorders modulated by Pim kinases.

Formula I compounds have the structure:

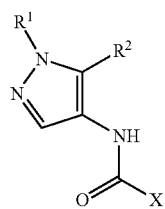

I and stereoisomers, geometric isomers, tautomers, or pharmaceutically acceptable salts thereof, wherein:

$R^1$ is selected from H, $C_1$-$C_{12}$ alkyl, $C_2$-$C_{12}$ alkenyl, $C_2$-$C_{12}$ alkynyl, $C_6$-$C_{20}$ aryl, $C_3$-$C_{12}$ carbocyclyl, $C_2$-$C_{20}$ heterocyclyl, $C_1$-$C_{20}$ heteroaryl, and —($C_1$-$C_{12}$ alkylene)-($C_2$-$C_{20}$ heterocyclyl);

$R^2$ is selected from the structures:

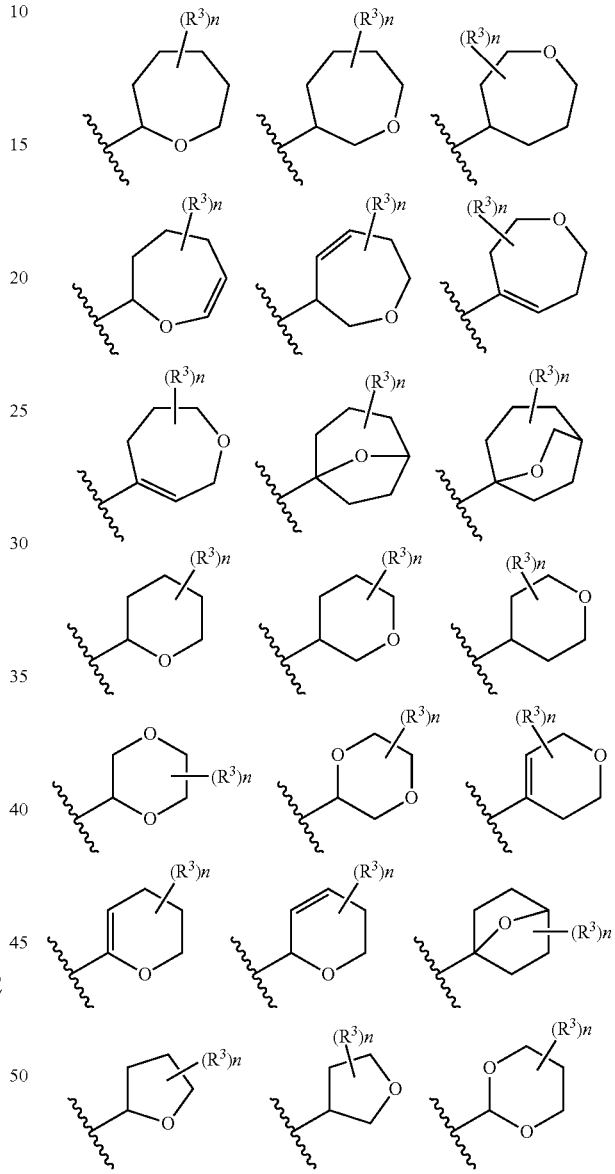

where the wavy line indicates the site of attachment;

$R^3$ is independently selected from F, Cl, Br, I, —$CH_3$, —$CH_2CH_3$, —$CH(CH_3)_2$, —$C(CH_3)_3$, —$CH_2CH(CH_3)_2$, —$CH=CH_2$, —$CH=C(CH_3)_2$, =$CH_2$, —$CH_2F$, —$CHF_2$, —$CF_3$, —$CH_2OH$, —$CH_2OCH_3$, —$CH_2NH_2$, —$CH_2NHCH_3$, —$CH_2CH_2NH_2$, —$CH_2CHCH_2NH_2$, —$CH_2CH(CH_3)NH_2$, —$CH_2OH$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —CN, —$CO_2H$, —$COCH_3$, —$COCH_2NH_2$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NO_2$, —$NH_2$, —$NHCH_3$, —N(CH₃)₂, —NHCH₂CHF₂, —NHCH₂CF₃, —NHCH₂CH₂OH, —NHCOCH₃, —N(CH₃)COCH₃, —NHC(O)OCH₂CH₃, —NHC(O)OCH₂Cl₃, —NHC(O)OC₆H₅, —NHS(O)₂CH₃, —N(CH₃)C(CH₃)₂CONH₂, —N(CH₃)CH₂CH₂S(O)₂CH₃, =O, —OH, —OCH₃, —OCHF₂, —OCH₂F, —OCH₂CH₃, —OCH(CH₃)₂, —OCH₂CH(CH₃)₂, —OC(CH₃)₃, —S(O)₂N(CH₃)₂, —SCH₃, —CH₂OCH₃, —S(O)₂CH₃, cyclopropyl, cyclobutyl, cyclopentyl, cyclohexyl, cycloheptyl, azetidinyl, azepanyl, oxetanyl, oxetan-3-ylmethylamino, (3-methyloxetan-3-yl)methylamino, pyrrolidinyl, piperazinyl, piperidinyl, (piperidin-4-yl)ethyl), pyranyl, (piperidin-4-ylmethyl), morpholinomethyl, and morpholino;

or where two geminal R³ groups form a spiro ring selected from a cyclopropyl, cyclobutyl, cyclopentyl, cyclohexyl, pyrrolidinyl, azetidinyl, azepanyl, oxetanyl, pyrrolidinyl, piperazinyl, or piperidinyl ring, where the spiro ring is optionally substituted with one or more groups independently selected from —F, —OH, =O, —CH₃, —NH₂, —CH₂F, —CH₂OH, —CH₂OCH₃, —CH₂NH₂, and —CF₃;

or where two vicinal R³ groups form a five-membered or six-membered heterocyclyl fused ring, where the heterocyclyl fused ring is optionally substituted with one or more groups independently selected from —F, —OH, =O, —CH₃, —NH₂, —CH₂F, —CH₂OH, —CH₂OCH₃, —CH₂NH₂, and —CF₃;

n is 0, 1, 2, 3, 4, 5, or 6;

X is selected from the structures:

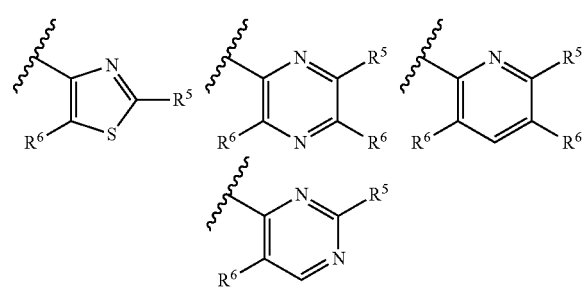

where the wavy line indicates the site of attachment;

R⁴ is independently H, F, —CH₃, or —NH₂; and

R⁵ is selected from H, Cl, Br, $C_1$-$C_{12}$ alkyl, —O—($C_1$-$C_{12}$ alkyl), —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_2$-$C_8$ alkenylene)-($C_3$-$C_{12}$ carbocyclyl), —($C_2$-$C_8$ alkenylene)-($C_2$-$C_{20}$ heterocyclyl), $C_6$-$C_{20}$ aryl, —($C_6$-$C_{20}$ arylene)-($C_2$-$C_{20}$ heterocyclyl), —($C_6$-$C_{20}$ arylene)-($C_6$-$C_{20}$ arylene), —($C_6$-$C_{20}$ arylene)-($C_1$-$C_{12}$ alkylene)-($C_2$-$C_{20}$ heterocyclyl), —($C_6$-$C_{20}$ arylene)-O—($C_2$-$C_{20}$ heterocyclyl), —($C_6$-$C_{20}$ arylene)-O—($C_1$-$C_{12}$ alkyl), $C_3$-$C_{12}$ carbocyclyl, $C_2$-$C_{20}$ heterocyclyl, $C_1$-$C_{20}$ heteroaryl, —($C_1$-$C_{20}$ heteroaryl)-($C_2$-$C_{20}$ heterocyclyl), and —($C_1$-$C_{20}$ heteroaryl)-($C_1$-$C_{12}$ alkyl); where alkyl, alkenyl, alkynyl, alkylene, carbocyclyl, heterocyclyl, aryl, and heteroaryl are optionally substituted with one or more groups independently selected from F, Cl, Br, I, —CH₃, —CH₂CH₃, —CH(CH₃)₂, —CH₂CH(CH₃)₂, —CH₂NH₂, —CH₂CH₂NH₂, —CH₂CHCH₂NH₂, —CH₂CH(CH₃)NH₂, —CH₂OH, —CH₂CH₂OH, —CH(CH₂OH)₂, —C(CH₂OH)₃, —CH(CH₃)OH, —C(CH₃)₂OH, —CH(OH)CH(CH₃)₂, —C(CH₃)₂CH₂OH, —CH₂CH₂SO₂CH₃, —CN, —CF₃, —CHF₂, —CH₂F, —CO₂H, —COCH₃, —COCH(CH₃)₂, —CO₂CH₃, —CO₂C(CH₃)₃, —COCH(OH)CH₃, —CONH₂, —CONHCH₃, —CON(CH₃)₂, —C(CH₃)₂CONH₂, —NO₂, —NH₂, —NHCH₃, —N(CH₃)₂, —NHCOCH₃, —N(CH₃)COCH₃, —NHS(O)₂CH₃, —N(CH₃)C(CH₃)₂CONH₂, —N(CH₃)CH₂CH₂S(O)₂CH₃, =O, —OH, —OCH₃, —OCF₃, —OCH(CH₃)₂, —S(O)₂N(CH₃)₂, —SCH₃, —CH₂OCH₃, —S(O)₂CH₃, cyclopropyl, cyclobutyl, cyclopentyl, cyclohexyl, cycloheptyl, azetidinyl, azepanyl, oxetanyl, phenyl, pyrrolidinyl, piperazinyl, piperidinyl, (piperidin-4-yl)ethyl), pyranyl, (piperidin-4-ylmethyl), morpholinomethyl, and morpholino.

Exemplary embodiments of Formula I compounds include wherein R¹ is H, $C_1$-$C_{12}$ alkyl including —CH₃, —CH₂CH₃, —CH₂CHF₂, and —CH₂CF₃, $C_3$-$C_{12}$ carbocyclyl, or —($C_1$-$C_{12}$ alkylene)-($C_2$-$C_{20}$ heterocyclyl) including oxetan-3-ylmethyl.

Exemplary embodiments of Formula I compounds include wherein R² has the structure:

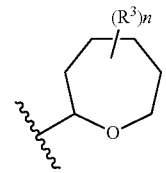

Exemplary embodiments of Formula I compounds include wherein R³ is independently selected from F, Cl, —OH, —CH₃, —CH₂CH₃, —CF₃, —NH₂, —NHCH₃, —N(CH₃)₂, —NHCH₂CHF₂, —NHCH₂CF₃, —CH₂NHCH₃, and —OCH₃; and n is 1, 2, or 3.

Exemplary embodiments of Formula I compounds include wherein R⁴ is —NH₂.

Exemplary embodiments of Formula I compounds include wherein R⁴ is H.

Exemplary embodiments of Formula I compounds include wherein R⁵ is $C_6$-$C_{20}$ aryl including phenyl substituted with one or more F.

Exemplary embodiments of Formula I compounds include the structures of Formula Ia-h, where R⁴ is NH₂ (Ia-d) and R⁴ is H (Ie-h):

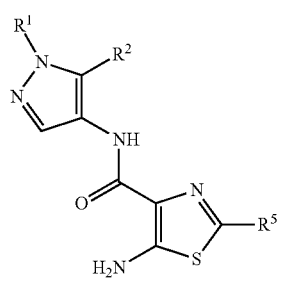

Ia

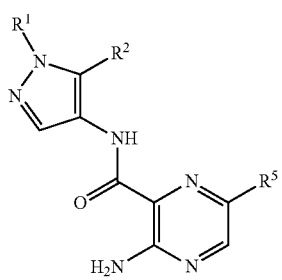

Ib

-continued

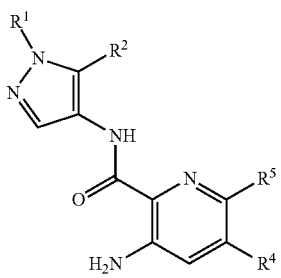
Ic

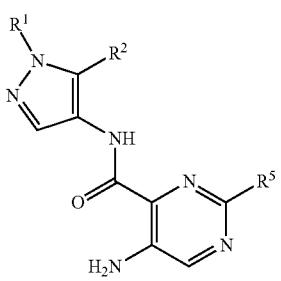
Id

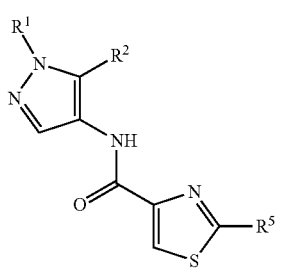
Ie

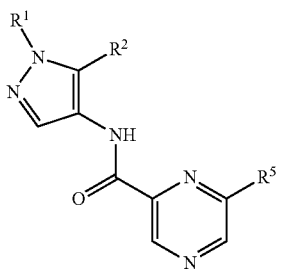
If

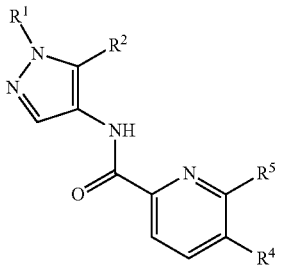
Ig

-continued

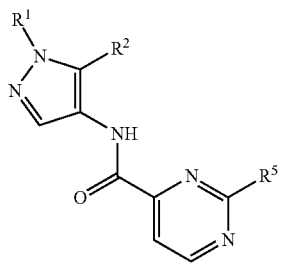
Ih

Biological Evaluation

Determination of the Pim kinase activity of a Formula I compound is possible by a number of direct and indirect detection methods. Certain exemplary compounds described herein were assayed for their Pim kinase binding activity, including isoforms Pim-1, Pim-2, and Pim-3, (Example 901) and in vitro activity against tumor cells (Example 902). Certain exemplary compounds of the invention had Pim binding activity $IC_{50}$ values less than about 1 micromolar (μM). Certain compounds of the invention had tumor cell-based activity $EC_{50}$ values less than about 1 micromolar (μM), for example against cell line BaF3, a murine interleukin-3 dependent pro-B cell line, useful as a model system for assessing both the potency and downstream signaling of kinase oncogenes ("Ba/F3 cells and their use in kinase drug discovery", Warmuth, M, et al, (January 2007) Current Opinion in Oncology, Vol 19(1):55-60), and against MM1.S, a multiple myeloma cell line, useful as a model system for assessing the efficacy of Pim inhibitors in the treatment of multiple myeloma patients (Greenstein et al (2003) Exper. Hematol. 31(4):271-282). Formula I compounds having $Ki/IC_{50}/EC_{50}$ of less than 1 μM in assays described in Examples 901 and 902, may be useful therapeutically as Pim kinase inhibitors (Pim-1, Pim-2 and/or Pim-3).

hERG (the human Ether-à-go-go-Related Gene) is a gene (KCNH2) that codes for a protein known as $K_v11.1$, the alpha subunit of a potassium ion channel. This ion channel (sometimes simply denoted as 'hERG') is best known for its contribution to the electrical activity of the heart that coordinates the heart's beating (i.e., the hERG channel mediates the repolarizing $I_{Kr}$ current in the cardiac action potential). When this channel's ability to conduct electrical current across the cell membrane is inhibited or compromised, either by application of drugs or by rare mutations in some families (Hedley P L et al. (2009) Human Mutation 30 (11): 1486-511), it can result in a potentially fatal disorder called long QT syndrome; a number of clinically successful drugs in the market have had the tendency to inhibit hERG, and create a concomitant risk of sudden death, as a side-effect, which has made hERG inhibition an important antitarget that must be avoided during drug development (Sanguinetti M C, Tristani-Firouzi M (March 2006) Nature 440(7083): 463-9). hERG has also been associated with modulating the functions of some cells of the nervous system (Chiesa N et al (June 1997) J. Physiol. (Lond.). 501 (Pt 2) (2): 313-8; Overholt J L, et al (2000) Adv. Exp. Med. Biol. 475: 241-8) and with establishing and maintaining cancer-like features in leukemic cells. hERG assays were conducted according to Example 903.

Exemplary Formula I compounds in Tables 1a, 1b, and 1c were made, characterized, and tested for inhibition of Pim kinase according to the methods of this invention, and have the following structures and corresponding names (Chem-BioDraw Ultra, Version 11.0, CambridgeSoft Corp., Cambridge Mass.). Some compounds with chiral atoms in Table 1 have not been fully characterized as to stereochemistry. A tentative assignment of stereochemistry or stereochemical relationship to other groups may be depicted in the structures. Means of separation of stereoisomers and characterization data are given in the Examples.

TABLE 1a

| No. | Structure | IUPAC Name | PIM1 LC3K (KI) uM |
|---|---|---|---|
| 101 | 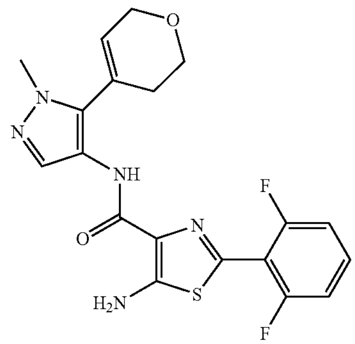 [SMILES: Cn1ncc(NC(=O)c2nc(-c3c(F)cccc3F)sc2N)c1C1=CCOCC1] | 5-amino-2-(2,6-difluorophenyl)-N-[5-(3,6-dihydro-2H-pyran-4-yl)-1-methyl-pyrazol-4-yl]thiazole-4-carboxamide | 0.000485 |
| 102 | 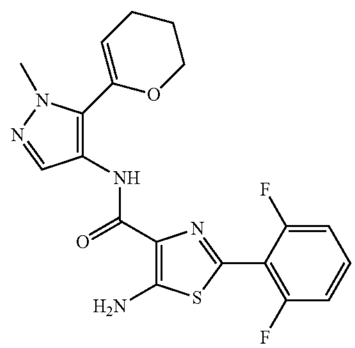 [SMILES: Cn1ncc(NC(=O)c2nc(-c3c(F)cccc3F)sc2N)c1C1=CCCCO1] | 5-amino-2-(2,6-difluorophenyl)-N-[5-(3,4-dihydro-2H-pyran-6-yl)-1-methyl-pyrazol-4-yl]thiazole-4-carboxamide | 0.000408 |
| 103 | 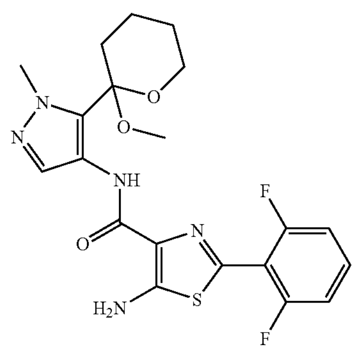 [SMILES: COC1(c2c(NC(=O)c3nc(-c4c(F)cccc4F)sc3N)cnn2C)CCCCO1] | 5-amino-2-(2,6-difluorophenyl)-N-[5-(2-methoxytetrahydropyran-2-yl)-1-methyl-pyrazol-4-yl]thiazole-4-carboxamide | 0.000209 |
| 104 | 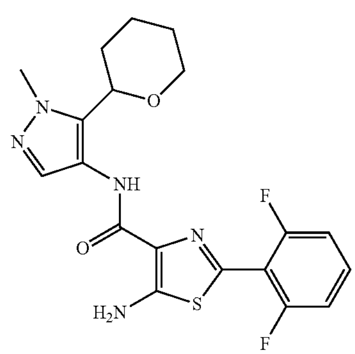 [SMILES: Cn1ncc(NC(=O)c2nc(-c3c(F)cccc3F)sc2N)c1C1CCCCO1] | 5-amino-2-(2,6-difluorophenyl)-N-(1-methyl-5-tetrahydropyran-2-yl-pyrazol-4-yl)thiazole-4-carboxamide | 0.000424 |

TABLE 1a-continued

| No. | Structure | IUPAC Name | PIM1 LC3K (KI) uM |
|---|---|---|---|
| 105 | 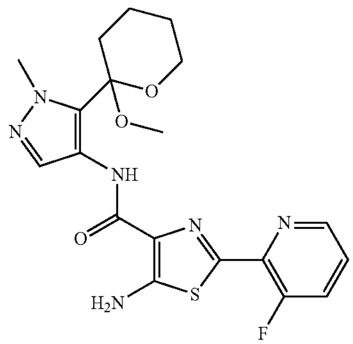 [SMILES: COC1(c2c(NC(=O)c3nc(-c4ncccc4F)sc3N)cnn2C)CCCCO1] | 5-amino-2-(3-fluoro-2-pyridyl)-N-[5-(2-methoxytetrahydropyran-2-yl)-1-methyl-pyrazol-4-yl]thiazole-4-carboxamide | 0.000118 |
| 106 | 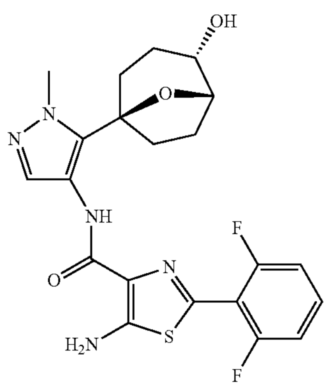 [SMILES: Cn1ncc(NC(=O)c2nc(-c3c(F)cccc3F)sc2N)c1[C@]12CC[C@H](O1)[C@@H](O)CC2] | 5-amino-2-(2,6-difluorophenyl)-N-(5-((1S,4S,5S)-4-hydroxy-8-oxabicyclo[3.2.1]octan-1-yl)-1-methyl-1H-pyrazol-4-yl)thiazole-4-carboxamide | 0.000032 |
| 107 | 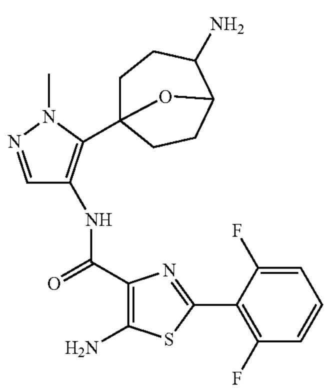 [SMILES: Cn1ncc(NC(=O)c2nc(-c3c(F)cccc3F)sc2N)c1C12CCC(N)C(CC1)O2] | 5-amino-N-[5-(2-amino-8-oxabicyclo[3.2.1]octan-5-yl)-1-methyl-pyrazol-4-yl]-2-(2,6-difluorophenyl)thiazole-4-carboxamide | 0.000008 |
| 108 | 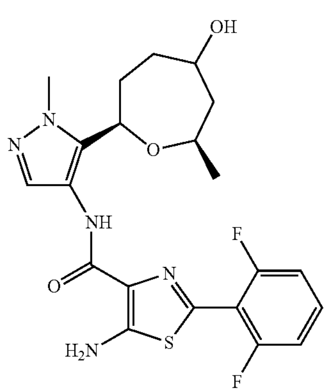 [SMILES: C[C@@H]1CC(O)CC[C@H](c2c(NC(=O)c3nc(-c4c(F)cccc4F)sc3N)cnn2C)O1] | 5-amino-2-(2,6-difluorophenyl)-N-(5-((2R,7R)-5-hydroxy-7-methyloxepan-2-yl)-1-methyl-1H-pyrazol-4-yl)thiazole-4-carboxamide | 0.000049 |

TABLE 1a-continued

| No. | Structure | IUPAC Name | PIM1 LC3K (KI) uM |
|---|---|---|---|
| 109 | 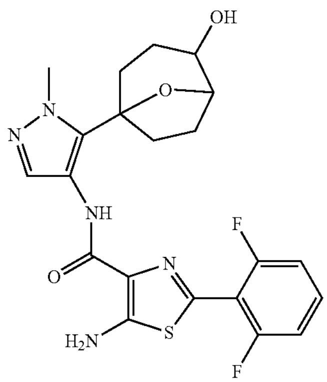 [SMILES: Cn1ncc(NC(=O)c2nc(-c3c(F)cccc3F)sc2N)c1C12CCC(O)C(CC1)O2] | 5-amino-2-(2,6-difluorophenyl)-N-[5-(2-hydroxy-8-oxabicyclo[3.2.1]octan-5-yl)-1-methyl-pyrazol-4-yl]thiazole-4-carboxamide | 0.000034 |
| 110 | 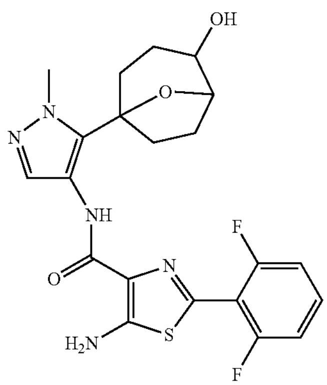 [SMILES: Cn1ncc(NC(=O)c2nc(-c3c(F)cccc3F)sc2N)c1C12CCC(O)C(CC1)O2] | 5-amino-2-(2,6-difluorophenyl)-N-[5-(2-hydroxy-8-oxabicyclo[3.2.1]octan-5-yl)-1-methyl-pyrazol-4-yl]thiazole-4-carboxamide | 0.000017 |
| 111 | 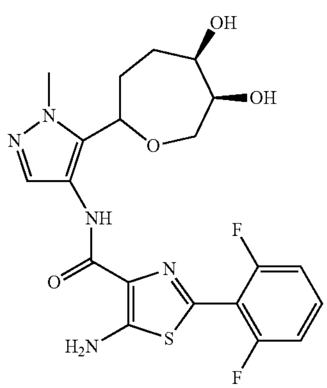 [SMILES: Cn1ncc(NC(=O)c2nc(-c3c(F)cccc3F)sc2N)c1C1CC[C@@H](O)[C@@H](O)CO1] | 5-amino-2-(2,6-difluorophenyl)-N-(5-((5R,6S)-5,6-dihydroxyoxepan-2-yl)-1-methyl-1H-pyrazol-4-yl)thiazole-4-carboxamide | 0.000425 |
| 112 | 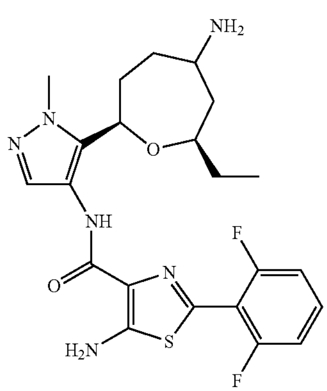 [SMILES: CC[C@@H]1CC(N)CC[C@H](c2c(NC(=O)c3nc(-c4c(F)cccc4F)sc3N)cnn2C)O1] | 5-amino-N-(5-((2R,7R)-5-amino-7-ethyloxepan-2-yl)-1-methyl-1H-pyrazol-4-yl)-2-(2,6-difluorophenyl)thiazole-4-carboxamide | 0.000502 |

TABLE 1a-continued

| No. | Structure | IUPAC Name | PIM1 LC3K (KI) uM |
|---|---|---|---|
| 113 | 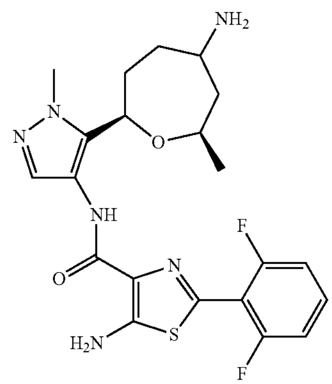 [SMILES: C[C@@H]1CC(N)CC[C@H](c2c(NC(=O)c3nc(-c4c(F)cccc4F)sc3N)cnn2C)O1] | 5-amino-N-(5-((2R,7R)-5-amino-7-methyloxepan-2-yl)-1-methyl-1H-pyrazol-4-yl)-2-(2,6-difluorophenyl)thiazole-4-carboxamide | 0.000019 |
| 114 | 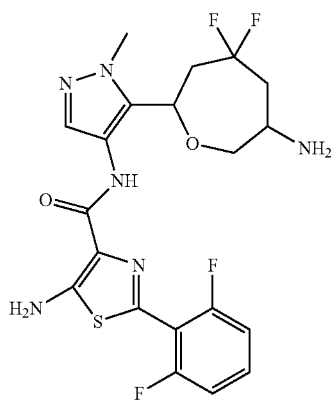 [SMILES: Cn1ncc(NC(=O)c2nc(-c3c(F)cccc3F)sc2N)c1C1CC(F)(F)CC(N)CO1] | 5-amino-N-[5-(6-amino-4,4-difluoro-oxepan-2-yl)-1-methyl-pyrazol-4-yl]-2-(2,6-difluorophenyl)thiazole-4-carboxamide | 0.000032 |
| 115 | 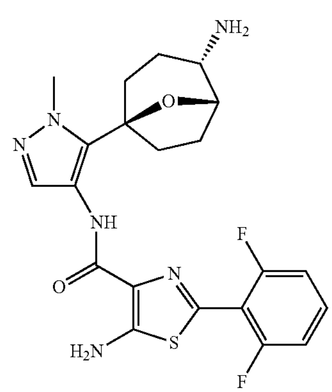 [SMILES: Cn1ncc(NC(=O)c2nc(-c3c(F)cccc3F)sc2N)c1[C@]12CC[C@H](O1)[C@@H](N)CC2] | 5-amino-N-(5-((1S,4S,5S)-4-amino-8-oxabicyclo[3.2.1]octan-1-yl)-1-methyl-1H-pyrazol-4-yl)-2-(2,6-difluorophenyl)thiazole-4-carboxamide | 0.000006 |
| 116 | 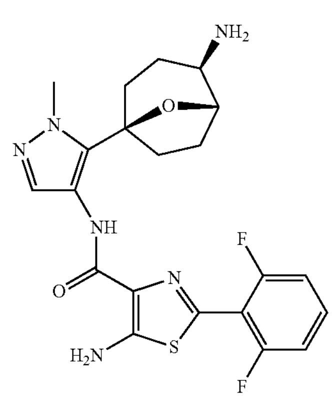 [SMILES: Cn1ncc(NC(=O)c2nc(-c3c(F)cccc3F)sc2N)c1[C@]12CC[C@@H](N)[C@H](CC1)O2] | 5-amino-N-(5-((1S,4R,5S)-4-amino-8-oxabicyclo[3.2.1]octan-1-yl)-1-methyl-1H-pyrazol-4-yl)-2-(2,6-difluorophenyl)thiazole-4-carboxamide | 0.000072 |

TABLE 1a-continued

| No. | Structure | IUPAC Name | PIM1 LC3K (KI) uM |
|---|---|---|---|
| 117 | 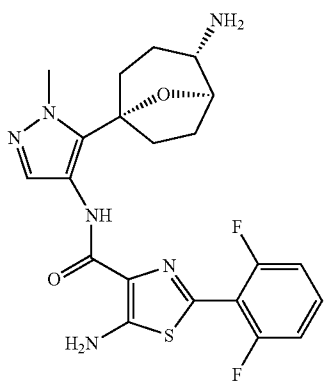 [SMILES: Cn1ncc(NC(=O)c2nc(-c3c(F)cccc3F)sc2N)c1[C@@]12CC[C@H](N)[C@@H](CC1)O2] | 5-amino-N-(5-((1R,4S,5R)-4-amino-8-oxabicyclo[3.2.1]octan-1-yl)-1-methyl-1H-pyrazol-4-yl)-2-(2,6-difluorophenyl)thiazole-4-carboxamide | 0.000002 |
| 118 | 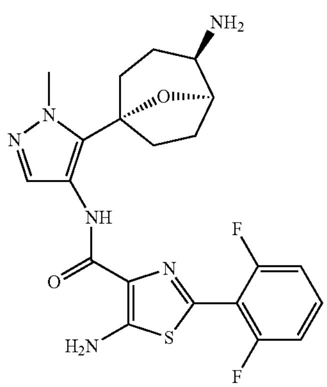 [SMILES: Cn1ncc(NC(=O)c2nc(-c3c(F)cccc3F)sc2N)c1[C@@]12CC[C@@H](N)[C@@H](CC1)O2] | 5-amino-N-(5-((1R,4R,5R)-4-amino-8-oxabicyclo[3.2.1]octan-1-yl)-1-methyl-1H-pyrazol-4-yl)-2-(2,6-difluorophenyl)thiazole-4-carboxamide | 0.000009 |
| 119 | 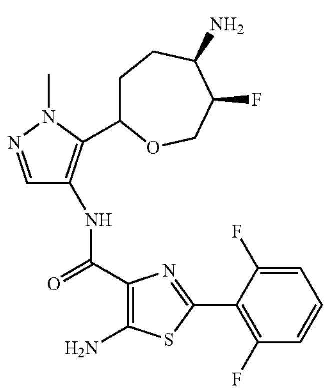 [SMILES: Cn1ncc(NC(=O)c2nc(-c3c(F)cccc3F)sc2N)c1C1CC[C@@H](N)[C@@H](F)CO1] | 5-amino-N-(5-((5R,6R)-5-amino-6-fluorooxepan-2-yl)-1-methyl-1H-pyrazol-4-yl)-2-(2,6-difluorophenyl)thiazole-4-carboxamide | 0.000021 |
| 120 | 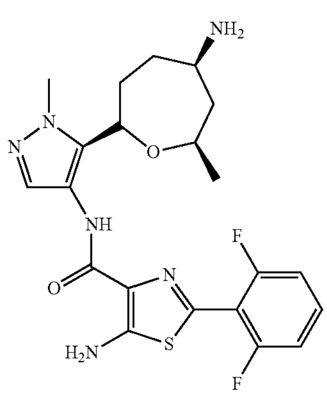 | 5-amino-N-(5-((2R,5R,7R)-5-amino-7-methyloxepan-2-yl)-1-methyl-1H-pyrazol-4-yl)-2-(2,6-difluorophenyl)thiazole-4-carboxamide | 0.000081 |

TABLE 1a-continued

| No. | Structure | IUPAC Name | PIM1 LC3K (KI) uM |
|---|---|---|---|
| 121 | 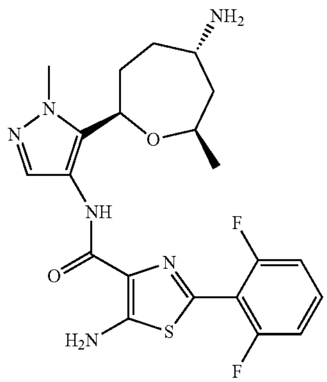 | 5-amino-N-(5-((2R,5S,7R)-5-amino-7-methyloxepan-2-yl)-1-methyl-1H-pyrazol-4-yl)-2-(2,6-difluorophenyl)thiazole-4-carboxamide | 0.000003 |
| 122 | 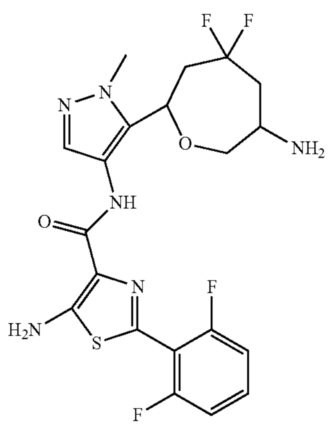 [SMILES: Cn1ncc(NC(=O)c2nc(-c3c(F)cccc3F)sc2N)c1C1CC(F)(F)CC(N)CO1] | 5-amino-N-[5-(6-amino-4,4-difluoro-oxepan-2-yl)-1-methyl-pyrazol-4-yl]-2-(2,6-difluorophenyl)thiazole-4-carboxamide | 0.000014 |
| 123 | 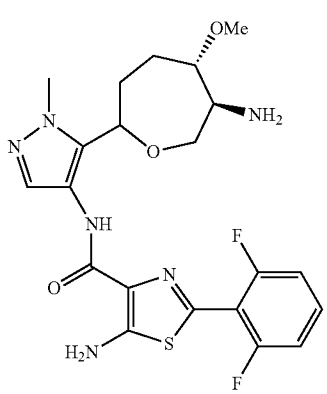 [SMILES: CO[C@H]1CCC(c2c(NC(=O)c3nc(-c4c(F)cccc4F)sc3N)cnn2C)OC[C@@H]1N] | 5-amino-N-(5-((5S,6S)-6-amino-5-methoxyoxepan-2-yl)-1-methyl-1H-pyrazol-4-yl)-2-(2,6-difluorophenyl)thiazole-4-carboxamide | 0.000125 |

TABLE 1a-continued

| No. | Structure | IUPAC Name | PIM1 LC3K (KI) uM |
|---|---|---|---|
| 124 | 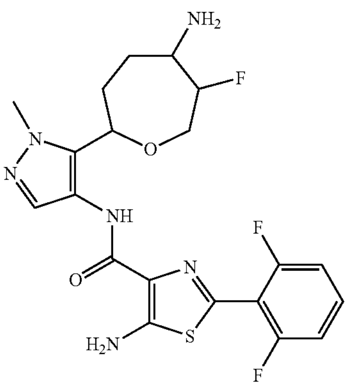 [SMILES: Cn1ncc(NC(=O)c2nc(-c3c(F)cccc3F)sc2N)c1C1CCC(N)C(F)CO1] | 5-amino-N-[5-(5-amino-6-fluoro-oxepan-2-yl)-1-methyl-pyrazol-4-yl]-2-(2,6-difluorophenyl)thiazole-4-carboxamide | 0.000015 |
| 125 | 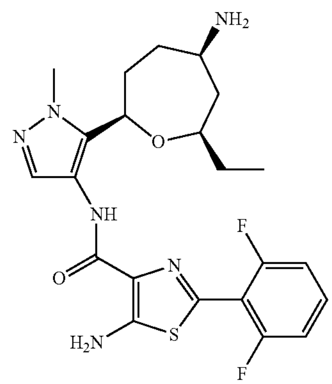 [SMILES: CC[C@@H]1C[C@H](N)CC[C@H](c2c(NC(=O)c3nc(-c4c(F)cccc4F)sc3N)cnn2C)O1] | 5-amino-N-(5-((2R,7R)-5-amino-7-ethyloxepan-2-yl)-1-methyl-1H-pyrazol-4-yl)-2-(2,6-difluorophenyl)thiazole-4-carboxamide | 0.0035 |
| 126 | 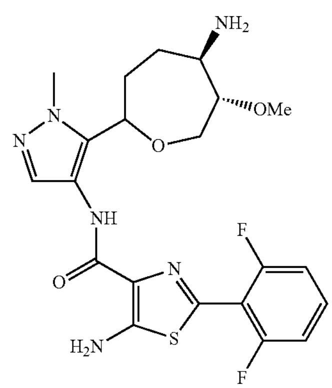 [SMILES: CO[C@@H]1COC(c2c(NC(=O)c3nc(-c4c(F)cccc4F)sc3N)cnn2C)CC[C@H]1N] | 5-amino-N-(5-((5R,6S)-5-amino-6-methoxyoxepan-2-yl)-1-methyl-1H-pyrazol-4-yl)-2-(2,6-difluorophenyl)thiazole-4-carboxamide | 0.000026 |
| 127 | 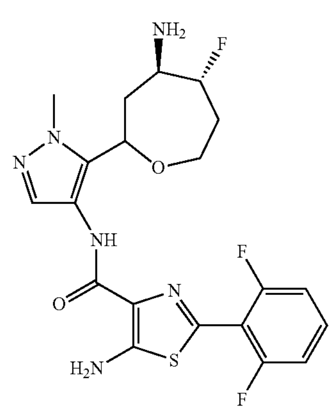 [SMILES: Cn1ncc(NC(=O)c2nc(-c3c(F)cccc3F)sc2N)c1C1C[C@@H](N)[C@H](F)CCO1] | 5-amino-N-(5-((4R,5R)-4-amino-5-fluorooxepan-2-yl)-1-methyl-1H-pyrazol-4-yl)-2-(2,6-difluorophenyl)thiazole-4-carboxamide | 0.000112 |

TABLE 1a-continued

| No. | Structure | IUPAC Name | PIM1 LC3K (KI) uM |
|---|---|---|---|
| 128 | 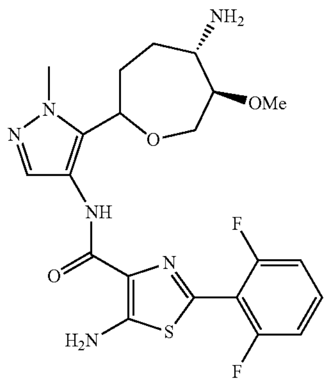 [SMILES: CO[C@H]1COC(c2c(NC(=O)c3nc(-c4c(F)cccc4F)sc3N)cnn2C)CC[C@@H]1N] | 5-amino-N-(5-((5S,6R)-5-amino-6-methoxyoxepan-2-yl)-1-methyl-1H-pyrazol-4-yl)-2-(2,6-difluorophenyl)thiazole-4-carboxamide | 0.000476 |
| 129 | 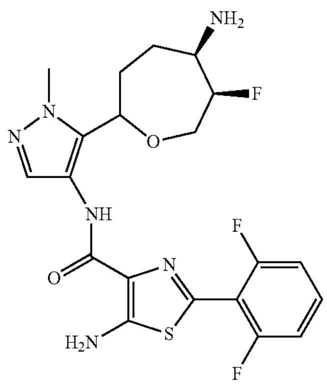 [SMILES: Cn1ncc(NC(=O)c2nc(-c3c(F)cccc3F)sc2N)c1C1CC[C@@H](N)[C@@H](F)CO1] | 5-amino-N-(5-((5R,6R)-5-amino-6-fluorooxepan-2-yl)-1-methyl-1H-pyrazol-4-yl)-2-(2,6-difluorophenyl)thiazole-4-carboxamide | 0.000006 |
| 130 | 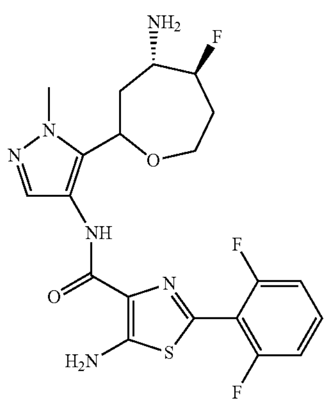 [SMILES: Cn1ncc(NC(=O)c2nc(-c3c(F)cccc3F)sc2N)c1C1C[C@H](N)[C@@H](F)CCO1] | 5-amino-N-(5-((4S,5S)-4-amino-5-fluorooxepan-2-yl)-1-methyl-1H-pyrazol-4-yl)-2-(2,6-difluorophenyl)thiazole-4-carboxamide | 0.000358 |
| 131 | 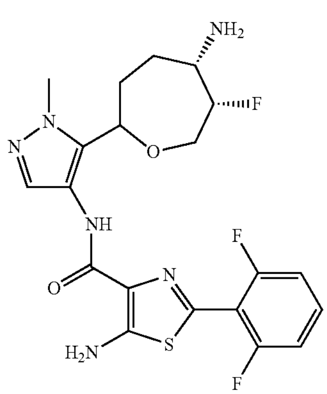 [SMILES: Cn1ncc(NC(=O)c2nc(-c3c(F)cccc3F)sc2N)c1C1CC[C@H](N)[C@H](F)CO1] | 5-amino-N-(5-((5S,6S)-5-amino-6-fluorooxepan-2-yl)-1-methyl-1H-pyrazol-4-yl)-2-(2,6-difluorophenyl)thiazole-4-carboxamide | 0.00027 |

TABLE 1a-continued

| No. | Structure | IUPAC Name | PIM1 LC3K (KI) uM |
|-----|-----------|------------|-------------------|
| 132 | 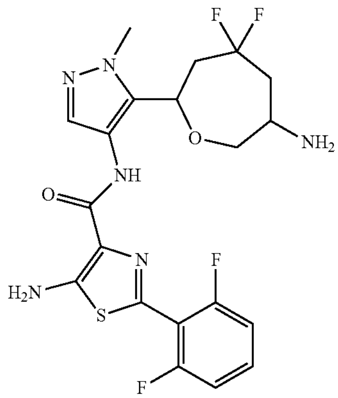 [SMILES: Cn1ncc(NC(=O)c2nc(-c3c(F)cccc3F)sc2N)c1C1CC(F)(F)CC(N)CO1] | 5-amino-N-[5-(6-amino-4,4-difluoro-oxepan-2-yl)-1-methyl-pyrazol-4-yl]-2-(2,6-difluorophenyl)thiazole-4-carboxamide | 0.000014 |
| 133 | 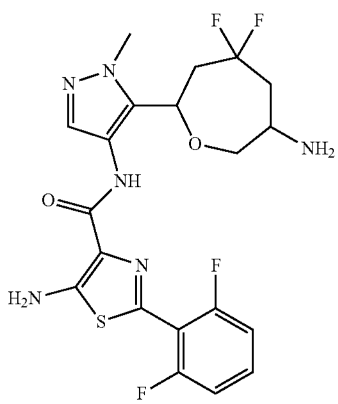 [SMILES: Cn1ncc(NC(=O)c2nc(-c3c(F)cccc3F)sc2N)c1C1CC(F)(F)CC(N)CO1] | 5-amino-N-[5-(6-amino-4,4-difluoro-oxepan-2-yl)-1-methyl-pyrazol-4-yl]-2-(2,6-difluorophenyl)thiazole-4-carboxamide | 0.000076 |
| 134 | 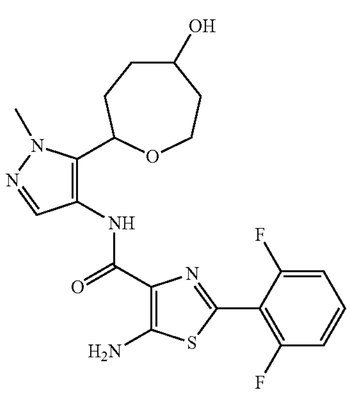 [SMILES: Cn1ncc(NC(=O)c2nc(-c3c(F)cccc3F)sc2N)c1C1CCC(O)CCO1] | 5-amino-2-(2,6-difluorophenyl)-N-[5-(5-hydroxyoxepan-2-yl)-1-methyl-pyrazol-4-yl]thiazole-4-carboxamide | 0.000054 |

TABLE 1a-continued

| No. | Structure | IUPAC Name | PIM1 LC3K (KI) uM |
|---|---|---|---|
| 135 | 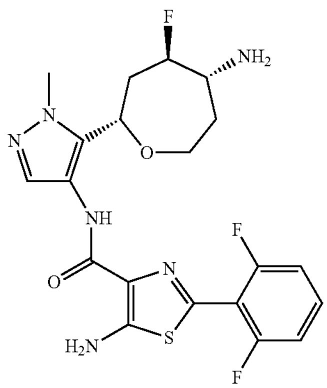 [SMILES: Cn1ncc(NC(=O)c2nc(-c3c(F)cccc3F)sc2N)c1[C@@H]1C[C@@H](F)[C@H](N)CCO1] | 5-amino-N-[5-(5-amino-4-fluoro-oxepan-2-yl)-1-methyl-pyrazol-4-yl]-2-(2,6-difluorophenyl)thiazole-4-carboxamide | 0.00001 |
| 136 | 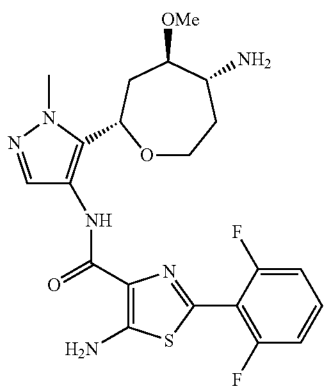 [SMILES: CO[C@@H]1C[C@@H](c2c(NC(=O)c3nc(-c4c(F)cccc4F)sc3N)cnn2C)OCC[C@H]1N] | 5-amino-N-(5-((2S,4R,5R)-5-amino-4-methoxyoxepan-2-yl)-1-methyl-1H-pyrazol-4-yl)-2-(2,6-difluorophenyl)thiazole-4-carboxamide | 0.000057 |
| 137 | 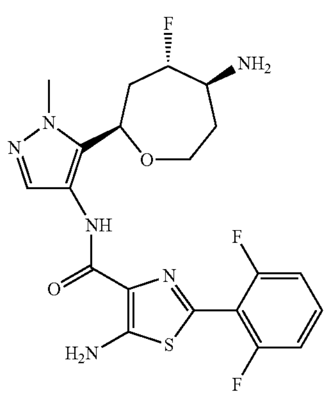 [SMILES: Cn1ncc(NC(=O)c2nc(-c3c(F)cccc3F)sc2N)c1[C@H]1C[C@H](F)[C@@H](N)CCO1] | 5-amino-N-(5-((2R,4S,5S)-5-amino-4-fluorooxepan-2-yl)-1-methyl-1H-pyrazol-4-yl)-2-(2,6-difluorophenyl)thiazole-4-carboxamide | 0.000099 |
| 138 | 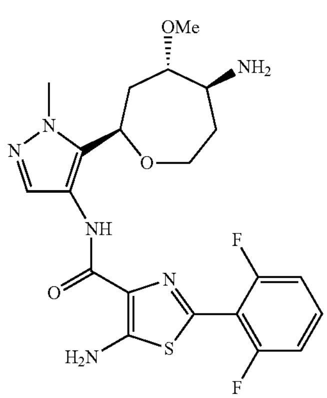 [SMILES: CO[C@H]1C[C@H](c2c(NC(=O)c3nc(-c4c(F)cccc4F)sc3N)cnn2C)OCC[C@@H]1N] | 5-amino-N-(5-((2R,4S,5S)-5-amino-4-methoxyoxepan-2-yl)-1-methyl-1H-pyrazol-4-yl)-2-(2,6-difluorophenyl)thiazole-4-carboxamide | 0.00187 |

TABLE 1a-continued

| No. | Structure | IUPAC Name | PIM1 LC3K (KI) uM |
|---|---|---|---|
| 139 | 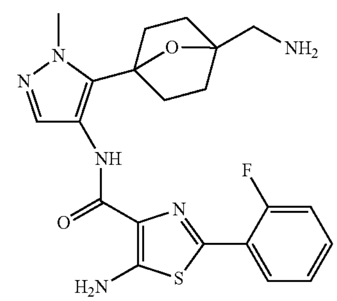 [SMILES: Cn1ncc(NC(=O)c2nc(-c3ccccc3F)sc2N)c1C12CCC(CN)(CC1)O2] | 5-amino-N-[5-[1-(aminomethyl)-7-oxabicyclo[2.2.1]heptan-4-yl]-1-methyl-pyrazol-4-yl]-2-(2-fluorophenyl)thiazole-4-carboxamide | 0.000053 |
| 140 | 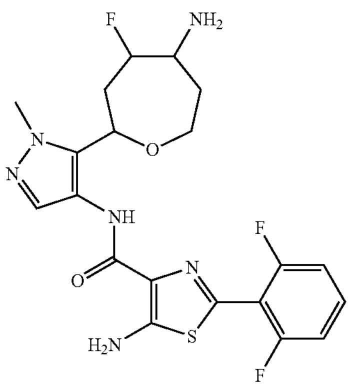 [SMILES: Cn1ncc(NC(=O)c2nc(-c3c(F)cccc3F)sc2N)c1C1CC(F)C(N)CCO1] | 5-amino-N-(5-(5-amino-4-fluorooxepan-2-yl)-1-methyl-1H-pyrazol-4-yl)-2-(2,6-difluorophenyl)thiazole-4-carboxamide | 0.000469 |
| 141 | 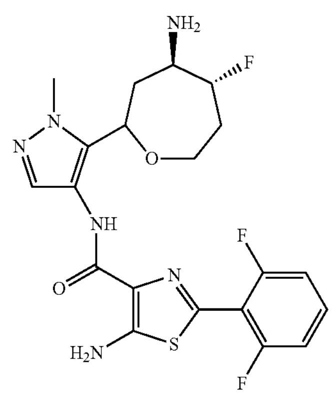 [SMILES: Cn1ncc(NC(=O)c2nc(-c3c(F)cccc3F)sc2N)c1C1C[C@@H](N)[C@H](F)CCO1] | 5-amino-N-(5-((4R,5R)-4-amino-5-fluorooxepan-2-yl)-1-methyl-1H-pyrazol-4-yl)-2-(2,6-difluorophenyl)thiazole-4-carboxamide | 0.00007 |
| 142 | 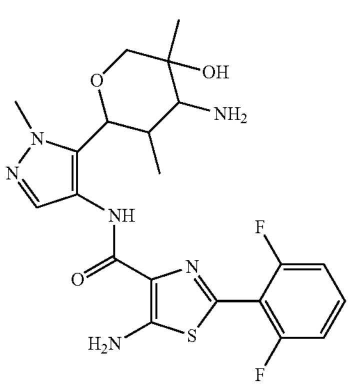 [SMILES: CC1C(c2c(NC(=O)c3nc(-c4c(F)cccc4F)sc3N)cnn2C)OCC(C)(O)C1N] | 5-amino-N-[5-(4-amino-5-hydroxy-3,5-dimethyl-tetrahydropyran-2-yl)-1-methyl-pyrazol-4-yl]-2-(2,6-difluorophenyl)thiazole-4-carboxamide | 0.000441 |

TABLE 1a-continued

| No. | Structure | IUPAC Name | PIM1 LC3K (KI) uM |
|---|---|---|---|
| 143 | 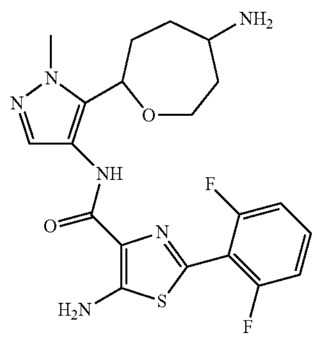 [SMILES: Cn1ncc(NC(=O)c2nc(-c3c(F)cccc3F)sc2N)c1C1CCC(N)CCO1] | 5-amino-N-[5-(6-aminooxepan-3-yl)-1-methyl-pyrazol-4-yl]-2-(2,6-difluorophenyl)thiazole-4-carboxamide | 0.000194 |
| 144 | 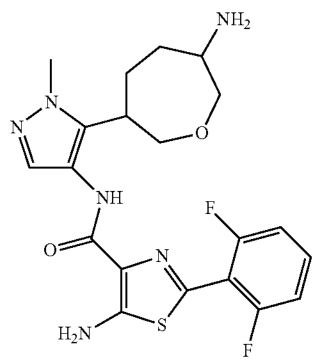 [SMILES: Cn1ncc(NC(=O)c2nc(-c3c(F)cccc3F)sc2N)c1C1CCC(N)COC1] | 5-amino-N-[5-(6-aminooxepan-3-yl)-1-methyl-pyrazol-4-yl]-2-(2,6-difluorophenyl)thiazole-4-carboxamide | 0.00145 |
| 145 | 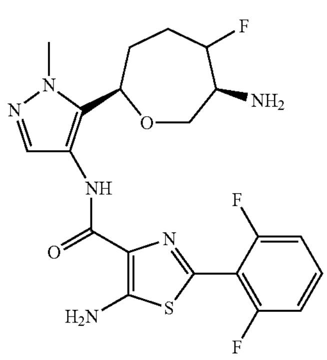 [SMILES: Cn1ncc(NC(=O)c2nc(-c3c(F)cccc3F)sc2N)c1[C@H]1CCC(F)[C@@H](N)CO1] | 5-Amino-N-[5-[6-amino-5-fluoro-oxepan-2-yl]-1-methyl-pyrazol-4-yl]-2-(2,6-difluorophenyl)thiazole-4-carboxamide | 0.000351 |
| 146 | 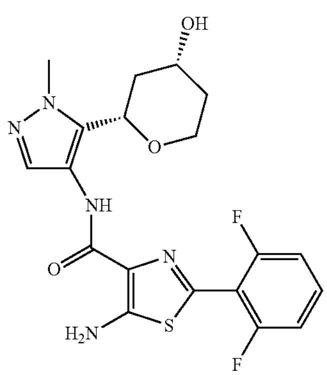 [SMILES: Cn1ncc(NC(=O)c2nc(-c3c(F)cccc3F)sc2N)c1[C@@H]1C[C@H](O)CCO1] | 5-amino-2-(2,6-difluorophenyl)-N-(5-((2S,4R)-4-hydroxytetrahydro-2H-pyran-2-yl)-1-methyl-1H-pyrazol-4-yl)thiazole-4-carboxamide | 0.000095 |

TABLE 1a-continued

| No. | Structure | IUPAC Name | PIM1 LC3K (KI) uM |
|---|---|---|---|
| 147 | 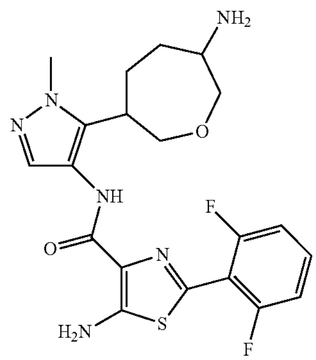 [SMILES: Cn1ncc(NC(=O)c2nc(-c3c(F)cccc3F)sc2N)c1C1CCC(N)COC1] | 5-amino-N-[5-(6-aminooxepan-3-yl)-1-methyl-pyrazol-4-yl]-2-(2,6-difluorophenyl)thiazole-4-carboxamide | 0.000141 |
| 148 | 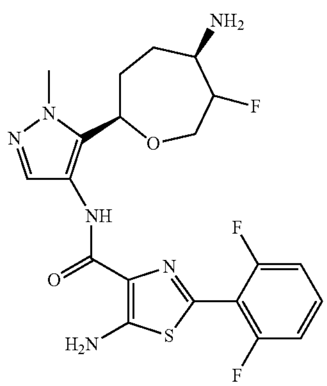 [SMILES: Cn1ncc(NC(=O)c2nc(-c3c(F)cccc3F)sc2N)c1[C@H]1CC[C@@H](N)C(F)CO1] | 5-Amino-N-[5-[5-amino-6-fluoro-oxepan-2-yl]-1-methyl-pyrazol-4-yl]-2-(2,6-difluorophenyl)thiazole-4-carboxamide | 0.000079 |
| 149 | 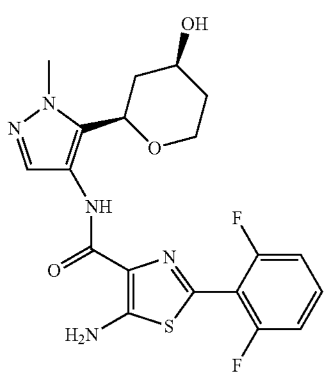 [SMILES: Cn1ncc(NC(=O)c2nc(-c3c(F)cccc3F)sc2N)c1[C@H]1C[C@@H](O)CCO1] | 5-amino-2-(2,6-difluorophenyl)-N-(5-((2R,4S)-4-hydroxytetrahydro-2H-pyran-2-yl)-1-methyl-1H-pyrazol-4-yl)thiazole-4-carboxamide | 0.000174 |
| 150 | 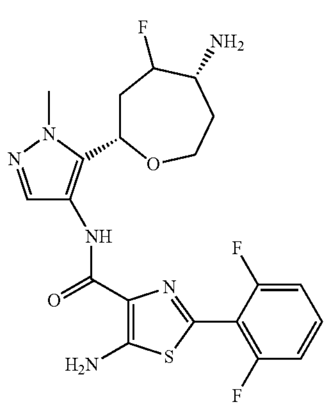 [SMILES: Cn1ncc(NC(=O)c2nc(-c3c(F)cccc3F)sc2N)c1[C@@H]1CC(F)[C@H](N)CCO1] | 5-Amino-N-[5-[(2S,5R)-5-amino-4-fluoro-oxepan-2-yl]-1-methyl-pyrazol-4-yl]-2-(2,6-difluorophenyl)thiazole-4-carboxamide | 0.000105 |

TABLE 1a-continued

| No. | Structure | IUPAC Name | PIM1 LC3K (KI) uM |
|---|---|---|---|
| 151 | 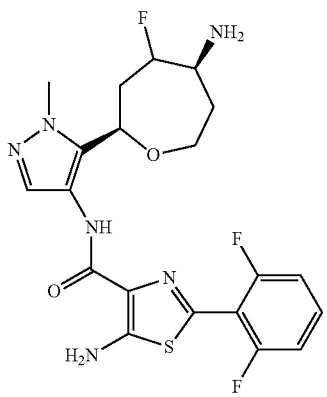 [SMILES: Cn1ncc(NC(=O)c2nc(-c3c(F)cccc3F)sc2N)c1[C@H]1CC(F)[C@@H](N)CCO1] | 5-Amino-N-[5-[(2R,5S)-5-amino-4-fluoro-oxepan-2-yl]-1-methyl-pyrazol-4-yl]-2-(2,6-difluorophenyl)thiazole-4-carboxamide | 0.000068 |
| 152 | 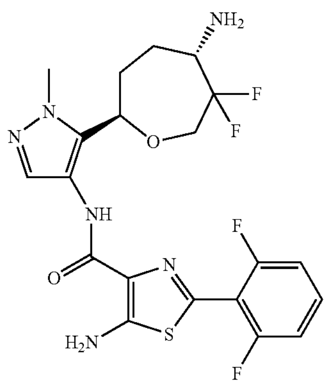 [SMILES: Cn1ncc(NC(=O)c2nc(-c3c(F)cccc3F)sc2N)c1[C@H]1CC[C@H](N)C(F)(F)CO1] | 5-Amino-N-[5-[(5-amino-6,6-difluoro-oxepan-2-yl]-1-methyl-pyrazol-4-yl]-2-(2,6-difluorophenyl)thiazole-4-carboxamide | 0.000031 |
| 153 | 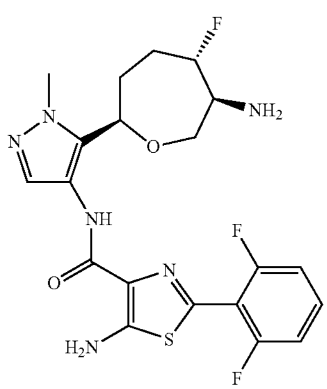 [SMILES: Cn1ncc(NC(=O)c2nc(-c3c(F)cccc3F)sc2N)c1[C@H]1CC[C@H](F)[C@@H](N)CO1] | 5-Amino-N-[5-[(2R,5S,6S)-6-amino-5-fluoro-oxepan-2-yl]-1-methyl-pyrazol-4-yl]-2-(2,6-difluorophenyl)thiazole-4-carboxamide | 0.000114 |
| 154 | 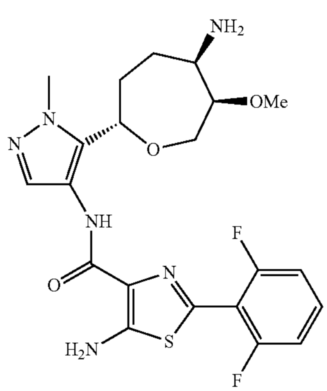 [SMILES: CO[C@H]1CO[C@H](c2c(NC(=O)c3nc(-c4c(F)cccc4F)sc3N)cnn2C)CC[C@H]1N] | 5-Amino-N-[5-[(2S,5R,6R)-5-amino-6-methoxy-oxepan-2-yl]-1-methyl-pyrazol-4-yl]-2-(2,6-difluorophenyl)thiazole-4-carboxamide | 0.0000080 |

TABLE 1a-continued

| No. | Structure | IUPAC Name | PIM1 LC3K (KI) uM |
|---|---|---|---|
| 155 | 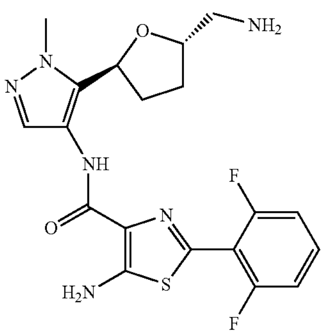 [SMILES: Cn1ncc(NC(=O)c2nc(-c3c(F)cccc3F)sc2N)c1[C@@H]1CC[C@@H](CN)O1] | 5-Amino-N-[5-[5-(aminomethyl)tetrahydrofuran-2-yl]-1-methyl-pyrazol-4-yl]-2-(2,6-difluorophenyl)thiazole-4-carboxamide | 0.000104 |

TABLE 1b

| No. | Structure | IUPAC Name | PIM1 LC3K (KI) μM |
|---|---|---|---|
| 156 | 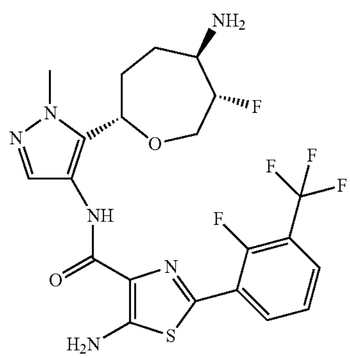 [SMILES: Cn1ncc(NC(=O)c2nc(-c3cccc(C(F)(F)F)c3F)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(2-fluoro-3-(trifluoromethyl)phenyl)thiazole-4-carboxamide | 0.000107 |
| 157 | 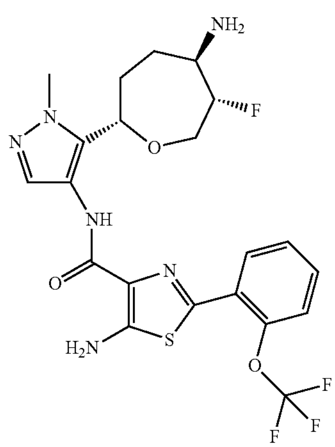 [SMILES: Cn1ncc(NC(=O)c2nc(-c3ccccc3OC(F)(F)F)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(2-(trifluoromethoxy)phenyl)thiazole-4-carboxamide | 0.000965 |

TABLE 1b-continued

| No. | Structure | IUPAC Name | PIM1 LC3K (KI) μM |
|---|---|---|---|
| 158 | 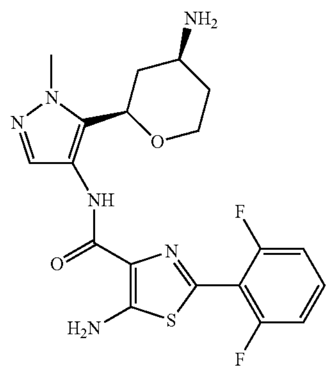 [SMILES: Cn1ncc(NC(=O)c2nc(-c3c(F)cccc3F)sc2N)c1[C@H]1C[C@@H](N)CCO1] | Amino-N-[5-[4-aminotetrahydropyran-2-yl]-1-methyl-pyrazol-4-yl]-2-(2,6-difluorophenyl)thiazole-4-carboxamide | 0.000032 |
| 159 | 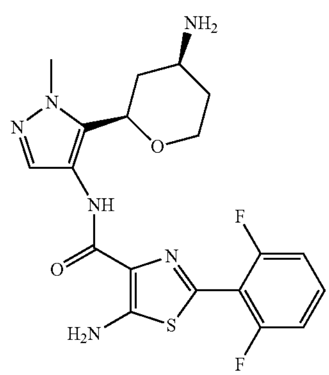 [SMILES: Cn1ncc(NC(=O)c2nc(-c3c(F)cccc3F)sc2N)c1[C@H]1C[C@@H](N)CCO1] | 5-Amino-N-[5-[(2R,4S)-4-aminotetrahydropyran-2-yl]-1-methyl-pyrazol-4-yl]-2-(2,6-difluorophenyl)thiazole-4-carboxamide | 0.000019 |
| 160 | 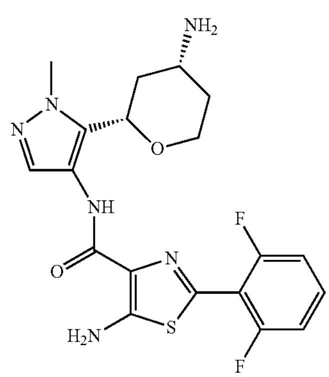 [SMILES: Cn1ncc(NC(=O)c2nc(-c3c(F)cccc3F)sc2N)c1[C@@H]1C[C@H](N)CCO1] | 5-Amino-N-[5-[(2S,4R)-4-aminotetrahydropyran-2-yl]-1-methyl-pyrazol-4-yl]-2-(2,6-difluorophenyl)thiazole-4-carboxamide | 0.000248 |
| 161 | 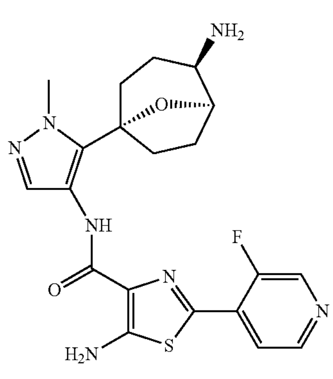 [SMILES: Cn1ncc(NC(=O)c2nc(-c3ccncc3F)sc2N)c1[C@@]12CC[C@@H](N)[C@@H](CC1)O2] | 5-Amino-N-[5-[2-amino-8-oxabicyclo[3.2.1]octan-5-yl]-1-methyl-pyrazol-4-yl]-2-(3-fluoro-4-pyridyl)thiazole-4-carboxamide | 0.000013 |

| No. | Structure | IUPAC Name | PIM1 LC3K (KI) μM |
|-----|-----------|------------|-------------------|
| 162 | 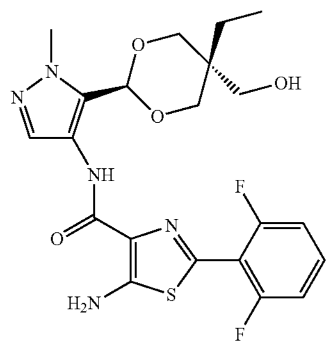 [SMILES: CC[C@]1(CO)CO[C@H](c2c(NC(=O)c3nc(-c4c(F)cccc4F)sc3N)cnn2C)OC1] | 5-Amino-2-(2,6-difluorophenyl)-N-[5-[5-ethyl-5-(hydroxymethyl)-1,3-dioxan-2-yl]-1-methyl-pyrazol-4-yl]thiazole-4-carboxamide | 0.000025 |
| 163 | 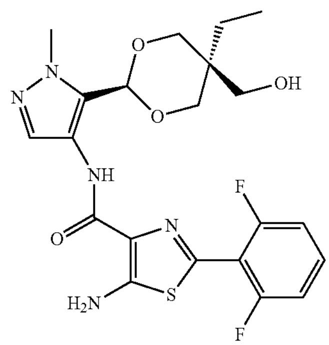 [SMILES: CC[C@]1(CO)CO[C@@H](c2c(NC(=O)c3nc(-c4c(F)cccc4F)sc3N)cnn2C)OC1] | 5-Amino-2-(2,6-difluorophenyl)-N-[5-[5-ethyl-5-(hydroxymethyl)-1,3-dioxan-2-yl]-1-methyl-pyrazol-4-yl]thiazole-4-carboxamide | 0.00126 |
| 164 | 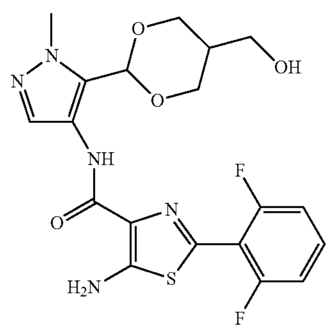 [SMILES: Cn1ncc(NC(=O)c2nc(-c3c(F)cccc3F)sc2N)c1C1OCC(CO)CO1] | 5-Amino-2-(2,6-difluorophenyl)-N-[5-[5-(hydroxymethyl)-1,3-dioxan-2-yl]-1-methyl-pyrazol-4-yl]thiazole-4-carboxamide | 0.000105 |
| 165 | 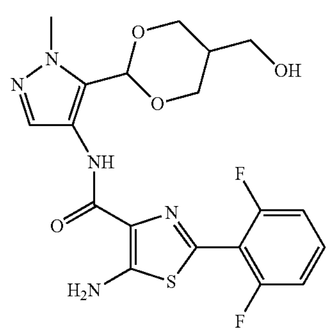 [SMILES: Cn1ncc(NC(=O)c2nc(-c3c(F)cccc3F)sc2N)c1C1OCC(CO)CO1] | 5-Amino-2-(2,6-difluorophenyl)-N-[5-[5-(hydroxymethyl)-1,3-dioxan-2-yl]-1-methyl-pyrazol-4-yl]thiazole-4-carboxamide | 0.000647 |

TABLE 1b-continued

| No. | Structure | IUPAC Name | PIM1 LC3K (KI) μM |
|---|---|---|---|
| 166 | 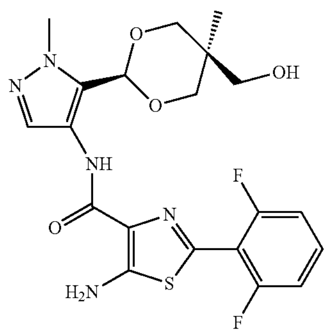 [SMILES: Cn1ncc(NC(=O)c2nc(-c3c(F)cccc3F)sc2N)c1[C@H]1OC[C@@](C)(CO)CO1] | 5-Amino-2-(2,6-difluorophenyl)-N-[5-[5-(hydroxymethyl)-5-methyl-1,3-dioxan-2-yl]-1-methyl-pyrazol-4-yl]thiazole-4-carboxamide | 0.000514 |
| 167 | 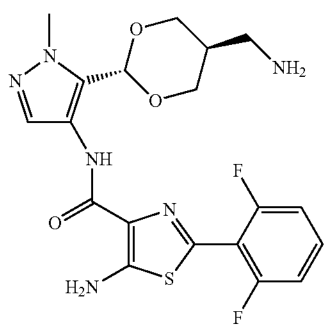 [SMILES: Cn1ncc(NC(=O)c2nc(-c3c(F)cccc3F)sc2N)c1[C@H]1OC[C@H](CN)CO1] | 5-Amino-N-[5-[5-(aminomethyl)-1,3-dioxan-2-yl]-1-methyl-pyrazol-4-yl]-2-(2,6-difluorophenyl)thiazole-4-carboxamide | 0.000029 |
| 168 | 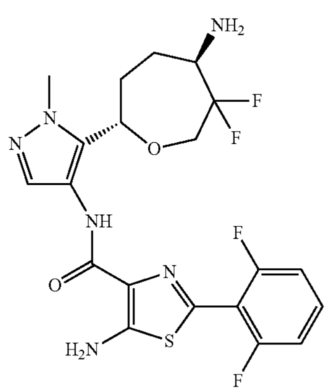 [SMILES: Cn1ncc(NC(=O)c2nc(-c3c(F)cccc3F)sc2N)c1[C@@H]1CC[C@@H](N)C(F)(F)CO1] | 5-Amino-N-[5-[(2S,5R)-5-amino-6,6-difluoro-oxepan-2-yl]-1-methyl-pyrazol-4-yl]-2-(2,6-difluorophenyl)thiazole-4-carboxamide | 0.000013 |
| 169 | 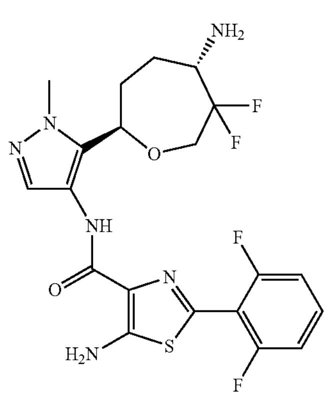 [SMILES: Cn1ncc(NC(=O)c2nc(-c3c(F)cccc3F)sc2N)c1[C@H]1CC[C@H](N)C(F)(F)CO1] | 5-Amino-N-[5-[(2R,5S)-5-amino-6,6-difluoro-oxepan-2-yl]-1-methyl-pyrazol-4-yl]-2-(2,6-difluorophenyl)thiazole-4-carboxamide | 0.000341 |

TABLE 1b-continued

| No. | Structure | IUPAC Name | PIM1 LC3K (KI) μM |
|---|---|---|---|
| 170 | 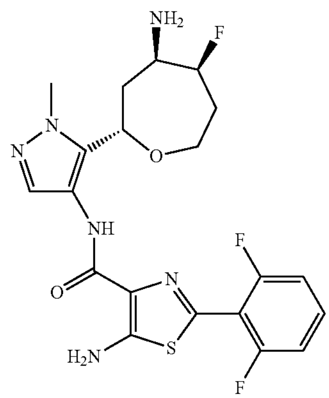 [SMILES: Cn1ncc(NC(=O)c2nc(-c3c(F)cccc3F)sc2N)c1[C@@H]1C[C@@H](N)[C@@H](F)CCO1] | 5-Amino-N-[5-[4-amino-5-fluoro-oxepan-2-yl]-1-methyl-pyrazol-4-yl]-2-(2,6-difluorophenyl)thiazole-4-carboxamide | 0.000126 |
| 171 | 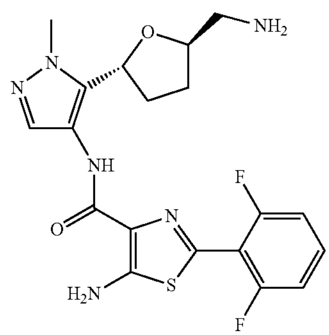 [SMILES: Cn1ncc(NC(=O)c2nc(-c3c(F)cccc3F)sc2N)c1[C@H]1CC[C@H](CN)O1] | 5-Amino-N-[5-[(2R,5R)-5-(aminomethyl)tetrahydrofuran-2-yl]-1-methyl-pyrazol-4-yl]-2-(2,6-difluorophenyl)thiazole-4-carboxamide | 0.000027 |
| 172 | 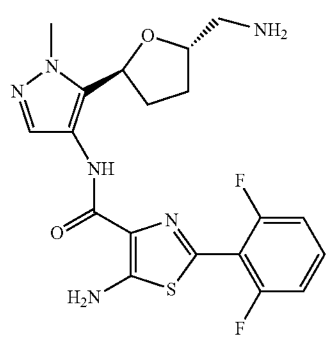 [SMILES: Cn1ncc(NC(=O)c2nc(-c3c(F)cccc3F)sc2N)c1[C@@H]1CC[C@@H](CN)O1] | 5-Amino-N-[5-[(2S,5S)-5-(aminomethyl)tetrahydrofuran-2-yl]-1-methyl-pyrazol-4-yl]-2-(2,6-difluorophenyl)thiazole-4-carboxamide | 0.00015 |
| 173 | 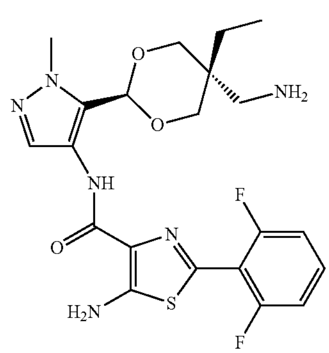 [SMILES: CC[C@]1(CN)CO[C@H](c2c(NC(=O)c3nc(-c4c(F)cccc4F)sc3N)cnn2C)OC1] | 5-Amino-N-[5-[5-(aminomethyl)-5-ethyl-1,3-dioxan-2-yl]-1-methyl-pyrazol-4-yl]-2-(2,6-difluorophenyl)thiazole-4-carboxamide | 0.000015 |

TABLE 1b-continued

| No. | Structure | IUPAC Name | PIM1 LC3K (KI) μM |
|---|---|---|---|
| 174 | 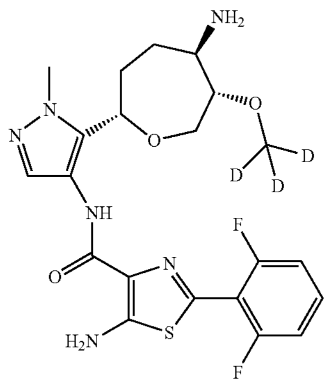 [SMILES: [2H]C([2H])([2H])O[C@@H]1CO[C@H](c2c(NC(=O)c3nc(-c4c(F)cccc4F)sc3N)cnn2C)CC[C@H]1N] | 5-Amino-N-[5-[(2S,5R,6S)-5-amino-6-(trideuteriomethoxy)oxepan-2-yl]-1-methyl-pyrazol-4-yl]-2-(2,6-difluorophenyl)thiazole-4-carboxamide | 0.000135 |
| 175 | 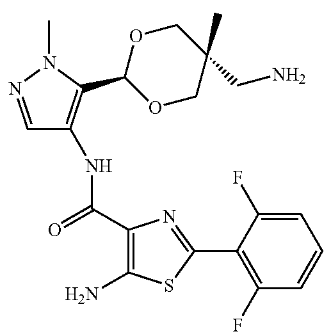 [SMILES: Cn1ncc(NC(=O)c2nc(-c3c(F)cccc3F)sc2N)c1[C@H]1OC[C@](C)(CN)CO1] | 5-Amino-N-[5-[5-(aminomethyl)-5-methyl-1,3-dioxan-2-yl]-1-methyl-pyrazol-4-yl]-2-(2,6-difluorophenyl)thiazole-4-carboxamide | 0.000036 |
| 176 | 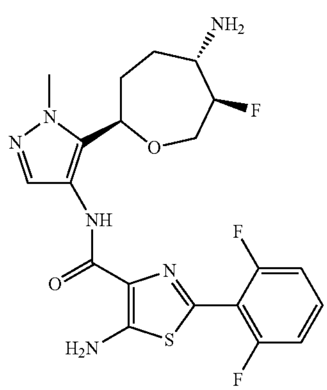 [SMILES: Cn1ncc(NC(=O)c2nc(-c3c(F)cccc3F)sc2N)c1[C@H]1CC[C@H](N)[C@@H](F)CO1] | 5-Amino-N-[5-[(2R,5S,6R)-5-amino-6-fluoro-oxepan-2-yl]-1-methyl-pyrazol-4-yl]-2-(2,6-difluorophenyl)thiazole-4-carboxamide | 0.000595 |
| 177 | 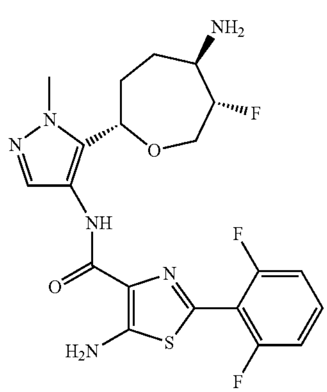 [SMILES: Cn1ncc(NC(=O)c2nc(-c3c(F)cccc3F)sc2N)c1[C@@H]1CC[C@@H](N)[C@H](F)CO1] | 5-Amino-N-[5-[(2S,5R,6S)-5-amino-6-fluoro-oxepan-2-yl]-1-methyl-pyrazol-4-yl]-2-(2,6-difluorophenyl)thiazole-4-carboxamide | 0.00000342 |

TABLE 1b-continued

| No. | Structure | IUPAC Name | PIM1 LC3K (KI) μM |
|---|---|---|---|
| 178 | 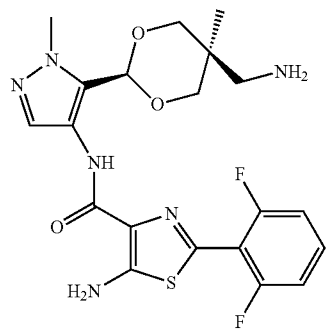 [SMILES: Cn1ncc(NC(=O)c2nc(-c3c(F)cccc3F)sc2N)c1[C@H]1OC[C@@](C)(CN)CO1] | 5-Amino-N-[5-[5-(aminomethyl)-5-methyl-1,3-dioxan-2-yl]-1-methyl-pyrazol-4-yl]-2-(2,6-difluorophenyl)thiazole-4-carboxamide | 0.000155 |
| 179 | 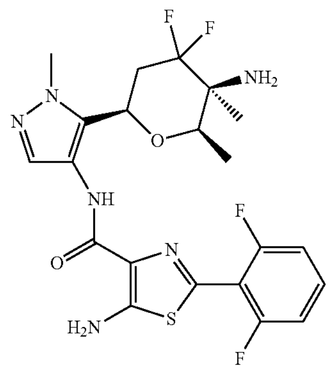 [SMILES: C[C@H]1O[C@@H](c2c(NC(=O)c3nc(-c4c(F)cccc4F)sc3N)cnn2C)CC(F)(F)[C@@]1(C)N] | 5-Amino-N-[5-[5-amino-4,4-difluoro-5,6-dimethyl-tetrahydropyran-2-yl]-1-methyl-pyrazol-4-yl]-2-(2,6-difluorophenyl)thiazole-4-carboxamide | 0.000456 |
| 180 | 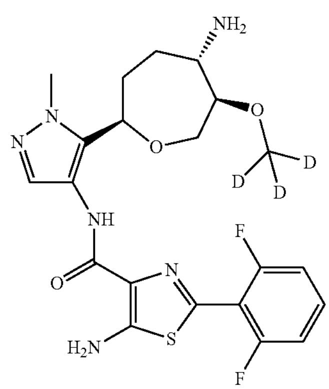 [SMILES: [2H]C([2H])([2H])O[C@H]1CO[C@@H](c2c(NC(=O)c3nc(-c4c(F)cccc4F)sc3N)cnn2C)CC[C@@H]1N] | 5-Amino-N-[5-[(2R,5S,6R)-5-amino-6-(trideuteriomethoxy)oxepan-2-yl]-1-methyl-pyrazol-4-yl]-2-(2,6-difluorophenyl)thiazole-4-carboxamide | 0.000017 |
| 181 | 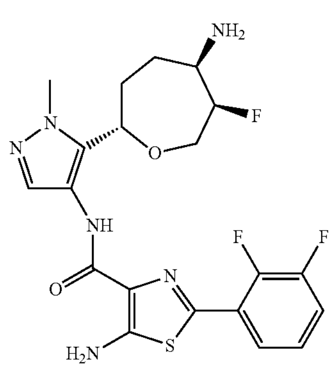 [SMILES: Cn1ncc(NC(=O)c2nc(-c3cccc(F)c3F)sc2N)c1[C@@H]1CC[C@@H](N)[C@@H](F)CO1] | 5-Amino-N-[5-[(2S,5R,6R)-5-amino-6-fluoro-oxepan-2-yl]-1-methyl-pyrazol-4-yl]-2-(2,3-difluorophenyl)thiazole-4-carboxamide | 0.000004 |

TABLE 1b-continued

| No. | Structure | IUPAC Name | PIM1 LC3K (KI) μM |
|---|---|---|---|
| 182 | 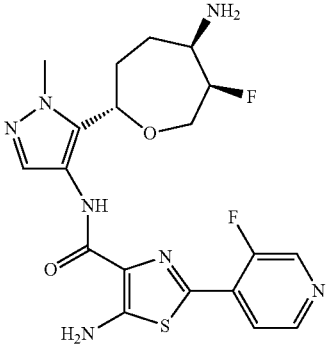 [SMILES: Cn1ncc(NC(=O)c2nc(-c3ccncc3F)sc2N)c1[C@@H]1CC[C@@H](N)[C@@H](F)CO1] | 5-Amino-N-[5-[(2S,5R,6R)-5-amino-6-fluoro-oxepan-2-yl]-1-methyl-pyrazol-4-yl]-2-(3-fluoro-4-pyridyl)thiazole-4-carboxamide | 0.000051 |
| 183 | 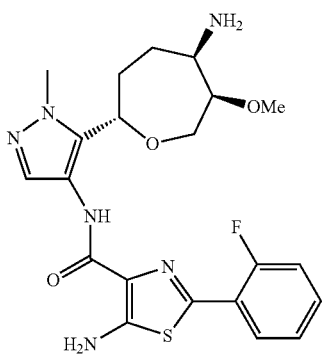 [SMILES: CO[C@H]1CO[C@H](c2c(NC(=O)c3nc(-c4ccccc4F)sc3N)cnn2C)CC[C@H]1N] | 5-Amino-N-[5-[(2S,5R,6R)-5-amino-6-methoxy-oxepan-2-yl]-1-methyl-pyrazol-4-yl]-2-(2-fluorophenyl)thiazole-4-carboxamide | 0.0000143 |
| 184 | 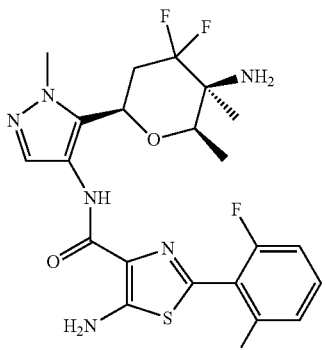 | 5-Amino-N-(5-((2R,5S,6R)-5-amino-4,4-difluoro-5,6-dimethyltetrahydro-2H-pyran-2-yl)-1-methyl-1H-pyrazol-4-yl)-2-(2,6-difluorophenyl)thiazole-4-carboxamide | 0.000484 |
| 185 | 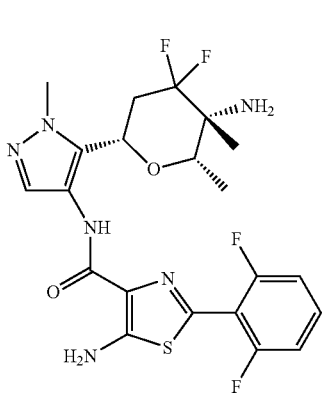 [SMILES: C[C@@H]1O[C@H](c2c(NC(=O)c3nc(-c4c(F)cccc4F)sc3N)cnn2C)CC(F)(F)[C@]1(C)N] | 5-Amino-N-(5-((2S,5R,6S)-5-amino-4,4-difluoro-5,6-dimethyltetrahydro-2H-pyran-2-yl)-1-methyl-1H-pyrazol-4-yl)-2-(2,6-difluorophenyl)thiazole-4-carboxamide | 0.00435 |

TABLE 1b-continued

| No. | Structure | IUPAC Name | PIM1 LC3K (KI) µM |
|---|---|---|---|
| 186 | 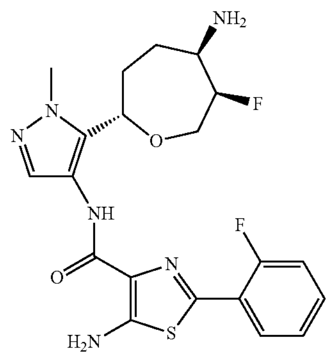 [SMILES: Cn1ncc(NC(=O)c2nc(-c3ccccc3F)sc2N)c1[C@@H]1CC[C@@H](N)[C@@H](F)CO1] | 5-Amino-N-(5-((2S,5R,6R)-5-amino-6-fluorooxepan-2-yl)-1-methyl-1H-pyrazol-4-yl)-2-(2-fluorophenyl)thiazole-4-carboxamide | 0.000007 |
| 187 | 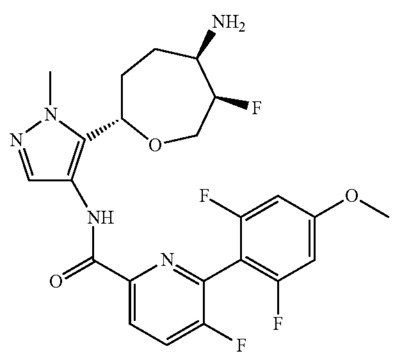 [SMILES: COc1cc(F)c(-c2nc(C(=O)Nc3cnn(C)c3[C@@H]3CC[C@@H](N)[C@@H](F)CO3)ccc2F)c(F)c1] | N-(5-((2S,5R,6R)-5-Amino-6-fluorooxepan-2-yl)-1-methyl-1H-pyrazol-4-yl)-6-(2,6-difluoro-4-methoxyphenyl)-5-fluoropicolinamide | 0.000027 |
| 188 | 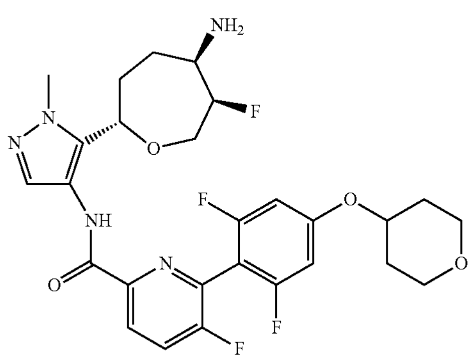 [SMILES: Cn1ncc(NC(=O)c2ccc(F)c(-c3c(F)cc(OC4CCOCC4)cc3F)n2)c1[C@@H]1CC[C@@H](N)[C@@H](F)CO1] | N-(5-((2S,5R,6R)-5-Amino-6-fluorooxepan-2-yl)-1-methyl-1H-pyrazol-4-yl)-6-(2,6-difluoro-4-((tetrahydro-2H-pyran-4-yl)oxy)phenyl)-5-fluoropicolinamide | 0.00003 |
| 189 | 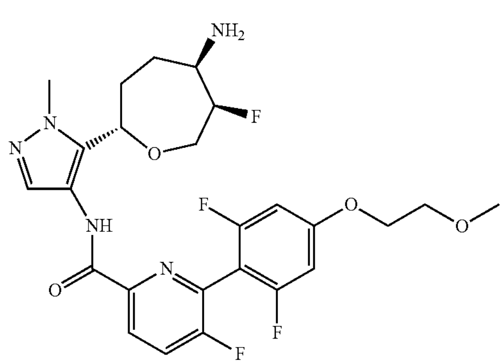 [SMILES: COCCOc1cc(F)c(-c2nc(C(=O)Nc3cnn(C)c3[C@@H]3CC[C@@H](N)[C@@H](F)CO3)ccc2F)c(F)c1] | N-(5-((2S,5R,6R)-5-Amino-6-fluorooxepan-2-yl)-1-methyl-1H-pyrazol-4-yl)-6-(2,6-difluoro-4-(2-methoxyethoxy)phenyl)-5-fluoropicolinamide | 0.000025 |

TABLE 1b-continued

| No. | Structure | IUPAC Name | PIM1 LC3K (KI) μM |
|---|---|---|---|
| 190 | 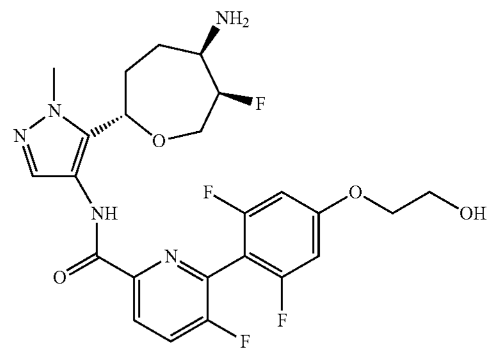 [SMILES: Cn1ncc(NC(=O)c2ccc(F)c(-c3c(F)cc(OCCO)cc3F)n2)c1[C@@H]1CC[C@@H](N)[C@@H](F)CO1] | N-(5-((2S,5R,6R)-5-Amino-6-fluorooxepan-2-yl)-1-methyl-1H-pyrazol-4-yl)-6-(2,6-difluoro-4-(2-hydroxyethoxy)phenyl)-5-fluoropicolinamide | 0.000014 |
| 191 | 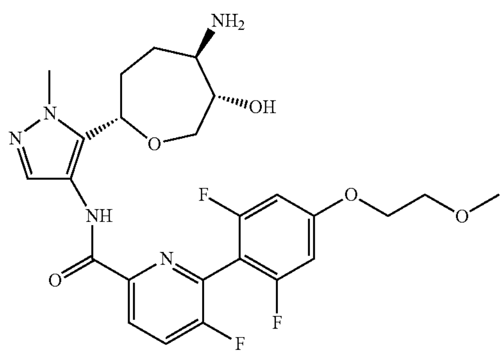 [SMILES: COCCOc1cc(F)c(-c2nc(C(=O)Nc3cnn(C)c3[C@@H]3CC[C@@H](N)[C@H](O)CO3)ccc2F)c(F)c1] | N-(5-((2S,5R,6S)-5-Amino-6-hydroxyoxepan-2-yl)-1-methyl-1H-pyrazol-4-yl)-6-(2,6-difluoro-4-(2-methoxyethoxy)phenyl)-5-fluoropicolinamide | 0.000056 |
| 192 | 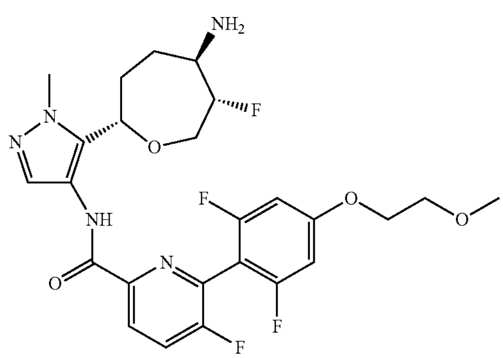 [SMILES: COCCOc1cc(F)c(-c2nc(C(=O)Nc3cnn(C)c3[C@@H]3CC[C@@H](N)[C@H](F)CO3)ccc2F)c(F)c1] | N-(5-((2S,5R,6S)-5-amino-6-fluorooxepan-2-yl)-1-methyl-1H-pyrazol-4-yl)-6-(2,6-difluoro-4-(2-methoxyethoxy)phenyl)-5-fluoropicolinamide | 0.000023 |
| 193 | 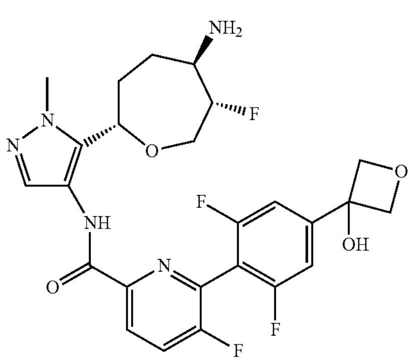 [SMILES: Cn1ncc(NC(=O)c2ccc(F)c(-c3c(F)cc(C4(O)COC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(2,6-difluoro-4-(3-hydroxyoxetan-3-yl)phenyl)-5-fluoropicolinamide | 0.000034 |

TABLE 1b-continued

| No. | Structure | IUPAC Name | PIM1 LC3K (KI) μM |
|---|---|---|---|
| 194 | 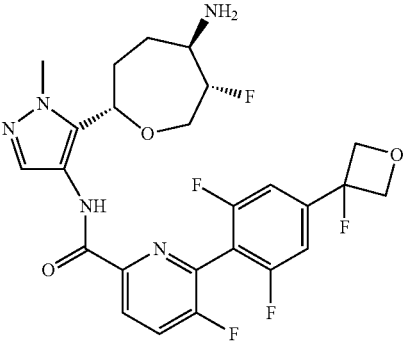 [SMILES: Cn1ncc(NC(=O)c2ccc(F)c(-c3c(F)cc(C4(F)COC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(2,6-difluoro-4-(3-fluorooxetan-3-yl)phenyl)-5 fluoropicolinamide | 0.000022 |
| 195 | 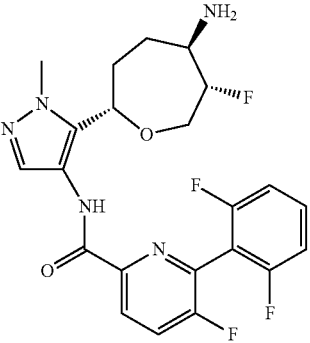 [SMILES: Cn1ncc(NC(=O)c2ccc(F)c(-c3c(F)cccc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(2,6-difluorophenyl)-5-fluoropicolinamide | 0.000025 |
| 196 | 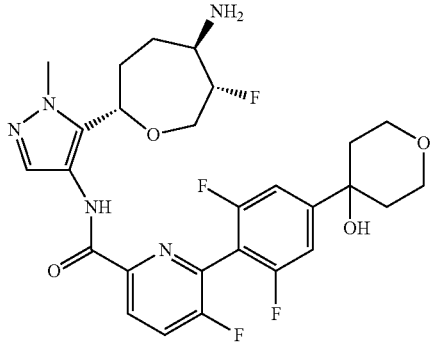 [SMILES: Cn1ncc(NC(=O)c2ccc(F)c(-c3c(F)cc(C4(O)CCOCC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(2,6-difluoro-4-(4-hydroxytetrahydro-2H-pyran-4-yl)phenyl)-5-fluoropicolinamide | 0.000006 |
| 197 | 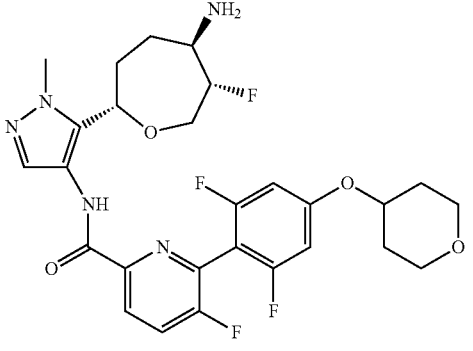 [SMILES: Cn1ncc(NC(=O)c2ccc(F)c(-c3c(F)cc(OC4CCOCC4)cc3F)n2)c1[C@@H]1CC[C@@H](N)[C@H](F)CO1] | N-(5-((2S,5R,6S)-5-Amino-6-fluorooxepan-2-yl)-1-methyl-1H-pyrazol-4-yl)-6-(2,6-difluoro-4-((tetrahydro-2H-pyran-4-yl)oxy)phenyl)-5-fluoropicolinamide | 0.000018 |

TABLE 1b-continued

| No. | Structure | IUPAC Name | PIM1 LC3K (KI) μM |
|---|---|---|---|
| 198 | 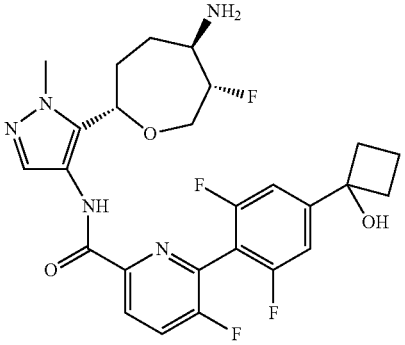 [SMILES: Cn1ncc(NC(=O)c2ccc(F)c(-c3c(F)cc(C4(O)CCC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(2,6-difluoro-4-(1-hydroxycyclobutyl)phenyl)-5-fluoropicolinamide | 0.000021 |
| 199 | 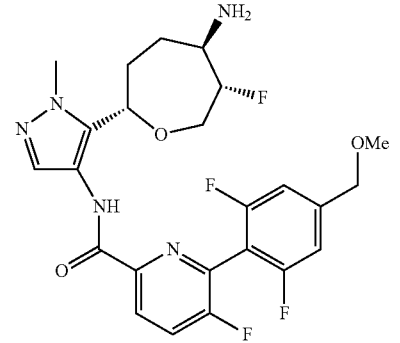 [SMILES: COCc1cc(F)c(-c2nc(C(=O)Nc3cnn(C)c3[C@@H]3CC[C@@H](N)[C@H](F)CO3)ccc2F)c(F)c1] | N-(5-((2S,5R,6S)-5-amino-6-fluorooxepan-2-yl)-1-methyl-1H-pyrazol-4-yl)-6-(2,6-difluoro-4-(methoxymethyl)phenyl)-5-fluoropicolinamide | 0.000031 |
| 200 | 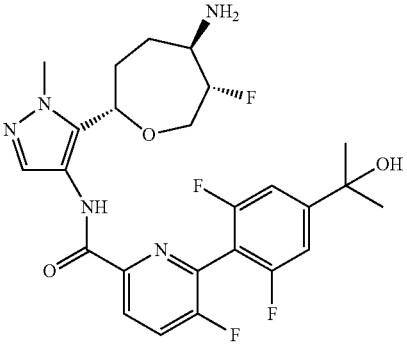 [SMILES: Cn1ncc(NC(=O)c2ccc(F)c(-c3c(F)cc(C(C)(C)O)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(2,6-difluoro-4-(2-hydroxypropan-2-yl)phenyl)-5-fluoropicolinamide | 0.000011 |
| 201 | 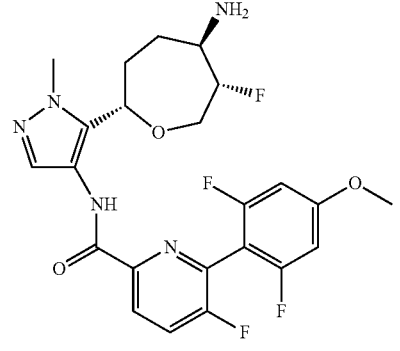 [SMILES: COc1cc(F)c(-c2nc(C(=O)Nc3cnn(C)c3[C@@H]3CC[C@@H](N)[C@H](F)CO3)ccc2F)c(F)c1] | N-(5-((2S,5R,6S)-5-amino-6-fluorooxepan-2-yl)-1-methyl-1H-pyrazol-4-yl)-6-(2,6-difluoro-4-methoxyphenyl)-5-fluoropicolinamide | 0.000019 |

TABLE 1b-continued

| No. | Structure | IUPAC Name | PIM1 LC3K (KI) μM |
|---|---|---|---|
| 202 | 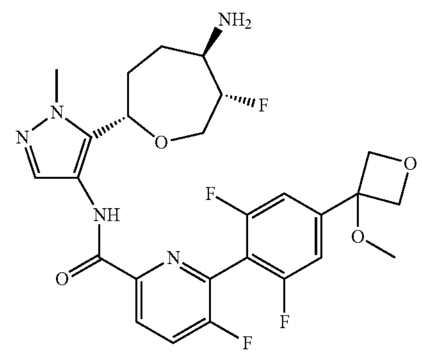 [SMILES: COC1(c2cc(F)c(-c3nc(C(=O)Nc4cnn(C)c4[C@@H]4CC[C@@H](N)[C@H](F)CO4)ccc3F)c(F)c2)COC1] | N-(5-((2S,5R,6S)-5-amino-6-fluorooxepan-2-yl)-1-methyl-1H-pyrazol-4-yl)-6-(2,6-difluoro-4-(3-methoxyoxetan-3-yl)phenyl)-5-fluoropicolinamide | 0.000056 |
| 203 | 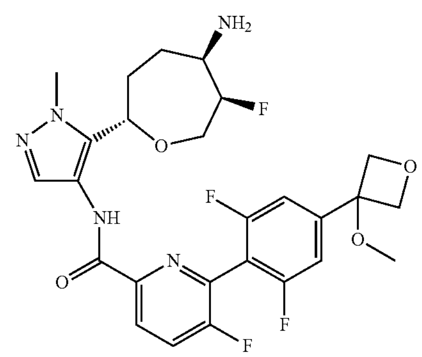 [SMILES: COC1(c2cc(F)c(-c3nc(C(=O)Nc4cnn(C)c4[C@@H]4CC[C@@H](N)[C@@H](F)CO4)ccc3F)c(F)c2)COC1] | N-(5-((2S,5R,6R)-5-amino-6-fluorooxepan-2-yl)-1-methyl-1H-pyrazol-4-yl)-6-(2,6-difluoro-4-(3-methoxyoxetan-3-yl)phenyl)-5-fluoropicolinamide | 0.000119 |
| 204 | 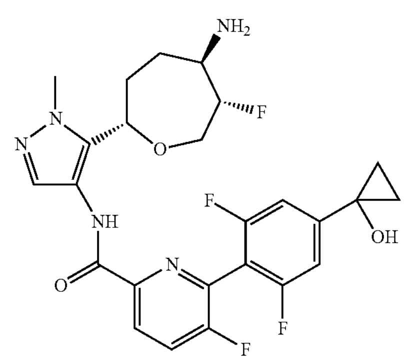 [SMILES: Cn1ncc(NC(=O)c2ccc(F)c(-c3c(F)cc(C4(O)CC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(2,6-difluoro-4-(1-hydroxycyclopropyl)phenyl)-5-fluoropicolinamide | 0.000001 |
| 205 | 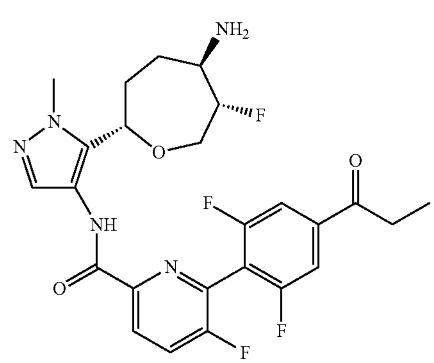 [SMILES: CCC(=O)c1cc(F)c(-c2nc(C(=O)Nc3cnn(C)c3[C@@H]3CC[C@@H](N)[C@H](F)CO3)ccc2F)c(F)c1] | N-(5-((2S,5R,6S)-5-amino-6-fluorooxepan-2-yl)-1-methyl-1H-pyrazol-4-yl)-6-(2,6-difluoro-4-propionylphenyl)-5-fluoropicolinamide | 0.000034 |

TABLE 1b-continued

| No. | Structure | IUPAC Name | PIM1 LC3K (KI) μM |
|---|---|---|---|
| 206 | 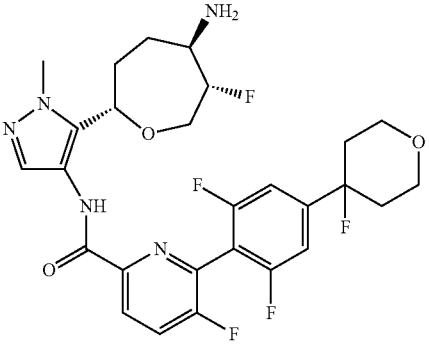 [SMILES: Cn1ncc(NC(=O)c2ccc(F)c(-c3c(F)cc(C4(F)CCOCC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(2,6-difluoro-4-(4-fluorotetrahydro-2H-pyran-4-yl)phenyl)-5-fluoropicolinamide | 0.000016 |
| 207 | 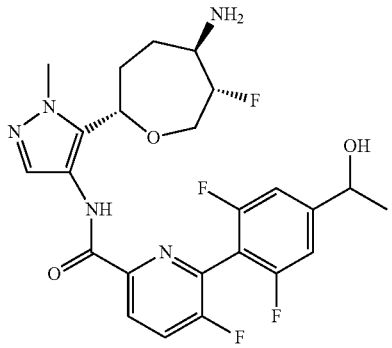 [SMILES: CC(O)c1cc(F)c(-c2nc(C(=O)Nc3cnn(C)c3[C@@H]3CC[C@@H](N)[C@H](F)CO3)ccc2F)c(F)c1] | N-(5-((2S,5R,6S)-5-amino-6-fluorooxepan-2-yl)-1-methyl-1H-pyrazol-4-yl)-6-(2,6-difluoro-4-(1-hydroxyethyl)phenyl)-5-fluoropicolinamide | 0.000017 |
| 208 | 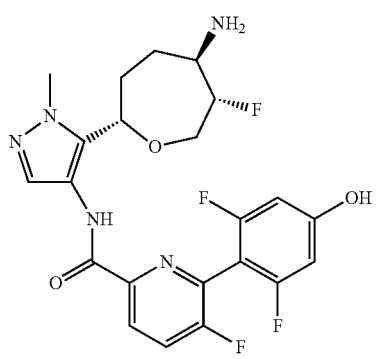 [SMILES: Cn1ncc(NC(=O)c2ccc(F)c(-c3c(F)cc(O)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(2,6-difluoro-4-hydroxyphenyl)-5-fluoropicolinamide | 0.000012 |
| 209 | 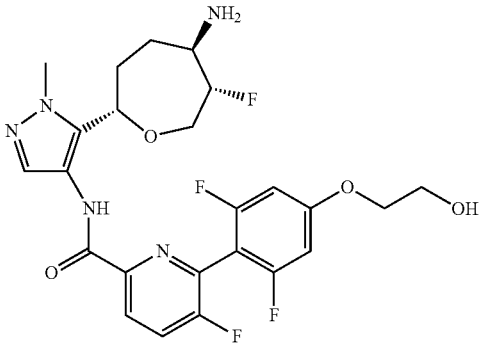 [SMILES: Cn1ncc(NC(=O)c2ccc(F)c(-c3c(F)cc(OCCO)cc3F)n2)c1[C@@H]1CC[C@@H](N)[C@H](F)CO1] | N-(5-((2S,5R,6S)-5-Amino-6-fluorooxepan-2-yl)-1-methyl-1H-pyrazol-4-yl)-6-(2,6-difluoro-4-(2-hydroxyethoxy)phenyl)-5-fluoropicolinamide | 0.000016 |

TABLE 1b-continued

| No. | Structure | IUPAC Name | PIM1 LC3K (KI) μM |
|---|---|---|---|
| 210 | 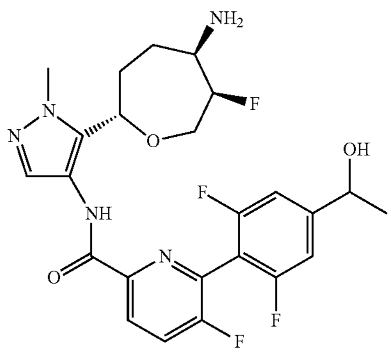 [SMILES: CC(O)c1cc(F)c(-c2nc(C(=O)Nc3cnn(C)c3[C@@H]3CC[C@@H](N)[C@@H](F)CO3)ccc2F)c(F)c1] | N-(5-((2S,5R,6R)-5-amino-6-fluorooxepan-2-yl)-1-methyl-1H-pyrazol-4-yl)-6-(2,6-difluoro-4-(1-hydroxyethyl)phenyl)-5-fluoropicolinamide | 0.000053 |
| 211 | 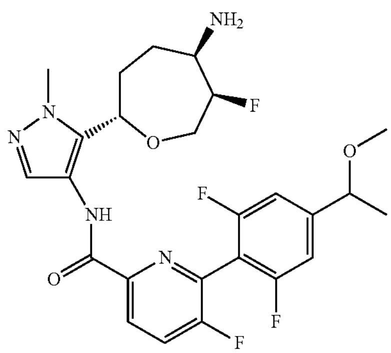 [SMILES: COC(C)c1cc(F)c(-c2nc(C(=O)Nc3cnn(C)c3[C@@H]3CC[C@@H](N)[C@@H](F)CO3)ccc2F)c(F)c1] | N-(5-((2S,5R,6R)-5-amino-6-fluorooxepan-2-yl)-1-methyl-1H-pyrazol-4-yl)-6-(2,6-difluoro-4-(1-methoxyethyl)phenyl)-5-fluoropicolinamide | 0.000037 |
| 212 | 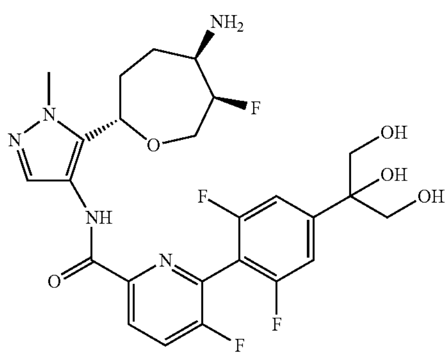 [SMILES: Cn1ncc(NC(=O)c2ccc(F)c(-c3c(F)cc(C(O)(CO)CO)cc3F)n2)c1[C@@H]1CC[C@@H](N)[C@@H](F)CO1] | N-(5-((2S,5R,6R)-5-amino-6-fluorooxepan-2-yl)-1-methyl-1H-pyrazol-4-yl)-6-(2,6-difluoro-4-(1,2,3-trihydroxypropan-2-yl)phenyl)-5-fluoropicolinamide | 0.000162 |
| 213 | 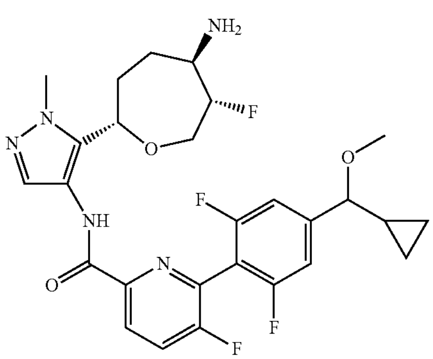 [SMILES: COC(c1cc(F)c(-c2nc(C(=O)Nc3cnn(C)c3[C@@H]3CC[C@@H](N)[C@H](F)CO3)ccc2F)c(F)c1)C1CC1] | N-(5-((2S,5R,6S)-5-amino-6-fluorooxepan-2-yl)-1-methyl-1H-pyrazol-4-yl)-6-(4-(cyclopropyl(methoxy)methyl)-2,6-difluorophenyl)-5-fluoropicolinamide | 0.000078 |

TABLE 1b-continued

| No. | Structure | IUPAC Name | PIM1 LC3K (KI) μM |
|---|---|---|---|
| 214 | 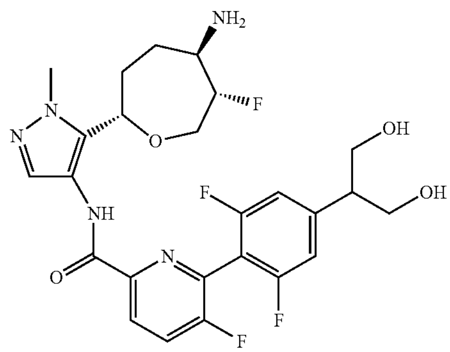 [SMILES: Cn1ncc(NC(=O)c2ccc(F)c(-c3c(F)cc(C(CO)CO)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(4-(1,3-dihydroxypropan-2-yl)-2,6-difluorophenyl)-5-fluoropicolinamide | 0.000075 |
| 215 | 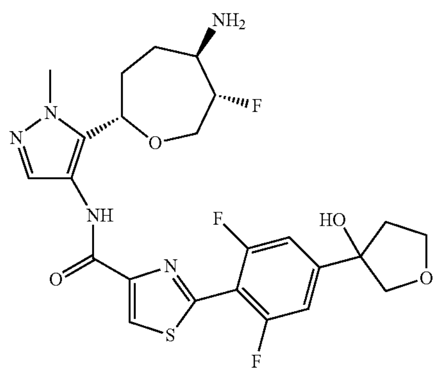 [SMILES: Cn1ncc(NC(=O)c2csc(-c3c(F)cc(C4(O)CCOC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,6-difluoro-4-(3-hydroxytetrahydrofuran-3-yl)phenyl)thiazole-4-carboxamide | 0.00000762 |
| 216 | 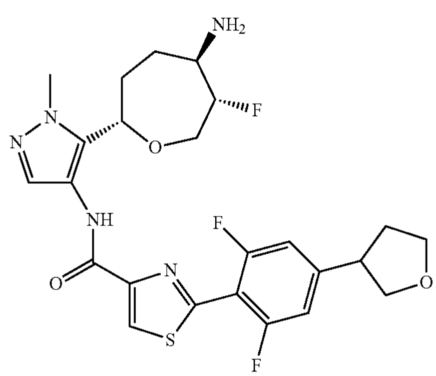 [SMILES: Cn1ncc(NC(=O)c2csc(-c3c(F)cc(C4CCOC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,6-difluoro-4-(tetrahydrofuran-3-yl)phenyl)thiazole-4-carboxamide | 0.000011+ |
| 217 | 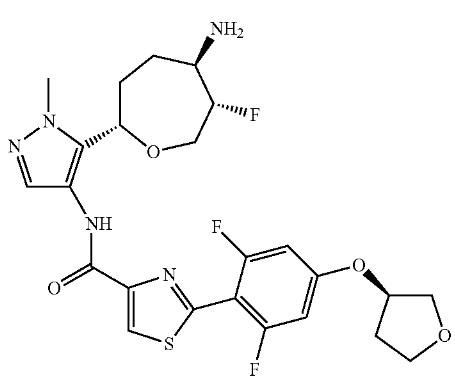 [SMILES: Cn1ncc(NC(=O)c2csc(-c3c(F)cc(O[C@@H]4CCOC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,6-difluoro-4-(((R)-tetrahydrofuran-3-yl)oxy)phenyl)thiazole-4-carboxamide | 0.000003 |

TABLE 1b-continued

| No. | Structure | IUPAC Name | PIM1 LC3K (KI) μM |
|---|---|---|---|
| 218 | 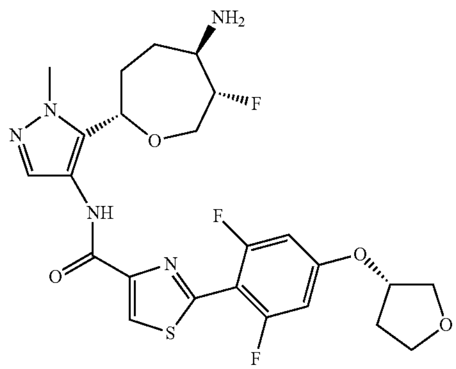 [SMILES: Cn1ncc(NC(=O)c2csc(-c3c(F)cc(O[C@H]4CCOC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,6-difluoro-4-(((S)-tetrahydrofuran-3-yl)oxy)phenyl)thiazole-4-carboxamide | 0.00000224 |
| 219 | 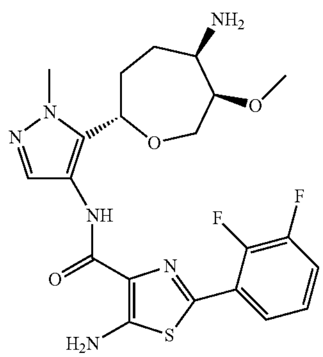 [SMILES: CO[C@H]1CO[C@H](c2c(NC(=O)c3nc(-c4cccc(F)c4F)sc3N)cnn2C)CC[C@H]1N] | 5-amino-N-(5-((2S,5R,6R)-5-amino-6-methoxyoxepan-2-yl)-1-methyl-1H-pyrazol-4-yl)-2-(2,3-difluorophenyl)thiazole-4-carboxamide | 0.00005 |
| 220 | 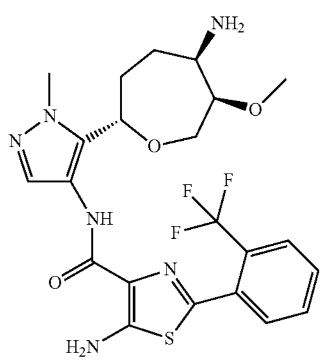 [SMILES: CO[C@H]1CO[C@H](c2c(NC(=O)c3nc(-c4ccccc4C(F)(F)F)sc3N)cnn2C)CC[C@H]1N] | 5-amino-N-(5-((2S,5R,6R)-5-amino-6-methoxyoxepan-2-yl)-1-methyl-1H-pyrazol-4-yl)-2-(2-(trifluoromethyl)phenyl)thiazole-4-carboxamide | 0.000083 |
| 221 | 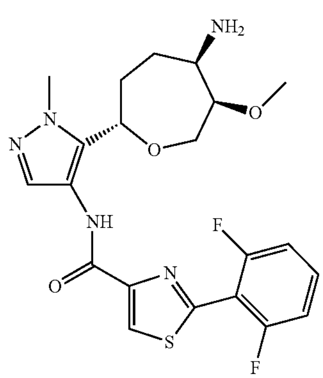 [SMILES: CO[C@H]1CO[C@H](c2c(NC(=O)c3csc(-c4c(F)cccc4F)n3)cnn2C)CC[C@H]1N] | N-(5-((2S,5R,6R)-5-amino-6-methoxyoxepan-2-yl)-1-methyl-1H-pyrazol-4-yl)-2-(2,6-difluorophenyl)thiazole-4-carboxamide | 0.000066 |

TABLE 1b-continued

| No. | Structure | IUPAC Name | PIM1 LC3K (KI) μM |
|---|---|---|---|
| 222 | 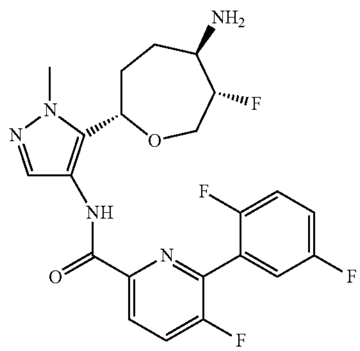 [SMILES: Cn1ncc(NC(=O)c2ccc(F)c(-c3cc(F)ccc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(2,6-difluorophenyl)-5-fluoropicolinamide | 0.000161 |
| 223 | 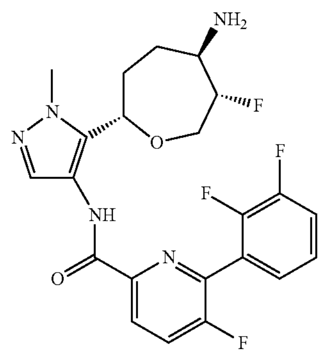 [SMILES: Cn1ncc(NC(=O)c2ccc(F)c(-c3cccc(F)c3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(2,3-difluorophenyl)-5-fluoropicolinamide | 0.000083 |
| 224 | 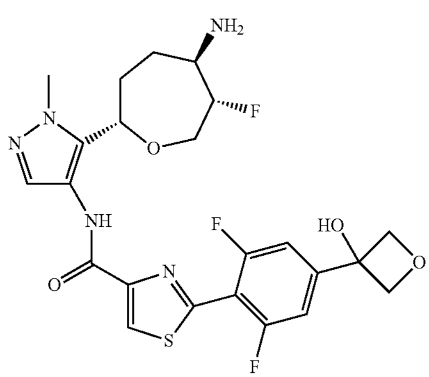 [SMILES: Cn1ncc(NC(=O)c2csc(-c3c(F)cc(C4(O)COC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,6-difluoro-4-(3-hydroxyoxetan-3-yl)phenyl)thiazole-4-carboxamide | 0.000035 |
| 225 | 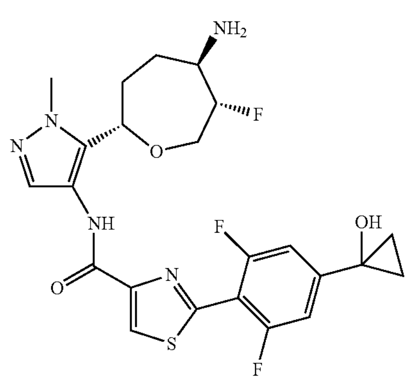 [SMILES: Cn1ncc(NC(=O)c2csc(-c3c(F)cc(C4(O)CC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,6-difluoro-4-(1-hydroxycyclopropyl)phenyl)thiazole-4-carboxamide | 0.000028 |

TABLE 1b-continued

| No. | Structure | IUPAC Name | PIM1 LC3K (KI) µM |
|---|---|---|---|
| 226 | 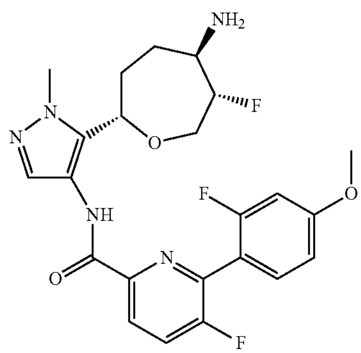 [SMILES: COc1ccc(-c2nc(C(=O)Nc3cnn(C)c3[C@@H]3CC[C@@H](N)[C@H](F)CO3)ccc2F)c(F)c1] | N-(5-((2S,5R,6S)-5-amino-6-fluorooxepan-2-yl)-1-methyl-1H-pyrazol-4-yl)-5-fluoro-6-(2-fluoro-4-methoxyphenyl)picolinamide | 0.000036 |
| 227 | 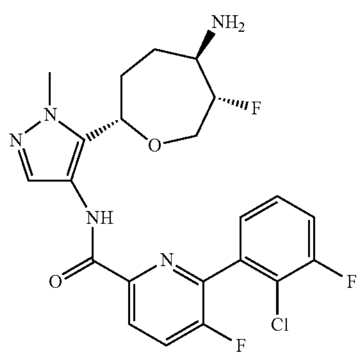 [SMILES: Cn1ncc(NC(=O)c2ccc(F)c(-c3cccc(F)c3Cl)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(2-chloro-3-fluorophenyl)-5-fluoropicolinamide | 0.00057 |
| 228 | 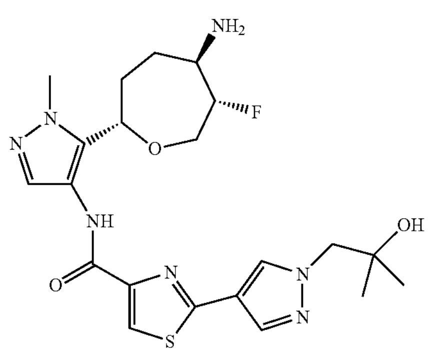 [SMILES: Cn1ncc(NC(=O)c2csc(-c3cnn(CC(C)(C)O)c3)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(1-(2-hydroxy-2-methylpropyl)-1H-pyrazol-4-yl)thiazole-4-carboxamide | 0.000124 |
| 229 | 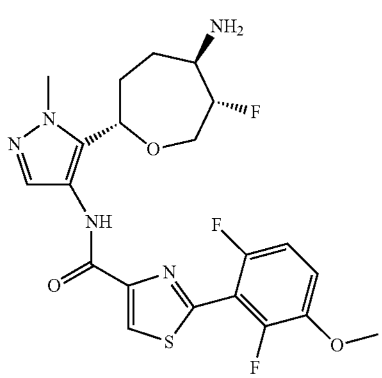 [SMILES: COc1ccc(F)c(-c2nc(C(=O)Nc3cnn(C)c3[C@@H]3CC[C@@H](N)[C@H](F)CO3)cs2)c1F] | N-(5-((2S,5R,6S)-5-amino-6-fluorooxepan-2-yl)-1-methyl-1H-pyrazol-4-yl)-2-(2,6-difluoro-3-methoxyphenyl)thiazole-4-carboxamide | 0.000001 |

TABLE 1b-continued

| No. | Structure | IUPAC Name | PIM1 LC3K (KI) μM |
|---|---|---|---|
| 230 | 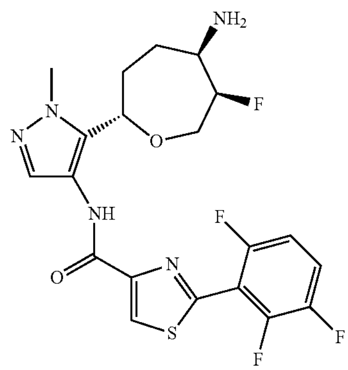 [SMILES: Cn1ncc(NC(=O)c2csc(-c3c(F)ccc(F)c3F)n2)c1[C@@H]1CC[C@@H](N)[C@@H](F)CO1] | N-(5-((2S,5R,6R)-5-amino-6-fluorooxepan-2-yl)-1-methyl-1H-pyrazol-4-yl)-2-(2,3,6-trifluorophenyl)thiazole-4-carboxamide | 0.000031 |
| 231 | 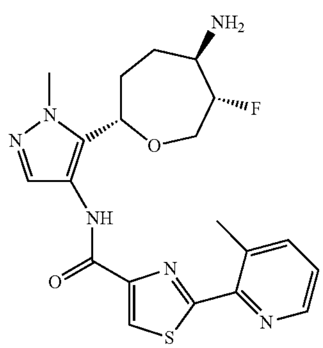 [SMILES: Cc1cccnc1-c1nc(C(=O)Nc2cnn(C)c2[C@@H]2CC[C@@H](N)[C@H](F)CO2)cs1] | N-(5-((2S,5R,6S)-5-amino-6-fluorooxepan-2-yl)-1-methyl-1H-pyrazol-4-yl)-2-(3-methylpyridin-2-yl)thiazole-4-carboxamide | 0.000045 |
| 232 | 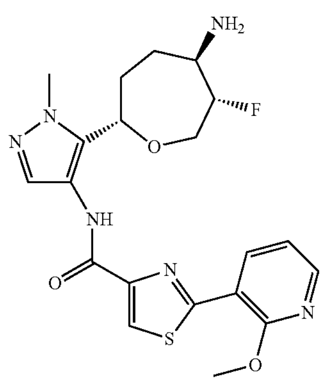 [SMILES: COc1ncccc1-c1nc(C(=O)Nc2cnn(C)c2[C@@H]2CC[C@@H](N)[C@H](F)CO2)cs1] | N-(5-((2S,5R,6S)-5-amino-6-fluorooxepan-2-yl)-1-methyl-1H-pyrazol-4-yl)-2-(2-methoxypyridin-3-yl)thiazole-4-carboxamide | 0.00111 |
| 233 | 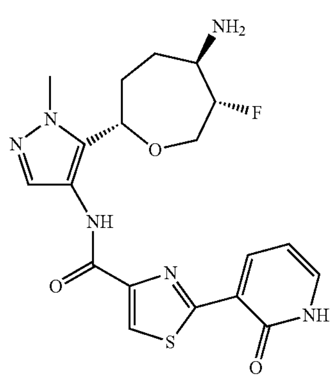 [SMILES: Cn1ncc(NC(=O)c2csc(-c3ccc[nH]c3=O)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2-oxo-1,2-dihydropyridin-3-yl)thiazole-4-carboxamide | 0.000103 |

TABLE 1b-continued

| No. | Structure | IUPAC Name | PIM1 LC3K (KI) μM |
|---|---|---|---|
| 234 | 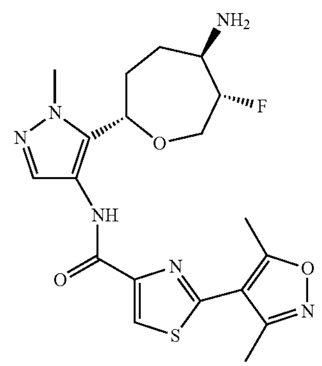 [SMILES: Cc1noc(C)c1-c1nc(C(=O)Nc2cnn(C)c2[C@@H]2CC[C@@H](N)[C@H](F)CO2)cs1] | N-(5-((2S,5R,6S)-5-amino-6-fluorooxepan-2-yl)-1-methyl-1H-pyrazol-4-yl)-2-(3,5-dimethylisoxazol-4-yl)thiazole-4-carboxamide | 0.000068 |
| 235 | 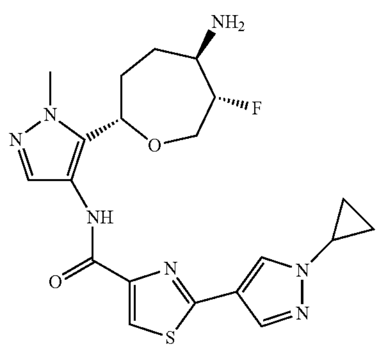 [SMILES: Cn1ncc(NC(=O)c2csc(-c3cnn(C4CC4)c3)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(1-cyclopropyl-1H-pyrazol-4-yl)thiazole-4-carboxamide | 0.000068 |
| 236 | 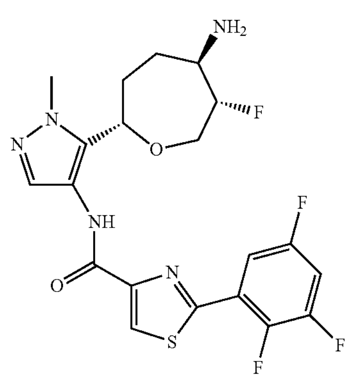 [SMILES: Cn1ncc(NC(=O)c2csc(-c3cc(F)cc(F)c3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,3,5-trifluorophenyl)thiazole-4-carboxamide | 0.000255 |
| 237 | 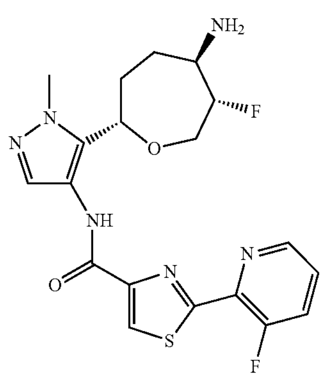 [SMILES: Cn1ncc(NC(=O)c2csc(-c3ncccc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(3-fluoropyridin-2-yl)thiazole-4-carboxamide | 0.000107 |

TABLE 1b-continued

| No. | Structure | IUPAC Name | PIM1 LC3K (KI) μM |
|---|---|---|---|
| 238 | 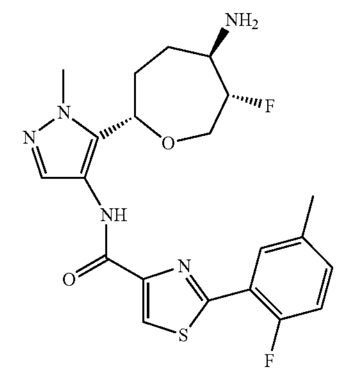 [SMILES: Cc1ccc(F)c(-c2nc(C(=O)Nc3cnn(C)c3[C@@H]3CC[C@@H](N)[C@H](F)CO3)cs2)c1] | N-(5-((2S,5R,6S)-5-amino-6-fluorooxepan-2-yl)-1-methyl-1H-pyrazol-4-yl)-2-(2-fluoro-5-methylphenyl)thiazole-4-carboxamide | 0.000048 |
| 239 | 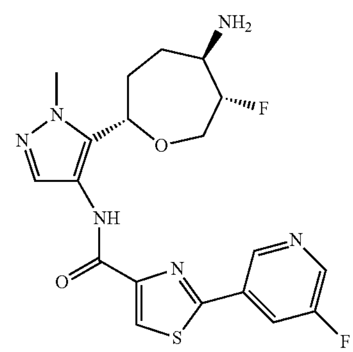 [SMILES: Cn1ncc(NC(=O)c2csc(-c3cncc(F)c3)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(5-fluoropyridin-3-yl)thiazole-4-carboxamide | 0.00266 |
| 240 | 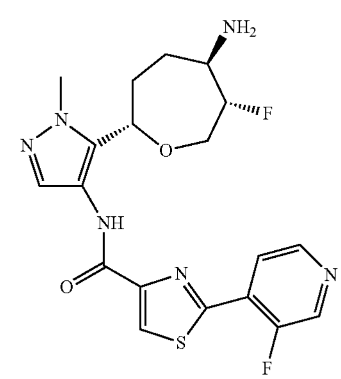 [SMILES: Cn1ncc(NC(=O)c2csc(-c3ccncc3F)n2)c1[C@@H]1CC[C@@H](N)[C@H](F)CO1] | N-(5-((2S,56R,6S)-5-amino-6-fluorooxepan-2-yl)-1-methyl-1H-pyrazol-4-yl)-2-(3-fluoropyriidn-4-yl)thiazole-4-carboxamide | 0.00034 |
| 241 | 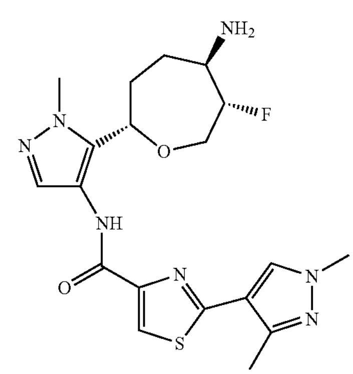 [SMILES: Cc1nn(C)cc1-c1nc(C(=O)Nc2cnn(C)c2[C@@H]2CC[C@@H](N)[C@H](F)CO2)cs1] | N-(5-((2S,5R,6S)-5-amino-6-fluorooxepan-2-yl)-1-methyl-1H-pyrazol-4-yl)-2-(1,3-dimethyl-1H-pyrazol-4-yl)thiazole-4-carboxamide | 0.000283 |

TABLE 1b-continued

| No. | Structure | IUPAC Name | PIM1 LC3K (KI) μM |
|---|---|---|---|
| 242 | 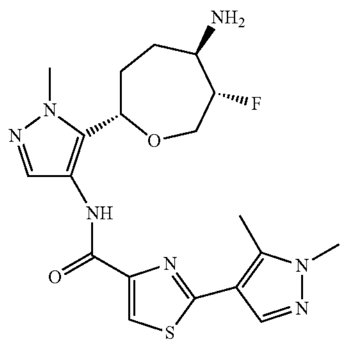 [SMILES: Cc1c(-c2nc(C(=O)Nc3cnn(C)c3[C@@H]3CC[C@@H](N)[C@H](F)CO3)cs2)cnn1C] | N-(5-((2S,5R,6S)-5-amino-6-fluorooxepan-2-yl)-1-methyl-1H-pyrazol-4-yl)-2-(1,5-dimethyl-1H-pyrazol-4-yl)thiazole-4-carboxamide | 0.000218 |
| 243 | 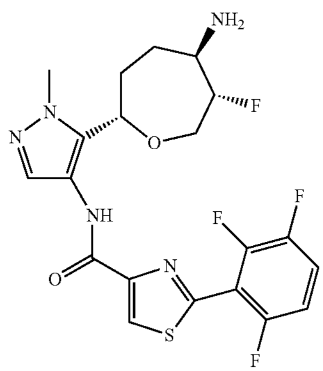 [SMILES: Cn1ncc(NC(=O)c2csc(-c3c(F)ccc(F)c3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,3,6-trifluorophenyl)thiazole-4-carboxamide | 0.000047 |
| 244 | 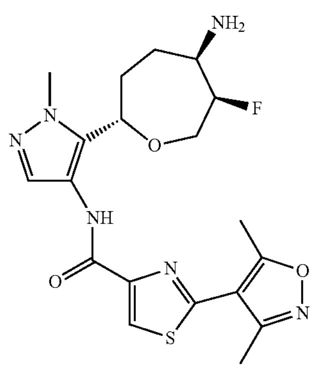 [SMILES: Cc1noc(C)c1-c1nc(C(=O)Nc2cnn(C)c2[C@@H]2CC[C@@H](N)[C@@H](F)CO2)cs1] | N-(5-((2S,5R,6R)-5-amino-6-fluorooxepan-2-yl)-1-methyl-1H-pyrazol-4-yl)-2-(3,5-dimethylisoxazol-4-yl)thiazole-4-carboxamide | 0.00598 |
| 245 | 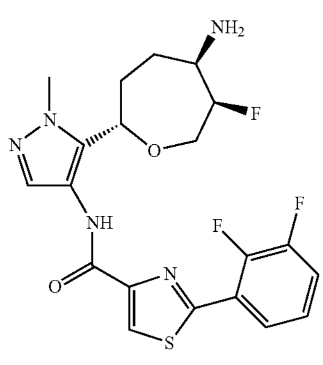 [SMILES: Cn1ncc(NC(=O)c2csc(-c3cccc(F)c3F)n2)c1[C@@H]1CC[C@@H](N)[C@@H](F)CO1] | N-(5-((2S,5R,6R)-5-amino-6-fluorooxepan-2-yl)-1-methyl-1H-pyrazol-4-yl)-2-(2,3-difluorophenyl)thiazole-4-carboxamide | 0.000104 |

TABLE 1b-continued

| No. | Structure | IUPAC Name | PIM1 LC3K (KI) μM |
|---|---|---|---|
| 246 | 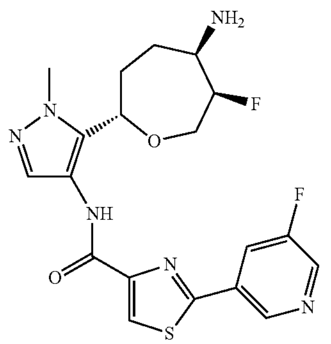 [SMILES: Cn1ncc(NC(=O)c2csc(-c3cncc(F)c3)n2)c1[C@@H]1CC[C@@H](N)[C@@H](F)CO1] | N-(5-((2S,5R,6R)-5-amino-6-fluorooxepan-2-yl)-1-methyl-1H-pyrazol-4-yl)-2-(5-fluoropyridin-3-yl)thiazole-4-carboxamide | 0.00576 |
| 247 | 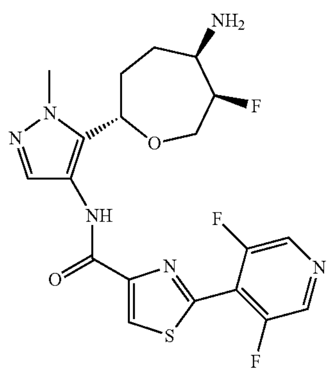 [SMILES: Cn1ncc(NC(=O)c2csc(-c3c(F)cncc3F)n2)c1[C@@H]1CC[C@@H](N)[C@@H](F)CO1] | N-(5-((2S,5R,6R)-5-amino-6-fluorooxepan-2-yl)-1-methyl-1H-pyrzol-4-yl)-2-(3,5-difluoropyridin-4-yl)thiazole-4-carboxamide | 0.000112 |
| 248 | 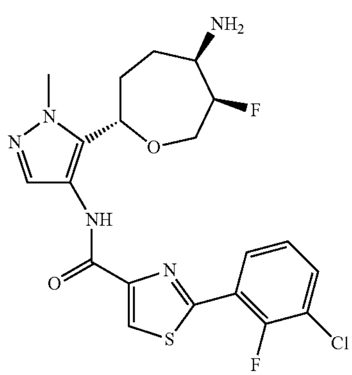 [SMILES: Cn1ncc(NC(=O)c2csc(-c3cccc(Cl)c3F)n2)c1[C@@H]1CC[C@@H](N)[C@@H](F)CO1] | N-(5-((2S,5R,6R)-5-amino-6-fluorooxepan-2-yl)-1-methyl-1H-pyrazol-4-yl)-2-(3-chloro-2-fluorophenyl)thiazole-4-carboxamide | 0.000064 |
| 249 | 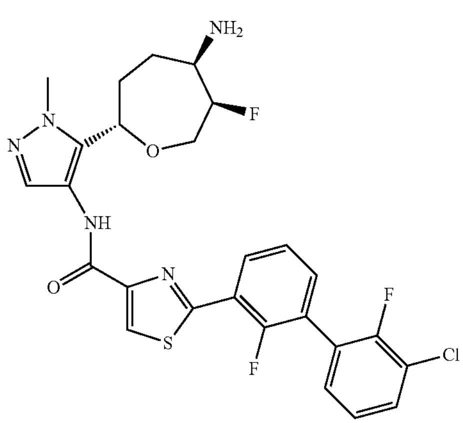 [SMILES: Cn1ncc(NC(=O)c2csc(-c3cccc(-c4cccc(Cl)c4F)c3F)n2)c1[C@@H]1CC[C@@H](N)[C@@H](F)CO1] | N-(5-((2S,5R,6R)-5-amino-6-fluorooxepan-2-yl)-1-methyl-1H-pyrazol-4-yl)-2-(3'-chloro-2,2'-difluoro-[1,1'-biphenyl]-3-yl)thiazole-4-carboxamide | 0.000533 |

TABLE 1b-continued

| No. | Structure | IUPAC Name | PIM1 LC3K (KI) μM |
|---|---|---|---|
| 250 | 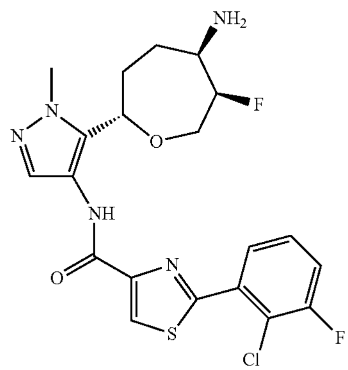 [SMILES: Cn1ncc(NC(=O)c2csc(-c3cccc(F)c3Cl)n2)c1[C@@H]1CC[C@@H](N)[C@@H](F)CO1] | N-(5-((2S,5R,6R)-5-amino-6-fluorooxepan-2-yl)-1-methyl-1H-pyrazol-4-yl)-2-(2-chloro-3-fluorophenyl)thiazole-4-carboxamide | 0.000132 |
| 251 | 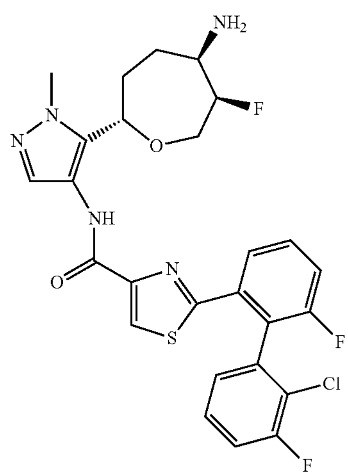 [SMILES: Cn1ncc(NC(=O)c2csc(-c3cccc(F)c3-c3cccc(F)c3Cl)n2)c1[C@@H]1CC[C@@H](N)[C@@H](F)CO1] | N-(5-((2S,5R,6R)-5-amino-6-fluorooxepan-2-yl)-1-methyl-1H-pyrazol-4-yl)-2-(2'-chloro-3',6-difluoro-[1,1'-biphenyl]-2-yl)thiazole-4-carboxamide | 0.63 |
| 252 | 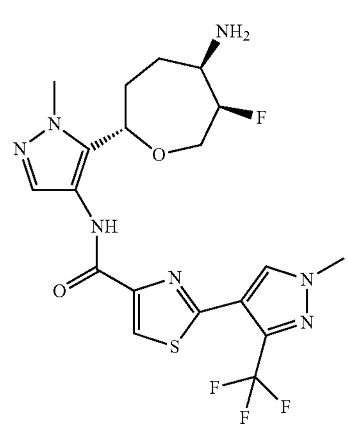 [SMILES: Cn1cc(-c2nc(C(=O)Nc3cnn(C)c3[C@@H]3CC[C@@H](N)[C@@H](F)CO3)cs2)c(C(F)(F)F)n1] | N-(5-((2S,5R,6R)-5-amino-6-fluorooxepan-2-yl)-1-methyl-1H-pyrazol-4-yl)-2-(1-methyl-3-(trifluoromethyl)-1H-pyrazol-4-yl)thiazole-4-carboxamide | 0.000281 |

TABLE 1b-continued

| No. | Structure | IUPAC Name | PIM1 LC3K (KI) μM |
|---|---|---|---|
| 253 | 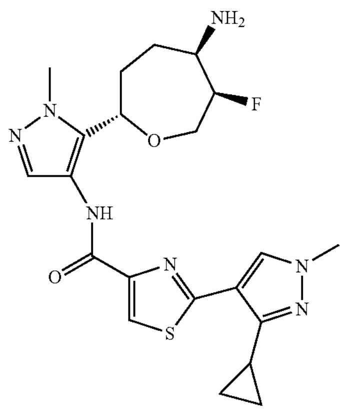 [SMILES: Cn1cc(-c2nc(C(=O)Nc3cnn(C)c3[C@@H]3CC[C@@H](N)[C@@H](F)CO3)cs2)c(C2CC2)n1] | N-(5-((2S,5R,6R)-5-amino-6-fluorooxepan-2-yl)-1-methyl-1H-pyrazol-4-yl)-2-(3-cyclopropyl-1-methyl-1H-pyrazol-4-yl)thiazole-4-carboxamide | 0.000253 |
| 254 | 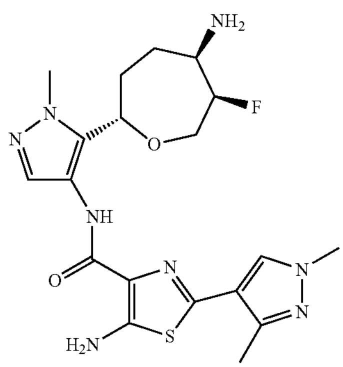 [SMILES: Cc1nn(C)cc1-c1nc(C(=O)Nc2cnn(C)c2[C@@H]2CC[C@@H](N)[C@@H](F)CO2)c(N)s1] | 5-amino-N-(5-((2S,5R,6R)-5-amino-6-fluorooxepan-2-yl)-1-methyl-1H-pyrazol-4-yl)-2-(1,3-dimethyl-1H-pyrazol-4-yl)thiazole-4-carboxamide | 0.000026 |
| 255 | 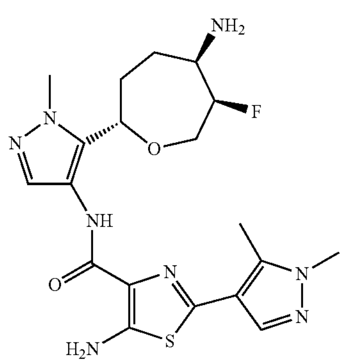 [SMILES: Cc1c(-c2nc(C(=O)Nc3cnn(C)c3[C@@H]3CC[C@@H](N)[C@@H](F)CO3)c(N)s2)cnn1C] | 5-amino-N-(5-((2S,5R,6R)-5-amino-6-fluorooxepan-2-yl)-1-methyl-1H-pyrazol-4-yl)-2-(1,5-dimethyl-1H-pyrazol-4-yl)thiazole-4-carboxamide | 0.000007 |
| 256 | 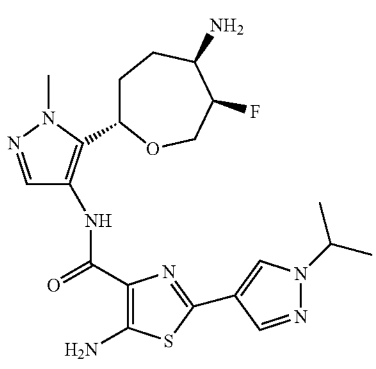 [SMILES: CC(C)n1cc(-c2nc(C(=O)Nc3cnn(C)c3[C@@H]3CC[C@@H](N)[C@@H](F)CO3)c(N)s2)cn1] | 5-amino-N-(5-((2S,5R,6R)-5-amino-6-fluorooxepan-2-yl)-1-methyl-1H-pyrazol-4-yl)-2-(1-isopropyl-1H-pyrazol-4-yl)thiazole-4-carboxamide | 0.000093 |

TABLE 1b-continued

| No. | Structure | IUPAC Name | PIM1 LC3K (KI) μM |
|---|---|---|---|
| 257 | 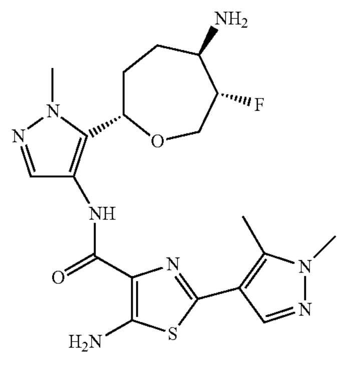 [SMILES: Cc1c(-c2nc(C(=O)Nc3cnn(C)c3[C@@H]3CC[C@@H](N)[C@H](F)CO3)c(N)s2)cnn1C] | 5-amino-N-(5-((2S,5R,6S)-5-amino-6-fluorooxepan-2-yl)-1-methyl-1H-pyrazol-4-yl)-2-(1,5-dimethyl-1H-pyrazol-4-yl)thiazole-4-carboxamide | 0.000025 |
| 258 | 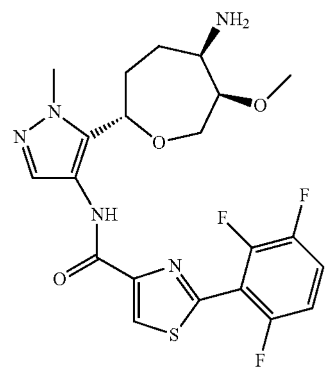 [SMILES: CO[C@H]1CO[C@H](c2c(NC(=O)c3csc(-c4c(F)ccc(F)c4F)n3)cnn2C)CC[C@H]1N] | N-(5-((2S,5R,6R)-5-amino-6-methoxyoxepan-2-yl)-1-methyl-1H-pyrazol-4-yl)-2-(2,3,6,-trifluorophenyl)thiazole-4-carboxamide | 0.000145 |
| 259 | 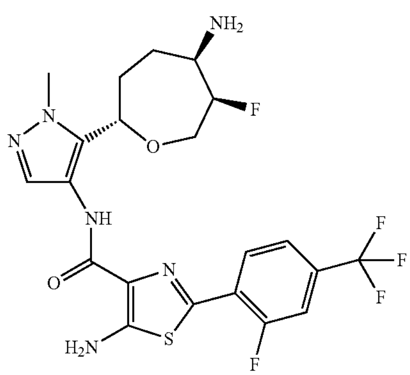 [SMILES: Cn1ncc(NC(=O)c2nc(-c3ccc(C(F)(F)F)cc3F)sc2N)c1[C@@H]1CC[C@@H](N)[C@@H](F)CO1] | 5-amino-N-(5-((2S,5R,6R)-5-amino-6-fluorooxepan-2-yl)-1-methyl-1H-pyrazol-4-yl)-2-(2-fluoro-4-(trifluoromethyl)phenyl)thiazole-4-carboxamide | 0.00001 |
| 260 | 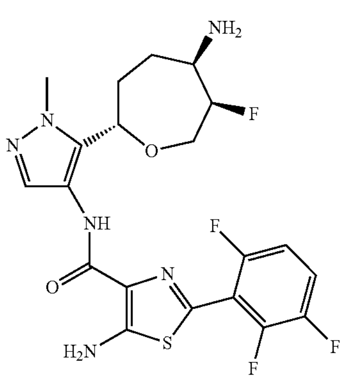 [SMILES: Cn1ncc(NC(=O)c2nc(-c3c(F)ccc(F)c3F)sc2N)c1[C@@H]1CC[C@@H](N)[C@@H](F)CO1] | 5-amino-N-(5-((2S,5R,6R)-5-amino-6-fluorooxepan-2-yl)-1-methyl-1H-pyrazol-4-yl)-2-(2,3,6-trifluorophenyl)thiazole-4-carboxamide | 0.000004 |

TABLE 1b-continued

| No. | Structure | IUPAC Name | PIM1 LC3K (KI) μM |
|---|---|---|---|
| 261 | 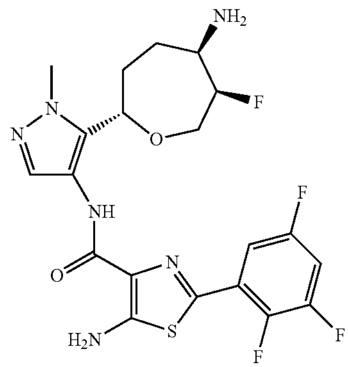 [SMILES: Cn1ncc(NC(=O)c2nc(-c3cc(F)cc(F)c3F)sc2N)c1[C@@H]1CC[C@@H](N)[C@@H](F)CO1] | 5-amino-N-(5-((2S,5R,6R)-5-amino-6-fluorooxepan-2-yl)-1-methyl-1H-pyrazol-4-yl)-2-(2,3,5-trifluorophenyl)thiazole-4-carboxamide | 0.000037 |
| 262 | 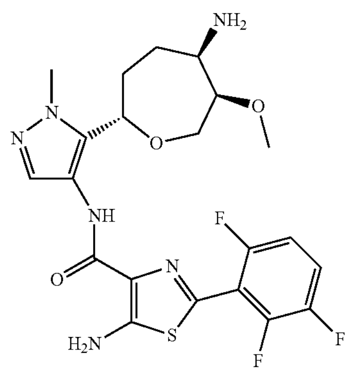 [SMILES: CO[C@H]1CO[C@H](c2c(NC(=O)c3nc(-c4c(F)ccc(F)c4F)sc3N)cnn2C)CC[C@H]1N] | 5-amino-N-(5-((2S,5R,6R)-5-amino-6-methoxyoxepan-2-yl)-1-methyl-1H-pyrazol-4-yl)-2-(2,3,6-trifluorophenyl)thiazole-4-carboxamide | 0.00001 |
| 263 | 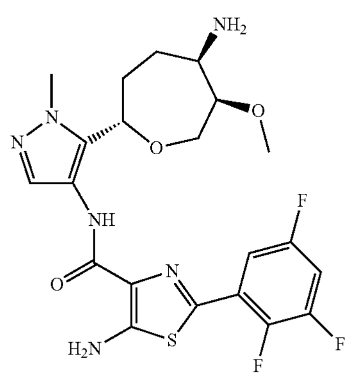 [SMILES: CO[C@H]1CO[C@H](c2c(NC(=O)c3nc(-c4cc(F)cc(F)c4F)sc3N)cnn2C)CC[C@H]1N] | 5-amino-N-(5-((2S,5R,6R)-5-amino-6-methoxyoxepan-2-yl)-1-methyl-1H-pyrazol-4-yl)-2-(2,3,5-trifluorophenyl)thiazole-4-carboxamide | 0.000127 |
| 264 | 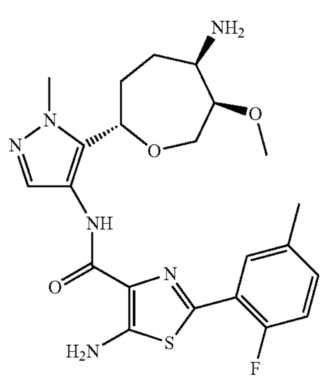 [SMILES: CO[C@H]1CO[C@H](c2c(NC(=O)c3nc(-c4cc(C)ccc4F)sc3N)cnn2C)CC[C@H]1N] | 5-amino-N-(5-((2S,5R,6R)-5-amino-6-methoxyoxepan-2-yl)-1-methyl-1H-pyrazol-4-yl)-2-(2-fluoro-5-methylphenyl)thiazole-4-carboxamide | 0.00002 |

TABLE 1b-continued

| No. | Structure | IUPAC Name | PIM1 LC3K (KI) μM |
|---|---|---|---|
| 265 | 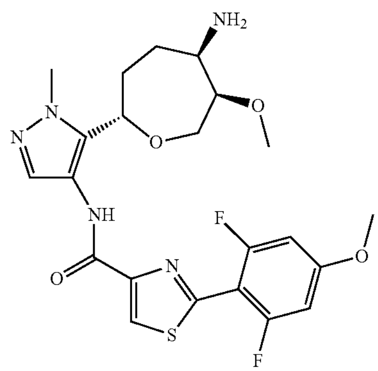 [SMILES: COc1cc(F)c(-c2nc(C(=O)Nc3cnn(C)c3[C@@H]3CC[C@@H](N)[C@@H](OC)CO3)cs2)c(F)c1] | N-(5-((2S,5R,6R)-5-amino-6-methoxyoxepan-2-yl)-1-methyl-1H-pyrazol-4-yl)-2-(2,6-difluoro-4-methoxyphenyl)thiazole-4-carboxamide | 0.000034 |
| 266 | 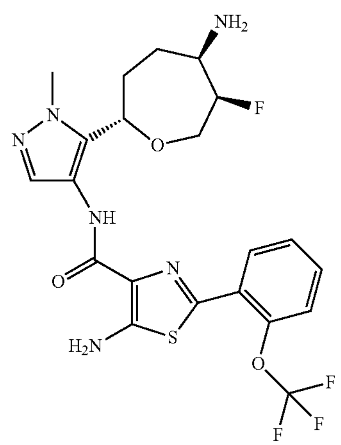 [SMILES: Cn1ncc(NC(=O)c2nc(-c3ccccc3OC(F)(F)F)sc2N)c1[C@@H]1CC[C@@H](N)[C@@H](F)CO1] | 5-amino-N-(5-((2S,5R,6R)-5-amino-6-fluorooxepan-2-yl)-1-methyl-1H-pyrazol-4-yl)-2-(2-(trifluoromethoxy)phenyl)thiazole-4-carboxamide | 0.000155 |
| 267 | 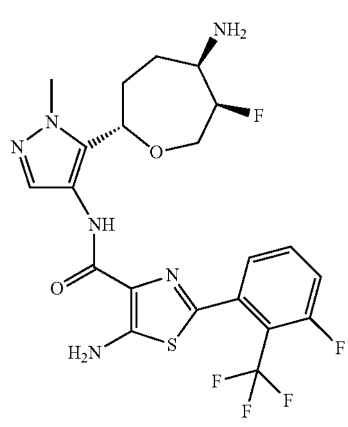 [SMILES: Cn1ncc(NC(=O)c2nc(-c3cccc(F)c3C(F)(F)F)sc2N)c1[C@@H]1CC[C@@H](N)[C@@H](F)CO1] | 5-amino-N-(5-((2S,5R,6R)-5-amino-6-fluorooxepan-2-yl)-1-methyl-1H-pyrazol-4-yl)-2-(3-fluoro-2-(trifluoromethyl)phenyl)thiazole-4-carboxamide | 0.000098 |

TABLE 1b-continued

| No. | Structure | IUPAC Name | PIM1 LC3K (KI) μM |
|---|---|---|---|
| 268 | 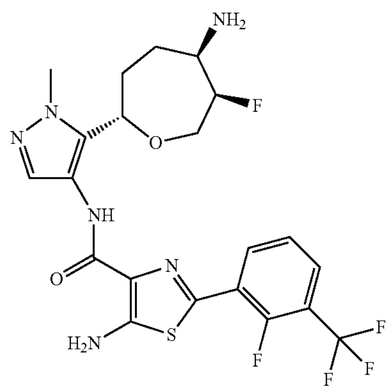 [SMILES: Cn1ncc(NC(=O)c2nc(-c3cccc(C(F)(F)F)c3F)sc2N)c1[C@@H]1CC[C@@H](N)[C@@H](F)CO1] | 5-amino-N-(5-((2S,5R,6R)-5-amino-6-fluorooxepan-2-yl)-1-methyl-1H-pyrazol-4-yl)-2-(2-fluoro-3-(trifluoromethyl)phenyl)thiazole-4-carboxamide | 0.000028 |
| 269 | 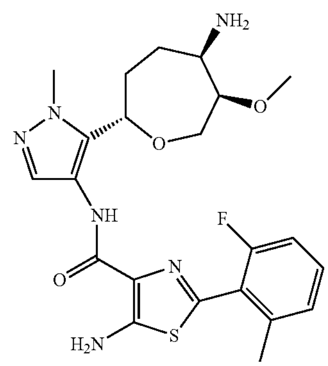 [SMILES: CO[C@H]1CO[C@H](c2c(NC(=O)c3nc(-c4c(C)cccc4F)sc3N)cnn2C)CC[C@H]1N] | 5-amino-N-(5-((2S,5R,6R)-5-amino-6-methoxyoxepan-2-yl)-1-methyl-1H-pyrazol-4-yl)-2-(2-fluoro-6-methylphenyl)thiazole-4-carboxamide | 0.000052 |
| 270 | 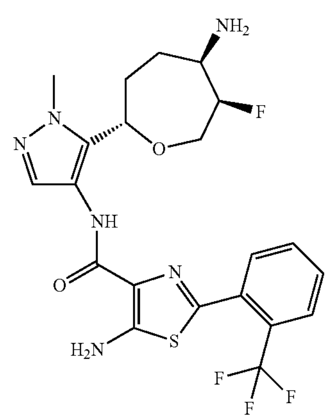 [SMILES: Cn1ncc(NC(=O)c2nc(-c3ccccc3C(F)(F)F)sc2N)c1[C@@H]1CC[C@@H](N)[C@@H](F)CO1] | 5-amino-N-(5-((2S,5R,6R)-5-amino-6-fluorooxepan-2-yl)-1-methyl-1H-pyrazol-4-yl)-2-(2-(trifluoromethyl)phenyl)thiazole-4-carboxamide | 0.000053 |
| 271 | 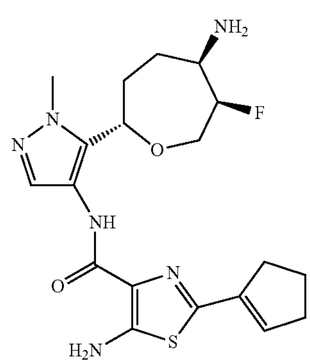 [SMILES: Cn1ncc(NC(=O)c2nc(C3=CCCC3)sc2N)c1[C@@H]1CC[C@@H](N)[C@@H](F)CO1] | 5-amino-N-(5-((2S,5R,6R)-5-amino-6-fluorooxepan-2-yl)-1-methyl-1H-pyrazol-4-yl)-2-(cyclopent-1-en-1-yl)thiazole-4-carboxamide | 0.000062 |

TABLE 1b-continued

| No. | Structure | IUPAC Name | PIM1 LC3K (KI) μM |
|-----|-----------|------------|------------------|
| 272 | 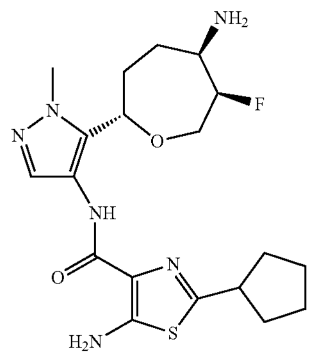 [SMILES: Cn1ncc(NC(=O)c2nc(C3CCCC3)sc2N)c1[C@@H]1CC[C@@H](N)[C@@H](F)CO1] | 5-amino-N-(5-((2S,5R,6R)-5-amino-6-fluorooxepan-2-yl)-1-methyl-1H-pyrazol-4-yl)-2-cyclopentylthiazole-4-carboxamide | 0.000992 |
| 273 | 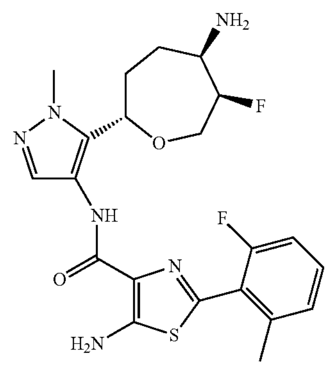 [SMILES: Cc1cccc(F)c1-c1nc(C(=O)Nc2cnn(C)c2[C@@H]2CC[C@@H](N)[C@@H](F)CO2)c(N)s1] | 5-amino-N-(5-((2S,5R,6R)-5-amino-6-fluorooxepan-2-yl)-1-methyl-1H-pyrazol-4-yl)-2-(2-fluoro-6-methylphenyl)thiazole-4-carboxamide | 0.000007 |
| 274 | 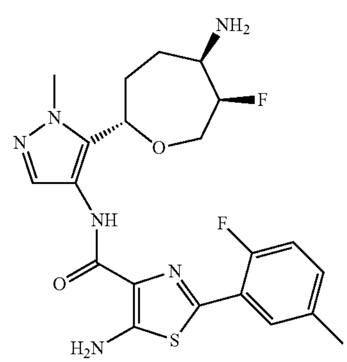 [SMILES: Cc1ccc(F)c(-c2nc(C(=O)Nc3cnn(C)c3[C@@H]3CC[C@@H](N)[C@@H](F)CO3)c(N)s2)c1] | 5-amino-N-(5-((2S,5R,6R)-5-amino-6-fluorooxepan-2-yl)-1-methyl-1H-pyrazol-4-yl)-2-(2-fluoro-5-methylphenyl)thiazole-4-carboxamide | 0.00002 |
| 275 | 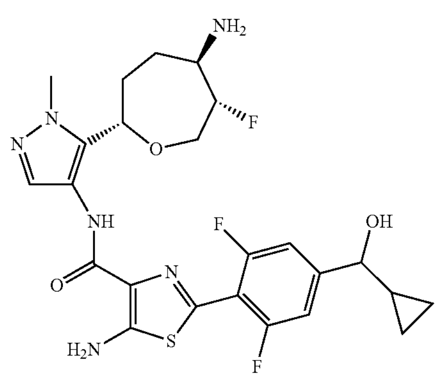 [SMILES: Cn1ncc(NC(=O)c2nc(-c3c(F)cc(C(O)C4CC4)cc3F)sc2N)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(4-(cyclopropyl(hydroxy)methyl)-2,6-difluorophenyl)thiazole-4-carboxamide | 0.000037 |

TABLE 1b-continued

| No. | Structure | IUPAC Name | PIM1 LC3K (KI) μM |
|---|---|---|---|
| 276 | 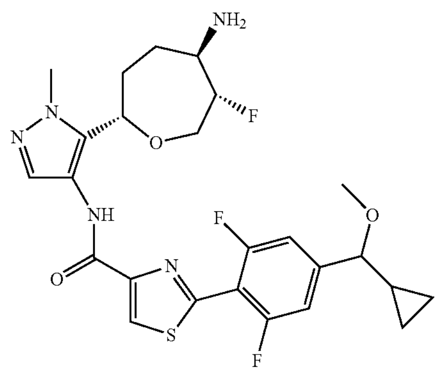 [SMILES: COC(c1cc(F)c(-c2nc(C(=O)Nc3cnn(C)c3[C@@H]3CC[C@@H](N)[C@H](F)CO3)cs2)c(F)c1)C1CC1] | N-(5-((2S,5R,6S)-5-amino-6-fluorooxepan-2-yl)-1-methyl-1H-pyrazol-4-yl)-2-(4-(cyclopropyl(methoxy)methyl)-2,6-difluorophenyl)thiazole-4-carboxamide | 0.000084 |
| 277 | 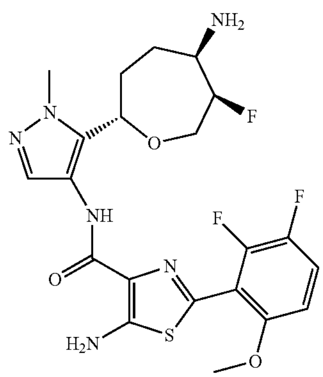 [SMILES: COc1ccc(F)c(F)c1-c1nc(C(=O)Nc2cnn(C)c2[C@@H]2CC[C@@H](N)[C@@H](F)CO2)c(N)s1] | 5-amino-N-(5-((2S,5R,6R)-5-amino-6-fluorooxepan-2-yl)-1-methyl-1H-pyrazol-4-yl)-2-(2,3-difluoro-6-methoxyphenyl)thiazole-4-carboxamide | 0.000143 |
| 278 | 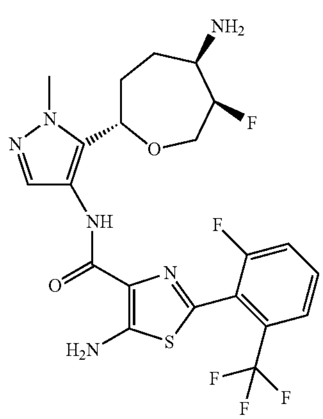 [SMILES: Cn1ncc(NC(=O)c2nc(-c3c(F)cccc3C(F)(F)F)sc2N)c1[C@@H]1CC[C@@H](N)[C@@H](F)CO1] | 5-amino-N-(5-((2S,5R,6R)-5-amino-6-fluorooxepan-2-yl)-1-methyl-1H-pyrazol-4-yl)-2-(2-fluoro-6-(trifluoromethyl)phenyl)thiazole-4-carboxamide | 0.000061 |
| 279 | 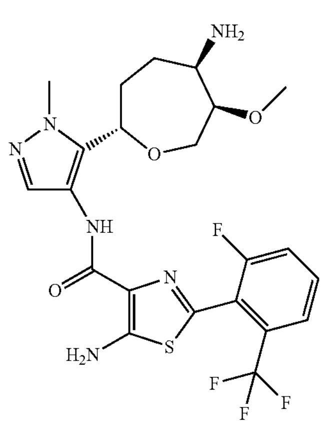 [SMILES: CO[C@H]1CO[C@H](c2c(NC(=O)c3nc(-c4c(F)cccc4C(F)(F)F)sc3N)cnn2C)CC[C@H]1N] | 5-amino-N-(5-((2S,5R,6R)-5-amino-6-methoxyoxepan-2-yl)-1-methyl-1H-pyrazol-4-yl)-2-(2-fluoro-6-(trifluoromethyl)phenl)thiazole-4-carboxamide | 0.000083 |

TABLE 1b-continued

| No. | Structure | IUPAC Name | PIM1 LC3K (KI) μM |
|---|---|---|---|
| 280 | 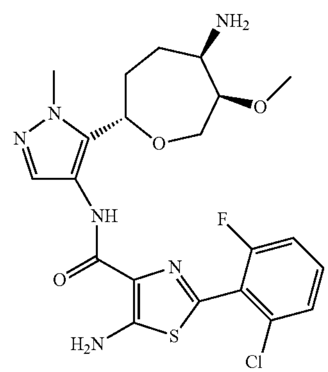 [SMILES: CO[C@H]1CO[C@H](c2c(NC(=O)c3nc(-c4c(F)cccc4Cl)sc3N)cnn2C)CC[C@H]1N] | 5-amino-N-(5-((2S,5R,6R)-5-amino-6-methoxyoxepan-2-yl)-1-methyl-1H-pyrazol-4-yl)-2-(2-chloro-6-fluorophenyl)thiazole-4-carboxamide | 0.000014 |
| 281 | 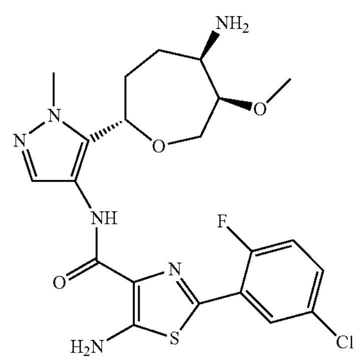 [SMILES: CO[C@H]1CO[C@H](c2c(NC(=O)c3nc(-c4cc(Cl)ccc4F)sc3N)cnn2C)CC[C@H]1N] | 5-amino-N-(5-((2S,5R,6R)-5-amino-6-methoxyoxepan-2-yl)-1-methyl-1H-pyrazol-4-yl)-2-(5-chloro-2-fluorophenyl)thiazole-4-carboxamide | 0.000007 |
| 282 | 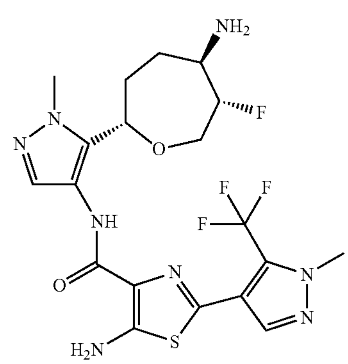 [SMILES: Cn1ncc(NC(=O)c2nc(-c3cnn(C)c3C(F)(F)F)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(1-methyl-5-(trifluoromethyl)-1H-pyrazol-4-yl)thiazole-4-carboxamide | 0.000058 |
| 283 | 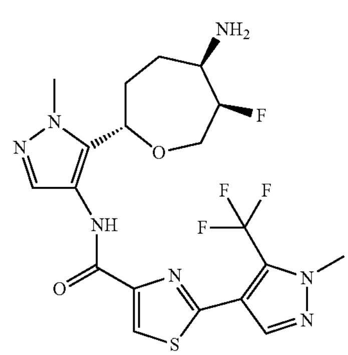 [SMILES: Cn1ncc(NC(=O)c2csc(-c3cnn(C)c3C(F)(F)F)n2)c1[C@@H]1CC[C@@H](N)[C@@H](F)CO1] | N-(5-((2S,5R,6R)-5-amino-6-fluorooxepan-2-yl)-1-methyl-1H-pyrazol-4-yl)-2-(1-methyl-5-(trifluoromethyl)-1H-pyrazol-4-yl)thiazole-4-carboxamide | 0.000171 |

TABLE 1b-continued

| No. | Structure | IUPAC Name | PIM1 LC3K (KI) μM |
|---|---|---|---|
| 284 | 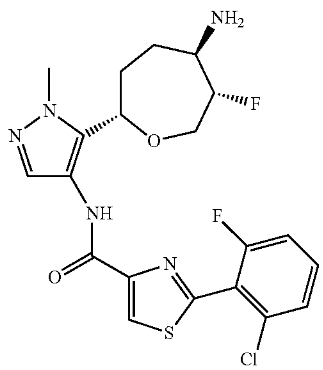 [SMILES: Cn1ncc(NC(=O)c2csc(-c3c(F)cccc3Cl)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2-chloro-6-fluorophenyl)thiazole-4-carboxamide | 0.00022 |
| 285 | 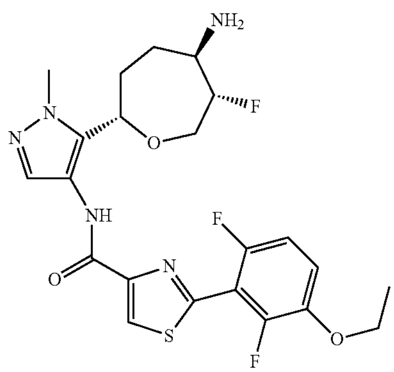 [SMILES: CCOc1ccc(F)c(-c2nc(C(=O)Nc3cnn(C)c3[C@@H]3CC[C@@H](N)[C@H](F)CO3)cs2)c1F] | N-(5-((2S,5R,6S)-5-amino-6-fluorooxepan-2-yl)-1-methyl-1H-pyrazol-4-yl)-2-(3-ethoxy-2,6-difluorophenyl)thiazole-4-carboxamide | 0.000001 |
| 286 | 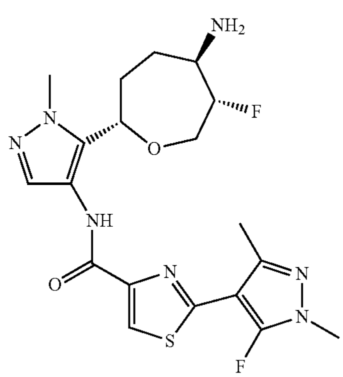 [SMILES: Cc1nn(C)c(F)c1-c1nc(C(=O)Nc2cnn(C)c2[C@@H]2CC[C@@H](N)[C@H](F)CO2)cs1] | N-(5-((2S,5R,6S)-5-amino-6-fluorooxepan-2-yl)-1-methyl-1H-pyrazol-4-yl)-2-(5-fluoro-1,3-dimethyl-1H-pyrazol-4-yl)thiazole-4-carboxamide | |
| 287 | 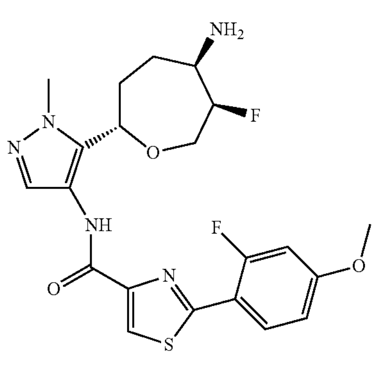 [SMILES: COc1ccc(-c2nc(C(=O)Nc3cnn(C)c3[C@@H]3CC[C@@H](N)[C@@H](F)CO3)cs2)c(F)c1] | N-(5-((2S,5R,6R)-5-amino-6-fluorooxepan-2-yl)-1-methyl-1H-pyrazol-4-yl)-2-(2-fluoro-4-methoxyphenyl)thiazole-4-carboxamide | 0.000053 |

TABLE 1b-continued

| No. | Structure | IUPAC Name | PIM1 LC3K (KI) μM |
|---|---|---|---|
| 288 | 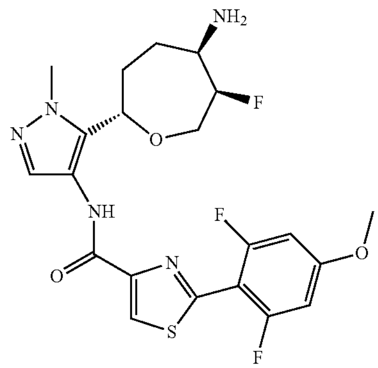 [SMILES: COc1cc(F)c(-c2nc(C(=O)Nc3cnn(C)c3[C@@H]3CC[C@@H](N)[C@@H](F)CO3)cs2)c(F)c1] | N-(5-((2S,5R,6R)-5-amino-6-fluorooxepan-2-yl)-1-methyl-1H-pyrazol-4-yl)-2-(2,6-difluoro-4-methoxyphenyl)thiazole-4-carboxamide | 0.000035 |
| 289 | 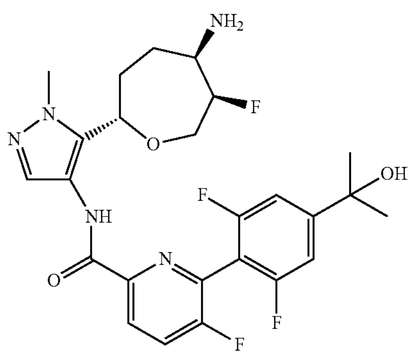 [SMILES: Cn1ncc(NC(=O)c2ccc(F)c(-c3c(F)cc(C(C)(C)O)cc3F)n2)c1[C@@H]1CC[C@@H](N)[C@@H](F)CO1] | N-(5-((2S,5R,6R)-5-amino-6-fluorooxepan-2-yl)-1-methyl-1H-pyrazol-4-yl)-6-(2,6-difluoro-4-(2-hydroxypropan-2-yl)phenyl)-5-fluoropicolinamide | 0.00008 |
| 290 | 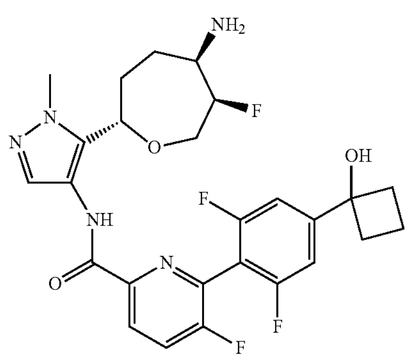 [SMILES: Cn1ncc(NC(=O)c2ccc(F)c(-c3c(F)cc(C4(O)CCC4)cc3F)n2)c1[C@@H]1CC[C@@H](N)[C@@H](F)CO1] | N-(5-((2S,5R,6R)-5-amino-6-fluorooxepan-2-yl)-1-methyl-1H-pyrazol-4-yl)-6-(2,6-difluoro-4-(1-hydroxycyclobutyl)phenyl)-5-fluoropicolinamide | 0.0000131 |
| 291 | 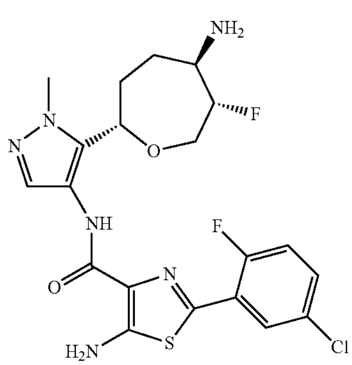 [SMILES: Cn1ncc(NC(=O)c2nc(-c3cc(Cl)ccc3F)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(5-chloro-2-fluorophenyl)thiazole-4-carboxamide | 0.000018 |

TABLE 1b-continued

| No. | Structure | IUPAC Name | PIM1 LC3K (KI) µM |
|---|---|---|---|
| 292 | 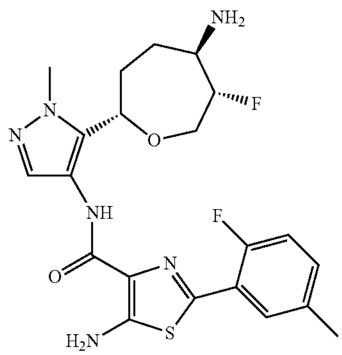 [SMILES: Cc1ccc(F)c(-c2nc(C(=O)Nc3cnn(C)c3[C@@H]3CC[C@@H](N)[C@H](F)CO3)c(N)s2)c1] | 5-amino-N-(5-((2S,5R,6S)-5-amino-6-fluorooxepan-2-yl)-1-methyl-1H-pyrazol-4-yl)-2-(2-fluoro-5-methyplhenyl)thiazole-4-carboxamide | 0.000024 |
| 293 | 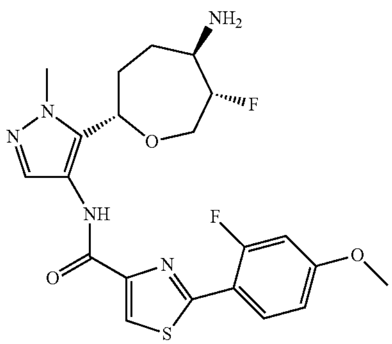 [SMILES: COc1ccc(-c2nc(C(=O)Nc3cnn(C)c3[C@@H]3CC[C@@H](N)[C@H](F)CO3)cs2)c(F)c1] | N-(5-((2S,5R,6S)-5-amino-6-fluorooxepan-2-yl)-1-methyl-1H-pyrazol-4-yl)-2-(2-fluoro-4-methoxyphenyl)thiazole-4-carboxamide | 0.000059 |
| 294 | 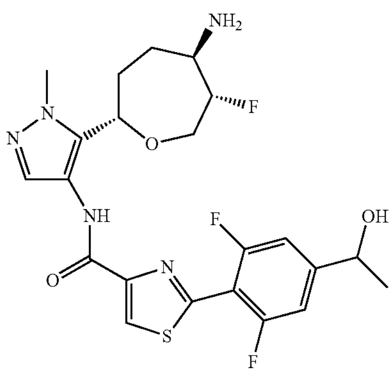 [SMILES: CC(O)c1cc(F)c(-c2nc(C(=O)Nc3cnn(C)c3[C@@H]3CC[C@@H](N)[C@H](F)CO3)cs2)c(F)c1] | N-(5-((2S,5R,6S)-5-amino-6-fluorooxepan-2-yl)-1-methyl-1H-pyrazol-4-yl)-2-(2,6-difluoro-4-(1-hydroxyethyl)phenyl)thiazole-4-carboxamide | 0.000029 |
| 295 | 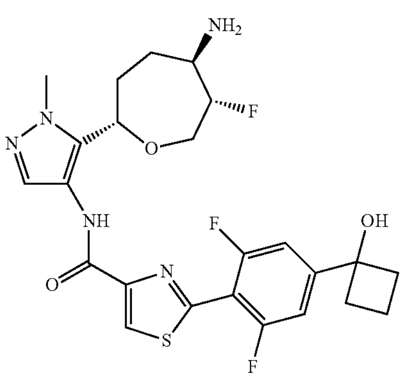 [SMILES: Cn1ncc(NC(=O)c2csc(-c3c(F)cc(C4(O)CCC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,6-difluoro-4-(1-hydroxycyclobutyl)phenyl)thiazole-4-carboxamide | 0.000027 |

TABLE 1b-continued

| No. | Structure | IUPAC Name | PIM1 LC3K (KI) μM |
|---|---|---|---|
| 296 | 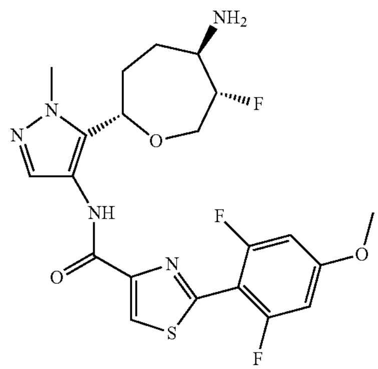 [SMILES: COc1cc(F)c(-c2nc(C(=O)Nc3cnn(C)c3[C@@H]3CC[C@@H](N)[C@H](F)CO3)cs2)c(F)c1] | N-(5-((2S,5R,6S)-5-amino-6-fluorooxepan-2-yl)-1-methyl-1H-pyrazol-4-yl)-2-(2,6-difluoro-4-methoxyphenyl)thiazole-4-carboxamide | 0.000031 |
| 297 | 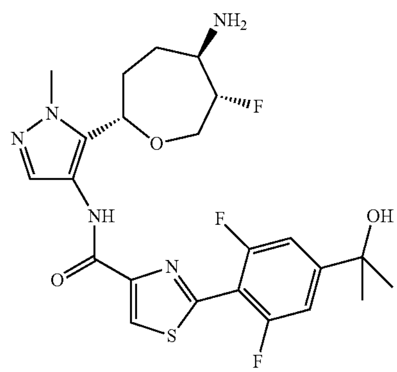 [SMILES: Cn1ncc(NC(=O)c2csc(-c3c(F)cc(C(C)(C)O)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,6-difluoro-4-(2-hydroxypropan-2-yl)phenyl)thiazole-4-carboxamide | 0.000021 |
| 298 | 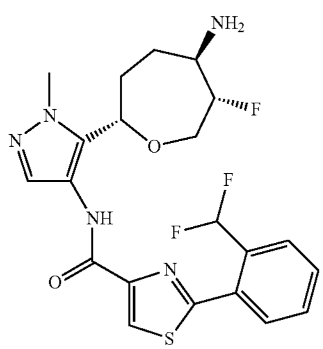 [SMILES: Cn1ncc(NC(=O)c2csc(-c3ccccc3C(F)F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2-(difluoromethyl)phenyl)thiazole-4-carboxamide | 0.000783 |
| 299 | 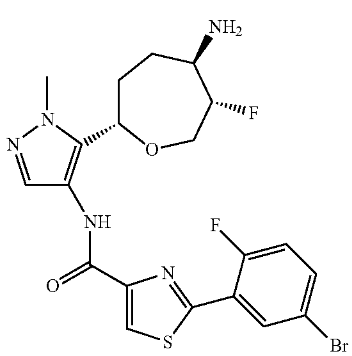 [SMILES: Cn1ncc(NC(=O)c2csc(-c3cc(Br)ccc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(5-bromo-2-fluorophenyl)thiazole-4-carboxamide | 0.000023 |

TABLE 1b-continued

| No. | Structure | IUPAC Name | PIM1 LC3K (KI) μM |
|---|---|---|---|
| 300 | 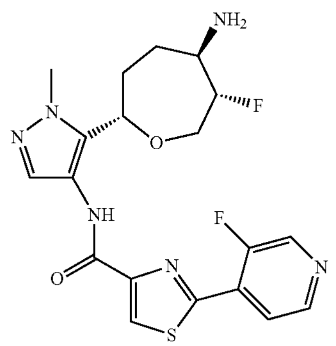 [SMILES: Cn1ncc(NC(=O)c2csc(-c3ccncc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(3-fluoropyridin-4-yl)thiazole-4-carboxamide | 0.000134 |
| 301 | 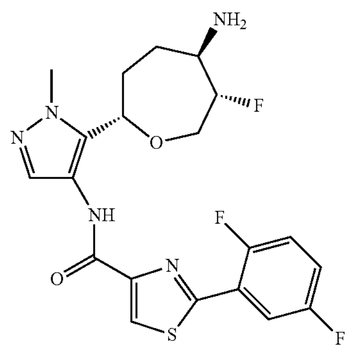 [SMILES: Cn1ncc(NC(=O)c2csc(-c3cc(F)ccc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,5-difluorophenyl)thiazole-4-carboxamide | 0.000058 |
| 302 | 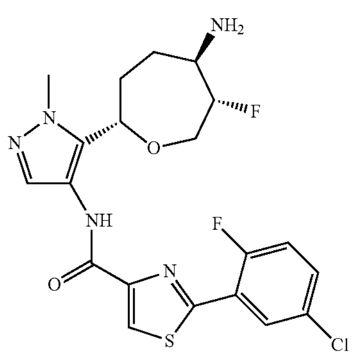 [SMILES: Cn1ncc(NC(=O)c2csc(-c3cc(Cl)ccc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(5-chloro-2-fluorophenyl)thiazole-4-carboxamide | 0.000031 |
| 303 | 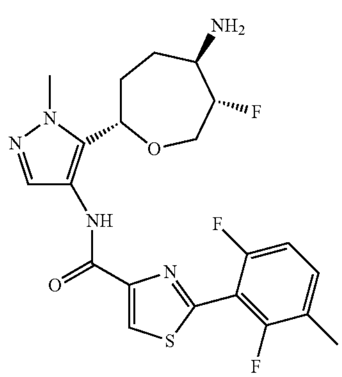 [SMILES: Cc1ccc(F)c(-c2nc(C(=O)Nc3cnn(C)c3[C@@H]3CC[C@@H](N)[C@H](F)CO3)cs2)c1F] | N-(5-((2S,5R,6S)-5-amino-6-fluorooxepan-2-yl)-1-methyl-1H-pyrazol-4-yl)-2-(2,6-difluoro-3-methylphenyl)thiazole-4-carboxamide | 0.000013 |

TABLE 1b-continued

| No. | Structure | IUPAC Name | PIM1 LC3K (KI) μM |
|---|---|---|---|
| 304 | 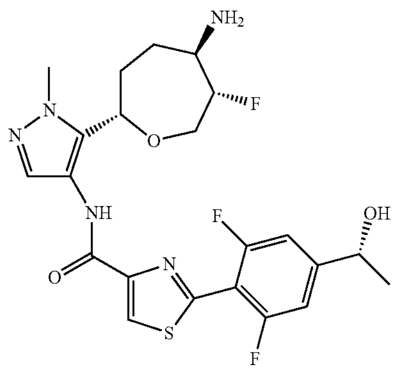 [SMILES: C[C@@H](O)c1cc(F)c(-c2nc(C(=O)Nc3cnn(C)c3[C@@H]3CC[C@@H](N)[C@H](F)CO3)cs2)c(F)c1] | N-(5-((2S,5R,6S)-5-amino-6-fluorooxepan-2-yl)-1-methyl-1H-pyrazol-4-yl)-2-(2,6-difluoro-4-((R)-1-hydroxyethyl)phenyl)thiazole-4-carboxamide | 0.000014 |
| 305 | 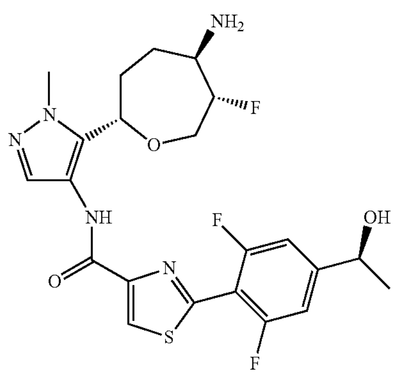 [SMILES: C[C@H](O)c1cc(F)c(-c2nc(C(=O)Nc3cnn(C)c3[C@@H]3CC[C@@H](N)[C@H](F)CO3)cs2)c(F)c1] | N-(5-((2S,5R,6S)-5-amino-6-fluorooxepan-2-yl)-1-methyl-1H-pyrazol-4-yl)-2-(2,6-difluoro-4-((S)-1-hydroxyethyl)phenyl)thiazole-4-carboxamide | 0.000008 |
| 306 | 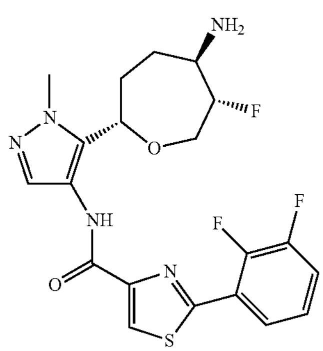 [SMILES: Cn1ncc(NC(=O)c2csc(-c3cccc(F)c3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,3-difluorophenyl)thiazole-4-carboxamide | 0.000044 |
| 307 | 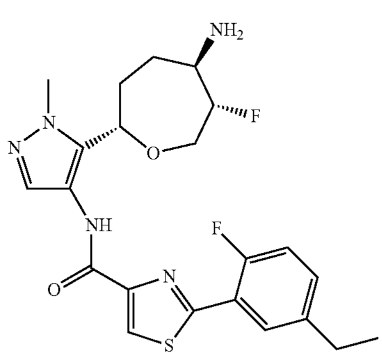 [SMILES: CCc1ccc(F)c(-c2nc(C(=O)Nc3cnn(C)c3[C@@H]3CC[C@@H](N)[C@H](F)CO3)cs2)c1] | N-(5-((2S,5R,6S)-5-amino-6-fluorooxepan-2-yl)-1-methyl-1H-pyrazol-4-yl)-2-(5-ethyl-2-fluorophenyl)thiazole-4-carboxamide | 0.000081 |

TABLE 1b-continued

| No. | Structure | IUPAC Name | PIM1 LC3K (KI) μM |
|---|---|---|---|
| 308 | 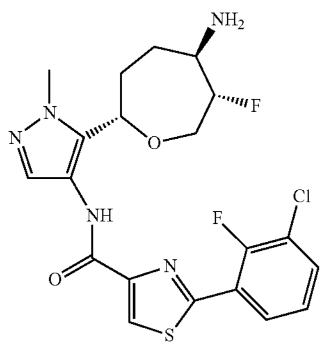 [SMILES: Cn1ncc(NC(=O)c2csc(-c3cccc(Cl)c3F)n2)c1[C@@H]1CC[C@@H](N)[C@H](F)CO1] | N-(5-((2S,56R,6S)-5-amino-6-fluorooxepan-2-yl)-1-methyl-1H-pyrazol-4-yl)-2-(3-chloro-2-fluorophenyl)thiazol-4-carboxamide | 0.000054 |
| 309 | 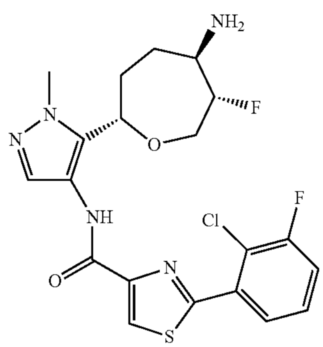 [SMILES: Cn1ncc(NC(=O)c2csc(-c3cccc(F)c3Cl)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2-chloro-3-fluorophenyl)thiazole-4-carboxamide | 0.000274 |
| 310 | 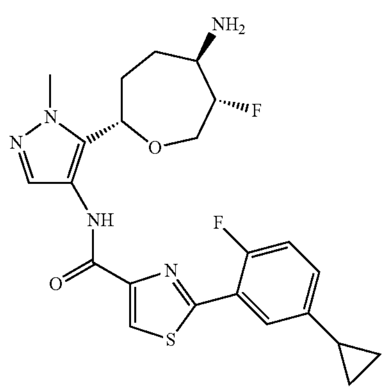 [SMILES: Cn1ncc(NC(=O)c2csc(-c3cc(C4CC4)ccc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(5-cyclopropyl-2-fluorophenyl)thiazole-4-carboxamide | 0.000093 |
| 311 | 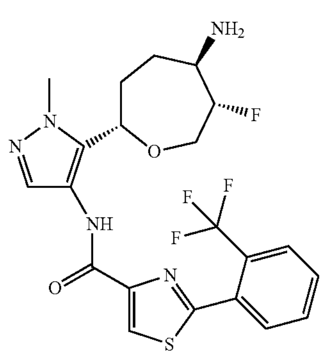 [SMILES: Cn1ncc(NC(=O)c2csc(-c3ccccc3C(F)(F)F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2-(trifluoromethyl)phenyl)thiazole-4-carboxamide | 0.00165 |

TABLE 1b-continued

| No. | Structure | IUPAC Name | PIM1 LC3K (KI) μM |
|---|---|---|---|
| 312 | 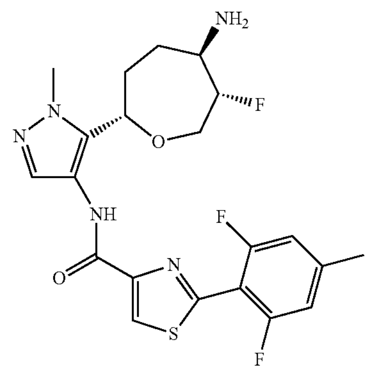 [SMILES: Cc1cc(F)c(-c2nc(C(=O)Nc3cnn(C)c3[C@@H]3CC[C@@H](N)[C@H](F)CO3)cs2)c(F)c1] | N-(5-((2S,5R,6S)-5-amino-6-fluorooxepan-2-yl)-1-methyl-1H-pyrazol-4-yl)-2-(2,6-difluoro-4-methylphenyl)thiazole-4-carboxamide | 0.000003 |
| 313 | 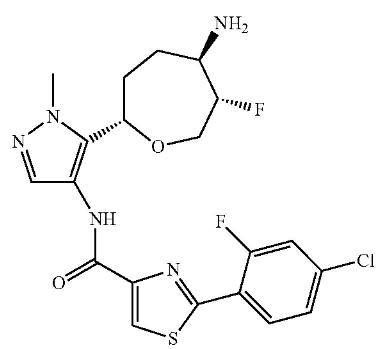 [SMILES: Cn1ncc(NC(=O)c2csc(-c3ccc(Cl)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(4-chloro-2-fluorophenyl)thiazole-4-carboxamide | 0.000002 |
| 314 | 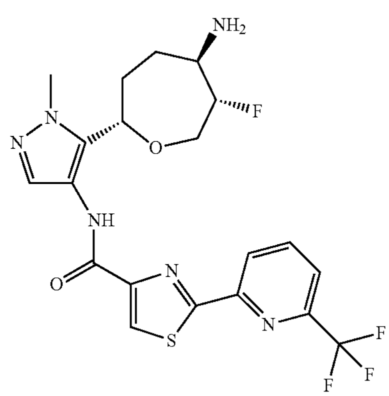 [SMILES: Cn1ncc(NC(=O)c2csc(-c3cccc(C(F)(F)F)n3)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(6-(trifluoromethyl)pyridin-2-yl)thiazole-4-carboxamide | 0.00208 |
| 315 | 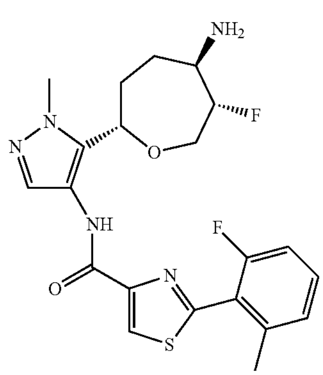 [SMILES: Cc1cccc(F)c1-c1nc(C(=O)Nc2cnn(C)c2[C@@H]2CC[C@@H](N)[C@H](F)CO2)cs1] | N-(5-((2S,5R,6S)-5-amino-6-fluorooxepan-2-yl)-1-methyl-1H-pyrazol-4-yl)-2-(2-fluoro-6-methylphenyl)thiazole-4-carboxamide | 0.000091 |

TABLE 1b-continued

| No. | Structure | IUPAC Name | PIM1 LC3K (KI) μM |
|---|---|---|---|
| 316 | 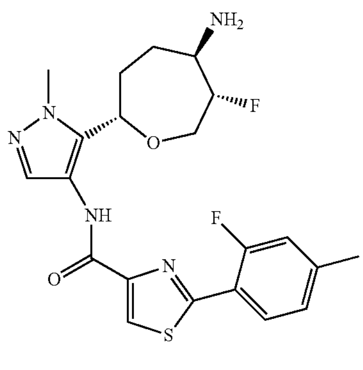 [SMILES: Cc1ccc(-c2nc(C(=O)Nc3cnn(C)c3[C@@H]3CC[C@@H](N)[C@H](F)CO3)cs2)c(F)c1] | N-(5-((2S,5R,6S)-5-amino-6-fluorooxepan-2-yl)-1-methyl-1H-pyrazol-4-yl)-2-(2-fluoro-4-methyphenyl)thiazole-4-carboxamide | |
| 317 | 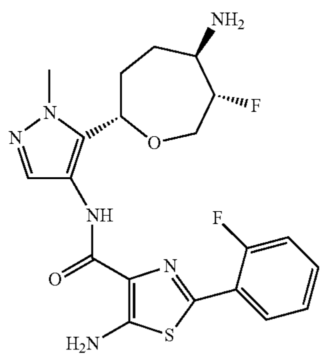 [SMILES: Cn1ncc(NC(=O)c2nc(-c3ccccc3F)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(2-fluorophenyl)thiazole-4-carboxamide | 0.00000509 |
| 318 | 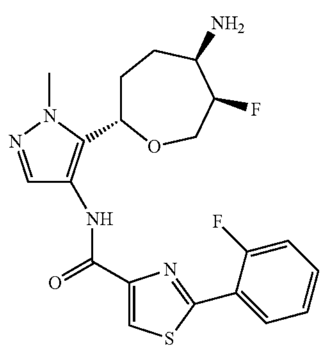 [SMILES: Cn1ncc(NC(=O)c2csc(-c3ccccc3F)n2)c1[C@@H]1CC[C@@H](N)[C@@H](F)CO1] | N-(5-((2S,5R,6R)-5-amino-6-fluorooxepan-2-yl)-1-methyl-1H-pyrazol-4-yl)-2-(2-fluorophenyl)thiazole-4-carboxamide | 0.000098 |
| 319 | 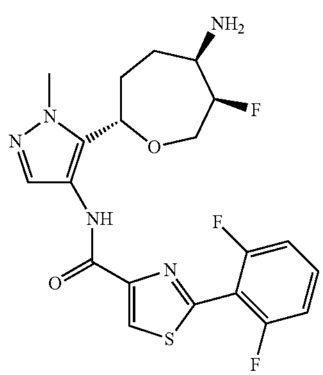 [SMILES: Cn1ncc(NC(=O)c2csc(-c3c(F)cccc3F)n2)c1[C@@H]1CC[C@@H](N)[C@@H](F)CO1] | N-(5-((2S,5R,6R)-5-amino-6-fluorooxepan-2-yl)-1-methyl-1H-pyrazol-4-yl)-2-(2,6-difluorophenyl)thiazole-4-carboxamide | 0.000038 |

TABLE 1b-continued

| No. | Structure | IUPAC Name | PIM1 LC3K (KI) μM |
|---|---|---|---|
| 320 | 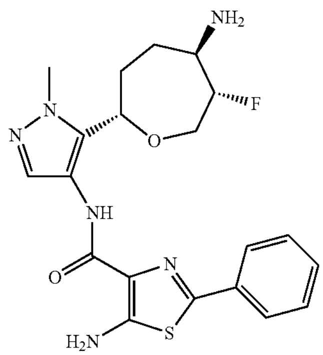 [SMILES: Cn1ncc(NC(=O)c2nc(-c3ccccc3)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-phneylthiazole-4-carboxamide | 0.000036 |
| 321 | 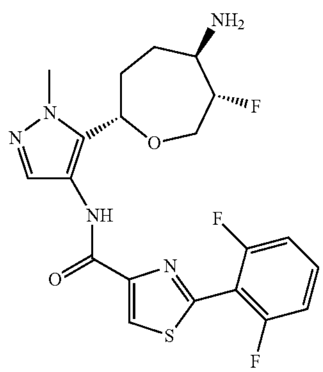 [SMILES: Cn1ncc(NC(=O)c2csc(-c3c(F)cccc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,6-difluorophenyl)thiazole-4-carboxamide | 0.0000137 |
| 322 | 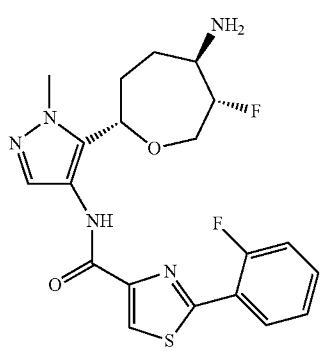 [SMILES: Cn1ncc(NC(=O)c2csc(-c3ccccc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2-fluorophenyl)thiazole-4-carboxamide | 0.000072 |
| 323 | 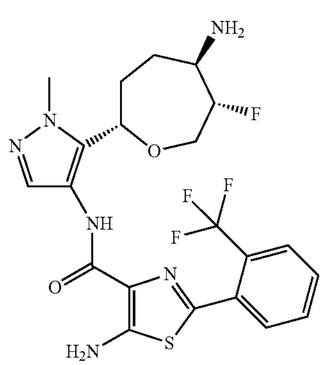 [SMILES: Cn1ncc(NC(=O)c2nc(-c3ccccc3C(F)(F)F)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(2-(trifluoromethyl)phenyl)thiazole-4-carboxamide | 0.000283 |

TABLE 1b-continued

| No. | Structure | IUPAC Name | PIM1 LC3K (KI) μM |
|---|---|---|---|
| 324 | 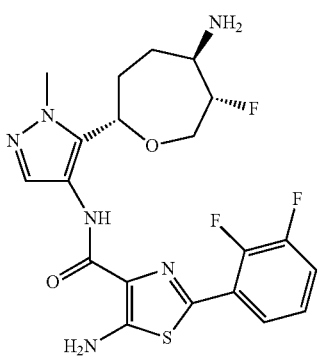 | 5-amino-N-(5-((2S,5R,6S)-5-amino-6-fluorooxepan-2-yl)-1-methyl-1H-pyrazol-4-yl)-2-(2,3-difluorophenyl)thiazole-4-carboxamide | 0.000019 |
| 325 | 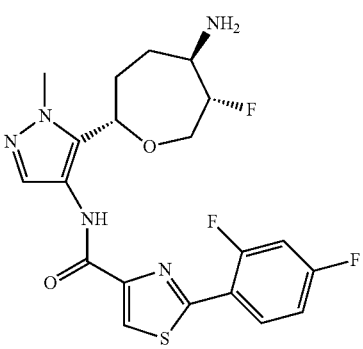 [SMILES: Cn1ncc(NC(=O)c2csc(-c3ccc(F)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,4-difluorophenyl)thiazole-4-carboxamide | 0.00005 |
| 326 | 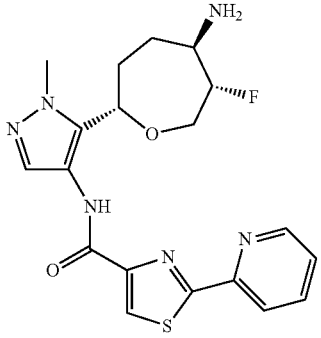 [SMILES: Cn1ncc(NC(=O)c2csc(-c3ccccn3)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(pyridin-2-yl)thiazole-4-carboxamide | 0.000031 |
| 327 | 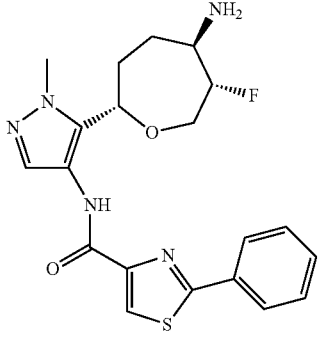 [SMILES: Cn1ncc(NC(=O)c2csc(-c3ccccc3)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-phenylthiazole-4-carboxamide | 0.000021 |

TABLE 1b-continued

| No. | Structure | IUPAC Name | PIM1 LC3K (KI) μM |
|---|---|---|---|
| 328 | 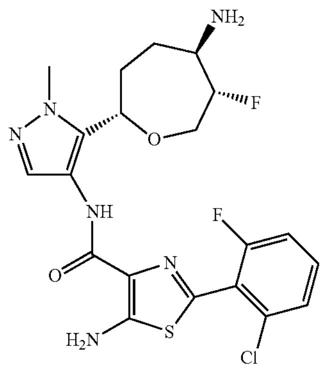 [SMILES: Cn1ncc(NC(=O)c2nc(-c3c(F)cccc3Cl)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(2-chloro-6-fluorophenyl)thiazole-4-carboxamide | 0.000036 |
| 329 | 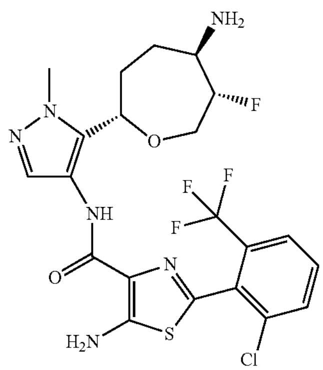 [SMILES: Cn1ncc(NC(=O)c2nc(-c3c(Cl)cccc3C(F)(F)F)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(2-chloro-6-(trifluoromethyl)phenyl)thiazole-4-carboxamide | 0.000071 |
| 330 | 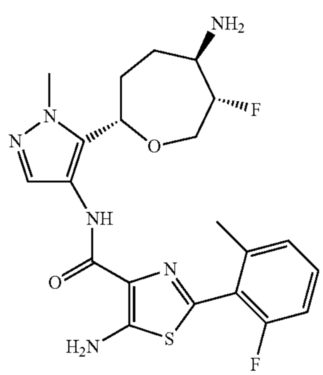 [SMILES: Cc1cccc(F)c1-c1nc(C(=O)Nc2cnn(C)c2[C@@H]2CC[C@@H](N)[C@H](F)CO2)c(N)s1] | 5-amino-N-(5-((2S,5R,6S)-5-amino-6-fluorooxepan-2-yl)-1-methyl-1H-pyrazol-4-yl)-2-(2-fluoro-6-methylphenyl)thiazole-4-carboxamide | 0.000016 |
| 331 | 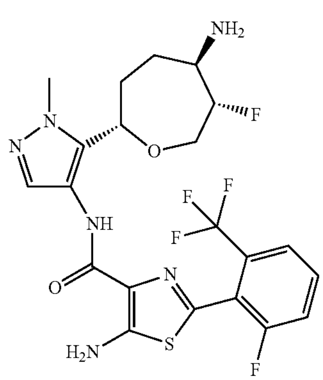 [SMILES: Cn1ncc(NC(=O)c2nc(-c3c(F)cccc3C(F)(F)F)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(2-fluoro-6-(trifluoromethyl)phenyl)thiazole-4-carboxamide | 0.000104 |

TABLE 1b-continued

| No. | Structure | IUPAC Name | PIM1 LC3K (KI) μM |
|---|---|---|---|
| 332 | 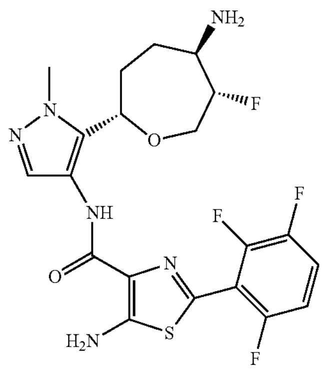 [SMILES: Cn1ncc(NC(=O)c2nc(-c3c(F)ccc(F)c3F)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(2,3,6,-trifluorophenyl)thiazole-4-carboxamide | 0.000003 |
| 333 | 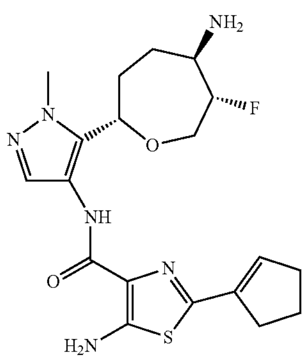 [SMILES: Cn1ncc(NC(=O)c2nc(C3=CCCC3)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(cyclopent-1-en-1-yl)thiazole-4-carboxamide | 0.00003 |
| 334 | 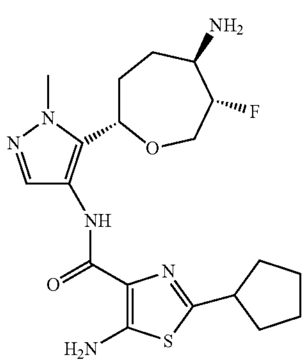 [SMILES: Cn1ncc(NC(=O)c2nc(C3CCCC3)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-cyclopentylthiazole-4-carboxamide | 0.000453 |
| 335 | 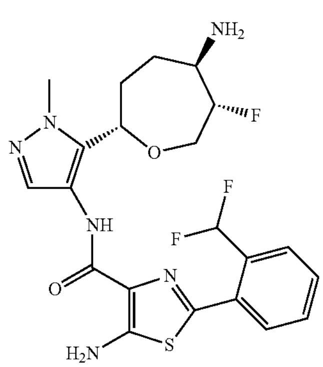 [SMILES: Cn1ncc(NC(=O)c2nc(-c3ccccc3C(F)F)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(2-(difluoromethyl)phenyl)thiazole-4-carboxamide | 0.000092 |

TABLE 1b-continued

| No. | Structure | IUPAC Name | PIM1 LC3K (KI) μM |
|---|---|---|---|
| 336 | 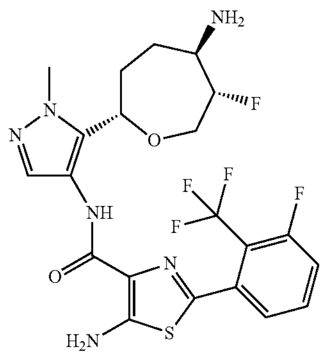 [SMILES: Cn1ncc(NC(=O)c2nc(-c3cccc(F)c3C(F)(F)F)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(3-fluoro-2-(trifluoromethyl)phenyl)thiazole-4-carboxamide | 0.000188 |
| 337 | 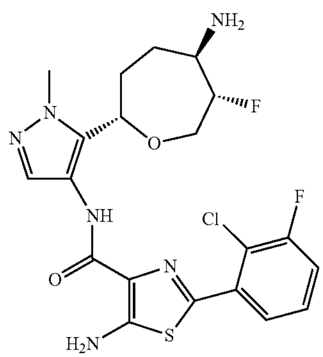 [SMILES: Cn1ncc(NC(=O)c2nc(-c3cccc(F)c3Cl)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(2-chloro-3-fluorophenyl)thiazole-4-carboxamide | 0.000015 |
| 338 | 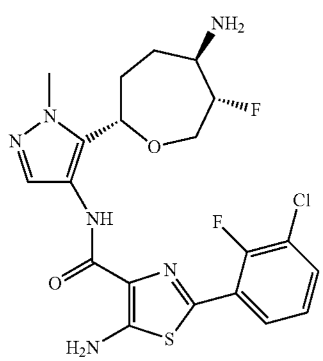 [SMILES: Cn1ncc(NC(=O)c2nc(-c3cccc(Cl)c3F)sc2N)c1[C@@H]1CC[C@@H](N)[C@H](F)CO1] | 5-amino-N-(5-((2S,5R,6S)-5-amino-6-fluorooxepan-2-yl)-1-methyl-1H-pyrazol-4-yl)-2-(3-chloro-2-fluorophenyl)thiazole-4-carboxamide | 0.000007 |
| 339 | 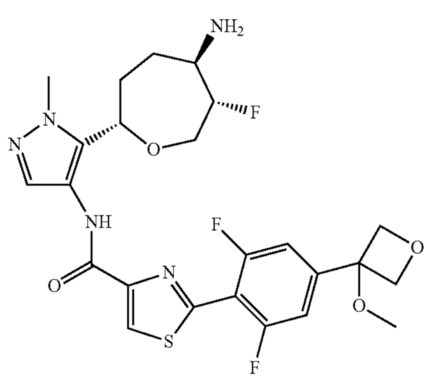 [SMILES: COC1(c2cc(F)c(-c3nc(C(=O)Nc4cnn(C)c4[C@@H]4CC[C@@H](N)[C@H](F)CO4)cs3)c(F)c2)COC1] | N-(5-((2S,5R,6S)-5-amino-6-fluorooxepan-2-yl)-1-methyl-1H-pyrazol-4-yl)-2-(2,6-difluoro-4-(3-methoxyoxetan-3-yl)phenyl)thiazole-4-carboxamide | 0.000014 |

TABLE 1b-continued

| No. | Structure | IUPAC Name | PIM1 LC3K (KI) μM |
|---|---|---|---|
| 340 | 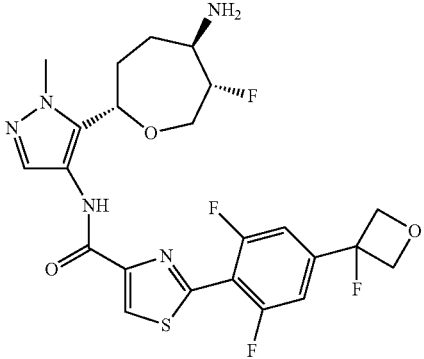 [SMILES: Cn1ncc(NC(=O)c2csc(-c3c(F)cc(C4(F)COC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,6-difluoro-4-(3-fluorooxetan-3-yl)phenyl)thiazole-4-carboxamide | 0.000010 |
| 341 | 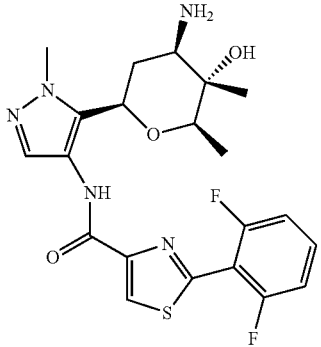 [SMILES: C[C@H]1O[C@@H](c2c(NC(=O)c3csc(-c4c(F)cccc4F)n3)cnn2C)C[C@@H](N)[C@]1(C)O] | N-(5-((2R,4R,5S,6R)-4-amino-5-hydroxy-5,6-dimethyltetrahydro-2H-pyran-2-yl)-1-methyl-1H-pyrazol-4-yl)-2-(2,6-difluorophenyl)thiazole-4-carboxamide | 0.0000030 |
| 342 | 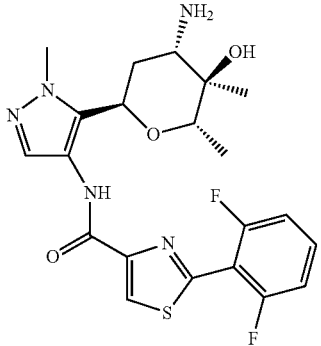 [SMILES: C[C@@H]1O[C@@H](c2c(NC(=O)c3csc(-c4c(F)cccc4F)n3)cnn2C)C[C@H](N)[C@@]1(C)O] | N-(5-((2S,4S,5R,6S)-4-amino-5-hydroxy-5,6-dimethyltetrahydro-2H-pyran-2-yl)-1-methyl-1H-pyrazol-4-yl)-2-(2,6-difluorophenyl)thiazole-4-carboxamide | 0.0023 |
| 343 | 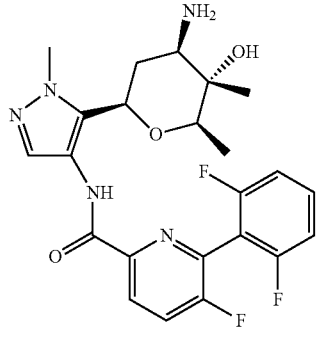 [SMILES: C[C@H]1O[C@@H](c2c(NC(=O)c3ccc(F)c(-c4c(F)cccc4F)n3)cnn2C)C[C@@H](N)[C@]1(C)O] | N-(5-((2R,4R,5S,6R)-4-amino-5-hydroxy-5,6-dimethyltetrahydro-2H-pyran-2-yl)-1-methyl-1H-pyrazol-4-yl)-6-(2,6-difluorophenyl)-5-fluoropicolinamide | |

TABLE 1b-continued

| No. | Structure | IUPAC Name | PIM1 LC3K (KI) μM |
|---|---|---|---|
| 344 | 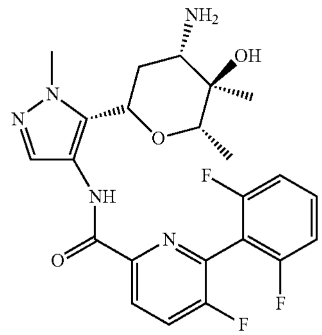 | N-(5-((2S,4S,5R,6S)-4-amino-5-hydroxy-5,6-dimethyltetrahydro-2H-pyran-2-yl)-1-methyl-1H-pyrazol-4-yl)-6-(2,6-difluorophenyl)-5-fluoropicolinamide | |
| 345 | 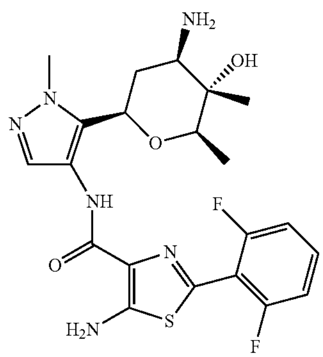 [SMILES: C[C@H]1O[C@@H](c2c(NC(=O)c3nc(-c4c(F)cccc4F)sc3N)cnn2C)C[C@@H](N)[C@]1(C)O] | 5-amino-N-(5-((2R,4R,5S,6R)-4-amino-5-hydroxy-5,6-dimethyltetrahydro-2H-pyran-2-yl)-1-methyl-1H-pyrazol-4-yl)-2-(2,6-difluorophenyl)thiazole-4-carboxamide | |
| 346 | 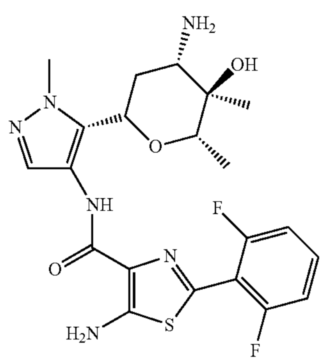 | 5-amino-N-(5-((2S,4S,5R,6S)-4-amino-5-hydroxy-5,6-dimethyltetrahydro-2H-pyran-2-yl)-1-methyl-1H-pyrazol-4-yl)-2-(2,6-difluorophenyl)thiazole-4-carboxamide | |
| 347 | 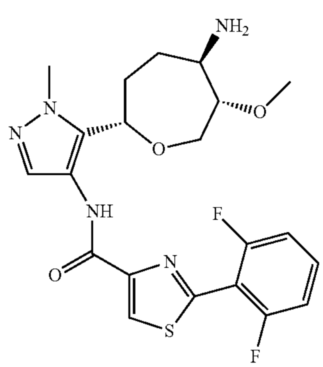 [SMILES: CO[C@@H]1CO[C@H](c2c(NC(=O)c3csc(-c4c(F)cccc4F)n3)cnn2C)CC[C@H]1N] | N-(5-((2S,5R,6S)-5-amino-6-methoxyoxepan-2-yl)-1-methyl-1H-pyrazol-4-yl)-2-(2,6-difluorophenyl)thiazole-4-carboxamide | 0.000014 |

TABLE 1b-continued

| No. | Structure | IUPAC Name | PIM1 LC3K (KI) μM |
|---|---|---|---|
| 348 | 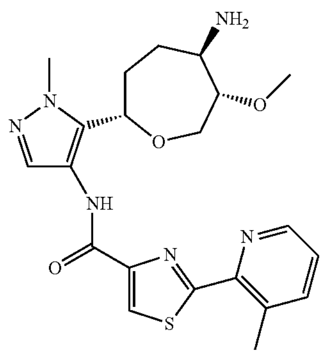 [SMILES: CO[C@@H]1CO[C@H](c2c(NC(=O)c3csc(-c4ncccc4C)n3)cnn2C)CC[C@H]1N] | N-(5-((2S,5R,6S)-5-amino-6-methoxyoxepan-2-yl)-1-methyl-1H-pyrazol-4-yl)-2-(3-methylpyridin-2-yl)thiazole-4-carboxamide | 0.000014 |

TABLE 1c

| No. | Structure | IUPAC Name | PIM1 LC3K (KI) μM |
|---|---|---|---|
| 349 | 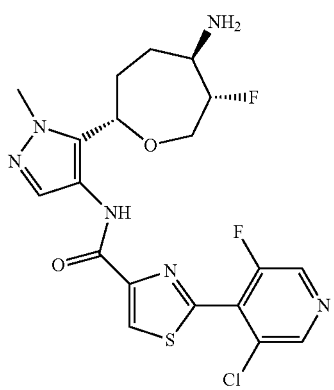 [SMILES: Cn1ncc(NC(=O)c2csc(-c3c(F)cncc3Cl)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(3-chloro-5-fluoropyridin-4-yl)thiazole-4-carboxamide | 0.00312 |
| 350 | 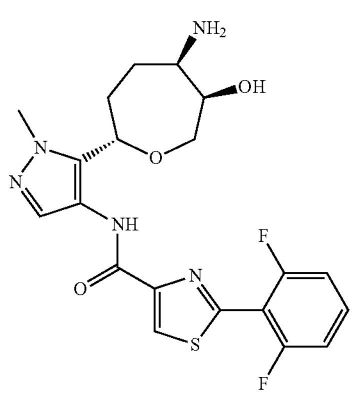 [SMILES: Cn1ncc(NC(=O)c2csc(-c3c(F)cccc3F)n2)c1[C@@H]1CC[C@@H](N)[C@@H](O)CO1] | N-(5-((2S,5R,6R)-5-amino-6-hydroxyoxepan-2-yl)-1-methyl-1H-pyrazol-4-yl)-2-(2,6-difluorophenyl)thiazole-4-carboxamide | >0.667 |

TABLE 1c-continued

| No. | Structure | IUPAC Name | PIM1 LC3K (KI) μM |
|---|---|---|---|
| 351 | 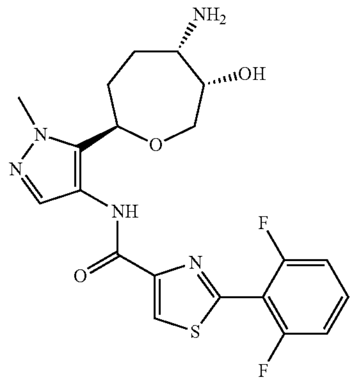 [SMILES: Cn1ncc(NC(=O)c2csc(-c3c(F)cccc3F)n2)c1[C@H]1CC[C@H](N)[C@H](O)CO1] | N-(5-((2R,5S,6S)-5-amino-6-hydroxyoxepan-2-yl)-1-methyl-1H-pyrazol-4-yl)-2-(2,6-difluorophenyl)thiazole-4-carboxamide | 0.000076 |
| 352 | 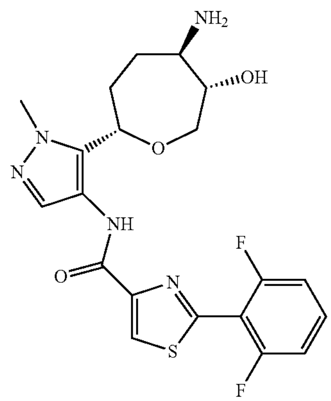 [SMILES: Cn1ncc(NC(=O)c2csc(-c3c(F)cccc3F)n2)c1[C@@H]1CC[C@@H](N)[C@H](O)CO1] | N-(5-((2S,5R,6S)-5-amino-6-hydroxyoxepan-2-yl)-1-methyl-1H-pyrazol-4-yl)-2-(2,6-difluorophenyl)thiazole-4-carboxamide | 0.000174 |
| 353 | 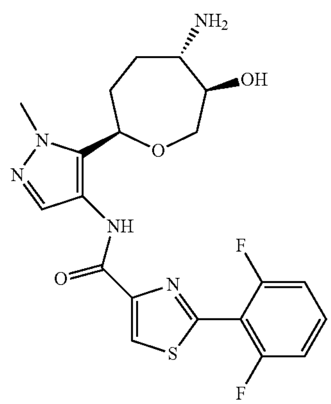 [SMILES: Cn1ncc(NC(=O)c2csc(-c3c(F)cccc3F)n2)c1[C@H]1CC[C@H](N)[C@@H](O)CO1] | N-(5-((2R,5S,6R)-5-amino-6-hydroxyoxepan-2-yl)-1-methyl-1H-pyrazol-4-yl)-2-(2,6-difluorophenyl)thiazole-4-carboxamide | 0.000111 |
| 354 | 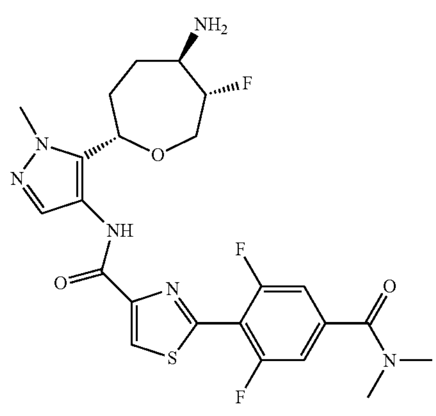 [SMILES: CN(C)C(=O)c1cc(F)c(-c2nc(C(=O)Nc3cnn(C)c3[C@@H]3CC[C@@H](N)[C@H](F)CO3)cs2)c(F)c1] | N-(5-((2S,5R,6S)-5-amino-6-fluorooxepan-2-yl)-1-methyl-1H-pyrazol-4-yl)-2-(4-(dimethylcarbamoyl)-2,6-difluorophenyl)thiazole-4-carboxamide | 0.000083 |

| No. | Structure | IUPAC Name | PIM1 LC3K (KI) μM |
|---|---|---|---|
| 355 | 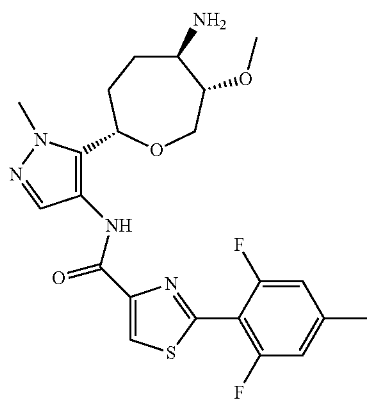 [SMILES: CO[C@@H]1CO[C@H](c2c(NC(=O)c3csc(-c4c(F)cc(C)cc4F)n3)cnn2C)CC[C@H]1N] | N-(5-((2S,5R,6S)-5-amino-6-methoxyoxepan-2-yl)-1-methyl-1H-pyrazol-4-yl)-2-(2,6-difluoro-4-methylphenyl)thiazole-4-carboxamide | 0.000035 |
| 356 | 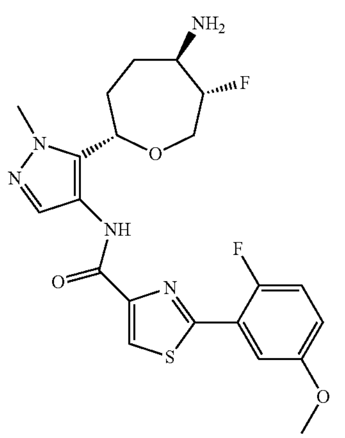 [SMILES: COc1ccc(F)c(-c2nc(C(=O)Nc3cnn(C)c3[C@@H]3CC[C@@H](N)[C@H](F)CO3)cs2)c1] | N-(5-((2S,5R,6S)-5-amino-6-fluorooxepan-2-yl)-1-methyl-1H-pyrazol-4-yl)-2-(2-fluoro-5-methoxyphenyl)thiazole-4-carboxamide | 0.000053 |
| 357 | 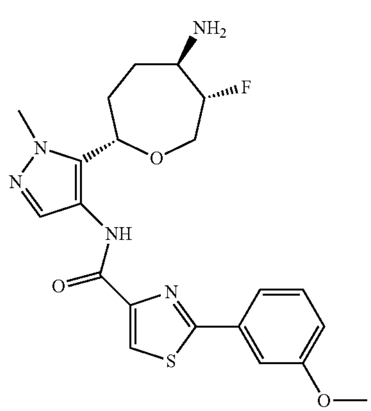 [SMILES: COc1cccc(-c2nc(C(=O)Nc3cnn(C)c3[C@@H]3CC[C@@H](N)[C@H](F)CO3)cs2)c1] | N-(5-((2S,5R,6S)-5-amino-6-fluorooxepan-2-yl)-1-methyl-1H-pyrazol-4-yl)-2-(3-methoxyphenyl)thiazole-4-carboxamide | 0.000035 |

TABLE 1c-continued

| No. | Structure | IUPAC Name | PIM1 LC3K (KI) μM |
|---|---|---|---|
| 358 | 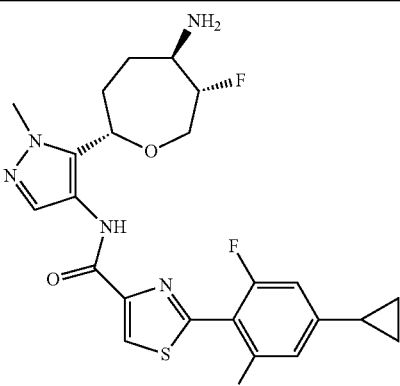 | N-(5-((2S,5R,6S)-5-amino-6-fluorooxepan-2-yl)-1-methyl-1H-pyrazol-4-yl)-2-(4-cyclopropyl-2,6-difluorophenyl)thiazole-4-carboxamide | 0.000009 |
| 359 | 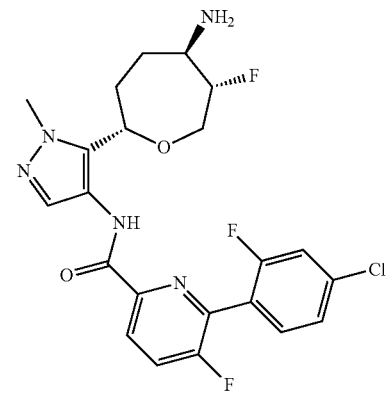 [SMILES: Cn1ncc(NC(=O)c2ccc(F)c(-c3ccc(Cl)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(4-chloro-2-fluorophenyl)-5-fluoropicolinamide | 0.000007 |
| 360 | 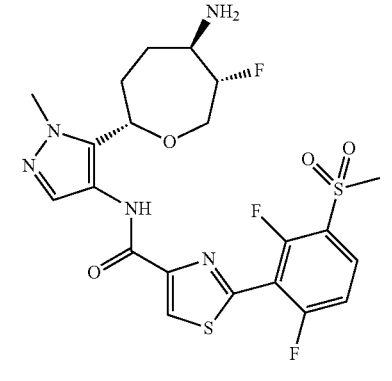 [SMILES: Cn1ncc(NC(=O)c2csc(-c3c(F)ccc(S(C)(=O)=O)c3F)n2)c1[C@@H]1CC[C@@H](N)[C@H](F)CO1] | N-[5-[(2S,5R,6S)-5-amino-6-fluoro-oxepan-2-yl]-1-methyl-pyrazol-4-yl]-2-(2,6-difluoro-3-methylsulfonyl-phenyl)thiazole-4-carboxamide | 0.00185 |
| 361 | 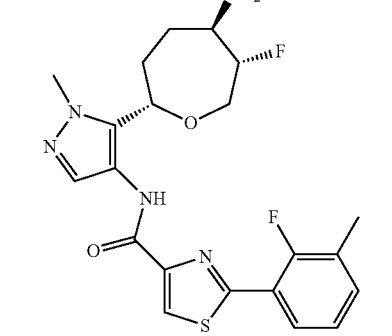 | N-[5-[(2S,5R,6S)-5-amino-6-fluoro-oxepan-2-yl]-1-methyl-pyrazol-4-yl]-2-(2-fluoro-3-methyl-phenyl)thiazole-4-carboxamide | 0.000068 |

TABLE 1c-continued

| No. | Structure | IUPAC Name | PIM1 LC3K (KI) μM |
|---|---|---|---|
| 362 | 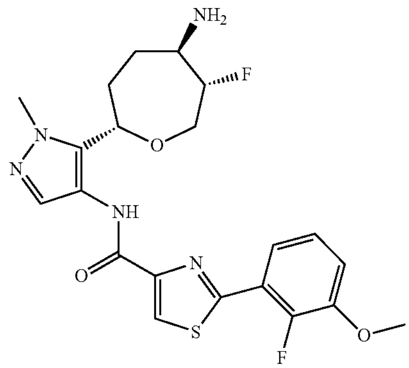 [SMILES: COc1cccc(-c2nc(C(=O)Nc3cnn(C)c3[C@@H]3CC[C@@H](N)[C@H](F)CO3)cs2)c1F] | N-(5-((2S,5R,6S)-5-amino-6-fluorooxepan-2-yl)-1-methyl-1H-pyrazol-4-yl)-2-(2-fluoro-3-methoxyphenyl)thiazole-4-carboxamide | 0.000036 |
| 363 | 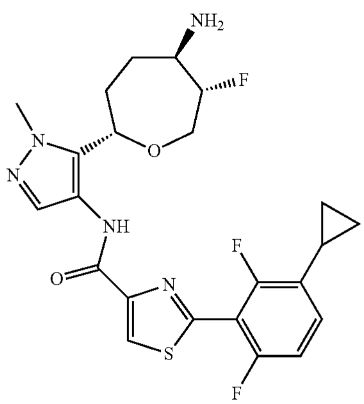 [SMILES: Cn1ncc(NC(=O)c2csc(-c3c(F)ccc(C4CC4)c3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(3-cyclopropyl-2,6-difluorophenyl)thiazole-4-carboxamide | 0.000034 |
| 364 | 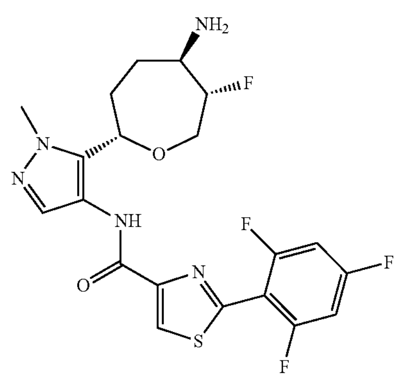 [SMILES: Cn1ncc(NC(=O)c2csc(-c3c(F)cc(F)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,4,6-trifluorophenyl)thiazole-4-carboxamide | 0.000039 |
| 365 | 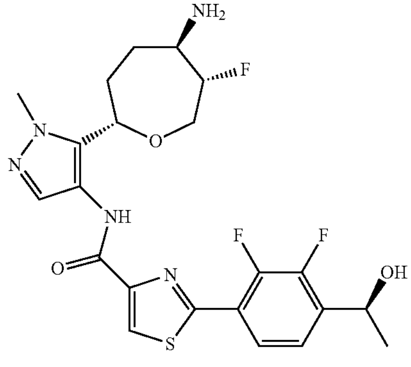 [SMILES: C[C@H](O)c1ccc(-c2nc(C(=O)Nc3cnn(C)c3[C@@H]3CC[C@@H](N)[C@H](F)CO3)cs2)c(F)c1F] | N-(5-((2S,5R,6S)-5-amino-6-fluorooxepan-2-yl)-1-methyl-1H-pyrazol-4-yl)-2-(2,3-difluoro-4-((S)-1-hydroxyethyl)phenyl)thiazole-4-carboxamide | 0.000069 |

TABLE 1c-continued

| No. | Structure | IUPAC Name | PIM1 LC3K (KI) μM |
|---|---|---|---|
| 366 | 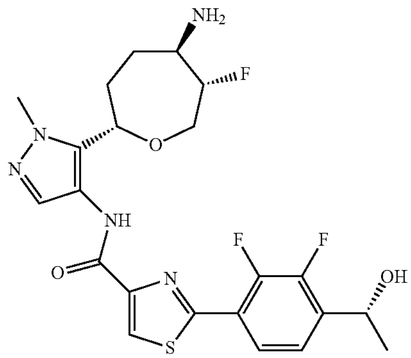 [SMILES: C[C@@H](O)c1ccc(-c2nc(C(=O)Nc3cnn(C)c3[C@@H]3CC[C@@H](N)[C@H](F)CO3)cs2)c(F)c1F] | N-(5-((2S,5R,6S)-5-amino-6-fluorooxepan-2-yl)-1-methyl-1H-pyrazol-4-yl)-2-(2,3-difluoro-4-((R)-1-hydroxyethyl)phenyl)thiazole-4-carboxamide | 0.00014 |
| 367 | 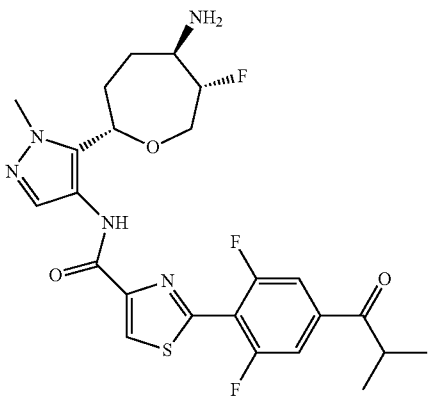 [SMILES: CC(C)C(=O)c1cc(F)c(-c2nc(C(=O)Nc3cnn(C)c3[C@@H]3CC[C@@H](N)[C@H](F)CO3)cs2)c(F)c1] | N-(5-((2S,5R,6S)-5-amino-6-fluorooxepan-2-yl)-1-methyl-1H-pyrazol-4-yl)-2-(2,6-difluoro-4-isobutyrylphenyl)thiazole-4-carboxamide | 0.000061 |
| 368 | 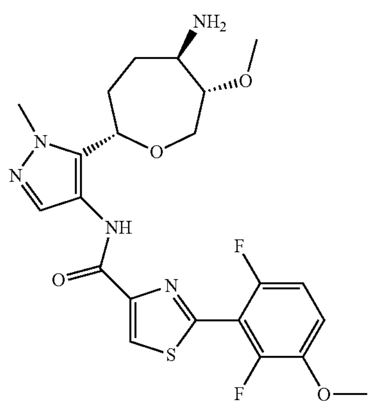 [SMILES: COc1ccc(F)c(-c2nc(C(=O)Nc3cnn(C)c3[C@@H]3CC[C@@H](N)[C@H](OC)CO3)cs2)c1F] | N-(5-((2S,5R,6S)-5-amino-6-methoxyoxepan-2-yl)-1-methyl-1H-pyrazol-4-yl)-2-(2,6-difluoro-3-methoxyphenyl)thiazole-4-carboxamide | 0.000030 |
| 369 | 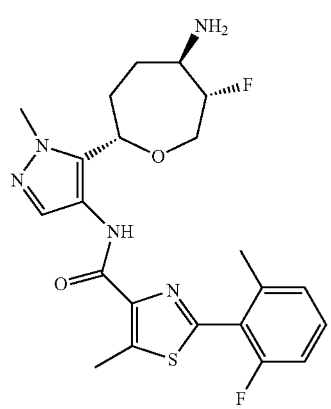 [SMILES: Cc1cccc(F)c1-c1nc(C(=O)Nc2cnn(C)c2[C@@H]2CC[C@@H](N)[C@H](F)CO2)c(C)s1] | N-[5-[(2S,5R,6S)-5-amino-6-fluoro-oxepan-2-yl]-1-methyl-pyrazol-4-yl]-2-(2-fluoro-6-methyl-phenyl)-5-methyl-thiazole-4-carboxamide | 0.00359 |

TABLE 1c-continued

| No. | Structure | IUPAC Name | PIM1 LC3K (KI) μM |
|---|---|---|---|
| 370 | 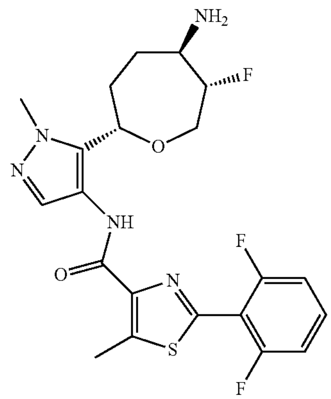 [SMILES: Cc1sc(-c2c(F)cccc2F)nc1C(=O)Nc1cnn(C)c1[C@@H]1CC[C@@H](N)[C@H](F)CO1] | N-[5-[(2S,5R,6S)-5-amino-6-fluoro-oxepan-2-yl]-1-methyl-pyrazol-4-yl]-2-(2,6-difluorophenyl)-5-methyl-thiazole-4-carboxamide | 0.000382 |
| 371 | 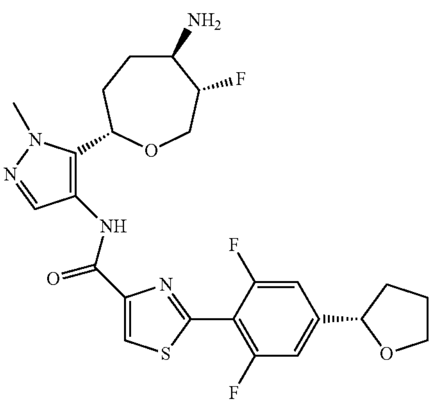 [SMILES: Cn1ncc(NC(=O)c2csc(-c3c(F)cc([C@@H]4CCCO4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,6-difluoro-4-((S)-tetrahydrofuran-2-yl)phenyl)thiazole-4-carboxamide | 0.000057 |
| 372 | 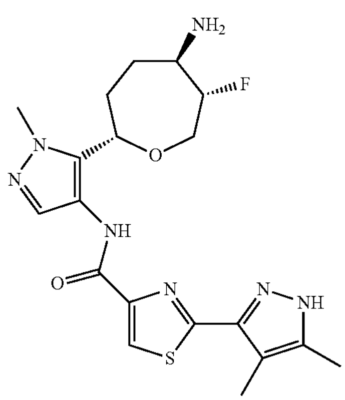 [SMILES: Cc1[nH]nc(-c2nc(C(=O)Nc3cnn(C)c3[C@@H]3CC[C@@H](N)[C@H](F)CO3)cs2)c1C] | N-(5-((2S,5R,6S)-5-amino-6-fluorooxepan-2-yl)-1-methyl-1H-pyrazol-4-yl)-2-(4,5-dimethyl-1H-pyrazol-3-yl)thiazole-4-carboxamide | 0.000064 |

TABLE 1c-continued

| No. | Structure | IUPAC Name | PIM1 LC3K (KI) μM |
|---|---|---|---|
| 373 | 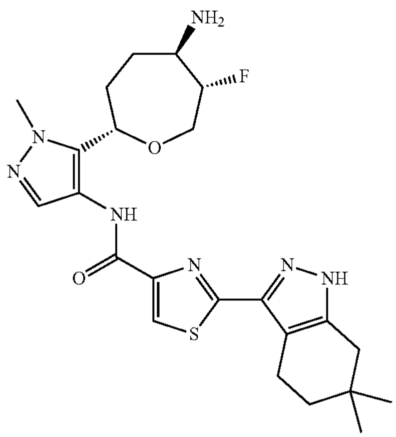 [SMILES: Cn1ncc(NC(=O)c2csc(-c3n[nH]c4c3CCC(C)(C)C4)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(6,6-dimethyl-4,5,6,7-tetrahydro-1H-indazol-3-yl)thiazole-4-carboxamide | 0.0000090 |
| 374 | 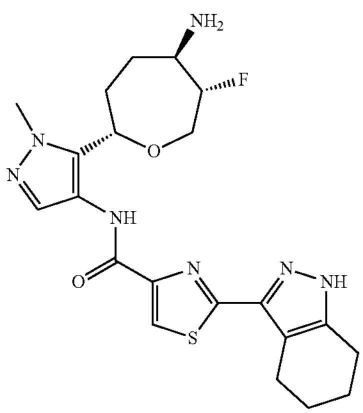 [SMILES: Cn1ncc(NC(=O)c2csc(-c3n[nH]c4c3CCCC4)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(4,5,6,7-tetrahydro-1H-indazol-3-yl)thiazole-4-carboxamide | 0.000023 |
| 375 | 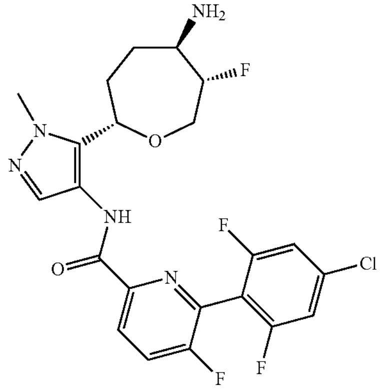 [SMILES: Cn1ncc(NC(=O)c2ccc(F)c(-c3c(F)cc(Cl)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-6-(4-chloro-2,6-difluorophenyl)-5-fluoropicolinamide | 0.000036 |

TABLE 1c-continued

| No. | Structure | IUPAC Name | PIM1 LC3K (KI) μM |
|---|---|---|---|
| 376 | 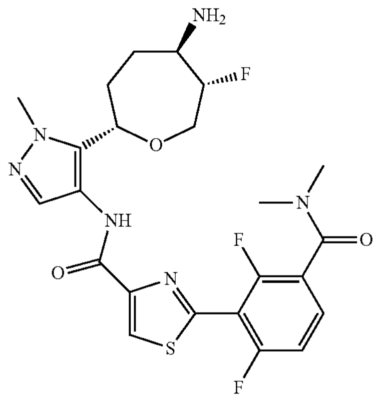 [SMILES: CN(C)C(=O)c1ccc(F)c(-c2nc(C(=O)Nc3cnn(C)c3[C@@H]3CC[C@@H](N)[C@H](F)CO3)cs2)c1F] | N-[5-[(2S,5R,6S)-5-amino-6-fluoro-oxepan-2-yl]-1-methyl-pyrazol-4-yl]-2-[3-(dimethylcarbamoyl)-2,6-difluoro-phenyl]thiazole-4-carboxamide | 0.000727 |
| 377 | 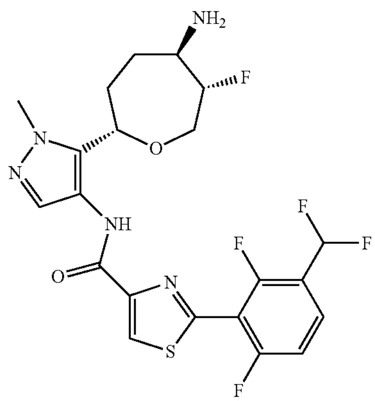 [SMILES: Cn1ncc(NC(=O)c2csc(-c3c(F)ccc(C(F)F)c3F)n2)c1[C@@H]1CC[C@@H](N)[C@H](F)CO1] | N-[5-[(2S,5R,6S)-5-amino-6-fluoro-oxepan-2-yl]-1-methyl-pyrazol-4-yl]-2-[3-(difluoromethyl)-2,6-difluoro-phenyl]thiazole-4-carboxamide | 0.000031 |
| 378 | 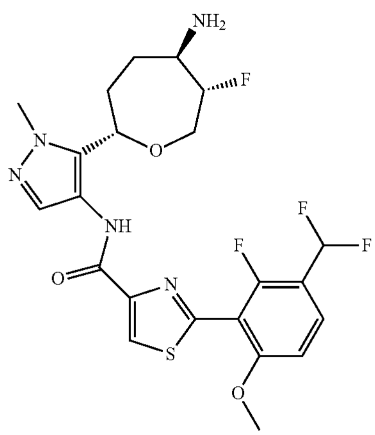 [SMILES: COc1ccc(C(F)F)c(F)c1-c1nc(C(=O)Nc2cnn(C)c2[C@@H]2CC[C@@H](N)[C@H](F)CO2)cs1] | N-[5-[(2S,5R,6S)-5-amino-6-fluoro-oxepan-2-yl]-1-methyl-pyrazol-4-yl]-2-[3-(difluoromethyl)-2-fluoro-6-methoxy-phenyl]thiazole-4-carboxamide | 0.00148 |
| 379 | 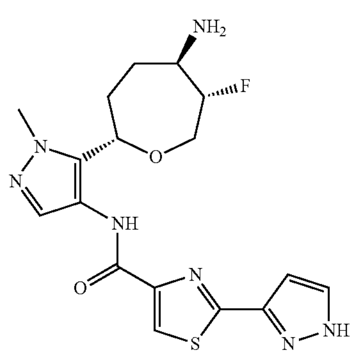 [SMILES: Cn1ncc(NC(=O)c2csc(-c3cc[nH]n3)n2)c1[C@@H]1CC[C@@H](N)[C@H](F)CO1] | N-[5-[(2S,5R,6S)-5-amino-6-fluoro-oxepan-2-yl]-1-methyl-pyrazol-4-yl]-2-(1H-pyrazol-3-yl)thiazole-4-carboxamide | 0.000129 |

TABLE 1c-continued

| No. | Structure | IUPAC Name | PIM1 LC3K (KI) μM |
|---|---|---|---|
| 380 | 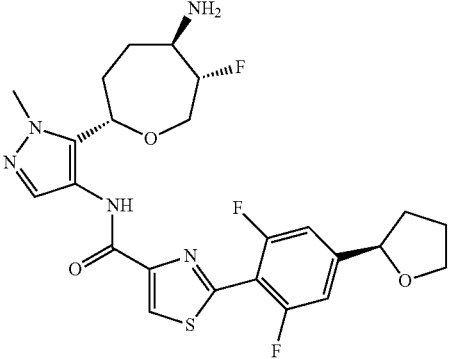 [SMILES: Cn1ncc(NC(=O)c2csc(-c3c(F)cc([C@H]4CCCO4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2,6-difluoro-4-((R)-tetrahydrofuran-2-yl)phenyl)thiazole-4-carboxamide | 0.000071 |
| 381 | 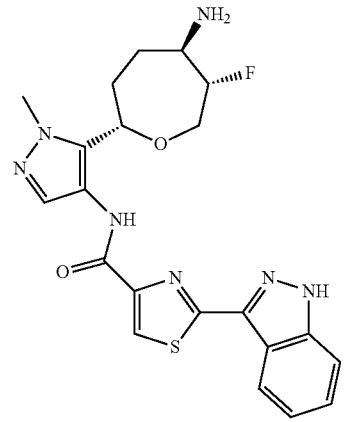 [SMILES: Cn1ncc(NC(=O)c2csc(-c3n[nH]c4ccccc34)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(1H-indazol-3-yl)thiazole-4-carboxamide | 0.000022 |
| 382 | 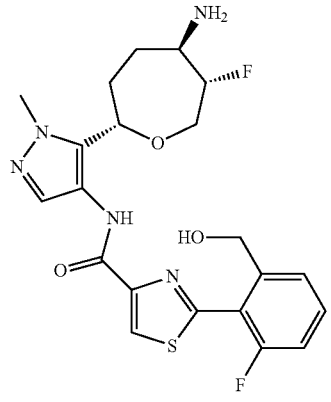 [SMILES: Cn1ncc(NC(=O)c2csc(-c3c(F)cccc3CO)n2)c1[C@@H]1CC[C@@H](N)[C@H](F)CO1] | N-[5-[(2S,5R,6S)-5-amino-6-fluoro-oxepan-2-yl]-1-methyl-pyrazol-4-yl]-2-[2-fluoro-6-(hydroxymethyl)phenyl]thiazole-4-carboxamide | 0.0072 |
| 383 | 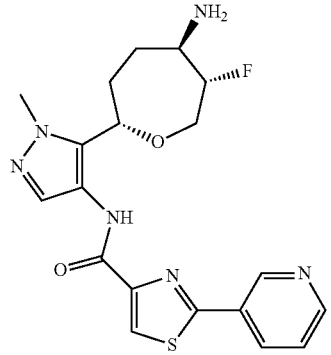 [SMILES: Cn1ncc(NC(=O)c2csc(-c3cccnc3)n2)c1[C@@H]1CC[C@@H](N)[C@H](F)CO1] | N-[5-[(2S,5R,6S)-5-amino-6-fluoro-oxepan-2-yl]-1-methyl-pyrazol-4-yl]-2-(3-pyridyl)thiazole-4-carboxamide | 0.000991 |

TABLE 1c-continued

| No. | Structure | IUPAC Name | PIM1 LC3K (KI) μM |
|---|---|---|---|
| 384 | 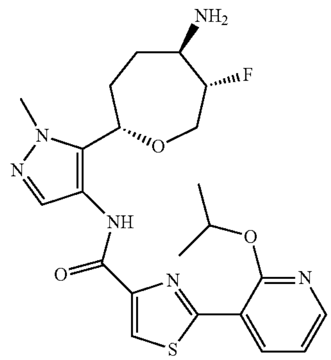 [SMILES: CC(C)Oc1ncccc1-c1nc(C(=O)Nc2cnn(C)c2[C@@H]2CC[C@@H](N)[C@H](F)CO2)cs1] | N-[5-[(2S,5R,6S)-5-amino-6-fluoro-oxepan-2-yl]-1-methyl-pyrazol-4-yl]-2-(2-isopropoxy-3-pyridyl)thiazole-4-carboxamide | 0.0097 |
| 385 | 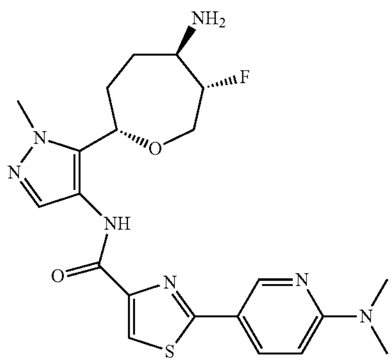 [SMILES: CN(C)c1ccc(-c2nc(C(=O)Nc3cnn(C)c3[C@@H]3CC[C@@H](N)[C@H](F)CO3)cs2)cn1] | N-[5-[(2S,5R,6S)-5-amino-6-fluoro-oxepan-2-yl]-1-methyl-pyrazol-4-yl]-2-[6-(dimethylamino)-3-pyridyl]thiazole-4-carboxamide | 0.0002 |
| 386 | 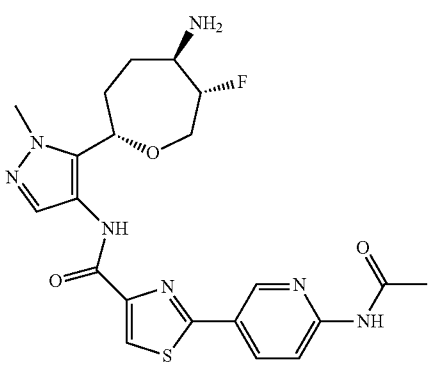 [SMILES: CC(=O)Nc1ccc(-c2nc(C(=O)Nc3cnn(C)c3[C@@H]3CC[C@@H](N)[C@H](F)CO3)cs2)cn1] | 2-(6-acetamido-3-pyridyl)-N-[5-[(2S,5R,6S)-5-amino-6-fluoro-oxepan-2-yl]-1-methyl-pyrazol-4-yl]thiazole-4-carboxamide | 0.000389 |
| 387 | 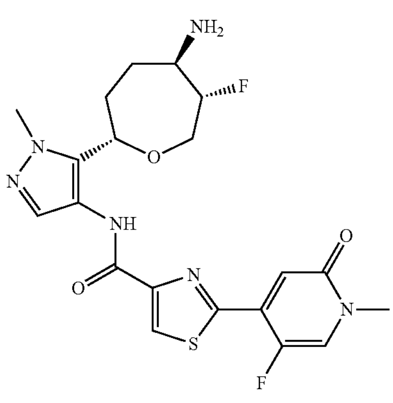 [SMILES: Cn1ncc(NC(=O)c2csc(-c3cc(=O)n(C)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(5-fluoro-1-methyl-2-oxo-1,2-dihydropyridin-4-yl)thiazole-4-carboxamide | 0.000954 |

TABLE 1c-continued

| No. | Structure | IUPAC Name | PIM1 LC3K (KI) μM |
|---|---|---|---|
| 388 | 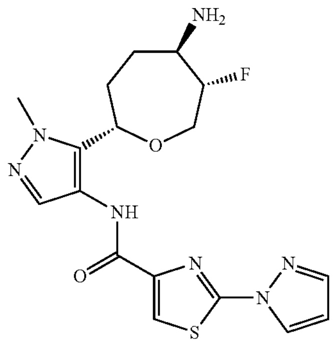 [SMILES: Cn1ncc(NC(=O)c2csc(-n3cccn3)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(1H-pyrazol-1-yl)thiazole-4-carboxamide | 0.000157 |
| 389 | 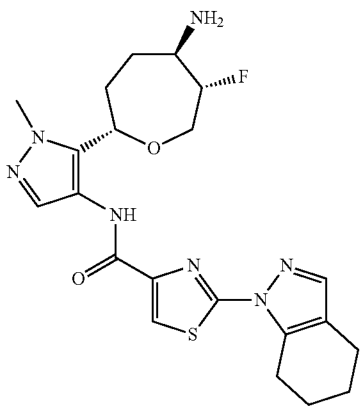 [SMILES: Cn1ncc(NC(=O)c2csc(-n3ncc4c3CCCC4)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(4,5,6,7-tetrahydro-1H-indazol-1-yl)thiazole-4-carboxamide | 0.000020 |
| 390 | 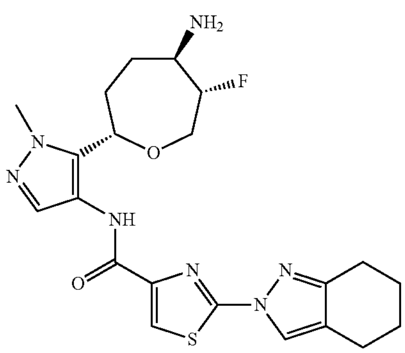 [SMILES: Cn1ncc(NC(=O)c2csc(-n3cc4c(n3)CCCC4)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(4,5,6,7-tetrahydro-2H-indazol-2-yl)thiazole-4-carboxamide | 0.000267 |
| 391 | 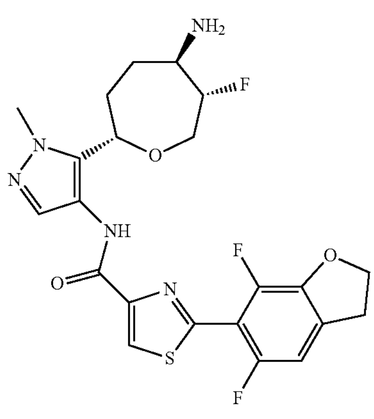 [SMILES: Cn1ncc(NC(=O)c2csc(-c3c(F)cc4c(c3F)OCC4)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(5,7-difluoro-2,3-dihydrobenzofuran-6-yl)thiazole-4-carboxamide | 0.000024 |

TABLE 1c-continued

| No. | Structure | IUPAC Name | PIM1 LC3K (KI) μM |
|---|---|---|---|
| 392 | 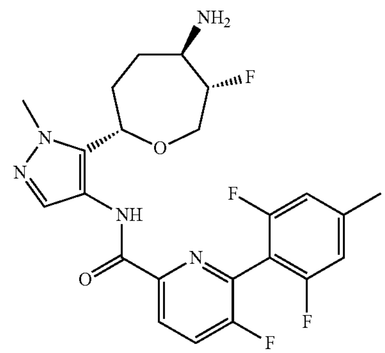 [SMILES: Cc1cc(F)c(-c2nc(C(=O)Nc3cnn(C)c3[C@@H]3CC[C@@H](N)[C@H](F)CO3)ccc2F)c(F)c1] | N-(5-((2S,5R,6S)-5-amino-6-fluorooxepan-2-yl)-1-methyl-1H-pyrazol-4-yl)-6-(2,6-difluoro-4-methylphenyl)-5-fluoropicolinamide | 0.000041 |
| 393 | 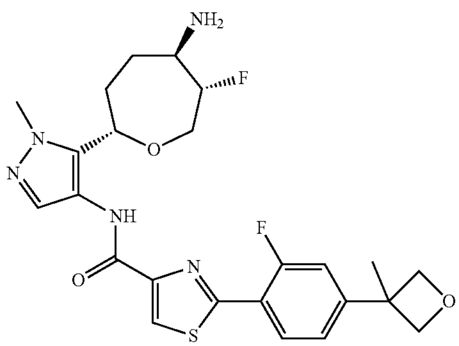 [SMILES: Cn1ncc(NC(=O)c2csc(-c3ccc(C4(C)COC4)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2-fluoro-4-(3-methyloxetan-3-yl)phenyl)thiazole-4-carboxamide | 0.000003 |
| 394 | 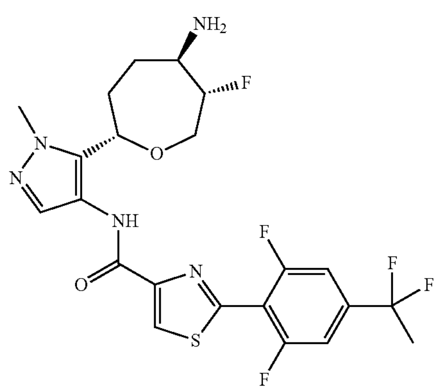 [SMILES: Cn1ncc(NC(=O)c2csc(-c3c(F)cc(C(C)(F)F)cc3F)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(4-(1,1-difluoroethyl)-2,6-difluorophenyl)thiazole-4-carboxamide | 0.000018 |
| 395 | 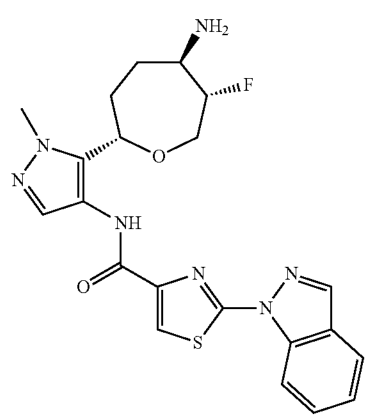 [SMILES: Cn1ncc(NC(=O)c2csc(-n3ncc4ccccc43)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(1H-indazol-1-yl)thiazole-4-carboxamide | 0.000085 |

TABLE 1c-continued

| No. | Structure | IUPAC Name | PIM1 LC3K (KI) μM |
|---|---|---|---|
| 396 | 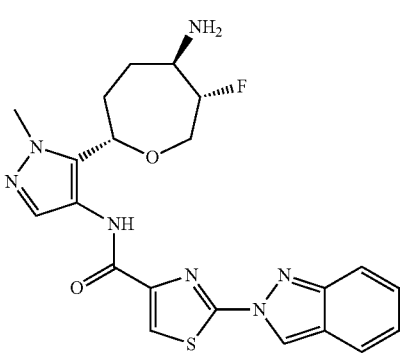 [SMILES: Cn1ncc(NC(=O)c2csc(-n3cc4ccccc4n3)n2)c1[C@@H]1CC[C@@H](N)[C@H](F)CO1] | N-(5-((2S,5R,6S)-5-amino-6-fluorooxepan-2-yl)-1-methyl-1H-pyrazol-4-yl)-2-(2H-indazol-2-yl)thiazole-4-carboxamide | 0.000002 |
| 397 | 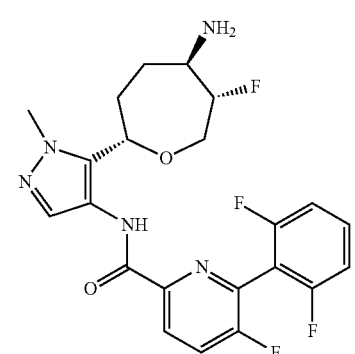 | N-[5-[(2S,5R,6S)-5-amino-6-fluoro-oxepan-2-yl]-1-methyl-pyrazol-4-yl]-6-(2,6-difluorophenyl)-5-fluoro-pyridine-2-carboxamide | 0.000016 |
| 398 | 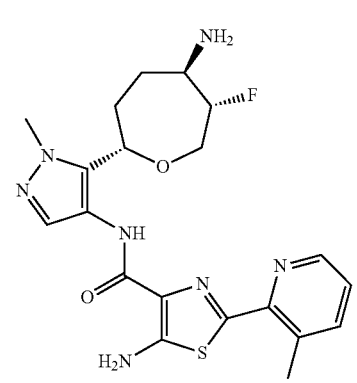 [SMILES: Cc1cccnc1-c1nc(C(=O)Nc2cnn(C)c2[C@@H]2CC[C@@H](N)[C@H](F)CO2)c(N)s1] | 5-amino-N-[5-[(2S,5R,6S)-5-amino-6-fluoro-oxepan-2-yl]-1-methyl-pyrazol-4-yl]-2-(3-methyl-2-pyridyl)thiazole-4-carboxamide | 0.0000040 |
| 399 | 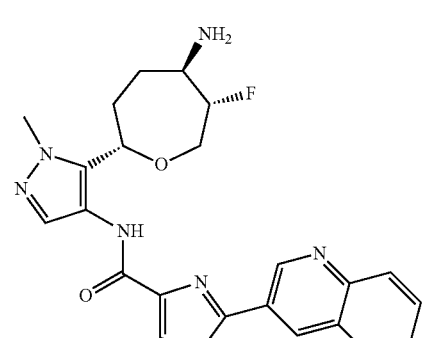 | N-[5-[(2S,5R,6S)-5-amino-6-fluoro-oxepan-2-yl]-1-methyl-pyrazol-4-yl]-2-(1,5-naphthyridin-3-yl)thiazole-4-carboxamide | 0.00021 |

TABLE 1c-continued

| No. | Structure | IUPAC Name | PIM1 LC3K (KI) μM |
|---|---|---|---|
| 400 | 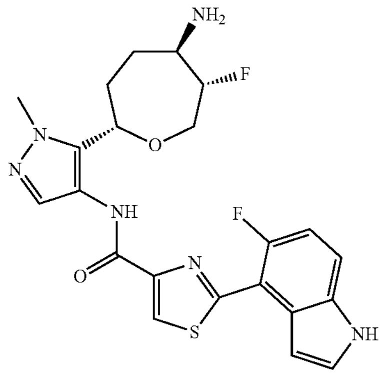 [SMILES: Cn1ncc(NC(=O)c2csc(-c3c(F)ccc4[nH]ccc34)n2)c1[C@@H]1CC[C@@H](N)[C@H](F)CO1] | N-[5-[(2S,5R,6S)-5-amino-6-fluoro-oxepan-2-yl]-1-methyl-pyrazol-4-yl]-2-(5-fluoro-1H-indol-4-yl)thiazole-4-carboxamide | 0.000011 |
| 401 | 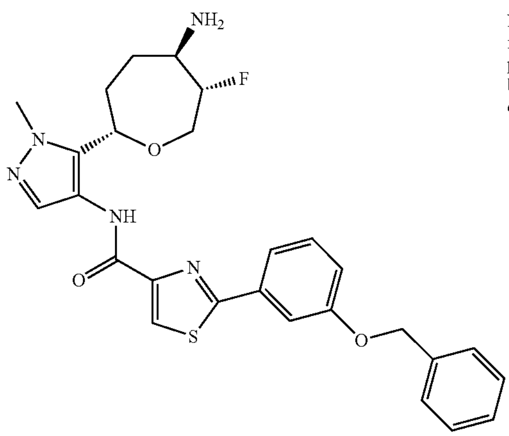 [SMILES: Cn1ncc(NC(=O)c2csc(-c3cccc(OCc4ccccc4)c3)n2)c1[C@@H]1CC[C@@H](N)[C@H](F)CO1] | N-[5-[(2S,5R,6S)-5-amino-6-fluoro-oxepan-2-yl]-1-methyl-pyrazol-4-yl]-2-(3-benzyloxyphenyl)thiazole-4-carboxamide | 0.000447 |
| 402 | 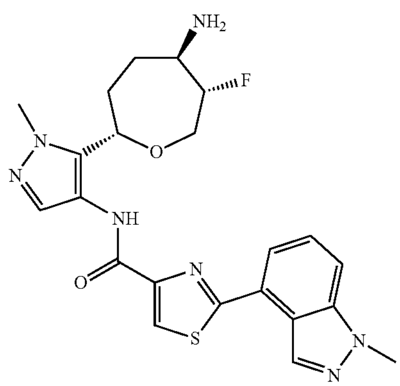 [SMILES: Cn1ncc(NC(=O)c2csc(-c3cccc4c3cnn4C)n2)c1[C@@H]1CC[C@@H](N)[C@H](F)CO1] | N-[5-[(2S,5R,6S)-5-amino-6-fluoro-oxepan-2-yl]-1-methyl-pyrazol-4-yl]-2-(1-methylindazol-4-yl)thiazole-4-carboxamide | 0.000117 |
| 403 | 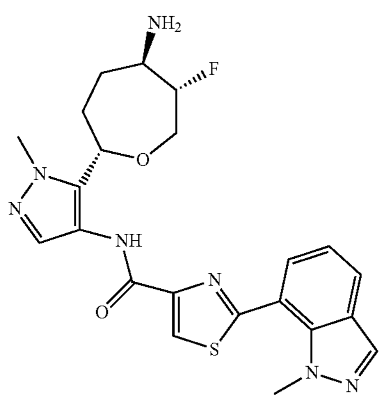 [SMILES: Cn1ncc(NC(=O)c2csc(-c3cccc4cnn(C)c34)n2)c1[C@@H]1CC[C@@H](N)[C@H](F)CO1] | N-[5-[(2S,5R,6S)-5-amino-6-fluoro-oxepan-2-yl]-1-methyl-pyrazol-4-yl]-2-(1-methylindazol-7-yl)thiazole-4-carboxamide | 0.00591 |

TABLE 1c-continued

| No. | Structure | IUPAC Name | PIM1 LC3K (KI) μM |
|---|---|---|---|
| 404 | 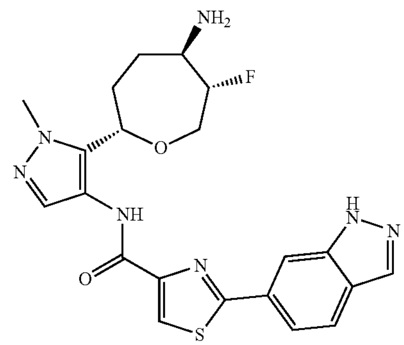 [SMILES: Cn1ncc(NC(=O)c2csc(-c3ccc4cn[nH]c4c3)n2)c1[C@@H]1CC[C@@H](N)[C@H](F)CO1] | N-[5-[(2S,5R,6S)-5-amino-6-fluoro-oxepan-2-yl]-1-methyl-pyrazol-4-yl]-2-(1H-indazol-6-yl)thiazole-4-carboxamide | |
| 405 | 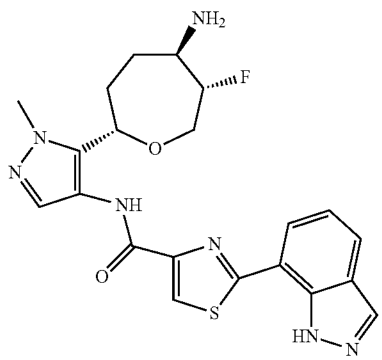 [SMILES: Cn1ncc(NC(=O)c2csc(-c3cccc4cn[nH]c34)n2)c1[C@@H]1CC[C@@H](N)[C@H](F)CO1] | N-[5-[(2S,5R,6S)-5-amino-6-fluoro-oxepan-2-yl]-1-methyl-pyrazol-4-yl]-2-(1H-indazol-7-yl)thiazole-4-carboxamide | |
| 406 | 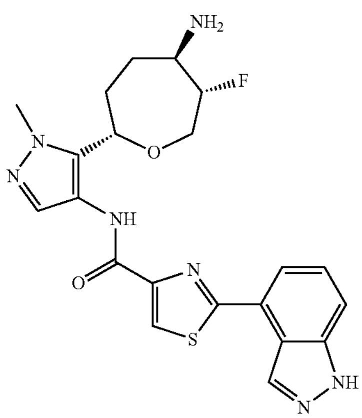 [SMILES: Cn1ncc(NC(=O)c2csc(-c3cccc4[nH]ncc34)n2)c1[C@@H]1CC[C@@H](N)[C@H](F)CO1] | N-[5-[(2S,5R,6S)-5-amino-6-fluoro-oxepan-2-yl]-1-methyl-pyrazol-4-yl]-2-(1H-indazol-4-yl)thiazole-4-carboxamide | |
| 407 | 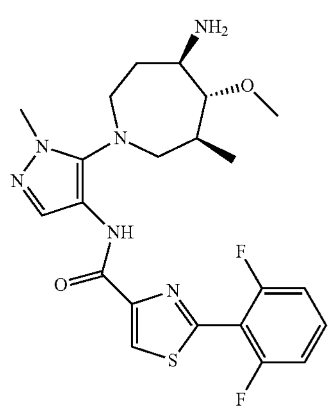 [SMILES: CO[C@H]1[C@H](N)CCN(c2c(NC(=O)c3csc(-c4c(F)cccc4F)n3)cnn2C)C[C@@H]1C] | N-(5-((3S,4R,5R)-5-amino-4-methoxy-3-methylazepan-1-yl)-1-methyl-1H-pyrazol-4-yl)-2-(2,6-difluorophenyl)thiazole-4-carboxamide | |

TABLE 1c-continued

| No. | Structure | IUPAC Name | PIM1 LC3K (KI) µM |
|---|---|---|---|
| 408 | 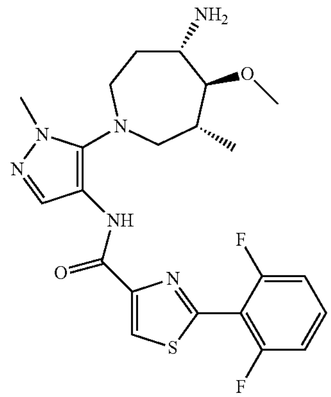 [SMILES: CO[C@H]1[C@H](C)CN(c2c(NC(=O)c3csc(-c4c(F)cccc4F)n3)cnn2C)CC[C@@H]1N] | N-(5-((3R,4S,5S)-5-amino-4-methoxy-3-methylazepan-1-yl)-1-methyl-1H-pyrazol-4-yl)-2-(2,6-difluorophenyl)thiazole-4-carboxamide | |
| 409 | 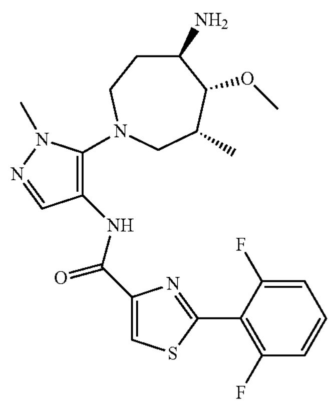 [SMILES: CO[C@@H]1[C@H](C)CN(c2c(NC(=O)c3csc(-c4c(F)cccc4F)n3)cnn2C)CC[C@H]1N] | N-(5-((3R,4R,5R)-5-amino-4-methoxy-3-methylazepan-1-yl)-1-methyl-1H-pyrazol-4-yl)-2-(2,6-difluorophenyl)thiazole-4-carboxamide | |
| 410 | 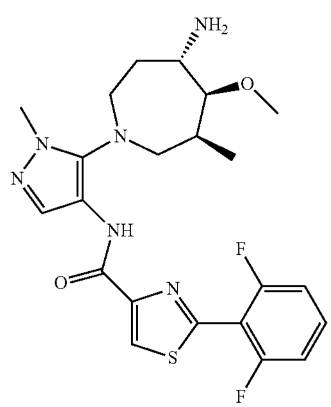 [SMILES: CO[C@H]1[C@@H](C)CN(c2c(NC(=O)c3csc(-c4c(F)cccc4F)n3)cnn2C)CC[C@@H]1N] | N-(5-((3S,4S,5S)-5-amino-4-methoxy-3-methylazepan-1-yl)-1-methyl-1H-pyrazol-4-yl)-2-(2,6-difluorophenyl)thiazole-4-carboxamide | |

The present invention includes a composition (e.g., a pharmaceutical composition) comprising a compound of Formula I, and/or solvates, hydrates and/or salts thereof, and a carrier (a pharmaceutically acceptable carrier). The present invention also includes a composition (e.g., a pharmaceutical composition) comprising a compound of Formula I and/or solvates, hydrates and/or salts thereof, and a carrier (a pharmaceutically acceptable carrier), further comprising a second chemotherapeutic agent such as those described herein. The present compositions are useful for inhibiting abnormal cell growth or treating a hyperproliferative disorder such as cancer in a mammal (e.g., human). For example, the present compounds and compositions are useful for treating multiple myeloma, lymphoma, acute myeloid leukemia, prostate cancer, breast cancer, hepatocellular carcinoma, pancreatic cancer, and/or colorectal cancer in a mammal (e.g., human).

The present invention includes a method of inhibiting abnormal cell growth or treating a hyperproliferative disorder such as cancer in a mammal (e.g., human) comprising administering to said mammal a therapeutically effective amount of a compound of Formula I, and/or solvates, hydrates and/or salts thereof, or a composition thereof. For example, the present invention includes a method of treating multiple myeloma, lymphoma, acute myeloid leukemia, prostate cancer, breast cancer, hepatocellular carcinoma, pancreatic cancer, and/or colorectal cancer in a mammal (e.g., human), comprising administering to said mammal a therapeutically effective amount of a compound of Formula I, and/or solvates, hydrates and/or salts thereof) or a composition thereof.

The present invention includes a method of inhibiting abnormal cell growth or treating a hyperproliferative disorder such as cancer in a mammal (e.g., human) comprising administering to said mammal a therapeutically effective amount of a compound of Formula I, and/or solvates, hydrates and/or salts thereof, or a composition thereof, in combination with a second chemotherapeutic agent such as those described herein. For example, the present invention includes a method of treating multiple myeloma, lymphoma, acute myeloid leukemia, prostate cancer, breast cancer, hepatocellular carcinoma, pancreatic cancer, and/or colorectal cancer in a mammal (e.g., human), comprising administering to said mammal a therapeutically effective amount of a compound of Formula I, and/or solvates, hydrates and/or salts thereof, or a composition thereof, in combination with a second chemotherapeutic agent such as those described herein.

The present invention includes a method of treating lymphoma in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as an anti-B-cell antibody therapeutic (e.g., RITUXAN® and/or dacetuzumab), gemcitabine, corticosteroids (e.g., prednisolone and/or dexamethasone), chemotherapy cocktails (e.g., CHOP (cyclophosphamide, doxorubicin, vincristine, prednisolone) and/or ICE (isfosfamide, cytoxan, etoposide)), a combination of biologics and chemotherapy (e.g., RITUXAN®-ICE, dacetuzumab-RITUXAN®-ICE, R-Gem, and/or D-R-Gem), an Akt inhibitor, a PI3K inhibitor (e.g, GDC-0941 (Genentech) and/or GDC-0980 (Genentech)), rapamycin, a rapamycin analog, mTOR inhibitor such as everolimus or sirolimus, a MEK inhibitor (GDC-0973), and a Bcl-2 inhibitor (ABT-263 or ABT-199).

The present invention includes a method of treating multiple myeloma in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as melphalan, "Imids" (immuno-modulators, e.g., thalidomide, lenalidomide, and/or pomolidamide), corticosteroids (e.g., dexamethasone and/or prednisolone), and bortezomib or other proteasome inhibitor.

The present invention includes a method of treating multiple myeloma, chronic lymphocytic leukemia (CLL), or acute myeloid leukemia (AML) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as cytarabine (araC), anthracyclines (e.g., daunorubicin and/or idarubicin), anti-myeloid antibody therapeutics (e.g., SGN-33), anti-myeloid antibody-drug conjugates (e.g., MYLOTARG®).

The present invention includes a method of treating chronic lymphocytic leukemia (CLL) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as fludarabine, cyclophosphamide, anti-B-cell antibody therapeutics (e.g., RITUXAN® and/or dacetuzumab).

The present invention includes a method of treating chronic myeloid leukemia (CML) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as a BCR-abl inhibitor (e.g., imatinib, nilotinib, and/or dasatinib).

The present invention includes a method of treating myelodysplastic diseases (MDS) and myeloproliferative disorders including polycythemia vera (PV), essential thrombocytosis (ET) or myelofibrosis (MF), in a mammal (e.g., human) comprising administering to said mammal a therapeutically effective amount of a compound of Formula I, and/or solvates, hydrates and/or salts thereof, or a composition thereof, either alone or in combination.

The present invention includes a method of using the present compounds for in vitro, in situ, and in vivo diagnosis or treatment of mammalian cells, organisms, or associated pathological conditions.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic agents, for example those described herein. Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension for parenteral injection as a sterile solution, suspension or emulsion for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of Formula I compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tabletting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

Administration of Formula I Compounds

The Formula I compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Compounds of the present invention are useful for treating hyperproliferative diseases, conditions and/or disorders including, but not limited to, those characterized by over expression of Pim kinases, e.g. Pim-1, Pim-2 and Pim-3 kinases. Accordingly, another aspect of this invention includes methods of treating or preventing diseases or conditions that can be treated or prevented by inhibiting Pim kinase. In one embodiment, the method comprises administering to a mammal in need thereof a therapeutically effective amount of a compound of Formula I, or a stereoisomer, geometric isomer, tautomer, or pharmaceutically acceptable salt thereof. In one embodiment, a human patient is treated with a compound of Formula I and a pharmaceutically acceptable carrier, adjuvant, or vehicle, wherein said compound of Formula I is present in an amount to detectably inhibit Pim kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a Formula I compound for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a Formula I compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the Formula I compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16$^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention comprising a Formula I compound will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the Formula I compound administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16$^{th}$ edition, Osol, A. Ed. (1980).

Sustained-release preparations of Formula I compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or oil, or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as a hyperproliferative disorder (e.g., cancer). In certain embodiments, a compound of Formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Formula I Compounds

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, may be useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. The kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or II or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The General Procedures and Examples provide exemplary methods for preparing Formula I compounds. Those skilled in the art will appreciate that other synthetic routes may be used to synthesize the Formula I compounds. Although specific starting materials and reagents are depicted and discussed in the Figures, General Procedures, and Examples, other starting materials and reagents can be easily substituted to provide a variety of derivatives and/or reaction conditions.

In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions, such as on a chiral adsorbent by HPLC or SFC (Supercritical Fluid Chromatography), see White and Burnett (2005) Jour. of Chrom. A1074:175-185; and "Drug Stereochemistry, Analytical Methods and Pharmacology," (1993) Irving W. Wainer, Ed., Marcel Dekker, Inc., New York).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

General Preparative Procedures

FIG. 1 shows an exemplary synthesis of 4-aminopyrazole compounds 5. 4-Nitro-1H-pyrazole 1 is converted to 1-substituted-4-nitro-1H-pyrazole compounds 2 by treatment with a base in a suitable solvent or neat, followed by the addition of an alkylation reagent such as dimethyl sulfate. Compound 2 may be converted to 5-chloro-4-nitro-1H-pyrazole 3 by treatment with a base such as lithium hexamethyldisilazide, or nBuLi in a suitable solvent such as THF (tetrahydrofuran) at an appropriate temperature, such as −78° C. Compound 3 may be converted to compound 4 by direct SnAr, or transition metal catalyzed cross coupling reactions, e.g. Suzuki, Sonogashira, Heck, Buchwald, Goldberg conditions under known methods. 4-Aminopyrazole 5 may be synthesized from 4 by a suitable reduction method, such as treatment with zinc powder and ammonium formate in tetrahydrofuran, or hydrogenation with $H_2$ and transitional metal catalysts such as palladium on carbon.

Buchwald coupling reactions may be conducted under Buchwald palladium catalysis conditions with the Buchwald pre-catalyst palladacycle and ligand reagents in the following table and as described in: Biscoe et al (2008) J. Am. Chem. Soc. 130:6686-6687; Kinzel et al (2010) J. Am. Chem. Soc. 132:14073-14075; Molander et al (2012) J. Am. Chem. Soc. 134:11667-11673; Walker et al (2004) Angew. Chem. Int. Ed. 43:1871; Billingsley et al (2007) Angew. Chem. Int. Ed. 46:5359-5363; U.S. Pat. No. 6,946,560; U.S. Pat. No. 7,026,498; U.S. Pat. No. 7,247,731; U.S. Pat. No. 7,560,582; U.S. Pat. No. 6,307,087; U.S. Pat. No. 6,395,916; U.S. Pat. No. 7,223,879; U.S. Pat. No. 7,858,784, which are incorporated by reference. Such reagents are commercially available (Johnson Matthey Inc., Wayne, Pa.; Sigma Aldrich Fine Chemical, St. Louis, Mo.; Strem Chemicals, Inc., Newburyport, Mass.).

| Buchwald Catalysts and Ligands | Name | CAS Reg. No. |
| --- | --- | --- |
| 2-Dicyclohexylphosphino-2'-(N,N-dimethylamino)biphenyl | DavePhos | 213697-53-1 |
| 2-Dicyclohexylphosphino-2',4',6'-triisopropylbiphenyl | XPhos | 564483-18-7 |
| 2-Dicyclohexylphosphino-2',6'-dimethoxybiphenyl | SPhos | 657408-07-6 |
| 2-Di-tert-butylphosphino-2',4',6'-triisopropylbiphenyl | tBuXPhos | 564483-19-8 |
| (2-Biphenyl)dicyclohexylphosphine | CyJohnPhos | 247940-06-3 |
| (2-Biphenyl)di-tert-butylphosphine | JohnPhos | 224311-51-7 |
| Sodium 2'-dicyclohexylphosphino-2,6 dimethoxy-1,1'-biphenyl-3-sulfonate hydrate | SPhos [water soluble] | 1049726-96-6 |
| 2-Di-tert-butylphosphino-3,4,5,6-tetramethyl-2',4',6'-triisopropyl-1,1'-biphenyl | Tetramethyl tBuXPhos | 857356-94-6 |
| 2-Dicyclohexylphosphino-2',6'-diisopropoxybiphenyl | RuPhos | 787618-22-8 |
| 2'-(Diphenylphosphino)-N,N'-dimethyl-(1,1'-biphenyl)-2-amine, 2-Diphenylphosphino-2'-(N,N-dimethylamino)biphenyl | PhDave-Phos | 240417-00-9 |
| 2'-(Di-tert-butylphosphino)-N,N-dimethylbiphenyl-2-amine | t-BuDavePhos | 224311-49-3 |
| 2-Dicyclohexylphosphino-2'-methylbiphenyl, 2-Methyl-2'-dicyclohexylphosphinobiphenyl | MePhos | 251320-86-2 |
| 2-Di-tert-butylphosphino-2'-methylbiphenyl | tBuMePhos | 255837-19-5 |
| Au(MeCN)SbF$_6$ | JohnPhos | 866641-66-9 |
| (2-Biphenyl)di-tert-butylphosphine gold(I) chloride, 2-(Di-tert-butylphosphino)biphenyl gold(I) chloride | JohnPhos AuCl | 854045-93-5 |
| 2-Dicyclohexylphosphino-2',4',6'-triisopropylbiphenyl gold(I) chloride | XPhos AuCl | 854045-94-6 |
| 2-Dicyclohexylphosphino-2',4',6'-triisopropylbiphenyl gold(I) bis(trifluoromethanesulfonyl)imide | XPhos AuNTf$_2$ | 934506-10-2 |
| 2-(Dicyclohexylphosphino)3,6-dimethoxy-2',4',6'-triisopropyl-1,1'-biphenyl | BrettPhos | 1070663-78-3 |
| RuPhos Pd G1 Methyl-t-Butyl Ether Adduct | | |
| Chloro(2-dicyclohexylphosphino-2',4',6'-triisopropyl-1,1'-biphenyl)[2-(2-aminoethyl)phenyl)]palladium(II) | XPhos Palladacycle | 1028206-56-5 |
| Chloro(2-dicyclohexylphosphino-2',6'-dimethoxy-1,1'-biphenyl)[2-(2-aminoethylphenyl)]palladium(II)-methyl-t-butyl ether adduct | SPhos Palladacycle | |
| t-BuXPhos palladium(II) phenethylamine chloride | tBuXPhos Pd G1 | 1142811-12-8 |
| 2-{Bis[3,5-bis(trifluoromethyl)phenyl]phosphino}-3,6-dimethoxy-2',4',6'-triisopropyl-1,1'-biphenyl | JackiePhos | 1160861-60-8 |
| 2-(Di-tert-butylphosphino)-2',4',6'- triisopropyl-3,6-dimethoxy-1,1'-biphenyl | tBuBrettPhos | 1160861-53-9 |
| Dicyclohexyl(2',4',6'-trimethoxy[1,1'-biphenyl]-2-yl)-phosphine | | 1000171-05-0 |
| BrettPhos Pd G1 Methyl-t-Butyl Ether Adduct | | |
| Chloro(2-dicyclohexylphosphino-2',4',6'-triisopropyl-1,1'-biphenyl)[2-(2'-amino-1,1'-biphenyl)]palladium(II) | Xphos Pd G2 | 1310584-14-5 |
| Chloro(2-dicyclohexylphosphino-2',6'-dimethoxy-1,1'-biphenyl)[2-(2'-amino-1,1'-biphenyl)]palladium(II) | SPhos Pd G2 | 1375325-64-6 |
| Chloro(2-dicyclohexylphosphino-2',6'-diisopropoxy-1,1'-biphenyl)[2-(2'-amino-1,1'-biphenyl)]palladium(II) | RuPhos Pd G2 | 1375325-68-0 |
| Chloro[(2-dicyclohexylphosphino-2',6'-bis(N,N-dimethylamino)-1,1'-biphenyl)-2-(2'-amino-1,1'-biphenyl)]palladium(II) | CPhos-Pd-G2 | |
| [(2-Dicyclohexylphosphino-2',6'-bis(N,N-dimethylamino)-1,1'-biphenyl)-2-(2'-amino-1,1'-biphenyl)] palladium(II) methanesulfonate | CPhos-Pd-G3 | |
| [(2-Di-tert-butylphosphino-2',4',6'-triisopropyl-1,1'-biphenyl)-2-(2'-amino-1,1'-biphenyl)] palladium(II) methanesulfonate | tBuXPhos-Pd-G3 | |

-continued

| Buchwald Catalysts and Ligands | Name | CAS Reg. No. |
|---|---|---|
| (2-Dicyclohexylphosphino-2',6'-diisopropoxy-1,1'-biphenyl)[2-(2'-amino-1,1'-biphenyl)]palladium(II) methanesulfonate | RuPhos-Pd-G3 | |
| (2-Dicyclohexylphosphino-2',4',6'-triisopropyl-1,1'-biphenyl)[2-(2'-amino-1,1'-biphenyl)]palladium(II) methanesulfonate | XPhos-Pd-G3 | |
| [(2-Di-cyclohexylphosphino-3,6-dimethoxy-2',4',6'-triisopropyl-1,1'-biphenyl)-2-(2'-amino-1,1'-biphenyl)]palladium(II) methanesulfonate | BrettPhos-Pd-G3 | |
| [(2-{Bis[3,5-bis(trifluoromethyl)phenyl]phosphine}-3,6-dimethoxy-2',4',6'- triisopropyl-1,1'-biphenyl)-2-(2'-amino-1,1'-biphenyl)]palladium(II) methanesulfonate | JackiePhos-Pd-G3 | |
| Me4-tert-butyl XPhos-AuMeCN SbF6 | | 1334547-72-6 |
| tBuXPhos Au(MeCN)SbF$_6$ | | 1140531-94-7 |
| RuPhos Au(MeCN)SbF$_6$ | | |
| SPhos Au(MeCN)SbF$_6$ | | 1236160-37-4 |
| XPhos Au(MeCN)SbF$_6$ | | 1215877-64-7 |
| Me4-tert-butyl XPhos-AuCl | | 1140907-91-0 |
| tBuXPhos AuCl | | |
| RuPhos AuCl | | 1261452-57-6 |
| SPhos AuCl | | 854045-95-7 |
| CyJohnPhos AuCl | | 854045-92-4 |
| BrettPhos AuCl | | 1334547-75-9 |
| JohnPhos AuNTf$_2$ | | 1036000-94-8 |
| Me$_4$-tert-butyl XPhos-AuNTf$_2$ | | |
| tBuXphos AuNTf$_2$ | | 1190991-33-3 |
| SPhos AuNTf$_2$ | | 1121960-90-4 |
| CyJohnPhos AuNTf$_2$ | | 1016161-75-3 |
| CPhos AuNTf$_2$ | | |
| RuPhos AuNTf$_2$ | | |
| BrettPhos AuNTf$_2$ | | 1296269-97-0 |
| DavePhos AuNTf$_2$ | | 1188507-66-5 |
| CPhos | | 1160556-64-8 |
| Chloro(sodium-2-dicyclohexylphosphino-2',6'-dimethoxy-1,1'-biphenyl-3'-sulfonate)[2-(2'-amino-1,1'-biphenyl)]palladium(II) | | |
| Di-Ad-BrettPhos | | 1160861-59-5 |
| Dicyclohexyl(2-(2-methoxynaphthalen-1-yl)phenyl)phosphine | | 1309570-98-6 |
| tert-BuBrettPhos-Pd-G3 | | |
| di-Ad-Johnphos-G3 | | |

Figure 2:
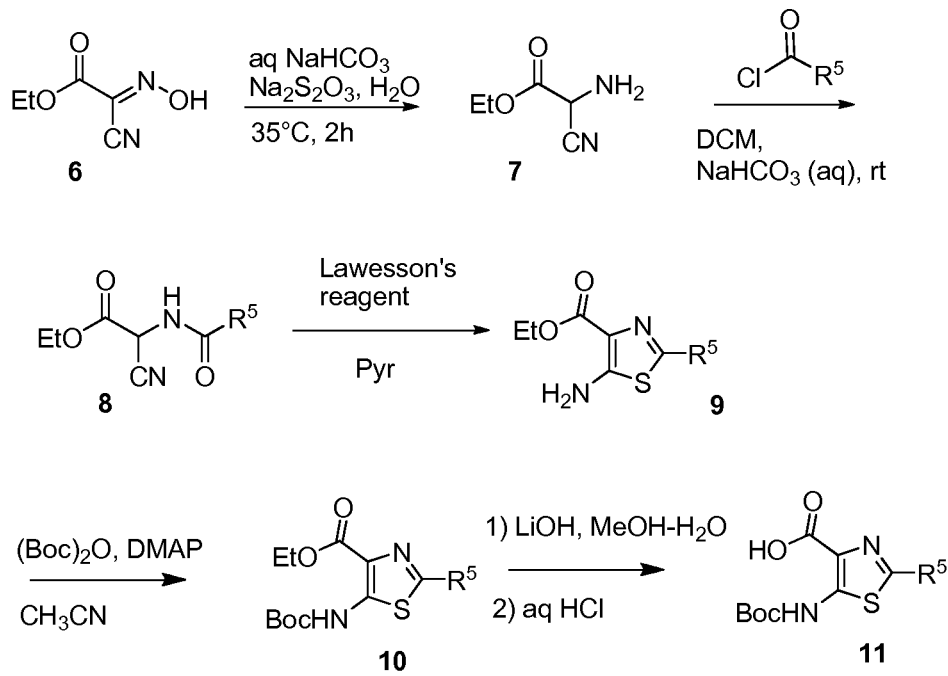
FIG. 2 shows an exemplary synthesis of 4-carboxy-thiazoles 11 from hydroxamide compounds 6.

FIG. 2 shows an exemplary synthesis of 4-carboxy-thiazoles 11 from hydroxamide compounds 6. Reduction of 6 by a reducing reagent in a suitable solvent such as $Na_2S_2O_3$ in water gives 7, which may be converted to 8 by an acylating reagent in a suitable solvent with a suitable base such as benzoyl chloride in dichloromethane with sodium bicarbonate. Compound 8 may be converted to 9 by a sulfur containing reagent in a suitable reagent such as Lawesson's reagent in pyridine, and protected to 10 by a suitable protecting group such as Boc (tert-butyloxycarbonyl). Ester hydrolysis of 10 using a suitable base and solvent, such as LiOH in methanol and water gives 11.

Figure 3:
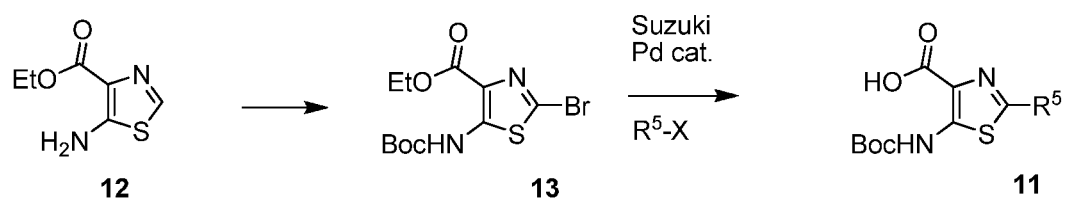
FIG. 3 shows an exemplary synthesis of 2-substituted, 4-carboxy-5-aminothiazoles 11 by C-2 bromination of 12 followed by Suzuki reaction of 13.

FIG. 3 shows an exemplary synthesis of 2-substituted, 4-carboxy-5-aminothiazoles 11 by C-2 bromination of 5-aminothiazole-4-carboxylate esters such as 12 followed by Suzuki reaction of 2-bromo-5-(tert-butoxycarbonylamino) thiazole-4-carboxylate esters such as 13. 5-Aminothiazole-4-carboxylate esters such as 12 may be brominated to give 13 with a brominating reagent in a suitable solvent, such as NBS (N-bromosuccinimide) in dichloromethane. The Suzuki-type coupling reaction is useful to attach a heterocycle or a heteroaryl by displacing a halide at the 2-position of the thiazole, pyridyl, pyrazinyl, or pyrimidinyl ring in the synthesis of a Formula I compound. For example, 2-bromo (or chloro) thiazole 13 may be reacted with about 1.5 equivalents of an aryl, heterocyclyl or heteroaryl boronic acid or ester reagent and an excess of aqueous sodium carbonate in acetonitrile. A catalytic amount, or more, of a low valent palladium reagent, such as bis(triphenylphosphine)palladium(II) dichloride, is added. A variety of boronic acids or boronic esters can be used. Boronic esters include pinacol esters (4,4,5,5-tetramethyl-1,3,2-dioxaborolan-2-yl). Also, a nitrogen atom of a heterocycle or heteroaryl may be protected, for example as N-THP. In some cases potassium acetate is used in place of sodium carbonate to adjust the pH of the aqueous layer. The reaction may be heated to about 140-150° C. under pressure in a microwave reactor such as the Biotage Optimizer (Biotage, Inc.) for 10 to 30 minutes. The contents are extracted with ethyl acetate, or another organic solvent. After evaporation of the organic layer the Suzuki coupling product may be purified on silica or by reverse phase HPLC.

A variety of palladium catalysts can be used during the Suzuki coupling step to form exemplary Formula I compounds. Low valent, Pd(II) and Pd(0) catalysts may be used in the Suzuki coupling reaction, including $PdCl2(PPh_3)_2$, $Pd(t-Bu)_3$, $PdCl_2$ dppf $CH_2Cl_2$, $Pd(PPh_3)_4$, $Pd(OAc)/PPh_3$, $Cl_2Pd[(Pet_3)]_2$, $Pd(DIPHOS)_2$, $Cl_2Pd(Bipy)$, $[PdCl(Ph_2PCH_2PPh_2)]_2$, $Cl_2Pd[P(o-tol)_3]_2$, $Pd_2(dba)_3/P(o-tol)_3$, $Pd_2(dba)/P(furyl)_3$, $Cl_2Pd[P(furyl)_3]_2$, $Cl_2Pd(PmePh_2)_2$, $Cl_2Pd[P(4-F-Ph)_3]_2$, $Cl_2Pd[P(C_6F_6)_3]_2$, $Cl_2Pd[P(2-COOH-Ph)(Ph)_2]_2$, $Cl_2Pd[P(4-COOH-Ph)(Ph)_2]_2$, and encapsulated catalysts Pd EnCat™ 30, Pd EnCat™ TPP30, and Pd(II) EnCat™ BINAP30 (US 2004/0254066).

A variety of solid adsorbent palladium scavengers can be used to remove palladium after the Suzuki, Suzuki-Miyaura, or Buchwald reactions. Exemplary embodiments of palladium scavengers include FLORISIL®, SILIABOND® Thiol, and SILIABOND® Thiourea. Other palladium scavengers include silica gel, controlled-pore glass (TosoHaas), and derivatized low crosslinked polystyrene QUADRAPURE™ AEA, QUADRAPURE™ IMDAZ, QUADRAPURE™ MPA, QUADRAPURE™ TU (Reaxa Ltd., Sigma-Aldrich Chemical Co.).

Figure 4:
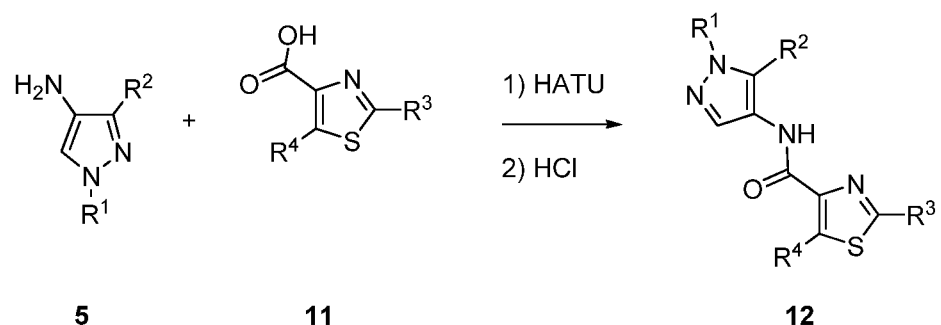
FIG. 4 shows an exemplary synthesis of coupled pyrazole-thiazole compounds 12 by coupling 4-aminopyrazole compounds 5 and 2-substituted, 4-carboxy-5-aminothiazoles 11.

FIG. 4 shows an exemplary synthesis of coupled pyrazole-thiazole compounds 12. Coupling of 4-aminopyrazole compounds 5 and 2-substituted, 4-carboxy-5-aminothiazoles 11 with an amide-forming (peptide) coupling reagent such as dicyclohexylcarbodiimide (DCC), diisopropylcarbodiimide (DIC), HATU (O-(7-azabenzotriazol-1-yl)-N,N,N',N'-tetramethyluronium hexafluorophosphate), HBTU (O-(Benzotriazol-1-yl)-N,N,N',N'-tetramethyluronium hexafluorophosphate, or PyBOP ((Benzotriazol-1-yloxy)tripyrrolidinophosphonium hexafluorophosphate) in a suitable solvent such as dichloromethane or DMF forms the amide bond in 12 (Hermanson, G. in Bioconjugate Techniques, 2nd Edition (2008) Academic Press, San Diego). Boc and other protecting groups of 12 can be removed under the usual conditions, to remove Boc, Fmoc or other acid-labile protecting groups from the 4-amino group of 5 under conditions such as HCl in dioxane and water or trifluoroacetic acid in dichloromethane.

Figure 5:
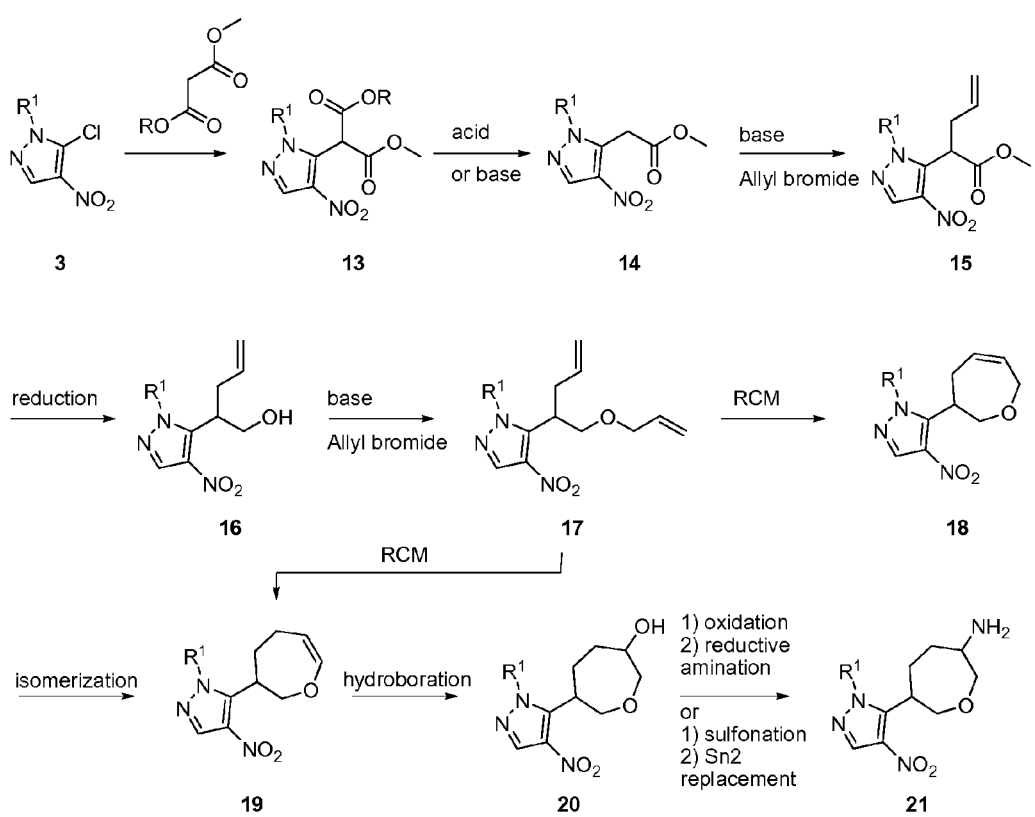
FIG. 5 shows an exemplary synthesis of 6-(4-nitro-1H-pyrazol-5-yl)oxepan-3-amine compounds 21 from 5-chloro-4-nitro-1H-pyrazole compounds 3.

FIG. 5 shows an exemplary synthesis of 6-(4-nitro-1H-pyrazol-5-yl)oxepan-3-amine compounds 21, such as 6-(1-methyl-4-nitro-1H-pyrazol-5-yl)oxepan-3-amine where R is methyl, from 5-chloro-4-nitro-1H-pyrazole compounds 3. Displacement of chloro from 3 with dimethyl malonate in the presence of a base such as potassium carbonate in a suitable solvent such as DMSO or by similar methods described in the literature yield 2-(1-substituted-4-nitro-1H-pyrazol-5-yl)malonate compounds 13. Decarboxylation of 13 in a basic, acidic or combination of both conditions described in the literature give alkyl 2-(4-nitro-1H-pyrazol-5-yl)acetate ester compounds 14. Allylation of 14 give alkyl 2-(4-nitro-1H-pyrazol-5-yl)pent-4-enoate ester compounds 15 using a suitable base such as sodium hydride in a suitable solvent such as DMF or by a method described in the literature. Reduction of 15 may be accomplished by a suitable reductive reagent such as DIBAL in a suitable solvent such as THF or by a method described in the literature to yield 2-(4-nitro-1H-pyrazol-5-yl)pent-4-en-1-ol compounds 16. Allylation of compounds of formula 16 may yield 5-(1-(allyloxy)pent-4-en-2-yl)-4-nitro-1H-pyrazole compounds 17 using a suitable base such as sodium hydride in a suitable solvent such as DMF or by a method described in the literature. Ring closing metathesis of 17 under suitable condition using Grubb's or related ruthenium catalyst (RCM=ruthenium-catalyzed metathesis) may yield 4-nitro-5-(2,3,4,7-tetrahydrooxepin-3-yl)-1H-pyrazole compounds 18. Isomerization of 18 with Grubb's or Wilkinson's catalyst may yield 4-nitro-5-(2,3,4,5-tetrahydrooxepin-3-yl)-1H-pyrazole compounds 19. Compounds 17 may be converted directly to 19 in a one pot procedure using ring closing metathesis conditions described in the literature. Hydroboration of 19 using conditions described in the literature may give 6-(4-nitro-1H-pyrazol-5-yl)oxepan-3-ol compounds 20, which may be oxidized to ketone followed by reductive amination to yield 6-(4-nitro-1H-pyrazol-5-yl)oxepan-3-amine compounds 21, or by sulfonation followed by displacement with an amine reagent.

Figure 6:
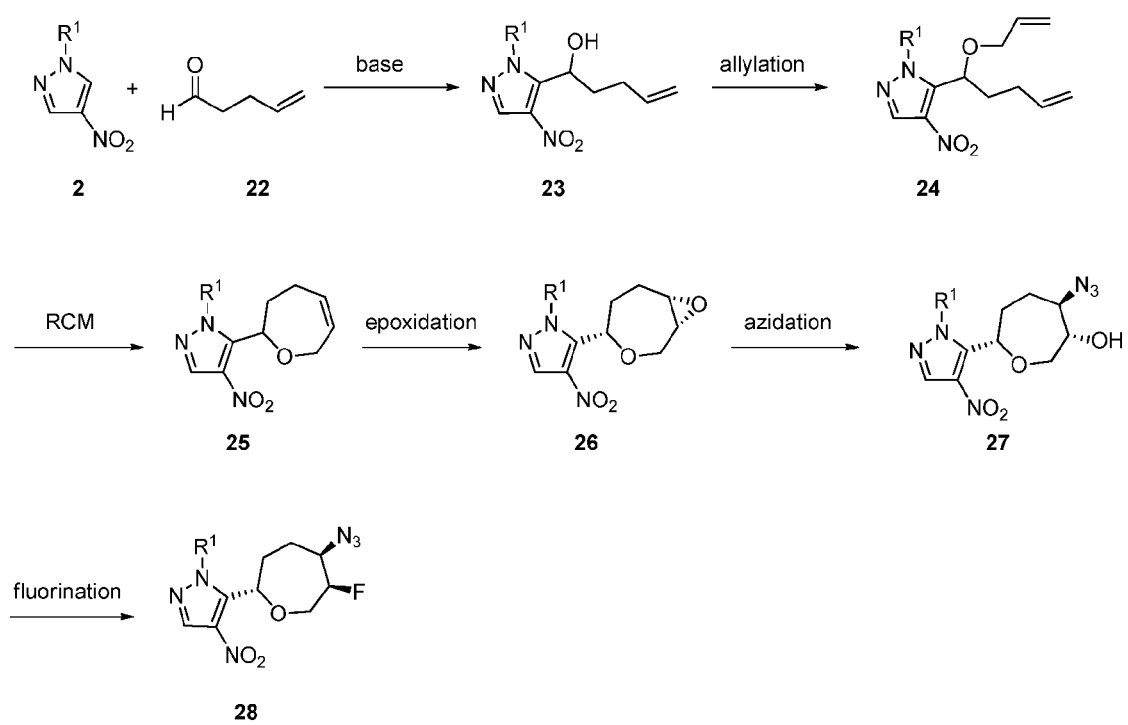
FIG. 6 shows an exemplary synthesis of 5-(5-azido-6-fluorooxepan-2-yl)-1-substituted-4-nitro-1H-pyrazole compounds 28 from 1-substituted-4-nitro-1H-pyrazole compounds 2.

FIG. 6 shows an exemplary synthesis of 5-(5-azido-6-fluorooxepan-2-yl)-1-substituted-4-nitro-1H-pyrazole compounds 28 from 1-substituted-4-nitro-1H-pyrazole compounds 2. Reaction of 2 and pent-4-enal 22 with a suitable base such as lithium hexamethyldisilazide in a suitable solvent such as THF at the required temperature or by procedures described in the literature gives 1-(1-substituted-4-nitro-1H-pyrazol-5-yl)pent-4-en-1-ol compounds 23. Heating 23 with bis-allylcarbonate in the presence of a suitable catalyst such as tris(dibenzylideneacetone)-dipalladium(0) and triphenylphoshine in solvents such as dioxane or using methods described in the literature gives 5-(1-(allyloxy)pent-4-enyl)-1-substituted-4-nitro-1H-pyrazole compounds 24. Cyclization of 24 by heating in a suitable solvent such as toluene with a suitable catalyst such as Grubbs 1st generation catalyst (RCM) or by methods described in the literature gives 1-substituted-4-nitro-5-(2,3,4,7-tetrahydrooxepin-2-yl)-1H-pyrazole compounds 25. Treatment of 25 with an epoxidizing reagent such as m-CPBA (meta-chloroperbenzoic acid) in a solvent such as dichloromethane or by similar methods described in the literature gives 5-(3,8-dioxabicyclo[5.1.0]octan-4-yl)-1-substituted-4-nitro-1H-pyrazole compounds 26. Opening of the epoxide of 26 with sodium azide according to literature methods gives 4-azido-7-(1-substituted-4-nitro-1H-pyrazol-5-yl)oxepan-3-ol compounds 27. Fluorination of 27 with a reagent such as deoxo-Fluor® in a suitable solvent such as DCM or by methods described in the literature gives 28.

Figure 7:
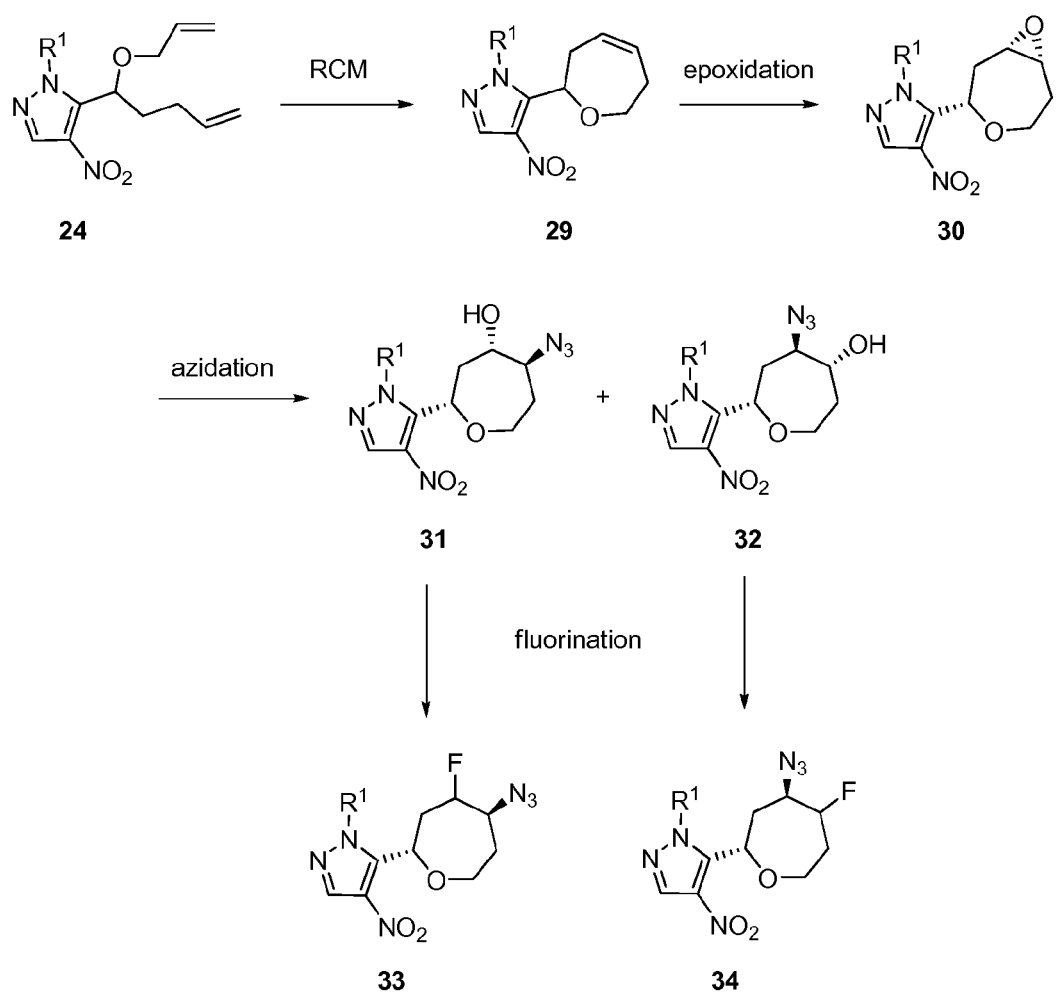
FIG. 7 shows an exemplary synthesis of 5-(5-azido-4-fluorooxepan-2-yl)-1-substituted-4-nitro-1H-pyrazole compounds 33 and 5-(4-azido-5-fluorooxepan-2-yl)-1-substituted-4-nitro-1H-pyrazole compounds 34 from 5-(1-(allyloxy)pent-4-enyl)-1-substituted-4-nitro-1H-pyrazole compounds 24.

FIG. 7 shows an exemplary synthesis of 5-(5-azido-4-fluorooxepan-2-yl)-1-substituted-4-nitro-1H-pyrazole compounds 33 and 5-(4-azido-5-fluorooxepan-2-yl)-1-substituted-4-nitro-1H-pyrazole compounds 34 from 5-(1-(allyloxy)pent-4-enyl)-1-substituted-4-nitro-1H-pyrazole compounds 24. Cyclization of 24 by heating in a suitable solvent such as dichloromethane with a suitable catalyst such as Grubbs $2^{nd}$ generation catalyst (RCM) or by methods described in the literature gives 1-substituted-4-nitro-5-(2,3,6,7-tetrahydrooxepin-2-yl)-1H-pyrazole compounds 29. Epoxidation of 29 with an epoxidizing reagent such as m-CPBA in a solvent such as dichloromethane or by similar methods described in the literature gives 5-(4,8-dioxabicyclo[5.1.0]octan-3-yl)-1-substituted-4-nitro-1H-pyrazole compounds 30. Treatment of 30 with an azide reagent (azidation) may give a mix of ring opened compounds 5-azido-2-(1-substituted-4-nitro-1H-pyrazol-5-yl)oxepan-4-ol 31 and 5-azido-7-(1-substituted-4-nitro-1H-pyrazol-5-yl)oxepan-4-ol 32. Fluorination of 31 and 32 with a fluorinating reagent such as deoxo-Fluor® in a suitable solvent such as DCM or by methods described in the literature gives 33 and 34, respectively.

Figure 8:
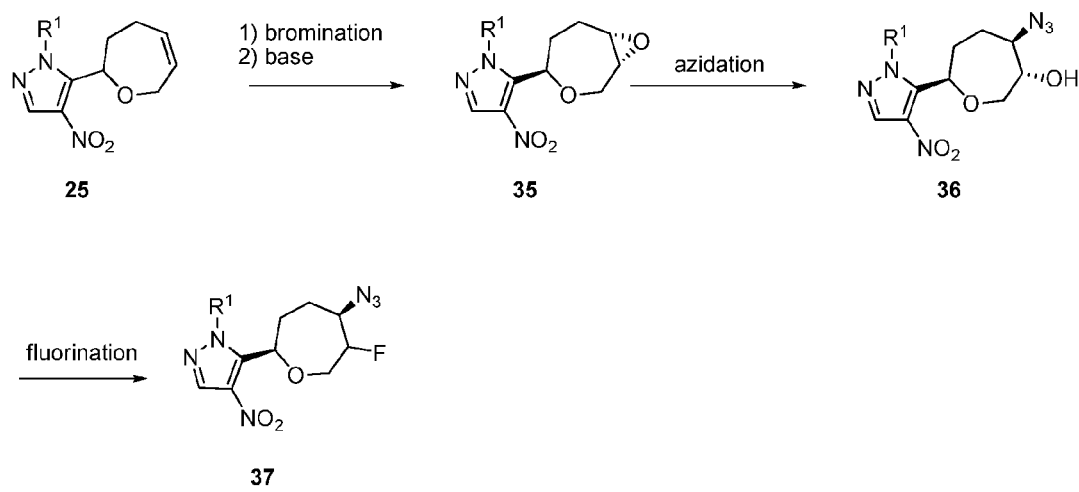
FIG. 8 shows an exemplary synthesis of 5-(5-azido-6-fluorooxepan-2-yl)-1-substituted-4-nitro-1H-pyrazole compounds 37 from 1-substituted-4-nitro-5-(2,3,4,7-tetrahydrooxepin-2-yl)-1H-pyrazole compounds 25.

FIG. 8 shows an exemplary synthesis of 5-(5-azido-6-fluorooxepan-2-yl)-1-substituted-4-nitro-1H-pyrazole compounds 37 from 1-substituted-4-nitro-5-(2,3,4,7-tetrahydrooxepin-2-yl)-1H-pyrazole compounds 25. Treatment of 25 with N-bromosuccinimide and acetic acid in the presence of molecular sieves in a suitable solvent such as dichloromethane followed by treatment with potassium carbonate in a suitable solvent such as methanol or by methods described in the literature gives 5-(3,8-dioxabicyclo[5.1.0]octan-4-yl)-1-substituted-4-nitro-1H-pyrazole compounds 35. Epoxide ring opening of 25 sodium azide according to literature methods gives 4-azido-7-(1-substituted-4-nitro-1H-pyrazol-5-yl)oxepan-3-ol compounds 36. Fluorination of 36 with a fluorinating reagent such as deoxo-Fluor® in a solvent such as DCM or by methods described in the literature gives 37.

Figure 9:
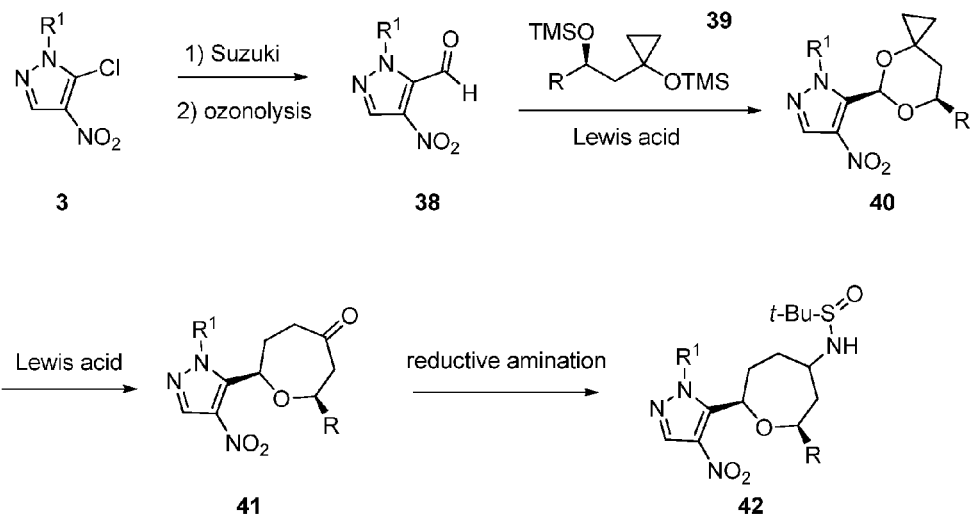
FIG. 9 shows an exemplary synthesis of 2-methyl-N-(2-substituted-7-(1-substituted-4-nitro-1H-pyrazol-5-yl)oxepan-4-yl)propane-2-sulfinamide compounds 42 from 5-chloro-4-nitro-1H-pyrazole compounds 3.

FIG. 9 shows an exemplary synthesis of 2-methyl-N-(2-substituted-7-(1-substituted-4-nitro-1H-pyrazol-5-yl)oxepan-4-yl)propane-2-sulfinamide compounds 42 from 5-chloro-4-nitro-1H-pyrazole compounds 3. Suzuki reaction of 3 by heating with potassium vinyltrifluoroborate and cesium carbonate in solvents such as DMF and water in the presence of a suitable catalyst such as 1,1'-bis(diphenylphosphino)ferrocene-palladium(II)dichloride dichloromethane complex followed by treatment of the resulting alkene with ozone in a suitable solvent such as dichloromethane or using methods described in the literature gives 1-substituted-4-nitro-1H-pyrazole-5-carbaldehyde compounds 38. Treatment of 38 with (R)-trimethyl(1-(1-(trimethylsilyloxy)cyclopropyl)propan-2-yloxy)silane compounds 39 and trimethylsilyl triflate in a suitable solvent such as dichloromethane or using methods described in the literature (Minbiole et al (2005) Org. Lett. 7:515) gives 5-((5R,7R)-7-substituted-4,6-dioxaspiro[2.5]octan-5-yl)-1-substituted-4-nitro-1H-pyrazole compounds 40. Treatment of 40 with a suitable Lewis acid such as titanium tetrachloride in a solvent such as dichloromethane or using methods described in the literature gives rearranged product, (2R,7R)-2-substituted-7-(1-substituted-4-nitro-1H-pyrazol-5-yl)oxepan-4-one compounds 41. Reductive amination of 41 by heating with (R)-2-methylpropane-2-sulfinamide in the presence of a suitable Lewis acid such as titanium(IV) ethoxide in a solvent such as THF followed by treatment with sodium borohydride in a suitable solvent or using methods described in the literature gives 42.

Figure 10:
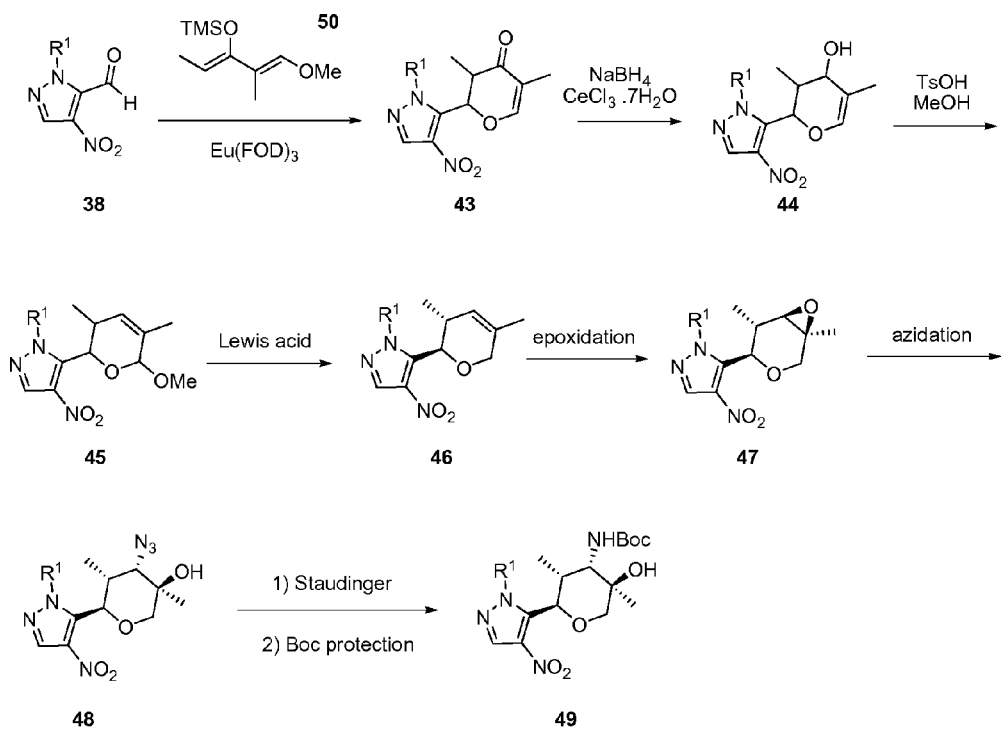
FIG. 10 shows an exemplary synthesis of tert-butyl (2R,3R,4S,5R)-5-hydroxy-3,5-dimethyl-2-(1-substituted-4-nitro-1H-pyrazol-5-yl)tetrahydro-2H-pyran-4-ylcarbamate compounds 49 from 1-substituted-4-nitro-1H-pyrazole-5-carbaldehyde compounds 38.

FIG. 10 shows an exemplary synthesis of tert-butyl (2R, 3R,4S,5R)-5-hydroxy-3,5-dimethyl-2-(1-substituted-4-nitro-1H-pyrazol-5-yl)tetrahydro-2H-pyran-4-ylcarbamate compounds 49 from 1-substituted-4-nitro-1H-pyrazole-5-carbaldehyde compounds 38. Heating 38 with diene ((1E, 3Z)-1-methoxy-2-methylpenta-1,3-dien-3-yloxy)trimethylsilane 50 in the presence of Resolve-Al™ EuFOD (Europium (III)-tris(11,1,2,2,3,3-heptafluoro-7,7-dimethyl-4,6-octanedionate), Sievers' Reagent, Tris(6,6,7,7,8,8,8-heptafluoro-2,2-dimethyl-3,5-octanedionato)europium, Sigma-Aldrich Product No. 160938, CAS No. 17631-68-4) in a suitable solvent such as chloroform or using methods described in the literature gives 3,5-dimethyl-2-(1-substituted-4-nitro-1H-pyrazol-5-yl)-2H-pyran-4(3H)-one compounds 43. Treatment of 43 with a suitable reducing agent such as sodium borohydride in the presence of cerium(III) chloride heptahydrate in an appropriate solvent such as methanol or using similar methods described in the literature gives 3,5-dimethyl-2-(1-substituted-4-nitro-1H-pyrazol-5-yl)-3,4-dihydro-2H-pyran-4-ol compounds 44. Heating 44 with p-toluene sulfonic acid in methanol or using methods described in the literature gives rearranged product, 5-(6-methoxy-3,5-dimethyl-3,6-dihydro-2H-pyran-2-yl)-1-substituted-4-nitro-1H-pyrazole compounds 45. Treatment of 45 with a Lewis acid such as boron trifluoride diethyl etherate and reducing agent such as triethylsilane in a suitable solvent such as dichloromethane or using methods described in the literature gives 5-(3,5-dimethyl-3,6-dihydro-2H-pyran-2-yl)-1-substituted-4-nitro-1H-pyrazole compounds 46. Epoxidation of 46 with an epoxidizing reagent such as m-CPBA or by similar procedures reported in the literature gives 5-(1,5-dimethyl-3,7-dioxabicyclo[4.1.0]heptan-4-yl)-1-substituted-4-nitro-1H-pyrazole compounds 47. Opening of the epoxide of 47 with sodium azide according to literature methods gives 4-azido-3,5-dimethyl-6-(1-substituted-4-nitro-1H-pyrazol-5-yl)tetrahydro-2H-pyran-3-ol compounds 48. Staudinger azide reduction of 48 by heating with trimethylphosphine in THF and water followed by protection of the resulting amine with a suitable protecting group such as a Boc-protecting group using the methods outlined or those described in the literature gives 49.

Figure 11:
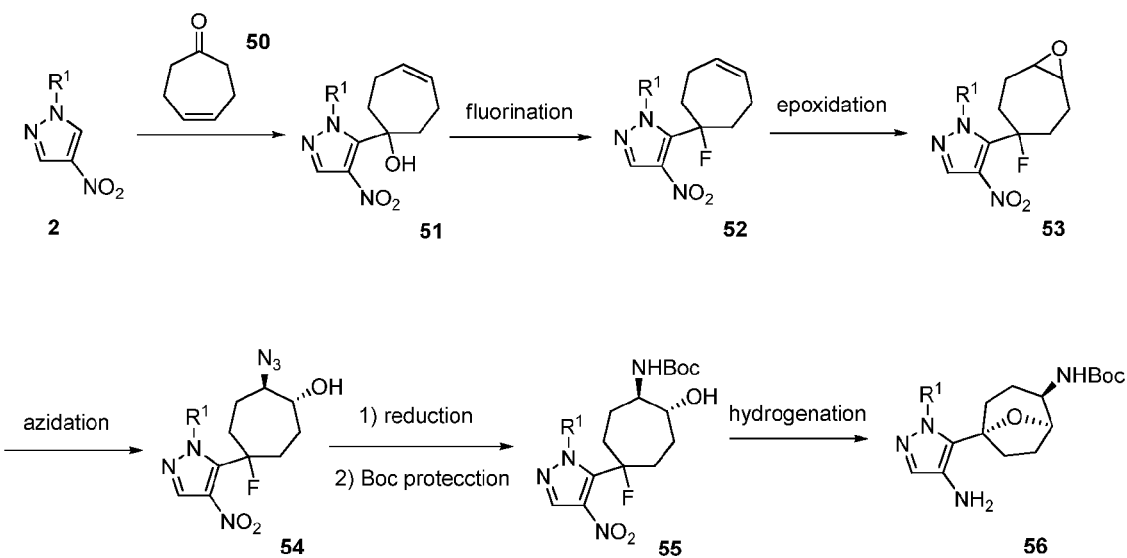
FIG. 11 shows an exemplary synthesis of tert-butyl (5-(4-amino-1-substituted-1H-pyrazol-5-yl)-8-oxabicyclo[3.2.1]octan-2-ylcarbamate compounds 56 from 1-substituted-4-nitro-1H-pyrazole compounds 2.

FIG. 11 shows an exemplary synthesis of tert-butyl (5-(4-amino-1-substituted-1H-pyrazol-5-yl)-8-oxabicyclo[3.2.1]octan-2-ylcarbamate compounds 56 from 1-substituted-4-nitro-1H-pyrazole compounds 2. Reaction of 2 with (Z)-cyclohept-4-enone 50 and a suitable base such as lithium hexamethyldisilazide at an appropriate temperature in a solvent such as THF or by methods described in the literature gives 1-(1-substituted-4-nitro-1H-pyrazol-5-yl)cyclohept-4-enol compounds 51. Fluorination of 51 with a fluorinating reagent such as deoxo-Fluor® in a suitable solvent such as DCM or by methods described in the literature gives 5-(1-fluorocyclohept-4-enyl)-1-substituted-4-nitro-1H-pyrazole compounds 52. Epoxidation of 52 with m-CPBA or similar methods described in the literature gives 5-(4-fluoro-8-oxabicyclo[5.1.0]octan-4-yl)-1-substituted-4-nitro-1H-pyrazole compounds 53. Opening the epoxide of 53 with sodium azide according to literature methods gives 2-azido-5-fluoro-5-(1-substituted-4-nitro-1H-pyrazol-5-yl)cycloheptanol compounds 54. Staudinger azide reduction of 54 by heating with triphenylphosphine in THF and water followed by protection of the resulting amine with a suitable protecting group such as a Boc-protecting group using the methods outlined or those described in the literature gives tert-butyl-(5-fluoro-2-hydroxy-5-(1-substituted-4-nitro-1H-pyrazol-5-yl)cycloheptylcarbamate compounds 55. Hydrogenation of 55 by heating at an appropriate temperature in the presence of a suitable catalyst such as 10% palladium on carbon under an atmosphere of hydrogen gas in suitable solvents such as a mixture of THF and methanol gives 56.

EXAMPLES

Example 1

5-chloro-1-methyl-4-nitro-1H-pyrazole

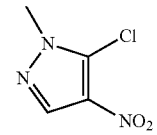

To a 500 mL round bottom flask containing 4-nitro-1-H-pyrazole (5 g, 44.2 mmol) was added sodium hydroxide (1M, 200 mL) and dimethyl sulfate (31 mL, 330 mmol). The mixture was stirred at room temperature for 72 h and the mixture was extracted with $CH_2Cl_2$ (2×150 mL). The organic layer was separated and the solvent was distilled off to yield 1-methyl-4-nitro-1H-pyrazole as a white solid (4.30 g, 76%).

Following WO 2007/99326, to a 500 mL 3-neck-round bottom flask was added 1-methyl-4-nitro-1H-pyrazole (4.30 g, 33.8 mmol) and THF (12 mL). The mixture was cooled to −78° C. and lithium hexamethyldisilazide in THF (1M, 88.4 mL, 90 mmol) was added dropwise via an addition funnel over 20 min. The brown mixture was stirred for 30 min and warmed to −45° C. over 30 min. The mixture was cooled back down to −78° C. and hexachloroethane (10.5 g, 44.2 mmol) dissolved in THF (20 mL) was added via an addition funnel over 15 min. The mixture was stirred for 2.5 h, warmed from −78° C. to −40° C. and the reaction was monitored by LCMS. Upon completion of the reaction, the reaction was quenched with a solution of saturated $NH_4Cl$ (150 mL), and ethyl acetate (100 mL) was added. The organic layer was separated and the aqueous layer was extracted with ethyl acetate (100 mL). The combined organic layer was washed with water (150 mL), dried over $Na_2SO_4$ and the organic solvent was distilled off. The crude product was purified via flash chromatography (CH$_2$Cl$_2$/7% MeOH) to yield 5-chloro-1-methyl-4-nitro-1H-pyrazole as a white solid (1.40 g, 20%). $^1$H NMR (400 MHz, CDCl$_3$) δ 8.13 (s, 1H), 3.92 (s, 3H); ESIMS m/z=162.0 (M+1)

Example 2 ethyl 2-amino-2-cyanoacetate

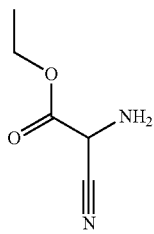

To a stirred solution of (E)-ethyl 2-cyano-2-(hydroxyimino)acetate (20 g, 0.14 mol) in water (250 mL) was added a saturated solution of NaHCO$_3$ in water (160 mL), followed by the addition of Na$_2$S$_2$O$_4$ (60 g, 0.423 mol). The reaction mixture was warmed up to 35° C. and stirred for additional 2 hr. It was then saturated with NaCl (150 g) and extracted with DCM (3×350 mL). Combined organic layers were washed with brine, dried over Na$_2$SO$_4$, filtered and concentrated in vacuo to give ethyl 2-amino-2-cyanoacetate as a red oil (7.8 g, 43%) that was used at the next step without additional purification. $^1$H-NMR (CDCl$_3$, 500 MHz) δ (ppm): 4.45 (s, 1H), 4.34 (q, J=7.0 Hz, 2H), 1.36 (t, J=7.0 Hz, 3H); MS (ESI) m/z: 129 [M+H$^+$].

Example 3 ethyl 2-benzamido-2-cyanoacetate

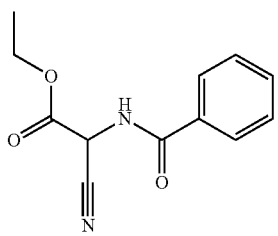 [SMILES: CCOC(=O)C(C#N)NC(=O)c1ccccc1]

To a stirred solution of compound ethyl 2-amino-2-cyanoacetate (0.64 g, 5 mmol) in DCM (15 mL) was added a saturate solution of NaHCO$_3$ in water (15 mL). With vigorously stirring, benzoyl chloride (0.84 g, 6 mmol) was added. The reaction mixture was stirred at ambient temperature for additional 30 min at which time it was extracted with DCM (3×15 mL). Combined organic layers were washed with brine (20 mL) and dried over Na$_2$SO$_4$, filtered, concentrated in vacuo. Resulted residue was purified by silica gel column chromatography (5:1 PE/EtOAc) to afford ethyl 2-benzamido-2-cyanoacetate (0.25 g, 22%) as white solid: $^1$H-NMR (CDCl$_3$, 500 MHz) δ (ppm): 7.83-7.85 (m, 2H), 7.59 (t, J=7.5 Hz, 1H), 7.49 (t, J=7.5 Hz, 2H), 7.02 (d, J=7.0 Hz, 1H), 5.72 (d, J=7.5 Hz, 1H), 4.40 (q, J=7.5 Hz, 2H), 1.39 (t, J=7.0 Hz, 3H); MS (ESI) m/z: 233 [M+H$^+$].

Example 4 ethyl 5-amino-2-phenylthiazole-4-carboxylate

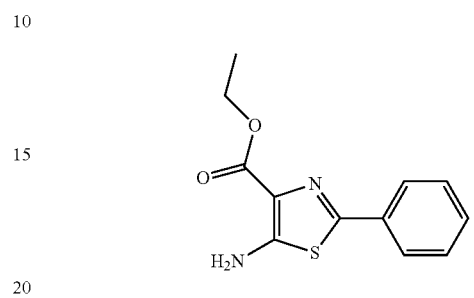

To a stirred solution of compound ethyl 2-benzamido-2-cyanoacetate (0.46 g, 2 mmol) in pyridine (20 mL) was added Lawesson's reagent (0.81 g, 2 mmol). The reaction mixture was heated at reflux for 15 hr. It was then concentrated and diluted with EtOAc (40 mL). The diluted mixture was washed with water (3×20 mL), brine (10 mL), dried over Na$_2$SO$_4$, filtered, and concentrated in vacuo. The residue was purified by silica gel column chromatography (10:1 PE/EtOAc) to afford ethyl 5-amino-2-phenylthiazole-4-carboxylate (0.2 g, 40%) as yellow solid: $^1$H-NMR (CDCl$_3$, 500 MHz) δ (ppm): 7.80 (d, J=6.5 Hz, 1H), 7.36-7.41 (m, 3H), 4.43 (q, J=7.0 Hz, 2H), 1.44 (t, J=7.0 Hz, 3H); MS (ESI) m/z: 249 [M+H$^+$].

Example 5 ethyl 5-(tert-butoxycarbonylamino)-2-phenylthiazole-4-carboxylate

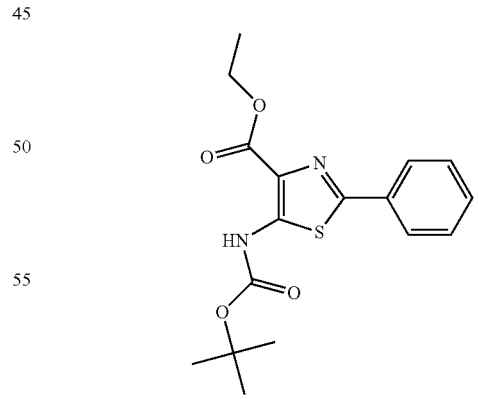

To a solution of compound ethyl 5-amino-2-phenylthiazole-4-carboxylate (248 mg, 1 mmol) in CH$_3$CN (10 mL) was added DMAP (6 mg, 0.05 mmol) followed by (Boc)$_2$O (262 mg, 1.2 mmol). The reaction mixture was maintained at ambient temperature for additional 30 min. The mixture was then evaporated in vacuo to give ethyl 5-(tert-butoxycarbonylamino)-2-phenylthiazole-4-carboxylate as a red solid (340 mg, 95%) that was used at the next step without further purification.

Example 6

5-(tert-butoxycarbonylamino)-2-phenylthiazole-4-carboxylic acid

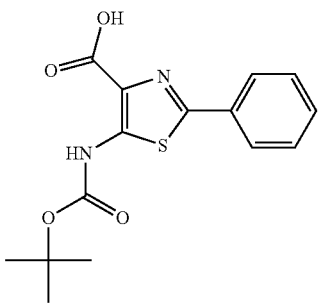 [SMILES: CC(C)(C)OC(=O)Nc1sc(-c2ccccc2)nc1C(=O)O]

To a solution of compound ethyl 5-(tert-butoxycarbonylamino)-2-phenylthiazole-4-carboxylate (348 mg, 1 mmol) in MeOH/$H_2O$ (10 mL, 1:1) was added LiOH.$H_2O$ (20 mg, 5 mmol). The reaction mixture was heated at 50-55° C. until starting material disappeared from TLC. It was cooled at about 0-4° C. and conc. HCl added dropwise until pH of about 5. The resulted mixture was then extracted with DCM (3×20 mL). Combined organic layers were washed with brine (2×20 mL), dried over $Na_2SO_4$, filtered, and concentrated in vacuo. The residue was purified by silica gel column chromatography (50:1 DCM:MeOH) to give the 5-(tert-butoxycarbonylamino)-2-phenylthiazole-4-carboxylic acid (0.22 g, 68%) as white solid: $^1$H-NMR (CDCl$_3$, 500 MHz) δ (ppm): 9.69 (s, 1H), 7.89-7.91 (m, 2H), 7.46-7.47 (m, 3H), 1.57 (s, 9H); MS (ESI) m/z: 321 [M+H$^+$]

Example 7

5-(tert-butoxycarbonylamino)-2-(2-fluorophenyl)thiazole-4-carboxylic acid

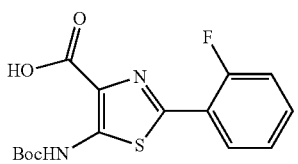 [SMILES: CC(C)(C)OC(=O)Nc1sc(-c2ccccc2F)nc1C(=O)O]

Following procedures from Examples 19-23 and shown in FIG. 2, 2-fluorobenzoyl chloride was converted to 5-(tert-butoxycarbonylamino)-2-(2-fluorophenyl)thiazole-4-carboxylic acid: $^1$H-NMR (CDCl$_3$, 500 MHz) δ (ppm): 9.70 (s, 1H), 8.19-8.23 (m, 1H), 7.42-7.45 (m, 1H), 7.20-7.30 (m, 2H), 1.57 (s, 9H); MS (ESI) m/z: 339 [M+H$^+$]

Example 8

5-(tert-butoxycarbonylamino)-2-(2,6-difluorophenyl)thiazole-4-carboxylic acid

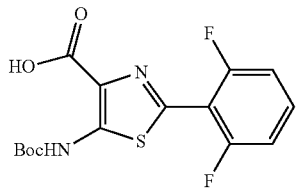 [SMILES: CC(C)(C)OC(=O)Nc1sc(-c2c(F)cccc2F)nc1C(=O)O]

Following procedures from Examples 19-23 and shown in FIG. 2, 2,6-difluorobenzoyl chloride was converted to 5-(tert-butoxycarbonylamino)-2-(2,6-difluorophenyl)thiazole-4-carboxylic acid: $^1$H-NMR (CD$_3$OD, 500 MHz) δ (ppm): 7.42-7.46 (m, 1H), 7.06 (t, J=8.5 Hz, 2H), 1.47 (s, 9H); MS (ESI) m/z: 355 [M+H$^+$].

Example 9

5-(tert-butoxycarbonylamino)-2-(2-chlorophenyl)thiazole-4-carboxylic acid

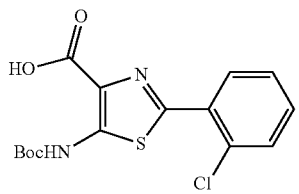 [SMILES: CC(C)(C)OC(=O)Nc1sc(-c2ccccc2Cl)nc1C(=O)O]

Following procedures from Examples 19-23 and shown in FIG. 2, 2-chlorobenzoyl chloride was converted to 5-(tert-butoxycarbonylamino)-2-(2-chlorophenyl)thiazole-4-carboxylic acid: $^1$H-NMR (DMSO, 500 MHz) δ (ppm): 13.57 (s, 1H), 10.05 (s, 1H), 8.14-8.17 (m, 1H), 7.63-7.65 (m, 1H), 7.49-7.51 (m, 2H), 1.53 (s, 9H); MS (ESI) m/z: 355 [M+H$^+$].

Example 10

2-(5-bromo-2-fluorophenyl)-5-(tert-butoxycarbonylamino)thiazole-4-carboxylic acid

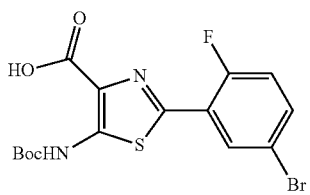 [SMILES: CC(C)(C)OC(=O)Nc1sc(-c2cc(Br)ccc2F)nc1C(=O)O]

Following procedures from Examples 1-9 and shown in FIG. 2, 5-bromo-2-fluorobenzoyl chloride was converted to 2-(5-bromo-2-fluorophenyl)-5-(tert-butoxycarbonylamino)thiazole-4-carboxylic acid: $^1$H-NMR (CDCl$_3$, 500 MHz) δ

(ppm): 9.70 (s, 1H), 8.32-8.34 (m, 1H), 7.49-7.52 (m, 1H), 7.09-7.13 (m, 1H), 1.57 (s, 9H); MS (ESI) m/z: 418 [M+H⁺].

Example 11

2-(5-bromo-2-chlorophenyl)-5-(tert-butoxycarbonylamino)thiazole-4-carboxylic acid

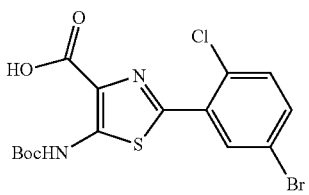 [SMILES: CC(C)(C)OC(=O)Nc1sc(-c2cc(Br)ccc2Cl)nc1C(=O)O]

Following procedures from Examples 1-9 and shown in FIG. 2, 5-bromo-2-chlorobenzoyl chloride was converted to 2-(5-bromo-2-chlorophenyl)-5-(tert-butoxycarbonylamino)thiazole-4-carboxylic acid: ¹H-NMR (CDCl₃, 500 MHz) δ (ppm): 9.70 (s, 1H), 8.31 (d, J=2.5 Hz, 1H), 7.47 (dd, J=2.5 Hz, J=8.5 Hz, 1H), 7.35 (d, J=9.0 Hz, 1H), 1.57 (s, 9H); MS (ESI) m/z: 433 [M+H⁺].

Example 12

2-(3-bromophenyl)-5-(tert-butoxycarbonylamino)thiazole-4-carboxylic acid

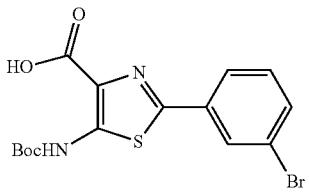 [SMILES: CC(C)(C)OC(=O)Nc1sc(-c2cccc(Br)c2)nc1C(=O)O]

Following procedures from Examples 1-9 and shown in FIG. 2, 3-bromobenzoyl chloride was converted to 2-(3-bromophenyl)-5-(tert-butoxycarbonylamino)thiazole-4-carboxylic acid: ¹H-NMR (CDCl₃, 500 MHz) δ (ppm): 9.68 (s, 1H), 8.08 (s, 1H), 7.78 (d, J=8.0 Hz, 1H), 7.56 (d, J=8.0 Hz, 1H), 7.32 (t, J=8.0 Hz, 1H), 1.57 (s, 9H); MS (ESI) m/z: 399 [M+H⁺]

Example 13

2-(4-bromo-2-fluorophenyl)-5-(tert-butoxycarbonylamino)thiazole-4-carboxylic acid

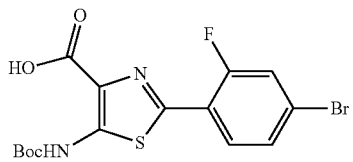 [SMILES: CC(C)(C)OC(=O)Nc1sc(-c2ccc(Br)cc2F)nc1C(=O)O]

Following procedures from Examples 1-9 and shown in FIG. 2, 4-bromo-2-fluorobenzoyl chloride was converted to 2-(4-bromo-2-fluorophenyl)-5-(tert-butoxycarbonylamino)thiazole-4-carboxylic acid: ¹H-NMR (CDCl₃, 500 MHz) δ (ppm): 9.67 (s, 1H), 8.07 (t, J=8.0 Hz, 1H), 7.42 (d, J=9.5 Hz, 1H), 1.57 (s, 9H); MS (ESI) m/z: 417 [M+H⁺]

Example 14

5-(tert-butoxycarbonylamino)-2-(yridine-2-yl)thiazole-4-carboxylic acid

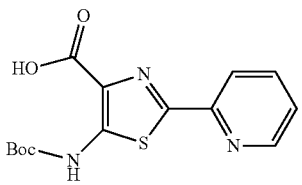 [SMILES: CC(C)(C)OC(=O)Nc1sc(-c2ccccn2)nc1C(=O)O]

To a solution of picolinic acid (1.23 g, 10 mmol), EDC.HCl (1.91 g, 10 mmol) and HOBT (1.35 g, 10 mmol) in THF (80 mL) was added DIPEA (3.6 g, 30 mmol) at ambient temperature. The reaction mixture was maintained at the same temperature for 1 hr at which time a solution of ethyl 2-amino-2-cyanoacetate (1.28 g, 10 mmol) in THF (5 mL) was added. The reaction mixture was stirred at ambient temperature for additional 6 hr. It was then concentrated, and the residue was purified by silica gel column chromatography (5:1 PE/EtOAc) to give ethyl 2-cyano-2-(picolinamido)acetate (0.7 g, 30%) as yellow solid.

Following procedures from Examples 19-23 and shown in FIG. 2, ethyl 2-cyano-2-(picolinamido)acetate was converted to 5-(tert-butoxycarbonylamino)-2-(pyridine-2-yl)thiazole-4-carboxylic acid: ¹H-NMR (CDCl₃, 500 MHz) δ (ppm): 9.72 (s, 1H), 8.61 (d, J=4.5 Hz, 1H), 8.09 (d, J=8.0 Hz, 1H), 7.81 (t, J=7.5 Hz, 1H), 7.34 (dd, J=5.5 Hz, J=7.0 Hz, 1H), 1.57 (s, 9H); MS (ESI) m/z: 322 [M+H⁺].

Example 15

5-(tert-butoxycarbonylamino)-2-isopropylthiazole-4-carboxylic acid

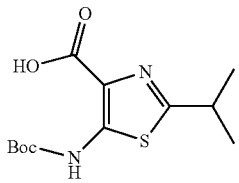

Following procedures from Examples 1-9 and shown in FIG. 2, isobutyryl chloride was converted to 5-(tert-butoxycarbonylamino)-2-isopropylthiazole-4-carboxylic acid: ¹H-NMR (CDCl₃, 500 MHz) δ (ppm): 9.54 (s, 1H), 3.16-3.21 (m, 1H), 1.54 (s, 9H), 1.37 (d, J=7.0 Hz, 6H); MS (ESI) m/z: 287 [M+H⁺].

Example 16

5-(tert-butoxycarbonylamino)-2-cyclohexylthiazole-4-carboxylic acid

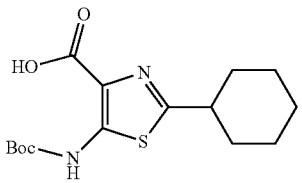 [SMILES: CC(C)(C)OC(=O)Nc1sc(C2CCCCC2)nc1C(=O)O]

Following procedures from Examples 1-9 and shown in FIG. 2, cyclohexanecarboxylic acid chloride was converted to 5-(tert-butoxycarbonylamino)-2-cyclohexylthiazole-4-carboxylic acid: $^1$H-NMR (CDCl$_3$, 500 MHz) δ (ppm): 9.53 (s, 1H), 2.84-2.89 (m, 1H), 2.08-2.12 (m, 2H), 1.84 (dd, J=3.5 Hz, J=10.0 Hz, 2H), 1.73 (d, J=13.0 Hz, 1H), 1.53 (s, 9H), 1.35-1.50 (m, 4H), 1.25-1.27 (m, 1H); MS (ESI) m/z: 327 [M+H$^+$].

Example 17

5-(tert-butoxycarbonylamino)-2-o-tolylthiazole-4-carboxylic acid

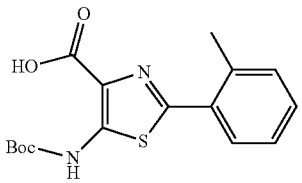 [SMILES: Cc1ccccc1-c1nc(C(=O)O)c(NC(=O)OC(C)(C)C)s1]

Following procedures from Examples 1-9 and shown in FIG. 2, 2-methylbenzoyl chloride was converted to 5-(tert-butoxycarbonylamino)-2-o-tolylthiazole-4-carboxylic acid: $^1$H-NMR (CD$_3$OD, 500 MHz) δ (ppm): 7.34 (s, 1H), 7.13-7.22 (m, 3H), 2.32 (s, 3H), 1.43 (s, 9H); MS (ESI) m/z: 335 [M+H$^+$].

Example 18

5-(tert-butoxycarbonylamino)-2-(2-methoxyphenyl)thiazole-4-carboxylic acid

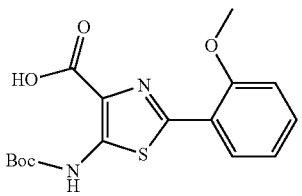 [SMILES: COc1ccccc1-c1nc(C(=O)O)c(NC(=O)OC(C)(C)C)s1]

Following procedures from Examples 1-9 and shown in FIG. 2, 2-methoxybenzoyl chloride was converted to 5-(tert-butoxycarbonylamino)-2-(2-methoxyphenyl)thiazole-4-carboxylic acid: $^1$H-NMR (CD$_3$OD, 500 MHz) δ (ppm): 9.63 (s, 1H), 8.27 (d, J=7.5 Hz, 1H), 7.42 (t, J=8.0 Hz, 1H), 7.09 (t, J=7.5 Hz, 1H), 7.04 (d, J=9.0 Hz, 1H), 1.57 (s, 9H); MS (ESI) m/z: 351 [M+H$^+$]

Example 19

5-(tert-butoxycarbonylamino)-2-(2-(trifluoromethyl)phenyl)thiazole-4-carboxylic acid

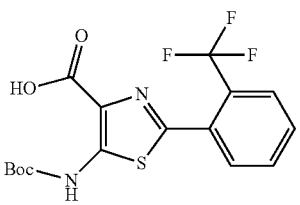 [SMILES: CC(C)(C)OC(=O)Nc1sc(-c2ccccc2C(F)(F)F)nc1C(=O)O]

Following procedures from Examples 1-9 and shown in FIG. 2, 2-(trifluoromethyl)benzoyl chloride was converted to 5-(tert-butoxycarbonylamino)-2-(2-(trifluoromethyl)phenyl)thiazole-4-carboxylic acid: $^1$H-NMR (CD$_3$OD, 500 MHz) δ (ppm): 7.76 (d, J=7.5 Hz, 1H), 7.58-7.64 (m, 3H), 1.46 (s, 9H); MS (ESI) m/z: 389 [M+H$^+$].

Example 20

5-(tert-butoxycarbonylamino)-2-methylthiazole-4-carboxylic acid

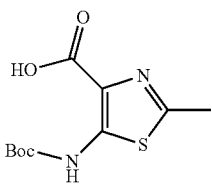 [SMILES: Cc1nc(C(=O)O)c(NC(=O)OC(C)(C)C)s1]

Following procedures from Examples 1-9 and shown in FIG. 2, acetyl chloride was converted to 5-(tert-butoxycarbonylamino)-2-methylthiazole-4-carboxylic acid: $^1$H-NMR (CDCl$_3$, 500 MHz) δ (ppm): 9.62 (s, 1H), 2.62 (s, 3H), 1.54 (s, 9H); MS (ESI) m/z: 259 [M+H$^+$]

Example 21

5-(tert-butoxycarbonylamino)thiazole-4-carboxylic acid

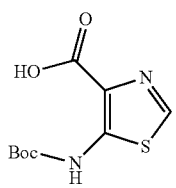

Under a nitrogen atmosphere (N$_2$), HCOOH (2.44 g, 53 mmol) was added to Ac$_2$O (6.48 g, 63.6 mmol) at 0° C. After it was allowed to warm to ambient temperature the reaction was heated at 50° C. for 15 hr. It was allowed to cool to ambient temperature. This mixed acid anhydride was then added dropwise to a solution of ethyl 2-amino-2-cyanoacetate (128 mg, 1 mmol) in dry THF (5 mL) at 0° C. After the cooling bath was removed, the reaction was maintained at ambient temperature for additional 1 hr. The reaction mixture was concentrated and purified by silica gel column chromatography (5:1 PE/EtOAc) to afford ethyl 2-cyano-2-formamidoacetate (110 mg, 70%) as a white solid.

Following procedures from Examples 1-9 and shown in FIG. 2, ethyl 2-cyano-2-formamidoacetate was converted to 5-(tert-butoxycarbonylamino)thiazole-4-carboxylic acid: $^1$H-NMR (CDCl$_3$, 500 MHz) δ (ppm): 9.70 (s, 1H), 8.29 (s, 1H), 1.55 (s, 9H); MS (ESI) m/z: 245 [M+H$^+$]

Example 22

2-bromo-5-(tert-butoxycarbonylamino)thiazole-4-carboxylic acid

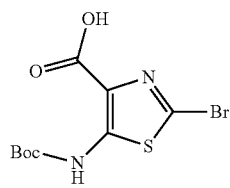 [SMILES: CC(C)(C)OC(=O)Nc1sc(Br)nc1C(=O)O]

To a solution of 5-(tert-butoxycarbonylamino)thiazole-4-carboxylic acid (1.72 g, 10 mmol) in DCM (50 mL) was added in three portions NBS (1.95 g, 11 mmol); the reaction mixture was stirred at ambient temperature for 1 h. Reaction was concentrated in vacuo; resulted residue was purified by silica gel column chromatography (6:1 Pet-ether-EtOAc) to afford 2-bromo-5-(tert-butoxycarbonylamino)thiazole-4-carboxylic acid (1.75 g, 70%) as white solid: $^1$H-NMR (CDCl$_3$, 500 MHz) δ (ppm): 13.65 (s, 1H), 10.03 (s, 1H), 1.49 (s, 9H). MS (ESI) m/z: 324 [M+H$^+$]

Example 23

5-(tert-butoxycarbonylamino)-2-(2,5-difluorophenyl)thiazole-4-carboxylic acid

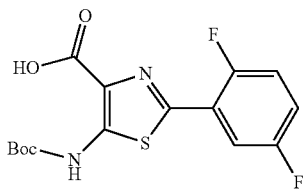 [SMILES: CC(C)(C)OC(=O)Nc1sc(-c2cc(F)ccc2F)nc1C(=O)O]

Following procedures from Examples 1-9 and shown in FIG. 2, 2,5-difluorobenzoyl chloride was converted to 5-(tert-butoxycarbonylamino)-2-(2,5-difluorophenyl)thiazole-4-carboxylic acid: $^1$H-NMR (CDCl$_3$, 500 MHz) δ (ppm): 9.68 (s, 1H), 7.87-7.91 (m, 1H), 7.15-7.26 (m, 1H), 7.08-7.13 (m, 1H), 1.57 (s, 9H); MS (ESI) m/z: 357 [M+H$^+$]

Example 24

5-(tert-butoxycarbonylamino)-2-(2,4-difluorophenyl)thiazole-4-carboxylic acid

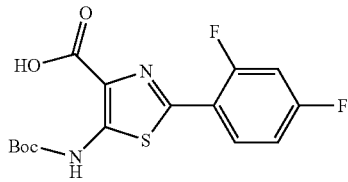 [SMILES: CC(C)(C)OC(=O)Nc1sc(-c2ccc(F)cc2F)nc1C(=O)O]

Following procedures from Examples 1-9 and shown in FIG. 2, 2,4-difluorobenzoyl chloride was converted to 5-(tert-butoxycarbonylamino)-2-(2,4-difluorophenyl)thiazole-4-carboxylic acid: $^1$H-NMR (CDCl$_3$, 500 MHz) δ (ppm): 9.66 (s, 1H), 8.16-8.21 (m, 1H), 6.95-7.04 (m, 2H), 1.62 (s, 9H); MS (ESI) m/z: 357 [M+H$^+$]

Example 25

5-(tert-butoxycarbonylamino)-2-(2,3-difluorophenyl)thiazole-4-carboxylic acid

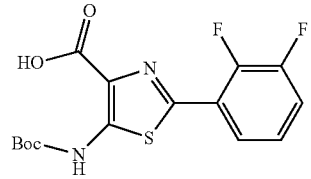 [SMILES: CC(C)(C)OC(=O)Nc1sc(-c2cccc(F)c2F)nc1C(=O)O]

Following procedures from Examples 1-9 and shown in FIG. 2, 2,3-difluorobenzoyl chloride was converted to 5-(tert-butoxycarbonylamino)-2-(2,3-difluorophenyl)thiazole-4-carboxylic acid: $^1$H-NMR (CD$_3$OD, 400 MHz) δ (ppm): 7.45 (s, 1H), 7.07-7.16 (m, 2H), 1.42 (s, 9H); MS (ESI) m/z: 357 [M+H$^+$].

Example 26

2-benzyl-5-(tert-butoxycarbonylamino)thiazole-4-carboxylic acid

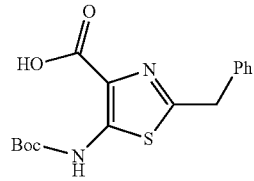 [SMILES: CC(C)(C)OC(=O)Nc1sc(Cc2ccccc2)nc1C(=O)O]

Following procedures from Examples 1-9 and shown in FIG. 2, 2-phenylacetyl chloride was converted to 2-benzyl-5-(tert-butoxycarbonylamino)thiazole-4-carboxylic acid:

¹H-NMR (CDCl₃, 500 MHz) δ (ppm): 9.63 (s, 1H), 7.27-7.35 (m, 5H), 4.25 (s, 2H), 1.50 (s, 9H); MS (ESI) m/z: 335 [M+H⁺].

Example 27

5-(tert-butoxycarbonylamino)-2-(quinolin-7-yl)thiazole-4-carboxylic acid

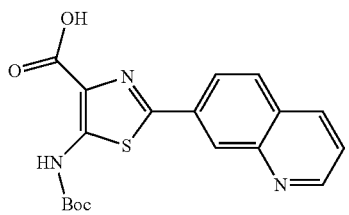 [SMILES: CC(C)(C)OC(=O)Nc1sc(-c2ccc3cccnc3c2)nc1C(=O)O]

Following procedures from Examples 1-9 and shown in FIG. 2, quinoline-7-carbonyl chloride was converted to 5-(tert-butoxycarbonylamino)-2-(quinolin-7-yl)thiazole-4-carboxylic acid: ¹H-NMR (DMSO, 500 MHz) δ (ppm): 10.14 (s, 1H), 9.11 (d, J=5 Hz, 1 h), 8.68 (s, 1H), 8.55 (s, 1H), 8.21-8.25 (m, 2H), 7.75-7.77 (m, 1H), 1.54 (s, 9H); MS (ESI) m/z: 372 [M+H⁺]

Example 28

5-(tert-butoxycarbonylamino)-2-(imidazo[1,2-a]yridine-2-yl)thiazole-4-carboxylic acid

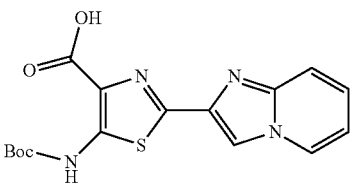 [SMILES: CC(C)(C)OC(=O)Nc1sc(-c2cn3ccccc3n2)nc1C(=O)O]

Following procedures from Examples 1-9 and shown in FIG. 2, imidazo[1,2-a]pyridine-2-carbonyl chloride was converted to 5-(tert-butoxycarbonylamino)-2-(imidazo[1,2-a]yridine-2-yl)thiazole-4-carboxylic acid: ¹H-NMR (DMSO, 500 MHz) δ (ppm): 10.12 (s, 1H), 8.58 (d, 5 Hz, 1H), 8.45 (s, 1H), 7.61 (d, 5 Hz, 1H), 7.31-7.34 (m, 1H), 6.97-6.99 (m, 1H), 1.53 (s, 9H); MS (ESI) m/z: 361 [M+H⁺].

Example 29

5-(tert-butoxycarbonylamino)-2-tert-butylthiazole-4-carboxylic acid

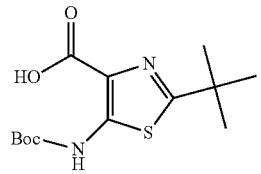 [SMILES: CC(C)(C)OC(=O)Nc1sc(C(C)(C)C)nc1C(=O)O]

Following procedures from Examples 1-9 and shown in FIG. 2, pivaloyl chloride was converted to 5-(tert-butoxycarbonylamino)-2-tert-butylthiazole-4-carboxylic acid: ¹H-NMR (CDCl₃, 500 MHz) δ (ppm): 9.55 (s, 9H), 1.42 (s, 9H); MS (ESI) m/z: 301 [M+H⁺].

Example 30

5-(tert-butoxycarbonylamino)-2-(3-chlorophenyl)thiazole-4-carboxylic acid

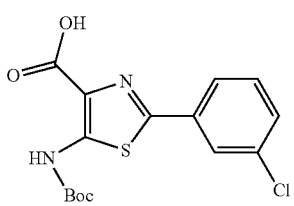 [SMILES: CC(C)(C)OC(=O)Nc1sc(-c2cccc(Cl)c2)nc1C(=O)O]

Following procedures from Examples 1-9 and shown in FIG. 2, 3-chlorobenzoyl chloride was converted to 5-(tert-butoxycarbonylamino)-2-(3-chlorophenyl)thiazole-4-carboxylic acid: ¹H-NMR (DMSO, 500 MHz) δ (ppm): 9.67 (s, 1H), 7.91 (s, 1H), 7.72 (d, J=7 Hz, 1H), 7.38-7.40 (m, 2H), 1.56 s, 9H); MS (ESI) m/z: 355 [M+H⁺].

Example 31

5-(tert-butoxycarbonylamino)-2-(4-chlorophenyl)thiazole-4-carboxylic acid

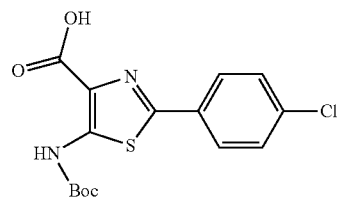 [SMILES: CC(C)(C)OC(=O)Nc1sc(-c2ccc(Cl)cc2)nc1C(=O)O]

Following procedures from Examples 1-9 and shown in FIG. 2, 4-chlorobenzoyl chloride was converted to 5-(tert-butoxycarbonylamino)-2-(4-chlorophenyl)thiazole-4-carboxylic acid: ¹H-NMR (DMSO, 500 MHz) δ (ppm): 9.66 (s, 1H), 7.81 (d, J=8.5 Hz, 2H), 7.42 (d, J=8.5 Hz, 2H), 1.56 (s, 9H); MS (ESI) m/z: 355 [M+H⁺].

Example 32

5-amino-N-(1-methyl-1H-pyrazol-4-yl)thiazole-4-carboxamide

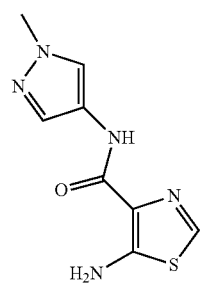

Following the procedures shown in FIG. 4, 1-methyl-1H-pyrazol-4-amine, 5-(tert-butoxycarbonylamino)thiazole-4-carboxylic acid were reacted to give 5-amino-N-(1-methyl-1H-pyrazol-4-yl)thiazole-4-carboxamide as a white solid (13 mg, 32%) over two steps. ESIMS m/z=336.1 (M+1)

Example 33

2-(4-Cyclopropyl-2-fluorophenyl)-4,4,5,5-tetramethyl-1,3,2-dioxaborolane

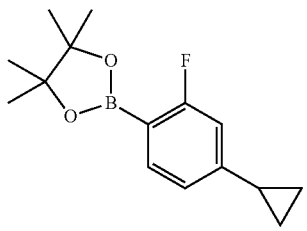 [SMILES: CC1(C)OB(c2ccc(C3CC3)cc2F)OC1(C)C]

Step A: 3-fluoro-4-nitrophenyl trifluoromethanesulfonate

To a stirred solution of 3-fluoro-4-nitrophenol (10.00 g, 63.65 mmol) and trifluoromethanesulfonic anhydride (20.0 mL, 119 mmol, 1.87 eq.) in anhydrous DCM (100.0 mL) at 0° C. was added dropwise triethylamine (33.27 mL, 238.7 mmol, 3.75 eq.). The resultant brown reaction mixture was stirred at 0° C. for 2 h and then stirred at ambient temperature for 16 h. The reaction mixture was slowly quenched with water and extracted with DCM (3×100 mL). The combined organic layers were washed with brine (1×), dried over $Na_2SO_4$, filtered, and concentrated under reduced pressure. The crude oil was purified via flash column chromatography eluted with 0 to 65% DCM/hexane to give 15.67 g (85.1%) of 3-fluoro-4-nitrophenyl trifluoromethanesulfonate as an oil. $^1$H NMR (500 MHz, $CDCl_3$) δ 8.23 (t, J=8.52 Hz, 1H), 7.34-7.27 (m, 2H).

Step B: 4-cyclopropyl-2-fluoro-1-nitrobenzene

A mixture of 3-fluoro-4-nitrophenyl trifluoromethanesulfonate (7.15 g, 24.73 mmol), cyclopropylboronic acid (2.55 g, 29.67 mmol), [1,1'-bis(diphenylphosphino)-ferrocene]dichloropalladium(II), complexed with dichloromethane (1:1) (1.62 g, 1.98 mmol), and 2M cesium carbonate in water (19.8 mL, 39.56 mmol) in toluene (39.5 mL) was degassed for 20 min. The reaction mixture was stirred at 90° C. under $N_2$ for 2.5 h. The reaction was cooled to RT, diluted with ethyl acetate (200 mL), and filtered through a pad of Celite. The filtrate was washed with brine, dried over $Na_2SO_4$, filtered, and concentrated under reduced pressure. The crude residue was purified via flash column chromatography eluted with 0 to 75% DCM/hexane to give 4.11 g (91.7%) of 4-cyclopropyl-2-fluoro-1-nitrobenzene as an oil. $^1$H NMR (400 MHz, MeOD) δ 7.98 (dd, J=10.2, 6.6 Hz, 1H), 7.12-7.02 (m, 2H), 2.11-1.97 (m, 1H), 1.20-1.11 (m, 2H), 0.89-0.82 (m, 2H).

Step C: 4-cyclopropyl-2-fluoroaniline

A mixture of 4-cyclopropyl-2-fluoro-1-nitrobenzene (3.36 g, 18.55 mmol), powdered iron (4.35 g, 77.9 mmol), and 2M ammonium chloride in water (19.8 mL) and 3:2:1 v/v EtOH:THF:$H_2O$ (86 mL) was stirred at reflux under $N_2$ for 17 h. The reaction mixture was cooled to RT and filtered through a pad of Celite. The Celite pad was rinsed well with ethyl acetate (~50 mL). Saturated aqueous $NaHCO_3$ solution was slowly added to the filtrate to neutralize the reaction mixture. The reaction mixture was extracted with ethyl acetate (3×200 mL). The combined organic layers were washed with water and brine, dried over $Na_2SO_4$, filtered, and concentrated under reduced pressure. The crude residue was purified via flash column chromatography eluted with 0 to 75% ethyl acetate/hexane to give 2.80 g (99%) of an orange oil, which solidified at 20° C. $^1$H NMR (400 MHz, $CDCl_3$) δ 6.75-6.63 (m, 3H), 3.57 (s, 2H), 1.87-1.72 (m, 1H), 0.93-0.83 (m, 2H), 0.64-0.51 (m, 2H); MS (ESI) m/z: 152.3 [M+H]$^+$.

Step D: 4-cyclopropyl-2-fluoro-1-iodobenzene

To a stirred mixture of 4-cyclopropyl-2-fluoroaniline (1.63 g, 10.78 mmol) in water (20 mL) at 0° C. was added concentrated sulfuric acid (8.6 mL, 15.0 eq.) dropwise, while keeping the temperature constant at 0° C. A solution of sodium nitrite (781.0 mg, 11.32 mmol, 1.05 eq.) in water (2.7 mL) was added and stirred for 5 minutes. This resulting reaction mixture was then added to a solution of potassium iodide (3.76 g, 22.64 mmol, 2.1 eq.) in water (9.7 mL), and the reaction mixture was stirred at 60° C. for 3 h. DCM (400 mL) was added to the cooled reaction. The biphasic layers were separated, and the aqueous layer was extracted with DCM (2×150 mL). The combined organic layers were washed with saturated aqueous $Na_2S_2O_4$, water, and brine, dried over $Na_2SO_4$, filtered, and concentrated under reduced pressure. The crude residue was purified via flash column chromatography eluted with 100% heptane to give 2.01 g (71.28%) of 4-cyclopropyl-2-fluoro-1-iodobenzene as a clear oil. $^1$H NMR (400 MHz, $CDCl_3$) δ 7.57 (dd, J=8.0, 6.9 Hz, 1H), 6.76 (dd, J=9.4, 1.9 Hz, 1H), 6.64 (dd, J=8.2, 1.9 Hz, 1H), 1.94-1.77 (m, 1H), 1.09-0.95 (m, 2H), 0.79-0.56 (m, 2H).

Step E

In a high pressure tube was placed 4-cyclopropyl-2-fluoro-1-iodobenzene (1.32 g, 5.04 mmol), bispinacol ester boronate (1.53 g, 6.04 mmol), potassium acetate (1.98 g, 20.15 mmol), [1,1'-bis(diphenylphosphino)ferrocene]dichloropalladium (II) (368.5 mg, 0.50 mmol), and N,N-dimethylformamide (35 mL). The reaction mixture was degassed with $N_2$ for 15 minutes. The vessel was sealed and the reaction mixture was stirred at 90° C. for 16 h. The cooled reaction mixture was diluted with ethyl acetate (75 mL) and water (25 mL) and then filtered through a pad of Celite. The biphasic layers were separated and the organic layer was washed with water and brine, dried over $Na_2SO_4$, filtered, and concentrated under reduced pressure. The crude residue was purified via flash column chromatography eluted with 0 to 75% EA/heptane to give 859.0 mg (65.1%) of 2-(4-cyclopropyl-2-fluorophenyl)-4,4,5,5-tetramethyl-1,3,2-dioxaborolane as a clear oil. $^1$H NMR (400 MHz, $CDCl_3$) δ 7.58 (s, 1H), 6.83 (d, J=7.7 Hz, 1H), 6.68 (d, J=10.8 Hz, 1H), 1.91-1.81 (m, 1H), 1.33 (s, 12H), 0.98 (dd, J=8.3, 2.0 Hz, 2H), 0.74-0.66 (m, 2H)

Example 34

5-Chloro-1-ethyl-4-nitro-1H-pyrazole

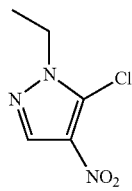

Following the procedure for Example 1 starting with 1-ethyl-4-nitropyrazole gave 5-chloro-1-ethyl-4-nitro-1H-pyrazole as a colorless solid (1.3 g, 74%). $^1$H-NMR (400 MHz, CDCl$_3$) δ 8.16 (s, 1H), 4.26 (q, J=7 Hz, 2H), 1.50 (t, J=7 Hz, 3H).

Example 35

5-Chloro-1-cyclopropylmethyl-4-nitro-1H-pyrazole

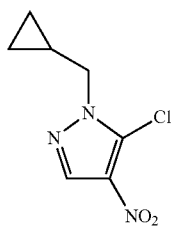 [SMILES: O=[N+]([O-])c1cnn(CC2CC2)c1Cl]

Following the procedure for Example 1 starting with 1-cyclopropylmethyl-4-nitropyrazole gave 5-chloro-1-cyclopropylmethyl-4-nitro-1H-pyrazole as a colorless oil (1.16 g, 56%). $^1$H-NMR (400 MHz, CDCl$_3$) δ 8.17 (s, 1H), 4.07 (d, J=7 Hz, 2H), 1.39-1.28 (m, 1H), 0.66-0.59 (m, 2H), 0.50-0.40 (m, 2H).

Example 36

5-Chloro-1-cyclopropyl-4-nitro-1H-pyrazole

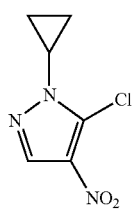 [SMILES: O=[N+]([O-])c1cnn(C2CC2)c1Cl]

Following the procedure for Example 1 starting with 1-cyclopropyl-4-nitropyrazole gave 5-chloro-1-cyclopropyl-4-nitro-1H-pyrazole as a colorless solid (0.23 g, 63%). $^1$H-NMR (400 MHz, CDCl$_3$) δ 8.09 (s, 1H), 3.62-3.54 (m, 1H), 1.38-1.28 (m, 2H), 1.25-1.13 (m, 2H).

Example 37

5-Chloro-1-(2,2-difluoroethyl)-4-nitro-1H-pyrazole

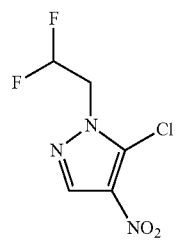 [SMILES: O=[N+]([O-])c1cnn(CC(F)F)c1Cl]

To a stirred solution of 1-(2,2-difluoroethyl)-4-nitro-1H-pyrazole (1.0 g, 5.13 mmol) in dry THF (20 mL) cooled to −70° C. was added dropwise a solution of lithium hexamethyldisilazide (1 M in THF, 8.47 mL, 8.47 mmol). After stirring at −70° C. for 40 min, the reaction mixture was allowed to warm to −55° C. over 20 min. After recooling to −70° C., a solution of perchloroethane (1.74 g, 7.34 mmol) in THF (10 mL) was added slowly and the reaction mixture was stirred at −70° C. for 1.5 hr. Saturated aqueous ammonium chloride solution (30 mL) was added followed by water (15 mL) and the mixture was extracted with EtOAc (3×100 mL). The combined organic layers were dried over MgSO$_4$ and the solvent removed under reduced pressure. Purification of the residue by silica gel column chromatography (0-100% EtOAc/isohexane) gave 5-chloro-1-(2,2-difluoroethyl)-4-nitro-1H-pyrazole as an off-white solid (438 mg, 37%). $^1$H NMR (400 MHz, CDCl$_3$) δ 8.24 (s, 1H), 6.18 (tt, J=54.8, 4.2 Hz, 1H), 4.58 (td, J=12.8, 4.2 Hz, 2H).

Example 38

5-Chloro-1-cyclopropyl-4-nitro-1H-pyrazole

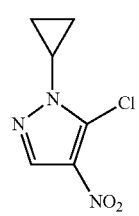

Following Example 37, chlorination of 1-cyclopropyl-4-nitropyrazole gave 5-chloro-1-cyclopropyl-4-nitro-1H-pyrazole as a colorless solid (0.23 g, 63%). $^1$H-NMR (400 MHz, CDCl$_3$) δ 8.09 (s, 1H), 3.62-3.54 (m, 1H), 1.38-1.28 (m, 2H), 1.25-1.13 (m, 2H).

Example 39

5-Chloro-1-(4-methoxybenzyl)-4-nitro-1H-pyrazole

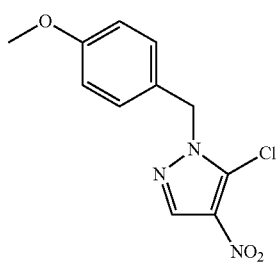 [SMILES: COc1ccc(Cn2ncc([N+](=O)[O-])c2Cl)cc1]

Following Example 37, chlorination of 1-(4-methoxybenzyl)-4-nitro-1H-pyrazole gave 5-chloro-1-(4-methoxybenzyl)-4-nitro-1H-pyrazole as a yellow solid (536 mg, 46%). $^1$H NMR (400 MHz, CDCl$_3$) δ 8.17 (s, 1H), 7.25 (d, J=8.3 Hz, 2H), 6.89 (d, J=8.3 Hz, 2H), 5.30 (s, 2H), 3.80 (s, 3H).

Example 40

5-Bromo-4-nitro-1-(2,2,2-trifluoroethyl)-1H-pyrazole

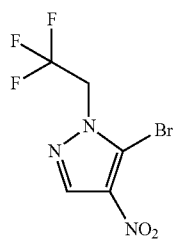

To a stirred solution of 1-(2,2,2-trifluoroethyl)-1H-pyrazol-5-amine (990 mg, 6.0 mmol) in acetic acid (5 mL) was added dropwise acetic anhydride (0.57 mL, 6.0 mmol) and the mixture was stirred at room temperature for 16 hr. More acetic anhydride (0.57 mL, 6.0 mmol) was added to the reaction mixture which was cooled in an ice bath for the addition of fuming nitric acid (0.28 mL, 6 mmol) to take place dropwise. The reaction mixture was stirred at room temperature for 7 hr and the solvent was removed under reduced pressure. The residue was dissolved in EtOH (15 mL) and concentrated hydrochloric acid (10 mL) was added. The mixture was heated at reflux for 16 hr. After concentrating under reduced pressure the residue was partitioned between DCM (50 mL) and 5% aqueous NaHCO$_3$ solution (100 mL). The mixture was filtered and the aqueous layer was extracted with DCM (100 mL). The organic layers were combined, dried over MgSO$_4$ and the solvent removed under reduced pressure to give a pale orange solid (540 mg). This solid (540 mg, 2.57 mmol) was dissolved in bromoform (2.9 mL, 33 mmol) and to the solution was added dropwise tert-butyl nitrite (0.92 mL, 7.71 mmol). The reaction mixture was stirred at room temperature for 15 min and then heated at 145° C. for 1.5 hr. The solvent was removed under reduced pressure and the residue purified by silica gel column chromatography (0-100% EtOAc/isohexane) to give 5-bromo-4-nitro-1-(2,2,2-trifluoroethyl)-1H-pyrazole as a pale yellow solid (536 mg, 33% over four steps). $^1$H NMR (400 MHz, CDCl$_3$) δ 8.30 (s, 1H), 4.86 (q, J=7.8 Hz, 2H).

Example 41

5-Chloro-1-ethyl-4-nitro-1H-pyrazole

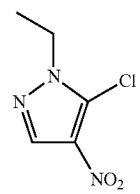

Following the procedure for Intermediate 5 starting with 1-ethyl-4-nitropyrazole gave 5-chloro-1-ethyl-4-nitro-1H-pyrazole as a colorless solid (1.3 g, 74%). $^1$H-NMR (400 MHz, CDCl$_3$) δ 8.16 (s, 1H), 4.26 (q, J=7 Hz, 2H), 1.50 (t, J=7 Hz, 3H).

Example 42

1-((3-Methyloxetan-3-yl)methyl)-1H-pyrazol-4-amine

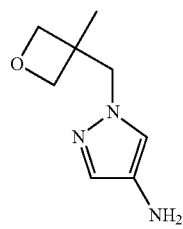

A mixture of 4-nitropyrazole (1.13 g, 10 mmol) and K$_2$CO$_3$ (3.4 g, 25 mmol) in MeCN (50 mL) was stirred at room temperature for 15 min prior to addition of 3-(bromomethyl)-3-methyloxetane (1.8 g, 11 mmol). The reaction mixture was stirred at room temperature for 18 hr, filtered and the filter cake washed with MeCN. The filtrate was concentrated under reduced pressure and the residue purified by silica gel column chromatography (0-100% EtOAc/isohexane) gradient to afford 1-((3-methyloxetan-3-yl)methyl)-4-nitro-1H-pyrazole as a colorless solid (1.43 g, 73%). A portion of this solid (206 mg, 1.04 mmol) dissolved in MeOH (20 mL) was treated with ammonium formate (260 mg, 4.13 mmol) and 10% palladium on carbon (50 mg). The mixture was heated at 80° C. for 1.5 hr, cooled, filtered through Celite® and the filtrate concentrated under reduced pressure to afford 1-((3-methyloxetan-3-yl)methyl)-1H-pyrazol-4-amine as a pale pink gum (160 mg, 92%). $^1$H NMR (400 MHz, CDCl$_3$) δ 7.15 (s, 1H), 6.97 (s, 1H), 4.66 (d, J=6.1 Hz, 2H), 4.37 (d, J=6.1 Hz, 2H), 4.19 (s, 2H), 2.91 (s, 2H), 1.23 (s, 3H).

Example 43

5-Chloro-1-cyclopropylmethyl-4-nitro-1H-pyrazole

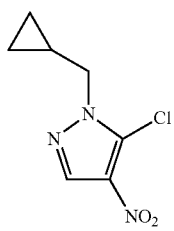

Following the procedure for Intermediate 5 starting with 1-cyclopropylmethyl-4-nitropyrazole gave 5-chloro-1-cyclopropylmethyl-4-nitro-1H-pyrazole as a colorless oil (1.16 g, 56%). $^1$H-NMR (400 MHz, CDCl$_3$) δ 8.17 (s, 1H), 4.07 (d, J=7 Hz, 2H), 1.39-1.28 (m, 1H), 0.66-0.59 (m, 2H), 0.50-0.40 (m, 2H).

Example 44

5-Amino-N-(5-chloro-1-methyl-1H-pyrazol-4-yl)-2-(2,6-difluorophenyl)thiazole-4-carboxamide

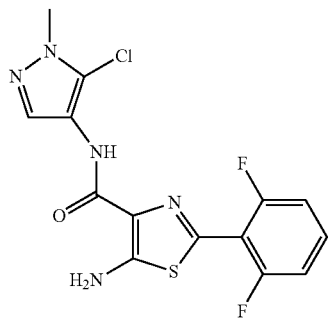 [SMILES: Cn1ncc(NC(=O)c2nc(-c3c(F)cccc3F)sc2N)c1Cl]

Following the procedure for Intermediate 1 starting from 3-chloro-1-methyl-1H-pyrazol-4-amine gave 5-Amino-N-(5-chloro-1-methyl-1H-pyrazol-4-yl)-2-(2,6-difluorophenyl)thiazole-4-carboxamide as an off-white solid (146 mg, 46% over 3 steps). $^1$H NMR (400 MHz, d$_6$-DMSO) δ 8.89 (s, 1H), 7.74 (s, 1H), 7.60-7.50 (m, 3H), 7.28 (t, J=8.6 Hz, 2H), 3.80 (s, 3H). LCMS (ES+) m/z 370 (M+1).

Example 45

5-Amino-2-(2,6-difluorophenyl)-N-(1-(3-methoxypropyl)-1H-pyrazol-4-yl)thiazole-4-carboxamide

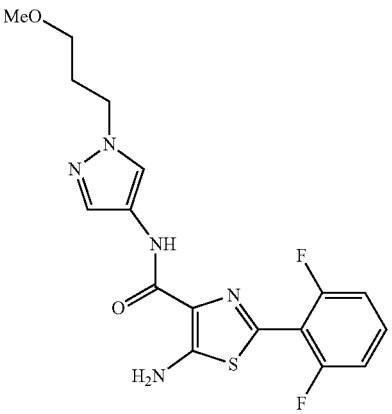 [SMILES: COCCCn1cc(NC(=O)c2nc(-c3c(F)cccc3F)sc2N)cn1]

Following the procedure for Intermediate 1 gave, after purification via preparative HPLC, 5-Amino-2-(2,6-difluorophenyl)-N-(1-(3-methoxypropyl)-1H-pyrazol-4-yl)thiazole-4-carboxamide (0.14 g, 28% over two steps) as a cream solid. $^1$H (400 MHz, d$_6$-DMSO) δ 9.75 (s, 1H), 7.97 (s, 1H), 7.67 (s, 1H), 7.58-7.52 (m, 3H), 7.30-7.25 (m, 2H), 4.09 (t, J=17.0 Hz, 2H), 3.27 (s, 3H), 3.23 (t, J=15.4 Hz, 2H), 1.98-1.93 (m, 2H). LCMS (ES+) m/z 394 (M+1)

Example 46

5-Amino-2-(2,6-difluorophenyl)-N-(1-(tetrahydro-2H-pyran-4-yl)-1H-pyrazol-4-yl)thiazole-4-carboxamide

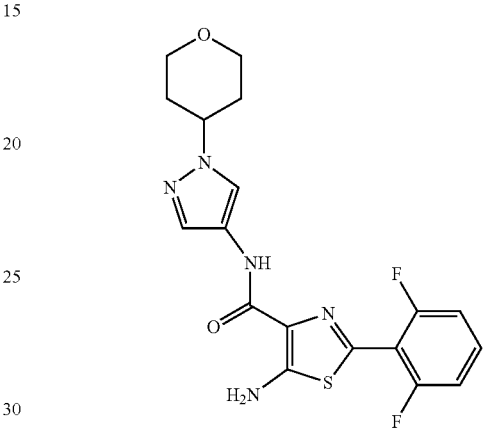

Following the procedure for Intermediate 1 gave, after purification via preparative HPLC, 5-Amino-2-(2,6-difluorophenyl)-N-(1-(tetrahydro-2H-pyran-4-yl)-1H-pyrazol-4-yl)thiazole-4-carboxamide (0.17 g, 43% over two steps) as a light brown solid. $^1$H (400 MHz, d$_6$-DMSO) δ 9.75 (s, 1H), 8.03 (s, 1H), 7.70 (s, 1H), 7.58-7.52 (m, 3H), 7.29-7.25 (m, 2H), 4.40-4.36 (m, 1H), 3.97-3.93 (m, 2H), 3.49-3.43 (m, 2H), 1.97-1.87 (m, 4H) LCMS (ES+) m/z 406 (M+1).

Intermediate 1 tert-Butyl 4-(5-chloro-1-methyl-1H-pyrazol-4-ylcarbamoyl)-2-(2,6-difluorophenyl)thiazol-5-ylcarbamate

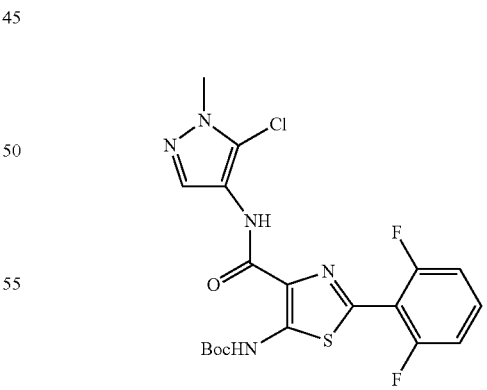

A solution of PyBOP (4.08 g, 7.84 mmol) and 5-((tert-butoxycarbonyl)amino)-2-(2,6-difluorophenyl)thiazole-4-carboxylic acid (2.20 g, 6.16 mmol) in DCM (50 mL) was stirred at room temperature for 30 min. A solution of 5-chloro-1-methyl-1H-pyrazol-4-amine (737 mg, 5.60 mmol) and DIPEA (1.6 mL, 9.0 mmol) in DCM (50 mL) was then added and the mixture stirred at room temperature for 16 hr. The mixture was diluted with DCM (50 mL) and washed with water (3×50 mL). The organic layer was separated, passed through a phase separation cartridge and concentrated under reduced pressure. Purification via silica gel chromatography (0-100% EtOAc/isohexane) followed by trituration with MeCN gave tert-butyl 4-(5-chloro-1-methyl-1H-pyrazol-4-ylcarbamoyl)-2-(2,6-difluorophenyl)thiazol-5-ylcarbamate as an off-white solid (1.71 g, 65%). $^1$H NMR (400 MHz, CDCl$_3$) δ 10.32 (s, 1H), 8.73 (s, 1H), 8.06 (s, 1H), 7.42-7.33 (m, 1H), 7.09-7.01 (m, 2H), 3.87 (s, 3H), 1.54 (s, 9H).

Intermediate 2 5-(3,4-Dihydro-2H-pyran-6-yl)-1-methyl-4-nitro-1H-pyrazole

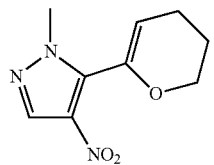

A mixture of 5-chloro-1-methyl-4-nitro-1H-pyrazole (200 mg, 1.25 mmol), potassium fluoride dihydrate (235 mg, 2.5 mmol) and 3,4-dihydro-2H-pyran-6-boronic acid pinacol ester (394 mg, 1.88 mmol) in THF (3 mL) was degassed by bubbling nitrogen through it for 15 min. Tris(dibenzylideneacetone)dipalladium/tri-tert-butyl phosphonium tetrafluoroborate mixture (mole ratio: 1/1.2, 151 mg, 0.13 mmol) was added and the mixture degassed for a further 10 min before being heated in the microwave at 85° C. for 2 hr. Water (10 mL) was added and the mixture extracted with EtOAc (3×5 mL). The combined organic layers were passed through a phase separation cartridge and concentrated under reduced pressure. Purification via silica gel chromatography (0-5% EtOAc/isohexane) gave 5-(3,4-dihydro-2H-pyran-6-yl)-1-methyl-4-nitro-1H-pyrazole as a yellow solid (215 mg, 82%). $^1$H NMR (400 MHz, CDCl$_3$) δ 8.04 (s, 1H), 5.22 (t, J=3.9 Hz, 1H), 4.20 (t, J=5.1 Hz, 2H), 3.88 (s, 3H), 2.31-2.24 (m, 2H), 2.05-1.96 (m, 2H).

Intermediate 3 2-Methyl-4-nitro-pyrazole-3-carbaldehyde

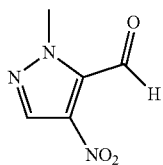

Nitrogen was bubbled through a solution of 3-chloro-2-methyl-4-nitro-pyrazole (16 g, 100 mmol), potassium vinyltrifluoroborate (18 g, 134 mmol) and cesium carbonate (3.7 M in water, 50 mL, 190 mmol) in DMF (100 mL). 1,1'-Bis(diphenylphosphino)ferrocene-palladium(II)dichloride dichloromethane complex (900 mg, 1.10 mmol) was added and degassing continued for 30 min. The reaction mixture was heated at 110° C. for 18 hr. More 1,1'-bis(diphenylphosphino)ferrocene-palladium(II)dichloride dichloromethane complex (900 mg, 1.10 mmol) was added and heating continued for 24 hr. More 1,1'-bis(diphenylphosphino)ferrocene-palladium(II)dichloride dichloromethane complex (400 mg, 0.49 mmol) was added and heating continued for 4 hr. The reaction was cooled to room temperature and brine (200 mL) and EtOAc (500 mL) were added. The organic layer was washed with water (4×300 mL), separated, dried over Na$_2$SO$_4$ and concentrated under reduced pressure. Purification via silica gel column chromatography (0-40% EtOAc/isohexane) gave 1-methyl-4-nitro-5-vinyl-1H-pyrazole as a colourless solid (9.1 g). Through a solution of this solid (9.1 g, 59 mmol) in DCM (400 mL) cooled to −78° C. was bubbled ozone. When the solution turned blue, ozone addition was stopped. Nitrogen was passed through the solution until the blue colour was discharged. The mixture was allowed to warm to room temperature and flushed with nitrogen for 15 min Anhydrous dimethyl sulfide (5 mL) was added and the mixture warmed to room temperature. After stirring for 12 hr, the solvents were removed under reduced pressure. DCM (150 mL) was added and the mixture was washed with water (50 mL). The aqueous layer was extracted with DCM (3×100 mL) and the combined organic layers were washed with brine (100 mL), separated, dried over Na$_2$SO$_4$ and concentrated to give 2-methyl-4-nitro-pyrazole-3-carbaldehyde as a yellow-orange solid (6.6 g, 43% over two steps). $^1$H NMR (400 MHz, CDCl$_3$) δ 10.51 (s, 1H), 8.11 (s, 1H), 4.23 (s, 3H).

Intermediate 4 1-Methyl-5-(5-methyl-6,8-dioxaspiro[2.5]octan-7-yl)-4-nitro-pyrazole

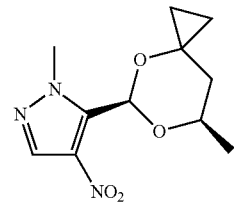 [SMILES: C[C@@H]1CC2(CC2)O[C@H](c2c([N+](=O)[O-])cnn2C)O1]

To a solution of 1-(2-hydroxypropyl)cyclopropanol (2.0 g, 17.2 mmol) in DCM (35 mL) at 0° C. was added 2,6-lutidine (5 mL, 42.9 mmol) followed by trimethylsilyl trifluoromethanesulfonate (6 mL, 32.9 mmol). The reaction mixture was warmed to room temperature and stirred for 18 hr. Additional amounts of 2,6-lutidine (5 mL, 42.9 mmol) and trimethylsilyl trifluoromethanesulfonate (6 mL, 32.9 mmol) were added at 0° C. The mixture was stirred for 1 hr and quenched with saturated aqueous NaHCO$_3$ (30 mL). The mixture was extracted with DCM (50 mL) and the organic layer was washed with aqueous 0.1 M HCl (2×15 mL) and passed through a phase separation cartridge. To this solution was added 2-methyl-4-nitro-pyrazole-3-carbaldehyde (1.40 g, 9.03 mmol) and the resulting solution was cooled to −78° C. and trimethylsilyl trifluoromethanesulfonate (4.11 mL, 22.6 mmol) added. The mixture was warmed to 0° C., stirred for 3 hr, cooled to −78° C. and additional trimethylsilyl trifluoromethanesulfonate (4.11 mL, 22.6 mmol) added. The mixture was warmed to 0° C. and stirred for 1 hr and solid sodium carbonate (2.5 g) added. The reaction mixture was stirred for 10 min before saturated aqueous NaHCO$_3$ (100 mL) was added. The organic layer was washed with water (100 mL) and brine (100 mL), separated, dried over Na$_2$SO$_4$ and concentrated under reduced pressure. Purification via silica gel column chromatography (0-100% EtOAc/isohexane) gave 1-methyl-5-(5-methyl-6,8-dioxaspiro[2.5]octan-7-yl)-4-nitro-pyrazole as a colourless solid (1.0 g, 44% over two steps). $^1$H NMR (400 MHz, CDCl$_3$) δ 8.00 (s, 1H), 6.59 (s, 1H), 4.29-4.02 (m, 4H), 2.33-2.23 (m, 1H), 1.33 (d, J=6.2 Hz, 3H), 1.17-1.12 (m, 1H), 1.02-0.89 (m, 2H), 0.70-0.52 (m, 2H).

Intermediate 5 2-Methyl-7-(2-methyl-4-nitro-pyrazol-3-yl)oxepan-4-one

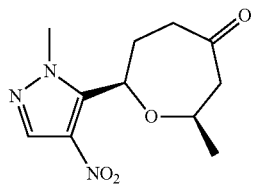 [SMILES: C[C@@H]1CC(=O)CC[C@H](c2c([N+](=O)[O-])cnn2C)O1]

To a solution of 1-methyl-5-(5-methyl-6,8-dioxaspiro[2.5]octan-7-yl)-4-nitro-pyrazole (1.0 g, 3.95 mmol) in DCM (20 mL) at −78° C. was added titanium tetrachloride (6.6 mL, 59.3 mmol) dropwise. Halfway through the addition, the reaction mixture became harder to stir so more DCM (10 mL) was added. The brown slurry was warmed to 0° C. and stirred for 1 hr. Solid sodium carbonate (5 g) was cautiously added followed by saturated aqueous NaHCO$_3$ (100 mL) and DCM (100 mL). The organic layer was washed with saturated aqueous NaHCO$_3$, (100 mL) and brine (100 mL), separated, dried over Na$_2$SO$_4$ and concentrated under reduced pressure. Purification via silica gel column chromatography (0-100% EtOAc/isohexane) gave 2-methyl-7-(2-methyl-4-nitro-pyrazol-3-yl)oxepan-4-one as a colourless solid (749 mg, 75%). $^1$H NMR (400 MHz, CDCl$_3$) δ 8.02 (s, 1H), 5.69 (dd, J=11.0, 2.4 Hz, 1H), 4.21-4.14 (m, 1H), 4.01 (s, 3H), 3.07-2.97 (m, 1H), 2.79-2.63 (m, 3H), 2.19-2.07 (m, 1H), 2.07-1.91 (m, 1H), 1.30 (d, J=6.2 Hz, 3H).

Intermediate 6 2-Methyl-7-(2-methyl-4-nitro-pyrazol-3-yl)oxepan-4-ol

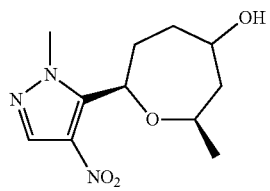 [SMILES: C[C@@H]1CC(O)CC[C@H](c2c([N+](=O)[O-])cnn2C)O1]

To a solution of 2-methyl-7-(2-methyl-4-nitro-pyrazol-3-yl)oxepan-4-one (65 mg, 0.26 mmol) in THF (1 mL) under nitrogen cooled to −78° C. was added dropwise a solution of L-selectride (1 M in THF, 0.28 mL, 0.28 mmol). After 1 hr the mixture was quenched with MeOH (1 mL) and warmed to room temperature. EtOAc (10 mL) and brine (10 mL) were added and the layers separated. The aqueous layer was extracted with EtOAc (3×10 mL) and the combined organic layers were washed with brine (10 mL), separated, dried over Na$_2$SO$_4$ and concentrated under reduced pressure. Purification via silica gel column chromatography (0-100% EtOAc/isohexane) gave 2-methyl-7-(2-methyl-4-nitro-pyrazol-3-yl)oxepan-4-ol as a colourless solid (54 mg, 81%). $^1$H NMR (400 MHz, CDCl$_3$) δ 8.01 (2s, 1H), 5.63-5.59 and 5.56-5.50 (2m, 1H), 4.26-4.01 (m, 5H), 3.88-3.73 (m, 1H), 2.21-1.72 (m, 4H), 1.28-1.23 (m, 3H), 0.99-0.81 (m, 2H).

Intermediate 7 5-Amino-2-(2,6-difluorophenyl)thiazole-4-carboxylic acid

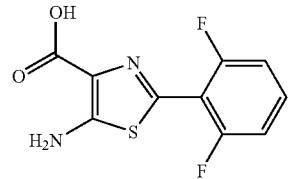 [SMILES: Nc1sc(-c2c(F)cccc2F)nc1C(=O)O]

To a solution of 5-(tert-butoxycarbonylamino)-2-(2,6-difluorophenyl)thiazole-4-carboxylic acid (530 mg, 1.49 mmol) in MeOH (10 mL) was added HCl in dioxane (4 M, 5 mL, 20.0 mmol). The reaction mixture was stirred at room temperature for 48 hr and the solvents removed under reduced pressure to give 5-amino-2-(2,6-difluorophenyl)thiazole-4-carboxylic acid as the hydrochloride salt. $^1$H NMR (400 MHz, d$_6$-DMSO) δ 7.57-7.45 (m, 1H), 7.29-7.18 (m, 2H), 5.30 (br s, 3H).

Intermediate 8 5-(1-Allyloxypent-4-enyl)-1-methyl-4-nitro-pyrazole

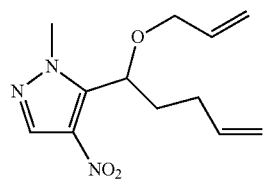 [SMILES: C=CCCC(OCC=C)c1c([N+](=O)[O-])cnn1C]

To a solution of 1-methyl-4-nitro-pyrazole (9.7 g, 76.7 mmol) and pent-4-enal (10.0 g, 84.4 mmol) in THF (250 mL) at −78° C. was added dropwise a solution of LiHMDS in THF (1 M, 192 mL, 191.7 mmol). The reaction mixture was allowed to warm to −40° C. and stirred for 4 hr. The reaction was quenched with a saturated solution of ammonium chloride (100 mL), warmed to room temperature and the solvents removed under reduced pressure. The residue was dissolved in EtOAc (100 mL) and washed with water (30 mL). The organic layer was separated, dried over MgSO$_4$ and concentrated under reduced pressure. Purification via silica gel column chromatography (0-30% EtOAc/isohexane) gave a clear oil. This oil (7.1 g, 33.6 mmol), diallyl carbonate (14.33 g, 100.9 mmol) and triphenylphosphine (880 mg, 3.35 mmol) were dissolved in dioxane (236 mL) under nitrogen before tris(dibenzylideneacetone)-dipalladium(0) (780 mg, 0.84 mmol) was added. The reaction mixture was heated at 50° C. for 1 hr and the solvent removed under reduced pressure. Purification via silica gel column chromatography (0-40% EtOAc/isohexane) gave 5-(1-allyloxypent-4-enyl)-1-methyl-4-nitro-pyrazole as a yellow oil (8.35 g, 43% over two steps). $^1$H NMR (400 MHz, CDCl$_3$) δ 8.06 (s, 1H), 5.90-5.73 (m, 2H), 5.46 (dd, J=8.8, 5.1 Hz, 1H), 5.29-5.16 (m, 2H), 5.10-

5.00 (m, 2H), 4.04 (s, 3H), 3.92 (d, J=5.8 Hz, 2H), 2.37-2.25 (m, 1H), 2.22-2.09 (m, 1H), 2.09-1.96 (m, 1H), 1.84 (dddd, J=13.7, 9.2, 6.9, 5.1 Hz, 1H).

Intermediate 9 1-Methyl-4-nitro-5-(2,3,4,7-tetrahydrooxepin-2-yl)pyrazole

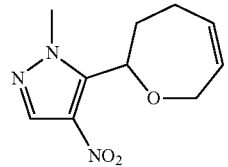

5-(1-Allyloxypent-4-enyl)-1-methyl-4-nitro-pyrazole (5 g, 19.92 mmol) was dissolved in toluene (1 L) and the mixture was degassed for 30 min before Benzylidene-bis(tricyclohexylphosphine)dichlororuthenium, Bis(tricyclohexylphosphine)benzylidine ruthenium(IV) dichloride, "Grubbs 1st generation catalyst" CAS No. 172222-30-9, Sigma-Aldrich Product No. 579726, U.S. Pat. No. 6,111,121, (878 mg, 0.99 mmol) was added. The reaction mixture was further degassed for 20 min, then heated at reflux for 2 hr, cooled to room temperature and filtered through Celite®. The filtrate was concentrated under reduced pressure. The residue was dissolved in EtOAc (200 mL), washed with aqueous 1 M HCl (150 mL), water (150 mL), saturated aqueous NaHCO$_3$ (2×150 mL) and brine (150 mL). The organic layer was separated, dried over MgSO$_4$ and concentrated under reduced pressure. Purification via silica gel column chromatography (0-20% EtOAc/isohexane) gave 1-methyl-4-nitro-5-(2,3,4,7-tetrahydrooxepin-2-yl)pyrazole as a clear oil (3.3 g, 75%). $^1$H NMR (400 MHz, CDCl$_3$) δ 8.02 (s, 1H), 5.99-5.91 (m, 1H), 5.83-5.76 (m, 1H), 5.59 (dd, J=9.4, 3.0 Hz, 1H), 4.42 (dd, J=15.8, 5.5 Hz, 1H), 4.24-4.17 (m, 1H), 4.06 (s, 3H), 2.58-2.48 (m, 1H), 2.46-2.36 (m, 1H), 2.14 (ddt, J=14.1, 6.8, 3.5 Hz, 1H), 1.99-1.88 (m, 1H).

Intermediate 10 7-(2-Methyl-4-nitro-pyrazol-3-yl)oxepane-3,4-diol

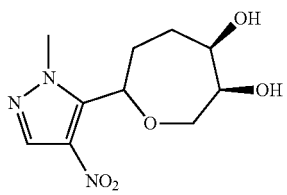 [SMILES: Cn1ncc([N+](=O)[O-])c1C1CC[C@@H](O)[C@@H](O)CO1]

To a solution of AD-mix α (1.51 g) in tert-butanol (5.4 mL) and water (5.5 mL) at 0° C. was added a solution of 1-methyl-4-nitro-5-(2,3,4,7-tetrahydrooxepin-2-yl)pyrazole (240 mg, 1.08 mmol) in tert-butanol (0.8 mL). The reaction mixture was stirred at 0° C. for 1 hr before solid sodium thiosulfate (1.4 g) was added slowly. The mixture was stirred for a further 1 hr and diluted with EtOAc (20 mL). The aqueous layer was extracted with EtOAc (4×15 mL) and the organic layers were combined, dried over MgSO$_4$ and concentrated under reduced pressure. Purification via silica gel column chromatography (0-2.5% MeOH/EtOAc) gave 7-(2-methyl-4-nitro-pyrazol-3-yl)oxepane-3,4-diol as a colourless solid (30 mg, 10%). $^1$H NMR (400 MHz, CDCl$_3$) δ 8.06-7.98 (m, 1H), 5.49 (dd, J=8.9, 5.7 Hz, 1H), 4.20 (dd, J=13.7, 3.2 Hz, 1H), 4.16-4.10 (m, 1H), 4.09 (s, 3H), 4.04-3.97 (m, 1H), 3.73 (dd, J=13.7, 2.5 Hz, 1H), 2.53-2.46 (m, 1H), 2.32 (dtd, J=14.3, 8.8, 4.9 Hz, 1H), 2.23 (d, J=5.8 Hz, 1H), 2.19-2.01 (m, 2H), 1.84-1.75 (m, 1H).

Intermediate 11 1-Methyl-5-(5-ethyl-6,8-dioxaspiro [2.5]octan-7-yl)-4-nitro-pyrazole

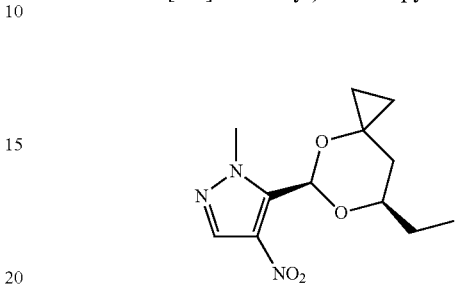

To a solution of (3R)-ethyl 3-hydroxybutanoate (2.5 g, 18.9 mmol) in THF (100 mL) under nitrogen was added a solution of titanium(IV) isopropoxide (6.02 mL, 19.9 mmol) in THF (15 mL) followed by a solution of ethyl magnesium bromide in diethyl ether (3 M, 30.2 mL, 90.7 mmol) dropwise over a period of 2 hr. The reaction mixture was stirred for a further 2 hr, before being cooled to 0° C. and quenched by the slow addition of a saturated aqueous ammonium chloride (75 mL). The solution was filtered and the filtrate extracted with DCM (3×20 mL). The combined organic layers were washed with brine (75 mL), separated, dried over MgSO$_4$ and concentrated under reduced pressure. Purification via silica gel column chromatography (0-100% EtOAc/isohexane) gave 1-[(2R)-2-hydroxybutyl]-cyclopropanol as a yellow oil (1.50 g). To a solution of this oil (900 mg, 7.76 mmol) in DCM (15 mL) cooled to 0° C. was added 2,6-lutidine (2.26 mL, 19.40 mmol) followed by trimethylsilyl trifluoromethanesulfonate (3.1 mL, 17.10 mmol). The reaction mixture was stirred at 0° C. for 2 hr before additional 2,6-lutidine (2.26 mL, 19.40 mmol) and trimethylsilyl trifluoromethanesulfonate (3.1 mL, 17.10 mmol) were added. The reaction mixture was allowed to warm to room temperature and stirred for 18 hr. The mixture was cooled to 0° C., quenched with 0.1 M aqueous HCl (15 mL) and extracted with DCM (50 mL). The organic layer was washed with 0.1 M aqueous HCl (2×15 mL) and passed through a phase separation cartridge. To this solution was added 2-methyl-4-nitro-pyrazole-3-carbaldehyde (1.90 g, 7.13 mmol) and the resulting solution was cooled to −78° C. before trimethylsilyl trifluoromethanesulfonate (0.64 mL, 3.56 mmol) was added dropwise. The mixture was warmed to 0° C. and stirred for 3 hr before being cooled to −78° C. and additional trimethylsilyl trifluoromethanesulfonate (1 mL, 5.49 mmol) was added. After stirring at 0° C. for 3 hr the procedure was repeated. The reaction mixture was stirred at 0° C. for a further 2 hr before solid sodium carbonate (2.5 g) was added. The reaction mixture was stirred for 10 min and a saturated solution of NaHCO$_3$ (10 mL) was added. The organic layer was washed with water (10 mL) and brine (10 mL), separated, dried over Na$_2$SO$_4$ and concentrated under reduced pressure. Purification via silica gel column chromatography (0-100% EtOAc/isohexane) gave 1-methyl-5-(5-ethyl-6,8-dioxaspiro[2.5]octan-7-yl)-4-nitro-pyrazole as a colourless solid (655 mg, 4% over three steps). $^1$H NMR (400 MHz, CDCl$_3$) δ 8.00 (s, 1H), 6.58 (s, 1H), 4.13 (s, 3H), 4.00-3.92 (m, 1H), 2.29 (t, J=12.4 Hz, 1H), 1.75-1.47 (m, 3H), 1.00-0.87 (m, 5H), 0.67-0.53 (m, 2H).

Intermediate 12 2-Ethyl-7-(2-methyl-4-nitro-pyrazol-3-yl)oxepan-4-one

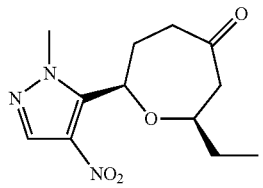 [SMILES: CC[C@@H]1CC(=O)CC[C@H](c2c([N+](=O)[O-])cnn2C)O1]

Following the procedure for Intermediate 5 starting from 1-methyl-5-(5-ethyl-6,8-dioxaspiro[2.5]octan-7-yl)-4-nitro-pyrazole gave 2-ethyl-7-(2-methyl-4-nitro-pyrazol-3-yl)oxepan-4-one as a colourless solid (240 mg, 13% over two steps). $^1$H NMR (400 MHz, CDCl$_3$) δ 8.04 (s, 1H), 5.67 (dd, J=11.0, 2.4 Hz, 1H), 4.02 (s, 3H), 3.94 (dd, J=10.2, 5.2 Hz, 1H), 3.04 (td, J=13.3, 3.3 Hz, 1H), 2.79-2.63 (m, 3H), 2.20-2.12 (m, 1H), 2.05-1.92 (m, 1H), 1.67-1.57 (m, 2H), 0.94 (t, J=7.4 Hz, 3H).

Intermediate 13 N-(2-Ethyl-7-(2-methyl-4-nitro-pyrazol-3-yl)oxepan-4-yl)-2-methyl-propane-2-sulfinamide

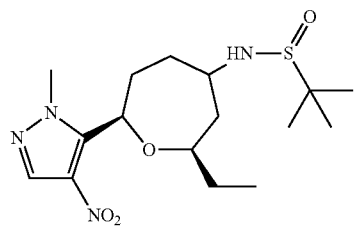 [SMILES: CC[C@@H]1CC(NS(=O)C(C)(C)C)CC[C@H](c2c([N+](=O)[O-])cnn2C)O1]

To a solution of 2-ethyl-7-(2-methyl-4-nitro-pyrazol-3-yl)oxepan-4-one (120 mg, 0.45 mmol) in THF (3 mL) was added (R)-2-methylpropane-2-sulfinamide (70 mg, 0.58 mmol) followed by titanium(IV) ethoxide (0.30 mL, 1.12 mmol). The reaction mixture was heated at reflux for 4 hr then allowed to cool to room temperature. The crude solution was added dropwise to a solution of sodium borohydride (69 mg, 1.80 mmol) in THF (3 mL) at −60° C. The reaction mixture was warmed to 0° C., quenched with MeOH (3 mL) and brine (50 mL), and stirred at room temperature for 18 hr. The mixture was filtered through Celite® washing with EtOAc (200 mL). The aqueous layer was extracted with EtOAc (3×50 mL) and the combined organic layers were washed with brine (150 mL), separated, dried over MgSO$_4$ and concentrated under reduced pressure. Purification via silica gel column chromatography (0-10% MeOH/DCM) gave N-(2-ethyl-7-(2-methyl-4-nitro-pyrazol-3-yl)oxepan-4-yl)-2-methyl-propane-2-sulfinamide as a mixture of diastereomers (ratio 5:2) as a colourless solid (118 mg, 71% over two steps). $^1$H NMR (400 MHz, CDCl$_3$) δ 8.03 and 8.02 (2s, 1H), 5.60-5.51 (m, 1H), 4.08 and 4.06 (2s, 3H), 3.83-3.66 (m, 2H), 3.62-3.50 (m, 1H), 3.22 and 3.15 (d, J=6.2 and 4.0 Hz, 1H), 2.11-1.96 (m, 4H), 1.76 (s, 1H), 1.63-1.54 (m, 2H), 1.28-1.15 (m, 9H), 0.91 (td, J=7.4, 2.4 Hz, 3H).

Intermediate 14 N-(2-Methyl-7-(2-methyl-4-nitro-pyrazol-3-yl)oxepan-4-yl)-2-methyl-propane-2-sulfinamide

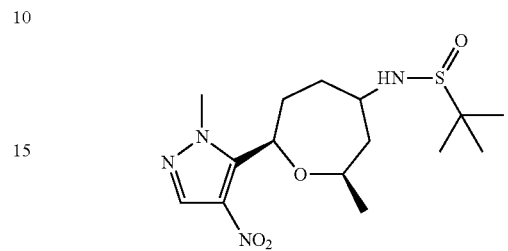

Following the procedure for Intermediate 13 starting from 2-methyl-7-(2-methyl-4-nitro-pyrazol-3-yl)oxepan-4-one gave N-(2-methyl-7-(2-methyl-4-nitro-pyrazol-3-yl)oxepan-4-yl)-2-methyl-propane-2-sulfinamide as an off-white solid (208 mg, 40% over two steps). $^1$H NMR (400 MHz, CDCl$_3$) δ 8.01 (s, 1H), 5.63-5.51 (m, 1H), 4.05 (s, 3H), 3.86-3.72 (m, 2H), 3.19-3.11 (m, 1H), 2.22-1.69 (m, 6H), 1.29-1.20 (m, 12H).

Intermediate 15 3-Allyloxy-3-(2-methyl-4-nitro-pyrazol-3-yl)propanoic acid

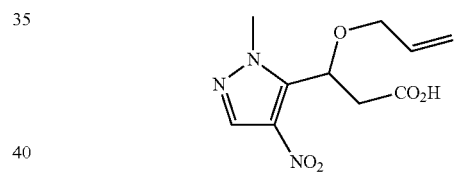

To a suspension of zinc dust (<10 μm, 10.3 g, 159 mmol) in dry Et$_2$O (120 mL) was added a few drops of trimethylsilyl chloride to initiate the reaction. The reaction mixture was then heated at reflux for 5 min and a few drops of 1,2-dibromoethane were carefully added. A solution of tert-butyl 2-bromoacetate (18.8 mL, 127 mmol) was added dropwise and the reaction mixture was heated at reflux for 1 hr. A solution of 2-methyl-4-nitro-pyrazole-3-carbaldehyde (77 wt % in DMSO, 6.4 g, 31.8 mmol) in THF (120 mL) was added at room temperature and stirring continued for 150 min. The reaction mixture was diluted with EtOAc (200 mL) and saturated ammonium chloride/1 M HCl (100 mL/100 mL) and stirred for 18 hr. The layers were separated and the aqueous layer was extracted with EtOAc (3×200 mL). The combined organic layers were washed with brine (100 mL), separated, dried over Na$_2$SO$_4$ and concentrated under reduced pressure. Purification via silica gel column chromatography (0-100% EtOAc/isohexane) gave tert-butyl 3-hydroxy-3-(1-methyl-4-nitro-1H-pyrazol-5-yl)propanoate as a colourless solid (6.52 g, 77%). To a solution of this solid (6.52 g, 24 mmol) in dioxane (168 mL) was added bisallylcarbonate (10.2 g, 72 mmol). The reaction mixture was degassed with nitrogen for 30 min. Tris(dibenzylideneacetone)-dipalladium(0) (557 mg, 0.60 mmol) and triphenylphosphine (630 mg, 2.40 mmol) were added in a single portion and degassing continued for 15 min. The reaction mixture was heated at 65° C. for 1 h and cooled to room temperature. Brine (100 mL) and EtOAc (150 mL) were added and the layers separated. The aqueous layer was extracted with EtOAc (3×150 mL) and the combined organic layers were washed with brine (100 mL), separated, dried over $Na_2SO_4$ and concentrated under reduced pressure. Purification via silica gel column chromatography (0-100% EtOAc/isohexane) gave tert-butyl 3-(allyloxy)-3-(1-methyl-4-nitro-1H-pyrazol-5-yl)propanoate as a colourless solid (7.7 g, 99%). To a solution of this solid (7.7 g, 24 mmol) in DCM (80 mL) was added TFA (40 mL) and the mixture was stirred at room temperature for 18 hr. After cooling to 0° C., sodium carbonate (5 g), saturated aqueous $NaHCO_3$ (100 mL) and DCM (200 mL) were carefully added until the effervescence stopped. Concentrated HCl was slowly added until the solution was pH4. The aqueous layer was extracted with DCM (3×200 mL) and the combined organic layers were separated, dried over $Na_2SO_4$ and concentrated under reduced pressure to give 3-allyloxy-3-(2-methyl-4-nitro-pyrazol-3-yl)propanoic acid as a yellow oil (4.33 g, 55% over three steps). $^1$H NMR (400 MHz, $CDCl_3$) δ 11.5-10.3 (br s, 1H), 8.08 (s, 1H), 5.90-5.78 (m, 3H), 5.28-5.18 (m, 1H), 4.07 (s, 3H), 4.06-3.96 (m, 2H), 2.99 (dd, J=16.2, 9.3 Hz, 1H), 2.87 (dd, J=16.2, 4.3 Hz, 1H).

Intermediate 16 2-(2-Methyl-4-nitro-pyrazol-3-yl)-3,7-dihydro-2H-oxepin-4-one

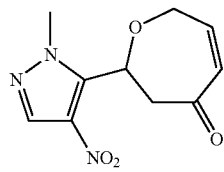 [SMILES: Cn1ncc([N+](=O)[O-])c1C1CC(=O)C=CCO1]

To a solution of 3-allyloxy-3-(2-methyl-4-nitro-pyrazol-3-yl)propanoic acid (4.33 g, 17 mmol) in DCM (48 mL) at 0° C. under nitrogen was added oxalyl chloride (4.37 mL, 51 mmol) followed by the cautious addition of DMF (0.05 mL) to initiate the acylation. The reaction mixture was stirred at room temperature for 3 hr and concentrated under reduced pressure. The residue was dissolved in DME (28 mL), vinyltributyltin (2.48 mL, 8.50 mmol) added and the mixture degassed with nitrogen for 30 min. trans-Benzyl(chloro)-bis(triphenylphosphine)palladium(II) (129 mg, 0.17 mmol) was added and degassing continued for 10 min. The reaction mixture was heated to 65° C. for 1 hr and cooled to room temperature. Concentration under reduced pressure and purification via silica gel column chromatography (0-100% EtOAc/isohexane) gave 5-(allyloxy)-5-(1-methyl-4-nitro-1H-pyrazol-5-yl)pent-1-en-3-one as a yellow syrup (2.76 g, 61%). A solution of this syrup (250 mg, 0.94 mmol) in toluene (90 mL) was degassed with nitrogen for 30 min at 35° C. Zhan 1B catalyst (26 mg, 0.04 mmol) dissolved in toluene (2 mL) was added to the reaction mixture and degassing continued for 15 min. After stirring at 35° C. for 1 h, the reaction mixture was cooled to room temperature and concentrated under reduced pressure. Purification via silica gel column chromatography (0-100% EtOAc/isohexane) gave 2-(2-methyl-4-nitro-pyrazol-3-yl)-3,7-dihydro-2H-oxepin-4-one as a colourless solid (107 mg, 30% over three steps). $^1$H NMR (400 MHz, $CDCl_3$) δ 8.05 (s, 1H), 6.44 (ddd, J=12.8, 3.4, 2.3 Hz, 1H), 6.15 (m, 1H), 6.01 (dd, J=11.1, 3.4 Hz, 1H), 4.72 (ddd, J=19.8, 3.4, 1.7 Hz, 1H), 4.61 (ddd, J=19.6, 2.4 Hz, 1H), 4.08 (s, 3H), 3.20-3.12 (m, 2H).

Intermediate 17 5-(6-Azido-4,4-difluoro-oxepan-2-yl)-1-methyl-4-nitro-pyrazole (Diastereomer 1)

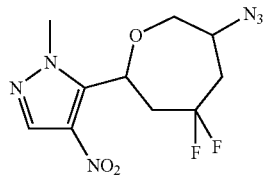 [SMILES: Cn1ncc([N+](=O)[O-])c1C1CC(F)(F)CC(N=[N+]=[N-])CO1]

To a solution of 2-(2-methyl-4-nitro-pyrazol-3-yl)-3,7-dihydro-2H-oxepin-4-one (440 mg, 0.42 mmol) in MeCN (3 mL) was added Amberlite IRA 900F resin (79 mg, 0.19 mmol) and trimethylsilylazide (1.2 mL, 9.35 mmol). The reaction mixture was heated at 65° C. behind a blast screen for 24 hr, cooled to room temperature and concentrated under reduced pressure. Purification via silica gel column chromatography (0-100% EtOAc/isohexane) gave pure 6-azido-2-(1-methyl-4-nitro-1H-pyrazol-5-yl)oxepan-4-one along with mixed fractions containing product and starting material. These were concentrated under reduced pressure and resubmitted to the same reaction conditions. Final purification via silica gel column chromatography (0-100% EtOAc/isohexane) gave 6-azido-2-(1-methyl-4-nitro-1H-pyrazol-5-yl)oxepan-4-one as a colourless solid (449 mg). To this solid (449 mg, 1.60 mmol) was added deoxo-Fluor® (50% in THF, 5 mL) and the mixture was stirred at room temperature for 18 hr. DCM (50 mL) was added and the reaction mixture cooled to 0° C. Saturated aqueous $NaHCO_3$ (30 mL) was then carefully added. The aqueous layer was extracted with DCM (3×30 mL) and the combined organic layers were dried over $Na_2SO_4$ and concentrated under reduced pressure. Purification via silica gel column chromatography (0-100% EtOAc/isohexane) gave 5-(6-azido-4,4-difluoro-oxepan-2-yl)-1-methyl-4-nitro-pyrazole (Diastereomer 1-major) as a colourless solid (264 mg, 47% over two steps). $^1$H NMR (400 MHz, $CDCl_3$) δ 8.03 (s, 1H), 5.67-5.58 (m, 1H), 4.18-3.91 (m, 3H), 4.08 (s, 3H), 2.79-2.63 (m, 1H), 2.63-2.40 (m, 3H).

Intermediate 18 5-(6-Azido-4,4-difluoro-oxepan-2-yl)-1-methyl-4-nitro-pyrazole (Diastereomer 2)

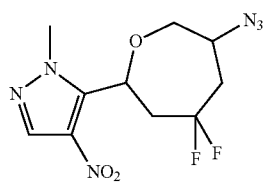 [SMILES: Cn1ncc([N+](=O)[O-])c1C1CC(F)(F)CC(N=[N+]=[N-])CO1]

Following the procedure for Intermediate 17 also gave 5-(6-azido-4,4-difluoro-oxepan-2-yl)-1-methyl-4-nitro-pyrazole (Diastereomer 2-minor) as a colourless solid (69 mg, 12% over two steps). $^1$H NMR (400 MHz, $CDCl_3$) δ 8.02

(s, 1H), 5.73 (dd, J=10.9, 4.5 Hz, 1H), 4.34-4.29 (m, 1H), 4.01 (s, 3H), 4.01-3.93 (m, 1H), 3.53 (dd, J=11.4, 11.4 Hz, 1H), 2.71-2.49 (m, 4H).

Intermediate 19 5-(5,8-Dioxabicyclo[5.1.0]octan-4-yl)-1-methyl-4-nitro-pyrazole

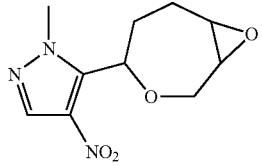 [SMILES: Cn1ncc([N+](=O)[O-])c1C1CCC2OC2CO1]

To a solution of 1-methyl-4-nitro-5-(2,3,4,7-tetrahydrooxepin-2-yl)pyrazole (1.00 g, 4.74 mmol) in DCM (25 mL) was added m-CPBA (70-75%, 1.75 g, 7.11 mmol) and the reaction mixture was stirred at room temperature for 18 hr. The reaction mixture was diluted with DCM (50 mL), washed with saturated aqueous NaHCO₃ (50 mL), water (50 mL) and brine (50 mL). The organic layer was separated, dried over MgSO₄, and concentrated under reduced pressure. Purification via silica gel column chromatography (0-30% EtOAc/isohexane) gave racemic 5-(5,8-dioxabicyclo[5.1.0]octan-4-yl)-1-methyl-4-nitro-pyrazole as a colourless solid (490 mg, 43%). ¹H NMR (400 MHz, CDCl₃) δ 8.22-7.87 (m, 1H), 5.07 (d, J=9.9 Hz, 1H), 4.50 (dd, J=14.5, 3.1 Hz, 1H), 4.05 (s, 3H), 3.93 (d, J=14.4 Hz, 1H), 3.35 (t, J=4.5 Hz, 1H), 3.13 (t, J=3.6 Hz, 1H), 2.55-2.47 (m, 1H), 2.31-2.21 (m, 1H), 2.16-2.04 (m, 1H), 1.79 (dd, J=14.4, 1.8 Hz, 1H).

Intermediate 20 tert-Butyl N-(4-methoxy-7-(2-methyl-4-nitro-pyrazol-3-yl)oxepan-3-yl]carbamate

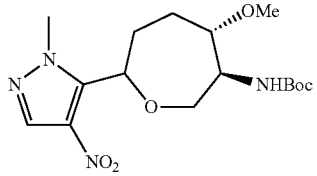 [SMILES: CO[C@H]1CCC(c2c([N+](=O)[O-])cnn2C)OC[C@@H]1NC(=O)OC(C)(C)C]

A solution of 5-(5,8-dioxabicyclo[5.1.0]octan-4-yl)-1-methyl-4-nitro-pyrazole (220 mg, 0.92 mmol) Intermediate 19 in MeOH/water (6 mL/1.2 mL) was treated with ammonium chloride (122 mg, 2.30 mmol) and sodium azide (299 mg, 4.60 mmol) and the mixture was heated at 70° C. behind a blast screen for 16 hr. The reaction mixture was extracted with EtOAc (100 mL) and the organic layer was washed with water (2×50 mL), dried over MgSO₄ and concentrated under reduced pressure. The residue (500 mg, 1.77 mmol) was dissolved in dry DMF (15 mL), cooled to 0° C., sodium hydride (60% in mineral oil, 106 mg, 2.66 mmol) was added and the mixture stirred for 15 min. Iodomethane (0.17 mL, 2.66 mmol) was added and the reaction mixture was warmed to room temperature and stirred for 16 hr. Water (20 mL) was added and the mixture was extracted with EtOAc (2×150 mL). The combined organic layers were dried over MgSO₄ and concentrated under reduced pressure. Purification via silica gel column chromatography (0-30% EtOAc/isohexane) gave 4-azido-5-methoxy-1-(1-methyl-4-nitro-1H-pyrazol-5-yl)azepane as a yellow oil (280 mg). A solution of this oil (270 mg, 0.91 mmol) in THF/water (13 mL/2.5 mL) was treated with triphenylphosphine (263 mg, 1.00 mmol) and the reaction mixture was heated at 70° C. behind a blast screen for 18 hr. The reaction mixture was concentrated under reduced pressure. The residue was dissolved in dry DCM (15 mL) at 0° C. and di-tert-butyl-dicarbonate (238 mg, 1.09 mmol) was added followed by DIPEA (0.66 mL, 4.55 mmol). The reaction mixture was warmed to room temperature and stirred for 3 hr before being quenched with water (20 mL) and extracted with DCM (100 mL). The organic layer was separated, dried over MgSO₄ and concentrated under reduced pressure. Purification via silica gel column chromatography (0-40% EtOAc/isohexane) isolated four diastereomers. The minor fraction gave tert-butyl N-(4-methoxy-7-(2-methyl-4-nitro-pyrazol-3-yl)oxepan-3-yl]carbamate (racemate) as a colourless solid (60 mg, 17% over four steps). ¹H NMR (400 MHz, CDCl₃) δ 8.02 (s, 1H), 5.58-5.51 (m, 1H), 4.82 (br s, 1H), 4.31 (dd, J=12.7, 3.0 Hz, 1H), 4.02 (s, 3H), 3.87 (br s, 1H), 3.62-3.48 (m, 2H), 3.41 (s, 3H), 2.28-2.09 (m, 2H), 2.03-1.83 (m, 2H), 1.47 (s, 9H).

Intermediate 21 tert-butyl ((3S,4R,7S)-3-methoxy-7-(1-methyl-4-nitro-1H-pyrazol-5-yl)oxepan-4-yl)carbamate

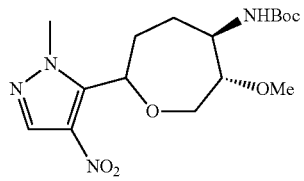 [SMILES: CO[C@@H]1COC(c2c([N+](=O)[O-])cnn2C)CC[C@H]1NC(=O)OC(C)(C)C]

Following the procedure for Intermediate 20, the major fraction isolated (290 mg) was further purified via chiral SFC to give tert-butyl ((3S,4R,7S)-3-methoxy-7-(1-methyl-4-nitro-1H-pyrazol-5-yl)oxepan-4-yl)carbamate as a colourless solid (101 mg, 29% over four steps). ¹H NMR (400 MHz, CDCl₃) δ 8.02 (s, 1H), 5.39 (dd, J=10.6, 3.6 Hz, 1H), 4.75 (br s, 1H), 4.33 (dd, J=14.2, 1.9 Hz, 1H), 4.06 (s, 3H), 3.91-3.83 (m, 1H), 3.75 (dd, J=14.2, 3.2 Hz, 1H), 3.43 (s, 3H), 3.39-3.34 (m, 1H), 2.22-2.12 (m, 1H), 2.12-2.03 (m, 1H), 2.03-1.82 (m, 2H), 1.47 (s, 9H).

Intermediate 22 tert-butyl ((3R,4S,7R)-3-methoxy-7-(1-methyl-4-nitro-1H-pyrazol-5-yl)oxepan-4-yl)carbamate

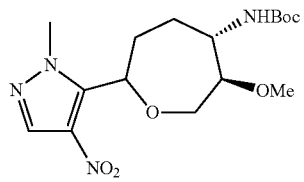

Following the procedure for Intermediate 21 also gave tert-butyl ((3R,4S,7R)-3-methoxy-7-(1-methyl-4-nitro-1H-pyrazol-5-yl)oxepan-4-yl)carbamate as a colourless solid (101 mg, 29% over four steps). ¹H NMR (400 MHz, CDCl₃) δ 8.05-7.99 (m, 1H), 5.39 (dd, J=10.6, 3.6 Hz, 1H), 4.75 (br s, 1H), 4.33 (dd, J=14.2, 1.9 Hz, 1H), 4.06 (s, 3H), 3.90-3.82 (m, 1H), 3.75 (dd, J=14.2, 3.2 Hz, 1H), 3.43 (s, 3H), 3.42-3.31 (m, 1H), 2.22-2.12 (m, 1H), 2.12-2.03 (m, 1H), 2.03-1.83 (m, 2H), 1.62-1.29 (m, 9H).

Intermediate 23 tert-Butyl N-(3-fluoro-7-(2-methyl-4-nitro-pyrazol-3-yl)oxepan-4-yl)carbamate

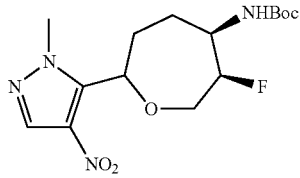 [SMILES: Cn1ncc([N+](=O)[O-])c1C1CC[C@@H](NC(=O)OC(C)(C)C)[C@@H](F)CO1]

A solution of 5-(5,8-dioxabicyclo[5.1.0]octan-4-yl)-1-methyl-4-nitro-pyrazole (130 mg, 0.54 mmol) Intermediate 19 in MeOH/water (3 mL/0.6 mL) was treated with ammonium chloride (72 mg, 1.35 mmol) and sodium azide (177 mg, 2.72 mmol) and the mixture was heated at 70° C. behind a blast screen for 18 hrs. The reaction mixture was extracted with EtOAc (100 mL) and the organic layer was washed with water (3×20 mL), washed with brine (20 mL), separated, dried over $MgSO_4$ and concentrated under reduced pressure. To a solution of the resulting residue (100 mg, 0.35 mmol) in DCM (3 mL) was added deoxo-Fluor® (50% in THF, 0.32 mL, 0.89 mmol) and the mixture was stirred at room temperature for 16 hr. The mixture was diluted with DCM (30 mL), cooled in an ice/water bath and quenched by the dropwise addition of saturated aqueous $NaHCO_3$ (30 mL). The resulting mixture was stirred for 10 min. The organic layer was separated, dried over $Na_2SO_4$ and the solvent removed under reduced pressure. Purification via silica gel column chromatography (0-40% EtOAc/isohexane) gave an oil (90 mg). A solution of this oil (90 mg, 0.35 mmol) in THF/water (4 mL/0.8 mL) was treated with triphenylphosphine (92 mg, 0.35 mmol) and the reaction mixture was heated at 70° C. behind a blast screen for 18 hr. The mixture was concentrated under reduced pressure. The resulting residue was dissolved in dry DCM (7 mL) at 0° C. and di-tert-butyl-dicarbonate (84 mg, 0.38 mmol) and DIPEA (0.22 mL, 1.6 mmol) were added. The reaction mixture was warmed to room temperature and stirred for 3 hr. Water (10 mL) was added and the mixture extracted with DCM (20 mL). The organic layer was separated, dried over $MgSO_4$ and concentrated under reduced pressure. Purification via silica gel column chromatography (0-40% EtOAc/isohexane) gave tert-butyl N-(3-fluoro-7-(2-methyl-4-nitro-pyrazol-3-yl)oxepan-4-yl)carbamate as a mixture of enantiomers as a mixture of enantiomers as an off-white solid (70 mg, 36% over four steps). $^1$H NMR (400 MHz, $CDCl_3$) δ 8.01 (s, 1H), 5.55-5.49 (m, 1H), 5.10-4.92 (m, 2H), 4.36-4.09 (m, 2H), 4.02 (s, 3H), 3.97-3.83 (m, 1H), 2.32-2.18 (m, 1H), 2.02-1.89 (m, 2H), 1.83 (d, J=14.0 Hz, 1H), 1.47 (s, 9H).

Intermediate 24 tert-butyl ((3R,4R,7S)-3-fluoro-7-(1-methyl-4-nitro-1H-pyrazol-5-yl)oxepan-4-yl)carbamate

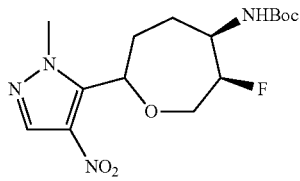

Further purification of tert-butyl N-(3-fluoro-7-(2-methyl-4-nitro-pyrazol-3-yl)oxepan-4-yl)carbamate via chiral SFC gave tert-butyl ((3R,4R,7S)-3-fluoro-7-(1-methyl-4-nitro-1H-pyrazol-5-yl)oxepan-4-yl)carbamate as an off-white solid (52 mg). $^1$H NMR (400 MHz, $CDCl_3$) δ 8.01 (s, 1H), 5.55-5.49 (m, 1H), 5.09-4.91 (m, 2H), 4.36-4.10 (m, 2H), 4.01 (s, 3H), 3.91 (ddd, J=26.6, 14.4, 2.2 Hz, 1H), 2.31-2.19 (m, 1H), 2.02-1.95 (m, 2H), 1.83 (d, J=13.9 Hz, 1H), 1.47 (s, 9H).

Intermediate 25 tert-butyl ((3S,4S,7R)-3-fluoro-7-(1-methyl-4-nitro-1H-pyrazol-5-yl)oxepan-4-yl)carbamate

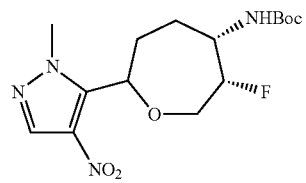

Following the procedure for Intermediate 24 also gave tert-butyl ((3S,4S,7R)-3-fluoro-7-(1-methyl-4-nitro-1H-pyrazol-5-yl)oxepan-4-yl)carbamate as an off-white solid (61 mg). $^1$H NMR (400 MHz, $CDCl_3$) δ 8.01 (s, 1H), 5.55-5.49 (m, 1H), 5.10-4.92 (m, 2H), 4.36-4.09 (m, 2H), 4.02 (s, 3H), 3.97-3.83 (m, 1H), 2.32-2.18 (m, 1H), 2.02-1.89 (m, 2H), 1.83 (d, J=14.0 Hz, 1H), 1.47 (s, 9H).

Intermediate 26 5-(4,8-Dioxabicyclo[5.1.0]octan-5-yl)-1-methyl-4-nitro-pyrazole

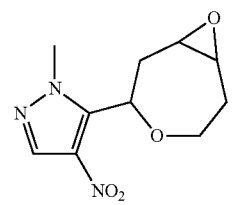

5-(1-Allyloxypent-4-enyl)-1-methyl-4-nitro-pyrazole (7.08 g, 28.2 mmol) was dissolved in DCM (910 mL) and the mixture degassed for 30 min before Grubbs 2nd generation catalyst (1.19 g, 1.41 mmol) was added. The reaction mixture was heated at 40° C. for 18 hr and concentrated under reduced pressure. Purification via silica gel column chromatography (0-10% EtOAc/isohexane) followed by reverse-phase preparative HPLC gave a mixture of isomers of 1-methyl-4-nitro-5-(tetrahydrooxepin-2-yl)pyrazole (66/34) as a clear oil (2.3 g). To a solution of this oil (2.3 g, 10.31 mmol) in DCM (50 mL) was added m-CPBA (70-75%, 3.56 g, 14.40 mmol) and the reaction mixture was stirred at room temperature for 4 hr. The reaction mixture was diluted with DCM (50 mL) and the organic layer was washed with saturated aqueous $NaHCO_3$ (2×50 mL), water (50 mL) and brine (50 mL), dried over $MgSO_4$, and concentrated under reduced pressure. Purification via silica gel column chromatography (0-30% EtOAc/isohexane) gave 5-(4,8-dioxabicyclo[5.1.0]octan-5-yl)-1-methyl-4-nitro-pyrazole as a colourless solid (1.0 g, 14% over two steps). $^1$H NMR (400 MHz, $CDCl_3$) δ 8.02 (s, 1H), 5.51-5.44 (m, 1H), 4.02 (s, 3H), 3.93 (dt, J=12.7, 3.4 Hz, 1H), 3.62-3.53 (m, 1H), 3.35-3.27 (m, 2H), 2.58-2.51 (m, 1H), 2.41-2.25 (m, 3H).

Intermediate 27

5-Azido-2-(2-methyl-4-nitro-pyrazol-3-yl)oxepan-4-ol

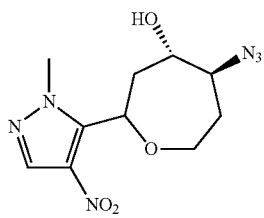 [SMILES: Cn1ncc([N+](=O)[O-])c1C1C[C@H](O)[C@@H](N=[N+]=[N-])CCO1]

To a solution of 5-(4,8-dioxabicyclo[5.1.0]octan-5-yl)-1-methyl-4-nitro-pyrazole (1.04 g, 4.35 mmol) in 4:1 MeOH:water (30 mL) was added ammonium chloride (0.58 g, 10.88 mmol) and sodium azide (1.41 g, 21.75 mmol). The mixture was heated at 70° C. behind a blast screen for 16 hr. The MeOH was removed under reduced pressure and EtOAc (20 mL) added. The organic layer was washed with saturated aqueous NaHCO$_3$ (20 mL), passed through a phase separation cartridge and concentrated under reduced pressure. Purification via silica gel chromatography (0-60% EtOAc/isohexane) gave 5-azido-2-(2-methyl-4-nitro-pyrazol-3-yl)oxepan-4-ol as a pale yellow gum (718 mg, 58% yield). $^1$H NMR (400 MHz, CDCl$_3$) δ 8.03 (s, 1H), 5.76 (dd, J=9.3, 3.2 Hz, 1H), 4.18-4.10 (m, 1H), 4.08-4.04 (m, 4H), 3.91 (ddd, J=9.4, 6.6, 6.2 Hz, 1H), 3.79 (ddd, J=12.6, 8.6, 3.5 Hz, 1H), 2.44 (ddd, J=15.3, 9.4, 3.8 Hz, 1H), 2.37-2.29 (m, 1H), 2.24 (d, J=3.2 Hz, 1H), 2.12 (ddd, J=15.3, 5.7, 3.2 Hz, 1H), 2.06-1.96 (m, 1H).

Intermediate 28 5-Azido-7-(2-methyl-4-nitro-pyrazol-3-yl)oxepan-4-ol

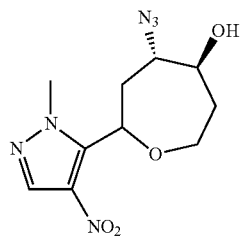 [SMILES: Cn1ncc([N+](=O)[O-])c1C1C[C@H](N=[N+]=[N-])[C@@H](O)CCO1]

Following the procedure for Intermediate 26 also gave 5-azido-7-(2-methyl-4-nitro-pyrazol-3-yl)oxepan-4-ol as a pale yellow gum (285 mg, 23% yield). $^1$H NMR (400 MHz, CDCl$_3$) δ 8.04 (s, 1H), 5.64 (dd, J=10.8, 1.4 Hz, 1H), 4.06-3.96 (m, 4H), 3.95-3.83 (m, 2H), 3.72 (ddd, J=10.8, 9.0, 4.9 Hz, 1H), 2.43 (d, J=2.5 Hz, 1H), 2.28 (ddd, J=14.1, 4.9, 1.4 Hz, 1H), 2.21-2.12 (m, 2H), 2.09-2.00 (m, 1H).

Intermediate 29 tert-Butyl N-(5-fluoro-2-(2-methyl-4-nitro-pyrazol-3-yl)oxepan-4-yl)carbamate To a solution of 5-azido-2-(2-methyl-4-nitro-pyrazol-3-yl)oxepan-4-ol (282 mg, 1.00 mmol) in DCM (6 mL) cooled to 0° C. was added dropwise a solution of deoxo-Fluor® in (50% in THF, 0.46 mL, 1.25 mmol). The mixture was warmed to room temperature and stirred for 16 hr. Additional deoxo-Fluor® (50% in THF, 0.23 mL, 0.63 mmol) was added and the mixture was stirred at room temperature for 5 hr. After cooling in an ice bath saturated aqueous NaHCO$_3$ (10 mL) was added slowly. The organic layer was passed through a phase separation cartridge and concentrated under reduced pressure. The residue was purified via silica gel chromatography (0-50% EtOAc/isohexane) to yield the fluoro compound as a clear gum (205 mg). To a solution of this gum (200 mg, 0.70 mmol) in THF (5 mL) and water (1 mL) was added triphenylphosphine (202 mg, 0.77 mmol) and the mixture heated at 60° C. for 2 hr. The mixture was diluted with EtOAc (10 mL) and washed with brine (2×5 mL). The organic layer was passed through a phase separation cartridge and concentrated under reduced pressure. The residue was dissolved in DCM (2 mL) and DIPEA (0.24 mL, 1.40 mmol) and di-tert-butyl dicarbonate (183 mg, 0.84 mmol) were added. The mixture was stirred at room temperature for 2 hr. Water (2 mL) was added and the mixture was extracted with DCM (3×2 mL). The combined organic layers were passed through a phase separation cartridge and concentrated under reduced pressure. Purification via silica gel chromatography (0-50% EtOAc/isohexane) gave tert-butyl N-(5-fluoro-2-(2-methyl-4-nitro-pyrazol-3-yl)oxepan-4-yl)carbamate as a clear gum (240 mg, 66% over three steps). $^1$H NMR (400 MHz, CDCl$_3$) δ 8.02 (s, 1H), 5.62 (dd, J=11.3, 2.3 Hz, 1H), 5.28-4.79 (m, 2H), 4.29-4.19 (m, 1H), 4.15-4.07 (m, 1H), 4.04 (s, 3H), 3.77 (ddd, J=12.9, 8.1, 4.5 Hz, 1H), 2.41-2.07 (m, 3H), 2.04 (d, J=10.8 Hz, 1H), 1.44 (s, 9H).

Intermediate 30 tert-Butyl N-(5-methoxy-7-(2-methyl-4-nitro-pyrazol-3-yl)oxepan-4-yl)carbamate To a solution of 5-azido-2-(2-methyl-4-nitro-pyrazol-3-yl) oxepan-4-ol (352 mg, 1.25 mmol) in dry THF (6 mL) under nitrogen cooled to 0° C. was added sodium hydride (60% in mineral oil, 55 mg, 1.38 mmol). After stirring for 20 min, iodomethane (0.09 mL, 1.38 mmol) was added and the reaction mixture was allowed to warm to room temperature and stirred for 90 min. The mixture was re-cooled to 0° C. and more sodium hydride (60% in mineral oil, 55 mg, 1.38 mmol) was added. After stirring for 20 min, more iodomethane (0.09 mL, 1.38 mmol) was added and the reaction mixture was allowed to warm to room temperature and stirred for 5 hr. Water (5 mL) was added and the mixture was extracted with EtOAc (3×5 mL). The combined organic layers were passed through a phase separation cartridge and concentrated under reduced pressure. Purification via silica gel column chromatography (0-50% EtOAc/isohexane) gave the intermediate methyl ether as a clear gum (155 mg). A solution of this gum (154 mg, 0.52 mmol) in THF/water (5 mL/1 mL) was treated with triphenylphosphine (150 mg, 0.57 mmol) and the reaction mixture was heated at 60° C. behind a blast screen for 2 hr. The mixture was diluted with EtOAc (10 mL) and washed with brine (2×5 mL). The organic layer was passed through a phase separation cartridge and concentrated under reduced pressure. The residue was dissolved in dry DCM (2 mL) and DIPEA (0.18 mL, 1.04 mmol) and di-tert-butyl-dicarbonate (136 mg, 0.62 mmol) were added. The reaction mixture was stirred at room temperature for 3 hr. Water (2 mL) was added and the mixture was extracted with DCM (3×2 mL). The organic layer was passed through a phase separation cartridge and concentrated under reduced pressure. Purification via silica gel column chromatography (0-50% EtOAc/isohexane) gave tert-butyl N-(5-methoxy-7-(2-methyl-4-nitro-pyrazol-3-yl)oxepan-4-yl)carbamate as a clear gum (190 mg, 41% over three steps). $^1$H NMR (400 MHz, CDCl$_3$) δ 8.03 (s, 1H), 5.67 (dd, J=10.5, 2.0 Hz, 1H), 4.96 (s, 1H), 4.33 (s, 1H), 4.06 (s, 3H), 4.02-3.84 (m, 2H), 3.62 (d, J=5.2 Hz, 1H), 3.44 (s, 3H), 2.52 (dddd, J=15.1, 9.9, 7.5, 2.1 Hz, 1H), 2.20-2.01 (m, 2H), 1.90-1.78 (m, 1H), 1.48 (s, 9H).

Intermediate 30 2-(2-Methyl-4-nitro-pyrazol-3-yl) tetrahydropyran-4-one

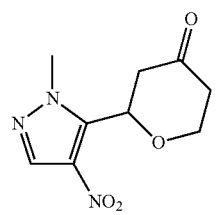 [SMILES: Cn1ncc([N+](=O)[O-])c1C1CC(=O)CCO1]

To a solution of 2-methyl-4-nitro-pyrazole-3-carbaldehyde (600 mg, 3.87 mmol) in CDCl$_3$ (20 mL) was added Danishefsky's diene (836 mg, 5.81 mmol) and Resolve-Al™ EuFOD (157 mg, 0.39 mmol). The reaction mixture was heated at 80° C. in a sealed tube for 24 hr. Additional Resolve-Al™ EuFOD (250 mg, 0.62 mmol) was added and heating continued for another 24 hr. The reaction mixture was concentrated under reduced pressure. Purification via silica gel column chromatography (0-100% EtOAc/isohexane) gave 2-(1-methyl-4-nitro-1H- pyrazol-5-yl)-2H-pyran-4(3H)-one as a yellow solid (710 mg, 82%). A portion of this solid (300 mg, 1.35 mmol) was dissolved in THF (10 mL) under nitrogen and cooled to −78° C. A solution of L-selectride (1 M in THF, 1.48 mL, 1.48 mmol) was added dropwise and the mixture was stirred at −78° C. for 30 min. The mixture was quenched with MeOH (2 mL) and warmed to room temperature. EtOAc (30 mL) and brine (30 mL) were added and the layers separated. The aqueous layer was extracted with EtOAc (3×20 mL) then the combined organic layers were washed with brine (30 mL), separated, dried over Na$_2$SO$_4$ and concentrated under reduced pressure. Purification via silica gel column chromatography (0-100% EtOAc/isohexane) gave 2-(2-methyl-4-nitro-pyrazol-3-yl)tetrahydropyran-4-one as a colourless solid (224 mg, 61% over two steps). $^1$H NMR (400 MHz, CDCl$_3$) δ 8.06 (s, 1H), 5.70 (dd, J=11.8, 3.3 Hz, 1H), 4.49 (ddd, J=11.8, 7.5, 1.3 Hz, 1H), 4.15 (s, 3H), 3.94-3.86 (m, 1H), 2.83-2.63 (m, 3H), 2.58-2.50 (m, 1H).

Intermediate 31 7-(2-Methyl-4-nitro-pyrazol-3-yl) oxepan-4-ol

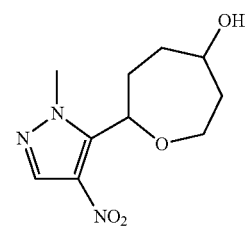 [SMILES: Cn1ncc([N+](=O)[O-])c1C1CCC(O)CCO1]

To a solution of 2-(2-methyl-4-nitro-pyrazol-3-yl)tetrahydropyran-4-one (300 mg, 1.33 mmol) in DCM (12 mL) at −70° C. was added boron trifluoride etherate (0.75 mL, 1.73 mmol) dropwise followed by a (trimethylsilyl)diazomethane solution (2 M in hexanes, 0.87 mL, 1.73 mmol). The reaction mixture was stirred at −70° C. for 90 min, quenched with water (10 mL), diluted with DCM (12 mL) and warmed to room temperature. The organic layer was passed through a phase separation cartridge and concentrated under reduced pressure. Purification via silica gel column chromatography (0-100% EtOAc/isohexane) gave 7-(1-methyl-4-nitro-1H-pyrazol-5-yl)oxepan-4-one as a colourless solid (121 mg) and its regioisomer 2-(1-methyl-4-nitro-1H-pyrazol-5-yl)oxepan-4-one (151 mg). To a solution of 7-(1-methyl-4-nitro-1H-pyrazol-5-yl)oxepan-4-one (121 mg, 0.51 mmol) in MeOH (5 mL) at 0° C. was added portionwise NaBH$_4$ (23 mg, 0.61 mmol). Stirring continued for 1 hr and the reaction mixture was quenched with 1 M HCl (5 mL) and EtOAc (10 mL). The aqueous layer was extracted with EtOAc (3×20 mL) and the combined organic layers were washed with brine (30 mL), separated, dried over Na$_2$SO$_4$ and concentrated under reduced pressure to give 7-(2-methyl-4-nitro-pyrazol-3-yl)oxepan-4-ol as a 1:1 mixture of diastereomers as a colourless oil (85 mg, 27% over two steps). The product was used without further purification as a 1/1 mixture of diastereoisomers. $^1$H NMR (400 MHz, CDCl$_3$) δ 8.02 and 8.01 (s, 1H), 5.61-5.56 and 5.54-5.50 (m, 1H), 4.26-4.14 (m, 1H), 4.07 and 4.04 (s, 3H), 3.90-3.80 and 3.81-3.63 (m, 1H), 2.20-1.80 (m, 8H).

Intermediate 32 tert-Butyl N-[2-(2,6-difluorophenyl)-4-[[5-[5,6-dihydroxyoxepan-2-yl]-1-methyl-pyrazol-4-yl]carbamoyl]thiazol-5-yl]carbamate

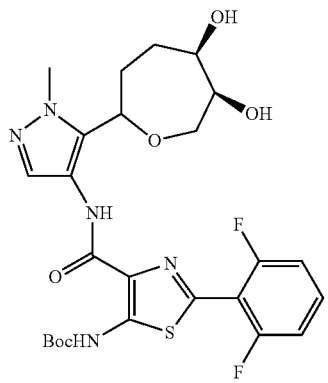 [SMILES: Cn1ncc(NC(=O)c2nc(-c3c(F)cccc3F)sc2NC(=O)OC(C)(C)C)c1C1CC[C@@H](O)[C@@H](O)CO1]

To a solution of AD-mix β (1.25 g) in tert-butanol (5.1 mL) and water (4.6 mL) at 0° C. was added a solution of 1-methyl-4-nitro-5-(2,3,4,7-tetrahydrooxepin-2-yl)pyrazole (200 mg, 0.89 mmol) in tert-butanol (1 mL). The reaction mixture was stirred at 0° C. for 66 hr before solid sodium thiosulfate (1.4 g) was added slowly. The mixture was stirred for a further 1 hr and diluted with EtOAc (20 mL). The aqueous layer was extracted with EtOAc (4×15 mL) and the combined organic layers were dried over MgSO₄ and concentrated under reduced pressure. Purification via silica gel column chromatography (0-2.5% MeOH/EtOAc) gave 7-(2-methyl-4-nitro-pyrazol-3-yl)oxepane-3,4-diol as a colourless solid. A solution of this diol in MeOH (18 mL) was passed through the H-Cube® (full hydrogen mode, 65° C., flow rate: 1 mL/min, 30 mm 10% Pd/C cartridge). The solvent was removed under reduced pressure to give the crude amine. To a solution of this amine in DCM (10 mL) was added 5-(tert-butoxycarbonylamino)-2-(2,6-difluorophenyl)thiazole-4-carboxylic acid (348 mg, 0.98 mmol), PyBOP (694 mg, 1.3 mmol) and DIPEA (0.44 mL, 2.67 mmol). The mixture was stirred at room temperature for 18 hr. The mixture was diluted with EtOAc (20 mL) and washed with brine (5 ml). The organic layer was dried over MgSO₄ and the solvent removed under reduced pressure. Purification via silica gel column chromatography (0-10% MeOH/EtOAc) gave tert-butyl N-[2-(2,6-difluorophenyl)-4-[[5-[5,6-dihydroxyoxepan-2-yl]-1-methyl-pyrazol-4-yl]carbamoyl]thiazol-5-yl]carbamate as an off-white solid (96 mg, 23% over three steps). $^1$H NMR (400 MHz, CDCl₃) δ 9.75 (s, 1H), 8.17-8.14 (m, 1H), 7.39-7.32 (m, 1H), 7.09-7.01 (m, 2H), 6.25 (s, 1H), 5.12 (t, J=4.5 Hz, 1H), 4.23 (dd, J=13.7, 4.0 Hz, 1H), 3.87 (d, J=3.9 Hz, 1H), 3.81-3.66 (m, 5H), 2.12-2.00 (m, 3H), 1.70 (t, J=14.4 Hz, 3H), 1.55 (s, 9H).

Intermediate 33 5-(5,8-Dioxabicyclo[5.1.0]octan-4-yl)-1-methyl-4-nitro-pyrazole

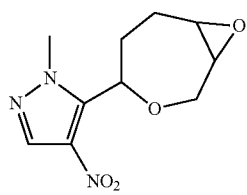 [SMILES: Cn1ncc([N+](=O)[O-])c1C1CCC2OC2CO1]

To a solution of 1-methyl-4-nitro-5-(2,3,4,7-tetrahydrooxepin-2-yl)pyrazole (1.0 g, 4.5 mmol) in DCM (18 mL) was added 3 Å molecular sieves followed by NBS (0.80 g, 4.48 mmol) and acetic acid (0.26 mL, 4.48 mol). The reaction mixture was stirred at room temperature for 60 hr. The mixture was diluted with DCM (30 mL) and washed with water (15 mL), saturated aqueous NaHCO₃ (15 mL) and brine (15 mL). The organic layer was separated, dried over MgSO₄ and the solvent removed under reduced pressure. Purification via silica gel column chromatography (0-100% EtOAc/isohexane) gave the intermediate bromoacetate as a mixture of regioisomers as a clear oil (1.17 g). The procedure was repeated to provide more material. To a solution of this oil (1.55 g, 4.3 mmol) in MeOH (60 mL) was added K₂CO₃ (2.66 g, 19.2 mmol) in a single portion. This mixture was stirred for 1 hr before water (50 mL) was added. EtOAc (150 mL) was added and the layers were separated. The organic layer was dried over MgSO₄ and the solvent removed under reduced pressure to give 5-(5,8-dioxabicyclo[5.1.0]-octan-4-yl)-1-methyl-4-nitro-pyrazole as a clear oil (0.86 g, 61% over two steps). $^1$H NMR (400 MHz, CDCl₃) δ 8.02 (s, 1H), 5.53-5.45 (m, 1H), 4.53 (dd, J=13.5, 5.2 Hz, 1H), 4.07 (s, 3H), 3.58-3.48 (m, 1H), 3.36-3.25 (m, 2H), 2.55-2.42 (m, 1H), 2.07-1.87 (m, 3H).

Intermediate 34 tert-Butyl N-(3-fluoro-7-(2-methyl-4-nitro-pyrazol-3-yl)oxepan-4-yl)carbamate

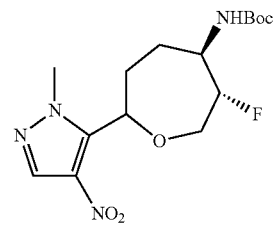

Following the procedure for Intermediate 23 starting from 5-(5,8-dioxabicyclo[5.1.0]octan-4-yl)-1-methyl-4-nitro-pyrazole (Intermediate 33) gave tert-butyl N-(3-fluoro-7-(2-methyl-4-nitro-pyrazol-3-yl)oxepan-4-yl)carbamate (290 mg, 53% over four steps) as an off-white solid. $^1$H NMR (400 MHz, CDCl₃) δ 8.02 (s, 1H), 5.50 (dd, J=9.9, 3.8 Hz, 1H), 4.96-4.73 (m, 2H), 4.14-3.95 (m, 3H), 4.03 (s, 3H), 2.30-2.16 (m, 3H), 1.95-1.84 (m, 1H), 1.47 (s, 9H).

Intermediate 35 5-(6-Methoxy-3,5-dimethyl-3,6-dihydro-2H-pyran-2-yl)-1-methyl-4-nitro-pyrazole

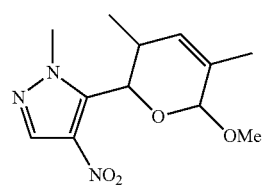 [SMILES: COC1OC(c2c([N+](=O)[O-])cnn2C)C(C)C=C1C]

To a solution of 2-methyl-4-nitro-pyrazole-3-carbaldehyde (487 mg, 3.14 mmol) in CDCl₃ (12 mL) was added [(Z)-1-[(E)-2-methoxy-1-methyl-vinyl]prop-1-enoxy]-trimethylsilane (944 mg, 4.71 mmol) and Resolve-Al™ EuFOD (127 mg, 0.31 mmol). The reaction mixture was heated at 80°

C. in a sealed tube for 18 hr. The reaction mixture was cooled to room temperature and concentrated under reduced pressure. Purification via silica gel column chromatography (0-100% EtOAc/isohexane) gave 3,5-dimethyl-2-(2-methyl-4-nitro-pyrazol-3-yl)-2,3-dihydropyran-4-one as a mixture of diastereomers as a yellow oil (829 mg). A solution of this oil (829 mg, 3.14 mmol) and cerium(III) chloride heptahydrate (4.8 g, 12.56 mmol) in MeOH (10 mL) was stirred at room temperature for 15 min. After cooling to 0° C., sodium borohydride (143 mg, 3.8 mmol) was added portionwise and the mixture was stirred at 0° C. for 1 hr. The reaction was quenched with 1 M aqueous HCl (10 mL) and extracted with EtOAc (50 mL). The organic layer was separated, dried over MgSO$_4$ and concentrated under reduced pressure. The residue was dissolved in MeOH (40 mL) and treated with tosic acid monohydrate (87 mg). The mixture was heated at reflux for 18 hr and concentrated under reduced pressure. The residue was dissolved in DCM (30 mL) and the organic layer was washed with aqueous NaHCO$_3$ (2×20 mL), washed with brine (20 mL), passed through a phase separation cartridge and concentrated under reduced pressure to give 5-(6-methoxy-3,5-dimethyl-3,6-dihydro-2H-pyran-2-yl)-1-methyl-4-nitro-pyrazole as a yellow oil (558 mg, 51% over three steps). $^1$H NMR (400 MHz, CDCl$_3$) δ 8.15-7.98 (m, 1H), 5.90 (d, J=3.6 Hz) and 5.78 (d, J=3.2 Hz) (1H), 5.72 (d, J=5.6 Hz) and 5.64 (d, J=10.8 Hz) (1H), 4.80 and 4.76 (2s, 1H), 4.16 and 4.06 (2s, 3H), 3.42 and 3.40 (2s, 3H), 2.65-2.58 (m, 1H), 1.77 and 1.65 (2s, 3H), 0.90 (d, J=7.2 Hz) and 0.83 (d, J=7.2 Hz) (3H).

Intermediate 36 5-(2,6-Dimethyl-4,7-dioxabicyclo[4.1.0]heptan-3-yl)-1-methyl-4-nitro-pyrazole

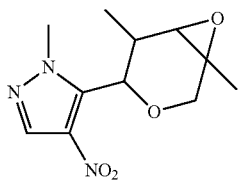 [SMILES: CC1C(c2c([N+](=O)[O-])cnn2C)OCC2(C)OC12]

To a solution of 5-(6-methoxy-3,5-dimethyl-3,6-dihydro-2H-pyran-2-yl)-1-methyl-4-nitro-pyrazole (100 mg, 0.38 mmol) in DCM (1 mL) cooled to −78° C. was added boron trifluoride diethyl etherate (0.14 mL, 1.13 mmol) and triethylsilane (0.36 mL), 2.68 mmol). After stirring at −78° C. for 1 hr, the reaction mixture was allowed to warm to room temperature and stirred for 18 hr. Saturated aqueous NaHCO$_3$ (5 mL) and DCM (5 mL) were added and the organic layer was passed through a phase separation cartridge and concentrated under reduced pressure. Purification via silica gel column chromatography (0-60% EtOAc/isohexane) gave 5-(3,5-dimethyl-3,6-dihydro-2H-pyran-2-yl)-1-methyl-4-nitro-pyrazole as a yellow oil. The reaction was repeated to provide more material. To a solution of 5-(3,5-dimethyl-3,6-dihydro-2H-pyran-2-yl)-1-methyl-4-nitro-pyrazole (305 mg, 1.29 mmol) in DCM (6.5 mL) cooled to 0° C. was added m-CPBA (70-75%, 382 mg, 1.54 mmol) and the mixture was stirred at 0° C. for 90 min. More m-CPBA (70-75%, 191 mg, 0.774 mmol) was added and the mixture was slowly warmed to room temperature over 6 hr. The mixture was filtered through Celite® washing with DCM (15 mL) and the filtrate washed with saturated aqueous NaHCO$_3$ (2×10 mL). The organic layer was passed through a phase separation cartridge and concentrated under reduced pressure. Purification via silica gel column chromatography (0-60% EtOAc/isohexane) gave 5-(2,6-dimethyl-4,7-dioxabicyclo[4.1.0]heptan-3-yl)-1-methyl-4-nitro-pyrazole as a single diastereomer as an off-white solid (189 mg, 53% over two steps). $^1$H NMR (400 MHz, CDCl$_3$) δ 8.08 (s, 1H), 5.32-5.28 (m, 1H), 4.15-4.08 (m, 1H), 4.06 (s, 3H), 3.78 (d, J=12.9 Hz, 1H), 3.30 (d, J=5.6 Hz, 1H), 2.71-2.61 (m, 1H), 1.38 (s, 3H), 0.92 (d, J=7.0 Hz, 3H).

Intermediate 37 4-Azido-3,5-dimethyl-6-(2-methyl-4-nitro-pyrazol-3-yl)tetrahydropyran-3-ol

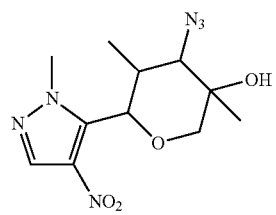

Following the procedure for Intermediate 27 starting from 5-(2,6-dimethyl-4,7-dioxabicyclo[4.1.0]heptan-3-yl)-1-methyl-4-nitro-pyrazole gave 4-azido-3,5-dimethyl-6-(2-methyl-4-nitro-pyrazol-3-yl)tetrahydropyran-3-ol as an off-white solid (140 mg, 63%). $^1$H NMR (400 MHz, CDCl$_3$) δ 8.09 (s, 1H), 5.74 (d, J=2.9 Hz, 1H), 4.14 (s, 2H), 3.79-3.64 (m, 3H), 3.58 (s, 1H), 2.58 (qdd, J=7.6, 2.9, 2.2 Hz, 1H), 1.81 (s, 1H), 1.25 (s, 3H), 1.18 (d, J=7.6 Hz, 3H).

Intermediate 38 tert-Butyl N-[5-hydroxy-3,5-dimethyl-2-(2-methyl-4-nitro-pyrazol-3-yl)tetrahydropyran-4-yl]carbamate

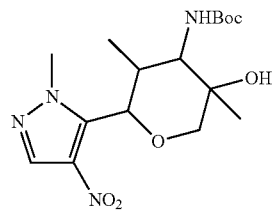 [SMILES: CC1C(c2c([N+](=O)[O-])cnn2C)OCC(C)(O)C1NC(=O)OC(C)(C)C]

A solution of 4-azido-3,5-dimethyl-6-(2-methyl-4-nitro-pyrazol-3-yl)tetrahydropyran-3-ol (140 mg, 0.47 mmol) in THF/water (1 mL/0.2 mL) was treated with triphenylphosphine (373 mg, 1.42 mmol) and the reaction mixture was heated at 65° C. behind a blast screen for 18 hr. More THF (1 mL) was added along with a solution of trimethylphosphine (1 M in toluene, 1 mL, 1.0 mmol). The mixture was heated at 65° C. behind a blast screen for 3 hr. The solvents were removed under reduced pressure and the residue was dissolved in dry DCM (4 mL). Di-tert-butyl-dicarbonate (115 mg, 0.53 mmol) was added followed by DIPEA (0.18 mL, 1.05 mmol) and the reaction mixture was stirred at room temperature for 72 hr. The mixture was concentrated under reduced pressure. Purification via silica gel column chromatography (0-60% EtOAc/isohexane) gave tert-butyl N-[5-hydroxy-3,5-dimethyl-2-(2-methyl-4-nitro-pyrazol-3-yl)tetrahydropyran-4-yl]carbamate an off-white solid (112 mg, 64% over two steps). $^1$H NMR (400 MHz, CDCl$_3$) δ 8.05 (s, 1H), 5.52 (d, J=2.7 Hz, 1H), 4.11-4.01 (m, 6H), 2.67-2.58 (m, 1H), 2.54 (s, 1H), 1.61 (s, 1H), 1.48 (s, 9H), 1.36 (s, 3H), 0.98 (d, J=7.2 Hz, 3H).

Intermediate 39 2-(2-Methyl-4-nitro-pyrazol-3-yl)tetrahydropyran-4-ol

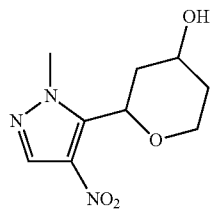

Following the procedure for Intermediate 30 also gave 2-(2-methyl-4-nitro-pyrazol-3-yl)tetrahydropyran-4-ol as a mixture of diastereomers as a yellow gum (91 mg, 12% over two steps). $^1$H NMR (400 MHz, CDCl$_3$) δ 8.06 and 8.03 (2s, 1H), 5.88 (dd, J=8.3, 6.1 Hz) and 5.70 (dd, J=11.8, 3.2 Hz) (1H), 4.49 (dd, J=11.8, 7.4 Hz) and 4.40 (s) (1H), 4.15-3.72 (m, 2H), 4.15 and 4.09 (s, 3H), 2.85-2.55 (m, 1H), 2.03-1.89 (m, 3H), 1.79-1.66 (m, 1H).

Intermediate 40 tert-Butyl N-(2-(2,6-difluorophenyl)-4-((1-methyl-5-(2-((2,2,2-trifluoroacetyl)amino)-8-oxabicyclo[3.2.1]octan-5-yl)pyrazol-4-yl)carbamoyl)thiazol-5-yl)carbamate

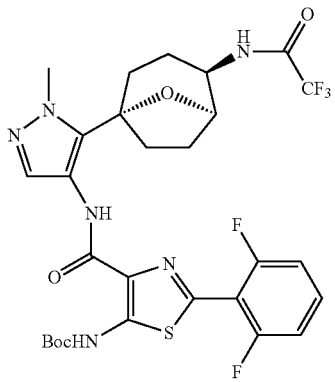 [SMILES: Cn1ncc(NC(=O)c2nc(-c3c(F)cccc3F)sc2NC(=O)OC(C)(C)C)c1[C@@]12CC[C@@H](NC(=O)C(F)(F)F)[C@@H](CC1)O2]

To a solution of 2,2,2-trifluoro-N-(5-fluoro-2-hydroxy-5-(2-methyl-4-nitro-pyrazol-3-yl)cycloheptyl)acetamide (120 mg, 0.32 mmol) in THF (10 mL) and MeOH (10 mL) was added 10% palladium on carbon (12 mg). The reaction mixture was heated at 40° C. under a 400 psi atmosphere of hydrogen for 3 hr, cooled to room temperature, filtered through Celite®, washing with methanol (50 mL) and concentrated under reduced pressure. The procedure was repeated using the same conditions except with additional aqueous HCl (2 M, 2 mL). To a solution of the residue in DCM (20 mL) was added DIPEA (1.00 mL, 5.74 mmol), 5-(tert-butoxycarbonylamino)-2-(2,6-difluorophenyl)thiazole-4-carboxylic acid (123 mg, 0.46 mmol) and PyBOP (409 mg, 0.78 mmol) and the mixture was stirred at room temperature for 16 hr. The reaction was quenched with water (20 mL) and extracted with DCM (150 mL). The organic layer was washed saturated solution of NaHCO$_3$ (30 mL) and water (30 mL), separated, dried over MgSO$_4$ and concentrated under reduced pressure. Purification via silica gel chromatography (80-100% EtOAc/isohexane) gave tert-butyl N-(2-(2,6-difluorophenyl)-4-((1-methyl-5-(2-((2,2,2-trifluoroacetyl)amino)-8-oxabicyclo[3.2.1]octan-5-yl)pyrazol-4-yl)carbamoyl)thiazol-5-yl)carbamate as an off-white solid (58 mg, 27% over two steps). $^1$H NMR (400 MHz, CDCl$_3$) δ 10.47 (s, 1H), 10.39 (s, 1H), 8.33 (s, 1H), 7.39-7.33 (m, 1H), 7.18-7.10 (m, 2H), 5.91 (d, J=7.7 Hz, 1H), 4.89-4.83 (m, 1H), 4.47-4.38 (m, 1H), 3.86 (s, 3H), 2.47-2.38 (m, 1H), 2.27-1.90 (m, 7H), 1.55 (s, 9H).

Intermediate 41 tert-Butyl N-[5-[4-[[5-(tert-butoxycarbonylamino)-2-(2,6-difluorophenyl)thiazole-4-carbonyl]amino]-2-methyl-pyrazol-3-yl]-8-oxabicyclo[3.2.1]octan-2-yl]carbamate

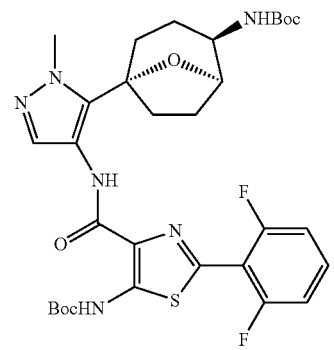 [SMILES: Cn1ncc(NC(=O)c2nc(-c3c(F)cccc3F)sc2NC(=O)OC(C)(C)C)c1[C@@]12CC[C@@H](NC(=O)OC(C)(C)C)[C@@H](CC1)O2]

Following the procedure for Intermediate 1 starting from tert-butyl N-(5-fluoro-2-hydroxy-5-(2-methyl-4-nitro-pyrazol-3-yl)cycloheptyl)carbamate gave tert-butyl N-(5-[4-[[5-(tert-butoxycarbonylamino)-2-(2,6-difluorophenyl)thiazole-4-carbonyl]amino]-2-methyl-pyrazol-3-yl]-8-oxabicyclo[3.2.1]octan-2-yl]carbamate as a pale pink solid (172 mg, 17% over two steps). $^1$H NMR (400 MHz, CDCl$_3$) δ 10.47 (s, 1H), 10.45 (s, 1H), 8.29 (s, 1H), 7.35-7.27 (m, 1H), 7.18-7.08 (m, 2H), 4.76 (br s, 1H), 4.29 (br s, 1H), 4.04 (br s, 1H), 3.85 (s, 3H), 2.38-2.33 (m, 1H), 2.19-1.86 (m, 7H), 1.55 (s, 9H), 1.48 (s, 9H).

Intermediate 42 tert-Butyl N-[5-[4-[[5-(tert-butoxycarbonylamino)-2-(2-fluorophenyl)thiazole-4-carbonyl]amino]-2-methyl-pyrazol-3-yl]-8-oxabicyclo[3.2.1]octan-2-yl]carbamate

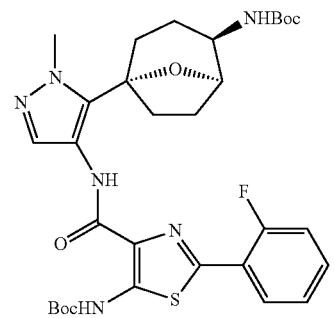 [SMILES: Cn1ncc(NC(=O)c2nc(-c3ccccc3F)sc2NC(=O)OC(C)(C)C)c1[C@@]12CC[C@@H](NC(=O)OC(C)(C)C)[C@@H](CC1)O2]

Following the procedure for Intermediate 1 starting from tert-butyl N-(5-fluoro-2-hydroxy-5-(2-methyl-4-nitro-pyrazol-3-yl)cycloheptyl)carbamate gave tert-butyl N-(5-[4-((5-(tert-butoxycarbonylamino)-2-(2-fluorophenyl)thiazole-4-carbonyl)amino)-2-methyl-pyrazol-3-yl]-8-oxabicyclo[3.2.1]octan-2-yl]carbamate as a pale pink solid (310 mg, 31% over two steps). $^1$H NMR (400 MHz, CDCl$_3$) δ 10.50 (br s, 1H), 10.48 (s, 1H), 8.39-8.29 (m, 2H), 7.60-7.51 (m, 1H), 7.38-7.31 (m, 1H), 7.18 (dd, J=11.4, 8.3 Hz, 1H), 4.86 (br s, 1H), 4.36 (br s, 1H), 4.07 (br s, 1H), 3.86 (s, 3H), 2.43-2.35 (m, 1H), 2.22-1.92 (m, 7H), 1.55 (s, 9H), 1.50 (s, 9H).

Intermediate 43 1-tert-butyl 3-methyl 2-(1-methyl-4-nitro-1H-pyrazol-5-yl)malonate

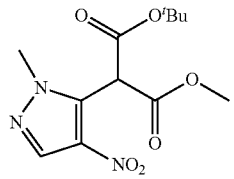 [SMILES: COC(=O)C(C(=O)OC(C)(C)C)c1c([N+](=O)[O-])cnn1C]

Potassium carbonate (15.40 g, 111.42 mmol) was added in one portion to a stirred, RT solution of 5-chloro-1-methyl-4-nitro-pyrazole (6.0 g, 37.140 mmol) and tert-butyl methyl melonate (8.74 g, 50.139 mmol) in anhydrous DMSO (100 mL) under nitrogen. The mixture was heated at 75° C. for 3 hours before being cooled and allowed to stand at RT overnight. The mixture was poured into water (500 mL), acidified with 2N HCl (80 ml, PH 5) and extracted with EtOAc (2×250 mL, 2×200 ml). The combined organics were dried (MgSO4) and the solvent removed under reduced pressure. The residue was purified via silica gel chromatography (0-30% EtOAc/heptane) to afford 1-tert-butyl 3-methyl 2-(1-methyl-4-nitro-1H-pyrazol-5-yl)malonate as a colorless solid (10.3 g, 92.7%).

Intermediate 44 methyl 2-(2-methyl-4-nitro-pyrazol-3-yl)acetate

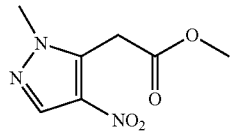

A mixture of 1-tert-butyl 3-methyl 2-(1-methyl-4-nitro-1H-pyrazol-5-yl)malonate (6.92 g, 23.1 mmol) and formic acid (100 mL) was heated at 50° C. for 5 hours before being cooled to room temperature. Formic acid was removed under reduced pressure; the residue was diluted with brine and extracted with DCM 3x. The combined organics were dried (MgSO4) and the solvent removed under reduced pressure. The residue was purified via silica gel chromatography (0-60% EtOAc/heptane) to afford methyl 2-(2-methyl-4-nitro-pyrazol-3-yl)acetate (4.15 g, 90%).

Intermediate 45 methyl 2-(2-methyl-4-nitro-pyrazol-3-yl)pent-4-enoate

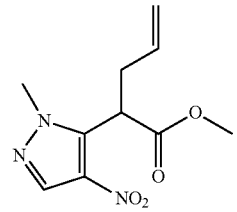

To a solution of methyl 2-(2-methyl-4-nitro-pyrazol-3-yl)acetate (869 mg, 4.36 mmol) in anhydrous DMF (10 mL) was added at 0° C. sodium hydride (218 mg, 5.45 mmol, 60 mass %), the mixture became dark red right away. After stirring at 0° C. for 15 min, allyl bromide (0.57 mL, 6.54 mmol) was added slowly, stirred at 0° C. for 10 min then room temp for 1 h. The reaction was quenched with water (20 mL) and extracted with EA (200 mL, 50 mL). Combined organic layer was washed with water (15×3 mL), brine (10 mL), dried (MgSO$_4$) and the solvent removed under reduced pressure. The residue was purified via silica gel chromatography (0-100% EtOAc/heptane) to afford methyl 2-(2-methyl-4-nitro-pyrazol-3-yl)pent-4-enoate (713 mg, 68%). $^1$H NMR (400 MHz, CDCl$_3$) δ 8.10 (s, 1H), 5.71-5.54 (m, 1H), 5.01 (d, J=13.1 Hz, 2H), 4.43 (dd, J=9.8, 5.5 Hz, 1H), 3.86 (s, 3H), 3.72 (s, 3H), 3.14-3.02 (m, 1H), 2.79-2.62 (m, 1H).

Intermediate 46 2-(2-methyl-4-nitro-pyrazol-3-yl)pent-4-en-1-ol

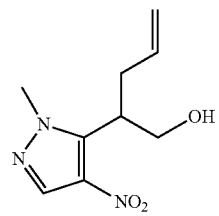

DIBAL-H (1.0 mol/L) in toluene (16.03 mmol, 16 mL) was added to a solution of methyl 2-(2-methyl-4-nitro-pyrazol-3-yl)pent-4-enoate (959 mg, 4.01 mmol) in THF (16 mL) under nitrogen atmosphere at 0° C. The mixture was stirred for 30 min at 0° C. 1N HCl (25 mL) solution was slowly added to the reaction mixture at 0° C., followed by ethyl acetate (30 mL). After separation, the organic layer was washed by saturated NaHCO$_3$ solution (30 mL) and saline (30 mL). The combined aqueous layers were extracted with ethyl acetate till there was no desired product in the aqueous layer. The organic layers were combined and subsequently dried (Na$_2$SO$_4$), filtered and evaporated to yield a light brown oil (610 mg). The crude material was purified on silica gel using 0-100% ethyl acetate in heptane to give 2-(2-methyl-4-nitro-pyrazol-3-yl)pent-4-en-1-ol as a light yellow solid (676 mg, 80%).

Intermediate 47 5-[1-(allyloxymethyl)but-3-enyl]-1-methyl-4-nitro-pyrazole

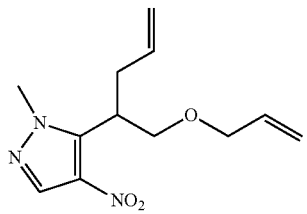 [SMILES: C=CCOCC(CC=C)c1c([N+](=O)[O-])cnn1C]

To a solution of 2-(2-methyl-4-nitro-pyrazol-3-yl)pent-4-en-1-ol (91 mg, 0.43) in anhydrous DMF (5 mL) was added at 0° C. sodium hydride (20 mg, 0.49 mmol, 60 mass %). After stirring at 0° C. for 15 min, allyl bromide (79, 0.64 mmol) was added slowly, stirred at 0° C. for 10 min then warm to room temperature for 2 h. The reaction was quenched with water (10 ml) and extracted with EA (3×50 ml). Combined organic layer was washed with brine (10 ml) and concentrated to dryness. The residue was purified via silica gel chromatography (0-100% EtOAc/heptane) to afford 5-[1-(allyloxymethyl)but-3-enyl]-1-methyl-4-nitro-pyrazole (84 mg, 78%).

Intermediate 48 1-methyl-4-nitro-5-(2,3,4,5-tetrahydrooxepin-3-yl)pyrazole

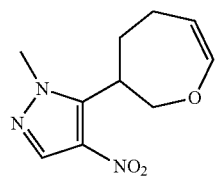 [SMILES: Cn1ncc([N+](=O)[O-])c1C1CCC=COC1]

A solution of 1,3-Bis(2,4,6-trimethylphenyl)-2-imidazolidinylidene)dichloro(phenylmethylene)(tricyclohexylphosphine)ruthenium, "Grubb's catalyst 2$^{nd}$ generation", CAS Reg. No. 246047-72-3, Sigma-Aldrich Product No. 569747, U.S. Pat. No. 6,111,121, U.S. Pat. No. 7,329,758 (375 mg, 0.42 mmol) in toluene (15 ml) was added to a solution of 5-[1-(allyloxymethyl)but-3-enyl]-1-methyl-4-nitro-pyrazole (527 mg, 2.10 mmol) in toluene (115 mL). The resulting solution was heated at reflux (120° C.) for 2.5 h. After cooling to room temperature, the solvent was removed under reduced pressure and the residue was purified via silica gel chromatography (0-100% EtOAc/heptane) to afford 1-methyl-4-nitro-5-(2,3,4,5-tetrahydrooxepin-3-yl)pyrazole (133 mg, 30%).

Intermediate 49 6-(2-methyl-4-nitro-pyrazol-3-yl)oxepan-3-ol

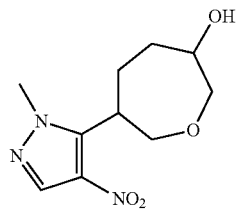

Borane dimethyl sulfide complex (2.0 mol/L) in THF (0.91 mL, 1.82 mmol) was added to a solution of 1-methyl-4-nitro-5-(2,3,4,5-tetrahydrooxepin-3-yl)pyrazole (204 mg, 0.91 mmol) in anhydrous THF (8 mL) at 0° C. The mixture was stirred at 0° C. for 15 min then warm to RT for 2 h. 1M NaOH (1.5 mL) and hydrogen peroxide (30 mass % in water) (0.8 mL) were added and the mixture was stirred at RT for 2 h. The reaction was quenched with water and extracted with DCM (2×) and EA (1×). Combined organic layers were washed with brine (10 ml) and concentrated to dryness. The residue was purified via silica gel chromatography (0-100% EtOAc/heptane) to afford 6-(2-methyl-4-nitro-pyrazol-3-yl)oxepan-3-ol (53 mg, 24%).

Intermediate 50 6-(2-methyl-4-nitro-pyrazol-3-yl)oxepan-3-one

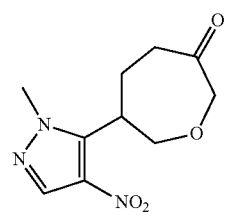

To a solution of 6-(2-methyl-4-nitro-pyrazol-3-yl)oxepan-3-ol (53 mg, 0.22 mmol) in DCM (6 mL) was added Dess-Martin periodinane (192 mg, 0.44 mmol) and sodium bicarbonate (93 mg, 1.10 mmol). The mixture was stirred at room temperature overnight, quenched with water, and extracted with DCM (3×). Combined organic layers were concentrated to dryness and purified via silica gel chromatography (0-100% EtOAc/heptane) to afford 6-(2-methyl-4-nitro-pyrazol-3-yl)oxepan-3-one (53 mg, quant.).

Intermediate 51 tert-butyl N-[6-(2-methyl-4-nitro-pyrazol-3-yl)oxepan-3-yl]carbamate

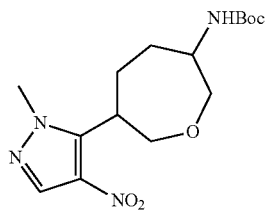

6-(2-Methyl-4-nitro-pyrazol-3-yl)oxepan-3-one (53 mg, 0.23 mmol), ammonium acetate (219 mg, 2.76 mmol), sodium cyanoborohydride (38 mg, 0.57 mmol) and a few pettets of 4A molecular seives were dissolved in methanol (2 mL). Acetic acid (35 mg, 0.57 mmol) was added and the mixture was stirred at RT under N2 atmosphere for three days. The reaction was quenched with sat. sodium bicarbonate and extracted with DCM (3×). Combined organic layers were dried (MgSO4) and the solvent removed under reduced pressure. The residue was dissolved in DCM (5 mL) and di-tert-butyl-dicarbonate (63 mg, 0.69 mmol) and DIPEA (0.067 mL, 0.38 mmol) were added. The mixture was stirred at room temperature overnight and then purified via silica gel chromatography (0-100% EtOAc/heptane) to afford tert-butyl N-[6-(2-methyl-4-nitro-pyrazol-3-yl)oxepan-3-yl]carbamate (53 mg, 81%).

Intermediate 52 tert-butyl N-[6-[4-[[5-(tert-butoxycarbonylamino)-2-(2,6-difluorophenyl)thiazole-4-carbonyl]amino]-2-methyl-pyrazol-3-yl]oxepan-3-yl]carbamate

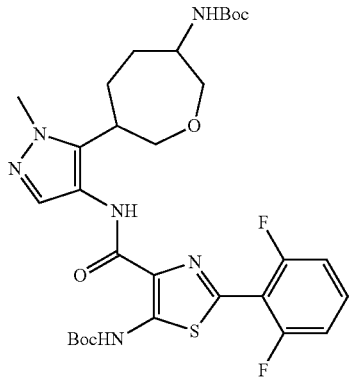 [SMILES: Cn1ncc(NC(=O)c2nc(-c3c(F)cccc3F)sc2NC(=O)OC(C)(C)C)c1C1CCC(NC(=O)OC(C)(C)C)COC1]

A solution of tert-butyl N-[6-(2-methyl-4-nitro-pyrazol-3-yl)oxepan-3-yl]carbamate (53 mg, 0.16 mmol) in MeOH (25 mL) was passed through the H-Cube® (50 bar, 50° C., flow rate: 1 mL/min, 30 mm 10% Pd/C cartridge). The solvent was removed under reduced pressure to afford tert-butyl N-[6-(4-amino-2-methyl-pyrazol-3-yl)oxepan-3-yl]carbamate as a brown oil. To a solution of this oil in DCM (5 mL) was added 5-(tert-butoxycarbonylamino)-2-(2,6-difluorophenyl)thiazole-4-carboxylic acid (72 mg, 0.20 mmol), PyBOP (133 g, 0.25 mmol) and DIPEA (0.17 mL, 0.94 mmol) and the mixture was stirred at room temperature for 16 hr. The reaction was quenched with water and extracted with EA (3×). The organic layers were combined and the solvent was removed under reduced pressure. Purification via silica gel column chromatography (0-100% EtOAc/heptane) gave tert-butyl N-[6-[4-[[5-(tert-butoxycarbonylamino)-2-(2,6-difluorophenyl)thiazole-4-carbonyl]amino]-2-methyl-pyrazol-3-yl]oxepan-3-yl]carbamate (100 mg, 99%).

Intermediate 53 tert-Butyl N-[4-fluoro-7-(2-methyl-4-nitro-pyrazol-3-yl)oxepan-3-yl]carbamate and tert-Butyl N-[3-fluoro-7-(2-methyl-4-nitro-pyrazol-3-yl)oxepan-4-yl]carbamate

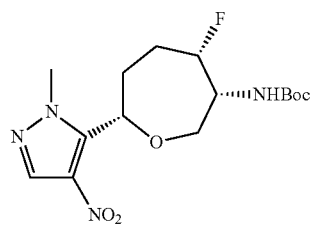

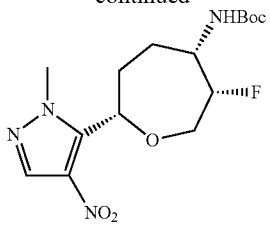

Following the procedure for Intermediate 23 starting from 5-(5,8-dioxabicyclo[5.1.0]octan-4-yl)-1-methyl-4-nitro-pyrazole (Intermediate 33) gave an inseparable mixture of tert-butyl N-[4-fluoro-7-(2-methyl-4-nitro-pyrazol-3-yl)oxepan-3-yl]carbamate and tert-butyl N-[3-fluoro-7-(2-methyl-4-nitro-pyrazol-3-yl)oxepan-4-yl]carbamate as an oil (290 mg, 53% over four steps). $^1$H NMR (400 MHz, CDCl$_3$) δ 8.02 (s, 1H), 5.58-5.47 (m, 1H), 4.96-4.73 (m, 2H), 4.14-3.93 (m, 5H), 2.30-2.16 (m, 3H), 2.04-1.83 (m, 2H), 1.47 (s, 9H).

Intermediate 54 tert-Butyl N-[5-fluoro-7-(2-methyl-4-nitro-pyrazol-3-yl)oxepan-4-yl]carbamate

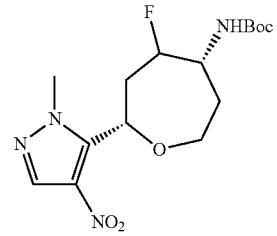

A solution of deoxo-Fluor (50% in THF, 0.576 mL, 1.56 mmol) was added dropwise to an ice-cooled solution of 5-azido-2-(2-methyl-4-nitro-pyrazol-3-yl)oxepan-4-ol (353 mg, 1.25 mmol, intermediate 27) in DCM (6 mL). The mixture was allowed to warm to room temperature whilst stirring for 16 hr before being cooled in an ice bath and saturated aqueous NaHCO$_3$ (10 mL) slowly added. The organic layer was passed through a phase separation cartridge and concentrated under reduced pressure. Purification via silica gel chromatography (0-50% EtOAc/isohexane) gave 5-(5-azido-4-fluorooxepan-2-yl)-1-methyl-4-nitro-1H-pyrazole as a clear gum. To a solution of this gum (145 mg, 0.51 mmol) in THF (5 mL) and water (1 mL) was added triphenylphosphine (147 mg, 0.56 mmol) and the mixture heated at 60° C. for 2 hr. The mixture was diluted with EtOAc (10 mL) and washed with brine (2×5 mL). The organic layer was passed through a phase separation cartridge and concentrated under reduced pressure. The residue was dissolved in DCM (2 mL) and DIPEA (0.178 mL, 1.02 mmol) and di-tert-butyl dicarbonate (134 mg, 0.61 mmol) were added. The mixture was stirred at room temperature for 2 hr. Water (2 mL) was added and the mixture extracted with DCM (3×2 mL). The combined organic layers were passed though a phase separation cartridge, concentrated under reduced pressure and the residue purified via silica gel chromatography (0-50% EtOAc/isohexane) to give tert-butyl N-[5-fluoro-7-(2-methyl-4-nitro-pyrazol-3-yl)oxepan-4-yl]carbamate as a clear gum (180 mg, 39% over three steps). $^1$H NMR (400 MHz, CDCl$_3$) δ 8.01 (s, 1H), 5.54 (dd, J=10.5, 4.2 Hz, 1H), 5.10-4.92 (m, 2H), 4.21-4.09 (m, 2H), 4.05 (s, 3H), 3.74-3.62 (m, 1H), 2.57-2.38 (m, 1H), 2.35-2.15 (m, 2H), 1.91-1.81 (m, 1H), 1.46 (s, 9H).

Intermediate 55 4-Azido-7-(2-methyl-4-nitro-pyrazol-3-yl)oxepan-3-one

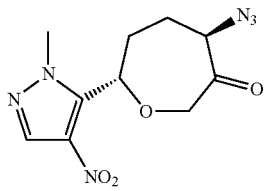

To a solution of 5-(5,8-dioxabicyclo[5.1.0]octan-4-yl)-1-methyl-4-nitro-pyrazole (2.85 g, 11.9 mmol, intermediate 19) in MeOH (60 mL) and water (11.5 mL) was added $NH_4Cl$ (1.58 g, 29.8 mmol) followed by sodium azide (3.87 g, 59.5 mmol). The reaction mixture was heated at 70° C. for 18 hr then allowed to cool to room temperature. The solvents were removed under reduced pressure and the residue was dissolved in EtOAc (150 mL). The organic layer was washed with brine (50 mL), separated, dried over $MgSO_4$ and concentrated under reduced pressure to give the azido alcohol as an orange oil as a 80/20 mixture of regioisomers. To a solution of this oil (1.9 g, 6.7 mmol) in DCM (40 mL) was added Dess-Martin periodinane (1.8 g, 4.26 mmol) and the mixture stirred at room temperature for 3 hr. Aqueous saturated $NaHCO_3$ (50 mL) and 20% sodium thiosulfate solution (50 mL) were added and the reaction mixture was stirred for 30 min until full dissolution of salts was observed. The mixture was diluted with DCM (50 mL) and the organic layer was separated, dried over $MgSO_4$ and concentrated under reduced pressure. Purification via silica gel column chromatography (0-50% EtOAc/isohexane) gave 4-azido-7-(2-methyl-4-nitro-pyrazol-3-yl)oxepan-3-one as an oil (1.05 g, 86% over two steps). $^1$H NMR (400 MHz, $CDCl_3$) δ 8.05 (s, 1H), 5.38 (dd, J=10.1, 2.7 Hz, 1H), 4.63-4.51 (m, 2H), 4.30-4.20 (m, 1H), 4.08 (s, 3H), 2.29-2.16 (m, 4H).

Intermediate 56 tert-Butyl N-[3,3-difluoro-7-(2-methyl-4-nitro-pyrazol-3-yl)oxepan-4-yl]carbamate

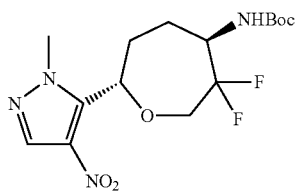 [SMILES: Cn1ncc([N+](=O)[O-])c1[C@@H]1CC[C@@H](NC(=O)OC(C)(C)C)C(F)(F)CO1]

To a solution of 4-azido-7-(2-methyl-4-nitro-pyrazol-3-yl)oxepan-3-one (440 mg, 1.57 mmol, intermediate 55) in DCM (10 mL) was added deoxo-Fluor® (50% in THF, 1.42 mL, 3.92 mmol) and the mixture stirred at room temperature for 18 hr. DCM (20 mL) was added, the mixture was cooled to 0° C. and saturated aqueous $NaHCO_3$ (20 mL) was carefully added. The aqueous layer was extracted with DCM (3×20 mL) and the combined organic layers were dried over $Na_2SO_4$ and concentrated under reduced pressure. Purification via silica gel column chromatography (0-30% EtOAc/isohexane) gave 5-(5-azido-6,6-difluorooxepan-2-yl)-1-methyl-4-nitro-1H-pyrazole as an oil (280 mg). A solution of this oil (280 mg, 0.93 mmol) in THF/water (10 mL/1.8 mL) was treated with triphenylphosphine (267 mg, 1.02 mmol) and the reaction mixture was heated at 70° C. behind a blast shield for 18 hr. The reaction mixture was concentrated under reduced pressure. The residue was dissolved in dry DCM (15 mL), cooled to 0° C. and di-tert-butyl-dicarbonate (243 mg, 1.12 mmol) was added followed by DIPEA (0.15 mL, 1.12 mmol). The reaction mixture was allowed to warm to room temperature and stirred for 72 hr. Water (20 mL) was added and the mixture was extracted with DCM (100 mL). The organic layer was separated, dried over $MgSO_4$ and concentrated under reduced pressure. Purification via silica gel column chromatography (0-35% EtOAc/isohexane) gave tert-butyl N-[3,3-difluoro-7-(2-methyl-4-nitro-pyrazol-3-yl)oxepan-4-yl]carbamate as a clear oil (310 mg, 59% over three steps). $^1$H NMR (400 MHz, $CDCl_3$) δ 8.03 (s, 1H), 5.48-5.42 (m, 1H), 5.10-5.01 (m, 1H), 4.49-4.35 (m, 2H), 4.04 (s, 3H), 3.99-3.80 (m, 1H), 2.17-1.98 (m, 4H), 1.48 (s, 9H).

Intermediate 57 4-Azido-7-(1-methyl-4-nitro-1H-pyrazol-5-yl)oxepan-3-ol

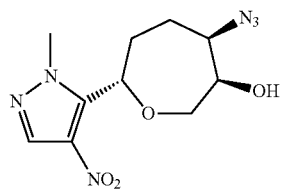 [SMILES: Cn1ncc([N+](=O)[O-])c1[C@@H]1CC[C@@H](N=[N+]=[N-])[C@@H](O)CO1]

To a solution of 4-azido-7-(2-methyl-4-nitro-pyrazol-3-yl)oxepan-3-one (Intermediate 55) (1 g, 3.57 mmol) in dry THF (25 mL) under nitrogen cooled to −78° C. was added L-selectride (1 M in THF, 4.3 mL, 4.3 mmol) and the mixture was stirred at −78° C. for 45 min. The mixture was allowed to warm to room temperature and water (10 mL) was added. The solvents were removed under reduced pressure and the residue was dissolved in EtOAc (100 mL). The organic layer was washed with water (40 mL) and brine (40 mL), dried over $Na_2SO_4$ and concentrated under reduced pressure. Purification via silica gel column chromatography (0-60% EtOAc/isohexane) gave racemic 4-azido-7-(1-methyl-4-nitro-1H-pyrazol-5-yl)oxepan-3-ol (relative stereochemistry as shown above) as a yellow oil (580 mg, 58%). $^1$H NMR (400 MHz, $CDCl_3$) δ 8.02 (s, 1H), 5.63 (dd, J=10.6, 3.5 Hz, 1H), 4.21-4.14 (m, 3H), 4.01 (s, 3H), 3.69-3.58 (m, 1H), 2.45-2.33 (m, 1H), 2.27-2.08 (m, 2H), 2.01-1.84 (m, 2H).

Intermediate 58 tert-Butyl N-[3-methoxy-7-(2-methyl-4-nitro-pyrazol-3-yl)oxepan-4-yl]carbamate

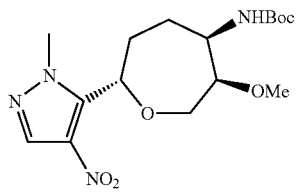

To a solution of 4-azido-7-(1-methyl-4-nitro-1H-pyrazol-5-yl)oxepan-3-ol, (Intermediate 57) (182 mg, 0.65 mmol) in anhydrous DMF (5 mL) under nitrogen was added sodium hydride (60% dispersion in mineral oil, 39 mg, 0.97 mmol) portionwise over 10 min. After a further 45 min, methyl iodide (0.06 mL, 0.97 mmol) was added dropwise and the mixture stirred for 18 hr at room temperature. Further sodium hydride (60% dispersion in mineral oil, 39 mg, 0.97 mmol) was added followed by methyl iodide (0.06 mL, 0.97 mmol) and the mixture stirred at room temperature for 48 hr. The mixture was quenched with water (20 mL) and extracted with EtOAc (3×20 mL). The combined organic layers were washed with water (20 mL) and brine (20 mL), separated, dried over MgSO$_4$ and the solvent removed under reduced pressure. Purification via silica gel column chromatography (0-50% EtOAc/isohexane) gave 5-(5-azido-6-methoxyoxepan-2-yl)-1-methyl-4-nitro-1H-pyrazole as an oil (100 mg). A solution of this oil (100 mg, 0.37 mmol) in THF/water (5 mL/1 mL) was treated with triphenylphosphine (97 mg, 0.37 mmol) and the reaction mixture heated at 70° C. behind a blast shield for 18 hr. The mixture was concentrated under reduced pressure. The residue was dissolved in dry DCM (3 mL) at 0° C. and di-tert-butyl-dicarbonate (89 mg, 0.4 mmol) and DIPEA (0.18 mL, 1.02 mmol) were added. The reaction mixture was warmed to room temperature and stirred for 3 hr. Water (10 mL) was added and the mixture extracted with DCM (20 mL). The organic layer was separated, dried over MgSO$_4$ and concentrated under reduced pressure. Purification via silica gel column chromatography (0-50% EtOAc/isohexane) gave racemic tert-butyl-(3-methoxy-7-(1-methyl-4-nitro-1H-pyrazol-5-yl)oxepan-4-yl)carbamate (relative stereochemistry as shown above) as a clear oil (119 mg, 47% over three steps). $^1$H NMR (400 MHz, CDCl$_3$) δ 8.02 (s, 1H), 5.39 (dd, J=10.6, 3.6 Hz, 1H), 4.75 (br s, 1H), 4.33 (dd, J=14.2, 1.9 Hz, 1H), 4.06 (s, 3H), 3.91-3.83 (m, 1H), 3.75 (dd, J=14.2, 3.2 Hz, 1H), 3.43 (s, 3H), 3.39-3.34 (m, 1H), 2.22-2.12 (m, 1H), 2.12-2.03 (m, 1H), 2.03-1.82 (m, 2H), 1.47 (s, 9H).

Intermediate 59 1-(1-Methyl-4-nitro-1H-pyrazol-5-yl)pent-4-en-1-ol

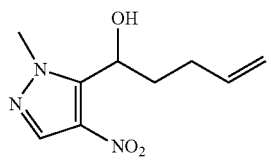

A solution of 1-methyl-4-nitro-1H-pyrazole (9.7 g, 76.7 mmol) and 4-pentenal (10 g, 84.4 mmol) in dry THF (250 mL) was cooled to −78° C. and stirred under nitrogen. A solution of LiHMDS (1 M in THF, 192 mL, 191.7 mmol) was added dropwise over a period of 3 hr. The reaction mixture was allowed to warm and to −40° C. and stirred for 2 hr, quenched by dropwise addition of saturated ammonium chloride solution (100 mL), warmed to room temperature and diluted with EtOAc (200 mL). The organic layer was washed with saturated ammonium chloride solution (50 mL), separated, dried over MgSO$_4$ and the solvent removed under reduced pressure. Purification via silica gel chromatography (0-100% EtOAc/DCM) followed by silica gel chromatography (0-100% EtOAc/isohexane) to gave 1-(1-methyl-4-nitro-1H-pyrazol-5-yl)pent-4-en-1-ol as a pale yellow oil (5.75 g, 36%). $^1$H NMR (400 MHz, CDCl$_3$) δ 8.06 (s, 1H), 5.85-5.78 (m, 1H), 5.32-5.26 (m, 1H), 5.12-5.04 (m, 2H), 3.98 (s, 3H), 3.45 (d, J=8.7 Hz, 1H), 2.92-2.09 (m, 3H), 1.90-1.86 (m, 1H).

Intermediate 60 5-(5-(Iodomethyl)tetrahydrofuran-2-yl)-1-methyl-4-nitro-1H-pyrazole

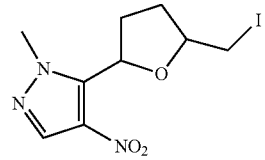 [SMILES: Cn1ncc([N+](=O)[O-])c1C1CCC(CI)O1]

To a stirred solution of 1-(1-methyl-4-nitro-1H-pyrazol-5-yl)pent-4-en-1-ol (0.84 g, 3.98 mmol, intermediate 59) in dry THF (25 mL) under nitrogen was added iodine (1.52 g, 5.97 mmol). After stirring for 5 min, Na$_2$CO$_3$ (0.63 g, 5.97 mmol) was added followed by silver triflate (3.07 g, 11.94 mmol) and the dark red solution turned yellow. The mixture was stirred at room temperature for 1 hr, diluted with THF (25 mL) and filtered through celite. The yellow solid was washed with THF/DCM and the filtrate concentrated under reduced pressure. Purification via silica gel chromatography (0-40% EtOAc/DCM) gave 5-(5-(iodomethyl)tetrahydrofuran-2-yl)-1-methyl-4-nitro-1H-pyrazole as a pale yellow gum (640 mg, 48%). $^1$H NMR (400 MHz, CDCl$_3$) δ 8.03 (s, 1H), 5.91-5.87 (m, 1H), 4.39-4.35 (m, 1H), 4.02 (s, 3H), 3.37-3.30 (m, 2H), 2.69-2.67 (m, 1H), 2.45-2.41 (m, 1H), 2.05-1.89 (m, 2H).

Intermediate 61 5-(5-(Azidomethyl)tetrahydrofuran-2-yl)-1-methyl-4-nitro-1H-pyrazole

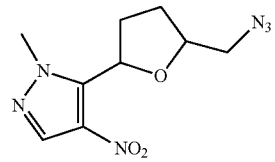

To a solution of 5-(5-(iodomethyl)tetrahydrofuran-2-yl)-1-methyl-4-nitro-1H-pyrazole (640 mg, 1.90 mmol, intermediate 60) in dry DMF (10 mL) was added sodium azide (250 mg, 3.80 mmol) and the mixture stirred at room temperature for 36 hr. The mixture was diluted with EtOAc (25 mL) and washed with water (2×10 mL) and brine (20 mL). The organic layer was passed through a phase separation cartridge and concentrated under reduced pressure to give 5-(5-(azidomethyl)tetrahydrofuran-2-yl)-1-methyl-4-nitro-1H-pyrazole as a yellow oil (480 mg, 100%). $^1$H NMR (400 MHz, CDCl$_3$) δ 8.05 (s, 1H), 5.84-5.70 (m, 1H), 4.49-4.45 (m, 1H), 4.03 (s, 3H), 3.56-3.39 (m, 2H), 2.66-2.65 (m, 1H), 2.29-2.22 (m, 1H), 2.02-1.92 (m, 2H).

Intermediate 62 tert-Butyl ((5-(1-methyl-4-nitro-1H-pyrazol-5-yl)tetrahydrofuran-2-yl)methyl)carbamate

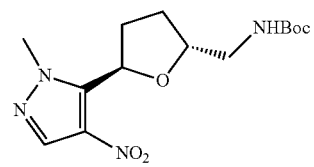 [SMILES: Cn1ncc([N+](=O)[O-])c1[C@H]1CC[C@H](CNC(=O)OC(C)(C)C)O1]

A solution of 5-(5-(azidomethyl)tetrahydrofuran-2-yl)-1-methyl-4-nitro-1H-pyrazole (520 mg, 2.07 mmol, intermediate 61) in THF/water (20 mL/4 mL) was treated with triphenylphosphine (600 mg, 2.28 mmol) and the reaction mixture heated at 70° C. behind a blast shield for 1.5 hr. The mixture was allowed to cool to room temperature and the organic solvent was removed under reduced pressure. The aqueous layer was extracted with DCM (40 mL) and the organic layer was passed through a phase separation cartridge and concentrated under reduced pressure to give a pale yellow oil. This oil was dissolved in DCM (20 mL) and DIPEA (0.72 mL, 4.14 mmol) was added followed by a solution of di-tert-butyl-dicarbonate (540 mg, 2.48 mmol) in DCM (1 mL) in two portions. The reaction mixture was stirred at room temperature for 1 hr. Water (10 mL) was added and the organic layer was passed through a phase separation cartridge and concentrated under reduced pressure. Purification via silica gel column chromatography (0-60% EtOAc/isohexane) gave tert-butyl ((5-(1-methyl-4-nitro-1H-pyrazol-5-yl)tetrahydrofuran-2-yl)methyl)carbamate as a colourless gum (145 mg, 21% over two steps). $^1$H NMR (400 MHz, CDCl$_3$) δ 8.04 (s, 1H), 5.80-5.76 (m, 1H), 4.85 (br s, 1H), 4.35 (br s, 1H), 4.01 (s, 3H), 3.50-3.40 (m, 1H), 3.25-3.19 (m, 1H), 2.65-2.55 (m, 1H), 2.25-2.20 (m, 1H), 2.00-1.80 (m, 2H), 1.46 (s, 9H).

Intermediate 63 2-Azido-5-fluoro-5-(1-methyl-4-nitro-1H-pyrazol-5-yl)cycloheptanol

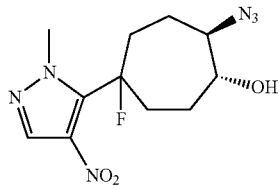 [SMILES: Cn1ncc([N+](=O)[O-])c1C1(F)CC[C@@H](O)[C@H](N=[N+]=[N-])CC1]

A solution of 5-(4-fluoro-8-oxabicyclo[5.1.0]octan-4-yl)-1-methyl-4-nitro-1H-pyrazole (2.75 g, 10.8 mmol, Intermediate 155) in DMF/water (35 mL/10 mL) was treated with ammonium chloride (1.43 g, 27.0 mmol) and sodium azide (3.5 g, 53.9 mmol) and the mixture was heated at 100° C. behind a blast shield for 18 hr. The reaction mixture was extracted with EtOAc (200 mL) and the organic layer was washed with water (8×30 mL), washed with brine (30 mL), separated, dried over MgSO$_4$, and concentrated under reduced pressure. Purification via silica gel column chromatography (30-40% EtOAc/isohexane) gave 2-azido-5-fluoro-5-(1-methyl-4-nitro-1H-pyrazol-5-yl)cycloheptanol as the second eluting isomer as a white solid (2.16 g, 67%). $^1$H NMR (400 MHz, CDCl$_3$) δ 8.06 and 8.05 (2s, 1H), 4.08 and 4.06 (2s, 3H), 3.88-3.78 (m, 1H), 3.65-3.58 (m, 1H), 2.87-2.55 (m, 2H), 2.31-2.21 (m, 2H), 2.18-2.00 (m, 3H), 1.98-1.85 (m, 2H).

Intermediate 64 tert-Butyl N-[5-fluoro-2-hydroxy-5-(2-methyl-4-nitro-pyrazol-3-yl)cycloheptyl]carbamate

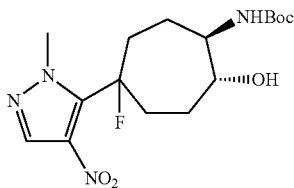 [SMILES: Cn1ncc([N+](=O)[O-])c1C1(F)CC[C@@H](O)[C@H](NC(=O)OC(C)(C)C)CC1]

A solution of 2-azido-5-fluoro-5-(1-methyl-4-nitro-1H-pyrazol-5-yl)cycloheptanol (300 mg, 1.05 mmol, intermediate 63) in THF/water (15 mL/3 mL) was treated with triphenylphosphine (290 mg, 1.11 mmol) and the mixture heated at 60° C. behind a blast shield for 18 hr. Brine (5 mL) was added and the mixture extracted with EtOAc (2×50 mL). The organic layers were combined, dried over MgSO$_4$ and concentrated under reduced pressure. To a solution of the resulting oil in dry DCM (20 mL) under nitrogen was added slowly DIPEA (0.88 mL, 5.03 mmol) followed by a solution of di-tert-butyl-dicarbonate (263 mg, 1.21 mmol) in dry DCM (10 mL). The reaction mixture was stirred at room temperature for 4 days. Water (30 mL) was added and the mixture was extracted with DCM (80 mL). The organic layer was separated, dried over MgSO$_4$ and concentrated under reduced pressure. Purification via silica gel column chromatography (40-50% EtOAc/isohexane) gave tert-butyl N-[5-fluoro-2-hydroxy-5-(2-methyl-4-nitro-pyrazol-3-yl)cycloheptyl]carbamate as a colourless oil (218 mg, 58% over two steps). $^1$H NMR (400 MHz, CDCl$_3$) δ 8.06 and 8.05 (2s, 1H), 4.86 (br s, 1H), 4.08 and 4.06 (2s, 3H), 3.88-3.79 (m, 1H), 3.75-3.67 (m, 2H), 2.77-2.48 (m, 2H), 2.40-2.30 (m, 1H), 2.21-1.95 (m, 3H), 1.95-1.67 (m, 2H), 1.47 (s, 9H).

Intermediate 65 tert-Butyl N-[2-bromo-4-[[5-[2-(tert-butoxycarbonylamino)-8-oxabicyclo[3.2.1]octan-5-yl]-1-methyl-pyrazol-4-yl]carbamoyl]thiazol-5-yl]carbamate

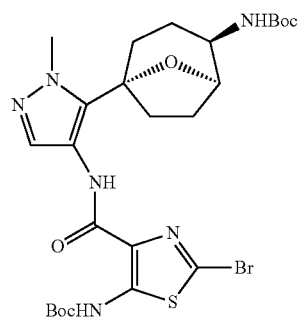 [SMILES: Cn1ncc(NC(=O)c2nc(Br)sc2NC(=O)OC(C)(C)C)c1[C@@]12CC[C@@H](NC(=O)OC(C)(C)C)[C@@H](CC1)O2]

To a solution of tert-butyl N-[5-fluoro-2-hydroxy-5-(2-methyl-4-nitro-pyrazol-3-yl)cycloheptyl]carbamate (210 mg, 0.565 mmol, intermediate 64) in THF (20 mL) and MeOH (20 mL) was added 10% palladium on carbon (20 mg). The reaction mixture was heated at 40° C. under a 400 psi atmosphere of hydrogen for 3 hr. After cooling to room temperature, the mixture was filtered through Celite®, washing with MeOH (50 mL) and concentrated under reduced pressure. To a solution of the residue in DCM (30 mL) was added DIPEA (2 mL, 1.40 mmol), 2-bromo-5-(tert-butoxycarbonylamino)thiazole-4-carboxylic acid (208 mg, 0.62 mmol, Example 22) and PyBOP (727 mg, 1.40 mmol) and the mixture was stirred at room temperature for 18 hr. Water (20 mL) was added and the mixture was extracted with DCM (100 mL). The organic layer was passed through a phase separation cartridge and concentrated under reduced pressure. Purification via silica gel chromatography (80-100% EtOAc/isohexane) gave tert-butyl N-[2-bromo-4-[[5-[2-(tert-butoxycarbonylamino)-8-oxabicyclo[3.2.1]octan-5-yl]-1-methyl-pyrazol-4-yl]carbamoyl]thiazol-5-yl]carbamate (120 mg, 34% over two steps). $^1$H NMR (400 MHz, CDCl$_3$) δ 10.40 (br s, 1H), 9.86 (br s, 1H), 8.12 (br s, 1H), 4.70-4.63 (m, 1H), 4.36-4.22 (m, 1H), 3.97-3.86 (m, 1H), 3.86 (s, 3H), 2.40-2.31 (m, 1H), 2.21-1.93 (m, 7H), 1.55 (s, 9H), 1.52 (s, 9H).

Intermediate 66 (5-Ethyl-2-(1-methyl-4-nitro-1H-pyrazol-5-yl)-1,3-dioxan-5-yl)methanol (trans isomer)

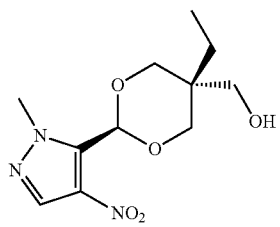 [SMILES: CC[C@]1(CO)CO[C@H](c2c([N+](=O)[O-])cnn2C)OC1]

To a solution of 2-methyl-4-nitro-pyrazole-3-carbaldehyde (370 mg, 2.39 mmol, intermediate 3) in toluene (50 mL) was added 2-ethyl-2-(hydroxymethyl)propane-1,3-diol (315 mg, 2.35 mmol) followed by p-toluenesulfonic acid (20 mg, 0.10 mmol). The reaction mixture was heated at reflux for 36 hr whilst azeotropically removing the water. The mixture was cooled to room temperature and concentrated under reduced pressure. Purification via silica gel column chromatography (0-100% EtOAc/isohexane) gave (5-ethyl-2-(1-methyl-4-nitro-1H-pyrazol-5-yl)-1,3-dioxan-5-yl)methanol (trans isomer) as the first eluting isomer as a colourless solid (244 mg, 38%). $^1$H NMR (400 MHz, CDCl$_3$) δ 8.02 (s, 1H), 6.38 (s, 1H), 4.16 (s, 3H), 4.02 (d, J=11.5 Hz, 2H), 3.97 (d, J=5.2 Hz, 2H), 3.42 (d, J=3.8 Hz, 2H), 1.90 (m, 3H), 0.99 (t, J=7.6 Hz, 3H).

Intermediate 67 (5-Ethyl-2-(1-methyl-4-nitro-1H-pyrazol-5-yl)-1,3-dioxan-5-yl)methanol (cis isomer)

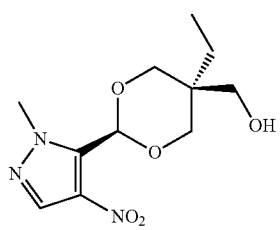 [SMILES: CC[C@]1(CO)CO[C@@H](c2c([N+](=O)[O-])cnn2C)OC1]

Following the procedure for Intermediate 66 also gave (5-ethyl-2-(1-methyl-4-nitro-1H-pyrazol-5-yl)-1,3-dioxan-5-yl)methanol (cis isomer) as the second eluting isomer as a colourless solid (118 mg, 18%). $^1$H NMR (400 MHz, CDCl$_3$) δ 8.02 (s, 1H), 6.37 (s, 1H), 4.13 (s, 3H), 4.12 (d, J=12.8 Hz, 2H), 3.98 (d, J=3.9 Hz, 2H), 3.73 (d, J=11.8 Hz, 2H), 1.74 (br s, 1H), 1.31 (q, J=7.7 Hz, 2H), 0.89 (t, J=7.7 Hz, 3H).

Intermediate 68 (2-(1-Methyl-4-nitro-1H-pyrazol-5-yl)-1,3-dioxan-5-yl)methanol (trans isomer)

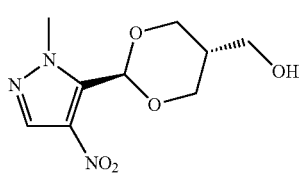

To a solution of 2-methyl-4-nitro-pyrazole-3-carbaldehyde (718 mg, 4.63 mmol, intermediate 3) in toluene (100 mL) was added 2-(hydroxymethyl)propane-1,3-diol (700 mg, 6.73 mmol) followed by p-toluenesulfonic acid (88 mg, 0.463 mmol). The reaction mixture was heated at reflux for 18 hr whilst azeotropically removing the water. The mixture was cooled to room temperature and concentrated under reduced pressure. The residue was diluted with DCM (50 mL) and washed with a saturated aqueous NaHCO$_3$ (50 mL). The organic layer was washed with water (20 mL) and brine (20 mL), separated, dried over Na$_2$SO$_4$ and concentrated under reduced pressure. Purification via silica gel column chromatography (0-100% EtOAc/isohexane) gave (2-(1-methyl-4-nitro-1H-pyrazol-5-yl)-1,3-dioxan-5-yl)methanol (trans isomer) as the first eluting isomer as a colourless solid (220 mg, 20%). $^1$H NMR (400 MHz, CDCl$_3$) δ 8.02 (s, 1H), 6.42 (s, 1H), 4.34 (dd, J=11.6, 4.7 Hz, 2H), 4.12 (s, 3H), 3.81 (t, J=11.5 Hz, 2H), 3.56 (t, J=5.1 Hz, 2H), 2.53-2.38 (m, 1H), 1.67 (t, J=4.6 Hz, 1H).

Intermediate 69 (2-(1-Methyl-4-nitro-1H-pyrazol-5-yl)-1,3-dioxan-5-yl)methanol (cis isomer)

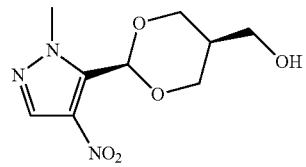 [SMILES: Cn1ncc([N+](=O)[O-])c1[C@H]1OC[C@@H](CO)CO1]

Following the procedure for Intermediate 68 also gave (2-(1-methyl-4-nitro-1H-pyrazol-5-yl)-1,3-dioxan-5-yl)methanol (cis isomer) as a colourless solid (268 mg, 24%). $^1$H NMR (400 MHz, CDCl$_3$) δ 8.02 (s, 1H), 6.49 (s, 1H), 4.28 (d, J=11.9 Hz, 2H), 4.20 (d, J=3.3 Hz, 2H), 4.12 (s, 3H), 4.06 (dd, J=7.8, 3.7 Hz, 2H), 1.82 (t, J=4.9 Hz, 1H), 1.78-1.71 (m, 1H).

Intermediate 70 (5-Methyl-2-(1-methyl-4-nitro-1H-pyrazol-5-yl)-1,3-dioxan-5-yl)methanol (trans isomer)

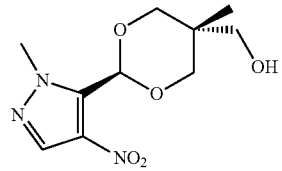 [SMILES: Cn1ncc([N+](=O)[O-])c1[C@H]1OC[C@](C)(CO)CO1]

Following the procedure for Intermediate 68 starting from 2-methyl-2-(hydroxymethyl)propane-1,3-diol gave (5-methyl-2-(1-methyl-4-nitro-1H-pyrazol-5-yl)-1,3-dioxan-5-yl)methanol as the first eluting isomer as a colourless solid (167 mg, 13%). $^1$H NMR (400 MHz, CDCl$_3$) δ 8.03 (s, 1H), 6.38 (s, 1H), 4.19 (s, 3H), 4.02 (d, J=11.3 Hz, 2H), 3.89 (d, J=11.3 Hz, 2H), 3.43 (d, J=4.5 Hz, 2H), 1.65-1.40 (m, 1H), 1.36 (s, 3H).

Intermediate 71 (5-Methyl-2-(1-methyl-4-nitro-1H-pyrazol-5-yl)-1,3-dioxan-5-yl)methanol (cis isomer)

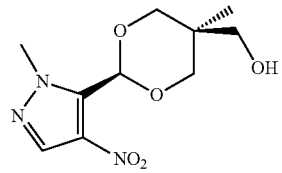 [SMILES: Cn1ncc([N+](=O)[O-])c1[C@H]1OC[C@@](C)(CO)CO1]

Following the procedure for Intermediate 70 also gave (5-methyl-2-(1-methyl-4-nitro-1H-pyrazol-5-yl)-1,3-dioxan-5-yl)methanol (cis isomer) as the second eluting isomer (480 mg, 38%). $^1$H NMR (400 MHz, CDCl$_3$) δ 8.02 (s, 1H), 6.40 (s, 1H), 4.16-4.06 (m, 5H), 3.91 (s, 2H), 3.72 (d, J=11.9 Hz, 2H), 0.85 (s, 3H). OH not observed.

Intermediate 72 tert-Butyl N-[(4R,7S)-3,3-difluoro-7-(2-methyl-4-nitro-pyrazol-3-yl)oxepan-4-yl]carbamate

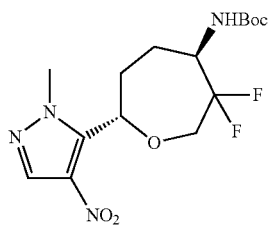 [SMILES: Cn1ncc([N+](=O)[O-])c1[C@@H]1CC[C@@H](NC(=O)OC(C)(C)C)C(F)(F)CO1]

tert-Butyl N-[3,3-difluoro-7-(2-methyl-4-nitro-pyrazol-3-yl)oxepan-4-yl]carbamate (intermediate 56) was further purified via chiral SFC to give tert-butyl N-[(4R)-3,3-difluoro-7-(2-methyl-4-nitro-pyrazol-3-yl)oxepan-4-yl]carbamate as the second eluting isomer as an off-white solid (57 mg, 47%). $^1$H NMR (400 MHz, CDCl$_3$) δ 8.04 (s, 1H), 5.48-5.42 (m, 1H), 5.06 (d, J=9.5 Hz, 1H), 4.49-4.38 (m, 2H), 4.05 (s, 3H), 3.98-3.82 (m, 1H), 2.18-2.00 (m, 4H), 1.48 (s, 9H).

Intermediate 73 tert-Butyl N-[(4S,7R)-3,3-difluoro-7-(2-methyl-4-nitro-pyrazol-3-yl)oxepan-4-yl]carbamate

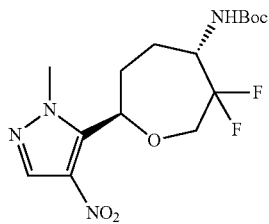 [SMILES: Cn1ncc([N+](=O)[O-])c1[C@H]1CC[C@H](NC(=O)OC(C)(C)C)C(F)(F)CO1]

Following the procedure for Intermediate 72 also gave tert-butyl N-[(4S,7R)-3,3-difluoro-7-(2-methyl-4-nitro-pyrazol-3-yl)oxepan-4-yl]carbamate as the first eluting isomer as an off-white solid (65 mg, 53%). $^1$H NMR (400 MHz, CDCl$_3$) δ 8.04 (s, 1H), 5.48-5.42 (m, 1H), 5.05 (d, J=9.2 Hz, 1H), 4.50-4.36 (m, 2H), 4.05 (s, 3H), 3.98-3.84 (m, 1H), 2.18-2.00 (m, 4H), 1.48 (s, 9H).

Intermediate 74 (5-Ethyl-2-(1-methyl-4-nitro-1H-pyrazol-5-yl)-1,3-dioxan-5-yl)methyl methanesulfonate

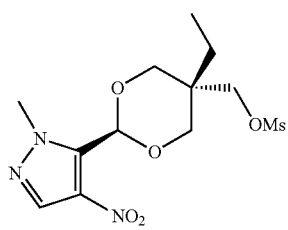 [SMILES: CC[C@]1(COS(C)(=O)=O)CO[C@H](c2c([N+](=O)[O-])cnn2C)OC1]

To a solution of (5-ethyl-2-(1-methyl-4-nitro-1H-pyrazol-5-yl)-1,3-dioxan-5-yl)methanol (trans isomer) (610 mg, 2.25 mmol, intermediate 66) in dry DCM (15 mL) at 0° C. was added Et$_3$N (0.45 mL, 3.38 mmol) followed by methanesulfonyl chloride (0.21 mL, 2.70 mmol). The reaction mixture was slowly warmed to room temperature over 1.5 hr. The mixture was re-cooled to 0° C. and diluted with aqueous 1 M HCl (10 mL) and DCM (20 mL). The organic layer was washed with aqueous saturated NaHCO$_3$ (15 mL) and water (15 mL), separated, dried over Na$_2$SO$_4$ and concentrated under reduced pressure to give (5-ethyl-2-(1-methyl-4-nitro-1H-pyrazol-5-yl)-1,3-dioxan-5-yl)methyl methanesulfonate as a white solid (816 mg, quantitative). $^1$H NMR (400 MHz, CDCl$_3$) δ 8.01 (s, 1H), 6.38 (s, 1H), 4.14 (s, 3H), 4.05-3.88 (m, 6H), 3.22-2.92 (m, 3H), 1.96 (q, J=7.6 Hz, 2H), 1.03 (t, J=7.6 Hz, 3H).

Intermediate 75 2-((5-Ethyl-2-(1-methyl-4-nitro-1H-pyrazol-5-yl)-1,3-dioxan-5-yl)methyl)isoindoline-1,3-dione

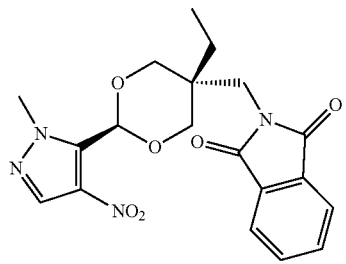 [SMILES: CC[C@]1(CN2C(=O)c3ccccc3C2=O)CO[C@H](c2c([N+](=O)[O-])cnn2C)OC1]

To a solution of (5-ethyl-2-(1-methyl-4-nitro-1H-pyrazol-5-yl)-1,3-dioxan-5-yl)methyl methanesulfonate (816 mg, 2.25 mmol, intermediate 74) in dry DMSO (10 mL) was added potassium phthalimide (2.1 g, 11.3 mmol) in a single portion. The reaction mixture was heated at 180° C. for 5 hr, cooled to room temperature and diluted with EtOAc (50 mL) and water (30 mL). The organic layer was washed with water (3×30 mL), 2 N NaOH (2×20 mL) and water (20 mL), separated, dried over Na$_2$SO$_4$ and concentrated under reduced pressure. Purification via silica gel column chromatography (0-100% EtOAc/isohexane) gave 2-((5-ethyl-2-(1-methyl-4-nitro-1H-pyrazol-5-yl)-1,3-dioxan-5-yl)methyl)isoindoline-1,3-dione as a colourless solid (317 mg, 35%). $^1$H NMR (400 MHz, CDCl$_3$) δ 8.00 (s, 1H), 7.93-7.88 (m, 2H), 7.82-7.76 (m, 2H), 6.31 (s, 1H), 4.14 (s, 3H), 4.06 (d, J=11.8 Hz, 2H), 3.85 (d, J=11.8 Hz, 2H), 3.51 (s, 2H), 1.92 (q, J=7.6 Hz, 2H), 1.14 (t, J=7.6 Hz, 3H).

Intermediate 76 tert-Butyl N-[7-(2-methyl-4-nitro-pyrazol-3-yl)-3-(trideuteriomethoxy)oxepan-4-yl]carbamate

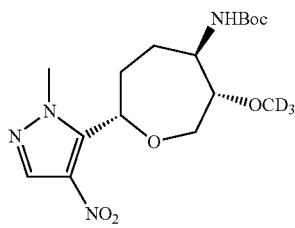

A solution of 5-(5,8-dioxabicyclo[5.1.0]octan-4-yl)-1-methyl-4-nitro-pyrazole (400 mg, 1.67 mmol, intermediate 19) in MeOH/water (9 mL/1.7 mL) was treated with ammonium chloride (221 mg, 4.2 mmol) and sodium azide (544 mg, 8.37 mmol) and the mixture was heated at 70° C. behind a blast shield for 18 hr. The reaction mixture was extracted with EtOAc (100 mL) and the organic layer washed with water (3×20 mL) and brine (20 mL), separated, dried over MgSO$_4$ and concentrated under reduced pressure. To a solution of the residue (310 mg, 1.1 mmol) in anhydrous DMF (5 mL) under nitrogen at room temperature was added sodium hydride (60% dispersion in mineral oil, 53 mg, 1.32 mmol) portionwise over 10 min. After a further 45 min, trideuteromethyl iodide (0.21 mL, 3.3 mmol) was added dropwise and the mixture stirred at room temperature for 18 hr. More sodium hydride (60% dispersion in mineral oil, 310 mg, 1.1 mmol) was added followed by more trideuteromethyl iodide (0.21 mL, 3.3 mmol) and the mixture stirred at room temperature for 48 hr. Water (20 mL) was added and the mixture extracted with EtOAc (3×20 mL). The combined organic layers were washed with water (20 mL) and brine (20 mL), dried over MgSO$_4$ and concentrated under reduced pressure. Purification via silica gel column chromatography (0-40% EtOAc/isohexane) gave 5-[5-azido-6-(trideuteriomethoxy)oxepan-2-yl]-1-methyl-4-nitro-pyrazole as an oil (140 mg). A solution of this oil (140 mg, 0.47 mmol) in THF/water (5 mL/0.9 mL) was treated with triphenylphosphine (135 mg, 0.52 mmol) and the reaction mixture was heated at 70° C. behind a blast shield for 18 hr. The mixture was concentrated under reduced pressure. The resulting residue was dissolved in dry DCM (9 mL) at 0° C. and di-tert-butyl-dicarbonate (123 mg, 0.56 mmol) and DIPEA (0.25 mL, 1.41 mmol) were added. The reaction mixture was warmed to room temperature and stirred for 3 hr. Water (10 mL) was added and the mixture extracted with DCM (20 mL). The organic layer was separated, dried over MgSO$_4$ and concentrated under reduced pressure. Purification via silica gel column chromatography (0-60% EtOAc/isohexane) gave racemic tert-butyl N-[7-(2-methyl-4-nitro-pyrazol-3-yl)-3-(trideuteriomethoxy)oxepan-4-yl]carbamate (relative stereochemistry as shown above) as an off-white solid (125 mg, 28% over four steps). $^1$H NMR (400 MHz, CDCl$_3$) δ 8.01 (s, 1H), 5.39 (dd, J=10.6, 3.6 Hz, 1H), 4.85-4.67 (m, 1H), 4.32 (dd, J=14.2, 1.9 Hz, 1H), 4.06 (s, 3H), 3.90-3.82 (m, 1H), 3.75 (dd, J=14.2, 3.2 Hz, 1H), 3.40-3.33 (m, 1H), 2.20-1.82 (m, 4H), 1.46 (m, 9H).

Intermediate 77 tert-Butyl N-[(3R,4S,7R)-7-(2-methyl-4-nitro-pyrazol-3-yl)-3-(trideuteriomethoxy)oxepan-4-yl]carbamate

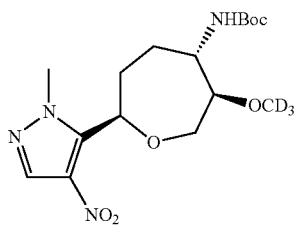

Further purification of tert-butyl N-[7-(2-methyl-4-nitro-pyrazol-3-yl)-3-(trideuteriomethoxy)oxepan-4-yl]carbamate via chiral SFC gave tert-butyl N-[(3R,4S)-7-(2-methyl-4-nitro-pyrazol-3-yl)-3-(trideuteriomethoxy)oxepan-4-yl]carbamate as the first eluting isomer as an off-white solid (54 mg, 43%). $^1$H NMR (400 MHz, CDCl$_3$) δ 8.01 (s, 1H), 5.39 (dd, J=10.6, 3.6 Hz, 1H), 4.85-4.68 (m, 1H), 4.32 (dd, J=14.2, 1.9 Hz, 1H), 4.06 (s, 3H), 3.90-3.82 (m, 1H), 3.75 (dd, J=14.0, 3.2 Hz, 1H), 3.40-3.33 (m, 1H), 2.20-1.83 (m, 4H), 1.46 (s, 9H).

Intermediate 78 tert-Butyl N-[(3S,4R,7S)-7-(2-methyl-4-nitro-pyrazol-3-yl)-3-(trideuteriomethoxy)oxepan-4-yl]carbamate

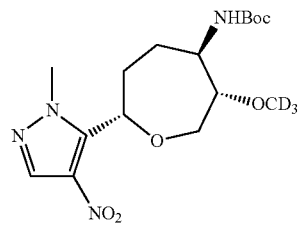

Following the procedure for Intermediate 77 also gave tert-butyl N-[(3S,4R,7S)-7-(2-methyl-4-nitro-pyrazol-3-yl)-3-(trideuteriomethoxy)oxepan-4-yl]carbamate as the second eluting isomer as an off-white solid (52 mg, 41%). $^1$H NMR (400 MHz, CDCl$_3$) δ 8.02 (s, 1H), 5.39 (dd, J=10.6, 3.6 Hz, 1H), 4.85-4.66 (m, 1H), 4.33 (dd, J=14.2, 1.9 Hz, 1H), 4.07 (s, 3H), 3.90-3.83 (m, 1H), 3.75 (dd, J=14.2, 3.2 Hz, 1H), 3.40-3.33 (m, 1H), 2.21-1.83 (m, 4H), 1.47 (m, 9H).

Intermediate 79 5-(5-(Azidomethyl)-5-methyl-1,3-dioxan-2-yl)-1-methyl-4-nitro-1H-pyrazole (trans isomer)

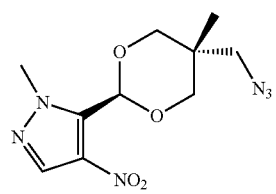 [SMILES: Cn1ncc([N+](=O)[O-])c1[C@H]1OC[C@](C)(CN=[N+]=[N-])CO1]

To a solution of (5-methyl-2-(1-methyl-4-nitro-1H-pyrazol-5-yl)-1,3-dioxan-5-yl)methanol (trans isomer) (248 mg, 1.02 mmol, intermediate 66) in dry DCM at 0° C. (10 mL) was added Et$_3$N (0.20 mL, 1.53 mmol) followed by methanesulfonyl chloride (0.10 mL, 1.22 mmol). The reaction mixture was slowly warmed to room temperature over 1.5 hr. The mixture was re-cooled to 0° C. and 1 M aqueous HCl (5 mL) and DCM (20 mL) were added. The organic layer was washed with saturated aqueous NaHCO$_3$ (10 mL) and water (10 mL), separated, dried over Na$_2$SO$_4$ and concentrated under reduced pressure to yield a colourless oil. This oil was dissolved in DMF (20 mL) and sodium azide (400 mg, 6.12 mmol) was added. The reaction mixture was heated at 140° C. for 18 hr behind a blast shield. The reaction mixture was cooled to room temperature and diluted with water (20 mL) and EtOAc (50 mL). The organic layer was washed with water (3×20 mL), separated, dried over Na$_2$SO$_4$ and concentrated under reduced pressure to give 5-(5-(azidomethyl)-5-methyl-1,3-dioxan-2-yl)-1-methyl-4-nitro-1H-pyrazole as a colourless solid (300 mg, quantitative over two steps). $^1$H NMR (400 MHz, CDCl$_3$) δ 8.03 (s, 1H), 6.36 (s, 1H), 4.17 (s, 3H), 3.88 (s, 4H), 3.20 (s, 2H), 1.40 (s, 3H).

Intermediate 80 tert-Butyl N-[(3S,4R,7S)-3-fluoro-7-(2-methyl-4-nitro-pyrazol-3-yl)oxepan-4-yl]carbamate

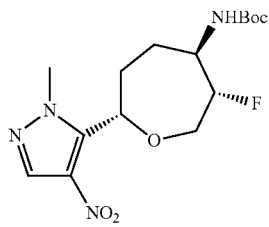 [SMILES: Cn1ncc([N+](=O)[O-])c1[C@@H]1CC[C@@H](NC(=O)OC(C)(C)C)[C@H](F)CO1]

To a solution of 4-azido-7-(2-methyl-4-nitro-pyrazol-3-yl)oxepan-3-ol (660 mg, 2.34 mmol, intermediate 57) in DCM (12 mL) was added deoxo-Fluor® (50% in THF, 2.12 mL) and the mixture was stirred at room temperature for 18 hr. The mixture was diluted with DCM (22 mL), cooled to 0° C. and saturated aqueous $NaHCO_3$ (20 mL) was carefully added. The aqueous layer was extracted with DCM (3×20 mL) and the combined organic layers were dried over $Na_2SO_4$ and concentrated under reduced pressure. Purification via silica gel column chromatography (0-30% EtOAc/isohexane) gave 5-(5-azido-6-fluorooxepan-2-yl)-1-methyl-4-nitro-1H-pyrazole as an oil (440 mg). A solution of this oil (440 mg, 1.54 mmol) in THF/water (15 mL/2.8 mL) was treated with triphenylphosphine (487 mg, 1.86 mmol) and the reaction mixture was heated at 70° C. behind a blast shield for 18 hr. The reaction mixture was concentrated under reduced pressure. The residue was dissolved in dry DCM (15 mL), cooled to 0° C. and di-tert-butyl-dicarbonate (402 mg, 1.84 mmol) was added followed by DIPEA (0.8 mL, 4.62 mmol). The reaction mixture was allowed to warm to room temperature and stirred for 18 hr. Water (20 mL) was added and the mixture extracted with DCM (100 mL). The organic layer was separated, dried over $MgSO_4$ and concentrated under reduced pressure. Purification via silica gel column chromatography (0-35% EtOAc/isohexane) followed by chiral prep SFC gave tert-butyl N-[(3S,4R,7S)-3-fluoro-7-(2-methyl-4-nitro-pyrazol-3-yl)oxepan-4-yl]carbamate as a white solid (223 mg, 27% over three steps). $^1$H NMR (400 MHz, $CDCl_3$) δ 8.02 (s, 1H), 5.37 (dd, J=10.5, 3.0 Hz, 1H), 4.89 (br s, 1H), 4.61 (ddd, J=49.1, 7.7, 3.2 Hz, 1H), 4.44 (dd, J=22.2, 15.0 Hz, 1H), 4.07 (s, 3H), 3.98-3.80 (m, 1H), 3.49 (d, J=5.3 Hz, 1H), 2.15-1.90 (m, 4H), 1.47 (s, 9H).

Intermediate 81 tert-Butyl N-[(3R,4S,7R)-3-fluoro-7-(2-methyl-4-nitro-pyrazol-3-yl)oxepan-4-yl]carbamate

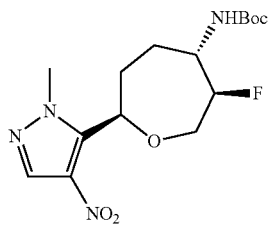 [SMILES: Cn1ncc([N+](=O)[O-])c1[C@H]1CC[C@H](NC(=O)OC(C)(C)C)[C@@H](F)CO1]

Following the procedure for Intermediate 80 also gave tert-butyl N-[(3R,4S,7R)-3-fluoro-7-(2-methyl-4-nitro-pyrazol-3-yl)oxepan-4-yl]carbamate as a white solid (247 mg, 91%). $^1$H NMR (400 MHz, $CDCl_3$) δ 8.05 (s, 1H), 5.39 (dd, J=10.7, 2.9 Hz, 1H), 4.85 (br s, 1H), 4.61 (ddd, J=49.3, 7.7, 3.17 Hz, 1H), 4.52-4.40 (m, 1H), 4.07 (s, 3H), 3.97-3.84 (m, 1H), 3.49 (d, J=5.3 Hz, 1H), 2.15-1.88 (m, 4H), 1.49 (s, 9H).

Intermediate 82 5-(5-(Azidomethyl)-5-methyl-1,3-dioxan-2-yl)-1-methyl-4-nitro-1H-pyrazole (cis isomer)

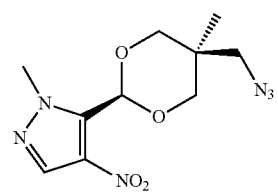 [SMILES: Cn1ncc([N+](=O)[O-])c1[C@H]1OC[C@@](C)(CN=[N+]=[N-])CO1]

Following the procedure for Intermediate 79 starting from (5-methyl-2-(1-methyl-4-nitro-1H-pyrazol-5-yl)-1,3-dioxan-5-yl)methanol (cis isomer, intermediate 67) gave 5-(5-(azidomethyl)-5-methyl-1,3-dioxan-2-yl)-1-methyl-4-nitro-1H-pyrazole as a colourless solid (519 mg, 87% over two steps). $^1$H NMR (400 MHz, $CDCl_3$) δ 8.02 (s, 1H), 6.39 (s, 1H), 4.14 (s, 3H), 4.04 (d, J=12.0 Hz, 2H), 3.73 (d, J=12.0 Hz, 2H), 3.70 (s, 2H), 0.87 (s, 3H).

Intermediate 83 2,2,2-Trifluoro-N-((5-methyl-2-(1-methyl-4-nitro-1H-pyrazol-5-yl)-1,3-dioxan-5-yl)methyl)acetamide (cis isomer)

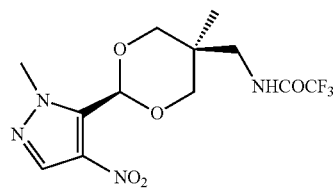

To a solution of 5-(5-(azidomethyl)-5-methyl-1,3-dioxan-2-yl)-1-methyl-4-nitro-1H-pyrazole (cis isomer) (519 mg, 1.84 mmol, intermediate 82) in dry MeOH (25 mL) and THF (10 mL) was added ammonium formate (300 mg, 4.76 mmol) and 10% Pd/C (300 mg, 0.28 mmol). The mixture was heated at reflux for 30 min and then cooled to room temperature. The suspension was filtered through celite and the cake washed with EtOAc (200 mL). The filtrate was concentrated under reduced pressure and the crude residue was dissolved in dry THF (11 mL) and DCM (2 mL) and cooled to 0° C. $Et_3N$ (0.38 mL, 2.86 mmol) was added followed by trifluoroacetic anhydride (0.30 mL, 2.10 mmol). The reaction mixture was slowly warmed to room temperature and stirred for 18 hr. The mixture was recooled to 0° C. and quenched with water (10 mL) and extracted with EtOAc (20 mL). The organic layer was washed with brine (10 mL), separated, dried over $Na_2SO_4$ and concentrated under reduced pressure. Purification via silica gel column chromatography (0-100% EtOAc/isohexane) gave 2,2,2-trifluoro-N-((5-methyl-2-(1-methyl-4-nitro-1H-pyrazol-5-yl)-1,3-dioxan-5-yl)methyl)acetamide as a colourless oil (410 mg, 63% over two steps). $^1$H NMR (400 MHz, CDCl$_3$) δ 7.95 (s, 1H), 7.24 (s, 1H), 6.33 (s, 1H), 4.17 (s, 3H), 3.92 (d, J=12.0 Hz, 2H), 3.75 (d, J=6.8 Hz, 2H), 3.71 (d, J=12.0 Hz, 2H), 0.80 (s, 3H).

Intermediate 84 2,2,2-Trifluoro-N-((5-methyl-2-(1-methyl-4-nitro-1H-pyrazol-5-yl)-1,3-dioxan-5-yl)methyl)acetamide (trans isomer)

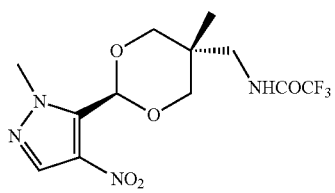

To a solution of 5-(5-(azidomethyl)-5-methyl-1,3-dioxan-2-yl)-1-methyl-4-nitro-1H-pyrazole (trans isomer; 300 mg, 1.02 mmol, intermediate 79) in THF (3 mL) and water (0.3 mL) was added triphenylphosphine (322 mg, 1.22 mmol). The reaction mixture was heated at 70° C. for 1 hr. The mixture was cooled to room temperature and concentrated under reduced pressure. To a solution of the crude residue in dry THF (10 mL) at 0° C. was added Et$_3$N (0.20 mL, 1.53 mmol) followed by trifluoromethanesulfonic anhydride (0.16 mL, 1.12 mmol). The reaction mixture was slowly warmed to room temperature and stirred for 18 hr. The mixture was re-cooled to 0° C. and more Et$_3$N (0.20 mL, 1.53 mmol) and trifluoromethanesulfonic anhydride (0.16 mL, 1.12 mmol) were added. The reaction mixture was slowly warmed to room temperature and stirred for 6 hr. The mixture was re-cooled to 0° C., quenched with water (10 mL) and extracted with DCM (20 mL). The organic layer was passed through a phase separation cartridge and concentrated under reduced pressure. Purification via silica gel column chromatography (0-100% EtOAc/isohexane) gave 2,2,2-trifluoro-N-((5-methyl-2-(1-methyl-4-nitro-1H-pyrazol-5-yl)-1,3-dioxan-5-yl)methyl)acetamide as a colourless solid (171 mg, 0.49 mmol).

Intermediate 85 5-(5,6-Dimethyl-4-((triethylsilyl)oxy)-3,6-dihydro-2H-pyran-2-yl)-1-methyl-4-nitro-1H-pyrazole

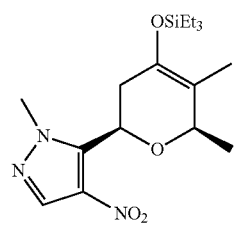

To a solution of (E)-3-methylpent-3-en-2-one (2.69 mL, 24.1 mmol) in DCM (200 mL) cooled to 0° C. was added Et$_3$N (10.5 mL, 79.5 mmol) followed by TESOTf (6.0 mL, 26.5 mmol). The mixture was warmed to room temperature and stirred for 18 hr. Saturated aqueous NaHCO$_3$ solution (100 mL) and DCM (200 mL) were added. The aqueous layer was extracted with DCM (3×200 mL) and the combined organic layers were washed with brine (100 mL), separated, dried over MgSO$_4$ and concentrated under reduced pressure to give (E)-triethyl((3-methylpenta-1,3-dien-2-yl)oxy)silane. To a solution of 2-methyl-4-nitro-pyrazole-3-carbaldehyde (1.0 g, 8 mmol, intermediate 3) in CDCl$_3$ (28 mL) was added (E)-triethyl((3-methylpenta-1,3-dien-2-yl)oxy)silane (1.6 g, 7.55 mmol) followed by EuFOD (220 mg, 0.50 mmol). The reaction mixture was heated at 65° C. behind a blast shield for 18 hr in a pressure tube. The mixture was cooled to room temperature and concentrated under reduced pressure. Purification via silica gel column chromatography (0-100% EtOAc/isohexane) gave 5-(5,6-dimethyl-4-((triethylsilyl)oxy)-3,6-dihydro-2H-pyran-2-yl)-1-methyl-4-nitro-1H-pyrazole as a colourless oil (2.92 g, quantitative). $^1$H NMR (400 MHz, CDCl$_3$) δ 8.07 (s, 1H), 5.64 (dd, J=10.9, 3.6 Hz, 1H), 4.33-4.28 (m, 1H), 4.25-3.94 (m, 3H), 2.50-2.41 (m, 1H), 2.31 (m, 1H), 1.61 (s, 3H), 1.31 (d, J=6.4 Hz, 3H), 1.05-0.97 (m, 6H), 0.73-0.61 (m, 9H).

Intermediate 86 3-Azido-2,3-dimethyl-6-(1-methyl-4-nitro-1H-pyrazol-5-yl)dihydro-2H-pyran-4(3H)-one

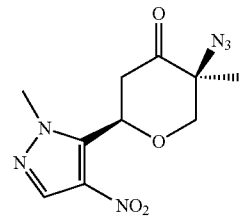 [SMILES: Cn1ncc([N+](=O)[O-])c1[C@H]1CC(=O)[C@@](C)(N=[N+]=[N-])CO1]

To a solution of 5-(5,6-dimethyl-4-((triethylsilyl)oxy)-3,6-dihydro-2H-pyran-2-yl)-1-methyl-4-nitro-1H-pyrazole (507 mg, 1.38 mmol, intermediate 85) in dry MeCN (3.5 mL) cooled to −20° C. was added sodium azide (404 mg, 6.22 mmol) followed by a solution of cerium ammonium nitrate (2.27 g, 4.15 mmol) in CH$_3$CN (10.4 mL) dropwise. The reaction mixture was stirred at −20° C. for 1 hr, slowly warmed to 0° C. over 1 hr then quenched with water (20 mL) and extracted with EtOAc (20 mL). The organic layer was washed with water (10 mL) and brine (10 mL), separated, dried over Na$_2$SO$_4$ and concentrated under reduced pressure. Purification via silica gel column chromatography (0-100% EtOAc/isohexane) gave 3-azido-2,3-dimethyl-6-(1-methyl-4-nitro-1H-pyrazol-5-yl)dihydro-2H-pyran-4(3H)-one as a white solid (187 mg, 46%). $^1$H NMR (400 MHz, CDCl$_3$) δ 8.05 (s, 1H), 5.78 (dd, J=12.3, 3.2 Hz, 1H), 4.21 (s, 3H), 3.73 (dd, J=12.3, 6.2 Hz, 1H), 3.13 (dd, J=14.6, 12.3 Hz, 1H), 2.73 (dd, J=14.6, 3.2 Hz, 1H), 1.44 (s, 3H), 1.41 (d, J=6.1 Hz, 3H).

Intermediate 87 5-(5-Azido-4,4-difluoro-5,6-dimethyltetrahydro-2H-pyran-2-yl)-1-methyl-4-nitro-1H-pyrazole

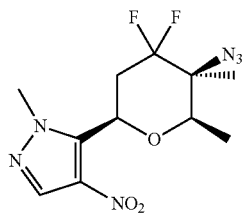 [SMILES: C[C@H]1O[C@@H](c2c([N+](=O)[O-])cnn2C)CC(F)(F)[C@@]1(C)N=[N+]=[N-]]

To a solution of 3-azido-2,3-dimethyl-6-(1-methyl-4-nitro-1H-pyrazol-5-yl)dihydro-2H-pyran-4(3H)-one (335 mg, 1.14 mmol, intermediate 86) in dry DCM (10 ml) was added a solution of deoxo-Fluor® (50% in THF, 830 mg, 1.88 mmol) and the mixture stirred at room temperature for 18 hr. Saturated aqueous NaHCO₃ solution (20 mL) and DCM (20 mL) were added. The aqueous layer was extracted with DCM (3×20 mL) and the combined organic layers were washed with brine (20 mL), separated, dried over MgSO₄ and concentrated under reduced pressure. Purification via silica gel column chromatography (20% EtOAc/isohexane) gave 5-(5-azido-4,4-difluoro-5,6-dimethyltetrahydro-2H-pyran-2-yl)-1-methyl-4-nitro-1H-pyrazole (contaminated with some vinyl fluoride) as a pale yellow oil (157 mg, 44%). ¹H NMR (400 MHz, CDCl₃) δ 8.04 (s, 1H), 5.69 (dd, J=12.2, 2.9 Hz, 1H), 4.13 (s, 3H), 3.76 (qd, J=6.3, 1.6 Hz, 1H), 2.59-2.40 (m, 1H), 2.38-2.28 (m, 1H), 1.48 (s, 3H), 1.32 (d, J=6.2 Hz, 3H).

Intermediate 88 tert-Butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate

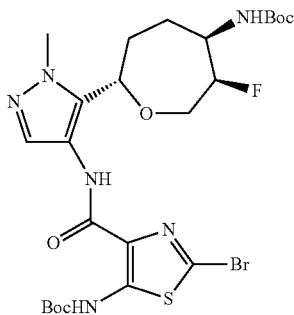 [SMILES: Cn1ncc(NC(=O)c2nc(Br)sc2NC(=O)OC(C)(C)C)c1[C@@H]1CC[C@@H](NC(=O)OC(C)(C)C)[C@@H](F)CO1]

Following the procedure for Intermediate 65 starting from tert-butyl ((3R,4R,7S)-3-fluoro-7-(1-methyl-4-nitro-1H-pyrazol-5-yl)oxepan-4-yl)carbamate (Intermediate 24) gave tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate as a solid (350 mg, 73% over two steps). ¹H NMR (400 MHz, CDCl₃) δ 10.34 (s, 1H), 9.31 (s, 1H), 7.98 (s, 1H), 5.15-4.98 (m, 1H), 4.93 (d, J=9.0 Hz, 1H), 4.77 (d, J=8.7 Hz, 1H), 4.39-3.94 (m, 2H), 3.80 (s, 3H), 2.12-1.93 (m, 4H), 1.85 (d, J=11.0 Hz, 1H), 1.52 (s, 9H), 1.46 (s, 9H).

Intermediate 89 tert-Butyl (2-(1-methyl-4-nitro-1H-pyrazol-5-yl)tetrahydro-2H-pyran-4-yl)carbamate

To a solution of 2-(2-methyl-4-nitro-pyrazol-3-yl)tetrahydropyran-4-ol (450 mg, 1.98 mmol, Intermediate 39) in dry DCM (24 mL) at 0° C. was added Et₃N (0.33 mL, 2.97 mmol) followed by MsCl (0.44 mL, 4.0 mmol). The reaction mixture was stirred at 0° C. for 30 min then at room temperature for 18 hr. The mixture was re-cooled to 0° C. and quenched with aqueous saturated NaHCO₃ (10 mL). The organic layer was washed with 0.1 M HCl (5 mL), passed through a phase separation cartridge and concentrated under reduced pressure to give a colourless oil. This oil was dissolved in DMF (10 mL) and sodium azide (660 mg, 10 mmol) was added. The reaction mixture was heated at 110° C. for 2 hr behind a blast shield. The reaction mixture was cooled to room temperature, diluted with water (20 mL) and extracted with EtOAc (50 mL). The organic layer was washed with water (3×20 mL), separated, dried over Na₂SO₄ and concentrated under reduced pressure to give a colourless solid (220 mg). To a solution of this solid (220 mg, 0.87 mmol) in THF (2.5 mL) and water (0.5 mL) was added triphenylphosphine (344 mg, 1.31 mmol). The reaction mixture was heated at 65° C. behind a blast shield for 4 hr. The mixture was re-cooled to room temperature and concentrated under reduced pressure. The residue was dissolved in DCM (5 mL), treated with di-tert-butyl-dicarbonate (287 mg, 1.31 mmol) and DIPEA (0.44 mL, 2.62 mmol) and the reaction mixture stirred at room temperature for 16 hr. The mixture was concentrated under reduced pressure. Purification via silica gel column chromatography (30% EtOAc/isohexane) gave tert-butyl (2-(1-methyl-4-nitro-1H-pyrazol-5-yl)tetrahydro-2H-pyran-4-yl)carbamate as a yellow oil (155 mg, 24% over four steps). ¹H NMR (400 MHz, CDCl₃) δ 8.03 (s, 1H), 5.44 (d, J=11.6 Hz, 1H), 4.52 (s, 1H), 4.19 (dd, J=11.9, 4.6 Hz, 1H), 4.06 (s, 3H), 3.68-3.60 (m, 1H), 2.29 (d, J=12.6 Hz, 1H), 2.03 (d, J=8.4 Hz, 1H), 1.75 (s, 1H), 1.61-1.47 (m, 2H), 1.45 (s, 9H).

Intermediate 90 (3S,4R,7S)-4-azido-7-(1-methyl-4-nitro-1H-pyrazol-5-yl)oxepan-3-ol

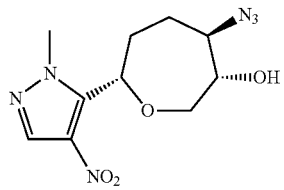 [SMILES: Cn1ncc([N+](=O)[O-])c1[C@@H]1CC[C@@H](N=[N+]=[N-])[C@H](O)CO1]

To a solution of 5-(5,8-dioxabicyclo[5.1.0]octan-4-yl)-1-methyl-4-nitro-pyrazole (2.7 g, 11.3 mmol, intermediate 19) in MeOH/water (60 mL/15 mL) was added ammonium chloride (1.51 g, 28.3 mmol) and sodium azide (3.67 g, 56.5 mmol). The mixture was heated at 70° C. behind a blast shield for 4 hr. The MeOH was removed under reduced pressure and the aqueous residue extracted with EtOAc (100 mL). The organic layer was washed with aqueous NaHCO₃ (3×20 mL), passed through a phase separation cartridge and concentrated under reduced pressure. Purification via silica gel column chromatography (0-100% EtOAc/isohexane) followed by chiral SFC chromatography gave (3S,4R,7S)-4-azido-7-(1-methyl-4-nitro-1H-pyrazol-5-yl)oxepan-3-ol as the second eluting isomer as a clear gum (1.4 g, 41%). ¹H NMR (400 MHz, CDCl₃) δ 8.03 (s, 1H), 5.43-5.37 (m, 1H), 4.18 (dd, J=13.9, 2.1 Hz, 1H), 4.06 (s, 3H), 3.97-3.77 (m, 3H), 2.45 (d, J=3.9 Hz, 1H), 2.32-2.09 (m, 2H), 2.10-1.85 (m, 2H).

Intermediate 91 (4R,7S)-4-Azido-7-(2-methyl-4-nitro-pyrazol-3-yl)oxepan-3-one

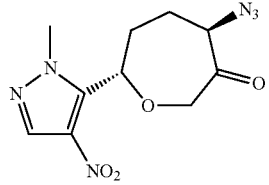

To a solution of (3S,4R,7S)-4-azido-7-(1-methyl-4-nitro-1H-pyrazol-5-yl)oxepan-3-ol (1.4 g, 4.96 mmol, intermediate 90) in DCM (35 mL) was added Dess-Martin peridionane (2.52 g, 5.96 mmol) and the mixture stirred at room temperature for 2 hr. Aqueous saturated NaHCO$_3$ (60 mL) and 20% sodium thiosulfate solution (50 mL) were added and the reaction mixture was stirred for 30 min until full dissolution of salts was observed. The organic layer was separated, dried over MgSO$_4$ and solvents removed under reduced pressure. Purification via silica gel column chromatography (0-40% EtOAc/isoHexane) gave (4R,7S)-4-azido-7-(2-methyl-4-nitro-pyrazol-3-yl)oxepan-3-one as an off-white solid (1.1 g, 82%). $^1$H NMR (400 MHz, CDCl$_3$) δ 8.05 (s, 1H), 5.38 (dd, J=10.2, 2.7 Hz, 1H), 4.62-4.49 (m, 2H), 4.31-4.22 (m, 1H), 4.08 (s, 3H), 2.31-2.17 (m, 3H), 2.15-2.04 (m, 1H).

Intermediate 92 (3R,4R,7S)-4-Azido-7-(2-methyl-4-nitro-pyrazol-3-yl)oxepan-3-ol

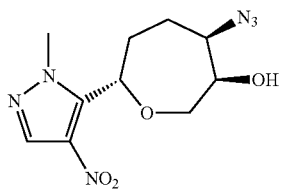 [SMILES: Cn1ncc([N+](=O)[O-])c1[C@@H]1CC[C@@H](N=[N+]=[N-])[C@@H](O)CO1]

Following the procedure for Intermediate 57 starting from (4R,7S)-4-azido-7-(2-methyl-4-nitro-pyrazol-3-yl)oxepan-3-one gave (3R,4R,7S)-4-azido-7-(2-methyl-4-nitro-pyrazol-3-yl)oxepan-3-ol as a dark orange oil (850 mg, 74%). $^1$H NMR (400 MHz, CDCl$_3$) δ 8.02 (s, 1H), 5.68-5.60 (m, 1H), 4.24-4.14 (m, 3H), 4.01 (s, 3H), 3.72-3.58 (m, 1H), 2.45-2.31 (m, 1H), 2.30-2.09 (m, 2H), 2.01-1.81 (m, 2H).

Intermediate 93 tert-Butyl N-[(3R,4R,7S)-3-methoxy-7-(2-methyl-4-nitro-pyrazol-3-yl)oxepan-4-yl]carbamate

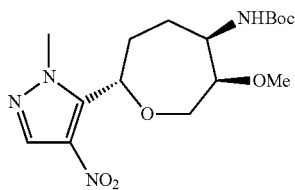 [SMILES: CO[C@H]1CO[C@H](c2c([N+](=O)[O-])cnn2C)CC[C@H]1NC(=O)OC(C)(C)C]

Following the procedure for Intermediate 58 starting from (3R,4R,7S)-4-azido-7-(2-methyl-4-nitro-pyrazol-3-yl)oxepan-3-ol gave tert-butyl N-[(3R,4R,7S)-3-methoxy-7-(2-methyl-4-nitro-pyrazol-3-yl)oxepan-4-yl]carbamate as a colourless oil (357 mg, 32% over three steps). $^1$H NMR (400 MHz, CDCl$_3$) δ 8.00 (s, 1H), 5.60-5.53 (m, 1H), 5.12-5.02 (m, 1H), 4.21-4.08 (m, 2H), 4.01 (s, 3H), 3.79 (dd, J=13.2, 4.4 Hz, 1H), 3.75-3.70 (m, 1H), 3.41 (s, 3H), 2.28-2.07 (m, 1H), 1.97-1.89 (m, 2H), 1.80-1.72 (m, 1H), 1.47 (s, 9H).

Intermediate 94 tert-Butyl ((3S,4R,7S)-3-hydroxy-7-(1-methyl-4-nitro-1H-pyrazol-5-yl)oxepan-4-yl)carbamate

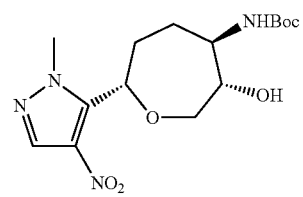 [SMILES: Cn1ncc([N+](=O)[O-])c1[C@@H]1CC[C@@H](NC(=O)OC(C)(C)C)[C@H](O)CO1]

To a solution of (3S,4R,7R)-4-azido-7-(2-methyl-4-nitro-pyrazol-3-yl)oxepan-3-ol (Intermediate 90) (1.19 g, 4.22 mmol) in THF (50 mL) and water (10 mL) was added triphenylphosphine (1.22 g, 4.64 mmol) and the mixture heated at 70° C. for 24 hr. The mixture was diluted with EtOAc (100 mL) and washed with brine (2×25 mL). The organic layer was separated, dried over MgSO$_4$ and concentrated under reduced pressure. The residue was passed through an SCX column washing with MeOH and eluting with 3% 7 N NH$_3$ in MeOH/DCM to give an oil. This oil was dissolved in DCM (13.5 mL) and DIPEA (1.08 mL, 6.21 mmol) and di-tert-butyl-dicarbonate (1.36 g, 6.21 mmol) were added. The mixture was stirred at room temperature for 3 hr then concentrated under reduced pressure. Purification via silica gel chromatography (0-60% EtOAc/isohexane) gave tert-butyl ((3S,4R,7S)-3-hydroxy-7-(1-methyl-4-nitro-1H-pyrazol-5-yl)oxepan-4-yl)carbamate (contaminated with some triphenylphosphine oxide) as a clear gum (895 mg, 60% over two steps). $^1$H NMR (400 MHz, CDCl$_3$) δ 8.02 (s, 1H), 5.42-5.36 (m, 1H), 4.83 (d, J=6.7 Hz, 1H), 4.22 (d, J=13.4 Hz, 2H), 4.08 (s, 3H), 3.86-3.76 (m, 3H), 2.18-2.07 (m, 1H), 2.02-1.89 (m, 3H), 1.47 (s, 9H).

Intermediate 95 tert-Butyl N-[(3R,4R,7S)-7-[4-[(6-bromo-5-fluoro-pyridine-2-carbonyl)amino]-2-methyl-pyrazol-3-yl]-3-methoxy-oxepan-4-yl]carbamate

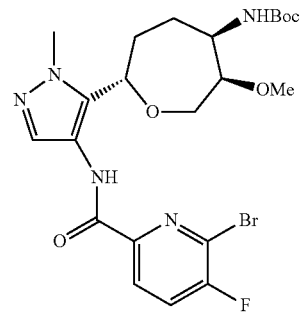 [SMILES: CO[C@H]1CO[C@H](c2c(NC(=O)c3ccc(F)c(Br)n3)cnn2C)CC[C@H]1NC(=O)OC(C)(C)C]

Following the procedure for Example 65, starting from tert-butyl N-[(3R,4R,7S)-3-methoxy-7-(2-methyl-4-nitropyrazol-3-yl)oxepan-4-yl]carbamate (intermediate 93) and replacing 2-bromo-5-(tert-butoxycarbonylamino)thiazole-4-carboxylic acid with 6-bromo-5-fluoro-pyridine-2-carboxylic acid (see US2010/56576 A1) gave tert-butyl N-[(3R,4R,7S)-7-[4-[(6-bromo-5-fluoro-pyridine-2-carbonyl)amino]-2-methyl-pyrazol-3-yl]-3-methoxy-oxepan-4-yl]carbamate (contaminated with tetramethylurea) as a clear oil (169 mg, 30% over two steps). ¹H NMR (400 MHz, CDCl₃) δ 10.37 (s, 1H), 8.26-8.17 (m, 2H), 7.63-7.55 (m, 1H), 5.02 (br s, 1H), 4.96 (dd, J=9.0, 3.6 Hz, 1H), 4.32 (dd, J=13.2, 4.4 Hz, 1H), 4.05-3.94 (m, 2H), 3.85-3.80 (m, 1H), 3.78 (s, 3H), 3.47 (s, 3H), 2.10-1.91 (m, 3H), 1.86-1.78 (m, 1H), 1.45 (s, 9H).

Intermediate 96 tert-Butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate

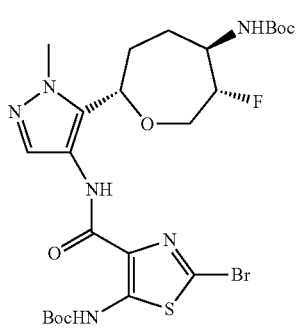 [SMILES: Cn1ncc(NC(=O)c2nc(Br)sc2NC(=O)OC(C)(C)C)c1[C@@H]1CC[C@@H](NC(=O)OC(C)(C)C)[C@H](F)CO1]

Following the procedure for Intermediate 65, starting from tert-butyl ((3S,4R,7S)-3-fluoro-7-(1-methyl-4-nitro-1H-pyrazol-5-yl)oxepan-4-yl)carbamate (Intermediate 80) gave tert-butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate.

Intermediate 97 tert-Butyl N-[2-bromo-4-[[5-[(2S,5R,6S)-5-(tert-butoxycarbonylamino)-6-methoxy-oxepan-2-yl]-1-methyl-pyrazol-4-yl]carbamoyl]thiazol-5-yl]carbamate

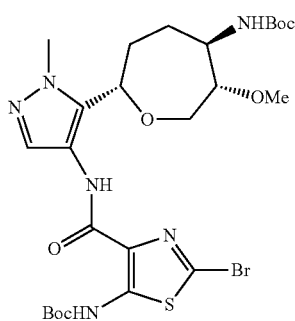 [SMILES: CO[C@@H]1CO[C@H](c2c(NC(=O)c3nc(Br)sc3NC(=O)OC(C)(C)C)cnn2C)CC[C@H]1NC(=O)OC(C)(C)C]

Following the procedure for Intermediate 65, starting from tert-butyl ((3S,4R,7S)-3-fluoro-7-(1-methyl-4-nitro-1H-pyrazol-5-yl)oxepan-4-yl)carbamate (Intermediate 21) gave tert-Butyl N-[2-bromo-4-[[5-[(2S,5R,6S)-5-(tert-butoxycarbonylamino)-6-methoxy-oxepan-2-yl]-1-methyl-pyrazol-4-yl]carbamoyl]thiazol-5-yl]carbamate.

Intermediate 98 tert-Butyl N-[2-bromo-4-[[5-[(2S,5R,6R)-5-(tert-butoxycarbonylamino)-6-methoxy-oxepan-2-yl]-1-methyl-pyrazol-4-yl]carbamoyl]thiazol-5-yl]carbamate

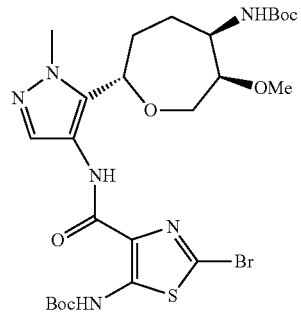 [SMILES: CO[C@H]1CO[C@H](c2c(NC(=O)c3nc(Br)sc3NC(=O)OC(C)(C)C)cnn2C)CC[C@H]1NC(=O)OC(C)(C)C]

Following the procedure for Intermediate 65, starting from tert-butyl ((3S,4R,7S)-3-fluoro-7-(1-methyl-4-nitro-1H-pyrazol-5-yl)oxepan-4-yl)carbamate (Intermediate 93) gave tert-Butyl N-[2-bromo-4-[[5-[(2S,5R,6R)-5-(tert-butoxycarbonylamino)-6-methoxy-oxepan-2-yl]-1-methyl-pyrazol-4-yl]carbamoyl]thiazol-5-yl]carbamate.

Intermediate 99 tert-butyl ((3S,4R,7S)-7-(4-(2-bromothiazole-4-carboxamido)-1-methyl-1H-pyrazol-5-yl)-3-fluorooxepan-4-yl)carbamate

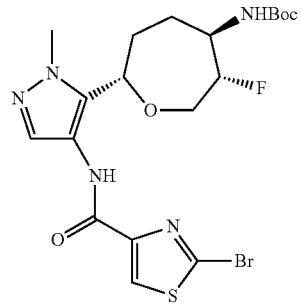 [SMILES: Cn1ncc(NC(=O)c2csc(Br)n2)c1[C@@H]1CC[C@@H](NC(=O)OC(C)(C)C)[C@H](F)CO1]

Following the procedure for Intermediate 65, starting from tert-butyl ((3S,4R,7S)-3-fluoro-7-(1-methyl-4-nitro-1H-pyrazol-5-yl)oxepan-4-yl)carbamate (Intermediate 80) and replacing 2-bromo-5-(tert-butoxycarbonylamino)thiazole-4-carboxylic acid with 2-bromothiazole-4-carboxylic acid (commercial) gave tert-butyl ((3S,4R,7S)-7-(4-(2-bromothiazole-4-carboxamido)-1-methyl-1H-pyrazol-5-yl)-3-fluorooxepan-4-yl)carbamate.

Intermediate 100 tert-butyl ((3R,4R,7S)-7-(4-(2-bromothiazole-4-carboxamido)-1-methyl-1H-pyrazol-5-yl)-3-fluorooxepan-4-yl)carbamate

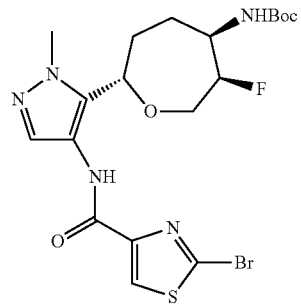 [SMILES: Cn1ncc(NC(=O)c2csc(Br)n2)c1[C@@H]1CC[C@@H](NC(=O)OC(C)(C)C)[C@@H](F)CO1]

Following the procedure for Intermediate 65, starting from tert-butyl ((3R,4R,7S)-3-fluoro-7-(1-methyl-4-nitro-1H-pyrazol-5-yl)oxepan-4-yl)carbamate (Intermediate 24) and replacing 2-bromo-5-(tert-butoxycarbonylamino)thiazole-4-carboxylic acid with 2-bromothiazole-4-carboxylic acid (commercial) gave tert-butyl ((3R,4R,7S)-7-(4-(2-bromothiazole-4-carboxamido)-1-methyl-1H-pyrazol-5-yl)-3-fluorooxepan-4-yl)carbamate.

Intermediate 101 tert-butyl ((3R,4R,7S)-7-(4-(2-bromothiazole-4-carboxamido)-1-methyl-1H-pyrazol-5-yl)-3-methoxyoxepan-4-yl)carbamate

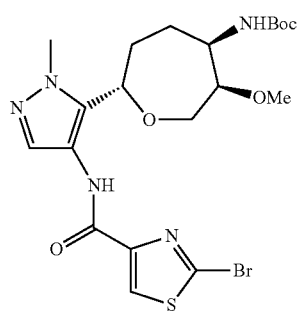 [SMILES: CO[C@H]1CO[C@H](c2c(NC(=O)c3csc(Br)n3)cnn2C)CC[C@H]1NC(=O)OC(C)(C)C]

Following the procedure for Intermediate 65, starting from tert-butyl ((3R,4R,7S)-3-methoxy-7-(1-methyl-4-nitro-1H-pyrazol-5-yl)oxepan-4-yl)carbamate (Intermediate 93) and replacing 2-bromo-5-(tert-butoxycarbonylamino)thiazole-4-carboxylic acid with 2-bromothiazole-4-carboxylic acid (commercial) gave tert-butyl ((3R,4R,7S)-7-(4-(2-bromothiazole-4-carboxamido)-1-methyl-1H-pyrazol-5-yl)-3-methoxyoxepan-4-yl)carbamate.

Intermediate 102 tert-butyl ((3S,4R,7S)-7-(4-(2-bromothiazole-4-carboxamido)-1-methyl-1H-pyrazol-5-yl)-3-methoxyoxepan-4-yl)carbamate

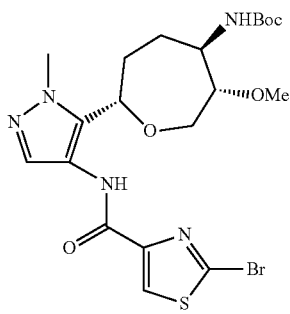 [SMILES: CO[C@@H]1CO[C@H](c2c(NC(=O)c3csc(Br)n3)cnn2C)CC[C@H]1NC(=O)OC(C)(C)C]

Following the procedure for Intermediate 65, starting from tert-butyl ((3S,4R,7S)-3-methoxy-7-(1-methyl-4-nitro-1H-pyrazol-5-yl)oxepan-4-yl)carbamate (Intermediate 21) and replacing 2-bromo-5-(tert-butoxycarbonylamino)thiazole-4-carboxylic acid with 2-bromothiazole-4-carboxylic acid (commercial) gave tert-butyl ((3S,4R,7S)-7-(4-(2-bromothiazole-4-carboxamido)-1-methyl-1H-pyrazol-5-yl)-3-methoxyoxepan-4-yl)carbamate.

Intermediate 103 tert-butyl ((3S,4R,7S)-7-(4-(6-bromo-5-fluoropicolinamido)-1-methyl-1H-pyrazol-5-yl)-3-fluorooxepan-4-yl)carbamate

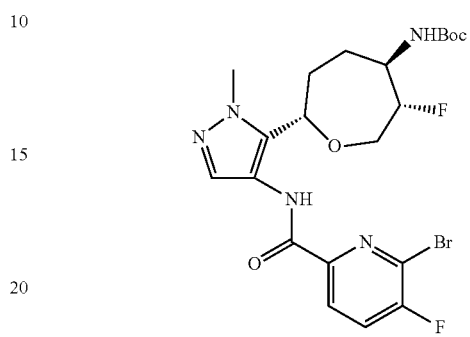

Following the procedure for Example 65, starting from tert-butyl N-[(3S,4R,7S)-3-fluoro-7-(2-methyl-4-nitro-pyrazol-3-yl)oxepan-4-yl]carbamate (intermediate 80) and replacing 2-bromo-5-(tert-butoxycarbonylamino)thiazole-4-carboxylic acid with 6-bromo-5-fluoro-pyridine-2-carboxylic acid (see US2010/56576 A1) gave tert-butyl ((3S,4R,7S)-7-(4-(6-bromo-5-fluoropicolinamido)-1-methyl-1H-pyrazol-5-yl)-3-fluorooxepan-4-yl)carbamate.

Intermediate 104 2-(2,6-difluoro-4-methoxyphenyl)thiazole-4-carboxylic acid

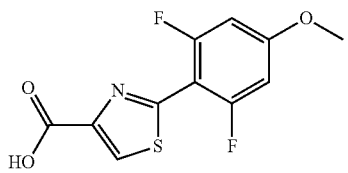 [SMILES: COc1cc(F)c(-c2nc(C(=O)O)cs2)c(F)c1]

To a solution of methyl 2-bromothiazole-4-carboxylate (3.27 mmol, 741 mg) in tetrahydrofuran (15 mL) and water (1.5 mL) was added 2,6-difluoro-4-methoxyphenylboronic acid (1.8 equiv., 5.88 mmol, 1160 mg) and potassium fluoride (3.3 equiv., 10.8 mmol, 627 mg). The mixture was degassed with nitrogen, then tris(dibenzylideneacetone)dipalladium (0) (0.2 equiv., 0.654 mmol, 617 mg) and tri-tert-butylphosphine (1.0 M in toluene; 0.4 equiv., 1.31 mmol, 1.3 mL) were added and the reaction mixture was heated under microwave at 100° C. for 30 minutes. The reaction mixture was concentrated and the residue was purified on silica eluted with 0 to 50% EtOAc in heptane to afford methyl 2-(2,6-difluoro-4-methoxy-phenyl)thiazole-4-carboxylate (2.40 mmol, 685 mg, 74% yield).

To a solution of methyl 2-(2,6-difluoro-4-methoxy-phenyl)thiazole-4-carboxylate (2.403 mmol, 685.5 mg) in methanol (15 mL) and water (5 mL) was added lithium hydroxide (1.9 equiv., 4.54 mmol, 111 mg). The reaction mixture was stirred at room temperature overnight. The reaction mixture was quenched with 1N HCl (aq.), then partitioned between EtOAc and brine. The organic layer was concentrated. The residue was dried on highvac to afford 2-(2,6-difluoro-4-methoxy-phenyl)thiazole-4-carboxylic acid (650 mg, quant.) as a brown solid.

Intermediate 105
2-(2-fluoro-4-methoxyphenyl)thiazole-4-carboxylic acid

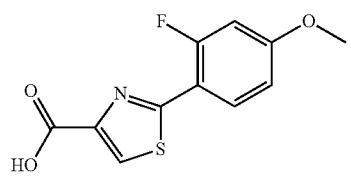 [SMILES: COc1ccc(-c2nc(C(=O)O)cs2)c(F)c1]

Following the procedure of Intermediate 104, replacing 2,6-difluoro-4-methoxyphenylboronic acid with 2-fluoro-4-methoxyphenylboronic acid gave the title compound.

Intermediate 106 1-(3,5-difluoro-4-(4,4,5,5-tetramethyl-1,3,2-dioxaborolan-2-yl)phenyl)ethanol

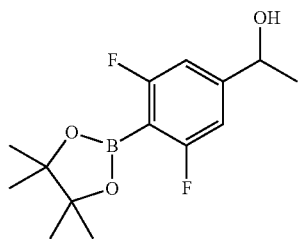 [SMILES: CC(O)c1cc(F)c(B2OC(C)(C)C(C)(C)O2)c(F)c1]

To a solution of 1-(3,5-difluorophenyl)ethanol (10.2 mmol, 1660 mg, commercial) in tetrahydrofuran (100 mL) at −78° C. was added n-butyllithium (2.5 mol/L) in hexane (2.4 equiv., 24.4 mmol, 9.8 mL) dropwise. The mixture was stirred at −78° C. for 2 hours. 2-isopropoxy-4,4,5,5-tetramethyl-1,3,2-dioxaborolane (2.50 equiv., 25.4 mmol, 5.29 mL) was added, and the reaction mixture was stirred over night allowing to warm to room temperature. The reaction mixture was quenched with saturated NaHCO$_3$(aq.) And extracted with etoac. The organic layer was washed with brine, dried with Na$_2$SO$_4$, filtered, and the filtrated was concentrated to afford the desired product which was used without further purification.

Intermediate 107 2-(3,5-difluoro-4-(4,4,5,5-tetramethyl-1,3,2-dioxaborolan-2-yl)phenyl)propan-2-ol

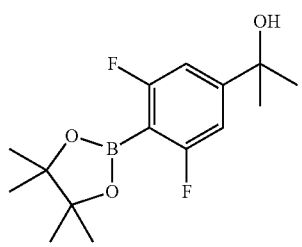 [SMILES: CC(C)(O)c1cc(F)c(B2OC(C)(C)C(C)(C)O2)c(F)c1]

Following the procedure of Intermediate 106, replacing 1-(3,5-difluorophenyl)ethanol with 2-(3,5-difluorophenyl)propan-2-ol (see US2012/225062) provided the title compound.

Intermediate 108 1-(3,5-difluoro-4-(4,4,5,5-tetramethyl-1,3,2-dioxaborolan-2-yl)phenyl)cyclobutanol

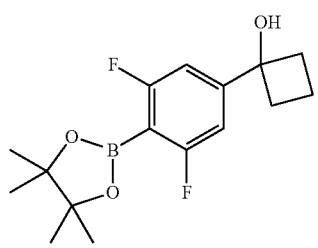 [SMILES: CC1(C)OB(c2c(F)cc(C3(O)CCC3)cc2F)OC1(C)C]

Following the procedure of Intermediate 106, replacing 1-(3,5-difluorophenyl)ethanol with 1-(3,5-difluorophenyl)cyclobutanol (see US2012/225062) provided the title compound.

Intermediate 109 2-(2,6-difluoro-4-(1-hydroxyethyl)phenyl)thiazole-4-carboxylic acid

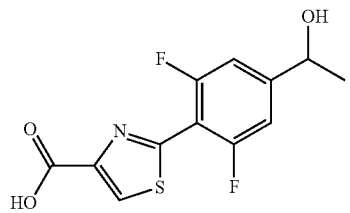 [SMILES: CC(O)c1cc(F)c(-c2nc(C(=O)O)cs2)c(F)c1]

Following the procedure of Intermediate 104, replacing 2,6-difluoro-4-methoxyphenylboronic acid with 1-(3,5-difluoro-4-(4,4,5,5-tetramethyl-1,3,2-dioxaborolan-2-yl)phenyl)ethanol (Intermediate 106) gave the title compound.

Intermediate 110 2-(2,6-difluoro-4-(1-hydroxycyclobutyl)phenyl)thiazole-4-carboxylic acid

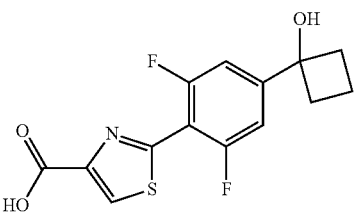 [SMILES: O=C(O)c1csc(-c2c(F)cc(C3(O)CCC3)cc2F)n1]

Following the procedure of Intermediate 104, replacing 2,6-difluoro-4-methoxyphenylboronic acid with 1-(3,5-difluoro-4-(4,4,5,5-tetramethyl-1,3,2-dioxaborolan-2-yl)phenyl)cyclobutanol (Intermediate 108) gave the title compound.

Intermediate 111 2-(2,6-difluoro-4-(2-hydroxypropan-2-yl)phenyl)thiazole-4-carboxylic acid

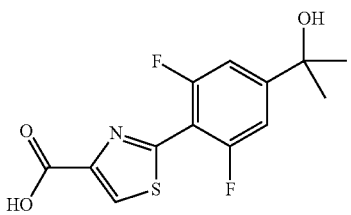 [SMILES: CC(C)(O)c1cc(F)c(-c2nc(C(=O)O)cs2)c(F)c1]

Following the procedure of Intermediate 104, replacing 2,6-difluoro-4-methoxyphenylboronic acid with 2-(3,5-difluoro-4-(4,4,5,5-tetramethyl-1,3,2-dioxaborolan-2-yl)phenyl)propan-2-ol (Intermediate 107) gave the title compound.

Intermediate 112 2-(2-(difluoromethyl)phenyl)thiazole-4-carboxylic acid

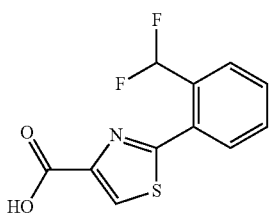 [SMILES: O=C(O)c1csc(-c2ccccc2C(F)F)n1]

Following the procedure of Intermediate 104, replacing 2,6-difluoro-4-methoxyphenylboronic acid with (2-(difluoromethyl)phenyl)boronic acid gave the title compound.

Intermediate 113 2-(3-fluoropyridin-4-yl)thiazole-4-carboxylic acid

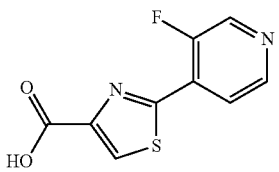 [SMILES: O=C(O)c1csc(-c2ccncc2F)n1]

Following the procedure of Intermediate 104, replacing 2,6-difluoro-4-methoxyphenylboronic acid with (3-fluoropyridin-4-yl)boronic acid gave the title compound.

Intermediate 114 2-(2,5-difluorophenyl)thiazole-4-carboxylic acid

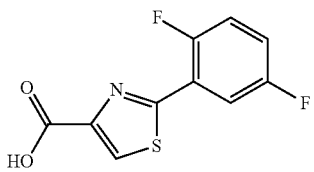 [SMILES: O=C(O)c1csc(-c2cc(F)ccc2F)n1]

Following the procedure of Intermediate 104, replacing 2,6-difluoro-4-methoxyphenylboronic acid with (2,5-difluorophenyl)boronic acid gave the title compound.

Intermediate 115 2-(5-chloro-2-fluorophenyl)thiazole-4-carboxylic acid

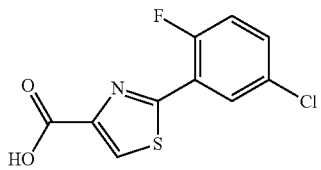 [SMILES: O=C(O)c1csc(-c2cc(Cl)ccc2F)n1]

Following the procedure of Intermediate 104, replacing 2,6-difluoro-4-methoxyphenylboronic acid with (5-chloro-2-fluorophenyl)boronic acid gave the title compound.

Intermediate 116 2-(2,6-difluoro-3-methylphenyl)thiazole-4-carboxylic acid

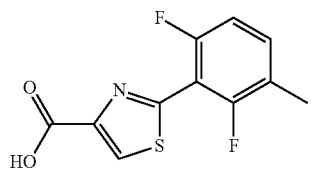 [SMILES: Cc1ccc(F)c(-c2nc(C(=O)O)cs2)c1F]

Following the procedure of Intermediate 104, replacing 2,6-difluoro-4-methoxyphenylboronic acid with (2,6-difluoro-3-methylphenyl)boronic acid gave the title compound.

Intermediate 117 (R)-2-(2,6-difluoro-4-(1-hydroxyethyl)phenyl)thiazole-4-carboxylic acid

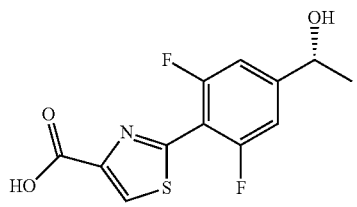 [SMILES: C[C@@H](O)c1cc(F)c(-c2nc(C(=O)O)cs2)c(F)c1]

Following the procedure of Intermediate 109, replacing 1-(3,5-difluorophenyl)ethanol in step 1 (Intermediate 106) with (R)-1-(3,5-difluorophenyl)ethanol (commercial).

Intermediate 118 (S)-2-(2,6-difluoro-4-(1-hydroxyethyl)phenyl)thiazole-4-carboxylic acid

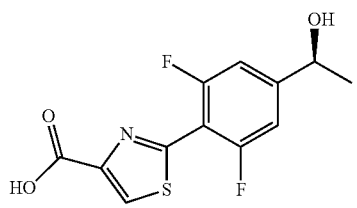 [SMILES: C[C@H](O)c1cc(F)c(-c2nc(C(=O)O)cs2)c(F)c1]

Following the procedure of Intermediate 109, replacing 1-(3,5-difluorophenyl)ethanol in step 1 (Intermediate 106) with (S)-1-(3,5-difluorophenyl)ethanol (commercial source).

Intermediate 119
2-(2,3-difluorophenyl)thiazole-4-carboxylic acid

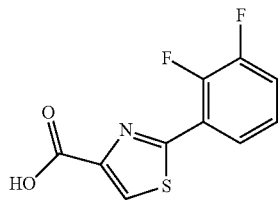 [SMILES: O=C(O)c1csc(-c2cccc(F)c2F)n1]

Following the procedure of Intermediate 104, replacing 2,6-difluoro-4-methoxyphenylboronic acid with (2,3-difluorophenyl)boronic acid gave the title compound.

Intermediate 120
2-(5-ethyl-2-fluorophenyl)thiazole-4-carboxylic acid

Following the procedure of Intermediate 104, replacing 2,6-difluoro-4-methoxyphenylboronic acid with (5-ethyl-2-fluorophenyl)boronic acid gave the title compound.

Intermediate 121
2-(3-chloro-2-fluorophenyl)thiazole-4-carboxylic acid

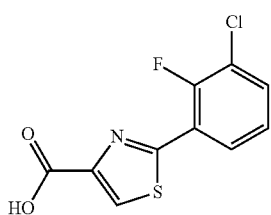 [SMILES: O=C(O)c1csc(-c2cccc(Cl)c2F)n1]

Following the procedure of Intermediate 104, replacing 2,6-difluoro-4-methoxyphenylboronic acid with (3-chloro-2-fluorophenyl)boronic acid gave the title compound.

Intermediate 122
2-(2-chloro-3-fluorophenyl)thiazole-4-carboxylic acid

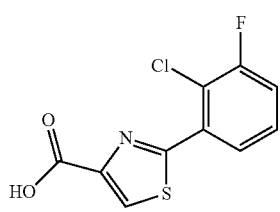 [SMILES: O=C(O)c1csc(-c2cccc(F)c2Cl)n1]

Following the procedure of Intermediate 104, replacing 2,6-difluoro-4-methoxyphenylboronic acid with (2-chloro-3-fluorophenyl)boronic acid gave the title compound.

Intermediate 123 2-(5-cyclopropyl-2-fluorophenyl)thiazole-4-carboxylic acid

Following the procedure of Intermediate 104, replacing 2,6-difluoro-4-methoxyphenylboronic acid with (5-cyclopropyl-2-fluorophenyl)boronic acid gave the title compound.

Intermediate 124
2-(2-(trifluoromethyl)phenyl)thiazole-4-carboxylic acid

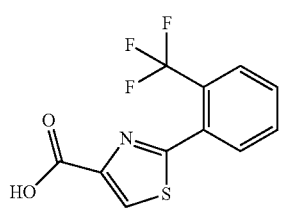 [SMILES: O=C(O)c1csc(-c2ccccc2C(F)(F)F)n1]

Following the procedure of Intermediate 104, replacing 2,6-difluoro-4-methoxyphenylboronic acid with (2-(trifluoromethyl)phenyl)boronic acid gave the title compound.

Intermediate 125 2-(2,6-difluoro-4-methylphenyl)-4,4,5,5-tetramethyl-1,3,2-dioxaborolane

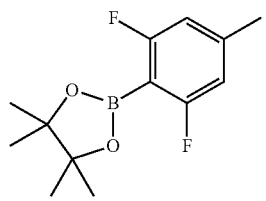

Following the procedure of Intermediate 106, replacing 1-(3,5-difluorophenyl)ethanol with 1,3-difluoro-5-methylbenzene, and reducing the number of equivalents of butyl lithium to 1.05 provided the title compound.

Intermediate 126 2-(2,6-difluoro-4-methylphenyl)thiazole-4-carboxylic acid

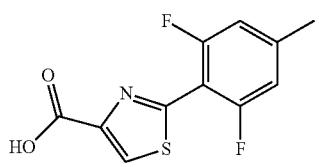 [SMILES: Cc1cc(F)c(-c2nc(C(=O)O)cs2)c(F)c1]

Following the procedure of Intermediate 104, replacing 2,6-difluoro-4-methoxyphenylboronic acid with 2-(2,6-difluoro-4-methylphenyl)-4,4,5,5-tetramethyl-1,3,2-dioxaborolane (Intermediate 125) gave the title compound.

Intermediate 127
2-(4-chloro-2-fluorophenyl)thiazole-4-carboxylic acid

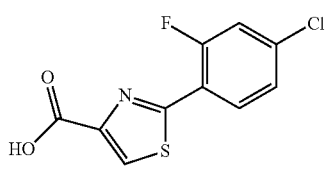 [SMILES: O=C(O)c1csc(-c2ccc(Cl)cc2F)n1]

Following the procedure of Intermediate 104, replacing 2,6-difluoro-4-methoxyphenylboronic acid with (4-chloro-2-fluorophenyl)boronic acid gave the title compound.

Intermediate 128
2-(2-fluoro-6-methylphenyl)thiazole-4-carboxylic acid

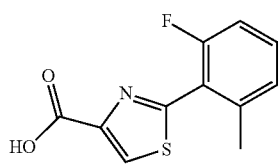 [SMILES: Cc1cccc(F)c1-c1nc(C(=O)O)cs1]

Following the procedure of Intermediate 104, replacing 2,6-difluoro-4-methoxyphenylboronic acid with (2-fluoro-6-methylphenyl)boronic acid gave the title compound.

Intermediate 129
2-(5-bromo-2-fluorophenyl)thiazole-4-carboxylic acid

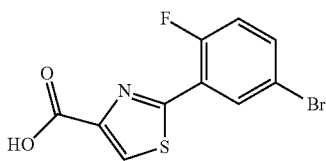 [SMILES: O=C(O)c1csc(-c2cc(Br)ccc2F)n1]

5-bromo-2-fluoro-benzonitrile (12.4 mmol, 2470 mg) in pyridine (6.5 mL) was treated with ammonium sulfide (40 mass % in water, 1.1 equiv., 13.6 mmol, 2.32 mL) and triethylamine (1.1 equiv., 13.6 mmol, 1.90 mL). The reaction mixture was heated at 50° C. for 3 hours, then cooled to room temperature. The reaction mixture was partitioned between EtOAc and water. The organic later was washed with water (3×), and brine (3×), dried with MgSO$_4$, then concentrated. The residue was purified on silica eluted with 0 to 50% EtOAc in Heptane to provide 5-bromo-2-fluoro-benzenecarbothioamide (2.84 g, 94% yield).

A mixture of 5-bromo-2-fluoro-benzenecarbothioamide (11.8 mmol, 2840 mg) and ethyl bromopyruvate (1.05 equiv., 12.4 mmol, 1.56 mL) in ethanol (30 mL) was heated at 80° C. overnight. The mixture was concentrated and the residue was purified on silica eluted with 0 to 20% EtOAc in Heptane to afford ethyl 2-(5-bromo-2-fluoro-phenyl)thiazole-4-carboxylate (2960 mg, 76.14% Yield) as a clear oil.

To a solution of ethyl 2-(5-bromo-2-fluoro-phenyl)thiazole-4-carboxylate (8.97 mmol, 2960 mg) in methanol (40 mL) and water (10 mL) was added lithium hydroxide (1.6 equiv., 14.2 mmol, 347 mg). The reaction mixture was stirred at 50° C. for 2 hours. The reaction mixture was cooled to room temperature, concentrated, suspended in water, and then quenched with 2N HCl(aq.). The solid was collected, washed with water, and dried under high vacuum to afford 2-(5-bromo-2-fluoro-phenyl)thiazole-4-carboxylic acid (2410 mg, 89% Yield) as a white solid.

Intermediate 130 2-(6-(trifluoromethyl)pyridin-2-yl)thiazole-4-carboxylic acid

Following the procedure of Intermediate 129, replacing 5-bromo-2-fluoro-benzonitrile with 6-(trifluoromethyl)picolinonitrile gave the title compound.

Intermediate 131
2-(2-fluoro-4-methylphenyl)thiazole-4-carboxylic acid

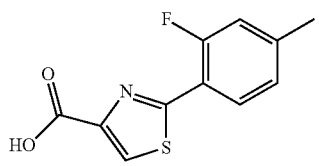 [SMILES: Cc1ccc(-c2nc(C(=O)O)cs2)c(F)c1]

Following the procedure of Intermediate 129, replacing 5-bromo-2-fluoro-benzonitrile with 2-fluoro-4-methylbenzonitrile gave the title compound.

Intermediate 132 5-((tert-butoxycarbonyl)amino)-2-(5-chloro-2-fluorophenyl)thiazole-4-carboxylic acid

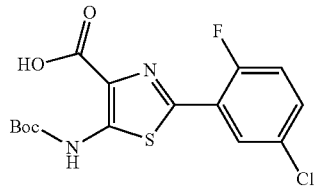 [SMILES: CC(C)(C)OC(=O)Nc1sc(-c2cc(Cl)ccc2F)nc1C(=O)O]

Following procedures from Examples 1-9, 5-chloro-2-fluorobenzoyl chloride was converted to the title compound.

Intermediate 133 5-((tert-butoxycarbonyl)amino)-2-(2-fluoro-5-methylphenyl)thiazole-4-carboxylic acid

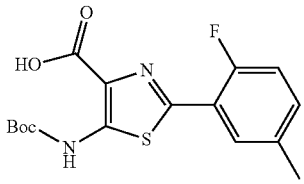 [SMILES: Cc1ccc(F)c(-c2nc(C(=O)O)c(NC(=O)OC(C)(C)C)s2)c1]

Following procedures from Examples 1-9, 2-fluoro-5-methylbenzoyl chloride was converted to the title compound.

Intermediate 134 6-(2,6-difluoro-4-(2-hydroxypropan-2-yl)phenyl)-5-fluoropicolinic acid

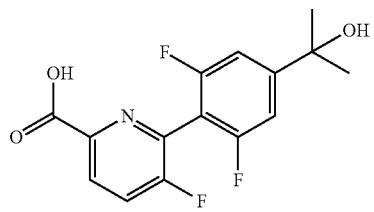 [SMILES: CC(C)(O)c1cc(F)c(-c2nc(C(=O)O)ccc2F)c(F)c1]

Following the procedure of Intermediate 104, replacing 2,6-difluoro-4-methoxyphenylboronic acid with 2-(3,5-difluoro-4-(4,4,5,5-tetramethyl-1,3,2-dioxaborolan-2-yl)phenyl)propan-2-ol (Intermediate 107) and replacing methyl 2-bromothiazole-4-carboxylate with methyl 6-bromo-5-fluoropicolinate (see US2012/225062) gave the title compound.

Intermediate 135 6-(2,6-difluoro-4-(1-hydroxycyclobutyl)phenyl)-5-fluoropicolinic acid

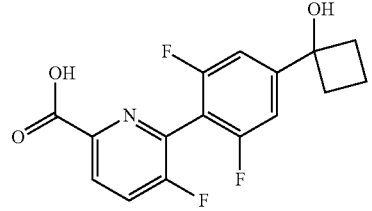 [SMILES: O=C(O)c1ccc(F)c(-c2c(F)cc(C3(O)CCC3)cc2F)n1]

Following the procedure of Intermediate 104, replacing 2,6-difluoro-4-methoxyphenylboronic acid with 1-(3,5-difluoro-4-(4,4,5,5-tetramethyl-1,3,2-dioxaborolan-2-yl)phenyl)cyclobutanol (Intermediate 108) and replacing methyl 2-bromothiazole-4-carboxylate with methyl 6-bromo-5-fluoropicolinate (see US2012/225062) gave the title compound.

Intermediate 136 6-(2,6-difluoro-4-(1-hydroxyethyl)phenyl)-5-fluoropicolinic acid

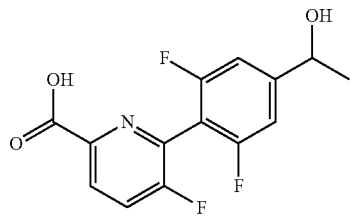 [SMILES: CC(O)c1cc(F)c(-c2nc(C(=O)O)ccc2F)c(F)c1]

Following the procedure of Intermediate 104, replacing 2,6-difluoro-4-methoxyphenylboronic acid with 1-(3,5-difluoro-4-(4,4,5,5-tetramethyl-1,3,2-dioxaborolan-2-yl)phenyl)ethanol (Intermediate 106) and replacing methyl 2-bromothiazole-4-carboxylate with methyl 6-bromo-5-fluoropicolinate (see US2012/225062) gave the title compound.

Intermediate 137 6-(2,6-difluoro-4-hydroxyphenyl)-5-fluoropicolinic acid

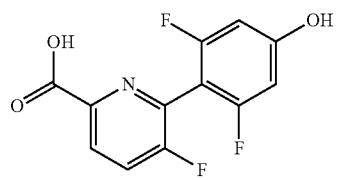 [SMILES: O=C(O)c1ccc(F)c(-c2c(F)cc(O)cc2F)n1]

Following the procedure of Intermediate 104, replacing 2,6-difluoro-4-methoxyphenylboronic acid with (2,6-difluoro-4-hydroxyphenyl)boronic acid and replacing methyl 2-bromothiazole-4-carboxylate with methyl 6-bromo-5-fluoropicolinate (see US2012/225062) gave the title compound.

Intermediate 138 6-(2,6-difluoro-4-(1-methoxyethyl)phenyl)-5-fluoropicolinic acid

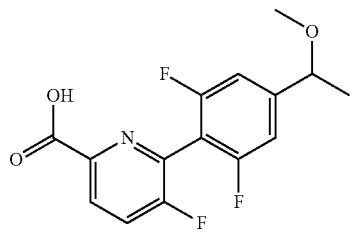 [SMILES: COC(C)c1cc(F)c(-c2nc(C(=O)O)ccc2F)c(F)c1]

To a solution of methyl 6-[2,6-difluoro-4-(1-hydroxyethyl)phenyl]-5-fluoro-pyridine-2-carboxylate (1.21 mmol, 376 mg; penultimate intermediate en route to Intermediate 136) in N,N-dimethylformamide (50 mL) at 0° C. was added sodium hydride (60 mass % in mineral oil, 1.5 equiv., 1.81 mmol, 72.5 mg). The mixture was stirred for 2 minutes, then iodomethane (3.0 equiv., 3.62 mmol, 0.226 mL) was added.

The reaction mixture was stirred at room temperature for 2 days. The reaction mixture was quenched with water and extracted with EtOAc. The organic layer was washed with brine, dried (Na₂SO₄) and concentrated. The residue was purified on silica eluted with 0 to 50% EtOAc in Heptane to provide methyl 6-(2,6-difluoro-4-(1-methoxyethyl)phenyl)-5-fluoropicolinate (392 mg, 63%). This ester was diluted with MeOH (15 mL) and water (5 mL) and lithium hydroxide (60 mg) was added. The mixture was stirred overnight at rt. The reaction was quenched by the addition of 1 N HCl(aq), then the mixture was diluted with EtOAc and washed with brine. The organic extracts were dried (Na₂SO₄) and concentrated in vacuo to provide the title compound (quant) which was used without purification.

Intermediate 139
cyclopropyl(3,5-difluorophenyl)methanol

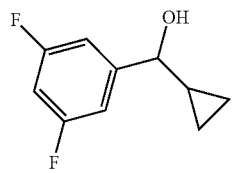 [SMILES: OC(c1cc(F)cc(F)c1)C1CC1]

A solution of 3,5-difluorobenzaldehyde (1.0 g, 7.0 mmol) was dissolved in tetrahydrofuran (10 mL) was cooled in an ice bath. cyclopropylmagnesium bromide (0.5 M in THF, 1.2 equiv., 8.4 mmol) was added slowly and the mixture was stirred at 0° C. for 60 min. The reaction was quenched with sat. ammonium chloride and extracted twice with EtOAc. The combined organic extracts were dried over Na₂SO₄, filtered and concentrated to give the title compound of sufficient purity to be used directly.

Intermediate 140 cyclopropyl(3,5-difluoro-4-(4,4,5,5-tetramethyl-1,3,2-dioxaborolan-2-yl)phenyl)methanol

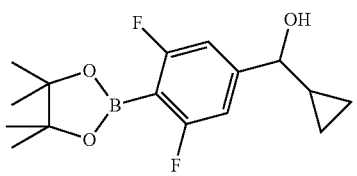 [SMILES: CC1(C)OB(c2c(F)cc(C(O)C3CC3)cc2F)OC1(C)C]

Following the procedure of Intermediate 106, replacing 1-(3,5-difluorophenyl)ethanol with cyclopropyl(3,5-difluorophenyl)methanol (Intermediate 139) provided the title compound.

Intermediate 141 6-(4-(cyclopropyl(hydroxy)methyl)-2,6-difluorophenyl)-5-fluoropicolinic acid

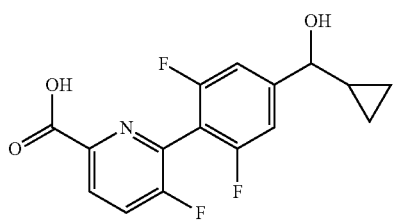 [SMILES: O=C(O)c1ccc(F)c(-c2c(F)cc(C(O)C3CC3)cc2F)n1]

Following the procedure of Intermediate 104, replacing 2,6-difluoro-4-methoxyphenylboronic acid with cyclopropyl (3,5-difluoro-4-(4,4,5,5-tetramethyl-1,3,2-dioxaborolan-2-yl)phenyl)methanol (Intermediate 141) and replacing methyl 2-bromothiazole-4-carboxylate with methyl 6-bromo-5-fluoropicolinate (see US2012/225062) gave the title compound.

Intermediate 142
3-(3,5-difluorophenyl)tetrahydrofuran-3-ol

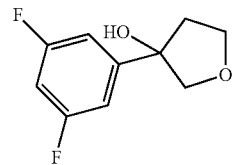 [SMILES: OC1(c2cc(F)cc(F)c2)CCOC1]

to a solution of 1-bromo-3,5-difluoro-benzene (4.00 g, 20.7 mmol) in tetrahydrofuran (70 mL) under nitrogen was added magnesium (6.0 equiv., 124 mmol) and the solution was heated at 85° C. for three hours. The solution was cooled to rt and 3-oxotetrahydrofuran (1 equiv., 20.726 mmol) in THF (20 mL) was added via syringe. The mixture was stirred at rt for three days. The reaction was quenched with sat NaHCO₃, extracted with EtOAc and washed with brine. Purification by CombiFlash (0 to 100% EtOAc in heptane) provided the title compound (405 mg, 9.7%).

Intermediate 143 3-(3,5-difluoro-4-(4,4,5,5-tetramethyl-1,3,2-dioxaborolan-2-yl)phenyl)tetrahydrofuran-3-ol

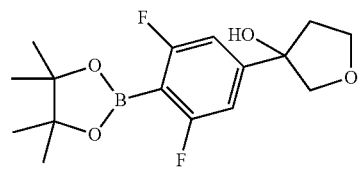 [SMILES: CC1(C)OB(c2c(F)cc(C3(O)CCOC3)cc2F)OC1(C)C]

Following the procedure of Intermediate 106, replacing 1-(3,5-difluorophenyl)ethanol with 3-(3,5-difluorophenyl) tetrahydrofuran-3-ol methanol (Intermediate 142) provided the title compound.

Intermediate 144 2-(2,6-difluoro-4-(3-hydroxytetrahydrofuran-3-yl)phenyl)thiazole-4-carboxylic acid

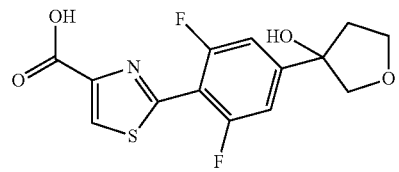 [SMILES: O=C(O)c1csc(-c2c(F)cc(C3(O)CCOC3)cc2F)n1]

Following the procedure of Intermediate 104, replacing 2,6-difluoro-4-methoxyphenylboronic acid with 3-(3,5-difluoro-4-(4,4,5,5-tetramethyl-1,3,2-dioxaborolan-2-yl)phenyl)tetrahydrofuran-3-ol (Intermediate 143) gave the title compound.

Intermediate 145 2-(2,6-difluoro-4-(tetrahydrofuran-3-yl)phenyl)thiazole-4-carboxylic acid

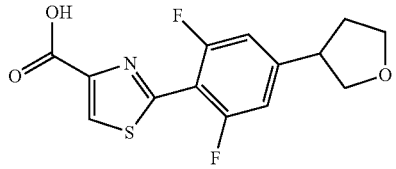 [SMILES: O=C(O)c1csc(-c2c(F)cc(C3CCOC3)cc2F)n1]

To a solution of methyl 2-[2,6-difluoro-4-(3-hydroxytetrahydrofuran-3-yl)phenyl]thiazole-4-carboxylate (250 mg, 0.732 mmol, precursor to Intermediate 144) in dichloromethane (1 mL) was added TRIFLUOROACETIC ACID (1 mL) The mixture was heated at 120° C. in microwave for 2 h. After in vacuo concentration, purification by CombiFlash (0 to 100% EtOAC in heptane) provided methyl 2-(4-(2,5-dihydrofuran-3-yl)-2,6-difluorophenyl)thiazole-4-carboxylate (57 mg, 24% yield) as a mixture of olefin isomers.

This mixture was diluted with 30 mL MeOH and ran through an H-cube hydrogenator (1 mL/min, 60 bar, 70 deg C.) to provide, after concentration, methyl 2-(2,6-difluoro-4-(tetrahydrofuran-3-yl)phenyl)thiazole-4-carboxylate (44 mg). This ester was diluted with THF (3 mL) and water (1.5 mL) and LiOH (6.5 mg, 2.0 equiv.) was added. After stirring for 2.5 hours at rt, the mixture was neutralized with 1 N HCl(aq), diluted with EtOAc and washed with brine. The organic extracts were dried ($Na_2SO_4$) and concentrated in vacuo to provide the title compound (42 mg, quant).

Intermediate 146 methyl 2-(2,6-difluoro-4-hydroxyphenyl)thiazole-4-carboxylate

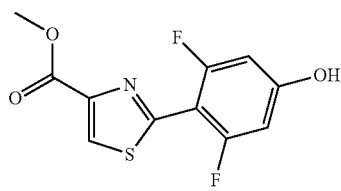 [SMILES: COC(=O)c1csc(-c2c(F)cc(O)cc2F)n1]

To a suspension of methyl 2-bromothiazole-4-carboxylate (500 mg, 2.16 mmol), 2,6-difluoro-4-hydroxyphenylboronic acid (2 equiv., 767 mg) and potassium fluoride (3.3 equiv., 414 mg) in tetrahydrofuran (10 mL) and water (1 mL) was added bis(tri-tert-butylphosphine)palladium(0) (0.1 equiv., 110 mg) and the mixture was heated to 120° C. for 15 min in the microwave reactor. After in vacuo concentration, the reaction mixture was purified by CombiFlash (0 to 100% EtOAc in heptane) to provide 241 mg of the title compound as a ~1:1 mixture with methyl 2-bromothiazole-4-carboxylate, which was used directly without further purification.

Intermediate 147 (R)-2-(2,6-difluoro-4-((tetrahydrofuran-3-yl)oxy)phenyl)thiazole-4-carboxylic acid

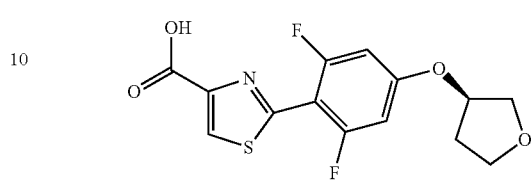

To a solution of methyl 2-(2,6-difluoro-4-hydroxy-phenyl)thiazole-4-carboxylate (207 mg, 0.763 mmol) and (R)-3-hydroxytetrahydrofuran (3 equiv., 206 mg) in tetrahydrofuran (5 mL) was added triphenylphosphine (3 equiv., 600 mg) and diisopropyl azodicarboxylate (3 equiv., 0.45 mL) The mixture was stirred at RT for 2 days. The mixture was concentrated and partitioned between EtOAc and water. The organic layer was washed with sat. $NaHCO_3$, brine, dried over $Na_2SO_4$ and concentrated. This residue was diluted with THF (3 mL) and water (1 mL) and LiOH (36 mg) was added. After stirring at rt for 2.5 hours, the reaction was neutralized with 1 N HCl(aq), diluted with EtOAc and washed with brine. The organic extracts were dried ($Na_2SO_4$) and concentrated in vacuo to provide the title compound, contaminated with triphenylphosphine oxide, and other by-products, which was used without further purification.

Intermediate 148 (S)-2-(2,6-difluoro-4-((tetrahydrofuran-3-yl)oxy)phenyl)thiazole-4-carboxylic acid

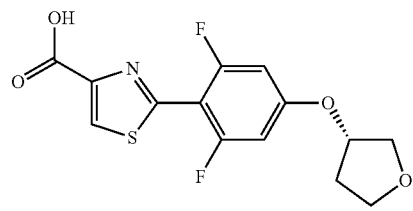 [SMILES: O=C(O)c1csc(-c2c(F)cc(O[C@H]3CCOC3)cc2F)n1]

Following the procedure for Intermediate 147, replacing (R)-3-hydroxytetrahydrofuran with (S)-3-hydroxytetrahydrofuran provided the title compound.

Intermediate 149 1-methyl-4-(4,4,5,5-tetramethyl-1,3,2-dioxaborolan-2-yl)-5-(trifluoromethyl)-1H-pyrazole

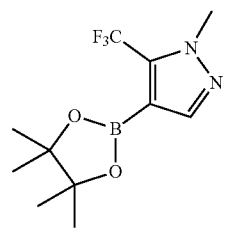 [SMILES: Cn1ncc(B2OC(C)(C)C(C)(C)O2)c1C(F)(F)F]

In a microwave reaction vial, 4-bromo-1-methyl-5-(trifluoromethyl)pyrazole (520 mg, 2.27 mmol, commercial), bis(pinacolato)diboron (1.3 equiv., 749 mg), bis(triphenylphosphine)palladium(II) dichloride (0.05 equiv., 79 mg) and POTASSIUM ACETATE (2 equiv., 4445 mg) were dissolved in toluene (15 mL). The mixture was heated in a microwave reactor to 150° C. for 10 min. After cooling to rt, the mixture was filtered over celite (EtOAc rinse). The filtrate was concentrated to give the title compound of sufficient purity to be used directly.

Intermediate 150 5-fluoro-1,3-dimethyl-4-(4,4,5,5-tetramethyl-1,3,2-dioxaborolan-2-yl)-1H-pyrazole

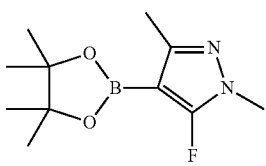

Following the procedure of Intermediate 149, replacing 4-bromo-1-methyl-5-(trifluoromethyl)pyrazole with 4-bromo-5-fluoro-1,3-dimethyl-1H-pyrazole (commercial) provided the title compound.

Intermediate 151 2-(2,6-difluoro-4-(3-fluorooxetan-3-yl)phenyl)thiazole-4-carboxylic acid

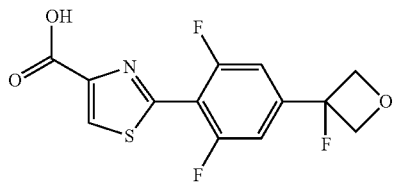 [SMILES: O=C(O)c1csc(-c2c(F)cc(C3(F)COC3)cc2F)n1]

Following the procedure of Intermediate 104, replacing 2,6-difluoro-4-methoxyphenylboronic acid with 3-(3,5-difluoro-4-(4,4,5,5-tetramethyl-1,3,2-dioxaborolan-2-yl)phenyl)oxetan-3-ol (see US2012/225062) gave the title compound, after adding the following fluorination step prior to ester hydrolysis: A solution of methyl 2-(2,6-difluoro-4-(3-hydroxyoxetan-3-yl)phenyl)thiazole-4-carboxylate (50 mg) in dichloromethane (5 mL) was cooled to −78° C., then deoxo-fluor (1.5 equiv., 50 wt % solution in toluene) was added. The mixture was allowed to slowly warm to rt over 30 minutes. The reaction was then quenched by the addition of sat. NaHCO$_3$(aq), then the mixture was diluted with EtOAc and washed with brine. The organic extracts were dried (Na$_2$SO$_4$) and concentrated in vacuo. Purification by CombiFlash (0 to 100% EtOAc in heptane) provided methyl 2-(2,6-difluoro-4-(3-fluorooxetan-3-yl)phenyl)thiazole-4-carboxylate.

Intermediate 152 tert-butyl ((2R*,3S*,4R*,6R*)-6-(4-amino-1-methyl-1H-pyrazol-5-yl)-3-hydroxy-2,3-dimethyltetrahydro-2H-pyran-4-yl)carbamate (racemic)

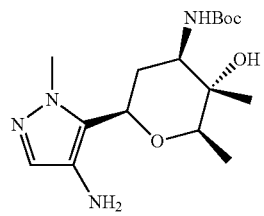 [SMILES: C[C@H]1O[C@@H](c2c(N)cnn2C)C[C@@H](NC(=O)OC(C)(C)C)[C@]1(C)O]

Prepared in an analogous manner to tert-butyl ((2R*,3S*,4R*,6R*)-6-(3-aminopyridin-4-yl)-3-hydroxy-2,3-dimethyltetrahydro-2H-pyran-4-yl)carbamate (WO2012/004217), replacing 3-nitroisonicotinaldehyde with 1-methyl-4-nitro-1H-pyrazole-5-carbaldehyde (Intermediate 3).

Intermediate 153 (Z)-1-(1-Methyl-4-nitro-1H-pyrazol-5-yl)cyclohept-4-enol

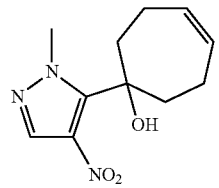 [SMILES: Cn1ncc([N+](=O)[O-])c1C1(O)CCC=CCC1]

To a solution of 1-methyl-4-nitro-1H-pyrazole (1.5 g, 11.8 mmol) and (Z)-cyclohept-4-enone (1.4 g, 13.0 mmol) in dry THF (30 mL) under nitrogen cooled to −78° C. was added dropwise a solution of lithium hexamethyldisilazide (1.0 M in THF, 30 mL, 29.5 mmol). The reaction mixture was allowed to warm to −40° C. and stirred for 90 min. Saturated aqueous ammonium chloride solution (30 mL) was added (dropwise initially) and the mixture was allowed to warm to room temperature and extracted with EtOAc (150 mL). The organic layer was washed with water (30 mL), washed with brine (20 mL), separated, dried over MgSO$_4$ and concentrated under reduced pressure. Purification via silica gel column chromatography (20-25% EtOAc) gave (Z)-1-(1-methyl-4-nitro-1H-pyrazol-5-yl)cyclohept-4-enol as a tan oil (1.37 g, 49%).

Intermediate 154 (Z)-5-(1-Fluorocyclohept-4-enyl)-1-methyl-4-nitro-1H-pyrazole

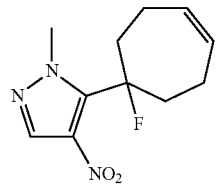 [SMILES: Cn1ncc([N+](=O)[O-])c1C1(F)CCC=CCC1]

To a solution of (Z)-1-(1-methyl-4-nitro-1H-pyrazol-5-yl)cyclohept-4-enol (1.35 g, 5.70 mmol) in dry DCM (60 mL) was added dropwise a solution of deoxo-Fluor® (50% in THF, 6.2 mL, 17.1 mmol) and the reaction mixture was stirred at room temperature for 90 min. The mixture was cooled to 0° C. and saturated aqueous NaHCO₃ solution (70 mL) was added, dropwise initially, and extracted with DCM (100 mL). The organic layer was separated, dried over MgSO₄, and concentrated under reduced pressure. Purification via silica gel column chromatography (15-20% EtOAc/hexane) gave (Z)-5-(1-fluorocyclohept-4-enyl)-1-methyl-4-nitro-1H-pyrazole as an off-white solid (615 mg, 45%).

Intermediate 155 5-(4-Fluoro-8-oxabicyclo[5.1.0]octan-4-yl)-1-methyl-4-nitro-1H-pyrazole

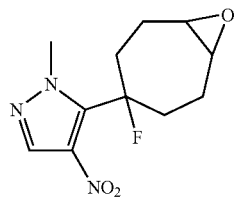 [SMILES: Cn1ncc([N+](=O)[O-])c1C1(F)CCC2OC2CC1]

To a solution of (Z)-5-(1-fluorocyclohept-4-enyl)-1-methyl-4-nitro-1H-pyrazole (900 mg, 3.77 mmol) in DCM (30 mL) at 0° C. was added portionwise meta-chloroperoxybenzoic acid (1.0 g, 4.14 mmol). The reaction mixture was allowed to warm to room temperature and stirred for 90 min before being quenched with a saturated solution of sodium hydrogencarbonate (30 mL). The mixture was extracted with DCM (100 mL), washed with aqueous 2 M NaOH (2×50 mL) and brine (30 mL). The organic layer was separated, dried over MgSO₄ and concentrated under reduced pressure to give 5-(4-fluoro-8-oxabicyclo[5.1.0]octan-4-yl)-1-methyl-4-nitro-1H-pyrazole as a colourless solid (982 mg, quantitative) as a 2:5 ratio of diastereomers.

Table 1a and 1b Formula I Compounds

Example 101

5-amino-2-(2,6-difluorophenyl)-N-[5-(3,6-dihydro-2H-pyran-4-yl)-1-methyl-pyrazol-4-yl]thiazole-4-carboxamide 101

A mixture of tert-butyl (4-((5-chloro-1-methyl-1H-pyrazol-4-yl)carbamoyl)-2-(2,6-difluorophenyl)thiazol-5-yl)carbamate (234 mg, 0.5 mmol), potassium fluoride dihydrate (155 mg, 1.65 mmol) and 3,6-dihydro-2H-pyran-4-boronic acid pinacol ester (210 mg, 1.0 mmol) in THF (5 mL) was degassed by bubbling nitrogen through it for 15 min. Tris(dibenzylideneacetone)dipalladium/tri-tert-butyl phosphonium tetrafluoroborate mixture (mole ratio: 1/1.2, 60 mg, 0.05 mmol) was added and the mixture degassed for a further 10 min before being heated in a microwave at 110° C. for 8 hr. Water (10 mL) was added and the mixture extracted with EtOAc (3×5 mL). The combined organic layers were passed through a phase separation cartridge and concentrated under reduced pressure. The residue was purified via silica gel chromatography (isohexane then 0-5% MeOH/EtOAc). The resulting intermediate was dissolved in MeOH (5 mL) and treated with a solution of HCl in dioxane (4 M, 5 mL). The mixture was stirred at room temperature for 16 hr and the solvent removed under reduced pressure. Purification via preparative HPLC gave 101 as a brown solid (37 mg, 17% over two steps). ¹H NMR (400 MHz, CDCl₃) δ 8.68 (s, 1H), 8.05 (s, 1H), 7.38-7.26 (m, 1H), 7.06-6.97 (m, 2H), 6.13 (s, 2H), 6.03-6.00 (m, 1H), 4.41 (d, J=2.8 Hz, 1H), 4.39 (d, J=2.8 Hz, 1H), 3.96 (t, J=5.3 Hz, 2H), 3.83 (s, 3H), 2.45-2.41 (m, 2H). LCMS (ES+) m/z 418 (M+1).

Example 102

5-amino-2-(2,6-difluorophenyl)-N-[5-(3,4-dihydro-2H-pyran-6-yl)-1-methyl-pyrazol-4-yl]thiazole-4-carboxamide 102

Following the procedure for Example 101 starting from tert-butyl (4-((5-chloro-1-methyl-1H-pyrazol-4-yl)carbamoyl)-2-(2,6-difluorophenyl)thiazol-5-yl)carbamate and 3,4-dihydro-2H-pyran-6-boronic acid pinacol ester gave 102 as a white solid (25 mg, 8% over two steps). ¹H NMR (400 MHz, CDCl₃) δ 9.25 (s, 1H), 8.18 (s, 1H), 7.34-7.28 (m, 1H), 7.06-6.98 (m, 2H), 6.13 (s, 2H), 5.11 (t, J=3.9 Hz, 1H), 4.25 (t, J=5.1 Hz, 2H), 3.89 (s, 3H), 2.32-2.26 (m, 2H), 2.03-1.96 (m, 2H). LCMS (ES+) m/z 418 (M+1).

Example 103

5-amino-2-(2,6-difluorophenyl)-N-[5-(2-methoxytetrahydropyran-2-yl)-1-methyl-pyrazol-4-yl]thiazole-4-carboxamide 103

A mixture of tert-butyl (4-((5-chloro-1-methyl-1H-pyrazol-4-yl)carbamoyl)-2-(2,6-difluorophenyl)thiazol-5-yl)carbamate (234 mg, 0.5 mmol), potassium fluoride dihydrate (155 mg, 1.65 mmol) and 3,4-dihydro-2H-pyran-6-boronic acid pinacol ester (210 mg, 1.0 mmol) in THF (5 mL) was degassed by bubbling nitrogen through it for 15 min. Tris(dibenzylideneacetone)dipalladium/tri-tert-butyl phosphonium tetrafluoroborate mixture (mole ratio: 1/1.2, 60 mg, 0.05 mmol) was then added and the mixture degassed for a further 10 min before being heated in a microwave at 85° C. for 6 hr. Water (10 mL) was added and the mixture extracted with EtOAc (3×5 mL). The combined organic layers were passed through a phase separation cartridge and concentrated under reduced pressure. Purification via silica gel chromatography (0-100% EtOAc/isohexane) gave a white solid (269 mg, 0.52 mmol). This was dissolved in DCM (20 mL) and EtOH (10 mL) and passed through the H-Cube® (full H₂, 100° C., flow rate: 1 mL/min, 30 mm 10% Raney Nickel cartridge). Removal of the solvent under reduced pressure gave tert-butyl 2-(2,6-difluorophenyl)-4-(5-(2-ethoxytetrahydro-2H-pyran-2-yl)-1-methyl-1H-pyrazol-4-ylcarbamoyl)thiazol-5-ylcarbamate as a white solid (250 mg, 92%). This solid was dissolved in MeOH (5 mL) and a solution of HCl in dioxane (4 M, 5 mL) and stirred at room temperature for 16 hr. Purification via silica gel chromatography (0-5% MeOH/DCM) and preparative HPLC gave 103 as a white solid (31 mg, 10% over three steps). ¹H NMR (400 MHz, CDCl₃) δ 10.08 (s, 1H), 8.34 (s, 1H), 7.35-7.26 (m, 1H), 7.05-6.97 (m, 2H), 6.19 (s, 2H), 4.03 (dd, J=11.1, 4.5 Hz, 1H), 3.92 (s, 3H), 3.92-3.78 (m, 1H), 3.16 (s, 3H), 2.15-2.05 (m, 1H), 2.03-1.89 (m, 1H), 1.92-1.64 (m, 4H). LCMS (ES+) m/z 450 (M+1).

Example 104

5-amino-2-(2,6-difluorophenyl)-N-(1-methyl-5-tetrahydropyran-2-yl-pyrazol-4-yl)thiazole-4-carboxamide 104

10% Palladium on carbon (43 mg, 0.4 mmol) was added to a solution of 5-(3,4-dihydro-2H-pyran-6-yl)-1-methyl-4-nitro-1H-pyrazole (209 mg, 1.0 mmol) and ammonium formate (465 mg, 8.0 mmol) in MeOH (20 mL) under nitrogen and the mixture heated at 80° C. for 2 hr. The mixture was filtered through Celite® to remove the catalyst and the resulting solution passed through the H-Cube (70 bar $H_2$, 70° C., flow rate: 1 mL/min, 10% Pt/C cartridge). The solvent was removed under reduced pressure to give a red gum (170 mg). This was dissolved in DCM (5 mL) and DIPEA (0.13 mL, 0.74 mmol) and added to a solution of PyBOP (335 mg, 0.64 mmol) and 5-((tert-butoxycarbonyl)amino)-2-(2,6-difluorophenyl)thiazole-4-carboxylic acid (180 mg, 0.506 mmol) in DCM (5 mL), which had been stirring at room temperature for 30 min. The mixture was stirred at room temperature for 16 hr before being diluted with DCM (5 mL) and washed with water (3×5 mL). The organic layer was separated, passed through a phase separation cartridge and concentrated under reduced pressure. Purification via silica gel chromatography (0-100% EtOAc/isohexane) gave a yellow gum (40 mg). This gum was dissolved in a solution of HCl in dioxane (4 M, 5 mL) and MeOH (5 mL) and stirred at room temperature for 3 hr. The solvents were removed under reduced pressure and the residue purified via preparative HPLC to give 104 as a white solid (15 mg, 7% over three steps). $^1$H NMR (400 MHz, $CDCl_3$) δ 9.61 (s, 1H), 8.14 (s, 1H), 7.34-7.24 (m, 1H), 7.04-6.96 (m, 2H), 6.18 (s, 2H), 4.66-4.56 (m, 1H), 4.29 (dd, J=11.4, 4.2 Hz, 1H), 3.81 (s, 3H), 3.59 (ddd, J=12.2, 11.4, 2.1 Hz, 1H), 1.98-1.92 (m, 1H), 1.90-1.71 (m, 3H), 1.71-1.58 (m, 2H). LCMS (ES+) m/z 420 (M+1).

Example 105

5-amino-2-(3-fluoro-2-pyridyl)-N-[5-(2-methoxytetrahydropyran-2-yl)-1-methyl-pyrazol-4-yl]thiazole-4-carboxamide 105

A solution of 5-(3,4-dihydro-2H-pyran-6-yl)-1-methyl-4-nitro-1H-pyrazole (209 mg, 1.0 mmol) in MeOH (20 mL) was passed through the H-Cube (Full $H_2$ mode, 70° C., flow rate: 1 mL/min, 30 mm 10% Pd/C cartridge). No reaction occurred so to the solution was added 10% palladium on carbon (43 mg, 0.4 mmol) and ammonium formate (465 mg, 8.0 mmol). The mixture was heated at 80° C. under nitrogen for 2 hr. The mixture was filtered through Celite® to remove the catalyst and the resulting solution passed through the H-Cube (70 bar $H_2$, 70° C., flow rate: 1 mL/min, 10% Pt/C cartridge). The solvent was removed under reduced pressure to give a red gum (170 mg). This gum (170 mg, 0.48 mmol) was dissolved in DCM (5 mL) and DIPEA (0.13 mL, 0.77 mmol) and added to a solution of PyBOP (350 mg, 0.67 mmol) and 5-(tert-butoxycarbonylamino)-2-(3-fluoro-2-pyridyl)thiazole-4-carboxylic acid (179 mg, 0.53 mmol) in DCM (5 mL), which had been stirring at room temperature for 30 min. The mixture was stirred at room temperature for 60 hr, diluted with DCM (5 mL) and washed with water (3×5 mL). The organic layer was passed through a phase separation cartridge and concentrated under reduced pressure. Purification via silica gel chromatography (0-100% EtOAc/isohexane) gave a yellow gum. This gum was dissolved in a solution of HCl in dioxane (4 M, 5 mL) and MeOH (5 mL) and stirred at room temperature for 60 hr. The solvents were removed under reduced pressure. Purification via silica gel column chromatography (0-100% EtOAc/isohexane) gave 105 as a pale yellow solid (27 mg, 12% over three steps). $^1$H NMR (400 MHz, $CDCl_3$) δ 10.01 (s, 1H), 8.39-8.34 (m, 2H), 7.50 (t, J=9.5 Hz, 1H), 7.33-7.20 (m, 1H), 6.36 (s, 2H), 4.15 (dd, J=11.1, 4.3 Hz, 1H), 3.95-3.84 (m, 4H), 3.17 (s, 3H), 2.11 (d, J=12.9 Hz, 1H), 2.04-1.66 (m, 5H). LCMS (ES+) m/z 433 (M+1).

Example 106

5-amino-2-(2,6-difluorophenyl)-N-(5-((1S,4S,5S)-4-hydroxy-8-oxabicyclo[3.2.1]octan-1-yl)-1-methyl-1H-pyrazol-4-yl)thiazole-4-carboxamide 106

To a solution of 5-(4-fluoro-8-oxabicyclo[5.1.0]octan-4-yl)-1-methyl-4-nitro-1H-pyrazole (100 mg, 0.39 mmol) in THF (25 mL) and water (5 mL) was added 10% palladium on carbon (10 mg). The mixture was heated at 40° C. under an atmosphere of $H_2$ (400 psi) for 3 hr. The mixture was filtered through Celite® washing with MeOH (30 mL) and concentrated under reduced pressure to give 5-(4-amino-1-methyl-1H-pyrazol-5-yl)-8-oxabicyclo[3.2.1]octan-2-ol as an orange solid (105 mg, quantitative). This solid (105 mg, 0.44 mmol) was dissolved in DCM (20 mL) and DIPEA (1 mL, 5.74 mmol) was added, followed by 5-(tert-butoxycarbonylamino)-2-(2,6-difluorophenyl)-thiazole-4-carboxylic acid (161 mg, 0.45 mmol) and PyBOP (535 mg, 1.03 mmol). The reaction mixture was stirred at room temperature for 18 hr before being quenched with water (20 mL), extracted with DCM (100 mL), dried over $MgSO_4$ and the solvent removed under reduced pressure. Purification via silica gel column chromatography (80-100% EtOAc/isohexane) gave tert-butyl 2-(2,6-difluorophenyl)-4-(5-(4-hydroxy-8-oxabicyclo[3.2.1]octan-1-yl)-1-methyl-1H-pyrazol-4-ylcarbamoyl) thiazol-5-ylcarbamate as a colourless oil (635 mg, 54%). To a solution of this oil (160 mg, 0.28 mmol) in MeOH (5 mL) was added HCl in dioxane (4 M, 3.6 mL, 14.4 mmol). The reaction mixture was stirred at room temperature for 18 hr. The solvents were removed under reduced pressure before being purified via preparative HPLC, then dissolved in $CHCl_3$/MeOH mixture (10 mL) and passed through an SCX cartridge, eluting with 3N $NH_3$ in MeOH. The solvents were removed under reduced pressure to give 106 as a pale pink solid (31 mg, 24% over three steps). $^1$H NMR (400 MHz, $CDCl_3$) δ 10.08 (s, 1H), 8.25 (s, 1H), 7.32-7.26 (m, 1H), 7.02 (t, J=8.8 Hz, 2H), 6.12 (s, 2H), 4.59-4.55 (m, 1H), 4.12-4.05 (m, 1H), 3.85 (s, 3H), 2.42-2.33 (m, 1H), 2.22-1.89 (m, 6H), 1.62-1.56 (m, 1H), 1.50-1.45 (m, 1H). LCMS (ES+) m/z 462 (M+1).

Example 107

5-amino-N-(5-((1S,4S,5S)-4-amino-8-oxabicyclo[3.2.1]octan-1-yl)-1-methyl-1H-pyrazol-4-yl)-2-(2,6-difluorophenyl)thiazole-4-carboxamide 107

To a solution of tert-butyl N-(2-(2,6-difluorophenyl)-4-((1-methyl-5-(2-((2,2,2-trifluoroacetyl)amino)-8-oxabicyclo[3.2.1]octan-5-yl)pyrazol-4-yl)carbamoyl)thiazol-5-yl) carbamate (58 mg, 0.08 mmol) in MeOH (2 mL) was added a solution of HCl in dioxane (4 M, 1.1 mL, 4.42 mmol). The reaction mixture was stirred at room temperature for 16 hr and concentrated under reduced pressure to give a beige solid. This solid was dissolved in MeOH (5 mL) and water (5 mL) and potassium carbonate (61 mg, 0.44 mmol) added. The reaction mixture was heated at reflux for 3 hr, cooled to room temperature and the MeOH was removed under reduced pressure. The aqueous layer was extracted with 5% MeOH in DCM (2×25 mL), the combined organic layers were dried over $MgSO_4$ and concentrated under reduced pressure. Purification via preparative HPLC gave the formate salt of 107 as a white solid (11 mg, 27% over two steps). $^1$H NMR (400

MHz, d$_4$-MeOD) δ 8.53 (s, 1H), 8.11 (s, 1H), 7.47-7.43 (m, 1H), 7.18 (t, J=8.9 Hz, 2H), 4.68 (s, 1H), 3.89 (s, 3H), 3.52-3.41 (m, 1H), 2.65-2.52 (m, 1H), 2.29-2.04 (m, 5H), 2.00-1.92 (m, 1H), 1.82-1.76 (m, 1H). LCMS (ES+) m/z 461 (M+1).

Example 108

5-amino-2-(2,6-difluorophenyl)-N-(5-((2R,7R)-5-hydroxy-7-methyloxepan-2-yl)-1-methyl-1H-pyrazol-4-yl)thiazole-4-carboxamide 108

A solution of 2-methyl-7-(2-methyl-4-nitro-pyrazol-3-yl)oxepan-4-ol (79 mg, 0.30 mmol) in MeOH (20 mL) was passed through the H-Cube® (full H$_2$, 70° C., flow rate: 1 mL/min, 30 mm 20% Pd(OH)$_2$/C cartridge). The solvent was removed under reduced pressure and the crude residue was re-dissolved in MeOH (1 mL). 5-Amino-2-(2,6-difluorophenyl)thiazole-4-carboxylic acid (94 mg, 0.37 mmol) and DIPEA (0.24 mL, 1.40 mmol) were added. Propylphosphonic anhydride solution (0.19 mL, 50% wt in EtOAc, 0.39 mmol) was added dropwise and the reaction mixture was stirred at room temperature for 16 hr. The reaction mixture was concentrated under reduced pressure and the residue was dissolved in EtOAc (10 mL). The organic layer was washed with 1 M aqueous NaOH (3×10 mL), 1 M aqueous HCl (2×10 mL) and brine (10 mL), separated, dried over Na$_2$SO$_4$ and concentrated under reduced pressure. Purification via silica gel chromatography (0-5% 7 M NH$_3$ in MeOH/DCM) gave 108 as a white solid (4 mg, 3% over two steps). $^1$H NMR (400 MHz, CDCl$_3$) δ 9.69 (d, J=11.8 Hz, 1H), 8.16 (d, J=5.6 Hz, 1H), 7.37-7.30 (m, 1H), 7.04-6.97 (m, 2H), 6.15 (s, 2H), 5.00-4.93 (m, 1H), 4.17 (s, 1H), 4.03 (dd, J=8.0, 6.9 Hz, 1H), 3.77 (s, 3H), 2.11-1.74 (m, 5H), 1.28 (d, J=3.3 Hz, 1H), 1.21 (dd, J=9.2, 6.3 Hz, 3H). Alkyl OH not observed. LCMS (ES+) m/z 464 (M+1).

Example 109

5-amino-2-(2,6-difluorophenyl)-N-[5-(2-hydroxy-8-oxabicyclo[3.2.1]octan-5-yl)-1-methyl-pyrazol-4-yl]thiazole-4-carboxamide 109

Chiral separation of 106 by SFC gave 109. 1H NMR (400 MHz, DMSO) δ 10.03 (s, 1H), 8.00 (s, 1H), 7.56-7.41 (m, 3H), 7.28 (t, J=8.9 Hz, 2H), 4.92 (d, J=4.5 Hz, 1H), 4.40-4.30 (m, 1H), 3.77 (s, 3H), 3.76-3.69 (m, 1H), 2.49-2.38 (m, 1H), 2.17-2.08 (m, 1H), 2.05-1.74 (m, 4H), 1.71-1.43 (m, 2H). LCMS (ES+) m/z 462 (M+1).

Example 110

5-amino-2-(2,6-difluorophenyl)-N-[5-(2-hydroxy-8-oxabicyclo[3.2.1]octan-5-yl)-1-methyl-pyrazol-4-yl]thiazole-4-carboxamide 110

Chiral separation of 106 by SFC gave 110. $^1$H NMR (400 MHz, DMSO) δ 10.03 (s, 1H), 8.00 (s, 1H), 7.59-7.41 (m, 3H), 7.28 (t, J=8.9 Hz, 2H), 4.92 (d, J=4.4 Hz, 1H), 4.42-4.29 (m, 1H), 3.77 (s, 3H), 3.76-3.66 (m, 1H), 2.49-2.37 (m, 1H), 2.17-2.06 (m, 1H), 2.04-1.75 (m, 4H), 1.71-1.43 (m, 2H). LCMS (ES+) m/z 462 (M+1)

Example 111

5-amino-2-(2,6-difluorophenyl)-N-(5-((5R,6S)-5,6-dihydroxyoxepan-2-yl)-1-methyl-1H-pyrazol-4-yl)thiazole-4-carboxamide 111

A solution of 7-(2-methyl-4-nitro-pyrazol-3-yl)oxepane-3,4-diol (Intermediate 10) (165 mg, 0.64 mmol) in MeOH (13 mL) was passed through the H-Cube (full H$_2$ mode, 80° C., flow rate: 1 mL/min, 30 mm 10% Pd/C cartridge). The solvent was removed under reduced pressure. To a solution of the resulting amine in DCM (10 mL) was added DIPEA (0.33 mL, 1.92 mmol), PyBOP (499 mg, 0.96 mmol) and 5-(tert-butoxycarbonylamino)-2-(2,6-difluorophenyl)-thiazole-4-carboxylic acid (249 mg, 0.70 mmol). The mixture was stirred at room temperature for 18 hr, diluted with DCM (5 mL) and washed with water (3×5 mL). The organic layer was passed through a phase separation cartridge and concentrated under reduced pressure. Purification via silica gel chromatography (0-10% MeOH/EtOAc) gave a pink solid. This solid (65 mg, 0.11 mmol) was dissolved in a solution of HCl in dioxane (4 M, 8.6 mL) and MeOH (2 mL) and stirred at room temperature for 18 hr. The solvents were removed under reduced pressure. Purification via preparative HPLC gave 111 as an off-white solid (28 mg, 9% over three steps). $^1$H NMR (400 MHz, CDCl$_3$) δ 9.75 (br s, 1H), 8.17 (s, 1H), 7.39-7.32 (m, 1H), 7.10-7.00 (m, 2H), 6.25 (br s, 2H), 5.14-5.10 (m, 1H), 4.23 (dd, J=13.7, 4.0 Hz, 1H), 3.90-3.85 (m, 1H), 3.79 (s, 3H), 3.75-3.56 (m, 2H), 2.12-2.00 (m, 3H), 1.76-1.70 (m, 1H). OH protons not observed. LCMS (ES+) m/z 466 (M+1).

Example 112

5-amino-N-(5-((2R,7R)-5-amino-7-ethyloxepan-2-yl)-1-methyl-1H-pyrazol-4-yl)-2-(2,6-difluorophenyl)thiazole-4-carboxamide 112

A solution of N-(2-ethyl-7-(2-methyl-4-nitro-pyrazol-3-yl)oxepan-4-yl)-2-methyl-propane-2-sulfinamide (118 mg, 0.31 mmol) in MeOH (20 mL) was passed through the H-Cube® (full H$_2$, 60° C., flow rate: 1 mL/min, 30 mm 20% Pd(OH)$_2$/C cartridge). The solvent was removed under reduced pressure and the crude residue was re-dissolved in MeOH (1 mL). 5-(tert-Butoxycarbonylamino)-2-(2,6-difluorophenyl)thiazole-4-carboxylic acid (119 mg, 0.33 mmol) was added followed by DIPEA (0.16 mL, 0.95 mmol) and the reaction mixture was heated at 50° C. for 15 min. After cooling to room temperature, propylphosphonic anhydride solution (0.17 mL, 50% wt in EtOAc, 0.34 mmol) was added dropwise and the reaction mixture was stirred at room temperature for 16 hr. The mixture was concentrated under reduced pressure and the residue was dissolved in EtOAc (10 mL), washed with 1 M aqueous NaOH (3×10 mL), 1 M aqueous HCl (2×10 mL) and brine (10 mL). The organic layer was separated, dried over Na$_2$SO$_4$, concentrated under reduced pressure and purified via silica gel chromatography (0-10% 7 M ammonia in MeOH/DCM) to give an oil as a mixture of isomers. This oil was dissolved in MeOH (2 mL) and HCl in dioxane (4 M, 4.0 mmol, 1 mL) was added. The reaction mixture was stirred at room temperature for 18 hr and the solvents removed under reduced pressure. Purification via chiral preparative HPLC gave 112 as a white solid (9 mg, 5% over three steps). $^1$H NMR (400 MHz, CDCl$_3$) δ 9.63 (s, 1H), 8.15 (s, 1H), 7.34 (tt, J=8.4, 6.1 Hz, 1H), 7.05-6.97 (m, 2H), 6.16 (s, 2H), 4.80 (dd, J=8.2, 3.9 Hz, 1H), 3.77 (s, 3H), 3.71-3.62 (m, 1H), 3.39-3.32 (m, 1H), 2.18-2.09 (m, 1H), 2.08-1.98 (m, 1H), 1.93-1.74 (m, 2H), 1.71-1.57 (m, 3H), 1.46-1.33 (m, 3H), 0.81 (t, J=7.4 Hz, 3H). LCMS (ES+) m/z 477 (M+1).

Example 113

5-amino-N-(5-((2R,7R)-5-amino-7-methyloxepan-2-yl)-1-methyl-1H-pyrazol-4-yl)-2-(2,6-difluorophenyl)thiazole-4-carboxamide 113

Following the procedure for Example 112 starting from N-(2-methyl-7-(2-methyl-4-nitro-pyrazol-3-yl)oxepan-4-yl)-2-methyl-propane-2-sulfinamide gave, after silica gel column chromatography (0-10% MeOH/DCM, 1% 7 M NH₃ in MeOH) and preparative HPLC, 113 as an off-white solid (45 mg, 17% over three steps). ¹H NMR (400 MHz, CDCl₃) δ 9.60 (s, 1H), 8.13 (s, 1H), 7.36-7.29 (m, 1H), 7.05-6.96 (m, 2H), 6.17 (s, 2H), 4.84-4.79 and 4.71-4.67 (m, 1H), 4.04-3.96 (m, 1H), 3.78 and 3.74 (s, 3H), 3.40-3.33 (m, 1H), 2.15-1.51 (m, 8H), 1.26-1.16 (m, 3H). LCMS (ES+) m/z 463 (M+1).

Example 114

5-Amino-N-(5-(6-amino-4,4-difluorooxepan-2-yl)-1-methyl-1H-pyrazol-4-yl)-2-(2,6-difluorophenyl)thiazole-4-carboxamide 114

To a solution of 5-(6-azido-4,4-difluoro-oxepan-2-yl)-1-methyl-4-nitro-pyrazole (69 mg, 0.23 mmol) in EtOH (2.3 mL) was added ammonium chloride (61 mg 1.14 mmol) and water (0.23 mL) followed by iron powder (51 mg, 0.9 µmol). The reaction mixture was heated at 80° C. for 6 hr and then recharged with the same amounts of iron and ammonium chloride. Heating was continued for 60 min and the reaction mixture was cooled to room temperature. The crude slurry was filtered through Celite® washing with DCM (20 mL). The solution was passed through a phase separation cartridge and concentrated under reduced pressure. The crude residue was dissolved in MeOH (1 mL) and 5-amino-2-(2,6-difluorophenyl)thiazole-4-carboxylic acid (94 mg, 0.37 mmol) and DIPEA (0.24 mL, 1.40 mmol) were added. Propylphosphonic anhydride solution (50% wt in EtOAc, 0.19 mL, 0.39 mmol) was added dropwise and the reaction mixture was stirred at room temperature for 16 hr. The reaction mixture was concentrated under reduced pressure and the residue dissolved in EtOAc (10 mL). The organic layer was washed with 1 M aqueous NaOH (3×10 mL), 1 M aqueous HCl (2×10 mL), brine (10 mL), dried over Na₂SO₄ and concentrated under reduced pressure. Purification via silica gel chromatography (0-5% 7 M NH₃ in MeOH/DCM) and preparative HPLC gave 5-amino-N-(5-(6-azido-4,4-difluorooxepan-2-yl)-1-methyl-1H-pyrazol-4-yl)-2-(2,6-difluorophenyl)thiazole-4-carboxamide as a colourless oil. The compound was dissolved in MeOH (10 mL) and passed through the H-Cube® (full H₂, 70° C., flow rate: 1 mL/min, 30 mm 10% Pd/C cartridge). Purification via silica gel column chromatography (0-10% MeOH/DCM, 1% 7 M NH₃ in MeOH) gave 114 (Diastereomer 1) as a colourless solid (2 mg, 2% over three steps). ¹H NMR (400 MHz, CDCl₃) δ 9.39 (s, 1H), 8.07 (s, 1H), 7.45-7.18 (m, 1H), 7.05-6.98 (m, 2H), 6.16 (s, 2H), 4.97-4.88 (m, 1H), 4.32-4.23 (m, 1H), 3.83 (s, 3H), 3.54-3.42 (m, 2H), 2.74-2.44 (m, 3H), 2.36-2.20 (m, 1H), 1.31-1.14 (m, 2H). LCMS (ES+) m/z 485 (M+1).

Example 115

5-amino-N-(5-((1S,4S,5S)-4-amino-8-oxabicyclo[3.2.1]octan-1-yl)-1-methyl-1H-pyrazol-4-yl)-2-(2,6-difluorophenyl)thiazole-4-carboxamide 115

Chiral separation of the racemic mixture tert-butyl N-[5-[4-[[5-(tert-butoxycarbonylamino)-2-(2,6-difluorophenyl)thiazole-4-carbonyl]amino]-2-methyl-pyrazol-3-yl]-8-oxabicyclo[3.2.1]octan-2-yl]carbamate by SFC followed by deprotection with 4N HCl in dioxane gave 115 as a single enantiomer. ¹H NMR (400 MHz, DMSO) δ 10.07 (s, 1H), 8.00 (s, 1H), 7.57-7.39 (m, 3H), 7.38-7.22 (m, 2H), 4.27 (dd, J=7.1, 3.4 Hz, 1H), 3.77 (s, 3H), 3.01-2.90 (m, 1H), 2.44-2.30 (m, 1H), 2.22-2.07 (m, 1H), 2.04-1.55 (m, 5H), 1.44-1.27 (m, 1H). LCMS (ES+) m/z 461 (M+1).

Example 116

5-amino-N-(5-((1S,4R,5S)-4-amino-8-oxabicyclo[3.2.1]octan-1-yl)-1-methyl-1H-pyrazol-4-yl)-2-(2,6-difluorophenyl)thiazole-4-carboxamide 116

Chiral separation of the racemic mixture tert-butyl N-[5-[4-[[5-(tert-butoxycarbonylamino)-2-(2,6-difluorophenyl)thiazole-4-carbonyl]amino]-2-methyl-pyrazol-3-yl]-8-oxabicyclo[3.2.1]octan-2-yl]carbamate by SFC followed by deprotection with 4N HCl in dioxane gave 116 as a single enantiomer. ¹H NMR (400 MHz, DMSO) δ 10.08 (s, 1H), 8.00 (s, 1H), 7.57-7.40 (m, 3H), 7.36-7.24 (m, 2H), 4.27 (dd, J=7.0, 3.4 Hz, 1H), 3.77 (s, 3H), 2.93 (dd, J=10.0, 5.7 Hz, 1H), 2.43-2.34 (m, 1H), 2.20-2.08 (m, 1H), 2.04-1.50 (m, 5H), 1.42-1.29 (m, 1H). LCMS (ES+) m/z 461 (M+1).

Example 117

5-amino-N-(5-((1R,4S,5R)-4-amino-8-oxabicyclo[3.2.1]octan-1-yl)-1-methyl-1H-pyrazol-4-yl)-2-(2,6-difluorophenyl)thiazole-4-carboxamide 117

Chiral separation of the racemic mixture tert-butyl N-[5-[4-[[5-(tert-butoxycarbonylamino)-2-(2-fluorophenyl)thiazole-4-carbonyl]amino]-2-methyl-pyrazol-3-yl]-8-oxabicyclo[3.2.1]octan-2-yl]carbamate by SFC followed by deprotection with 4N HCl in dioxane gave 117 as a single enantiomer. ¹H NMR (400 MHz, DMSO) δ 10.23 (s, 1H), 8.18-8.09 (m, 1H), 7.97 (s, 1H), 7.51-7.29 (m, 5H), 4.37 (dd, J=7.0, 3.6 Hz, 1H), 3.79 (s, 3H), 3.07-2.96 (m, 1H), 2.45-2.34 (m, 1H), 2.23-2.12 (m, 1H), 2.09-1.97 (m, 1H), 1.94-1.83 (m, 2H), 1.80-1.59 (m, 4H), 1.47-1.30 (m, 1H). LCMS (ES+) m/z 443 (M+1).

Example 118

5-amino-N-(5-((1R,4R,5R)-4-amino-8-oxabicyclo[3.2.1]octan-1-yl)-1-methyl-1H-pyrazol-4-yl)-2-(2,6-difluorophenyl)thiazole-4-carboxamide 118

Chiral separation of the racemic mixture tert-butyl N-[5-[4-[[5-(tert-butoxycarbonylamino)-2-(2-fluorophenyl)thiazole-4-carbonyl]amino]-2-methyl-pyrazol-3-yl]-8-oxabicyclo[3.2.1]octan-2-yl]carbamate by SFC followed by deprotection with 4N HCl in dioxane gave 118 as a single enantiomer. ¹H NMR (400 MHz, DMSO) δ 10.23 (s, 1H), 8.19-8.09 (m, 1H), 7.97 (s, 1H), 7.54-7.27 (m, 5H), 4.37 (dd, J=7.2, 3.4 Hz, 1H), 3.79 (s, 3H), 3.09-2.96 (m, 1H), 2.46-2.36 (m, 1H), 2.23-2.13 (m, 1H), 2.12-1.98 (m, 1H), 1.96-1.82 (m, 2H), 1.79-1.58 (m, 3H), 1.45-1.29 (m, 1H). LCMS (ES+) m/z 443 (M+1).

Example 119

5-amino-N-(5-((5R,6R)-5-amino-6-fluorooxepan-2-yl)-1-methyl-1H-pyrazol-4-yl)-2-(2,6-difluorophenyl)thiazole-4-carboxamide 119

Following the procedure for Example 111 starting from tert-butyl N-3-fluoro-7-(2-methyl-4-nitro-pyrazol-3-yl)oxepan-4-yl)carbamate (Intermediate 23) gave 119 as a colourless solid (7 mg, 9% over three steps). ¹H NMR (400 MHz, DMSO) δ 9.49 (s, 1H), 7.87 (s, 1H), 7.60-7.44 (m, 3H), 7.32-7.23 (m, 2H), 5.01-4.83 (m, 2H), 4.12-3.90 (m, 2H), 3.72 (s, 3H), 3.36-3.19 (m, 1H), 2.22-2.14 (m, 1H), 1.92-1.57 (m, 3H). Alkyl $NH_2$ not observed. LCMS (ES+) m/z 467 (M+1).

Example 120

5-amino-N-(5-((2R,5R,7R)-5-amino-7-methyloxepan-2-yl)-1-methyl-1H-pyrazol-4-yl)-2-(2,6-difluorophenyl)thiazole-4-carboxamide 120

Chiral separation of 113 by SFC gave 120. $^1$H NMR (400 MHz, DMSO) δ 9.66 (s, 1H), 7.91 (s, 1H), 7.61-7.50 (m, 1H), 7.46 (s, 2H), 7.26 (t, J=8.5 Hz, 2H), 5.05-4.94 (m, 1H), 4.07-3.90 (m, 1H), 3.70 (s, 3H), 3.15-3.03 (m, 1H), 2.23-2.11 (m, 1H), 1.91-1.64 (m, 3H), 1.64-1.46 (m, 3H), 1.05 (d, J=6.3 Hz, 3H). LCMS (ES+) m/z 463 (M+1).

Example 121

5-amino-N-(5-((2R,5S,7R)-5-amino-7-methyloxepan-2-yl)-1-methyl-1H-pyrazol-4-yl)-2-(2,6-difluorophenyl)thiazole-4-carboxamide 121

Chiral separation of 113 by SFC gave 121. $^1$H NMR (400 MHz, DMSO) δ 9.56 (s, 1H), 7.90 (s, 1H), 7.61-7.52 (m, 1H), 7.48 (s, 2H), 7.27 (t, J=8.5 Hz, 2H), 4.99 (dd, J=9.0, 2.9 Hz, 1H), 4.05 (dd, J=11.5, 6.5 Hz, 1H), 3.72 (s, 3H), 2.09 (d, J=14.1 Hz, 1H), 1.98-1.51 (m, 6H), 1.09 (d, J=6.3 Hz, 3H). LCMS (ES+) m/z 463 (M+1).

Example 122

5-amino-N-[5-(6-amino-4,4-difluoro-oxepan-2-yl)-1-methyl-pyrazol-4-yl]-2-(2,6-difluorophenyl)thiazole-4-carboxamide 122

To a solution of 5-(6-azido-4,4-difluoro-oxepan-2-yl)-1-methyl-4-nitro-pyrazole (264 mg, 0.87 mmol) in EtOH (8.8 mL) was added ammonium chloride (360 mg 6.73 mmol) water (0.88 mL) and iron powder (51 mg, 0.91 mmol). The reaction mixture was heated at 80° C. for 16 hr and then cooled to room temperature. The crude slurry was filtered through Celite® washing with DCM (200 mL). The solution was passed through a phase separation cartridge and concentrated under reduced pressure. The residue was dissolved in isopropanol (10 mL) and 5-amino-2-(2,6-difluorophenyl)thiazole-4-carboxylic acid (255 mg, 0.92 mmol) and DIPEA (0.59 mL, 3.50 mmol) were added. Propylphosphonic anhydride solution (50% wt in EtOAc, 0.46 mL, 0.96 mmol) was added dropwise and the reaction mixture was stirred at room temperature for 16 hr. The reaction mixture was concentrated under reduced pressure. Purification via silica gel chromatography (0-5% 7 M $NH_3$ in MeOH/DCM) followed by preparative HPLC gave 122 (Diastereomer 2) as a colourless solid (24 mg, 6% over two steps). $^1$H NMR (400 MHz, $CDCl_3$) δ 9.43 and 9.39 (2s, 1H), 8.09 and 8.07 (2s, 1H), 7.32 (tt, J=8.4, 6.1 Hz, 1H), 7.06-6.96 (m, 2H), 6.19 (s, 2H), 4.92 and 4.81 (d, J=11.4 Hz, 1H), 4.27 and 4.08 (2dd, J=12.5, 5.2 Hz, 1H), 3.88 (dd, J=12.5, 6.4 Hz, 1H), 3.83 and 3.81 (2s, 3H), 3.46-3.36 (m, 1H), 2.65-2.46 (m, 1H), 2.45-2.27 (m, 2H), 1.25 (s, 3H). LCMS (ES+) m/z 485 (M+1).

Example 123

5-amino-N-(5-((5S,6S)-6-amino-5-methoxyoxepan-2-yl)-1-methyl-1H-pyrazol-4-yl)-2-(2,6-difluorophenyl)thiazole-4-carboxamide 123

Following the procedure for Example 111 starting from tert-butyl N-(4-methoxy-7-(2-methyl-4-nitro-pyrazol-3-yl)oxepan-3-yl]carbamate (Intermediate 20) gave the formate salt of 123 as a colorless solid (9 mg, 11% over three steps). $^1$H NMR (400 MHz, $d_6$-DMSO) δ 9.61 (s, 1H), 8.23 (s, 1H), 7.91 (s, 1H), 7.57-7.48 (m, 3H), 7.30 (t, J=8.8 Hz, 2H), 5.13 (dd, J=6.0, 3.4 Hz, 1H), 3.80 (dd, J=12.6, 3.8 Hz, 1H), 3.71 (s, 3H), 3.18 (s, 3H), 3.05-2.97 (m, 1H), 2.93 (t, J=8.6 Hz, 1H), 2.34 (s, 1H), 2.07-1.96 (m, 1H), 1.94-1.82 (m, 2H), 1.53-1.42 (m, 1H). Alkyl $NH_2$ not observed. LCMS (ES+) m/z 479 (M+1).

Example 125

5-amino-N-(5-((2R,7R)-5-amino-7-ethyloxepan-2-yl)-1-methyl-1H-pyrazol-4-yl)-2-(2,6-difluorophenyl)thiazole-4-carboxamide 125

Following the procedure for Example 112 gave another stereoisomer 125 as a colorless oil (1.3 mg, 1% over three steps). $^1$H NMR (400 MHz, $d_6$-DMSO) δ 9.73 (s, 1H), 7.89 (s, 1H), 7.53-7.44 (m, 2H), 7.41 (s, 2H), 7.23-7.14 (m, 3H), 5.09 (t, J=5.0 Hz, 1H), 3.62 (s, 3H), 3.49-3.39 (m, 1H), 3.09-2.96 (m, 1H), 2.10-1.96 (m, 1H), 1.84-1.71 (m, 2H), 1.68-1.60 (m, 1H), 1.54-1.35 (m, 3H), 1.27-1.16 (m, 1H), 0.66 (t, J=7.3 Hz, 3H). LCMS (ES+) m/z 477 (M+1).

Example 126

5-amino-N-(5-((5R,6S)-5-amino-6-methoxyoxepan-2-yl)-1-methyl-1H-pyrazol-4-yl)-2-(2,6-difluorophenyl)thiazole-4-carboxamide 126

Following the procedure for Example 111 starting from tert-butyl N-((3S,4R)-3-methoxy-7-(2-methyl-4-nitro-pyrazol-3-yl)oxepan-4-yl)carbamate (Intermediate 21) gave 126 as an off-white solid (33 mg, 25% over three steps). $^1$H NMR (400 MHz, $d_6$-DMSO) δ 9.23 (s, 1H), 7.77 (s, 1H), 7.59-7.47 (m, 3H), 7.31-7.23 (m, 2H), 4.79 (dd, J=10.9, 3.6 Hz, 1H), 4.04 (dd, J=13.8, 3.1 Hz, 1H), 3.84-3.75 (m, 1H), 3.75 (s, 3H), 3.09 (s, 3H), 3.08-2.94 (m, 2H), 2.06-1.97 (m, 1H), 1.84-1.67 (m, 2H), 1.64-1.55 (m, 1H), Alkyl $NH_2$ not observed. LCMS (ES+) m/z 479 (M+1).

Example 127

5-amino-N-(5-((4R,5R)-4-amino-5-fluorooxepan-2-yl)-1-methyl-1H-pyrazol-4-yl)-2-(2,6-difluorophenyl)thiazole-4-carboxamide 127

Following the procedure for Example 130 also gave 127 as a white solid (5 mg, 1% over three steps). $^1$H NMR (400 MHz, $CDCl_3$) δ 10.91 (s, 1H), 7.96 (s, 1H), 7.36-7.26 (m, 1H), 7.05-6.96 (m, 2H), 6.22 (s, 2H), 4.89 (t, J=6.1 Hz, 1H), 4.82-4.76 and 4.70-4.64 (m, 1H), 4.13 (dq, J=12.9, 4.2 Hz, 1H), 3.85 (s, 3H), 3.60-3.47 (m, 2H), 2.72-2.62 (m, 1H), 2.33-2.18 (m, 1H), 2.18-1.97 (m, 2H). Alkyl $NH_2$ not observed. LCMS (ES+) m/z 467 (M+1).

Example 128

5-amino-N-(5-((5S,6R)-5-amino-6-methoxyoxepan-2-yl)-1-methyl-1H-pyrazol-4-yl)-2-(2,6-difluorophenyl)thiazole-4-carboxamide 128

Following the procedure for Example 111 from tert-butyl N-((3R,4S)-3-methoxy-7-(2-methyl-4-nitro-pyrazol-3-yl)oxepan-4-yl)carbamate (Intermediate 22) gave 128 as a white solid (28 mg, 21% over three steps). $^1$H NMR (400 MHz, d$_6$-DMSO) δ 9.23 (s, 1H), 7.77 (s, 1H), 7.59-7.47 (m, 3H), 7.31-7.23 (m, 2H), 4.79 (dd, J=11.0, 3.6 Hz, 1H), 4.04 (dd, J=13.8, 3.1 Hz, 1H), 3.82 (dd, J=13.9, 3.4 Hz, 1H), 3.75 (s, 3H), 3.09 (s, 3H), 3.08-2.93 (m, 2H), 2.07-1.97 (m, 1H), 1.85-1.69 (m, 2H), 1.66-1.55 (m, 1H). Alkyl NH$_2$ not observed. LCMS (ES+) m/z 479 (M+1).

Example 129

5-amino-N-(5-((5R,6R)-5-amino-6-fluorooxepan-2-yl)-1-methyl-1H-pyrazol-4-yl)-2-(2,6-difluorophenyl)thiazole-4-carboxamide 129

Following the procedure for Example 111 starting from tert-butyl N-((3R,4R)-3-fluoro-7-(2-methyl-4-nitro-pyrazol-3-yl)oxepan-4-yl)carbamate (Intermediate 24) gave 129 as a colourless solid (30 mg, 38% over three steps). $^1$H NMR (400 MHz, d$_6$-DMSO) δ 9.49 (s, 1H), 7.86 (s, 1H), 7.55-7.48 (m, 3H), 7.28 (t, J=8.9 Hz, 2H), 4.98-4.78 (m, 2H), 4.08-3.93 (m, 2H), 3.72 (s, 3H), 3.28-3.20 (m, 1H), 2.22-1.92 (m, 3H), 1.91-1.58 (m, 3H). LCMS (ES+) m/z 467 (M+1).

Example 130

5-amino-N-(5-((4S,5S)-4-amino-5-fluorooxepan-2-yl)-1-methyl-1H-pyrazol-4-yl)-2-(2,6-difluorophenyl)thiazole-4-carboxamide 130

Following the procedure for Example 111 starting from tert-butyl N-(5-fluoro-2-(2-methyl-4-nitro-pyrazol-3-yl)oxepan-4-yl)carbamate gave 130 as a white solid (13 mg, 4% over three steps). $^1$H NMR (400 MHz, CDCl$_3$) δ 10.91 (s, 1H), 7.96 (s, 1H), 7.36-7.26 (m, 1H), 7.05-6.96 (m, 2H), 6.22 (s, 2H), 4.89 (t, J=6.1 Hz, 1H), 4.82-4.76 and 4.70-4.64 (m, 1H), 4.13 (dq, J=12.9, 4.2 Hz, 1H), 3.85 (s, 3H), 3.60-3.47 (m, 2H), 2.72-2.62 (m, 1H), 2.33-2.18 (m, 1H), 2.18-1.97 (m, 2H). Alkyl NH$_2$ not observed. LCMS (ES+) m/z 467 (M+1).

Example 131

5-amino-N-(5-((5S,6S)-5-amino-6-fluorooxepan-2-yl)-1-methyl-1H-pyrazol-4-yl)-2-(2,6-difluorophenyl)thiazole-4-carboxamide 131

Following the procedure for Example 111 from tert-butyl N-((3S,4S)-3-fluoro-7-(2-methyl-4-nitro-pyrazol-3-yl)oxepan-4-yl)carbamate (Intermediate 25) gave 131 as a colorless solid (30 mg, 38% over three steps). $^1$H NMR (400 MHz, d$_6$-DMSO) δ 9.49 (s, 1H), 7.86 (s, 1H), 7.55-7.48 (m, 3H), 7.31-7.22 (m, 2H), 4.95-4.76 (m, 2H), 4.08-3.91 (m, 2H), 3.72 (s, 3H), 3.30-3.22 (m, 1H), 2.22-1.57 (m, 6H). LCMS (ES+) m/z 467 (M+1).

Example 134

5-amino-2-(2,6-difluorophenyl)-N-[5-(5-hydroxyoxepan-2-yl)-1-methyl-pyrazol-4-yl]thiazole-4-carboxamide 134

Following the procedure for Example 108 starting from 7-(1-methyl-4-nitro-1H-pyrazol-5-yl)oxepan-4-ol (85 mg 0.35 mmol), using a Raney Nickel cartridge, gave, after preparative HPLC, 134 as a light pink solid and a 1/1 mixture of diastereoisomers (15 mg, 9% over two steps). $^1$H NMR δ (ppm) (CDCl$_3$) 9.72 (2s, 1H), 8.15 (2s, 1H), 7.37-7.26 (m, 1H), 7.06-6.96 (m, 2H), 6.17 (s, 2H), 5.01-4.92 (m, 1H), 4.23-4.15 (m, 1H), 4.06 (dt, J=12.7, 4.6 Hz, 1H), 4.01-3.62 (m, 5H), 2.42-2.25 (m, 1H), 2.17-1.90 (m, 5H). LCMS (ES+) m/z 450 (M+1).

Example 135

5-amino-N-(5-((2S,4R,5R)-5-amino-4-fluorooxepan-2-yl)-1-methyl-1H-pyrazol-4-yl)-2-(2,6-difluorophenyl)thiazole-4-carboxamide 135

To a solution of 5-azido-7-(2-methyl-4-nitro-pyrazol-3-yl)oxepan-4-ol (353 mg, 1.25 mmol) in DCM (6 mL) at 0° C. was added Bis(2-methoxyethyl)aminosulfur trifluoride, Sigma-Aldrich Product No. 494119, CAS No. 202289-38-1, deoxo-Fluor®, (50% in THF, 0.58 mL, 1.56 mmol) and the mixture was stirred at room temperature for 16 hr. The mixture was cooled in an ice/water bath and quenched by the dropwise addition of saturated aqueous NaHCO$_3$ (10 mL). The organic layer was passed through a phase separation cartridge and the solvent removed under reduced pressure. Purification via silica gel column chromatography (0-50% EtOAc/isohexane) gave a clear gum. A solution of this gum (145 mg, 0.51 mmol) in THF/water (2.5 mL/0.5 mL) was treated with triphenylphosphine (147 mg, 0.56 mmol) and the reaction mixture was heated at 60° C. behind a blast screen for 2 hr. The mixture was diluted with EtOAc (10 mL) and washed with brine (2×5 mL). The organic layer was passed through a phase separation cartridge and concentrated under reduced pressure. The resulting residue was dissolved in dry DCM (2 mL) and DIPEA (0.18 mL, 1.02 mmol) and di-tert-butyl-dicarbonate (134 mg, 0.61 mmol) was added. The reaction mixture was stirred at room temperature for 2 hr. Water (2 mL) was added and the mixture extracted with DCM (3×2 mL). The organic layer was passed through a phase separation cartridge and concentrated under reduced pressure. Purification via silica gel column chromatography (0-50% EtOAc/isohexane) gave the intermediate nitro-pyrazole as a clear gum (180 mg). To a solution of this gum (179 mg, 0.5 mmol) was added 10% palladium on carbon (27 mg, 0.25 mmol) and 1-methyl-1,4-cyclohexadiene (0.56 mL, 5.0 mmol). The mixture was heated at 70° C. for 1 hr. No reaction occurred so the mixture was filtered and to the filtrate added 10% palladium on carbon (27 mg, 0.25 mmol) and ammonium formate (126 mg, 2.0 mmol). The mixture was heated at 80° C. under nitrogen for 2 hr. The mixture was cooled to room temperature, filtered through Celite® and concentrated under reduced pressure to give the amino-pyrazole as a pale yellow gum (132 mg). This gum (131 mg, 0.40 mmol) was dissolved in DCM (2 mL) and DIPEA (0.10 mL, 0.56 mmol) and added to a solution of PyBOP (255 mg, 0.49 mmol) and 5-(tert-butoxycarbonylamino)-2-(3-fluoro-2-pyridyl)thiazole-4-carboxylic acid (131 mg, 0.37 mmol) in DCM (2 mL) which had been stirring at room temperature for 30 min. The mixture was stirred at room temperature for 16 hr, diluted with DCM (10 mL) and washed with saturated aqueous NaHCO$_3$ (10 mL) and water (10 mL). The organic layer was passed through a phase separation cartridge and concentrated under reduced pressure. Purification via silica gel chromatography (0-3% MeOH/DCM) gave a pale yellow gum (65 mg). Further purification via chiral preparative HPLC gave an off-white solid (22 mg). This solid (22 mg, 0.033 mmol) was dissolved in a solution of HCl in dioxane (4 M, 5 mL) and MeOH (2 mL) and stirred at room temperature for 16 hr. The solvents were removed under reduced pressure and residue was passed through an SCX cartridge washing with MeOH and eluting with 3% 7 M NH$_3$ in MeOH/DCM. Purification via silica gel column chromatography (0-5% 7 M NH$_3$ in MeOH/DCM) gave 135 as a white solid (10 mg, 1% over 6 steps). $^1$H NMR (400 MHz, CDCl$_3$) δ 9.68 (s, 1H), 8.19 (s, 1H), 7.35-7.27 (m, 1H), 7.01 (t, J=8.7 Hz, 2H), 6.16 (s, 2H), 5.07-5.02 (m, 1H), 4.60 (dddd, J=43.2, 9.0, 6.5, 3.8 Hz, 1H), 4.23 (ddd, J=12.5, 7.0, 4.4 Hz, 1H), 3.88-3.74 (m, 4H), 3.36-3.26 (m, 1H), 2.46-2.30 (m, 2H), 2.18-2.07 (m, 1H), 1.98-1.87 (m, 1H). Alkyl NH$_2$ not observed. LCMS (ES+) m/z 467 (M+1).

Example 136

5-amino-N-(5-((2S,4R,5R)-5-amino-4-methoxyoxepan-2-yl)-1-methyl-1H-pyrazol-4-yl)-2-(2,6-difluorophenyl)thiazole-4-carboxamide 136

Following the procedure for Example 140 starting from tert-butyl N-(5-methoxy-7-(2-methyl-4-nitro-pyrazol-3-yl)oxepan-4-yl)carbamate gave 136 as an off-white solid (28 mg, 12% over three steps). $^1$H NMR (400 MHz, CDCl$_3$) δ 9.76 (s, 1H), 8.20 (s, 1H), 7.35-7.26 (m, 1H), 7.01 (t, J=8.7 Hz, 2H), 6.16 (s, 2H), 5.04 (dd, J=6.5, 3.7 Hz, 1H), 4.24-4.16 (m, 1H), 3.87-3.69 (m, 4H), 3.34-3.11 (m, 4H), 3.15-3.08 (m, 1H), 2.24-2.04 (m, 3H), 1.94-1.84 (m, 1H). Alkyl NH$_2$ not observed. LCMS (ES+) m/z 479 (M+1).

Example 137

5-amino-N-(5-((2R,4S,5S)-5-amino-4-fluorooxepan-2-yl)-1-methyl-1H-pyrazol-4-yl)-2-(2,6-difluorophenyl)thiazole-4-carboxamide 137

Following the procedure for Example 140 also gave 137 as a white solid (10 mg, 1%, over 6 steps). $^1$H NMR (400 MHz, CDCl$_3$) δ 9.68 (s, 1H), 8.19 (s, 1H), 7.35-7.27 (m, 1H), 7.01 (t, J=8.7 Hz, 2H), 6.16 (s, 2H), 5.07-5.02 (m, 1H), 4.60 (dddd, J=43.2, 9.0, 6.5, 3.8 Hz, 1H), 4.23 (ddd, J=12.5, 7.0, 4.4 Hz, 1H), 3.88-3.74 (m, 4H), 3.36-3.26 (m, 1H), 2.46-2.30 (m, 2H), 2.18-2.07 (m, 1H), 1.98-1.87 (m, 1H). Alkyl NH$_2$ not observed. LCMS (ES+) m/z 467 (M+1).

Example 138

5-amino-N-(5-((2R,4S,5S)-5-amino-4-methoxyoxepan-2-yl)-1-methyl-1H-pyrazol-4-yl)-2-(2,6-difluorophenyl)thiazole-4-carboxamide 138

Following the procedure for Example 137 also gave 138 as an off-white solid (25 mg, 10% over three steps). $^1$H NMR (400 MHz, CDCl$_3$) δ 9.76 (s, 1H), 8.20 (s, 1H), 7.35-7.26 (m, 1H), 7.01 (t, J=8.7 Hz, 2H), 6.16 (s, 2H), 5.04 (dd, J=6.5, 3.7 Hz, 1H), 4.24-4.16 (m, 1H), 3.87-3.69 (m, 4H), 3.34-3.11 (m, 4H), 3.15-3.08 (m, 1H), 2.24-2.04 (m, 3H), 1.94-1.84 (m, 1H). Alkyl NH$_2$ not observed. LCMS (ES+) m/z 479 (M+1).

Example 139

5-amino-N-[5-[1-(aminomethyl)-7-oxabicyclo[2.2.1]heptan-4-yl]-1-methyl-pyrazol-4-yl]-2-(2-fluorophenyl)thiazole-4-carboxamide 139

Following the procedure for Example 106 starting from tert-butyl N-[[4-fluoro-1-hydroxy-4-(2-methyl-4-nitro-pyrazol-3-yl)cyclohexyl]methyl]carbamate gave, after purification via silica gel column chromatography (5% MeOH/DCM with 1% NH$_3$ in MeOH), 139 as a cream solid (142 mg, 22% over three steps). $^1$H NMR (400 MHz, CDCl$_3$) δ 9.70 (s, 1H), 8.23 (s, 1H), 8.12 (td, J=7.7, 1.9 Hz, 1H), 7.39-7.33 (m, 1H), 7.29-7.19 (s, 1H), 7.16 (dd, J=11.3, 8.3 Hz, 1H), 6.13 (s, 2H), 3.90 (s, 3H), 3.19 (s, 2H), 2.35-2.26 (m, 2H), 2.07-1.89 (m, 4H), 1.78-1.69 (m, 2H). Alkyl NH$_2$ not observed. LCMS (ES+) m/z 443 (M+1).

Example 141

5-amino-N-(5-((4R,5R)-4-amino-5-fluorooxepan-2-yl)-1-methyl-1H-pyrazol-4-yl)-2-(2,6-difluorophenyl)thiazole-4-carboxamide 141

Following the procedure for Example 130 also gave 141 as a white solid (5 mg, 1% over three steps). $^1$H NMR (400 MHz, CDCl$_3$) δ 10.91 (s, 1H), 7.96 (s, 1H), 7.36-7.26 (m, 1H), 7.05-6.96 (m, 2H), 6.22 (s, 2H), 4.89 (t, J=6.1 Hz, 1H), 4.82-4.76 and 4.70-4.64 (m, 1H), 4.13 (dq, J=12.9, 4.2 Hz, 1H), 3.85 (s, 3H), 3.60-3.47 (m, 2H), 2.72-2.62 (m, 1H), 2.33-2.18 (m, 1H), 2.18-1.97 (m, 2H). Alkyl NH$_2$ not observed. LCMS (ES+) m/z 467 (M+1).

Example 142

5-amino-N-[5-(4-amino-5-hydroxy-3,5-dimethyl-tetrahydropyran-2-yl)-1-methyl-pyrazol-4-yl]-2-(2,6-difluorophenyl)thiazole-4-carboxamide 142

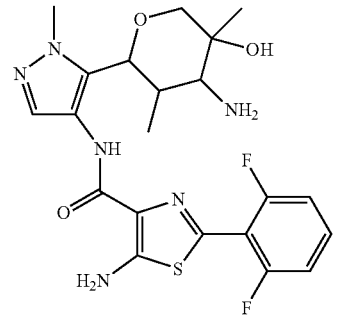 [SMILES: CC1C(c2c(NC(=O)c3nc(-c4c(F)cccc4F)sc3N)cnn2C)OCC(C)(O)C1N]

Following the procedure for Example 112 starting from tert-butyl N-[5-hydroxy-3,5-dimethyl-2-(2-methyl-4-nitro-pyrazol-3-yl)tetrahydropyran-4-yl]carbamate gave, after purification via preparative HPLC, 142 as an off-white solid (15 mg, 10% over three steps). $^1$H NMR (400 MHz, CDCl$_3$) δ 9.84 (s, 1H), 8.22 (s, 1H), 7.31 (ddd, J=8.5, 6.1, 2.3 Hz, 1H), 7.07-6.97 (m, 2H), 6.14 (s, 2H), 5.31 (d, J=3.3 Hz, 1H), 4.00 (d, J=12.1 Hz, 1H), 3.83 (d, J=12.1 Hz, 1H), 3.77 (s, 3H), 3.09 (s, 1H), 1.79-1.72 (m, 1H), 1.13 (s, 3H), 1.11 (d, J=7.6 Hz, 3H). Alkyl NH$_2$ and OH not observed. LCMS (ES+) m/z 479 (M+1).

Example 143

5-amino-N-[5-(6-aminooxepan-3-yl)-1-methyl-pyrazol-4-yl]-2-(2,6-difluorophenyl)thiazole-4-carboxamide 143 tert-Butyl N-[6-[4-[[5-(tert-butoxycarbonylamino)-2-(2,6-difluorophenyl)thiazole-4-carbonyl]amino]-2-methyl-pyrazol-3-yl]oxepan-3-yl]carbamate was stirred with 4N HCl in dioxane (5 mL) and methanol (2 mL) at room temperature for 3 h. The solvent was removed under reduced pressure, basified with saturated NaHCO$_3$, and extracted with ethyl acetate (3×). The combined organic layers were dried over MgSO$_4$ and the solvent removed under reduced pressure and the residue purified by preparative HPLC to afford 143 (24 mg, 32%). 1H NMR (400 MHz, DMSO) δ 9.73, 9.56 (s, 1H), 7.83, 7.78 (s, 1H), 7.62-7.42 (m, 3H), 7.36-7.18 (m, 2H), 3.96-3.71 (m, 6H), 3.59 (ddd, J=71.3, 12.2, 4.1 Hz, 1H), 3.03-2.91 (m, 1H), 2.94-2.79 (m, 1H), 2.10-1.89 (m, 1H), 1.85-1.68 (m, 1H), 1.68-1.56 (m, 1H), 1.54-1.39 (m, 1H). LCMS (ES+) m/z 449 (M+1).

Example 144

5-amino-N-[5-(6-aminooxepan-3-yl)-1-methyl-pyrazol-4-yl]-2-(2,6-difluorophenyl)thiazole-4-carboxamide 144

Chiral separation of 143 by SFC afforded 144 as a mixture of enantiomers. 1H NMR (400 MHz, DMSO) δ 9.56 (s, 1H), 7.78 (s, 1H), 7.60-7.52 (m, 1H), 7.50 (s, 2H), 7.26 (t, J=8.6 Hz, 2H), 3.91-3.79 (m, 2H), 3.77 (s, 3H), 3.68 (dd, J=12.3, 3.8 Hz, 1H), 3.50 (dd, J=12.2, 4.0 Hz, 1H), 2.97 (s, 1H), 2.13-2.00 (m, 1H), 1.81-1.66 (m, 2H), 1.66-1.53 (m, 1H). LCMS (ES+) m/z 449 (M+1).

Example 145

5-amino-N-(5-((5R,6S)-5-amino-6-fluorooxepan-2-yl)-1-methyl-1H-pyrazol-4-yl)-2-(2,6-difluorophenyl)thiazole-4-carboxamide 145

Following the procedure for Example 111 starting from tert-butyl N-(3-fluoro-7-(2-methyl-4-nitro-pyrazol-3-yl)oxepan-4-yl)carbamate (Intermediate 34) gave the formate salt of 145 as a colorless solid (5 mg, 5% over three steps). 1H NMR (400 MHz, DMSO) δ 9.31 (s, 1H), 8.20 (s, 1H), 7.80 (s, 1H), 7.59-7.50 (m, 3H), 7.32-7.22 (m, 2H), 4.93 (dd, J=8.8, 4.2 Hz, 1H), 4.58-4.39 (m, 1H), 3.90 (dd, J=13.2, 3.8 Hz, 1H), 3.78-3.72 (m, 1H), 3.75 (s, 3H), 3.08-2.98 (m, 1H), 2.17-1.91 (m, 3H), 1.88-1.78 (m, 1H). Alkyl NH$_2$ not observed. LCMS (ES+) m/z 467 (M+1).

Example 146

5-amino-2-(2,6-difluorophenyl)-N-(5-((2S,4R)-4-hydroxytetrahydro-2H-pyran-2-yl)-1-methyl-1H-pyrazol-4-yl)thiazole-4-carboxamide 146

Following the procedure for Example 108 starting from 2-(2-methyl-4-nitro-pyrazol-3-yl)tetrahydropyran-4-ol gave, after purification via chiral SFC, 146 (Enantiomer 1) as an off-white solid (4 mg, 2% over two steps). 1H NMR (400 MHz, CDCl$_3$) δ 9.59 (s, 1H), 8.13 (s, 1H), 7.41-7.14 (m, 1H), 7.06-6.96 (m, 2H), 6.15 (s, 2H), 5.13 (dd, J=11.8, 2.5 Hz, 1H), 4.37-4.34 (m, 1H), 4.11-4.06 (m, 2H), 3.82 (s, 3H), 2.18-2.00 (m, 2H), 1.92-1.83 (m, 1H), 1.68-1.60 (m, 1H). OH not observed. LCMS (ES+) m/z 436 (M+1).

Example 147

5-amino-N-[5-(6-aminooxepan-3-yl)-1-methyl-pyrazol-4-yl]-2-(2,6-difluorophenyl)thiazole-4-carboxamide 147

Chiral separation of 143 by SFC afforded 147 as a mixture of enantiomers. 1H NMR (400 MHz, DMSO) δ 9.74 (s, 1H), 7.83 (s, 1H), 7.62-7.51 (m, 1H), 7.47 (s, 2H), 7.27 (t, J=8.5 Hz, 2H), 3.94-3.75 (m, 3H), 3.73 (s, 3H), 3.03-2.93 (m, 1H), 2.93-2.81 (m, 1H), 2.02-1.90 (m, 1H), 1.85-1.71 (m, 1H), 1.71-1.54 (m, 1H), 1.52-1.39 (m, 1H). LCMS (ES+) m/z 449 (M+1).

Example 148

5-Amino-N-[5-[5-amino-6-fluoro-oxepan-2-yl]-1-methyl-pyrazol-4-yl]-2-(2,6-difluorophenyl)thiazole-4-carboxamide 148

Following the procedure for Example 111 starting from tert-Butyl N-[3-fluoro-7-(2-methyl-4-nitro-pyrazol-3-yl)oxepan-4-yl]carbamate (from Intermediate 53) gave 148 as a formate salt as a solid (3 mg, 22%). 1H NMR (400 MHz, d$_6$-DMSO) δ 9.64 (s, 1H), 7.94 (s, 1H), 7.57-7.45 (m, 4H), 7.29-7.20 (m, 3H), 5.21-5.16 (m, 1H), 4.06-4.01 (m, 1H), 3.82-3.69 (m, 4H), 2.96 (s, 1H), 2.21-2.15 (m, 2H), 2.03-1.74 (m, 1H), 1.79-1.55 (m, 1H), 1.42-1.37 (m, 1H). Alkyl NH$_2$ not observed. LCMS (ES+) m/z 467 (M+1).

Example 149

5-amino-2-(2,6-difluorophenyl)-N-(5-((2R,4S)-4-hydroxytetrahydro-2H-pyran-2-yl)-1-methyl-1H-pyrazol-4-yl)thiazole-4-carboxamide 149

Following the procedure for Example 146 also gave 149 (Enantiomer 2) as an off-white solid (4 mg, 2% over two steps). 1H NMR (400 MHz, CDCl$_3$) δ 9.59 (s, 1H), 8.13 (s, 1H), 7.34-7.27 (m, 1H), 7.05-6.96 (m, 2H), 6.15 (s, 2H), 5.14 (d, J=2.5 Hz, 1H), 5.11 (d, J=2.5 Hz, 1H), 4.36 (s, 1H), 4.11-4.07 (m, 2H), 3.82 (s, 3H), 2.62 (s, 1H), 2.19-2.01 (m, 2H), 1.91-1.85 (m, 1H), 1.73-1.63 (m, 1H). OH not observed. LCMS (ES+) m/z 436 (M+1).

Example 150

5-Amino-N-[5-[(2S,5R)-5-amino-4-fluoro-oxepan-2-yl]-1-methyl-pyrazol-4-yl]-2-(2,6-difluorophenyl)thiazole-4-carboxamide 150

Following the procedure for Example 111 starting from tert-Butyl N-[5-fluoro-7-(2-methyl-4-nitro-pyrazol-3-yl)oxepan-4-yl]carbamate (Intermediate 54) gave 150 as a white solid (28 mg, 12% over three steps). 1H NMR (400 MHz, d$_6$-DMSO) δ 9.52 (s, 1H), 7.85 (s, 1H), 7.56-7.48 (m, 3H), 7.27 (t, J=8.8 Hz, 2H), 4.99 (dd, J=9.9, 3.0 Hz, 1H), 4.93-4.76 (m, 1H), 4.08-3.99 (m, 1H), 3.79-3.67 (m, 4H), 3.33-3.20 (m, 1H), 2.31-2.12 (m, 2H), 1.89-1.83 (m, 2H). Alkyl NH$_2$ not observed. LCMS (ES+) m/z 467 (M+1).

Example 151

5-Amino-N-[5-[(2R,5S)-5-amino-4-fluoro-oxepan-2-yl]-1-methyl-pyrazol-4-yl]-2-(2,6-difluorophenyl)thiazole-4-carboxamide 151

Following the procedure for Example 150 also gave 151 as a white solid (24 mg, 17%). 1H NMR (400 MHz, d$_6$-DMSO) δ 9.52 (s, 1H), 7.85 (s, 1H), 7.56-7.48 (m, 3H), 7.27 (t, J=8.8 Hz, 2H), 4.99 (dd, J=9.9, 3.0 Hz, 1H), 4.93-4.76 (m, 1H), 4.08-3.99 (m, 1H), 3.79-3.67 (m, 4H), 3.33-3.20 (m, 1H), 2.31-2.12 (m, 2H), 1.89-1.83 (m, 2H). Alkyl NH$_2$ not observed. LCMS (ES+) m/z 467 (M+1).

Example 152

5-Amino-N-[5-[(5-amino-6,6-difluoro-oxepan-2-yl]-1-methyl-pyrazol-4-yl]-2-(2,6-difluorophenyl)thiazole-4-carboxamide 152

Following the procedure for Example 111 starting from tert-Butyl N-[3,3-difluoro-7-(2-methyl-4-nitro-pyrazol-3-yl) oxepan-4-yl]carbamate (Intermediate 56) gave 152 as a pale brown solid (60 mg, 73%). $^1$H NMR (400 MHz, d$_6$-DMSO) δ 9.28 (s, 1H), 7.81 (s, 1H), 7.57-7.48 (m, 3H), 7.30-7.20 (m, 2H), 5.06-5.00 (m, 1H), 4.19-3.98 (m, 2H), 3.76 (s, 3H), 2.22-2.14 (m, 1H), 1.92-1.76 (m, 4H). 2H partially masked by water peak. LCMS (ES+) m/z 485 (M+1).

Example 153

5-Amino-N-[5-[(2R,5S,6S)-6-amino-5-fluoro-oxepan-2-yl]-1-methyl-pyrazol-4-yl]-2-(2,6-difluorophenyl)thiazole-4-carboxamide 153

Prior to Boc deprotection of Example 150, SFC purification of tert-butyl N-[(3S,4S,7R)-7-[4-[[5-(tert-butoxycarbonylamino)-2-(2,6-difluorophenyl)thiazole-4-carbonyl] amino]-2-methyl-pyrazol-3-yl]-4-fluoro-oxepan-3-yl] carbamate on a chiral stationary phase gave 153 as a golden solid (25 mg, 59%). $^1$H NMR (400 MHz, d$_6$-DMSO) δ 9.34 (s, 1H), 7.84 (s, 1H), 7.62-7.53 (m, 3H), 7.34-7.26 (m, 2H), 4.97 (dd, J=8.8, 4.2 Hz, 1H), 4.61-4.44 (m, 1H), 3.96-3.88 (m, 1H), 3.86-3.68 (m, 4H), 3.10-3.01 (m, 1H), 2.18-1.92 (m, 3H), 1.93-1.78 (m, 1H). Alkyl NH$_2$ not observed. LCMS (ES+) m/z 467 (M+1).

Example 154

5-Amino-N-[5-[(2S,5R,6R)-5-amino-6-methoxy-oxepan-2-yl]-1-methyl-pyrazol-4-yl]-2-(2,6-difluorophenyl)thiazole-4-carboxamide 154

Following the procedure for Example 111 starting from tert-Butyl N-[(3R,4R,7S)-3-methoxy-7-(2-methyl-4-nitro-pyrazol-3-yl)oxepan-4-yl]carbamate (Intermediate 93) gave 154 as the hydrochloride salt as a beige solid (33 mg, 89%). $^1$H NMR (400 MHz, d$_6$-DMSO) δ 9.41 (s, 1H), 8.06 (s, 3H), 7.84 (s, 1H), 7.60-7.48 (m, 3H), 7.38-7.29 (m, 2H), 4.97-4.92 (m, 1H), 4.15 (dd, J=13.4, 4.7 Hz, 1H), 3.93 (dd, J=13.3, 5.4 Hz, 1H), 3.86-3.82 (m, 1H), 3.80-3.62 (m, 4H), 3.29 (s, 3H), 2.13-1.98 (m, 2H), 1.86-1.73 (m, 2H). LCMS (ES+) m/z 479 (M+1).

Example 155

5-Amino-N-[5-[5-(aminomethyl)tetrahydrofuran-2-yl]-1-methyl-pyrazol-4-yl]-2-(2,6-difluorophenyl) thiazole-4-carboxamide 155

Following the procedure for Example 111 starting from tert-Butyl ((5-(1-methyl-4-nitro-1H-pyrazol-5-yl)tetrahydrofuran-2-yl)methyl)carbamate (Intermediate 62) gave 155 as a cream solid (19 mg, 90%). $^1$H NMR (400 MHz, d$_4$-MeOD) δ 7.95 (s, 1H), 7.52-7.45 (m, 1H), 7.20-7.14 (m, 2H), 5.33-5.29 (m, 1H), 4.50-4.47 (m, 1H), 3.85 (s, 3H), 2.96-2.87 (m, 2H), 2.54-2.49 (m, 1H), 2.31-2.25 (m, 1H), 2.08-2.00 (m, 1H), 1.91-1.86 (m, 1H). LCMS (ES+) m/z 435 (M+1). Exchangeable protons not observed.

Example 156

5-amino-N-(5-((2S,5R,6S)-5-amino-6-fluorooxepan-2-yl)-1-methyl-1H-pyrazol-4-yl)-2-(2-fluoro-3-(trifluoromethyl)phenyl)thiazole-4-carboxamide 156

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl] carbamoyl]thiazol-5-yl]carbamate (Intermediate 95), and replacing 3,6-dihydro-2H-pyran-4-boronic acid pinacol ester with (2-fluoro-3-(trifluoromethyl)phenyl)boronic acid gave 156. 1H NMR (400 MHz, DMSO-d6) δ 9.37 (s, 1H), 8.56 (t, J=7.7 Hz, 1H), 7.85 (s, 1H), 7.79 (t, J=7.3 Hz, 1H), 7.57 (s, 2H), 7.49 (t, J=7.9 Hz, 1H), 4.91-4.82 (m, 1H), 4.67-4.49 (m, 1H), 4.42-4.26 (m, 1H), 4.21-4.00 (m, 1H), 3.77 (s, 3H), 2.13-2.01 (m, 1H), 1.90-1.67 (m, 4H). LCMS (ES+) m/z 517 (M+1).

Example 157

5-amino-N-(5-((2S,5R,6S)-5-amino-6-fluorooxepan-2-yl)-1-methyl-1H-pyrazol-4-yl)-2-(2-(trifluoromethoxy)phenyl)thiazole-4-carboxamide 157

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl] carbamoyl]thiazol-5-yl]carbamate (Intermediate 95), and replacing 3,6-dihydro-2H-pyran-4-boronic acid pinacol ester with (2-(trifluoromethoxy)phenyl)boronic acid gave 157. 1H NMR (400 MHz, DMSO-d6) δ 9.33 (s, 1H), 8.40 (dd, J=7.9, 2.3 Hz, 1H), 7.84 (s, 1H), 7.54-7.44 (m, 5H), 4.89-4.80 (m, 1H), 4.69-4.53 (m, 1H), 4.41-4.28 (m, 1H), 4.21-4.02 (m, 1H), 3.77 (s, 3H), 3.48-3.38 (m, 1H), 2.13-2.02 (m, 1H), 1.91-1.72 (m, 3H). LCMS (ES+) m/z 515 (M+1).

Example 158

5-Amino-N-[5-[4-aminotetrahydropyran-2-yl]-1-methyl-pyrazol-4-yl]-2-(2,6-difluorophenyl)thiazole-4-carboxamide 158

Following the procedure for Example 111 starting from tert-Butyl ((5-(1-methyl-4-nitro-1H-pyrazol-5-yl)tetrahydrofuran-2-yl)methyl)carbamate (Intermediate 89) gave 158 as a white solid (11 mg, 5% over two steps). $^1$H NMR (400 MHz, CDCl$_3$) δ 9.49 (s, 1H), 8.12 (s, 1H), 7.34-7.27 (m, 1H), 7.06-6.96 (m, 2H), 6.16 (s, 2H), 4.62 (dd, J=11.6, 2.3 Hz, 1H), 4.31 (dd, J=11.7, 4.5 Hz, 1H), 3.82 (s, 3H), 3.59 (td, J=12.0, 2.1 Hz, 1H), 3.06-2.96 (m, 1H), 2.12-1.98 (m, 1H), 1.89 (ddd, J=13.1, 4.4, 2.2 Hz, 1H), 1.71-1.46 (m, 2H). Alkyl NH$_2$ not observed. LCMS (ES+) m/z 435 (M+1).

Example 159

5-Amino-N-[5-[(2R,4S)-4-aminotetrahydropyran-2-yl]-1-methyl-pyrazol-4-yl]-2-(2,6-difluorophenyl) thiazole-4-carboxamide 159

Purification of Example 158 via chiral preparative HPLC gave 159 as the first eluting isomer as the formate salt as a white solid (5 mg, 13%). $^1$H NMR (400 MHz, d$_6$-DMSO) 9.53 (s, 1H), 8.38 (s, 1H), 7.90 (s, 1H), 7.55-7.46 (m, 3H), 7.32-7.23 (m, 2H), 4.81 (dd, J=11.4, 2.3 Hz, 1H), 4.12 (dd, J=11.7, 4.4 Hz, 1H), 3.76 (s, 3H), 3.62-3.50 (m, 1H), 3.19-3.05 (m, 1H), 2.05 (d, J=12.6 Hz, 1H), 1.84 (d, J=12.8 Hz, 1H), 1.51 (qd, J=12.2, 4.6 Hz, 1H), 1.39 (q, J=11.9 Hz, 1H). Alkyl $NH_2$ not observed. LCMS (ES+) m/z 435 (M+1).

Example 160

5-Amino-N-[5-[(2S,4R)-4-aminotetrahydropyran-2-yl]-1-methyl-pyrazol-4-yl]-2-(2,6-difluorophenyl)thiazole-4-carboxamide 160

Following the procedure for Example 159 also gave 160 as the second eluting isomer as the formate salt as a white solid (5 mg, 13%). $^1$H NMR (400 MHz, $d_6$-DMSO) δ 9.53 (s, 1H), 8.38 (s, 1H), 7.90 (s, 1H), 7.55-7.46 (m, 3H), 7.32-7.23 (m, 2H), 4.81 (dd, J=11.4, 2.3 Hz, 1H), 4.12 (dd, J=11.7, 4.4 Hz, 1H), 3.76 (s, 3H), 3.62-3.50 (m, 1H), 3.19-3.05 (m, 1H), 2.05 (d, J=12.6 Hz, 1H), 1.84 (d, J=12.8 Hz, 1H), 1.51 (qd, J=12.2, 4.6 Hz, 1H), 1.39 (q, J=11.9 Hz, 1H). Alkyl $NH_2$ not observed. LCMS (ES+) m/z 435 (M+1).

Example 161

5-Amino-N-[5-[2-amino-8-oxabicyclo[3.2.1]octan-5-yl]-1-methyl-pyrazol-4-yl]-2-(3-fluoro-4-pyridyl)thiazole-4-carboxamide 161

A solution of tert-butyl N-[2-bromo-4-[[5-[2-(tert-butoxycarbonylamino)-8-oxabicyclo[3.2.1]octan-5-yl]-1-methyl-pyrazol-4-yl]carbamoyl]thiazol-5-yl]carbamate (110 mg, 0.175 mmol, Intermediate 65) in dry dioxane (15 mL) was treated with 3-fluoro-4-(tributylstannyl)-pyridine (0.053 mL, 0.246 mmol), lithium chloride (22 mg, 0.526 mmol), copper (I) iodide (10 mg, 0.053 mmol) and tetrakis(triphenylphosphine)palladium(0) (12 mg, 0.011 mmol). Nitrogen gas was bubbled through the mixture for 10 min and the mixture was heated at 120° C. under microwave irradiation for 90 min. Water (20 mL) was added and the mixture was extracted with EtOAc (60 mL). The organic layer was washed with brine (20 mL), separated, dried over $MgSO_4$, and concentrated under reduced pressure. Purification via silica gel chromatography (75% EtOAc/isohexane) gave the desired intermediate as a peach solid (59 mg). This solid was suspended in MeOH (3 mL), treated with a solution of HCl in dioxane (4 M, 2.2 mL, 9.18 mmol) and stirred at room temperature for 18 hr. More HCl in dioxane (4 M, 1.1 mL, 4.59 mmol) was added and the mixture was stirred for 6 hr. The solvent was removed under reduced pressure and the residue was passed through an SCX column washing with MeOH and eluting with 3 N $NH_3$ in MeOH. Further purification via silica gel chromatography (5% MeOH/$CH_2Cl_2$ with 1% 7 N $NH_3$ in MeOH) gave 161 as a yellow solid (26 mg, 32%). $^1$H NMR (400 MHz, $CDCl_3$) δ 10.26 (s, 1H), 8.57 (d, J=2.6 Hz, 1H), 8.45 (d, J=5.1 Hz, 1H), 8.24 (s, 1H), 8.03-7.97 (m, 1H), 6.28 (s, 2H), 4.51-4.44 (s, 1H), 3.86 (s, 3H), 3.31-3.23 (m, 1H), 2.40-2.33 (m, 1H), 2.21-2.05 (m, 3H), 1.98-1.86 (m, 3H), 1.67-1.29 (m, 3H). LCMS (ES+) m/z 444 (M+1).

Example 162

5-Amino-2-(2,6-difluorophenyl)-N-[5-[5-ethyl-5-(hydroxymethyl)-1,3-dioxan-2-yl]-1-methyl-pyrazol-4-yl]thiazole-4-carboxamide 162

Following the procedure for Example 111 starting from (5-Ethyl-2-(1-methyl-4-nitro-1H-pyrazol-5-yl)-1,3-dioxan-5-yl)methanol (trans isomer, Intermediate 66) gave 162 as a colourless solid (25 mg, 12% over two steps). $^1$H NMR (400 MHz, $CDCl_3$) δ 9.76 (s, 1H), 8.24 (s, 1H), 7.32-7.30 (m, 1H), 7.04-6.97 (m, 2H), 6.15 (s, 2H), 5.72 (s, 1H), 4.07 (d, J=11.3 Hz, 2H), 3.91 (d, J=11.3 Hz, 2H), 3.85 (s, 3H), 3.44 (d, J=4.9 Hz, 2H), 1.81 (q, J=7.6 Hz, 1H), 1.27 (t, J=5.0 Hz, 2H), 0.83 (t, J=7.6 Hz, 3H). LCMS (ES+) m/z 480 (M+1).

Example 163

5-Amino-2-(2,6-difluorophenyl)-N-[5-[5-ethyl-5-(hydroxymethyl)-1,3-dioxan-2-yl]-1-methyl-pyrazol-4-yl]thiazole-4-carboxamide 163

Following the procedure for Example 111 starting from (5-Ethyl-2-(1-methyl-4-nitro-1H-pyrazol-5-yl)-1,3-dioxan-5-yl)methanol (cis isomer, Intermediate 67) gave 163 as a colourless solid (42 mg, 10% over two steps). $^1$H NMR (400 MHz, $CDCl_3$) δ 9.78 (s, 1H), 8.24 (s, 1H), 7.36-7.28 (m, 1H), 7.07-6.97 (m, 2H), 6.18 (s, 2H), 5.73 (s, 1H), 4.19 (d, J=11.5 Hz, 2H), 3.93 (d, J=5.7 Hz, 2H), 3.84 (s, 3H), 3.66 (d, J=11.6 Hz, 2H), 1.73 (t, J=5.8 Hz, 1H), 1.28 (q, J=7.6 Hz, 2H), 0.92-0.83 (m, 3H). LCMS (ES+) m/z 480 (M+1).

Example 164

5-Amino-2-(2,6-difluorophenyl)-N-[5-[5-(hydroxymethyl)-1,3-dioxan-2-yl]-1-methyl-pyrazol-4-yl]thiazole-4-carboxamide 164

Following the procedure for Example 111 starting from (2-(1-Methyl-4-nitro-1H-pyrazol-5-yl)-1,3-dioxan-5-yl)methanol (trans isomer, Intermediate 68) gave 164 as a 91/9 ratio of trans/cis isomers as a colourless solid (79 mg, 19% over two steps). $^1$H NMR (400 MHz, $d_6$-DMSO) δ 9.73 (s, 1H), 7.99 (s, 1H), 7.54-7.46 (m, 3H), 7.32-7.22 (m, 2H), 5.89 (s, 1H), 4.67 (t, J=5.2 Hz, 1H), 4.21 (dd, J=11.2, 4.6 Hz, 2H), 3.80-3.70 (m, 5H), 3.35-3.30 (m, 2H), 2.28-2.16 (m, 1H). LCMS (ES+) m/z 452 (M+1).

Example 165

5-Amino-2-(2,6-difluorophenyl)-N-[5-[5-(hydroxymethyl)-1,3-dioxan-2-yl]-1-methyl-pyrazol-4-yl]thiazole-4-carboxamide 165

Following the procedure for Example 111 starting from (2-(1-Methyl-4-nitro-1H-pyrazol-5-yl)-1,3-dioxan-5-yl)methanol (cis isomer, Intermediate 69) gave 164 as a 86/14 ratio of cis/trans isomers of 48 as a colourless solid (45 mg, 9% over two steps). $^1$H NMR (400 MHz, $d_6$-DMSO) δ 9.63 (s, 1H), 7.98 (s, 1H), 7.56-7.47 (m, 3H), 7.31-7.22 (m, 2H), 5.97 (s, 1H), 4.62 (t, J=5.1 Hz, 1H), 4.12 (s, 4H), 3.90-3.60 (m, 3H), 3.67 (dd, J=7.8, 5.1 Hz, 2H), 1.57 (t, J=7.8 Hz, 1H). LCMS (ES+) m/z 452 (M+1).

Example 166

5-Amino-2-(2,6-difluorophenyl)-N-[5-[5-(hydroxymethyl)-5-methyl-1,3-dioxan-2-yl]-1-methyl-pyrazol-4-yl]thiazole-4-carboxamide 166

Following the procedure for Example 111 starting from (5-Methyl-2-(1-methyl-4-nitro-1H-pyrazol-5-yl)-1,3-dioxan-5-yl)methanol (cis isomer, Intermediate 71) gave 166 as a colourless solid (83 mg, 10% over two steps). $^1$H NMR (400 MHz, $d_6$-DMSO) δ 9.65 (s, 1H), 7.98 (s, 1H), 7.57-7.46 (m, 3H), 7.33-7.25 (m, 2H), 5.90 (s, 1H), 4.61 (t, J=5.2 Hz, 1H), 3.96 (d, J=11.2 Hz, 2H), 3.77 (s, 3H), 3.68 (d, J=11.2 Hz, 2H), 3.53 (d, J=5.2 Hz, 2H), 0.70 (s, 3H). LCMS (ES+) m/z 466 (M+1).

Example 167

5-Amino-N-[5-[5-(aminomethyl)-1,3-dioxan-2-yl]-1-methyl-pyrazol-4-yl]-2-(2,6-difluorophenyl)thiazole-4-carboxamide 167

To a solution of (2-(1-methyl-4-nitro-1H-pyrazol-5-yl)-1,3-dioxan-5-yl)methanol (360 mg, 1.48 mmol, intermediate 68) in dry THF (12 mL) was added polymer supported triphenylphosphine (~3 mmol/g, 1.5 g, 4.44 mmol) and phthalamide (326 mg, 2.22 mmol) followed by diisopropylazodicarboxylate (450 mg, 2.22 mmol). The reaction mixture was stirred at room temperature for 18 hr then heated at 35° C. for 4 hr. The reaction mixture was filtered and the filtrate diluted with DCM (50 mL) and washed with a saturated aqueous $NaHCO_3$ (25 mL). The organic layer was washed with water (25 mL) and brine (25 mL), separated, dried over $Na_2SO_4$ and concentrated under reduced pressure. Purification via silica gel column chromatography (0-100% EtOAc/isohexane) gave 2-((2-(1-methyl-4-nitro-1H-pyrazol-5-yl)-1,3-dioxan-5-yl)methyl)isoindoline-1,3-dione as a colourless solid (226 mg) contaminated with diisopropyl azodicarboxylate byproduct. To a suspension of this solid (165 mg, 0.44 mmol) in MeOH (150 mL) and THF (20 mL) was added ammonium formate (300 mg, mmol) and 10% Pd/C (300 mg). The mixture was heated at reflux for 2 hr. The mixture was quickly filtered whilst hot and the cake washed with DCM (50 mL) and EtOAC (50 mL). The filtrate was concentrated under reduced pressure and the crude residue was dissolved in IPA (5 mL) and 5-amino-2-(2,6-difluorophenyl)thiazole-4-carboxylic acid (134 mg, 0.46 mmol) and DIPEA (0.31 mL, 1.76 mmol) were then added. Propylphosphonic anhydride solution (50% wt in EtOAc, 0.33 mL, 0.48 mmol) was added dropwise and the reaction mixture was stirred at room temperature for 16 hr. The mixture was concentrated under reduced pressure and purified via silica gel chromatography (0-5% 7 N $NH_3$ in MeOH/DCM) to give an oil. This oil was dissolved in EtOH (1 mL), hydrazine (1 mL) was added and the mixture heated at reflux for 16 hr. The solvents were removed under reduced pressure and the residue was dissolved in MeOH and passed through an SCX column eluting with 0-5% 7 N $NH_3$ in MeOH/DCM. Purification via preparative HPLC gave 167 as a colourless solid (4 mg, 1% over four steps). $^1$H NMR (400 MHz, $CDCl_3$) δ 9.82 (s, 1H), 8.25 (s, 1H), 7.36-7.29 (m, 1H), 7.07-6.99 (m, 2H), 6.18 (s, 2H), 5.74 (s, 1H), 4.46 (dd, J=11.4, 4.5 Hz, 2H), 3.88 (s, 3H), 3.67 (t, J=11.3 Hz, 2H), 2.64 (d, J=6.7 Hz, 2H), 2.41-2.32 (m, 1H). Alkyl $NH_2$ not observed. LCMS (ES+) m/z 451 (M+1).

Example 168

5-Amino-N-[5-[(2S,5R)-5-amino-6,6-difluoro-oxepan-2-yl]-1-methyl-pyrazol-4-yl]-2-(2,6-difluorophenyl)thiazole-4-carboxamide 168

Following the procedure for Example 111 starting from tert-Butyl N-[(4R,7S)-3,3-difluoro-7-(2-methyl-4-nitropyrazol-3-yl)oxepan-4-yl]carbamate (intermediate 72) gave 168 as the hydrochloride salt as a pale brown solid (57 mg, 79% over three steps). $^1$H NMR (400 MHz, $d_6$-DMSO) δ 9.22 (s, 1H), 8.78-8.64 (m, 3H), 7.79 (s, 1H), 7.59-7.48 (m, 2H), 7.34-7.25 (m, 3H), 5.10-5.04 (m, 1H), 4.53-4.07 (m, 2H), 3.97-3.77 (m, 1H), 3.79 (s, 3H), 2.26-1.94 (m, 4H). LCMS (ES+) m/z 485 (M+1).

Example 169

5-Amino-N-[5-[(2R,5S)-5-amino-6,6-difluoro-oxepan-2-yl]-1-methyl-pyrazol-4-yl]-2-(2,6-difluorophenyl)thiazole-4-carboxamide 169

Following the procedure for Example 111 starting from tert-Butyl N-[(4S,7R)-3,3-difluoro-7-(2-methyl-4-nitropyrazol-3-yl)oxepan-4-yl]carbamate (intermediate 73) gave 168 as the hydrochloride salt as a pale brown solid (13 mg, 16% over three steps). $^1$H NMR (400 MHz, $d_6$-DMSO) δ 9.22 (s, 1H), 8.69 (s, 3H), 7.79 (s, 1H), 7.59-7.48 (m, 2H), 7.34-7.25 (m, 3H), 5.06 (d, J=10.9 Hz, 1H), 4.48-4.36 (m, 1H), 4.47-3.72 (m, 2H), 3.79 (s, 3H), 2.27-2.17 (m, 1H), 2.14-1.93 (m, 3H). LCMS (ES+) m/z 485 (M+1).

Example 170

5-Amino-N-[5-[4-amino-5-fluoro-oxepan-2-yl]-1-methyl-pyrazol-4-yl]-2-(2,6-difluorophenyl)thiazole-4-carboxamide 170

Following the procedure for Example 111 starting from tert-Butyl N-(5-fluoro-2-(2-methyl-4-nitro-pyrazol-3-yl)oxepan-4-yl)carbamate (intermediate 29) gave 170 as a pink solid (8 mg, 100%). $^1$H NMR (400 MHz, $d_6$-DMSO) δ 9.71 (s, 1H), 7.96 (s, 1H), 7.57-7.49 (m, 3H), 7.31-7.22 (m, 2H), 5.22 (t, J=4.5 Hz, 1H), 4.46-4.28 (m, 1H), 3.97-3.90 (m, 1H), 3.75-3.60 (m, 4H), 3.06 (q, J=8.4 Hz, 1H), 2.16-1.99 (m, 5H), 1.85 (d, J=15.6 Hz, 1H). LCMS (ES+) m/z 467 (M+1).

Example 171

5-Amino-N-[5-[(2R,5R)-5-(aminomethyl)tetrahydrofuran-2-yl]-1-methyl-pyrazol-4-yl]-2-(2,6-difluorophenyl)thiazole-4-carboxamide 171

Purification of 5-Amino-N-[5-[5-(aminomethyl)tetrahydrofuran-2-yl]-1-methyl-pyrazol-4-yl]-2-(2,6-difluorophenyl)thiazole-4-carboxamide Example 157) by chiral SFC gave 171 as an off-white solid (34 mg). $^1$H NMR (400 MHz, $d_6$-DMSO) δ 9.40 (s, 1H), 7.88 (s, 1H), 7.57-7.50 (m, 3H), 7.31-7.25 (m, 2H), 5.23-5.20 (m, 1H), 4.30-4.27 (m, 1H), 3.75 (s, 3H), 2.71-2.70 (m, 2H), 2.42-2.41 (m, 1H), 2.10-2.07 (m, 1H), 1.87-1.79 (m, 2H). Alkyl $NH_2$ not observed. LCMS (ES+) m/z 435 (M+1).

Example 172

5-Amino-N-[5-[(2S,5S)-5-(aminomethyl)tetrahydrofuran-2-yl]-1-methyl-pyrazol-4-yl]-2-(2,6-difluorophenyl)thiazole-4-carboxamide 172

Following the procedure for Example 171 also gave 172 as an off-white solid (33 mg). $^1$H NMR (400 MHz, $d_6$-DMSO) δ 9.42 (s, 1H), 7.88 (s, 1H), 7.57-7.50 (m, 3H), 7.31-7.25 (m, 2H), 5.24-5.20 (m, 1H), 4.29-4.25 (m, 1H), 3.74 (s, 3H), 2.69-2.68 (m, 2H), 2.42-2.41 (m, 1H), 2.08-2.04 (m, 1H), 1.88-1.80 (m, 2H). Alkyl $NH_2$ not observed. LCMS (ES+) m/z 435 (M+1).

Example 173

5-Amino-N-[5-[5-(aminomethyl)-5-ethyl-1,3-dioxan-2-yl]-1-methyl-pyrazol-4-yl]-2-(2,6-difluorophenyl)thiazole-4-carboxamide 173

To a solution of 2-((2-(1-methyl-4-nitro-1H-pyrazol-5-yl)-1,3-dioxan-5-yl)methyl)isoindoline-1,3-dione (317 mg, 0.793 mmol, intermediate 75) in MeOH (10 mL) and THF (10 mL) was added ammonium formate (300 mg, 4.76 mmol) and 10% Pd/C (300 mg, 0.28 mmol) and the mixture was heated at reflux for 2 hr. The mixture was quickly filtered whilst hot and the cake washed with DCM (50 mL) and EtOAC (50 mL). The solvent was removed under reduced pressure and the crude residue was dissolved in EtOAc (10 mL) and 5-amino-2-(2,6-difluorophenyl)thiazole-4-carboxylic acid (170 mg, 0.66 mmol) and N-methylmorpholine (0.4 mL, 1.89 mmol) were added. Propylphosphonic anhydride solution (50% wt in EtOAc, 0.32 mL, 0.695 mmol) was added dropwise and the reaction mixture was stirred at room temperature for 16 hr. The solvent was removed under reduced pressure and the residue purified via silica gel chromatography (0-5% 7 N $NH_3$ in MeOH/DCM) to give a colourless solid. To a solution of this solid in EtOH (2 mL) was added hydrazine hydrate (64-65% solution, 2 mL) and the mixture was heated at 70° C. for 16 hr. After concentration under reduced pressure, MeOH was added to the residue and the solids filtered off. The filtrate was concentrated under reduced pressure. Purification via K—NH column (0-5% 7 N $NH_3$ in MeOH/DCM) followed by preparative HPLC gave 173 as a colourless solid (18 mg, 17% over three steps). $^1$H NMR (400 MHz, $CDCl_3$) δ 9.78 (s, 1H), 8.26 (s, 1H), 7.36-7.29 (m, 1H), 7.06-6.99 (m, 2H), 6.18 (s, 2H), 5.73 (s, 1H), 4.11 (d, J=11.2 Hz, 2H), 3.87 (s, 3H), 3.78 (d, J=11.2 Hz, 2H), 2.53 (s, 2H), 1.83 (q, J=7.6 Hz, 2H), 0.84 (t, J=7.6 Hz, 3H). Alkyl $NH_2$ not observed. LCMS (ES+) m/z 479 (M+1).

Example 174

5-Amino-N-[5-[(2S,5R,6S)-5-amino-6-(trideuteriomethoxy)oxepan-2-yl]-1-methyl-pyrazol-4-yl]-2-(2,6-difluorophenyl)thiazole-4-carboxamide 174

Following the procedure for Example 111 starting from tert-Butyl N-[(3S,4R,7S)-7-(2-methyl-4-nitro-pyrazol-3-yl)-3-(trideuteriomethoxy)oxepan-4-yl]carbamate (intermediate 78) gave 170 as a pale brown solid (32 mg, 79% over three steps). $^1$H NMR (400 MHz, $d_6$-DMSO) δ 9.22 (s, 1H), 8.34 (s, 1H), 7.77 (s, 1H), 7.58-7.49 (m, 2H), 7.33-7.24 (m, 2H), 4.82-4.77 (m, 1H), 4.08 (dd, J=13.9, 3.1 Hz, 1H), 3.86 (dd, J=13.9, 3.7 Hz, 1H), 3.76 (s, 3H), 3.20-3.15 (m, 1H), 3.12-3.04 (m, 1H), 2.09-2.01 (m, 1H), 1.85-1.66 (m, 3H). Alkyl $NH_2$ not observed. LCMS (ES+) m/z 482 (M+1).

Example 175

5-Amino-N-[5-[5-(aminomethyl)-5-methyl-1,3-dioxan-2-yl]-1-methyl-pyrazol-4-yl]-2-(2,6-difluorophenyl)thiazole-4-carboxamide 175

2,2,2-trifluoro-N-((5-methyl-2-(1-methyl-4-nitro-1H-pyrazol-5-yl)-1,3-dioxan-5-yl)methyl)acetamide (171 mg, 0.49 mmol, intermediate 84) was dissolved in MeOH (30 mL) and ammonium formate (170 mg, 2.69 mmol) and 10% Pd/C (140 mg, 0.13 mmol) were added. The mixture was heated at reflux for 18 hr before being cooled to room temperature. The suspension was filtered, the cake washed with EtOAc (100 mL) and the filtrate concentrated under reduced pressure. The crude residue was dissolved in EtOAc (10 mL) and 5-amino-2-(2,6-difluorophenyl)thiazole-4-carboxylic acid (131 mg, 0.51 mmol) was then added followed by N-methylmorpholine (0.11 mL, 1.46 mmol). Propylphosphonic anhydride solution (50% wt in EtOAc, 338 mg, 0.53 mmol) was added dropwise and the reaction mixture was stirred at room temperature for 16 hr. The reaction mixture was concentrated under reduced pressure and purified via silica gel chromatography (0-5% 7 N $NH_3$ in MeOH/DCM) to give 5-amino-2-(2,6-difluorophenyl)-N-(1-methyl-5-(5-methyl-5-((2,2,2-trifluoroacetamido)methyl)-1,3-dioxan-2-yl)-1H-pyrazol-4-yl)thiazole-4-carboxamide as a white solid (102 mg, 18% over three steps). A mixture of 5-amino-2-(2,6-difluorophenyl)-N-(1-methyl-5-(5-methyl-5-((2,2,2-trifluoroacetamido)methyl)-1,3-dioxan-2-yl)-1H-pyrazol-4-yl)thiazole-4-carboxamide (101 mg, 0.18 mmol) in MeOH (6 mL) and aqueous saturated $K_2CO_3$ solution (0.6 mL) was heated in a microwave at 100° C. for 1 hr. The reaction mixture was cooled to room temperature, concentrated under reduced pressure and purified via silica gel chromatography (0-20% MeOH/DCM) to give 175 as a white solid (4 mg, 5%). $^1$H NMR (400 MHz, $CDCl_3$) δ 9.80 (s, 1H), 8.24 (s, 1H), 7.34-7.27 (m, 1H), 7.05-6.97 (m, 2H), 6.15 (s, 2H), 5.70 (s, 1H), 3.98-3.91 (m, 2H), 3.86 (s, 3H), 3.80 (d, J=11.0 Hz, 2H), 2.54 (s, 2H), 1.26 (s, 3H). Alkyl $NH_2$ not observed. LCMS (ES+) m/z 465 (M+1).

Example 176

5-Amino-N-[5-[(2R,5S,6R)-5-amino-6-fluoro-oxepan-2-yl]-1-methyl-pyrazol-4-yl]-2-(2,6-difluorophenyl)thiazole-4-carboxamide 176

Following the procedure for Example 111 starting from tert-butyl N-[(3S,4R,7S)-3-fluoro-7-(2-methyl-4-nitro-pyrazol-3-yl)oxepan-4-yl]carbamate (intermediate 81) gave 176 as a beige solid (17 mg, 11% over three steps). $^1$H NMR (400 MHz, $d_6$-DMSO) δ 9.29 (s, 1H), 7.80 (s, 1H), 7.56-7.46 (m, 3H), 7.29-7.19 (m, 2H), 4.78 (dd, J=10.90, 3.48 Hz, 1H), 4.44-4.26 (m, 1H), 4.21-3.91 (m, 2H), 3.76 (s, 3H), 3.40-3.15 (m, 1H), 2.08-2.00 (m, 1H), 1.88-1.60 (m, 3H). Alkyl $NH_2$ not observed. LCMS (ES+) m/z 467 (M+1).

Example 177

5-Amino-N-[5-[(2S,5R,6S)-5-amino-6-fluoro-oxepan-2-yl]-1-methyl-pyrazol-4-yl]-2-(2,6-difluorophenyl)thiazole-4-carboxamide 177

Following the procedure for Example 111 starting from tert-butyl N-[(3R,4S,7R)-3-fluoro-7-(2-methyl-4-nitro-pyrazol-3-yl)oxepan-4-yl]carbamate (intermediate 80) gave 177 as a beige solid (37 mg, 19% over three steps). $^1$H NMR (400 MHz, $d_6$-DMSO) δ 9.29 (s, 1H), 7.80 (s, 1H), 7.56-7.46 (m, 3H), 7.29-7.19 (m, 2H), 4.78 (dd, J=10.87, 3.53 Hz, 1H), 4.44-4.26 (m, 1H), 4.20-3.89 (m, 2H), 3.77 (s, 3H), 3.40-3.15 (m, 1H), 2.10-1.60 (m, 6H). LCMS (ES+) m/z 467 (M+1).

Example 178

5-Amino-N-[5-[5-(aminomethyl)-5-methyl-1,3-dioxan-2-yl]-1-methyl-pyrazol-4-yl]-2-(2,6-difluorophenyl)thiazole-4-carboxamide 178

To a solution of 2,2,2-trifluoro-N-((5-methyl-2-(1-methyl-4-nitro-1H-pyrazol-5-yl)-1,3-dioxan-5-yl)methyl)acetamide (410 mg, 1.16 mmol, intermediate 83) in MeOH (20 mL) was added ammonium formate (400 mg, 6.34 mmol) and 10% Pd/C (400 mg). The mixture was heated at reflux for 5 hr then cooled to room temperature. The suspension was filtered and the filtrate concentrated under reduced pressure. The residue was dissolved in IPA (10 mL) and 5-amino-2-(2,6-difluorophenyl)thiazole-4-carboxylic acid (312 mg, 1.22 mmol) and DIPEA (0.62 mL, 3.47 mmol) were then added. Propylphosphonic anhydride solution (50% wt in EtOAc, 0.61 mL, 1.28 mmol) was added dropwise and the reaction mixture was stirred at room temperature for 16 hr. Saturated aqueous NaHCO$_3$ solution (10 mL) and DCM (20 mL) were added. The organic layer was washed with 1 N HCl (10 mL), separated, dried over MgSO$_4$ and concentrated under reduced pressure. Purification via silica gel chromatography (0-5% 7 N NH$_3$ in MeOH/DCM) gave 5-amino-2-(2,6-difluorophenyl)-N-(1-methyl-5-(5-methyl-5-((2,2,2-trifluoroacetamido)methyl)-1,3-dioxan-2-yl)-1H-pyrazol-4-yl)thiazole-4-carboxamide as an oil. To a solution of this oil in IPA (2 mL), THF (2 mL) and water (1 mL) was added K$_2$CO$_3$ (31 mg, 0.22 mmol) and the mixture heated at 50° C. for 18 hr. More K$_2$CO$_3$ (300 mg, 2.2 mmol) was added and the mixture heated in a microwave at 120° C. for 2.5 hr. The reaction mixture was cooled to room temperature, filtered washing with EtOAc (20 mL) and the filtrate concentrated under reduced pressure. The residue was passed through an SCX column eluting with 0-5% 7 N NH$_3$ in MeOH/DCM) and purified by preparative HPLC to give 178 as a colourless solid (1 mg, 0.2% over three steps). $^1$H NMR (400 MHz, d$_4$-MeOD) δ 8.45 (s, 2H), 8.01 (s, 1H), 7.39-7.32 (m, 1H), 7.06 (t, J=8.8 Hz, 2H), 5.82 (s, 1H), 3.98 (d, J=11.6 Hz, 2H), 3.74-3.65 (m, 5H), 2.86 (s, 2H), 0.69 (s, 3H). LCMS (ES+) m/z 465 (M+1).

Example 179

5-Amino-N-[5-[5-amino-4,4-difluoro-5,6-dimethyl-tetrahydropyran-2-yl]-1-methyl-pyrazol-4-yl]-2-(2,6-difluorophenyl)thiazole-4-carboxamide 179

A solution of 5-(5-azido-4,4-difluoro-5,6-dimethyltetrahydro-2H-pyran-2-yl)-1-methyl-4-nitro-1H-pyrazole (152 mg, 0.481 mmol, intermediate 87) in THF/water (5 mL/0.5 mL) was treated with triphenylphosphine (190 mg, 0.72 mmol) and the mixture was heated at 65° C. behind a blast shield for 18 hr. The mixture was concentrated under reduced pressure to give a colourless oil (74 mg). A solution of this oil (74 mg, 0.255 mmol) in MeOH (20 mL) was passed through the H-Cube® (full H$_2$, 85° C., flow rate: 1 mL/min, 30 mm RaNi cartridge). The solvent was removed under reduced pressure and the residue dissolved in EtOAc (1 mL). 5-Amino-2-(2,6-difluorophenyl)thiazole-4-carboxylic acid (69 mg, 0.268 mmol) and N-methylmorpholine (0.08 mL, 0.765 mmol) were added. Propylphosphonic anhydride solution (50% wt in EtOAc, 0.1 mL, 0.281 mmol) was added dropwise and the reaction mixture was stirred at room temperature for 16 hr. The reaction mixture was concentrated under reduced pressure and purified via silica gel chromatography (0-5% 7 N NH$_3$ in MeOH/DCM) to give 179 as a colourless solid (33 mg, 13% over three steps). $^1$H NMR (400 MHz, CDCl$_3$) δ 9.13 (s, 1H), 8.00 (s, 1H), 7.40-7.31 (m, 1H), 7.06-6.96 (m, 2H), 6.16 (s, 2H), 4.87 (dd, J=12.1, 2.7 Hz, 1H), 3.84 (s, 3H), 3.77-3.71 (m, 1H), 2.68-2.50 (m, 1H), 2.18-2.08 (m, 1H), 1.34 (s, 2H), 1.22 (d, J=6.4 Hz, 3H), 1.08 (d, J=1.8 Hz, 3H). LCMS (ES+) m/z 499 (M+1).

Example 180

5-Amino-N-[5-[(2R,5S,6R)-5-amino-6-(trideuteriomethoxy)oxepan-2-yl]-1-methyl-pyrazol-4-yl]-2-(2,6-difluorophenyl)thiazole-4-carboxamide 180

Following the procedure for Example 111 starting from tert-butyl N-[(3R,4S)-7-(2-methyl-4-nitro-pyrazol-3-yl)-3-(trideuteriomethoxy)oxepan-4-yl]carbamate (intermediate 77) gave 180 as a solid (15 mg, 22% over three steps). $^1$H NMR (400 MHz, d$_6$-DMSO) δ 9.24 (s, 1H), 7.77 (s, 1H), 7.57-7.48 (m, 3H), 7.31-7.23 (m, 2H), 4.79 (dd, J=10.8, 3.6 Hz, 1H), 4.02 (dd, J=13.8, 3.0 Hz, 1H), 3.80 (dd, J=13.8, 3.1 Hz, 1H), 3.75 (s, 3H), 3.01-2.93 (m, 2H), 2.00 (s, 1H), 1.83-1.54 (m, 3H). Alkyl NH$_2$ not observed. LCMS (ES+) m/z 482 (M+1).

Example 181

5-Amino-N-[5-[(2S,5R,6R)-5-amino-6-fluoro-oxepan-2-yl]-1-methyl-pyrazol-4-yl]-2-(2,3-difluorophenyl)thiazole-4-carboxamide 181

Following the procedure for Example 111 starting from tert-butyl N-[(3S,4R,7S)-3-fluoro-7-(2-methyl-4-nitro-pyrazol-3-yl)oxepan-4-yl]carbamate (Intermediate 88), and replacing 5-((tert-butoxycarbonyl)amino)-2-(2,6-difluorophenyl)thiazole-4-carboxylic acid with 5-(tert-butoxycarbonylamino)-2-(2,3-difluorophenyl)thiazole-4-carboxylic acid (Example 25) gave 181 as the hydrochloride salt as a pale pink solid (30 mg, 38% over three steps). $^1$H NMR (400 MHz, d$_6$-DMSO) δ 9.42 (s, 1H), 8.54-8.41 (m, 4H), 7.96-7.89 (m, 1H), 7.67 (s, 1H), 7.50-7.39 (m, 3H), 5.28 (m, 1H), 4.84 (d, J=10.4 Hz, 1H), 4.33-4.17 (m, 1H), 4.11-3.99 (m, 1H), 3.78 (s, 3H), 3.74-3.52 (m, 1H), 2.16-1.81 (m, 4H). LCMS (ES+) m/z 467 (M+1).

Example 182

5-Amino-N-[5-[(2S,5R,6R)-5-amino-6-fluoro-oxepan-2-yl]-1-methyl-pyrazol-4-yl]-2-(3-fluoro-4-pyridyl)thiazole-4-carboxamide 182

A mixture of tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (100 mg, 0.16 mmol, intermediate 88), 3-fluoro-4-tri-n-butylstannyl pyridine (93 mg, 0.24 mmol), tetrakis(triphenylphosphine)palladium(0) (9.3 mg, 0.008 mmol), copper (I) iodide (9 mg, 0.047 mmol) and lithium chloride (21 mg, 0.48 mmol) in dioxane (1.5 mL) was degassed by bubbling nitrogen gas through it for 5 min. The mixture was heated at 135° C. under microwave irradiation for 45 min. After cooling to room temperature, more 3-fluoro-4-tri-n-butylstannyl pyridine (93 mg, 0.24 mmol), tetrakis(triphenylphosphine)palladium(0) (9.3 mg, 0.008 mmol), copper (I) iodide (9 mg, 0.047 mmol) and lithium chloride (21 mg, 0.48 mmol) were added and the mixture was degassed by bubbling nitrogen gas through it for 5 min. The mixture was heated at 135° C. for 45 min, cooled to room temperature, filtered through celite and the filtrate concentrated under reduced pressure. Purification via silica gel column chromatography (0-80% EtOAc/isohexane) gave tert-butyl N-[4-[[5-[(2S,5R,6R)-5-(tert-butoxycarbonylamino)-6-fluoro-oxepan-2-yl]-1-methyl-pyrazol-4-yl]carbamoyl]-2-(3-fluoro-4-pyridyl)thiazol-5-yl]carbamate as a pale brown solid. This solid was stirred in a solution of HCl (4.0 M in dioxane, 3 mL) and MeOH (0.5 mL) at room temperature for 18 hr. The solvents were removed under reduced pressure. Purification via preparative HPLC gave 182 as the formate salt as a pale pink solid (26 mg, 33%). $^1$H NMR (400 MHz, d$_6$-DMSO) δ 9.27 (s, 1H), 8.43 (d, J=2.8 Hz, 1H), 8.28-8.23 (m, 1H), 8.00 (s, 1H), 7.78-7.72 (m, 1H), 7.47 (s, 1H), 7.42 (br s, 2H), 4.78-4.58 (m, 2H), 3.99-3.85 (m, 1H), 3.79-3.67 (m, 1H), 3.49 (s, 3H), 3.17-3.02 (m, 1H), 1.90-1.80 (m, 1H), 1.67-1.51 (m, 2H), 1.41 (d, J=13.1 Hz, 1H). Alkyl NH$_2$ not observed. LCMS (ES+) m/z 450 (M+1).

Example 183

5-Amino-N-[5-[(2S,5R,6R)-5-amino-6-methoxy-oxepan-2-yl]-1-methyl-pyrazol-4-yl]-2-(2-fluorophenyl)thiazole-4-carboxamide 183

Following the procedure for Example 111 starting from tert-butyl ((3R,4R,7S)-3-methoxy-7-(1-methyl-4-nitro-1H-pyrazol-5-yl)oxepan-4-yl)carbamate (Intermediate 93), and replacing 5-((tert-butoxycarbonyl)amino)-2-(2,6-difluorophenyl)thiazole-4-carboxylic acid with 5-(tert-butoxycarbonylamino)-2-(2-fluorophenyl)thiazole-4-carboxylic acid (Example 7) gave 183 as the hydrochloride salt as a dark salmon pink solid (68 mg, 45%). $^1$H NMR (400 MHz, d$_6$-DMSO) δ 9.47 (s, 1H), 8.18-8.09 (m, 5H), 7.74 (s, 1H), 7.52-7.36 (m, 4H), 4.96 (dd, J=9.9, 2.8 Hz, 1H), 4.19 (dd, J=13.6, 5.0 Hz, 1H), 4.00 (dd, J=13.6, 5.3 Hz, 1H), 3.86 (d, J=4.5 Hz, 1H), 3.78 (s, 3H), 3.62-3.49 (m, 1H), 3.33 (s, 3H), 2.14-1.97 (m, 2H), 1.98-1.74 (m, 2H). LCMS (ES+) m/z 461 (M+1).

Example 184

5-Amino-N-(5-((2R,5S,6R)-5-amino-4,4-difluoro-5,6-dimethyltetrahydro-2H-pyran-2-yl)-1-methyl-1H-pyrazol-4-yl)-2-(2,6-difluorophenyl)thiazole-4-carboxamide 184

5-Amino-N-(5-(5-amino-4,4-difluoro-5,6-dimethyltetrahydro-2H-pyran-2-yl)-1-methyl-1H-pyrazol-4-yl)-2-(2,6 difluorophenyl)thiazole-4-carboxamide (Example 179) was further purified via chiral preparative HPLC to give 184 as the first eluting enantiomer as a colourless solid (15 mg, 50%). $^1$H NMR (400 MHz, CDCl$_3$) δ 9.13 (s, 1H), 8.00 (s, 1H), 7.35 (d, J=7.81 Hz, 1H), 7.04-6.97 (m, 2H), 6.15 (s, 2H), 4.87 (dd, J=12.1, 2.7 Hz, 1H), 3.84 (s, 3H), 3.76-3.69 (m, 1H), 2.66-2.52 (m, 1H), 2.18-2.08 (m, 1H), 1.22 (d, J=6.4 Hz, 3H), 1.08 (d, J=1.8 Hz, 3H). Alkyl NH$_2$ not observed. LCMS (ES+) m/z 499 (M+1).

Example 185

5-Amino-N-(5-((2S,5R,6S)-5-amino-4,4-difluoro-5,6-dimethyltetrahydro-2H-pyran-2-yl)-1-methyl-1H-pyrazol-4-yl)-2-(2,6-difluorophenyl)thiazole-4-carboxamide 185

Following the procedure for Example 184 also gave 185 as the second eluting enantiomer as a colourless solid (15 mg, 50%). $^1$H NMR (400 MHz, CDCl$_3$) δ 9.13 (s, 1H), 8.00 (s, 1H), 7.41-7.31 (m, 1H), 7.05-6.95 (m, 2H), 6.16 (s, 2H), 4.87 (dd, J=12.1, 2.6 Hz, 1H), 3.84 (s, 3H), 3.77-3.71 (m, 1H), 2.69-2.51 (m, 1H), 2.18-2.08 (m, 1H), 1.34 (s, 2H), 1.23 (t, J=8.2 Hz, 3H), 1.08 (d, J=1.8 Hz, 3H). LCMS (ES+) m/z 499 (M+1).

Example 186

5-Amino-N-(5-((2S,5R,6R)-5-amino-6-fluorooxepan-2-yl)-1-methyl-1H-pyrazol-4-yl)-2-(2-fluorophenyl)thiazole-4-carboxamide 186

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 5-(tert-butoxycarbonylamino)-2-(2-fluorophenyl)thiazole-4-carboxylic acid (Example 7) gave 186 as the hydrochloride salt as a white solid (38 mg, 71%). $^1$H NMR (400 MHz, d$_6$-DMSO) δ 9.47 (s, 1H), 8.60-8.40 (m, 3H), 8.19-8.13 (m, 1H), 7.71 (s, 1H), 7.49-7.35 (m, 3H), 5.40-5.23 (m, 1H), 4.87 (d, J=10.5 Hz, 1H), 4.28 (ddd, J=32.0, 14.5, 4.7 Hz, 1H), 4.07 (ddd, J=23.4, 14.5, 2.8 Hz, 1H), 3.80 (s, 3H), 3.78-3.60 (m, 1H), 2.19-1.82 (m, 4H). LCMS (ES+) m/z 449 (M+1). Alkyl NH$_2$ not observed.

Example 187

N-(5-((2S,5R,6R)-5-Amino-6-fluorooxepan-2-yl)-1-methyl-1H-pyrazol-4-yl)-6-(2,6-difluoro-4-methoxyphenyl)-5-fluoropicolinamide 187

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 6-(2,6-difluoro-4-methoxyphenyl)-5-fluoropicolinic acid (see WO2010/56576) gave 187 as a white solid (22 mg, 26%). $^1$H NMR (400 MHz, CDCl$_3$) δ 10.40 (s, 1H), 8.31 (dd, J=8.6, 4.0 Hz, 1H), 8.21 (s, 1H), 7.71-7.63 (m, 1H), 6.64 (d, J=10.1 Hz, 2H), 4.84-4.73 (m, 2H), 4.07-3.89 (m, 3H), 3.87 (s, 3H), 3.77 (s, 3H), 3.41 (dd, J=23.1, 9.5 Hz, 1H), 2.67 (br s, 1H), 2.15-2.08 (m, 1H), 2.08-1.94 (m, 1H), 1.95-1.84 (m, 1H), 1.85-1.73 (m, 1H). LCMS (ES+) m/z 494 (M+1).

Example 188

N-(5-((2S,5R,6R)-5-Amino-6-fluorooxepan-2-yl)-1-methyl-1H-pyrazol-4-yl)-6-(2,6-difluoro-4-((tetrahydro-2H-pyran-4-yl)oxy)phenyl)-5-fluoropicolinamide 188

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 6-(2,6-difluoro-4-((tetrahydro-2H-pyran-4-yl)oxy)phenyl)-5-fluoropicolinic acid (see US2012/225062) gave 188 as a white solid (12 mg, 27%). $^1$H NMR (400 MHz, d$_6$-DMSO) δ 10.24 (s, 1H), 8.25 (dd, J=8.6, 3.9 Hz, 1H), 8.17-8.09 (m, 1H), 7.85 (s, 1H), 7.40-7.00 (br s, 2H), 7.20 (d, J=11.6 Hz, 2H), 5.30 (d, J=48 Hz, 1H), 4.92-4.86 (m, 2H), 4.11-4.00 (m, 2H), 3.92-3.84 (m, 2H), 3.75 (s, 3H), 3.62-3.50 (m, 3H), 2.07 (m, 4H), 1.95-1.70 (m, 2H), 1.68-1.55 (m, 2H). LCMS (ES+) m/z 564 (M+1).

Example 189

N-(5-((2S,5R,6R)-5-Amino-6-fluorooxepan-2-yl)-1-methyl-1H-pyrazol-4-yl)-6-(2,6-difluoro-4-(2-methoxyethoxy)phenyl)-5-fluoropicolinamide 189

Following the procedure for Example 111 starting from tert-butyl ((3R,4R,7S)-3-fluoro-7-(1-methyl-4-nitro-1H- pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 6-(2,6-difluoro-4-(2-methoxyethoxy)phenyl)-5-fluoropicolinic acid (see US2012/225062) gave 189 as a white solid (19 mg, 50%). $^1$H NMR (400 MHz, $d_6$-DMSO) δ 10.45 (s, 1H), 8.26 (dd, J=8.6, 3.9 Hz, 1H), 8.19-8.09 (m, 1H), 7.95 (s, 1H), 7.03 (d, J=10.5 Hz, 2H), 4.95 (dd, J=8.3, 3.6 Hz, 1H), 4.69 (s, 1H), 4.57 (s, 1H), 4.24 (t, J=4.2 Hz, 2H), 3.98-3.78 (m, 2H), 3.73 (s, 3H), 3.70 (t, J=4.2 Hz, 2H), 3.30 (s, 3H), 3.15 (m, 1H), 2.20-2.11 (m, 1H), 1.89-1.72 (m, 2H), 1.72-1.62 (m, 1H), 1.59-1.50 (m, 1H). LCMS (ES+) m/z 538 (M+1).

Example 190

N-(5-((2S,5R,6R)-5-Amino-6-fluorooxepan-2-yl)-1-methyl-1H-pyrazol-4-yl)-6-(2,6-difluoro-4-(2-hydroxyethoxy)phenyl)-5-fluoropicolinamide 190

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 6-(4-(2-((tert-butyldimethylsilyl)oxy)ethoxy)-2,6-difluorophenyl)-5-fluoropicolinic acid (see US2012/225062) gave 190 as a white solid (29 mg, 62%). $^1$H NMR (400 MHz, $d_6$-DMSO) δ 10.59 (s, 1H), 8.40 (dd, J=8.6, 3.9 Hz, 1H), 8.27 (dd, J=8.6, 8.6 Hz, 1H), 8.10 (s, 1H), 7.15 (d, J=10.5 Hz, 2H), 5.09 (dd, J=8.4, 3.6 Hz, 1H), 4.86-4.83 (d, J=48 Hz, 1H), 4.28 (t, J=4.8 Hz, 2H), 4.12-3.92 (m, 2H), 3.92-3.86 (m, 5H), 3.70-3.38 (br s, 1H), 3.36-3.24 (m, 1H), 2.33-2.25 (m, 1H), 2.02-1.87 (m, 1H), 1.87-1.75 (m, 1H), 1.75-1.63 (m, 1H). Alkyl NH$_2$ not observed. LCMS (ES+) m/z 524 (M+1).

Example 191

N-(5-((2S,5R,6S)-5-Amino-6-hydroxyoxepan-2-yl)-1-methyl-1H-pyrazol-4-yl)-6-(2,6-difluoro-4-(2-methoxyethoxy)phenyl)-5-fluoropicolinamide 191

Following the procedure for Example 111 starting from tert-butyl ((3S,4R,7S)-3-hydroxy-7-(1-methyl-4-nitro-1H-pyrazol-5-yl)oxepan-4-yl)carbamate (Intermediate 94), and replacing 5-((tert-butoxycarbonyl)amino)-2-(2,6-difluorophenyl)thiazole-4-carboxylic acid with 6-(2,6-difluoro-4-(2-methoxyethoxy)phenyl)-5-fluoropicolinic acid (see US2012/225062) gave 191 as a white solid (73 mg, 71%). $^1$H NMR (400 MHz, $d_6$-DMSO) δ 10.22 (s, 1H), 8.25 (dd, J=8.6, 4.0 Hz, 1H), 8.12 (t, J=8.9 Hz, 1H), 7.82 (s, 1H), 6.97 (d, J=10.2 Hz, 2H), 4.79 (dd, J=10.8, 3.4 Hz, 2H), 4.26-4.20 (m, 2H), 3.90-3.67 (m, 4H), 3.73-3.67 (m, 2H), 3.63 (dd, J=12.8, 5.8 Hz, 1H), 3.62-3.02 (m, 3H), 2.73-2.64 (m, 1H), 2.00-1.92 (m, 1H), 1.92-1.79 (m, 1H), 1.79-1.72 (m, 1H), 1.55-1.42 (m, 1H). Alkyl NH$_2$ not observed. LCMS (ES+) m/z 536 (M+1).

Example 192

N-(5-((2S,5R,6S)-5-amino-6-fluorooxepan-2-yl)-1-methyl-1H-pyrazol-4-yl)-6-(2,6-difluoro-4-(2-methoxyethoxy)phenyl)-5-fluoropicolinamide 192

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-(2-methoxyethoxy)phenyl)-5-fluoropicolinic acid (see US2012/225062) gave 192. $^1$H NMR (400 MHz, DMSO-$d_6$) δ 10.20 (s, 1H), 8.26 (dd, J=8.6, 4.0 Hz, 1H), 8.11 (t, J=8.9 Hz, 1H), 7.91 (s, 1H), 7.01-6.91 (m, 2H), 4.82 (dd, J=10.3, 3.8 Hz, 1H), 4.32-4.12 (m, 3H), 4.05-3.85 (m, 2H), 3.75 (s, 3H), 3.74-3.65 (m, 2H), 3.32 (s, 3H), 3.06 (dd, J=16.5, 7.8 Hz, 1H), 2.10-2.02 (m, 1H), 1.82-1.57 (m, 5H). LCMS (ES+) m/z 538 (M+1).

Example 193

N-(5-((2S,5R,6S)-5-amino-6-fluorooxepan-2-yl)-1-methyl-1H-pyrazol-4-yl)-6-(2,6-difluoro-4-(3-hydroxyoxetan-3-yl)phenyl)-5-fluoropicolinamide 193

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-(3-hydroxyoxetan-3-yl)phenyl)-5-fluoropicolinic acid (see US2012/225062) gave 193. $^1$H NMR (400 MHz, DMSO-$d_6$) δ 10.20 (s, 1H), 8.30 (dd, J=8.7, 4.0 Hz, 1H), 8.23-8.12 (m, 1H), 7.90 (s, 1H), 7.49 (d, J=9.7 Hz, 2H), 4.81 (t, J=5.7 Hz, 3H), 4.73 (dd, J=7.0, 1.4 Hz, 2H), 4.41-4.17 (m, 1H), 4.10-3.87 (m, 2H), 3.76 (s, 3H), 3.19-3.09 (m, 1H), 2.11-2.02 (m, 1H), 1.69 (s, 3H). LCMS (ES+) m/z 536 (M+1).

Example 194

N-(5-((2S,5R,6S)-5-amino-6-fluorooxepan-2-yl)-1-methyl-1H-pyrazol-4-yl)-6-(2,6-difluoro-4-(3-fluorooxetan-3-yl)phenyl)-5-fluoropicolinamide 194

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-(3-fluorooxetan-3-yl)phenyl)-5-fluoropicolinic acid (see US2012/225062) gave 194. $^1$H NMR (400 MHz, DMSO-$d_6$) δ 10.22 (s, 1H), 8.32 (dd, J=8.7, 4.0 Hz, 1H), 8.18 (t, J=8.9 Hz, 1H), 7.93 (s, 1H), 7.54 (d, J=8.8 Hz, 2H), 5.02 (s, 2H), 4.97 (s, 2H), 4.82 (dd, J=10.3, 3.7 Hz, 1H), 4.31-4.05 (m, 1H), 4.07-3.84 (m, 2H), 3.75 (s, 3H), 3.09-2.95 (m, 1H), 2.10-1.99 (m, 1H), 1.80-1.57 (m, 5H). LCMS (ES+) m/z 538 (M+1).

Example 195

N-(5-((2S,5R,6S)-5-amino-6-fluorooxepan-2-yl)-1-methyl-1H-pyrazol-4-yl)-6-(2,6-difluorophenyl)-5-fluoropicolinamide 195

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluorophenyl)-5-fluoropicolinic acid (see US2012/225061) gave 195. $^1$H NMR (400 MHz, DMSO-$d_6$) δ 10.20 (s, 1H), 8.30 (dd, J=8.7, 4.0 Hz, 1H), 8.15 (t, J=8.9 Hz, 1H), 7.91 (s, 1H), 7.72-7.59 (m, 1H), 7.30 (t, J=8.4 Hz, 2H), 4.86-4.78 (m, 1H), 4.31-4.05 (m, 1H), 4.02-3.83 (m, 2H), 3.75 (s, 3H), 3.11-2.97 (m, 1H), 2.11-2.00 (m, 1H), 1.82-1.50 (m, 5H). LCMS (ES+) m/z 464 (M+1).

Example 196

N-(5-((2S,5R,6S)-5-amino-6-fluorooxepan-2-yl)-1-methyl-1H-pyrazol-4-yl)-6-(2,6-difluoro-4-(4-hydroxytetrahydro-2H-pyran-4-yl)phenyl)-5-fluoropicolinamide 196

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-(4-hydroxytetrahydro-2H-pyran-4-yl)phenyl)-5-fluoropicolinic acid (see US2012/225062) gave 196. $^1$H NMR (400 MHz, DMSO-d$_6$) δ 10.19 (s, 1H), 8.29 (dd, J=8.7, 4.0 Hz, 1H), 8.23-8.10 (m, 1H), 7.88 (s, 1H), 7.49-7.35 (m, 2H), 4.85-4.76 (m, 1H), 4.39-4.11 (m, 1H), 4.07-3.68 (m, 9H), 3.17-3.03 (m, 1H), 2.11-1.99 (m, 3H), 1.84-1.51 (m, 5H). LCMS (ES+) m/z 564 (M+1).

Example 197

N-(5-((2S,5R,6S)-5-Amino-6-fluorooxepan-2-yl)-1-methyl-1H-pyrazol-4-yl)-6-(2,6-difluoro-4-((tetrahydro-2H-pyran-4-yl)oxy)phenyl)-5-fluoropicolinamide 197

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-((tetrahydro-2H-pyran-4-yl)oxy)phenyl)-5-fluoropicolinic acid (see US2012/225062) gave 197. $^1$H NMR (400 MHz, DMSO-d$_6$) δ 10.19 (s, 1H), 8.25 (dd, J=8.7, 4.0 Hz, 1H), 8.11 (t, J=8.9 Hz, 1H), 7.91 (s, 1H), 6.99 (d, J=10.2 Hz, 2H), 4.82 (dd, J=10.4, 3.7 Hz, 1H), 4.77-4.66 (m, 1H), 4.21 (ddd, J=49.1, 7.8, 2.9 Hz, 1H), 4.10-3.90 (m, 2H), 3.90-3.80 (m, 2H), 3.75 (s, 3H), 3.51 (ddd, J=12.0, 9.4, 2.8 Hz, 2H), 3.14-3.01 (m, 1H), 2.10-1.97 (m, 3H), 1.85-1.55 (m, 5H). LCMS (ES+) m/z 564 (M+1).

Example 198

N-(5-((2S,5R,6S)-5-amino-6-fluorooxepan-2-yl)-1-methyl-1H-pyrazol-4-yl)-6-(2,6-difluoro-4-(1-hydroxycyclobutyl)phenyl)-5-fluoropicolinamide 198

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-(1-hydroxycyclobutyl)phenyl)-5-fluoropicolinic acid (see US2012/225062) gave 198. $^1$H NMR (400 MHz, DMSO-d$_6$) δ 10.19 (s, 1H), 8.29 (dd, J=8.7, 4.0 Hz, 1H), 8.14 (t, J=8.8 Hz, 1H), 7.90 (s, 1H), 7.35 (d, J=9.5 Hz, 2H), 5.89 (br, 1H), 4.80 (dd, J=10.5, 3.7 Hz, 1H), 4.32-4.07 (m, 1H), 4.07-3.84 (m, 2H), 3.75 (s, 3H), 3.11-3.00 (m, 1H), 2.50-2.39 (m, 2H), 2.38-2.26 (m, 2H), 2.09-1.88 (m, 2H), 1.84-1.68 (m, 2H), 1.67-1.57 (m, 2H). LCMS (ES+) m/z 534 (M+1).

Example 199

N-(5-((2S,5R,6S)-5-amino-6-fluorooxepan-2-yl)-1-methyl-1H-pyrazol-4-yl)-6-(2,6-difluoro-4-(methoxymethyl)phenyl)-5-fluoropicolinamide 199

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-(methoxymethyl)phenyl)-5-fluoropicolinic acid (see US2012/225062) gave 199. $^1$H NMR (400 MHz, DMSO-d$_6$) δ 10.20 (s, 1H), 8.29 (dd, J=8.6, 4.0 Hz, 1H), 8.15 (t, J=8.8 Hz, 1H), 7.91 (s, 1H), 7.24 (d, J=9.0 Hz, 2H), 4.81 (dd, J=10.3, 3.7 Hz, 1H), 4.53 (s, 2H), 4.31-4.07 (m, 1H), 4.02-3.83 (m, 2H), 3.75 (s, 3H), 3.36 (s, 3H), 3.11-2.98 (m, 1H), 2.10-2.00 (m, 1H), 1.82-1.57 (m, 3H). LCMS (ES+) m/z 508 (M+1).

Example 200

N-(5-((2S,5R,6S)-5-amino-6-fluorooxepan-2-yl)-1-methyl-1H-pyrazol-4-yl)-6-(2,6-difluoro-4-(2-hydroxypropan-2-yl)phenyl)-5-fluoropicolinamide 200

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-(2-hydroxypropan-2-yl)phenyl)-5-fluoropicolinic acid (see US2012/225062) gave 200. $^1$H NMR (400 MHz, DMSO-d$_6$) δ 10.20 (s, 1H), 8.28 (dd, J=8.7, 4.0 Hz, 1H), 8.14 (t, J=8.9 Hz, 1H), 7.89 (s, 1H), 7.34 (d, J=9.8 Hz, 2H), 5.36 (br, 1H), 4.80 (dd, J=10.4, 3.7 Hz, 1H), 4.37-4.06 (m, 1H), 4.02-3.87 (m, 2H), 3.75 (s, 3H), 3.13-3.00 (m, 1H), 2.10-1.99 (m, 1H), 1.85-1.57 (m, 3H), 1.47 (s, 6H). LCMS (ES+) m/z 522 (M+1).

Example 201

N-(5-((2S,5R,6S)-5-amino-6-fluorooxepan-2-yl)-1-methyl-1H-pyrazol-4-yl)-6-(2,6-difluoro-4-methoxyphenyl)-5-fluoropicolinamide 201

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-methoxyphenyl)-5-fluoropicolinic acid (see US2012/225062) gave 201. $^1$H NMR (400 MHz, DMSO-d$_6$) δ 10.20 (s, 1H), 8.26 (dd, J=8.7, 4.0 Hz, 1H), 8.11 (t, J=8.9 Hz, 1H), 7.90 (s, 1H), 6.94 (d, J=10.2 Hz, 2H), 4.82 (dd, J=10.4, 3.7 Hz, 1H), 4.40-4.14 (m, 1H), 4.08-3.91 (m, 2H), 3.86 (s, 3H), 3.76 (s, 3H), 3.18-3.04 (m, 1H), 2.12-2.02 (m, 1H), 1.83-1.60 (m, 3H). LCMS (ES+) m/z 494 (M+1).

Example 202

N-(5-((2S,5R,6S)-5-amino-6-fluorooxepan-2-yl)-1-methyl-1H-pyrazol-4-yl)-6-(2,6-difluoro-4-(3-methoxyoxetan-3-yl)phenyl)-5-fluoropicolinamide 202

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-(3-methoxyoxetan-3-yl)phenyl)-5-fluoropicolinic acid (see US2012/225062) gave 202. $^1$H NMR (400 MHz, DMSO-d$_6$) δ 10.24 (s, 1H), 8.32 (dd, J=8.7, 4.0 Hz, 1H), 8.17 (t, J=8.9 Hz, 1H), 7.94 (s, 1H), 7.42 (d, J=9.3 Hz, 2H), 4.87-4.75 (m, 5H), 4.17 (ddt, J=49.0, 6.1, 2.6 Hz, 1H), 4.03-3.84 (m, 2H), 3.75 (s, 3H), 3.14 (s, 3H), 3.12-2.98 (m, 1H), 2.11-2.00 (m, 1H), 1.80-1.57 (m, 3H). LCMS (ES+) m/z 550 (M+1).

Example 203

N-(5-((2S,5R,6R)-5-amino-6-fluorooxepan-2-yl)-1-methyl-1H-pyrazol-4-yl)-6-(2,6-difluoro-4-(3-methoxyoxetan-3-yl)phenyl)-5-fluoropicolinamide 203

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 6-(2,6-difluoro-4-(3-methoxyoxetan-3-yl)phenyl)-5-fluoropicolinic acid (see WO2012/225062) gave 203. $^1$H NMR (400 MHz, DMSO-d$_6$) δ 10.43 (s, 1H), 8.31 (dd, J=8.7, 4.0 Hz, 1H), 8.19 (t, J=8.9 Hz, 1H), 7.95 (s, 1H), 7.49 (d, J=9.3 Hz, 2H), 4.96 (dd, J=8.1, 4.0 Hz, 1H), 4.81 (d, J=1.7 Hz, 4H), 4.65-4.37 (m, 1H), 3.97-3.73 (m, 2H), 3.72 (s, 3H), 3.41-3.25 (m, 2H), 3.15 (s, 3H), 3.12-2.99 (m, 1H), 2.22-2.12 (m, 1H), 1.81-1.71 (m, 1H), 1.70-1.60 (m, 1H), 1.57-1.52 (m, 3H). LCMS (ES+) m/z 550 (M+1).

Example 204

N-(5-((2S,5R,6S)-5-amino-6-fluorooxepan-2-yl)-1-methyl-1H-pyrazol-4-yl)-6-(2,6-difluoro-4-(1-hydroxycyclopropyl)phenyl)-5-fluoropicolinamide 204

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-(1-hydroxycyclopropyl)phenyl)-5-fluoropicolinic acid (see US2012/225062) gave 204. $^1$H NMR (400 MHz, DMSO-d$_6$) δ 10.17 (s, 1H), 8.27 (dd, J=8.7, 4.0 Hz, 1H), 8.13 (t, J=8.9 Hz, 1H), 7.90 (s, 1H), 7.09 (d, J=9.8 Hz, 2H), 6.26 (s, 1H), 4.81 (dd, J=10.5, 3.7 Hz, 1H), 4.34-4.09 (m, 1H), 4.07-3.84 (m, 2H), 3.75 (s, 3H), 3.12-2.99 (m, 1H), 2.11-1.99 (m, 1H), 1.83-1.53 (m, 5H), 1.27-1.08 (m, 4H). LCMS (ES+) m/z 520 (M+1).

Example 205

N-(5-((2S,5R,6S)-5-amino-6-fluorooxepan-2-yl)-1-methyl-1H-pyrazol-4-yl)-6-(2,6-difluoro-4-propionylphenyl)-5-fluoropicolinamide 205

The title compound 205 was prepared as a second product during the formation of Example 204, and was separated during the final HPLC purification. $^1$H NMR (400 MHz, DMSO-d$_6$) δ 10.23 (s, 1H), 8.34 (dd, J=8.7, 4.1 Hz, 1H), 8.20 (t, J=8.9 Hz, 1H), 7.93 (s, 1H), 7.84 (d, J=8.6 Hz, 2H), 4.81 (ddd, J=10.8, 6.7, 3.7 Hz, 1H), 4.31-4.05 (m, 1H), 4.05-3.82 (m, 2H), 3.76 (s, 3H), 3.13 (q, J=7.1 Hz, 2H), 3.07-2.97 (m, 1H), 2.10-2.01 (m, 1H), 1.79-1.56 (m, 3H), 1.54 (br, 2H), 1.12 (t, J=7.1 Hz, 3H). LCMS (ES+) m/z 520 (M+1).

Example 206

N-(5-((2S,5R,6S)-5-amino-6-fluorooxepan-2-yl)-1-methyl-1H-pyrazol-4-yl)-6-(2,6-difluoro-4-(4-fluorotetrahydro-2H-pyran-4-yl)phenyl)-5-fluoropicolinamide 206

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-(4-fluorotetrahydro-2H-pyran-4-yl)phenyl)-5-fluoropicolinic acid (see US2012/225062) gave 206. $^1$H NMR (400 MHz, DMSO-d$_6$) δ 10.22 (s, 1H), 8.30 (dd, J=8.7, 4.0 Hz, 1H), 8.17 (t, J=8.9 Hz, 1H), 7.92 (s, 1H), 7.41 (d, J=9.2 Hz, 2H), 4.81 (dd, J=10.3, 3.8 Hz, 1H), 4.17 (ddd, J=49.1, 5.9, 3.1 Hz, 1H), 4.02-3.96 (m, 1H), 3.96-3.84 (m, 3H), 3.75 (s, 3H), 3.74-3.64 (m, 2H), 3.09-2.99 (m, 1H), 2.33-2.13 (m, 2H), 2.10-1.99 (m, 1H), 1.93-1.80 (m, 2H), 1.80-1.52 (m, 5H). LCMS (ES+) m/z 566 (M+1).

Example 207

N-(5-((2S,5R,6S)-5-amino-6-fluorooxepan-2-yl)-1-methyl-1H-pyrazol-4-yl)-6-(2,6-difluoro-4-(1-hydroxyethyl)phenyl)-5-fluoropicolinamide 207

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-(1-hydroxyethyl)phenyl)-5-fluoropicolinic acid (Intermediate 136) gave 207. The product was isolated as a mixture of diastereomers. $^1$H NMR (400 MHz, DMSO-d$_6$) δ 10.19 (s, 1H), 8.28 (dd, J=8.6, 4.0 Hz, 1H), 8.14 (t, J=8.9 Hz, 1H), 7.89 (s, 1H), 7.24 (d, J=8.9 Hz, 2H), 5.51 (br, 1H), 4.87-4.76 (m, 2H), 4.36-4.08 (m, 1H), 4.03-3.84 (m, 2H), 3.75 (s, 3H), 3.10-3.00 (m, 1H), 2.10-2.00 (m, 1H), 1.85-1.68 (m, 1H), 1.67-1.57 (m, 2H), 1.37 (d, J=6.4 Hz, 3H). LCMS (ES+) m/z 508 (M+1).

Example 208

N-(5-((2S,5R,6S)-5-amino-6-fluorooxepan-2-yl)-1-methyl-1H-pyrazol-4-yl)-6-(2,6-difluoro-4-hydroxyphenyl)-5-fluoropicolinamide 208

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-hydroxyphenyl)-5-fluoropicolinic acid (Intermediate 137) gave 208. $^1$H NMR (400 MHz, DMSO-d$_6$) δ 10.18 (s, 1H), 8.23 (dd, J=8.6, 4.0 Hz, 1H), 8.08 (t, J=8.8 Hz, 1H), 7.91 (s, 1H), 6.62 (d, J=10.1 Hz, 2H), 4.81 (dd, J=10.4, 3.6 Hz, 1H), 4.39-4.14 (m, 1H), 4.10-3.87 (m, 2H), 3.75 (s, 3H), 3.16-3.03 (m, 1H), 2.10-1.99 (m, 1H), 1.82-1.56 (m, 3H). LCMS (ES+) m/z 480 (M+1).

Example 209

N-(5-((2S,5R,6S)-5-Amino-6-fluorooxepan-2-yl)-1-methyl-1H-pyrazol-4-yl)-6-(2,6-difluoro-4-(2-hydroxyethoxy)phenyl)-5-fluoropicolinamide 209

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(4-(2-((tert-butyldimethylsilyl)oxy)ethoxy)-2,6-difluorophenyl)-5-fluoropicolinic acid (see US2012/225062) gave 209. $^1$H NMR (400 MHz, DMSO-d$_6$) δ 10.20 (s, 1H), 8.26 (dd, J=8.6, 4.0

Hz, 1H), 8.11 (t, J=8.9 Hz, 1H), 7.92 (s, 1H), 6.93 (d, J=10.2 Hz, 2H), 4.98 (br, 1H), 4.82 (dd, J=10.3, 3.7 Hz, 1H), 4.24 (ddt, J=49.2, 6.1, 2.6 Hz, 1H), 4.11 (t, J=4.8 Hz, 2H), 4.07-3.84 (m, 2H), 3.80-3.69 (m, 5H), 3.15-3.01 (m, 1H), 2.12-2.01 (m, 1H), 1.83-1.58 (m, 3H). LCMS (ES+) m/z 524 (M+1).

Example 210

N-(5-((2S,5R,6R)-5-amino-6-fluorooxepan-2-yl)-1-methyl-1H-pyrazol-4-yl)-6-(2,6-difluoro-4-(1-hydroxyethyl)phenyl)-5-fluoropicolinamide 210

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 6-(2,6-difluoro-4-(1-hydroxyethyl)phenyl)-5-fluoropicolinic acid (Intermediate 136) gave 210. The product was isolated as a mixture of diastereomers. $^1$H NMR (400 MHz, DMSO-$d_6$) δ 10.45 (s, 1H), 8.34-8.24 (m, 1H), 8.16 (t, J=8.9 Hz, 1H), 7.91 (s, 1H), 7.38-7.28 (m, 2H), 4.94-4.79 (m, 2H), 4.76-4.49 (m, 1H), 4.02-3.77 (m, 2H), 3.73 (s, 3H), 3.20-3.04 (m, 1H), 2.16-2.04 (m, 1H), 1.91-1.77 (m, 1H), 1.74-1.55 (m, 2H), 1.39 (d, J=6.5 Hz, 3H). LCMS (ES+) m/z 508 (M+1).

Example 211

N-(5-((2S,5R,6R)-5-amino-6-fluorooxepan-2-yl)-1-methyl-1H-pyrazol-4-yl)-6-(2,6-difluoro-4-(1-methoxyethyl)phenyl)-5-fluoropicolinamide 211

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 6-(2,6-difluoro-4-(1-methoxyethyl)phenyl)-5-fluoropicolinic acid (Intermediate 138) gave 211. The product was isolated as a mixture of diastereomers. $^1$H NMR (400 MHz, DMSO-$d_6$) δ 10.43 (s, 1H), 8.29 (dd, J=8.7, 4.0 Hz, 1H), 8.17 (t, J=8.9 Hz, 1H), 7.94 (s, 1H), 7.35-7.26 (m, 2H), 4.95 (dd, J=8.3, 3.9 Hz, 1H), 4.67-4.38 (m, 2H), 3.99-3.75 (m, 2H), 3.72 (s, 3H), 3.23 (s, 3H), 3.17-3.04 (m, 1H), 2.21-2.10 (m, 1H), 1.82-1.74 (m, 1H), 1.71-1.60 (m, 1H), 1.62-1.50 (m, 1H), 1.39 (d, J=6.4 Hz, 3H). LCMS (ES+) m/z 522 (M+1).

Example 212

N-(5-((2S,5R,6R)-5-amino-6-fluorooxepan-2-yl)-1-methyl-1H-pyrazol-4-yl)-6-(2,6-difluoro-4-(1,2,3-trihydroxypropan-2-yl)phenyl)-5-fluoropicolinamide 212

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 6-(2,6-difluoro-4-(3-hydroxyoxetan-3-yl)phenyl)-5-fluoropicolinic acid (see US2012/225062) gave 212. Oxetane hydrolysis occurs during acidic deprotection. $^1$H NMR (400 MHz, DMSO-$d_6$) δ 10.54 (s, 1H), 8.26 (dd, J=8.6, 3.9 Hz, 1H), 8.16 (t, J=8.8 Hz, 1H), 7.92 (s, 1H), 7.44-7.36 (m, 2H), 4.84 (d, J=9.5 Hz, 1H), 4.76-4.50 (m, 1H), 3.88 (d, J=4.5 Hz, 1H), 3.82 (d, J=4.4 Hz, 1H), 3.72 (s, 3H), 3.67 (d, J=11.7 Hz, 1H), 3.57 (dd, J=11.1, 5.4 Hz, 2H), 2.96 (dd, J=26.7, 10.0 Hz, 1H), 2.04-1.95 (m, 1H), 1.90-1.82 (m, 1H), 1.73-1.62 (m, 1H), 1.61-1.53 (m, 1H). LCMS (ES+) m/z 554 (M+1).

Example 213

N-(5-((2S,5R,6S)-5-amino-6-fluorooxepan-2-yl)-1-methyl-1H-pyrazol-4-yl)-6-(4-(cyclopropyl(methoxy)methyl)-2,6-difluorophenyl)-5-fluoropicolinamide Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(4-(cyclopropyl(methoxy)methyl)-2,6-difluorophenyl)-5-fluoropicolinic acid (Intermediate 141) gave 213. The product was isolated as a mixture of diastereomers. $^1$H NMR (400 MHz, DMSO-$d_6$) δ 10.22 (d, J=4.5 Hz, 1H), 8.30 (dd, J=8.6, 4.0 Hz, 1H), 8.15 (t, J=8.8 Hz, 1H), 7.91 (d, J=1.3 Hz, 1H), 7.26 (d, J=9.2 Hz, 2H), 4.82 (ddd, J=10.3, 3.9, 1.5 Hz, 1H), 4.30-4.04 (m, 1H), 4.06-3.83 (m, 2H), 3.75 (s, 3H), 3.71 (d, J=8.0 Hz, 1H), 3.24 (s, 3H), 3.14-3.00 (m, 1H), 2.04 (s, 1H), 1.81-1.56 (m, 5H), 1.16-1.02 (m, 1H), 0.66-0.33 (m, 4H). LCMS (ES+) m/z 548 (M+1).

Example 214

N-(5-((2S,5R,6S)-5-amino-6-fluorooxepan-2-yl)-1-methyl-1H-pyrazol-4-yl)-6-(4-(1,3-dihydroxypropan-2-yl)-2,6-difluorophenyl)-5-fluoropicolinamide 214

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 6-(2,6-difluoro-4-(oxetan-3-yl)phenyl)-5-fluoropicolinic acid (see US2012/225062) gave 214. Oxetane hydrolysis occurs during acidic deprotection. $^1$H NMR (400 MHz, DMSO-$d_6$) δ 10.11 (s, 1H), 8.28 (dd, J=8.7, 4.0 Hz, 1H), 8.14 (t, J=8.8 Hz, 1H), 7.73 (s, 1H), 7.20 (d, J=9.7 Hz, 2H), 4.90-4.76 (m, 1H), 4.77-4.54 (m, 1H), 4.23-3.94 (m, 2H), 3.80 (s, 3H), 3.77-3.61 (m, 4H), 3.55-3.38 (m, 1H), 3.01-2.92 (m, 1H), 2.20-2.03 (m, 1H), 2.00-1.70 (m, 3H). LCMS (ES+) m/z 538 (M+1).

Example 215

N-(5-((2S,5R,6S)-5-amino-6-fluorooxepan-2-yl)-1-methyl-1H-pyrazol-4-yl)-2-(2,6-difluoro-4-(3-hydroxytetrahydrofuran-3-yl)phenyl)thiazole-4-carboxamide 215

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2,6-difluoro-4-(3-hydroxytetrahydrofuran-3-yl)phenyl)thiazole-4-carboxylic acid (Intermediate 144) gave 215. The product was isolated as a mixture of diastereomers. $^1$H NMR (400 MHz, DMSO-$d_6$) δ 9.85 (s, 1H), 8.62 (s, 1H), 7.81 (s, 1H), 7.43 (d, J=10.3 Hz, 2H), 5.81 (s, 1H), 4.81 (dd, J=10.8, 3.7 Hz, 1H), 4.44-4.24 (m, 1H), 4.24-4.08 (m, 1H), 4.09-3.90 (m, 3H), 3.79 (d, J=8.1 Hz, 5H), 3.34-3.16 (m, 2H), 2.54-2.49 (m, 1H), 2.39-2.27 (m, 1H), 2.21-2.01 (m, 2H), 1.88-1.76 (m, 1H), 1.72-1.62 (m, 4H). LCMS (ES+) m/z 538 (M+1).

Example 216

N-(5-((2S,5R,6S)-5-amino-6-fluorooxepan-2-yl)-1-methyl-1H-pyrazol-4-yl)-2-(2,6-difluoro-4-(tetrahydrofuran-3-yl)phenyl)thiazole-4-carboxamide 216

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2,6-difluoro-4-(tetrahydrofuran-3-yl)phenyl)thiazole-4-carboxylic acid (Intermediate 145) gave 216. The product was isolated as a mixture of diastereomers. $^1$H NMR (400 MHz, DMSO-d$_6$) δ 9.85 (s, 1H), 8.61 (s, 1H), 7.80 (s, 1H), 7.27 (d, J=10.0 Hz, 2H), 4.81 (dd, J=10.8, 3.7 Hz, 1H), 4.46-4.22 (m, 1H), 4.24-4.09 (m, 1H), 4.08-3.89 (m, 3H), 3.86-3.75 (m, 4H), 3.63 (dd, J=8.4, 6.9 Hz, 1H), 3.58-3.45 (m, 1H), 3.34-3.16 (m, 3H), 2.42-2.29 (m, 1H), 2.11-1.91 (m, 2H), 1.87-1.79 (m, 1H), 1.72-1.62 (m, 4H). LCMS (ES+) m/z 522 (M+1).

Example 217

N-(5-((2S,5R,6S)-5-amino-6-fluorooxepan-2-yl)-1-methyl-1H-pyrazol-4-yl)-2-(2,6-difluoro-4-4(R)-tetrahydrofuran-3-yl)oxy)phenyl)thiazole-4-carboxamide 217

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with (R)-2-(2,6-difluoro-4-((tetrahydrofuran-3-yl)oxy)phenyl)thiazole-4-carboxylic acid (Intermediate 147) gave 217. $^1$H NMR (400 MHz, DMSO-d$_6$) δ 9.84 (s, 1H), 8.56 (s, 1H), 7.80 (s, 1H), 7.44 (s, 3H), 7.06-6.95 (m, 2H), 5.18 (td, J=4.6, 2.4 Hz, 1H), 4.95-4.59 (m, 2H), 4.37-4.04 (m, 2H), 3.95-3.72 (m, 8H), 3.55 (dt, J=17.6, 8.8 Hz, 1H), 2.38-2.24 (m, 1H), 2.13 (d, J=11.6 Hz, 1H), 2.06-1.80 (m, 5H). LCMS (ES+) m/z 538 (M+1).

Example 218

N-(5-((2S,5R,6S)-5-amino-6-fluorooxepan-2-yl)-1-methyl-1H-pyrazol-4-yl)-2-(2,6-difluoro-4-4(S)-tetrahydrofuran-3-yl)oxy)phenyl)thiazole-4-carboxamide 218

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with (S)-2-(2,6-difluoro-4-((tetrahydrofuran-3-yl)oxy)phenyl)thiazole-4-carboxylic acid (Intermediate 148) gave 218. $^1$H NMR (400 MHz, DMSO-d$_6$) δ 9.86 (s, 1H), 8.55 (s, 1H), 7.80 (s, 1H), 7.02-6.92 (m, 2H), 5.19 (dd, J=6.2, 4.2 Hz, 1H), 4.80 (dd, J=10.8, 3.6 Hz, 1H), 4.46-4.07 (m, 2H), 4.08-3.72 (m, 8H), 3.30-3.14 (m, 1H), 2.36-2.22 (m, 1H), 2.02 (ddd, J=19.6, 14.6, 9.1 Hz, 2H), 1.81 (ddd, J=14.3, 10.2, 4.9 Hz, 1H), 1.68 (s, 4H). LCMS (ES+) m/z 538 (M+1).

Example 219

5-amino-N-(5-((2S,5R,6R)-5-amino-6-methoxyoxepan-2-yl)-1-methyl-1H-pyrazol-4-yl)-2-(2,3-difluorophenyl)thiazole-4-carboxamide 219

Following the procedure for Example 101 starting from tert-butyl N-[2-bromo-4-[[5-[(2S,5R,6R)-5-(tert-butoxycarbonylamino)-6-methoxy-oxepan-2-yl]-1-methyl-pyrazol-4-yl]carbamoyl]thiazol-5-yl]carbamate (Intermediate 98), and replacing 3,6-dihydro-2H-pyran-4-boronic acid pinacol ester with (2,3-difluorophenyl)boronic acid gave 219. $^1$H NMR (400 MHz, DMSO-d$_6$) δ 9.60 (s, 1H), 7.90-7.82 (m, 2H), 7.56-7.42 (m, 3H), 7.38-7.30 (m, 1H), 5.07 (t, J=5.7 Hz, 1H), 3.98-3.90 (m, 1H), 3.88-3.80 (m, 1H), 3.71 (s, 3H), 3.50-3.45 (m, 1H), 3.14 (d, J=1.5 Hz, 3H), 2.36-2.31 (m, 2H), 1.76-1.71 (m, 1H), 1.63-1.58 (m, 4H), 1.50-1.45 (m, 1H). LCMS (ES+) m/z 479 (M+1).

Example 220

5-amino-N-(5-((2S,5R,6R)-5-amino-6-methoxyoxepan-2-yl)-1-methyl-1H-pyrazol-4-yl)-2-(2-(trifluoromethyl)phenyl)thiazole-4-carboxamide 220

Following the procedure for Example 101 starting from tert-butyl N-[2-bromo-4-[[5-[(2S,5R,6R)-5-(tert-butoxycarbonylamino)-6-methoxy-oxepan-2-yl]-1-methyl-pyrazol-4-yl]carbamoyl]thiazol-5-yl]carbamate (Intermediate 98), and replacing 3,6-dihydro-2H-pyran-4-boronic acid pinacol ester with (2-(trifluoromethyl)phenyl)boronic acid gave 220. $^1$H NMR (400 MHz, DMSO-d$_6$) δ 9.39 (s, 1H), 7.93-7.86 (m, 2H), 7.81-7.63 (m, 3H), 7.44 (s, 2H), 5.04 (t, J=5.1 Hz, 1H), 3.73-3.57 (m, 5H), 3.29-3.15 (m, 2H), 2.74 (s, 3H), 2.48-2.35 (m, 1H), 1.65-1.47 (m, 3H), 1.41 (br, 2H). LCMS (ES+) m/z 511 (M+1).

Example 221

N-(5-((2S,5R,6R)-5-amino-6-methoxyoxepan-2-yl)-1-methyl-1H-pyrazol-4-yl)-2-(2,6-difluorophenyl)thiazole-4-carboxamide 221

Following the procedure for Example 101 starting from tert-butyl ((3R,4R,7S)-7-(4-(2-bromothiazole-4-carboxamido)-1-methyl-1H-pyrazol-5-yl)-3-methoxyoxepan-4-yl)carbamate (Intermediate 101), and replacing 3,6-dihydro-2H-pyran-4-boronic acid pinacol ester with (2,6-difluorophenyl)boronic acid gave 221. $^1$H NMR (400 MHz, DMSO-d$_6$) δ 10.11 (s, 1H), 8.65 (s, 1H), 7.92 (s, 1H), 7.74-7.62 (m, 1H), 7.38 (t, J=8.8 Hz, 2H), 5.08 (t, J=5.7 Hz, 1H), 3.93-3.75 (m, 2H), 3.72 (s, 3H), 3.52-3.44 (m, 1H), 3.03 (s, 3H), 2.44-2.32 (m, 1H), 1.81-1.53 (m, 3H). LCMS (ES+) m/z 464 (M+1).

Example 222

N-(5-((2S,5R,6S)-5-amino-6-fluorooxepan-2-yl)-1-methyl-1H-pyrazol-4-yl)-6-(2,5-difluorophenyl)-5-fluoropicolinamide 222

Following the procedure for Example 101 starting from tert-butyl ((3S,4R,7S)-7-(4-(6-bromo-5-fluoropicolinamido)-1-methyl-1H-pyrazol-5-yl)-3-fluorooxepan-4-yl)carbamate (Intermediate 103), and replacing 3,6-dihydro-2H-pyran-4-boronic acid pinacol ester with (2,5-difluorophenyl)boronic acid gave 222. $^1$H NMR (400 MHz, DMSO-d$_6$) δ

10.17 (s, 1H), 8.21 (dd, J=8.6, 3.7 Hz, 1H), 8.09 (dd, J=11.0, 8.6 Hz, 1H), 7.85-7.75 (m, 3H), 7.43 (tt, J=9.2, 2.4 Hz, 1H), 4.83 (dd, J=10.3, 3.8 Hz, 1H), 4.46-4.21 (m, 1H), 4.20-3.89 (m, 2H), 3.80 (s, 3H), 3.18-3.04 (m, 1H), 2.16-2.04 (m, 1H), 1.94-1.79 (m, 1H), 1.75-1.55 (m, 4H). LCMS (ES+) m/z 464 (M+1).

Example 223

N-(5-((2S,5R,6S)-5-amino-6-fluorooxepan-2-yl)-1-methyl-1H-pyrazol-4-yl)-6-(2,3-difluorophenyl)-5-fluoropicolinamide 223

Following the procedure for Example 101 starting from tert-butyl ((3S,4R,7S)-7-(4-(6-bromo-5-fluoropicolinamido)-1-methyl-1H-pyrazol-5-yl)-3-fluorooxepan-4-yl)carbamate (Intermediate 103), and replacing 3,6-dihydro-2H-pyran-4-boronic acid pinacol ester with (2,3-difluorophenyl) boronic acid gave 223. $^1$H NMR (400 MHz, DMSO-$d_6$) δ 10.17 (s, 1H), 8.27 (dd, J=8.7, 3.9 Hz, 1H), 8.12 (t, J=9.1 Hz, 1H), 7.90 (s, 1H), 7.69-7.52 (m, 2H), 7.47-7.37 (m, 1H), 4.84 (dd, J=10.3, 3.7 Hz, 1H), 4.39-4.16 (m, 1H), 4.12-3.86 (m, 2H), 3.76 (s, 3H), 3.15-3.02 (m, 1H), 2.12-2.01 (m, 1H), 1.84-1.70 (m, 1H), 1.70-1.56 (m, 4H). LCMS (ES+) m/z 464 (M+1).

Example 224

N-(5-((2S,5R,6S)-5-amino-6-fluorooxepan-2-yl)-1-methyl-1H-pyrazol-4-yl)-2-(2,6-difluoro-4-(3-hydroxyoxetan-3-yl)phenyl)thiazole-4-carboxamide 224

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with 3-(3,5-difluoro-4-(4,4,5,5-tetramethyl-1,3,2-dioxaborolan-2-yl)phenyl)oxetan-3-ol (see US2012/225062) gave 224. LCMS (ES+) m/z 524 (M+1).

Example 225

N-(5-((2S,5R,6S)-5-amino-6-fluorooxepan-2-yl)-1-methyl-1H-pyrazol-4-yl)-2-(2,6-difluoro-4-(1-hydroxycyclopropyl)phenyl)thiazole-4-carboxamide 225

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with 1-(3,5-difluoro-4-(4,4,5,5-tetramethyl-1,3,2-dioxaborolan-2-yl)phenyl) cyclopropanol (see US2012/225062) gave 225. LCMS (ES+) m/z 508 (M+1).

Example 226

N-(5-((2S,5R,6S)-5-amino-6-fluorooxepan-2-yl)-1-methyl-1H-pyrazol-4-yl)-5-fluoro-6-(2-fluoro-4-methoxyphenyl)picolinamide 226

Following the procedure for Example 101 starting from tert-butyl ((3S,4R,7S)-7-(4-(6-bromo-5-fluoropicolinamido)-1-methyl-1H-pyrazol-5-yl)-3-fluorooxepan-4-yl)carbamate (Intermediate 103), and replacing 3,6-dihydro-2H-pyran-4-boronic acid pinacol ester with (2-fluoro-4-methoxyphenyl)boronic acid gave 226. $^1$H NMR (400 MHz, DMSO-$d_6$) δ 10.12 (s, 1H), 8.18 (dd, J=8.6, 3.8 Hz, 1H), 8.03 (dd, J=9.6, 8.6 Hz, 1H), 7.88 (s, 1H), 7.69 (t, J=8.8 Hz, 1H), 7.04-6.95 (m, 2H), 4.83 (dd, J=10.5, 3.7 Hz, 1H), 4.32 (ddt, J=48.7, 6.0, 2.6 Hz, 1H), 4.16-3.89 (m, 2H), 3.86 (s, 3H), 3.77 (s, 3H), 3.20-3.06 (m, 1H), 2.13-2.01 (m, 1H), 1.88-1.74 (m, 1H), 1.73-1.56 (m, 4H). LCMS (ES+) m/z 476 (M+1).

Example 227

N-(5-((2S,5R,6S)-5-amino-6-fluorooxepan-2-yl)-1-methyl-1H-pyrazol-4-yl)-6-(2-chloro-3-fluorophenyl)-5-fluoropicolinamide 227

Following the procedure for Example 101 starting from tert-butyl ((3S,4R,7S)-7-(4-(6-bromo-5-fluoropicolinamido)-1-methyl-1H-pyrazol-5-yl)-3-fluorooxepan-4-yl)carbamate (Intermediate 103), and replacing 3,6-dihydro-2H-pyran-4-boronic acid pinacol ester with (2-chloro-3-fluorophenyl)boronic acid gave 227. $^1$H NMR (400 MHz, DMSO-$d_6$) δ 10.18 (s, 1H), 8.28 (dd, J=8.6, 3.9 Hz, 1H), 8.12 (t, J=8.9 Hz, 1H), 7.89 (s, 1H), 7.64-7.45 (m, 3H), 4.81 (dd, J=10.3, 3.8 Hz, 1H), 4.20 (ddt, J=49.1, 5.7, 2.7 Hz, 1H), 4.05-3.80 (m, 2H), 3.75 (s, 3H), 3.09-2.95 (m, 1H), 2.10-1.99 (m, 1H), 1.82-1.64 (m, 1H), 1.66-1.56 (m, 2H), 1.53 (br, 2H). LCMS (ES+) m/z 480 (M+1).

Example 228

N-(5-((2S,5R,6S)-5-amino-6-fluorooxepan-2-yl)-1-methyl-1H-pyrazol-4-yl)-2-(1-(2-hydroxy-2-methylpropyl)-1H-pyrazol-4-yl)thiazole-4-carboxamide 228

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with 2-methyl-1-(4-(4,4,5,5-tetramethyl-1,3,2-dioxaborolan-2-yl)-1H-pyrazol-1-yl) propan-2-ol (see US2011/76291) gave 228. $^1$H NMR (400 MHz, DMSO-$d_6$) δ 9.77 (s, 1H), 8.32 (s, 1H), 8.22 (s, 1H), 8.04 (s, 1H), 7.88 (s, 1H), 4.88 (dd, J=10.0, 3.9 Hz, 1H), 4.69-4.42 (m, 1H), 4.39-4.24 (m, 1H), 4.17-3.95 (m, 4H), 3.77 (s, 3H), 2.15-2.05 (m, 1H), 1.89-1.68 (m, 3H), 1.10 (d, J=4.4 Hz, 6H). LCMS (ES+) m/z 478 (M+1).

Example 229

N-(5-((2S,5R,6S)-5-amino-6-fluorooxepan-2-yl)-1-methyl-1H-pyrazol-4-yl)-2-(2,6-difluoro-3-methoxyphenyl)thiazole-4-carboxamide 229

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with (2,6-difluoro-3-methoxyphenyl)boronic acid gave 229. $^1$H NMR (400 MHz, DMSO-$d_6$) δ 9.88 (s, 1H), 8.63 (s, 1H), 7.78 (s, 1H), 7.40 (td, J=9.3, 5.1 Hz, 1H), 7.27 (td, J=9.5, 1.9 Hz, 1H), 4.81 (dd, J=10.9, 3.6 Hz, 1H), 4.37 (d, J=47.9 Hz, 1H), 4.24-4.10 (m, 1H), 4.10-3.92 (m, 1H), 3.90 (s, 3H), 3.78 (s, 3H), 3.29-3.19 (m, 1H), 2.11-2.01 (m, 1H), 1.87-1.77 (m, 1H), 1.75-1.66 (m, 2H). LCMS (ES+) m/z 482 (M+1).

Example 230

N-(5-((2S,5R,6R)-5-amino-6-fluorooxepan-2-yl)-1-methyl-1H-pyrazol-4-yl)-2-(2,3,6-trifluorophenyl)thiazole-4-carboxamide 230

Following the procedure for Example 101 starting from tert-butyl ((3R,4R,7S)-7-(4-(2-bromothiazole-4-carboxamido)-1-methyl-1H-pyrazol-5-yl)-3-fluorooxepan-4-yl)carbamate (Intermediate 100), and replacing 3,6-dihydro-2H-pyran-4-boronic acid pinacol ester with (2,3,6-trifluorophenyl)boronic acid gave 230. $^1$H NMR (400 MHz, DMSO-$d_6$) δ 10.00 (s, 1H), 8.68 (s, 1H), 7.85 (s, 1H), 7.75 (qd, J=9.4, 4.9 Hz, 1H), 7.43 (tdd, J=9.7, 4.0, 2.1 Hz, 1H), 5.09-4.78 (m, 2H), 4.19-3.91 (m, 2H), 3.75 (s, 3H), 3.44-3.30 (m, 1H), 2.24-2.12 (m, 1H), 1.93-1.65 (m, 3H). LCMS (ES+) m/z 470 (M+1).

Example 231

N-(5-((2S,5R,6S)-5-amino-6-fluorooxepan-2-yl)-1-methyl-1H-pyrazol-4-yl)-2-(3-methylpyridin-2-yl)thiazole-4-carboxamide 231

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with (3-methylpyridin-2-yl)boronic acid gave 231. $^1$H NMR (400 MHz, DMSO-$d_6$) δ 9.51 (s, 1H), 8.53 (dd, J=4.7, 1.5 Hz, 1H), 8.47 (s, 1H), 7.91-7.83 (m, 1H), 7.81 (s, 1H), 7.45 (dd, J=7.7, 4.6 Hz, 1H), 4.84 (dd, J=10.7, 3.6 Hz, 1H), 4.53-4.30 (m, 1H), 4.25-3.94 (m, 2H), 3.79 (s, 3H), 3.29-3.12 (m, 1H), 2.85 (s, 3H), 2.51 (s, 1H), 2.13-2.02 (m, 1H), 1.94-1.79 (m, 1H), 1.76-1.62 (m, 4H). LCMS (ES+) m/z 431 (M+1).

Example 232

N-(5-((2S,5R,6S)-5-amino-6-fluorooxepan-2-yl)-1-methyl-1H-pyrazol-4-yl)-2-(2-methoxypyridin-3-yl)thiazole-4-carboxamide 232

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with (2-methoxypyridin-3-yl)boronic acid gave 232. LCMS (ES+) m/z 447 (M+1).

Example 233

N-(5-((2S,5R,6S)-5-amino-6-fluorooxepan-2-yl)-1-methyl-1H-pyrazol-4-yl)-2-(2-oxo-1,2-dihydropyridin-3-yl)thiazole-4-carboxamide 233

The title compound was isolated as a second product formed during the synthesis of Example 232. $^1$H NMR (400 MHz, DMSO-$d_6$) δ 9.87 (s, 1H), 8.72 (dd, J=7.1, 2.1 Hz, 1H), 8.30 (s, 1H), 7.91 (s, 1H), 7.70 (dd, J=6.3, 2.1 Hz, 1H), 6.49 (t, J=6.7 Hz, 1H), 4.87 (dd, J=10.4, 3.6 Hz, 1H), 4.50 (ddd, J=49.4, 7.1, 2.9 Hz, 1H), 4.40-4.25 (m, 1H), 4.20-3.94 (m, 1H), 3.78 (s, 3H), 3.40-3.29 (m, 1H), 2.13-2.00 (m, 1H), 1.90-1.65 (m, 3H). LCMS (ES+) m/z 433 (M+1).

Example 234

N-(5-((2S,5R,6S)-5-amino-6-fluorooxepan-2-yl)-1-methyl-1H-pyrazol-4-yl)-2-(3,5-dimethylisoxazol-4-yl)thiazole-4-carboxamide 234

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with (3,5-dimethylisoxazol-4-yl)boronic acid gave 234. $^1$H NMR (400 MHz, DMSO-$d_6$) δ 9.57 (s, 1H), 8.47 (s, 1H), 7.78 (s, 1H), 4.82 (dd, J=10.8, 3.6 Hz, 1H), 4.56-4.32 (m, 1H), 4.25-3.93 (m, 2H), 3.79 (s, 3H), 3.27-3.13 (m, 1H), 2.74 (s, 3H), 2.53 (s, 3H), 2.13-2.01 (m, 1H), 1.93-1.78 (m, 1H), 1.77-1.64 (m, 2H). LCMS (ES+) m/z 435 (M+1).

Example 235

N-(5-((2S,5R,6S)-5-amino-6-fluorooxepan-2-yl)-1-methyl-1H-pyrazol-4-yl)-2-(1-cyclopropyl-1H-pyrazol-4-yl)thiazole-4-carboxamide 235

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with 1-cyclopropyl-4-(4,4,5,5-tetramethyl-1,3,2-dioxaborolan-2-yl)-1H-pyrazole gave 235. $^1$H NMR (400 MHz, DMSO-$d_6$) δ 9.75 (s, 1H), 8.44 (s, 1H), 8.22 (s, 1H), 8.03 (s, 1H), 7.90 (s, 1H), 4.92-4.83 (m, 1H), 4.59-4.40 (m, 1H), 4.32 (dd, J=22.2, 15.0 Hz, 1H), 4.19-3.93 (m, 1H), 3.80 (dd, J=7.4, 3.7 Hz, 1H), 3.77 (s, 3H), 3.38-3.31 (m, 1H), 2.12-2.03 (m, 1H), 1.87-1.66 (m, 5H), 1.17-0.96 (m, 4H). LCMS (ES+) m/z 446 (M+1).

Example 236

N-(5-((2S,5R,6S)-5-amino-6-fluorooxepan-2-yl)-1-methyl-1H-pyrazol-4-yl)-2-(2,3,5-trifluorophenyl)thiazole-4-carboxamide 236

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with (2,3,5-trifluorophenyl)boronic acid gave 236. $^1$H NMR (400 MHz, DMSO-$d_6$) δ 9.92 (s, 1H), 8.63 (s, 1H), 8.14-8.04 (m, 1H), 7.83-7.71 (m, 2H), 4.85 (dd, J=10.7, 3.5 Hz, 1H), 4.71-4.46 (m, 1H), 4.36-4.22 (m, 1H), 4.20-3.94 (m, 1H), 3.81 (s, 3H), 3.45-3.31 (m, 1H), 2.16-2.07 (m, 1H), 1.98-1.76 (m, 3H). LCMS (ES+) m/z 470 (M+1).

Example 237

N-(5-((2S,5R,6S)-5-amino-6-fluorooxepan-2-yl)-1-methyl-1H-pyrazol-4-yl)-2-(3-fluoropyridin-2-yl)thiazole-4-carboxamide 237

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with (3-fluoropyridin-2-yl)boronic acid gave 237. LCMS (ES+) m/z 435 (M+1).

Example 238

N-(5-((2S,5R,6S)-5-amino-6-fluorooxepan-2-yl)-1-methyl-1H-pyrazol-4-yl)-2-(2-fluoro-5-methylphenyl)thiazole-4-carboxamide 238

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with (2-fluoro-5-methylphenyl)boronic acid gave 238. $^1$H NMR (400 MHz, DMSO-d$_6$) δ 9.86 (s, 1H), 8.52 (s, 1H), 8.22 (dd, J=7.3, 2.2 Hz, 1H), 7.84 (s, 1H), 7.43-7.29 (m, 2H), 4.89 (dd, J=10.1, 3.9 Hz, 1H), 4.57-4.37 (m, 1H), 4.35-4.20 (m, 1H), 4.17-3.94 (m, 1H), 3.79 (s, 3H), 3.29-3.17 (m, 1H), 2.40 (s, 3H), 2.19-2.07 (m, 1H), 1.92-1.77 (m, 1H), 1.76-1.66 (m, 4H). LCMS (ES+) m/z 448 (M+1).

Example 239

N-(5-((2S,5R,6S)-5-amino-6-fluorooxepan-2-yl)-1-methyl-1H-pyrazol-4-yl)-2-(5-fluoropyridin-3-yl)thiazole-4-carboxamide 239

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with (5-fluoropyridin-3-yl)boronic acid gave 239. $^1$H NMR (400 MHz, DMSO-d$_6$) δ 9.87 (s, 1H), 9.15 (t, J=1.7 Hz, 1H), 8.74 (d, J=2.7 Hz, 1H), 8.55 (s, 1H), 8.37 (dt, J=9.5, 2.3 Hz, 1H), 7.84 (s, 1H), 4.87 (dd, J=10.5, 3.9 Hz, 1H), 4.58-4.36 (m, 1H), 4.34-4.20 (m, 1H), 4.16-3.92 (m, 1H), 3.79 (s, 3H), 3.37-3.23 (m, 2H), 2.15-2.05 (m, 1H), 1.91-1.67 (m, 5H). LCMS (ES+) m/z 435 (M+1).

Example 240

N-(5-((2S,5R,6S)-5-amino-6-fluorooxepan-2-yl)-1-methyl-1H-pyrazol-4-yl)-2-(3-fluoropyridin-4-yl)thiazole-4-carboxamide 240

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with (3-fluoropyridin-4-yl)boronic acid gave 240. $^1$H NMR (400 MHz, DMSO-d$_6$) δ 10.09 (s, 1H), 8.87 (d, J=2.4 Hz, 1H), 8.73-8.64 (m, 2H), 8.23 (dd, J=6.4, 5.0 Hz, 1H), 7.78 (s, 1H), 5.04-4.77 (m, 2H), 4.25-4.09 (m, 1H), 4.06-3.92 (m, 1H), 3.78 (s, 3H), 3.27-3.20 (m, 1H), 2.19-2.08 (m, 1H), 1.91-1.76 (m, 3H), 1.69-1.59 (m, 1H). LCMS (ES+) m/z 435 (M+1).

Example 241

N-(5-((2S,5R,6S)-5-amino-6-fluorooxepan-2-yl)-1-methyl-1H-pyrazol-4-yl)-2-(1,3-dimethyl-1H-pyrazol-4-yl)thiazole-4-carboxamide 241

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with (1,3-dimethyl-1H-pyrazol-4-yl)boronic acid gave 241. $^1$H NMR (400 MHz, DMSO-d$_6$) δ 9.63 (s, 1H), 8.28 (s, 1H), 8.24 (s, 1H), 7.84 (s, 1H), 4.95-4.83 (m, 1H), 4.83-4.62 (m, 1H), 4.42-4.28 (m, 1H), 4.24-4.05 (m, 1H), 3.83 (s, 3H), 3.78 (s, 3H), 3.48 (dd, J=17.3, 8.4 Hz, 1H), 2.47 (s, 3H), 2.15-2.06 (m, 1H), 1.87 (d, J=14.4 Hz, 4H). LCMS (ES+) m/z 434 (M+1).

Example 242

N-(5-((2S,5R,6S)-5-amino-6-fluorooxepan-2-yl)-1-methyl-1H-pyrazol-4-yl)-2-(1,5-dimethyl-1H-pyrazol-4-yl)thiazole-4-carboxamide 242

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with 1,5-dimethyl-4-(4,4,5,5-tetramethyl-1,3,2-dioxaborolan-2-yl)-1H-pyrazole gave 242. $^1$H NMR (400 MHz, DMSO-d$_6$) δ 9.61 (s, 1H), 8.24 (s, 1H), 7.95 (s, 1H), 7.83 (s, 1H), 4.84 (dd, J=10.6, 3.8 Hz, 1H), 4.55-4.32 (m, 1H), 4.28-4.14 (m, 1H), 4.13-3.94 (m, 1H), 3.81 (s, 3H), 3.78 (s, 3H), 3.29-3.16 (m, 1H), 2.61 (s, 3H), 2.12-2.02 (m, 1H), 1.91-1.78 (m, 1H), 1.75-1.64 (m, 4H). LCMS (ES+) m/z 434 (M+1).

Example 243

N-(5-((2S,5R,6S)-5-amino-6-fluorooxepan-2-yl)-1-methyl-1H-pyrazol-4-yl)-2-(2,3,6-trifluorophenyl)thiazole-4-carboxamide 243

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with (2,3,6-trifluorophenyl)boronic acid gave 243. $^1$H NMR (400 MHz, DMSO-d$_6$) δ 9.93 (s, 1H), 8.67 (s, 1H), 7.83 (s, 1H), 7.73 (qd, J=9.5, 5.0 Hz, 1H), 7.38 (tdd, J=9.5, 3.9, 2.1 Hz, 1H), 4.83 (dd, J=10.7, 3.6 Hz, 1H), 4.45-4.23 (m, 1H), 4.17 (ddd, J=21.9, 15.0, 1.8 Hz, 1H), 4.08-3.89 (m, 1H), 3.77 (s, 3H), 3.29-3.13 (m, 1H), 2.12-2.01 (m, 1H), 1.87-1.72 (m, 1H), 1.72-1.60 (m, 4H). LCMS (ES+) m/z 470 (M+1).

Example 244

N-(5-((2S,5R,6R)-5-amino-6-fluorooxepan-2-yl)-1-methyl-1H-pyrazol-4-yl)-2-(3,5-dimethylisoxazol-4-yl)thiazole-4-carboxamide 244

Following the procedure for Example 101 starting from tert-butyl ((3R,4R,7S)-7-(4-(2-bromothiazole-4-carboxamido)-1-methyl-1H-pyrazol-5-yl)-3-fluorooxepan-4-yl)carbamate (Intermediate 100), and replacing 3,6-dihydro-2H-pyran-4-boronic acid pinacol ester with (3,5-dimethylisoxazol-4-yl)boronic acid gave 244. $^1$H NMR (400 MHz, DMSO-d$_6$) δ 9.63 (s, 1H), 8.47 (s, 1H), 7.83 (s, 1H), 5.01 (d, J=50.4 Hz, 1H), 4.84 (d, J=10.2 Hz, 1H), 4.24-4.06 (m, 1H), 4.06-3.88 (m, 1H), 3.78 (s, 3H), 3.45-3.31 (m, 1H), 2.77 (s, 3H), 2.56 (s, 3H), 2.09-1.84 (m, 3H), 1.76-1.68 (m, 1H). LCMS (ES+) m/z 435 (M+1).

Example 245

N-(5-((2S,5R,6R)-5-amino-6-fluorooxepan-2-yl)-1-methyl-1H-pyrazol-4-yl)-2-(2,3-difluorophenyl)thiazole-4-carboxamide 245

Following the procedure for Example 101 starting from tert-butyl ((3R,4R,7S)-7-(4-(2-bromothiazole-4-carboxamido)-1-methyl-1H-pyrazol-5-yl)-3-fluorooxepan-4-yl)carbamate (Intermediate 100), and replacing 3,6-dihydro-2H-pyran-4-boronic acid pinacol ester with (2,3-difluorophenyl) boronic acid gave 245. $^1$H NMR (400 MHz, DMSO-d$_6$) δ 10.04 (s, 1H), 8.59 (s, 1H), 8.15-8.06 (m, 1H), 7.77 (s, 1H), 7.72-7.60 (m, 1H), 7.51-7.41 (m, 1H), 5.12-4.82 (m, 2H), 4.26-4.10 (m, 1H), 4.07-3.93 (m, 1H), 3.78 (s, 3H), 3.44-3.30 (m, 1H), 2.15 (ddd, J=11.7, 6.2, 3.5 Hz, 1H), 1.97-1.79 (m, 2H), 1.69 (d, J=13.1 Hz, 1H). LCMS (ES+) m/z 452 (M+1).

Example 246

N-(5-((2S,5R,6R)-5-amino-6-fluorooxepan-2-yl)-1-methyl-1H-pyrazol-4-yl)-2-(5-fluoropyridin-3-yl)thiazole-4-carboxamide 246

Following the procedure for Example 101 starting from tert-butyl ((3R,4R,7S)-7-(4-(2-bromothiazole-4-carboxamido)-1-methyl-1H-pyrazol-5-yl)-3-fluorooxepan-4-yl)carbamate (Intermediate 100), and replacing 3,6-dihydro-2H-pyran-4-boronic acid pinacol ester with (5-fluoropyridin-3-yl)boronic acid gave 246. $^1$H NMR (400 MHz, DMSO-d$_6$) δ 10.01 (s, 1H), 9.13 (t, J=1.7 Hz, 1H), 8.76 (d, J=2.8 Hz, 1H), 8.55 (s, 1H), 8.40-8.32 (m, 1H), 7.72 (s, 1H), 5.05-4.73 (m, 2H), 4.21-4.05 (m, 1H), 4.05-3.91 (m, 1H), 3.79 (s, 3H), 3.29-3.24 (m, 1H), 2.21-2.10 (m, 1H), 1.94-1.77 (m, 2H), 1.71-1.61 (m, 1H). LCMS (ES+) m/z 435 (M+1).

Example 247

N-(5-((2S,5R,6R)-5-amino-6-fluorooxepan-2-yl)-1-methyl-1H-pyrazol-4-yl)-2-(3,5-difluoropyridin-4-yl)thiazole-4-carboxamide 247

Following the procedure for Example 101 starting from tert-butyl ((3R,4R,7S)-7-(4-(2-bromothiazole-4-carboxamido)-1-methyl-1H-pyrazol-5-yl)-3-fluorooxepan-4-yl)carbamate (Intermediate 100), and replacing 3,6-dihydro-2H-pyran-4-boronic acid pinacol ester with (3,5-difluoropyridin-4-yl)boronic acid gave 247. LCMS (ES+) m/z 453 (M+1).

Example 248

N-(5-((2S,5R,6R)-5-amino-6-fluorooxepan-2-yl)-1-methyl-1H-pyrazol-4-yl)-2-(3-chloro-2-fluorophenyl)thiazole-4-carboxamide 248

Following the procedure for Example 101 starting from tert-butyl ((3R,4R,7S)-7-(4-(2-bromothiazole-4-carboxamido)-1-methyl-1H-pyrazol-5-yl)-3-fluorooxepan-4-yl)carbamate (Intermediate 100), and replacing 3,6-dihydro-2H-pyran-4-boronic acid pinacol ester with (3-chloro-2-fluorophenyl)boronic acid gave 248. $^1$H NMR (400 MHz, DMSO-d$_6$) δ 10.10 (s, 1H), 8.59 (s, 1H), 8.30-8.21 (m, 1H), 7.86-7.77 (m, 2H), 7.52-7.43 (m, 1H), 5.05-4.77 (m, 2H), 4.16 (ddd, J=24.7, 13.6, 4.7 Hz, 1H), 3.99 (ddd, J=17.9, 13.5, 4.8 Hz, 1H), 3.77 (s, 3H), 3.27-3.22 (m, 1H), 2.18-2.09 (m, 1H), 1.88-1.78 (m, 2H), 1.71-1.60 (m, 3H). LCMS (ES+) m/z 468 (M+1).

Example 249

N-(5-((2S,5R,6R)-5-amino-6-fluorooxepan-2-yl)-1-methyl-1H-pyrazol-4-yl)-2-(3'-chloro-2,2'-difluoro-[1,1'-biphenyl]-3-yl)thiazole-4-carboxamide 249

The title compound was isolated as a second product during the synthesis of Example 248. $^1$H NMR (400 MHz, DMSO-d$_6$) δ 10.13 (s, 1H), 8.58 (s, 1H), 8.47-8.38 (m, 1H), 7.84-7.67 (m, 3H), 7.64-7.52 (m, 2H), 7.42 (t, J=7.9 Hz, 1H), 5.04-4.75 (m, 2H), 4.26-4.10 (m, 1H), 4.08-3.94 (m, 1H), 3.78 (s, 3H), 3.28-3.23 (m, 1H), 2.20-2.10 (m, 1H), 1.87-1.78 (m, 2H), 1.71-1.61 (m, 3H). LCMS (ES+) m/z 562 (M+1).

Example 250

N-(5-((2S,5R,6R)-5-amino-6-fluorooxepan-2-yl)-1-methyl-1H-pyrazol-4-yl)-2-(2-chloro-3-fluorophenyl)thiazole-4-carboxamide 250

Following the procedure for Example 101 starting from tert-butyl ((3R,4R,7S)-7-(4-(2-bromothiazole-4-carboxamido)-1-methyl-1H-pyrazol-5-yl)-3-fluorooxepan-4-yl)carbamate (Intermediate 100), and replacing 3,6-dihydro-2H-pyran-4-boronic acid pinacol ester with (2-chloro-3-fluorophenyl)boronic acid gave 250. $^1$H NMR (400 MHz, DMSO-d$_6$) δ 10.08 (s, 1H), 8.62 (s, 1H), 8.19-8.11 (m, 1H), 7.81 (s, 1H), 7.70-7.57 (m, 2H), 5.02-4.71 (m, 2H), 4.18-3.90 (m, 2H), 3.77 (s, 3H), 3.34-3.18 (m, 1H), 2.20-2.10 (m, 1H), 1.86-1.72 (m, 2H), 1.68-1.59 (m, 3H). LCMS (ES+) m/z 468 (M+1).

Example 251

N-(5-((2S,5R,6R)-5-amino-6-fluorooxepan-2-yl)-1-methyl-1H-pyrazol-4-yl)-2-(2'-chloro-3',6-difluoro-[1,1'-biphenyl]-2-yl)thiazole-4-carboxamide 251

The title compound was isolated as a second product during the synthesis of Example 250. $^1$H NMR (400 MHz, DMSO-d$_6$) δ 9.95 (s, 1H), 8.31 (s, 1H), 8.26-8.18 (m, 1H), 7.80-7.53 (m, 6H), 7.42-7.33 (m, 1H), 5.02-4.77 (m, 2H), 4.25-4.06 (m, 1H), 4.05-3.92 (m, 1H), 3.77 (s, 3H), 3.25 (s, 1H), 2.14 (s, 1H), 1.91-1.55 (m, 5H). LCMS (ES+) m/z 562 (M+1).

Example 252

N-(5-((2S,5R,6R)-5-amino-6-fluorooxepan-2-yl)-1-methyl-1H-pyrazol-4-yl)-2-(1-methyl-3-(trifluoromethyl)-1H-pyrazol-4-yl)thiazole-4-carboxamide 252

Following the procedure for Example 101 starting from tert-butyl ((3R,4R,7S)-7-(4-(2-bromothiazole-4-carboxamido)-1-methyl-1H-pyrazol-5-yl)-3-fluorooxepan-4-yl)carbamate (Intermediate 100), and replacing 3,6-dihydro-2H-pyran-4-boronic acid pinacol ester with (1-methyl-3-(trifluoromethyl)-1H-pyrazol-4-yl)boronic acid gave 252. $^1$H NMR (400 MHz, DMSO-d$_6$) δ 9.64 (s, 1H), 8.63 (s, 1H), 8.42 (s, 1H), 7.88 (s, 1H), 4.98-4.72 (m, 2H), 4.22-4.03 (m, 1H), 4.00 (s, 3H), 3.97-3.88 (m, 1H), 3.75 (s, 3H), 3.30-3.17 (m, 1H), 2.14-2.03 (m, 1H), 1.92-1.68 (m, 3H), 1.66-1.57 (m, 1H). LCMS (ES+) m/z 488 (M+1).

Example 253

N-(5-((2S,5R,6R)-5-amino-6-fluorooxepan-2-yl)-1-methyl-1H-pyrazol-4-yl)-2-(3-cyclopropyl-1-methyl-1H-pyrazol-4-yl)thiazole-4-carboxamide 253

Following the procedure for Example 101 starting from tert-butyl ((3R,4R,7S)-7-(4-(2-bromothiazole-4-carboxamido)-1-methyl-1H-pyrazol-5-yl)-3-fluorooxepan-4-yl)carbamate (Intermediate 100), and replacing 3,6-dihydro-2H-pyran-4-boronic acid pinacol ester with 3-cyclopropyl-1-methyl-4-(4,4,5,5-tetramethyl-1,3,2-dioxaborolan-2-yl)-1H-pyrazole gave 253. $^1$H NMR (400 MHz, DMSO-$d_6$) δ 9.76 (s, 1H), 8.27 (s, 1H), 8.20 (s, 1H), 7.81 (s, 1H), 5.02-4.76 (m, 2H), 4.16-3.90 (m, 2H), 3.80 (s, 3H), 3.76 (s, 3H), 3.29-3.16 (m, 1H), 2.41-2.30 (m, 1H), 2.18-2.09 (m, 1H), 1.86-1.74 (m, 2H), 1.66-1.58 (m, 1H), 1.02-0.90 (m, 2H), 0.89-0.80 (m, 2H). LCMS (ES+) m/z 460 (M+1).

Example 254

5-amino-N-(5-((2S,5R,6R)-5-amino-6-fluorooxepan-2-yl)-1-methyl-1H-pyrazol-4-yl)-2-(1,3-dimethyl-1H-pyrazol-4-yl)thiazole-4-carboxamide 254

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (1,3-dimethyl-1H-pyrazol-4-yl)boronic acid gave 254. $^1$H NMR (400 MHz, DMSO-$d_6$) δ 9.15 (s, 1H), 7.84 (s, 1H), 7.65 (s, 1H), 7.25 (s, 2H), 5.00-4.73 (m, 2H), 4.16-3.89 (m, 2H), 3.78 (s, 3H), 3.72 (s, 3H), 3.22 (dd, J=25.0, 9.5 Hz, 1H), 2.56 (s, 3H), 2.10-2.01 (m, 1H), 1.90-1.71 (m, 3H), 1.66-1.58 (m, 1H). LCMS (ES+) m/z 449 (M+1).

Example 255

5-amino-N-(5-((2S,5R,6R)-5-amino-6-fluorooxepan-2-yl)-1-methyl-1H-pyrazol-4-yl)-2-(1,5-dimethyl-1H-pyrazol-4-yl)thiazole-4-carboxamide 255

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (1,5-dimethyl-1H-pyrazol-4-yl)boronic acid gave 255. $^1$H NMR (400 MHz, DMSO-$d_6$) δ 9.15 (s, 1H), 7.84 (s, 1H), 7.65 (s, 1H), 7.25 (s, 2H), 4.96-4.76 (m, 2H), 4.16-3.89 (m, 2H), 3.79 (s, 3H), 3.72 (s, 3H), 3.29-3.15 (m, 1H), 2.56 (s, 3H), 2.11-2.00 (m, 1H), 1.90-1.71 (m, 4H), 1.66-1.58 (m, 1H). LCMS (ES+) m/z 449 (M+1).

Example 256

5-amino-N-(5-((2S,5R,6R)-5-amino-6-fluorooxepan-2-yl)-1-methyl-1H-pyrazol-4-yl)-2-(1-isopropyl-1H-pyrazol-4-yl)thiazole-4-carboxamide 256

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (1-isopropyl-1H-pyrazol-4-yl)boronic acid gave 256. $^1$H NMR (400 MHz, DMSO-$d_6$) δ 9.37 (s, 1H), 8.15 (s, 1H), 7.83 (s, 1H), 7.77 (s, 1H), 7.25 (s, 2H), 5.12-4.80 (m, 2H), 4.60-4.45 (m, 1H), 4.18-3.95 (m, 2H), 3.72 (s, 3H), 3.38-3.26 (m, 1H), 2.33-2.22 (m, 1H), 1.83-1.56 (m, 5H), 1.44 (d, J=6.7 Hz, 6H). LCMS (ES+) m/z 463 (M+1).

Example 257

5-amino-N-(5-((2S,5R,6S)-5-amino-6-fluorooxepan-2-yl)-1-methyl-1H-pyrazol-4-yl)-2-(1,5-dimethyl-1H-pyrazol-4-yl)thiazole-4-carboxamide 257

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate (Intermediate 95), and replacing 3,6-dihydro-2H-pyran-4-boronic acid pinacol ester with (1,5-dimethyl-1H-pyrazol-4-yl)boronic acid gave 257. $^1$H NMR (400 MHz, DMSO-$d_6$) δ 9.01 (s, 1H), 7.80 (s, 1H), 7.72 (s, 1H), 7.25 (s, 2H), 4.79 (dd, J=10.7, 3.6 Hz, 1H), 4.41 (ddd, J=49.5, 4.9, 2.7 Hz, 1H), 4.26-3.94 (m, 2H), 3.76 (d, J=5.4 Hz, 6H), 3.30-3.16 (m, 1H), 2.52 (s, 3H), 2.04 (dq, J=11.8, 4.1 Hz, 1H), 1.81 (dd, J=13.6, 10.0 Hz, 1H), 1.73-1.64 (m, 2H). LCMS (ES+) m/z 449 (M+1).

Example 258

N-(5-((2S,5R,6R)-5-amino-6-methoxyoxepan-2-yl)-1-methyl-1H-pyrazol-4-yl)-2-(2,3,6-trifluorophenyl)thiazole-4-carboxamide 258

Following the procedure for Example 101 starting from tert-butyl ((3R,4R,7S)-7-(4-(2-bromothiazole-4-carboxamido)-1-methyl-1H-pyrazol-5-yl)-3-methoxyoxepan-4-yl)carbamate (Intermediate 101), and replacing 3,6-dihydro-2H-pyran-4-boronic acid pinacol ester with (2,3,6-trifluorophenyl)boronic acid gave 258. $^1$H NMR (400 MHz, DMSO-$d_6$) δ 10.15 (s, 1H), 8.69 (s, 1H), 7.95 (s, 1H), 7.77 (qd, J=9.4, 4.9 Hz, 1H), 7.49-7.38 (m, 1H), 5.12 (t, J=5.6 Hz, 1H), 3.91-3.76 (m, 2H), 3.71 (s, 3H), 3.46-3.36 (m, 1H), 3.32-3.21 (m, 1H), 3.01 (s, 3H), 2.49-2.36 (m, 1H), 1.73-1.49 (m, 3H), 1.41 (br, 2H). LCMS (ES+) m/z 482 (M+1).

Example 259

5-amino-N-(5-((2S,5R,6R)-5-amino-6-fluorooxepan-2-yl)-1-methyl-1H-pyrazol-4-yl)-2-(2-fluoro-4-(trifluoromethyl)phenyl)thiazole-4-carboxamide 259

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (2-fluoro-4-(trifluoromethyl)phenyl)boronic acid gave 259. $^1$H NMR (400 MHz, DMSO-$d_6$) δ 9.54 (s, 1H), 8.31 (q, J=9.1, 8.5 Hz, 1H), 7.93-7.84 (m, 1H), 7.83-7.71 (m, 2H), 7.61 (s, 2H), 5.17-4.82 (m, 2H), 4.31-4.14 (m, 1H), 4.08-3.93 (m, 1H), 3.77 (s, 3H), 3.51-3.37 (m, 1H), 2.19-2.05 (m, 1H), 1.98-1.81 (m, 2H), 1.75-1.67 (m, 1H). LCMS (ES+) m/z 517 (M+1).

Example 260

5-amino-N-(5-((2S,5R,6R)-5-amino-6-fluorooxepan-2-yl)-1-methyl-1H-pyrazol-4-yl)-2-(2,3,6-trifluorophenyl)thiazole-4-carboxamide 260

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (2,3,6-trifluorophenyl)boronic acid gave 260. $^1$H NMR (400 MHz, DMSO-$d_6$) δ 9.47 (s, 1H), 7.85 (s, 1H), 7.65-7.52 (m, 3H), 7.39-7.27 (m, 1H), 5.03-4.83 (m, 2H), 4.16-3.90 (m, 2H), 3.73 (s, 3H), 3.39 (dd, J=7.1, 4.6 Hz, 1H), 2.18 (ddd, J=15.1, 6.7, 3.5 Hz, 1H), 1.87 (dt, J=14.1, 10.3 Hz, 1H), 1.69 (dtd, J=18.1, 13.8, 11.5, 7.4 Hz, 2H). LCMS (ES+) m/z 485 (M+1).

Example 261

5-amino-N-(5-((2S,5R,6R)-5-amino-6-fluorooxepan-2-yl)-1-methyl-1H-pyrazol-4-yl)-2-(2,3,5-trifluorophenyl)thiazole-4-carboxamide 261

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (2,3,5-trifluorophenyl)boronic acid gave 261. $^1$H NMR (400 MHz, DMSO-$d_6$) δ 9.52 (s, 1H), 7.80 (d, J=9.1 Hz, 1H), 7.67 (s, 1H), 7.60 (d, J=9.5 Hz, 3H), 5.05-4.71 (m, 2H), 4.20-3.90 (m, 2H), 3.77 (s, 3H), 3.31-3.26 (m, 1H), 2.19-2.09 (m, 1H), 1.91-1.78 (m, 2H), 1.69-1.64 (m, 1H). LCMS (ES+) m/z 485 (M+1).

Example 262

5-amino-N-(5-((2S,5R,6R)-5-amino-6-methoxyoxepan-2-yl)-1-methyl-1H-pyrazol-4-yl)-2-(2,3,6-trifluorophenyl)thiazole-4-carboxamide 262

Following the procedure for Example 101 starting from tert-butyl N-[2-bromo-4-[[5-[(2S,5R,6R)-5-(tert-butoxycarbonylamino)-6-methoxy-oxepan-2-yl]-1-methyl-pyrazol-4-yl]carbamoyl]thiazol-5-yl]carbamate (Intermediate 98), and replacing 3,6-dihydro-2H-pyran-4-boronic acid pinacol ester with (2,3,6-trifluorophenyl)boronic acid gave 262. $^1$H NMR (400 MHz, DMSO-$d_6$) δ 9.60 (s, 1H), 7.91 (s, 1H), 7.66-7.53 (m, 3H), 7.37-7.26 (m, 1H), 5.08 (t, J=5.6 Hz, 1H), 3.92-3.71 (m, 2H), 3.69 (s, 3H), 3.46-3.33 (m, 1H), 3.33-3.21 (m, 1H), 3.02 (s, 3H), 2.47-2.35 (m, 1H), 1.76-1.63 (m, 1H), 1.62-1.50 (m, 2H). LCMS (ES+) m/z 497 (M+1).

Example 263

5-amino-N-(5-((2S,5R,6R)-5-amino-6-methoxyoxepan-2-yl)-1-methyl-1H-pyrazol-4-yl)-2-(2,3,5-trifluorophenyl)thiazole-4-carboxamide 263

Following the procedure for Example 101 starting from tert-butyl N-[2-bromo-4-[[5-[(2S,5R,6R)-5-(tert-butoxycarbonylamino)-6-methoxy-oxepan-2-yl]-1-methyl-pyrazol-4-yl]carbamoyl]thiazol-5-yl]carbamate (Intermediate 98), and replacing 3,6-dihydro-2H-pyran-4-boronic acid pinacol ester with (2,3,5-trifluorophenyl)boronic acid gave 263. $^1$H NMR (400 MHz, DMSO-$d_6$) δ 9.51 (s, 1H), 7.88-7.79 (m, 1H), 7.68-7.54 (m, 4H), 4.96 (dd, J=8.7, 3.5 Hz, 1H), 4.06 (dd, J=13.1, 4.2 Hz, 1H), 3.92 (dd, J=13.2, 6.0 Hz, 1H), 3.77 (s, 3H), 3.70-3.64 (m, 1H), 3.46-3.41 (m, 1H), 3.27 (s, 3H), 2.18-2.10 (m, 1H), 1.94-1.82 (m, 2H), 1.75-1.67 (m, 1H). LCMS (ES+) m/z 497 (M+1).

Example 264

5-amino-N-(5-((2S,5R,6R)-5-amino-6-methoxyoxepan-2-yl)-1-methyl-1H-pyrazol-4-yl)-2-(2-fluoro-5-methylphenyl)thiazole-4-carboxamide 264

Following the procedure for Example 101 starting from tert-butyl N-[2-bromo-4-[[5-[(2S,5R,6R)-5-(tert-butoxycarbonylamino)-6-methoxy-oxepan-2-yl]-1-methyl-pyrazol-4-yl]carbamoyl]thiazol-5-yl]carbamate (Intermediate 98), and replacing 3,6-dihydro-2H-pyran-4-boronic acid pinacol ester with (2-fluoro-5-methylphenyl)boronic acid gave 264. $^1$H NMR (400 MHz, DMSO-$d_6$) δ 9.64 (s, 1H), 7.92-7.82 (m, 2H), 7.44 (br, 2H), 7.29-7.19 (m, 2H), 5.12 (t, J=5.4 Hz, 1H), 3.97-3.88 (m, 2H), 3.71 (s, 3H), 3.53-3.44 (m, 1H), 3.34-3.23 (m, 1H), 3.04 (s, 3H), 2.37 (s, 3H), 1.78-1.50 (m, 4H). LCMS (ES+) m/z 475 (M+1).

Example 265

N-(5-((2S,5R,6R)-5-amino-6-methoxyoxepan-2-yl)-1-methyl-1H-pyrazol-4-yl)-2-(2,6-difluoro-4-methoxyphenyl)thiazole-4-carboxamide 265

Following the procedure for Example 101 starting from tert-butyl ((3R,4R,7S)-7-(4-(2-bromothiazole-4-carboxamido)-1-methyl-1H-pyrazol-5-yl)-3-methoxyoxepan-4-yl)carbamate (Intermediate 101), and replacing 3,6-dihydro-2H-pyran-4-boronic acid pinacol ester with (2,6-difluoro-4-methoxyphenyl)boronic acid gave 265. $^1$H NMR (400 MHz, DMSO-$d_6$) δ 10.12 (s, 1H), 8.56 (s, 1H), 7.94 (s, 1H), 7.08-6.97 (m, 2H), 5.11 (t, J=5.5 Hz, 1H), 3.88 (s, 3H), 3.84-3.75 (m, 1H), 3.71 (s, 3H), 3.47-3.38 (m, 1H), 3.31-3.22 (m, 1H), 3.04 (s, 3H), 2.49-2.36 (m, 1H), 1.75-1.49 (m, 3H), 1.41 (br, 2H). LCMS (ES+) m/z 494 (M+1).

Example 266

5-amino-N-(5-((2S,5R,6R)-5-amino-6-fluorooxepan-2-yl)-1-methyl-1H-pyrazol-4-yl)-2-(2-(trifluoromethoxy)phenyl)thiazole-4-carboxamide 266

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (2-(trifluoromethoxy)phenyl)boronic acid gave 266. $^1$H NMR (400 MHz, DMSO-$d_6$) δ 9.50 (s, 1H), 8.28-8.20 (m, 1H), 7.78 (s, 1H), 7.57-7.43 (m, 6H), 5.00-4.77 (m, 2H), 4.22-4.06 (m, 1H), 4.06-3.92 (m, 1H), 3.75 (s, 3H), 3.29-3.21 (m, 1H), 2.18-2.09 (m, 1H), 1.95-1.54 (m, 5H). LCMS (ES+) m/z 515 (M+1).

Example 267

5-amino-N-(5-((2S,5R,6R)-5-amino-6-fluorooxepan-2-yl)-1-methyl-1H-pyrazol-4-yl)-2-(3-fluoro-2-(trifluoromethyl)phenyl)thiazole-4-carboxamide 267

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (3-fluoro-2-(trifluoromethyl)phenyl)boronic acid gave 267. $^1$H NMR (400 MHz, DMSO-d$_6$) δ 9.25 (s, 1H), 7.87-7.76 (m, 2H), 7.66-7.50 (m, 2H), 7.44 (s, 2H), 4.90 (dd, J=7.6, 3.8 Hz, 1H), 4.82-4.50 (m, 1H), 3.95-3.75 (m, 2H), 3.70 (s, 3H), 3.13 (dd, J=21.1, 8.4 Hz, 1H), 2.22-2.11 (m, 1H), 1.79-1.51 (m, 5H). LCMS (ES+) m/z 517 (M+1).

Example 268

5-amino-N-(5-((2S,5R,6R)-5-amino-6-fluorooxepan-2-yl)-1-methyl-1H-pyrazol-4-yl)-2-(2-fluoro-3-(trifluoromethyl)phenyl)thiazole-4-carboxamide 268

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (2-fluoro-3-(trifluoromethyl)phenyl)boronic acid gave 268. $^1$H NMR (400 MHz, DMSO-d$_6$) δ 9.53 (s, 1H), 8.38 (t, J=7.5 Hz, 1H), 7.90-7.75 (m, 2H), 7.62-7.50 (m, 3H), 5.05-4.71 (m, 2H), 4.22-4.06 (m, 1H), 4.05-3.92 (m, 1H), 3.75 (s, 3H), 3.34-3.21 (m, 1H), 2.18-2.10 (m, 1H), 1.88-1.72 (m, 4H), 1.69-1.60 (m, 1H). LCMS (ES+) m/z 517 (M+1).

Example 269

5-amino-N-(5-((2S,5R,6R)-5-amino-6-methoxyoxepan-2-yl)-1-methyl-1H-pyrazol-4-yl)-2-(2-fluoro-6-methylphenyl)thiazole-4-carboxamide 269

Following the procedure for Example 101 starting from tert-butyl N-[2-bromo-4-[[5-[(2S,5R,6R)-5-(tert-butoxycarbonylamino)-6-methoxy-oxepan-2-yl]-1-methyl-pyrazol-4-yl]carbamoyl]thiazol-5-yl]carbamate (Intermediate 98), and replacing 3,6-dihydro-2H-pyran-4-boronic acid pinacol ester with (2-fluoro-6-methylphenyl)boronic acid gave 269. $^1$H NMR (400 MHz, DMSO-d$_6$) δ 9.44 (s, 1H), 7.88 (s, 1H), 7.48-7.33 (m, 3H), 7.25-7.13 (m, 2H), 5.05 (t, J=5.3 Hz, 1H), 3.77-3.63 (m, 5H), 3.34-3.25 (m, 1H), 3.26-3.17 (m, 1H), 2.83 (s, 3H), 2.44 (s, 3H), 1.68-1.50 (m, 4H). LCMS (ES+) m/z 475 (M+1).

Example 270

5-amino-N-(5-((2S,5R,6R)-5-amino-6-fluorooxepan-2-yl)-1-methyl-1H-pyrazol-4-yl)-2-(2-(trifluoromethyl)phenyl)thiazole-4-carboxamide 270

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (2-(trifluoromethyl)phenyl)boronic acid gave 270. $^1$H NMR (400 MHz, DMSO-d$_6$) δ 9.18 (s, 1H), 7.88 (t, J=8.7 Hz, 1H), 7.83 (s, 1H), 7.77 (dd, J=6.5, 1.5 Hz, 2H), 7.72-7.62 (m, 1H), 7.46 (s, 2H), 4.87 (dd, J=8.5, 3.4 Hz, 1H), 4.82-4.60 (m, 1H), 3.97-3.83 (m, 2H), 3.71 (s, 3H), 3.17 (ddt, J=23.0, 9.2, 2.5 Hz, 1H), 2.15-2.04 (m, 1H), 1.86-1.54 (m, 4H). LCMS (ES+) m/z 499 (M+1).

Example 271

5-amino-N-(5-((2S,5R,6R)-5-amino-6-fluorooxepan-2-yl)-1-methyl-1H-pyrazol-4-yl)-2-(cyclopent-1-en-1-yl)thiazole-4-carboxamide 271

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with 2-(cyclopent-1-en-1-yl)-4,4,5,5-tetramethyl-1,3,2-dioxaborolane gave 271. $^1$H NMR (400 MHz, DMSO-d$_6$) δ 9.25 (s, 1H), 7.80 (s, 1H), 7.35 (br, J=8.5 Hz, 2H), 6.21-6.14 (m, 1H), 5.22-4.76 (m, 2H), 4.22-3.94 (m, 2H), 3.71 (s, 3H), 3.53-3.40 (m, 1H), 2.76-2.66 (m, 2H), 2.22-2.10 (m, 1H), 2.02-1.87 (m, 3H), 1.84-1.67 (m, 2H). LCMS (ES+) m/z 421 (M+1).

Example 272

5-amino-N-(5-((2S,5R,6R)-5-amino-6-fluorooxepan-2-yl)-1-methyl-1H-pyrazol-4-yl)-2-cyclopentylthiazole-4-carboxamide 272

To a solution of 5-amino-N-(5-((2S,5R,6R)-5-amino-6-fluorooxepan-2-yl)-1-methyl-1H-pyrazol-4-yl)-2-(cyclopent-1-en-1-yl)thiazole-4-carboxamide (Example 271) in methanol was added 10% palladium on carbon, and the mixture was stirred overnight under an atmosphere of hydrogen. The mixture was then filtered through Celite and concentrated in vacuo. HPLC purification provided 272. $^1$H NMR (400 MHz, DMSO-d$_6$) δ 9.26 (s, 1H), 7.77 (s, 1H), 7.05 (s, 2H), 5.17-4.78 (m, 2H), 4.17-3.92 (m, 2H), 3.71 (s, 3H), 3.47-3.34 (m, 1H), 3.27-3.15 (m, 1H), 2.23-2.11 (m, 1H), 2.11-1.95 (m, 2H), 1.94-1.83 (m, 1H), 1.82-1.57 (m, 9H). LCMS (ES+) m/z 423 (M+1).

Example 273

5-amino-N-(5-((2S,5R,6R)-5-amino-6-fluorooxepan-2-yl)-1-methyl-1H-pyrazol-4-yl)-2-(2-fluoro-6-methylphenyl)thiazole-4-carboxamide 273

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (2-fluoro-6-methylphenyl)boronic acid gave 273. $^1$H NMR (400 MHz, DMSO-d$_6$) δ 9.19 (s, 1H), 7.74 (s, 1H), 7.45-7.33 (m, 3H), 7.26-7.14 (m, 2H), 5.02-4.77 (m, 2H), 4.10-3.85 (m, 2H), 3.75 (s, 3H), 3.37 (s, 3H), 2.15-2.04 (m, 1H), 1.98-1.75 (m, 2H), 1.72-1.63 (m, 1H). LCMS (ES+) m/z 463 (M+1).

Example 274

5-amino-N-(5-((2S,5R,6R)-5-amino-6-fluorooxepan-2-yl)-1-methyl-1H-pyrazol-4-yl)-2-(2-fluoro-5-methylphenyl)thiazole-4-carboxamide 274

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (2-fluoro-5-methylphenyl)boronic acid gave 274. $^1$H NMR (400 MHz, DMSO-$d_6$) δ 9.51 (s, 1H), 7.90 (d, J=7.4 Hz, 1H), 7.82 (s, 1H), 7.41 (br, 2H), 7.24 (d, J=8.8 Hz, 2H), 5.09-4.68 (m, 2H), 4.22-3.97 (m, 2H), 3.74 (s, 3H), 2.36 (s, 3H), 2.23-2.12 (m, 1H), 1.88-1.73 (m, 2H), 1.68-1.63 (m, 3H). LCMS (ES+) m/z 463 (M+1).

Example 275

N-(5-((2S,5R,6S)-5-amino-6-fluorooxepan-2-yl)-1-methyl-1H-pyrazol-4-yl)-2-(4-(cyclopropyl(hydroxy)methyl)-2,6-difluorophenyl)thiazole-4-carboxamide 275

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with cyclopropyl(3,5-difluoro-4-(4,4,5,5-tetramethyl-1,3,2-dioxaborolan-2-yl)phenyl)methanol (Intermediate 140) gave 275, which was isolated as a mixture of diastereomers. LCMS (ES+) m/z 522 (M+1).

Example 276

N-(5-((2S,5R,6S)-5-amino-6-fluorooxepan-2-yl)-1-methyl-1H-pyrazol-4-yl)-2-(4-(cyclopropyl(methoxy)methyl)-2,6-difluorophenyl)thiazole-4-carboxamide 276

The title compound was isolated as a second compound formed during the synthesis of Example 275. LCMS (ES+) m/z 536 (M+1).

Example 277

5-amino-N-(5-((2S,5R,6R)-5-amino-6-fluorooxepan-2-yl)-1-methyl-1H-pyrazol-4-yl)-2-(2,3-difluoro-6-methoxyphenyl)thiazole-4-carboxamide 277

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (2,3-difluoro-6-methoxyphenyl)boronic acid gave 277. $^1$H NMR (400 MHz, DMSO-$d_6$) δ 9.42 (s, 1H), 7.84 (s, 1H), 7.47 (t, J=9.4 Hz, 1H), 7.39 (s, 2H), 7.01 (ddd, J=9.4, 4.0, 1.9 Hz, 1H), 5.02-4.76 (m, 2H), 4.18-3.93 (m, 2H), 3.92 (s, 3H), 3.72 (s, 3H), 2.23-2.13 (m, 1H), 1.90-1.60 (m, 4H). LCMS (ES+) m/z 497 (M+1).

Example 278

5-amino-N-(5-((2S,5R,6R)-5-amino-6-fluorooxepan-2-yl)-1-methyl-1H-pyrazol-4-yl)-2-(2-fluoro-6-(trifluoromethyl)phenyl)thiazole-4-carboxamide 278

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with (2-fluoro-6-(trifluoromethyl)phenyl)boronic acid gave 278. $^1$H NMR (400 MHz, DMSO-$d_6$) δ 9.19 (s, 1H), 7.85-7.69 (m, 4H), 7.47 (s, 2H), 5.03-4.74 (m, 2H), 4.00-3.86 (m, 2H), 3.74 (s, 3H), 2.13 (ddt, J=14.4, 6.1, 2.8 Hz, 1H), 2.01-1.61 (m, 3H). LCMS (ES+) m/z 517 (M+1).

Example 279

5-amino-N-(5-((2S,5R,6R)-5-amino-6-methoxyoxepan-2-yl)-1-methyl-1H-pyrazol-4-yl)-2-(2-fluoro-6-(trifluoromethyl)phenyl)thiazole-4-carboxamide 279

Following the procedure for Example 101 starting from tert-butyl N-[2-bromo-4-[[5-[(2S,5R,6R)-5-(tert-butoxycarbonylamino)-6-methoxy-oxepan-2-yl]-1-methyl-pyrazol-4-yl]carbamoyl]thiazol-5-yl]carbamate (Intermediate 98), and replacing 3,6-dihydro-2H-pyran-4-boronic acid pinacol ester with (2-fluoro-6-(trifluoromethyl)phenyl)boronic acid gave 279. $^1$H NMR (400 MHz, DMSO-$d_6$) δ 9.41 (s, 1H), 7.90 (s, 1H), 7.84-7.68 (m, 3H), 7.47 (s, 2H), 5.03 (t, J=5.2 Hz, 1H), 3.71-3.52 (m, 5H), 3.29-3.13 (m, 2H), 2.72 (s, 3H), 2.48-2.40 (m, 1H), 1.63-1.47 (m, 5H). LCMS (ES+) m/z 529 (M+1).

Example 280

5-amino-N-(5-((2S,5R,6R)-5-amino-6-methoxyoxepan-2-yl)-1-methyl-1H-pyrazol-4-yl)-2-(2-chloro-6-fluorophenyl)thiazole-4-carboxamide 280

Following the procedure for Example 101 starting from tert-butyl N-[2-bromo-4-[[5-[(2S,5R,6R)-5-(tert-butoxycarbonylamino)-6-methoxy-oxepan-2-yl]-1-methyl-pyrazol-4-yl]carbamoyl]thiazol-5-yl]carbamate (Intermediate 98), and replacing 3,6-dihydro-2H-pyran-4-boronic acid pinacol ester with (2-chloro-6-fluorophenyl)boronic acid gave 280. $^1$H NMR (400 MHz, DMSO-$d_6$) δ 9.51 (s, 1H), 7.89 (s, 1H), 7.61-7.46 (m, 4H), 7.40 (ddd, J=9.6, 8.2, 1.4 Hz, 1H), 5.06 (t, J=5.2 Hz, 1H), 3.68 (d, J=2.8 Hz, 5H), 3.33-3.17 (m, 2H), 2.82 (s, 3H), 1.66-1.49 (m, 4H). LCMS (ES+) m/z 495 (M+1).

Example 281

5-amino-N-(5-((2S,5R,6R)-5-amino-6-methoxyoxepan-2-yl)-1-methyl-1H-pyrazol-4-yl)-2-(5-chloro-2-fluorophenyl)thiazole-4-carboxamide 281

Following the procedure for Example 101 starting from tert-butyl N-[2-bromo-4-[[5-[(2S,5R,6R)-5-(tert-butoxycarbonylamino)-6-methoxy-oxepan-2-yl]-1-methyl-pyrazol-4-yl]carbamoyl]thiazol-5-yl]carbamate (Intermediate 98), and replacing 3,6-dihydro-2H-pyran-4-boronic acid pinacol ester with (2-chloro-5-fluorophenyl)boronic acid gave 281. $^1$H NMR (400 MHz, DMSO-$d_6$) δ 9.62 (s, 1H), 8.12 (dd, J=6.4, 2.7 Hz, 1H), 7.79 (s, 1H), 7.55-7.39 (m, 4H), 5.07 (dd, J=7.0, 4.5 Hz, 1H), 3.99-3.84 (m, 2H), 3.72 (s, 3H), 3.52-3.43 (m, 1H), 3.33-3.24 (m, 1H), 3.15 (s, 3H), 2.33-2.22 (m, 1H), 1.82-1.52 (m, 4H). LCMS (ES+) m/z 495 (M+1).

Example 282

5-amino-N-(5-((2S,5R,6S)-5-amino-6-fluorooxepan-2-yl)-1-methyl-1H-pyrazol-4-yl)-2-(1-methyl-5-(trifluoromethyl)-1H-pyrazol-4-yl)thiazole-4-carboxamide 282

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate (Intermediate 95), and replacing 3,6-dihydro-2H-pyran-4-boronic acid pinacol ester with 1-methyl-4-(4,4,5,5-tetramethyl-1,3,2-dioxaborolan-2-yl)-5-(trifluoromethyl)-1H-pyrazole (Intermediate 149) gave 282. $^1$H NMR (400 MHz, DMSO-d$_6$) δ 9.10 (s, 1H), 8.00 (s, 1H), 7.78 (s, 1H), 7.41 (s, 2H), 4.78 (dd, J=10.8, 3.6 Hz, 1H), 4.54-4.27 (m, 1H), 4.24-4.10 (m, 1H), 4.04 (s, 3H), 3.95 (dd, J=14.9, 3.4 Hz, 1H), 3.76 (s, 3H), 3.29-3.14 (m, 1H), 2.10-1.98 (m, 1H), 1.85-1.76 (m, 3H), 1.73-1.63 (m, 2H). LCMS (ES+) m/z 503 (M+1).

Example 283

N-(5-((2S,5R,6R)-5-amino-6-fluorooxepan-2-yl)-1-methyl-1H-pyrazol-4-yl)-2-(1-methyl-5-(trifluoromethyl)-1H-pyrazol-4-yl)thiazole-4-carboxamide 283

Following the procedure for Example 101 starting from tert-butyl N-[2-bromo-4-[[5-[(2S,5R,6R)-5-(tert-butoxycarbonylamino)-6-fluoro-oxepan-2-yl]-1-methyl-pyrazol-4-yl]carbamoyl]thiazol-5-yl]carbamate (Intermediate 88), and replacing 3,6-dihydro-2H-pyran-4-boronic acid pinacol ester with 1-methyl-4-(4,4,5,5-tetramethyl-1,3,2-dioxaborolan-2-yl)-5-(trifluoromethyl)-1H-pyrazole (Intermediate 149) gave 283. $^1$H NMR (400 MHz, DMSO-d$_6$) δ 9.76 (s, 1H), 8.49 (s, 1H), 8.16 (s, 1H), 7.85 (s, 1H), 4.99-4.67 (m, 2H), 4.10 (s, 3H), 4.08-3.85 (m, 2H), 3.75 (s, 3H), 3.30-3.16 (m, 1H), 2.16-2.05 (m, 1H), 1.90-1.67 (m, 2H), 1.66-1.58 (m, 1H). LCMS (ES+) m/z 488 (M+1).

Example 284

N-(5-((2S,5R,6S)-5-amino-6-fluorooxepan-2-yl)-1-methyl-1H-pyrazol-4-yl)-2-(2-chloro-6-fluorophenyl)thiazole-4-carboxamide 284

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with (2-chloro-6-fluorophenyl)boronic acid gave 284. $^1$H NMR (400 MHz, DMSO-d$_6$) δ 9.90 (s, 1H), 8.66 (s, 1H), 7.72 (s, 1H), 7.64 (td, J=8.3, 6.0 Hz, 1H), 7.58-7.51 (m, 1H), 7.50-7.40 (m, 1H), 4.77 (dd, J=10.9, 3.7 Hz, 1H), 4.38-4.17 (m, 1H), 4.17-4.03 (m, 1H), 4.02-3.83 (m, 1H), 3.78 (s, 3H), 3.23-3.09 (m, 1H), 2.10-1.98 (m, 1H), 1.91-1.76 (m, 3H), 1.70-1.56 (m, 4H). LCMS (ES+) m/z 468 (M+1).

Example 285

N-(5-((2S,5R,6S)-5-amino-6-fluorooxepan-2-yl)-1-methyl-1H-pyrazol-4-yl)-2-(3-ethoxy-2,6-difluorophenyl)thiazole-4-carboxamide 285

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with (3-ethoxy-2,6-difluorophenyl)boronic acid gave 285. $^1$H NMR (400 MHz, DMSO-d$_6$) δ 9.87 (s, 1H), 8.63 (s, 1H), 7.79 (s, 1H), 7.39 (td, J=9.3, 5.2 Hz, 1H), 7.24 (td, J=9.6, 1.9 Hz, 1H), 4.80 (dd, J=11.0, 3.6 Hz, 1H), 4.49-4.25 (m, 1H), 4.16 (q, J=6.9 Hz, 3H), 4.08-3.90 (m, 1H), 3.78 (s, 3H), 3.29-3.18 (m, 1H), 2.10-2.02 (m, 1H), 1.91-1.77 (m, 1H), 1.74-1.64 (m, 2H), 1.36 (t, J=6.9 Hz, 3H). LCMS (ES+) m/z 496 (M+1).

Example 286

N-(5-((2S,5R,6S)-5-amino-6-fluorooxepan-2-yl)-1-methyl-1H-pyrazol-4-yl)-2-(5-fluoro-1,3-dimethyl-1H-pyrazol-4-yl)thiazole-4-carboxamide 286

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with 5-fluoro-1,3-dimethyl-4-(4,4,5,5-tetramethyl-1,3,2-dioxaborolan-2-yl)-1H-pyrazole (Intermediate 150) gave 286. $^1$H NMR (400 MHz, DMSO-d$_6$) δ 9.56 (s, 1H), 8.33 (s, 1H), 7.81 (s, 1H), 4.82 (dd, J=10.7, 3.6 Hz, 1H), 4.39 (ddt, J=49.2, 6.4, 2.8 Hz, 1H), 4.24-3.94 (m, 2H), 3.78 (s, 3H), 3.72 (s, 3H), 3.25-3.12 (m, 1H), 2.54 (s, 3H), 2.12-2.01 (m, 1H), 1.92-1.56 (m, 4H). LCMS (ES+) m/z 452 (M+1).

Example 287

N-(5-((2S,5R,6R)-5-amino-6-fluorooxepan-2-yl)-1-methyl-1H-pyrazol-4-yl)-2-(2-fluoro-4-methoxyphenyl)thiazole-4-carboxamide 287

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 2-(2-fluoro-4-methoxyphenyl)thiazole-4-carboxylic acid (Intermediate 105) gave 287. 1H NMR (400 MHz, DMSO-d6) δ 10.04 (s, 1H), 8.42 (d, J=4.3 Hz, 1H), 8.21 (t, J=8.9 Hz, 1H), 7.81 (s, 1H), 7.15-7.00 (m, 2H), 5.00-4.80 (m, 2H), 4.22-3.92 (m, 2H), 3.88 (s, 3H), 3.77 (s, 3H), 2.20-2.09 (m, 1H), 1.90-1.75 (m, 2H), 1.65 (d, J=15.7 Hz, 3H). LCMS (ES+) m/z 464 (M+1).

Example 288

N-(5-((2S,5R,6R)-5-amino-6-fluorooxepan-2-yl)-1-methyl-1H-pyrazol-4-yl)-2-(2,6-difluoro-4-methoxyphenyl)thiazole-4-carboxamide 288

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 2-(2,6-difluoro-4-methoxyphenyl)thiazole-4-carboxylic acid (Intermediate 104) gave 288. 1H NMR (400 MHz, DMSO-d6) δ 10.01 (s, 1H), 8.54 (s, 1H), 7.88 (s, 1H), 7.05-6.98 (m, 2H), 4.99-4.81 (m, 2H), 4.16-3.94 (m, 2H), 3.88 (s, 3H), 3.73 (s, 3H), 2.20-2.11 (m, 1H), 1.92-1.67 (m, 2H), 1.62 (d, J=14.4 Hz, 1H). LCMS (ES+) m/z 482 (M+1).

Example 289

N-(5-((2S,5R,6R)-5-amino-6-fluorooxepan-2-yl)-1-methyl-1H-pyrazol-4-yl)-6-(2,6-difluoro-4-(2-hydroxypropan-2-yl)phenyl)-5-fluoropicolinamide 289

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 6-(2,6-difluoro-4-

(2-hydroxypropan-2-yl)phenyl)-5-fluoropicolinic acid (Intermediate 134) gave 289. 1H NMR (400 MHz, DMSO-d6) δ 10.45 (s, 1H), 8.31-8.24 (m, 1H), 8.21-8.09 (m, 1H), 7.92 (s, 1H), 7.40 (d, J=10.5 Hz, 2H), 4.91 (dd, J=8.8, 3.5 Hz, 1H), 3.91-3.79 (m, 2H), 3.72 (s, 3H), 3.08 (dd, J=23.4, 9.4 Hz, 1H), 2.16-2.06 (m, 1H), 1.87-1.74 (m, 1H), 1.71-1.53 (m, 2H). LCMS (ES+) m/z 522 (M+1).

Example 290

N-(5-((2S,5R,6R)-5-amino-6-fluorooxepan-2-yl)-1-methyl-1H-pyrazol-4-yl)-6-(2,6-difluoro-4-(1-hydroxycyclobutyl)phenyl)-5-fluoropicolinamide 290

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 6-(2,6-difluoro-4-(1-hydroxycyclobutyl)phenyl)-5-fluoropicolinic acid (Intermediate 135) gave 290. 1H NMR (400 MHz, DMSO-d6) δ 10.44 (s, 1H), 8.31-8.23 (m, 1H), 8.23-8.13 (m, 2H), 7.91 (s, 1H), 7.42 (dd, J=9.6, 3.6 Hz, 2H), 4.90 (dd, J=9.2, 3.5 Hz, 1H), 4.67 (d, J=5.4 Hz, 1H), 3.92-3.81 (m, 2H), 3.76-3.70 (m, 3H), 3.11 (dd, J=23.9, 9.5 Hz, 1H), 2.32 (q, J=9.9 Hz, 2H), 2.14-2.05 (m, 1H), 2.03-1.91 (m, 1H), 1.88-1.54 (m, 4H). LCMS (ES+) m/z 534 (M+1).

Example 291

5-amino-N-(5-((2S,5R,6S)-5-amino-6-fluorooxepan-2-yl)-1-methyl-1H-pyrazol-4-yl)-2-(5-chloro-2-fluorophenyl)thiazole-4-carboxamide 291

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 5-((tert-butoxycarbonyl)amino)-2-(5-chloro-2-fluorophenyl)thiazole-4-carboxylic acid (Intermediate 132) gave 291. 1H NMR (400 MHz, DMSO-d6) δ 9.41 (s, 1H), 8.29 (dd, J=6.5, 2.7 Hz, 1H), 7.73 (bs, 1H), 7.51 (s, 2H), 7.48-7.36 (m, 2H), 7.08-6.53 (m, 1H), 4.85 (dd, J=9.9, 4.1 Hz, 1H), 4.51-4.31 (m, 1H), 4.29-3.93 (m, 2H), 3.78 (s, 3H), 2.18-2.07 (m, 1H), 1.93-1.79 (m, 1H), 1.78-1.62 (m, 3H). LCMS (ES+) m/z 483 (M+1).

Example 292

5-amino-N-(5-((2S,5R,6S)-5-amino-6-fluorooxepan-2-yl)-1-methyl-1H-pyrazol-4-yl)-2-(2-fluoro-5-methylphenyl)thiazole-4-carboxamide 292

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 5-((tert-butoxycarbonyl)amino)-2-(2-fluoro-5-methylphenyl)thiazole-4-carboxylic acid (Intermediate 133) gave 292. 1H NMR (400 MHz, DMSO-d6) δ 9.29 (s, 1H), 8.03 (d, J=7.1 Hz, 1H), 7.82 (s, 1H), 7.44 (s, 2H), 7.26-7.17 (m, 2H), 4.86 (dd, J=10.2, 3.8 Hz, 1H), 4.54-4.36 (m, 1H), 4.34-4.18 (m, 1H), 4.15-3.96 (m, 1H), 3.77 (s, 3H), 2.35 (s, 3H), 2.14-2.03 (m, 1H), 1.88-1.65 (m, 4H). LCMS (ES+) m/z 463 (M+1).

Example 293

N-(5-((2S,5R,6S)-5-amino-6-fluorooxepan-2-yl)-1-methyl-1H-pyrazol-4-yl)-2-(2-fluoro-4-methoxyphenyl)thiazole-4-carboxamide 293

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2-fluoro-4-methoxyphenyl)thiazole-4-carboxylic acid (Intermediate 105) gave 293. 1H NMR (400 MHz, DMSO-d6) δ 9.86 (s, 1H), 9.10 (s, 1H), 8.44-8.34 (m, 2H), 7.88 (d, J=1.0 Hz, 1H), 7.14-7.05 (m, 1H), 7.02-6.91 (m, 3H), 6.67-6.58 (m, 2H), 4.87 (dd, J=10.5, 3.6 Hz, 1H), 4.58-4.39 (m, 1H), 4.38-4.23 (m, 1H), 4.18-3.99 (m, 1H), 3.87 (s, 3H), 3.78 (s, 3H), 2.13-2.02 (m, 1H), 1.88-1.67 (m, 5H). LCMS (ES+) m/z 464 (M+1).

Example 294

N-(5-((2S,5R,6S)-5-amino-6-fluorooxepan-2-yl)-1-methyl-1H-pyrazol-4-yl)-2-(2,6-difluoro-4-(1-hydroxyethyl)phenyl)thiazole-4-carboxamide 294

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2,6-difluoro-4-(1-hydroxyethyl)phenyl)thiazole-4-carboxylic acid (Intermediate 109) gave 294 as a mixture of diastereomers. 1H NMR (400 MHz, DMSO-d6) δ 9.88 (s, 1H), 8.61 (s, 1H), 7.81 (s, 1H), 7.31-7.24 (m, 2H), 5.57 (d, J=4.5 Hz, 1H), 4.86-4.75 (m, 2H), 4.41-4.23 (m, 1H), 4.23-3.92 (m, 2H), 3.78 (s, 3H), 3.26-3.15 (m, 1H), 2.11-2.01 (m, 1H), 1.87-1.76 (m, 1H), 1.74-1.59 (m, 4H), 1.35 (d, J=6.5 Hz, 3H). LCMS (ES+) m/z 496 (M+1).

Example 295

N-(5-((2S,5R,6S)-5-amino-6-fluorooxepan-2-yl)-1-methyl-1H-pyrazol-4-yl)-2-(2,6-difluoro-4-(1-hydroxycyclobutyl)phenyl)thiazole-4-carboxamide 295

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2,6-difluoro-4-(1-hydroxycyclobutyl)phenyl)thiazole-4-carboxylic acid (Intermediate 110) gave 295. 1H NMR (400 MHz, DMSO-d6) δ 9.87 (s, 1H), 8.62 (s, 1H), 7.80 (s, 1H), 7.44-7.35 (m, 2H), 7.01-6.57 (m, 1H), 5.95 (s, 1H), 4.82 (dd, J=10.9, 3.5 Hz, 1H), 4.42 (d, J=46.7 Hz, 1H), 4.27-3.93 (m, 2H), 3.78 (s, 3H), 2.46-2.38 (m, 2H), 2.36-2.26 (m, 2H), 2.11-1.92 (m, 2H), 1.87-1.67 (m, 4H). LCMS (ES+) m/z 522 (M+1).

Example 296

N-(5-((2S,5R,6S)-5-amino-6-fluorooxepan-2-yl)-1-methyl-1H-pyrazol-4-yl)-2-(2,6-difluoro-4-methoxyphenyl)thiazole-4-carboxamide 296

Following the procedure for Example 111 starting from tert-butyl ((3S,4R,7S)-3-fluoro-7-(1-methyl-4-nitro-1H- pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2,6-difluoro-4-methoxyphenyl)thiazole-4-carboxylic acid (Intermediate 104) gave 296. 1H NMR (400 MHz, DMSO-d6) δ 9.87 (s, 1H), 8.55 (s, 1H), 7.80 (s, 1H), 7.02-6.94 (m, 2H), 4.80 (dd, J=10.8, 3.6 Hz, 1H), 4.41-4.25 (m, 1H), 4.22-3.91 (m, 2H), 3.87 (s, 3H), 3.77 (s, 3H), 3.26-3.15 (m, 1H), 2.11-2.01 (m, 1H), 1.88-1.75 (m, 1H), 1.67 (q, J=9.0, 7.7 Hz, 3H). LCMS (ES+) m/z 482 (M+1).

Example 297

N-(5-((2S,5R,6S)-5-amino-6-fluorooxepan-2-yl)-1-methyl-1H-pyrazol-4-yl)-2-(2,6-difluoro-4-(2-hydroxypropan-2-yl)phenyl)thiazole-4-carboxamide 297

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2,6-difluoro-4-(2-hydroxypropan-2-yl)phenyl)thiazole-4-carboxylic acid (Intermediate 111) gave 297. 1H NMR (400 MHz, DMSO-d6) δ 9.86 (s, 1H), 8.61 (s, 1H), 7.80 (s, 1H), 7.41-7.31 (m, 2H), 5.43 (s, 1H), 4.80 (dd, J=10.9, 3.6 Hz, 1H), 4.23-4.10 (m, 1H), 4.08-3.90 (m, 1H), 3.78 (s, 3H), 3.26-3.15 (m, 1H), 2.10-2.01 (m, 1H), 1.88-1.76 (m, 1H), 1.74-1.60 (m, 4H), 1.46 (s, 6H). LCMS (ES+) m/z 510 (M+1).

Example 298

N-(5-((2S,5R,6S)-5-amino-6-fluorooxepan-2-yl)-1-methyl-1H-pyrazol-4-yl)-2-(2-(difluoromethyl)phenyl)thiazole-4-carboxamide 298

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2-(difluoromethyl)phenyl)thiazole-4-carboxylic acid (Intermediate 112) gave 298. 1H NMR (400 MHz, DMSO-d6) δ 9.70 (s, 1H), 8.54 (s, 1H), 8.11-7.80 (m, 3H), 7.76-7.67 (m, 3H), 4.78 (dd, J=10.8, 3.8 Hz, 1H), 4.48-4.29 (m, 1H), 4.20-3.89 (m, 2H), 3.81 (s, 3H), 2.11-2.02 (m, 1H), 1.98-1.86 (m, 1H), 1.74-1.64 (m, 2H). LCMS (ES+) m/z 466 (M+1).

Example 299

N-(5-((2S,5R,6S)-5-amino-6-fluorooxepan-2-yl)-1-methyl-1H-pyrazol-4-yl)-2-(5-bromo-2-fluorophenyl)thiazole-4-carboxamide 299

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(5-bromo-2-fluorophenyl)thiazole-4-carboxylic acid (Intermediate 129) gave 299. 1H NMR (400 MHz, DMSO-d6) δ 10.02 (s, 1H), 8.65 (dd, J=6.6, 2.6 Hz, 1H), 8.57 (s, 1H), 7.81-7.74 (m, 1H), 7.71 (s, 1H), 7.48 (dd, J=11.0, 8.9 Hz, 1H), 4.86 (dd, J=10.0, 3.9 Hz, 1H), 4.59-4.42 (m, 1H), 4.31-3.97 (m, 2H), 3.82 (s, 3H), 2.21-2.10 (m, 1H), 1.96-1.84 (m, 1H), 1.81-1.67 (m, 2H). LCMS (ES+) m/z 512 (M+1).

Example 300

N-(5-((2S,5R,6S)-5-amino-6-fluorooxepan-2-yl)-1-methyl-1H-pyrazol-4-yl)-2-(3-fluoropyridin-4-yl)thiazole-4-carboxamide 300

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(3-fluoropyridin-4-yl)thiazole-4-carboxylic acid (Intermediate 113) gave 300. 1H NMR (400 MHz, DMSO-d6) δ 9.97 (s, 1H), 8.86 (d, J=2.4 Hz, 1H), 8.72 (s, 1H), 8.66 (dd, J=5.0, 1.2 Hz, 1H), 8.36 (dd, J=6.5, 5.0 Hz, 1H), 7.84 (s, 1H), 7.59 (s, 2H), 4.98-4.79 (m, 2H), 4.43 (dd, J=23.7, 15.4 Hz, 1H), 4.27-4.09 (m, 1H), 3.81 (s, 3H), 3.68-3.54 (m, 1H), 2.19-2.10 (m, 1H), 2.03-1.83 (m, 3H). LCMS (ES+) m/z 435 (M+1).

Example 301

N-(5-((2S,5R,6S)-5-amino-6-fluorooxepan-2-yl)-1-methyl-1H-pyrazol-4-yl)-2-(2,5-difluorophenyl)thiazole-4-carboxamide 301

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2,5-difluorophenyl)thiazole-4-carboxylic acid (Intermediate 114) gave 301. 1H NMR (400 MHz, DMSO-d6) δ 9.91 (s, 1H), 8.58 (s, 1H), 8.27-8.20 (m, 1H), 7.79 (s, 1H), 7.59-7.52 (m, 1H), 7.51-7.42 (m, 1H), 4.85 (dd, J=10.6, 3.8 Hz, 1H), 4.51-4.35 (m, 1H), 4.31-4.18 (m, 1H), 4.13-3.95 (m, 1H), 3.80 (s, 3H), 3.27-3.19 (m, 1H), 2.14-2.05 (m, 1H), 1.98 (s, 1H), 1.92-1.82 (m, 1H), 1.76-1.66 (m, 2H). LCMS (ES+) m/z 452 (M+1).

Example 302

N-(5-((2S,5R,6S)-5-amino-6-fluorooxepan-2-yl)-1-methyl-1H-pyrazol-4-yl)-2-(5-chloro-2-fluorophenyl)thiazole-4-carboxamide 302

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(5-chloro-2-fluorophenyl)thiazole-4-carboxylic acid (Intermediate 115) gave 302. 1H NMR (400 MHz, DMSO-d6) δ 10.01 (s, 1H), 8.58 (s, 1H), 8.52 (dd, J=6.4, 2.7 Hz, 1H), 7.72 (s, 1H), 7.69-7.62 (m, 1H), 7.55 (dd, J=10.8, 8.9 Hz, 1H), 4.85 (dd, J=10.3, 3.9 Hz, 1H), 4.60-4.44 (m, 1H), 4.32-4.20 (m, 1H), 4.13-3.98 (m, 1H), 3.82 (s, 3H), 2.19-2.10 (m, 1H), 1.96-1.83 (m, 1H), 1.80-1.69 (m, 2H). LCMS (ES+) m/z 468 (M+1).

Example 303

N-(5-((2S,5R,6S)-5-amino-6-fluorooxepan-2-yl)-1-methyl-1H-pyrazol-4-yl)-2-(2,6-difluoro-3-methylphenyl)thiazole-4-carboxamide 303

Following the procedure for Example 111 starting from tert-butyl ((3S,4R,7S)-3-fluoro-7-(1-methyl-4-nitro-1H- pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2,6-difluoro-3-methylphenyl)thiazole-4-carboxylic acid (Intermediate 116) gave 303. 1H NMR (400 MHz, DMSO-d6) δ 9.92 (s, 1H), 8.63 (s, 1H), 7.80 (s, 1H), 7.57-7.48 (m, 1H), 7.29-7.19 (m, 1H), 4.83 (dd, J=10.4, 3.7 Hz, 1H), 4.54 (dd, J=50.8, 6.9 Hz, 1H), 4.30-4.17 (m, 1H), 4.15-3.97 (m, 1H), 3.78 (s, 3H), 2.30 (s, 3H), 2.13-2.04 (m, 1H), 1.89-1.72 (m, 3H). LCMS (ES+) m/z 466 (M+1).

Example 304

N-(5-((2S,5R,6S)-5-amino-6-fluorooxepan-2-yl)-1-methyl-1H-pyrazol-4-yl)-2-(2,6-difluoro-4-((R)-1-hydroxyethyl)phenyl)thiazole-4-carboxamide 304

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with (R)-2-(2,6-difluoro-4-(1-hydroxyethyl)phenyl)thiazole-4-carboxylic acid (Intermediate 117) gave 304. 1H NMR (400 MHz, DMSO-d6) δ 9.84 (s, 1H), 8.61 (s, 1H), 7.80 (s, 1H), 7.29 (d, J=10.1 Hz, 2H), 5.56 (s, 1H), 4.86-4.77 (m, 2H), 4.67-4.47 (m, 1H), 4.30-3.97 (m, 2H), 3.79 (s, 3H), 2.14-2.05 (m, 1H), 1.93-1.75 (m, 3H), 1.37 (d, J=6.5 Hz, 3H). LCMS (ES+) m/z 496 (M+1).

Example 305

N-(5-((2S,5R,6S)-5-amino-6-fluorooxepan-2-yl)-1-methyl-1H-pyrazol-4-yl)-2-(2,6-difluoro-4-((S)-1-hydroxyethyl)phenyl)thiazole-4-carboxamide 305

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with (S)-2-(2,6-difluoro-4-(1-hydroxyethyl)phenyl)thiazole-4-carboxylic acid (Intermediate 118) gave 305. 1H NMR (400 MHz, DMSO-d6) δ 9.84 (s, 1H), 8.61 (s, 1H), 7.80 (s, 1H), 7.30 (d, J=10.1 Hz, 2H), 5.56 (s, 1H), 4.87-4.77 (m, 2H), 4.68-4.49 (m, 1H), 4.29-3.99 (m, 2H), 3.79 (s, 3H), 2.15-2.05 (m, 1H), 1.92-1.73 (m, 3H), 1.37 (d, J=6.5 Hz, 3H). LCMS (ES+) m/z 496 (M+1).

Example 306

N-(5-((2S,5R,6S)-5-amino-6-fluorooxepan-2-yl)-1-methyl-1H-pyrazol-4-yl)-2-(2,3-difluorophenyl)thiazole-4-carboxamide 306

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2,3-difluorophenyl)thiazole-4-carboxylic acid (Intermediate 119) gave 306. 1H NMR (400 MHz, DMSO-d6) δ 9.90 (s, 1H), 8.59 (s, 1H), 8.28-8.21 (m, 1H), 7.87 (s, 1H), 7.68-7.58 (m, 1H), 7.44-7.36 (m, 1H), 4.88 (dd, J=10.5, 3.5 Hz, 1H), 4.67-4.49 (m, 1H), 4.41-4.29 (m, 1H), 4.20-4.03 (m, 2H), 3.79 (s, 3H), 3.45-3.35 (m, 1H), 2.15-2.05 (m, 1H), 1.91-1.73 (m, 3H). LCMS (ES+) m/z 452 (M+1).

Example 307

N-(5-((2S,5R,6S)-5-amino-6-fluorooxepan-2-yl)-1-methyl-1H-pyrazol-4-yl)-2-(5-ethyl-2-fluorophenyl)thiazole-4-carboxamide 307

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(5-ethyl-2-fluorophenyl)thiazole-4-carboxylic acid (Intermediate 120) gave 307. 1H NMR (400 MHz, DMSO-d6) δ 9.85 (s, 1H), 8.52 (s, 1H), 8.23 (dd, J=7.3, 2.3 Hz, 1H), 7.81 (s, 1H), 7.46-7.32 (m, 2H), 4.88 (dd, J=10.2, 4.0 Hz, 1H), 4.51-4.33 (m, 1H), 4.30-4.17 (m, 1H), 4.15-3.95 (m, 1H), 3.80 (s, 3H), 2.71 (q, J=7.6 Hz, 2H), 2.19-2.08 (m, 1H), 1.91-1.79 (m, 2H), 1.79-1.63 (m, 2H), 1.23 (t, J=7.6 Hz, 3H). LCMS (ES+) m/z 462 (M+1).

Example 308

N-(5-((2S,5R,6S)-5-amino-6-fluorooxepan-2-yl)-1-methyl-1H-pyrazol-4-yl)-2-(3-chloro-2-fluorophenyl)thiazole-4-carboxamide 308

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(3-chloro-2-fluorophenyl)thiazole-4-carboxylic acid (Intermediate 121) gave 308. 1H NMR (400 MHz, DMSO-d6) δ 9.91 (s, 1H), 8.59 (s, 1H), 8.44-8.39 (m, 1H), 7.87 (s, 1H), 7.81-7.76 (m, 1H), 7.45-7.39 (m, 1H), 4.88 (dd, J=10.4, 3.5 Hz, 1H), 4.63-4.47 (m, 1H), 4.40-4.27 (m, 1H), 4.20-4.03 (m, 1H), 3.79 (s, 3H), 3.43-3.37 (m, 1H), 2.15-2.06 (m, 1H), 1.91-1.70 (m, 3H). LCMS (ES+) m/z 468 (M+1).

Example 309

N-(5-((2S,5R,6S)-5-amino-6-fluorooxepan-2-yl)-1-methyl-1H-pyrazol-4-yl)-2-(2-chloro-3-fluorophenyl)thiazole-4-carboxamide 309

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2-chloro-3-fluorophenyl)thiazole-4-carboxylic acid (Intermediate 122) gave 309. 1H NMR (400 MHz, DMSO-d6) δ 9.88 (s, 1H), 8.62 (s, 1H), 8.33-8.27 (m, 1H), 7.85 (s, 1H), 7.64-7.53 (m, 2H), 4.86 (dd, J=10.7, 3.7 Hz, 1H), 4.54-4.34 (m, 1H), 4.27 (ddd, J=22.1, 15.0, 1.5 Hz, 1H), 4.05 (ddd, J=39.0, 15.0, 3.3 Hz, 1H), 3.79 (s, 3H), 2.13-2.03 (m, 1H), 1.89-1.79 (m, 1H), 1.75-1.68 (m, 3H). LCMS (ES+) m/z 468 (M+1).

Example 310

N-(5-((2S,5R,6S)-5-amino-6-fluorooxepan-2-yl)-1-methyl-1H-pyrazol-4-yl)-2-(5-cyclopropyl-2-fluorophenyl)thiazole-4-carboxamide 310

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluororophenyl)thiazole-4-carboxylic acid with 2-(5-cyclopropyl-2-fluorophenyl)thiazole-4-carboxylic acid (Intermediate 123) gave 310. 1H NMR (400 MHz, DMSO-d6) δ 9.86 (s, 1H), 8.51 (s, 1H), 8.16 (dd, J=7.2, 2.4 Hz, 1H), 7.76 (s, 1H), 7.33 (dd, J=11.2, 8.6 Hz, 1H), 7.28-7.20 (m, 1H), 4.86 (dd, J=10.2, 4.0 Hz, 1H), 4.29-4.16 (m, 1H), 4.12-3.94 (m, 1H), 3.81 (s, 3H), 3.26-3.15 (m, 1H), 2.18-2.04 (m, 2H), 1.96-1.82 (m, 1H), 1.80-1.61 (m, 4H), 1.04-0.94 (m, 2H), 0.80-0.71 (m, 2H). LCMS (ES+) m/z 474 (M+1).

Example 311

N-(5-((2S,5R,6S)-5-amino-6-fluorooxepan-2-yl)-1-methyl-1H-pyrazol-4-yl)-2-(2-(trifluoromethyl)phenyl)thiazole-4-carboxamide 311

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2-(trifluoromethyl)phenyl)thiazole-4-carboxylic acid (Intermediate 124) gave 311. 1H NMR (400 MHz, DMSO-d6) δ 9.75 (s, 1H), 8.58 (s, 1H), 7.97-7.93 (m, 1H), 7.89-7.75 (m, 4H), 4.78 (dd, J=10.9, 3.7 Hz, 1H), 4.37-4.19 (m, 1H), 4.14-4.02 (m, 1H), 4.02-3.84 (m, 1H), 3.78 (s, 3H), 3.20-3.08 (m, 1H), 2.08-1.99 (m, 1H), 1.88-1.76 (m, 1H), 1.71-1.59 (m, 3H). LCMS (ES+) m/z 484 (M+1).

Example 312

N-(5-((2S,5R,6S)-5-amino-6-fluorooxepan-2-yl)-1-methyl-1H-pyrazol-4-yl)-2-(2,6-difluoro-4-methylphenyl)thiazole-4-carboxamide 312

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2,6-difluoro-4-methylphenyl)thiazole-4-carboxylic acid (Intermediate 126) gave 312. 1H NMR (400 MHz, DMSO-d6) δ 9.86 (s, 1H), 8.59 (s, 1H), 7.81 (s, 1H), 7.18 (dd, J=10.3, 1.2 Hz, 2H), 4.81 (dd, J=10.8, 3.6 Hz, 1H), 4.43-4.27 (m, 1H), 4.23-4.11 (m, 1H), 4.08-3.90 (m, 1H), 3.78 (s, 3H), 3.24-3.17 (m, 1H), 2.41 (s, 3H), 2.11-2.02 (m, 1H), 1.99-1.76 (m, 3H), 1.73-1.62 (m, 2H). LCMS (ES+) m/z 466 (M+1).

Example 313

N-(5-((2S,5R,6S)-5-amino-6-fluorooxepan-2-yl)-1-methyl-1H-pyrazol-4-yl)-2-(4-chloro-2-fluorophenyl)thiazole-4-carboxamide 313

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(4-chloro-2-fluorophenyl)thiazole-4-carboxylic acid (Intermediate 127) gave 313. 1H NMR (400 MHz, DMSO-d6) δ 9.90 (s, 1H), 8.55 (s, 1H), 8.47 (t, J=8.4 Hz, 1H), 7.88 (s, 1H), 7.75 (dd, J=11.3, 2.0 Hz, 1H), 7.48 (dd, J=8.6, 2.0 Hz, 1H), 4.88 (dd, J=10.3, 3.5 Hz, 1H), 4.64-4.46 (m, 1H), 4.40-4.28 (m, 1H), 4.20-3.99 (m, 1H), 3.79 (s, 3H), 3.41-3.32 (m, 1H), 2.14-2.03 (m, 1H), 1.90-1.67 (m, 3H). LCMS (ES+) m/z 468 (M+1).

Example 314

N-(5-((2S,5R,6S)-5-amino-6-fluorooxepan-2-yl)-1-methyl-1H-pyrazol-4-yl)-2-(6-(trifluoromethyl)pyridin-2-yl)thiazole-4-carboxamide 314

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(6-(trifluoromethyl)pyridin-2-yl)thiazole-4-carboxylic acid (Intermediate 130) gave 314. 1H NMR (400 MHz, DMSO-d6) δ 9.84 (s, 1H), 9.11 (s, 1H), 9.04 (dd, J=5.1, 0.9 Hz, 1H), 8.66 (s, 1H), 7.98 (d, J=5.2 Hz, 1H), 7.80 (s, 1H), 4.80 (dd, J=10.7, 3.8 Hz, 1H), 4.35-4.17 (m, 1H), 4.14-4.03 (m, 1H), 4.02-3.85 (m, 1H), 3.78 (s, 3H), 3.19-3.09 (m, 1H), 2.10-2.01 (m, 1H), 1.88-1.76 (m, 1H), 1.71-1.54 (m, 4H). LCMS (ES+) m/z 485 (M+1).

Example 315

N-(5-((2S,5R,6S)-5-amino-6-fluorooxepan-2-yl)-1-methyl-1H-pyrazol-4-yl)-2-(2-fluoro-6-methylphenyl)thiazole-4-carboxamide 315

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2-fluoro-6-methylphenyl)thiazole-4-carboxylic acid (Intermediate 128) gave 315. 1H NMR (400 MHz, DMSO-d6) δ 9.77 (s, 1H), 8.60 (s, 1H), 7.73 (s, 1H), 7.56-7.38 (m, 1H), 7.24 (dd, J=10.0, 8.0 Hz, 2H), 4.79 (dd, J=11.1, 3.6 Hz, 1H), 4.52-4.27 (m, 1H), 4.22-3.87 (m, 2H), 3.79 (s, 3H), 2.42 (s, 3H), 2.10-2.01 (m, 1H), 1.93-1.80 (m, 1H), 1.71 (td, J=8.5, 7.7, 3.1 Hz, 2H). LCMS (ES+) m/z 448 (M+1).

Example 316

N-(5-((2S,5R,6S)-5-amino-6-fluorooxepan-2-yl)-1-methyl-1H-pyrazol-4-yl)-2-(2-fluoro-4-methylphenyl)thiazole-4-carboxamide 316

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2-fluoro-4-methylphenyl)thiazole-4-carboxylic acid (Intermediate 131) gave 316. 1H NMR (400 MHz, DMSO-d6) δ 9.87 (s, 1H), 8.48 (s, 1H), 8.36 (t, J=8.1 Hz, 1H), 7.89 (s, 1H), 7.34-7.18 (m, 2H), 4.87 (dd, J=10.6, 3.6 Hz, 1H), 4.57-4.39 (m, 1H), 4.38-4.25 (m, 1H), 4.19-4.01 (m, 1H), 3.78 (s, 3H), 2.40 (s, 3H), 2.12-2.03 (m, 1H), 1.88-1.78 (m, 1H), 1.77-1.66 (m, 3H). LCMS (ES+) m/z 448 (M+1).

Example 317

5-amino-N-(5-((2S,5R,6S)-5-amino-6-fluorooxepan-2-yl)-1-methyl-1H-pyrazol-4-yl)-2-(2-fluorophenyl)thiazole-4-carboxamide 317

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 5-(tert-butoxycarbonylamino)-2-(2-fluorophenyl)thiazole-4-carboxylic acid (Example 7) gave 317. 1H NMR (400 MHz, DMSO-d6) δ 9.34 (s, 1H), 8.30 (td, J=7.9, 1.8 Hz, 1H), 7.87 (s, 1H), 7.48-7.26 (m, 5H), 7.02-6.56 (m, 1H), 4.84 (dd, J=10.6, 3.5 Hz, 1H), 4.58-4.39 (m, 1H), 4.36-4.22 (m, 1H), 4.20-3.98 (m, 1H), 3.76 (s, 3H), 2.09-1.91 (m, 2H), 1.87-1.67 (m, 3H). LCMS (ES+) m/z 449 (M+1).

Example 318

N-(5-((2S,5R,6R)-5-amino-6-fluorooxepan-2-yl)-1-methyl-1H-pyrazol-4-yl)-2-(2-fluorophenyl)thiazole-4-carboxamide 318

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 2-(2-fluorophenyl)thiazole-4-carboxylic acid (see *Bioorg. Med. Chem. Lett.* 2010, 20, 1758) gave 318. 1H NMR (400 MHz, DMSO-d6) δ 10.08 (s, 1H), 8.53 (s, 1H), 8.35-8.28 (m, 1H), 7.81 (s, 1H), 7.66-7.58 (m, 1H), 7.53-7.41 (m, 2H), 5.02-4.81 (m, 2H), 4.24-4.09 (m, 1H), 4.09-3.92 (m, 1H), 3.77 (s, 3H), 2.20-2.09 (m, 1H), 2.07-1.92 (m, 1H), 1.87-1.74 (m, 2H), 1.66 (d, J=13.1 Hz, 1H). LCMS (ES+) m/z 434 (M+1).

Example 319

N-(5-((2S,5R,6R)-5-amino-6-fluorooxepan-2-yl)-1-methyl-1H-pyrazol-4-yl)-2-(2,6-difluorophenyl)thiazole-4-carboxamide 319

Following the procedure for Example 111 starting from tert-butyl ((3R,4R,7S)-3-fluoro-7-(1-methyl-4-nitro-1H-pyrazol-5-yl)oxepan-4-yl)carbamate (Intermediate 24), and replacing 5-((tert-butoxycarbonyl)amino)-2-(2,6-difluorophenyl)thiazole-4-carboxylic acid with 2-(2,6-difluorophenyl)thiazole-4-carboxylic acid (see US2012/225061) gave 319. 1H NMR (400 MHz, DMSO-d6) δ 10.02 (s, 1H), 8.63 (s, 1H), 7.86 (s, 1H), 7.74-7.59 (m, 1H), 7.38 (t, J=8.9 Hz, 2H), 5.03-4.81 (m, 2H), 4.19-3.88 (m, 2H), 3.75 (s, 2H), 2.24-2.10 (m, 1H), 1.93-1.81 (m, 1H), 1.82-1.70 (m, 1H), 1.65 (d, J=14.0 Hz, 1H). LCMS (ES+) m/z 452 (M+1).

Example 320

5-amino-N-(5-((2S,5R,6S)-5-amino-6-fluorooxepan-2-yl)-1-methyl-1H-pyrazol-4-yl)-2-phenylthiazole-4-carboxamide 320

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 5-((tert-butoxycarbonyl)amino)-2-phenylthiazole-4-carboxylic acid (Example 6) gave 320. 1H NMR (400 MHz, DMSO-d6) δ 9.29 (s, 1H), 7.89-7.81 (m, 2H), 7.50-7.34 (m, 4H), 7.01-6.59 (m, 1H), 4.83 (dd, J=10.7, 3.5 Hz, 1H), 4.57-4.39 (m, 1H), 4.37-3.99 (m, 2H), 3.80-3.70 (m, 3H), 2.04 (d, J=13.7 Hz, 1H), 2.00-1.66 (m, 4H). LCMS (ES+) m/z 431 (M+1).

Example 321

N-(5-((2S,5R,6S)-5-amino-6-fluorooxepan-2-yl)-1-methyl-1H-pyrazol-4-yl)-2-(2,6-difluorophenyl)thiazole-4-carboxamide 321

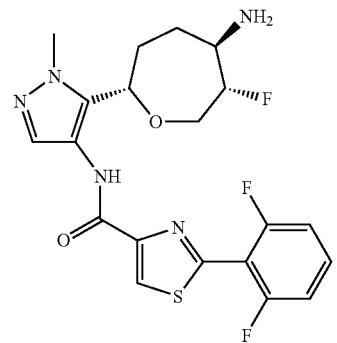 [SMILES: Cn1ncc(NC(=O)c2csc(-c3c(F)cccc3F)n2)c1[C@@H]1CC[C@@H](N)[C@H](F)CO1]

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2,6-difluorophenyl)thiazole-4-carboxylic acid (see US2012/225061) gave 321. 1H NMR (400 MHz, DMSO-d6) δ 9.94-9.85 (m, 1H), 8.63 (d, J=1.2 Hz, 1H), 7.81 (d, J=1.1 Hz, 1H), 7.69-7.60 (m, 1H), 7.33 (t, J=8.7 Hz, 2H), 4.81 (dd, J=10.9, 3.5 Hz, 1H), 4.44-4.24 (m, 1H), 4.23-4.10 (m, 1H), 3.99 (ddd, J=37.2, 14.8, 3.5 Hz, 1H), 3.77 (s, 3H), 2.11-2.02 (m, 1H), 1.90-1.76 (m, 1H), 1.75-1.63 (m, 2H). LCMS (ES+) m/z 452 (M+1).

Example 322

N-(5-((2S,5R,6S)-5-amino-6-fluorooxepan-2-yl)-1-methyl-1H-pyrazol-4-yl)-2-(2-fluorophenyl)thiazole-4-carboxamide 322

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2-fluorophenyl)thiazole-4-carboxylic acid (see *Bioorg. Med. Chem. Lett.* 2010, 20, 1758) gave 322. 1H NMR (400 MHz, DMSO-d6) δ 9.90 (s, 1H), 8.53 (s, 1H), 8.52-8.44 (m, 1H), 7.89 (s, 1H), 7.63-7.56 (m, 1H), 7.51-7.37 (m, 2H), 4.88 (dd, J=10.6, 3.6 Hz, 1H), 4.57-4.39 (m, 1H), 4.38-4.25 (m, 1H), 4.20-3.99 (m, 1H), 3.79 (s, 3H), 2.13-2.05 (m, 1H), 1.90-1.78 (m, 1H), 1.75 (d, J=9.6 Hz, 3H). LCMS (ES+) m/z 434 (M+1).

Example 323

5-amino-N-(5-((2S,5R,6S)-5-amino-6-fluorooxepan-2-yl)-1-methyl-1H-pyrazol-4-yl)-2-(2-(trifluoromethyl)phenyl)thiazole-4-carboxamide 323

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 5-((tert-butoxycarbonyl)amino)-2-(2-(trifluoromethyl)phenyl)thiazole-4-carboxylic acid (Example 19) gave 323. 1H NMR (400 MHz, DMSO-d6) δ 9.05 (s, 1H), 7.87 (d, J=7.8 Hz, 1H), 7.81-7.73 (m, 3H), 7.70-7.64 (m, 1H), 7.43 (s, 2H), 4.74 (dd, J=11.0, 3.4 Hz, 1H), 4.50-4.30 (m, 1H), 4.19-3.89 (m, 2H), 3.76 (s, 3H), 2.06-1.97 (m, 1H), 1.91-1.79 (m, 1H), 1.76-1.66 (m, 2H). LCMS (ES+) m/z 499 (M+1).

Example 324

5-amino-N-(5-((2S,5R,6S)-5-amino-6-fluorooxepan-2-yl)-1-methyl-1H-pyrazol-4-yl)-2-(2,3-difluorophenyl)thiazole-4-carboxamide 324

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 5-((tert-butoxycarbonyl)amino)-2-(2,3-difluorophenyl)thiazole-4-carboxylic acid (Example 25) gave 324. 1H NMR (400 MHz, DMSO-d6) δ 9.34 (s, 1H), 8.07 (dd, J=8.3, 6.5 Hz, 1H), 7.87 (s, 1H), 7.52 (s, 2H), 7.48-7.38 (m, 1H), 7.31-7.22 (m, 1H), 4.87-4.80 (m, 1H), 4.56-4.38 (m, 1H), 4.36-4.23 (m, 1H), 4.16-3.99 (m, 1H), 3.76 (s, 3H), 2.09-2.01 (m, 1H), 1.87-1.66 (m, 5H). LCMS (ES+) m/z 467 (M+1).

Example 325

N-(5-((2S,5R,6S)-5-amino-6-fluorooxepan-2-yl)-1-methyl-1H-pyrazol-4-yl)-2-(2,4-difluorophenyl)thiazole-4-carboxamide 325

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2,4-difluorophenyl)thiazole-4-carboxylic acid (see US2008/76771) gave 325. $^1$H NMR (400 MHz, DMSO-d$_6$) δ 9.89 (s, 1H), 8.56-8.46 (m, 2H), 7.88 (s, 1H), 7.59-7.50 (m, 1H), 7.32-7.24 (m, 1H), 4.87 (dd, J=10.4, 3.5 Hz, 1H), 4.57-4.38 (m, 1H), 4.38-4.23 (m, 1H), 4.18-3.98 (m, 1H), 3.78 (s, 3H), 2.14-2.02 (m, 1H), 1.88-1.66 (m, 4H). LCMS (ES+) m/z 452 (M+1).

Example 326

N-(5-((2S,5R,6S)-5-amino-6-fluorooxepan-2-yl)-1-methyl-1H-pyrazol-4-yl)-2-(pyridin-2-yl)thiazole-4-carboxamide 326

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(pyridin-2-yl)thiazole-4-carboxylic acid (see *Tetrahedron* 2011, 67, 267) gave 326. 1H NMR (400 MHz, DMSO-d6) δ 9.91 (s, 1H), 8.70-8.65 (m, 1H), 8.50 (s, 1H), 8.35-8.30 (m, 1H), 8.04-7.97 (m, 1H), 7.87 (s, 1H), 7.59-7.53 (m, 1H), 4.94-4.88 (m, 1H), 4.84-4.67 (m, 1H), 4.48-4.34 (m, 1H), 4.24-4.07 (m, 1H), 3.80 (s, 3H), 3.60-3.47 (m, 1H), 2.17-2.09 (m, 1H), 1.96-1.78 (m, 3H). LCMS (ES+) m/z 417 (M+1).

Example 327

N-(5-((2S,5R,6S)-5-amino-6-fluorooxepan-2-yl)-1-methyl-1H-pyrazol-4-yl)-2-phenylthiazole-4-carboxamide 327

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(pyridin-2-yl)thiazole-4-carboxylic acid (see *J. Med. Chem.* (2005), 48:2584) gave 327. 1H NMR (400 MHz, DMSO-d6) δ 9.87 (s, 1H), 8.41 (s, 1H), 8.14-8.06 (m, 2H), 7.88 (s, 1H), 7.57-7.50 (m, 3H), 4.88 (dd, J=10.5, 3.6 Hz, 1H), 4.64-4.46 (m, 1H), 4.40-4.27 (m, 1H), 4.21-4.01 (m, 1H), 3.79 (s, 3H), 3.45-3.35 (m, 1H), 2.14-2.06 (m, 1H), 1.91-1.70 (m, 3H). LCMS (ES+) m/z 416 (M+1).

Example 328

5-amino-N-(5-((2S,5R,6S)-5-amino-6-fluorooxepan-2-yl)-1-methyl-1H-pyrazol-4-yl)-2-(2-chloro-6-fluorophenyl)thiazole-4-carboxamide 328

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate (Intermediate 95), and replacing 3,6-dihydro-2H-pyran-4-boronic acid pinacol ester with (2-chloro-6-fluorophenyl)boronic acid gave 328. 1H NMR (400 MHz, DMSO-d6) δ 9.26 (s, 1H), 7.69 (s, 1H), 7.58-7.51 (m, 1H), 7.49-7.45 (m, 1H), 7.40-7.33 (m, 1H), 7.00-6.60 (m, 2H), 4.74 (dd, J=11.1, 3.6 Hz, 1H), 4.41-4.23 (m, 1H), 4.16-3.86 (m, 2H), 3.76 (s, 3H), 2.07-1.97 (m, 1H), 1.89-1.77 (m, 1H), 1.69 (d, J=9.1 Hz, 2H). LCMS (ES+) m/z 483 (M+1).

Example 329

5-amino-N-(5-((2S,5R,6S)-5-amino-6-fluorooxepan-2-yl)-1-methyl-1H-pyrazol-4-yl)-2-(2-chloro-6-(trifluoromethyl)phenyl)thiazole-4-carboxamide 329

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate (Intermediate 95), and replacing 3,6-dihydro-2H-pyran-4-boronic acid pinacol ester with (2-chloro-6-(trifluoromethyl)phenyl)boronic acid gave 329. 1H NMR (400 MHz, DMSO-d6) δ 9.38 (s, 1H), 8.59-8.53 (m, 1H), 7.99-7.96 (m, 1H), 7.85 (s, 1H), 7.75-7.70 (m, 1H), 7.61 (s, 2H), 4.85 (dd, J=10.4, 3.6 Hz, 1H), 4.57-4.39 (m, 1H), 4.37-4.24 (m, 1H), 4.16-3.97 (m, 2H), 3.76 (s, 3H), 2.11-2.03 (m, 1H), 1.89-1.67 (m, 4H). LCMS (ES+) m/z 433 (M+1).

Example 330

5-amino-N-(5-((2S,5R,6S)-5-amino-6-fluorooxepan-2-yl)-1-methyl-1H-pyrazol-4-yl)-2-(2-fluoro-6-methylphenyl)thiazole-4-carboxamide 330

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate (Intermediate 95), and replacing 3,6-dihydro-2H-pyran-4-boronic acid pinacol ester with (2-fluoro-6-methylphenyl)boronic acid gave 330. 1H NMR (400 MHz, DMSO-d6) δ 9.13 (s, 1H), 7.72 (s, 1H), 7.43-7.32 (m, 3H), 7.21-7.11 (m, 2H), 4.74 (dd, J=11.0, 3.6 Hz, 1H), 4.40-4.17 (m, 2H), 4.16-4.03 (m, 1H), 4.03-3.85 (m, 1H), 3.76 (s, 3H), 3.20-3.09 (m, 1H), 2.46 (s, 3H), 2.06-1.97 (m, 1H), 1.89-1.77 (m, 1H), 1.70-1.58 (m, 3H). LCMS (ES+) m/z 463 (M+1).

Example 331

5-amino-N-(5-((2S,5R,6S)-5-amino-6-fluorooxepan-2-yl)-1-methyl-1H-pyrazol-4-yl)-2-(2-fluoro-6-(trifluoromethyl)phenyl)thiazole-4-carboxamide 331

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate (Intermediate 95), and replacing 3,6-dihydro-2H-pyran-4-boronic acid pinacol ester with (2-fluoro-6-(trifluoromethyl)phenyl)boronic acid gave 331. 1H NMR (400 MHz, DMSO-d6) δ 9.18 (s, 1H), 7.81-7.68 (m, 3H), 7.42 (s, 2H), 4.78-4.68 (m, 1H), 4.45-4.26 (m, 1H), 4.14-3.86 (m, 2H), 3.76 (s, 3H), 2.07-1.97 (m, 1H), 1.88-1.76 (m, 1H), 1.76-1.65 (m, 2H). LCMS (ES+) m/z 517 (M+1).

Example 332

5-amino-N-(5-((2S,5R,6S)-5-amino-6-fluorooxepan-2-yl)-1-methyl-1H-pyrazol-4-yl)-2-(2,3,6-trifluorophenyl)thiazole-4-carboxamide 332

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate (Intermediate 95), and replacing 3,6-dihydro-2H-pyran-4-boronic acid pinacol ester with (2,3,6-trifluorophenyl)boronic acid gave 332. 1H NMR (400 MHz, DMSO-d6) δ 9.32 (s, 1H), 7.81 (s, 1H), 7.63-7.51 (m, 3H), 7.31-7.23 (m, 1H), 4.79 (dd, J=10.7, 3.5 Hz, 1H), 4.46-4.29 (m, 2H), 4.24-4.11 (m, 1H), 4.09-3.92 (m, 1H), 3.75 (s, 3H), 2.08-2.00 (m, 1H), 1.84-1.75 (m, 1H), 1.74-1.66 (m, 2H). LCMS (ES+) m/z 485 (M+1).

Example 333

5-amino-N-(5-((2S,5R,6S)-5-amino-6-fluorooxepan-2-yl)-1-methyl-1H-pyrazol-4-yl)-2-(cyclopent-1-en-1-yl)thiazole-4-carboxamide 333

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate (Intermediate 95), and replacing 3,6-dihydro-2H-pyran-4-boronic acid pinacol ester with 2-(cyclopent-1-en-1-yl)-4,4,5,5-tetramethyl-1,3,2-dioxaborolane gave 333. 1H NMR (400 MHz, DMSO-d6) δ 9.09 (s, 1H), 7.85 (s, 1H), 7.34 (s, 2H), 6.20-6.15 (m, 1H), 4.80 (dd, J=10.4, 3.7 Hz, 1H), 4.50-4.29 (m, 1H), 4.27-4.16 (m, 1H), 4.12-3.95 (m, 1H), 3.74 (s, 3H), 2.79-2.69 (m, 2H), 2.07-1.99 (m, 1H), 1.97-1.86 (m, 2H), 1.81-1.66 (m, 4H). LCMS (ES+) m/z 421 (M+1).

Example 334

5-amino-N-(5-((2S,5R,6S)-5-amino-6-fluorooxepan-2-yl)-1-methyl-1H-pyrazol-4-yl)-2-cyclopentylthiazole-4-carboxamide 334

To a solution of 5-amino-N-(5-((2S,5R,6S)-5-amino-6-fluorooxepan-2-yl)-1-methyl-1H-pyrazol-4-yl)-2-(cyclopent-1-en-1-yl)thiazole-4-carboxamide (Example 333) in methanol was added 10% palladium on carbon, and the mixture was stirred under an atmosphere of hydrogen overnight. After filtration and in vacuo concentration, purification by HPLC provided the title compound. 1H NMR (400 MHz, DMSO-d6) δ 9.13 (s, 1H), 7.79 (s, 1H), 7.05 (s, 2H), 4.83-4.74 (m, 1H), 4.48-4.30 (m, 1H), 4.26-4.12 (m, 1H), 4.11-3.91 (m, 1H), 3.74 (s, 3H), 2.07-1.97 (m, 3H), 1.88-1.52 (m, 11H). LCMS (ES+) m/z 423 (M+1).

Example 335

5-amino-N-(5-((2S,5R,6S)-5-amino-6-fluorooxepan-2-yl)-1-methyl-1H-pyrazol-4-yl)-2-(2-(difluoromethyl)phenyl)thiazole-4-carboxamide 335

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate (Intermediate 95), and replacing 3,6-dihydro-2H-pyran-4-boronic acid pinacol ester with (2-(difluoromethyl)phenyl)boronic acid gave 335. 1H NMR (400 MHz, DMSO-d6) δ 9.05 (s, 1H), 8.09-7.80 (m, 1H), 7.77 (d, J=7.6 Hz, 1H), 7.71-7.66 (m, 2H), 7.65-7.59 (m, 1H), 7.59-7.50 (m, 3H), 4.75 (dd, J=10.6, 3.8 Hz, 1H), 4.42-4.26 (m, 1H), 4.19-4.07 (m, 1H), 4.04-3.87 (m, 1H), 3.79 (s, 3H), 3.21-3.08 (m, 1H), 2.08-1.99 (m, 1H), 1.97-1.85 (m, 1H), 1.74-1.58 (m, 4H). LCMS (ES+) m/z 481 (M+1).

Example 336

5-amino-N-(5-((2S,5R,6S)-5-amino-6-fluorooxepan-2-yl)-1-methyl-1H-pyrazol-4-yl)-2-(3-fluoro-2-(trifluoromethyl)phenyl)thiazole-4-carboxamide 336

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate (Intermediate 95), and replacing 3,6-dihydro-2H-pyran-4-boronic acid pinacol ester with (3-fluoro-2-(trifluoromethyl)phenyl)boronic acid gave 336. 1H NMR (400 MHz, DMSO-d6) δ 9.13 (s, 1H), 7.85-7.77 (m, 1H), 7.72 (s, 1H), 7.66-7.57 (m, 1H), 7.54 (d, J=7.8 Hz, 1H), 7.44 (s, 2H), 4.81-4.73 (m, 1H), 4.63-4.44 (m, 1H), 4.22-4.10 (m, 1H), 4.08-3.91 (m, 1H), 3.76 (s, 3H), 2.10-2.00 (m, 1H), 1.90-1.73 (m, 3H). LCMS (ES+) m/z 517 (M+1).

Example 337

5-amino-N-(5-((2S,5R,6S)-5-amino-6-fluorooxepan-2-yl)-1-methyl-1H-pyrazol-4-yl)-2-(2-chloro-3-fluorophenyl)thiazole-4-carboxamide 337

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate (Intermediate 95), and replacing 3,6-dihydro-2H-pyran-4-boronic acid pinacol ester with (2-chloro-3-fluorophenyl)boronic acid gave 337. 1H NMR (400 MHz, DMSO-d6) δ 9.32 (s, 1H), 8.20-8.12 (m, 1H), 7.84 (s, 1H), 7.52 (s, 2H), 7.50-7.39 (m, 2H), 4.82 (dd, J=10.7, 3.6 Hz, 1H), 4.53-4.36 (m, 1H), 4.33-4.20 (m, 1H), 4.14-3.98 (m, 1H), 3.76 (s, 3H), 2.09-2.01 (m, 1H), 1.88-1.66 (m, 4H). LCMS (ES+) m/z 483 (M+1).

Example 338

5-amino-N-(5-((2S,5R,6S)-5-amino-6-fluorooxepan-2-yl)-1-methyl-1H-pyrazol-4-yl)-2-(3-chloro-2-fluorophenyl)thiazole-4-carboxamide 338

Following the procedure for Example 101 starting from tert-butyl N-[2-bromo-4-[[5-[(2S,5R,6S)-5-(tert-butoxycarbonylamino)-6-fluoro-oxepan-2-yl]-1-methyl-pyrazol-4-yl]carbamoyl]thiazol-5-yl]carbamate (Intermediate 95), and replacing 3,6-dihydro-2H-pyran-4-boronic acid pinacol ester with (3-chloro-2-fluorophenyl)boronic acid gave 338. 1H NMR (400 MHz, DMSO-d6) δ 9.34 (s, 1H), 8.47-8.06 (m, 1H), 7.86 (s, 1H), 7.66-7.55 (m, 1H), 7.52 (s, 2H), 7.30 (t, J=8.1 Hz, 1H), 4.83 (dd, J=10.5, 3.6 Hz, 1H), 4.58-4.37 (m, 1H), 4.36-4.22 (m, 1H), 4.18-3.97 (m, 1H), 3.76 (s, 3H), 2.10-2.00 (m, 1H), 1.89-1.60 (m, 4H). LCMS (ES+) m/z 483 (M+1).

Example 339

N-(5-((2S,5R,6S)-5-amino-6-fluorooxepan-2-yl)-1-methyl-1H-pyrazol-4-yl)-2-(2,6-difluoro-4-(3-methoxyoxetan-3-yl)phenyl)thiazole-4-carboxamide 339

Following the procedure for Example 101 starting from tert-butyl ((3S,4R,7S)-7-(4-(2-bromothiazole-4-carboxamido)-1-methyl-1H-pyrazol-5-yl)-3-fluorooxepan-4-yl)carbamate (Intermediate 99), and replacing 3,6-dihydro-2H-pyran-4-boronic acid pinacol ester with 2-(2,6-difluoro-4-(3-methoxyoxetan-3-yl)phenyl)-4,4,5,5-tetramethyl-1,3,2-dioxaborolane (US2012/225062) gave 339. 1H NMR (500 MHz, DMSO-d6) δ 9.91 (s, 1H), 8.65 (s, 1H), 7.88 (s, 1H), 7.46-7.44 (m, 2H), 4.82-4.79 (m, 5H), 4.37-3.93 (m, 3H), 3.78 (s, 3H), 3.24-3.17 (m, 1H), 3.12 (s, 3H), 2.07-1.67 (m, 4H). LCMS (ES+) m/z 538 (M+1).

Example 340

N-(5-((2S,5R,6S)-5-amino-6-fluorooxepan-2-yl)-1-methyl-1H-pyrazol-4-yl)-2-(2,6-difluoro-4-(3-fluorooxetan-3-yl)phenyl)thiazole-4-carboxamide 340

Following the procedure for Example 111 starting from tert-butyl ((3S,4R,7S)-3-fluoro-7-(1-methyl-4-nitro-1H-pyrazol-5-yl)oxepan-4-yl)carbamate (Intermediate 80), and replacing 5-((tert-butoxycarbonyl)amino)-2-(2,6-difluorophenyl)thiazole-4-carboxylic acid with 2-(2,6-difluoro-4-(3-fluorooxetan-3-yl)phenyl)thiazole-4-carboxylic acid (Intermediate 151) gave 340. ¹H NMR (500 MHz, CDCl₃) δ 9.81 (s, 1H), 8.38 (s, 1H), 8.16 (s, 1H), 7.36-7.34 (m, 2H), 5.21-5.16 (m, 2H), 4.86-4.81 (m, 2H), 4.63-4.45 (m, 3H), 4.05-3.86 (m, 1H), 3.85 (s, 3H), 3.52-3.49 (m, 1H), 2.10-2.05 (m, 2H), 1.85-1.72 (m, 2H). LCMS (ES+) m/z 526 (M+1).

Example 341

N-(5-((2R,4R,5S,6R)-4-amino-5-hydroxy-5,6-dimethyltetrahydro-2H-pyran-2-yl)-1-methyl-1H-pyrazol-4-yl)-2-(2,6-difluorophenyl)thiazole-4-carboxamide 341

Following the procedure for Example 111 (nitro reduction step not necessary) starting from tert-butyl ((2R*,3S*,4R*,6R*)-6-(4-amino-1-methyl-1H-pyrazol-5-yl)-3-hydroxy-2,3-dimethyltetrahydro-2H-pyran-4-yl)carbamate (Intermediate 152), and replacing 5-((tert-butoxycarbonyl)amino)-2-(2,6-difluorophenyl)thiazole-4-carboxylic acid with 2-(2,6-difluorophenyl)thiazole-4-carboxylic acid (see US2012/225061), and separation of the enantiomers prior to Boc deprotection (SFC; Chiralpak IC) provided 341. Note: absolute stereochemistry is arbitrary. 1H NMR (500 MHz, CDCl3) δ 9.75 (s, 1H), 8.36 (s, 1H), 8.14 (s, 1H), 7.46-7.43 (m, 1H), 7.07-7.04 (m, 2H), 4.82-4.79 (d, 1H), 3.79 (s, 3H), 3.47-3.45 (d, 1H), 2.99-2.98 (s, 1H), 2.09-2.05 (m, 1H), 1.92-1.81 (m, 4H), 1.50-1.10 (m, 3H), 1.09 (s, 3H). LCMS (ES+) m/z 464 (M+1).

Example 342

N-(5-((2S,4S,5R,6S)-4-amino-5-hydroxy-5,6-dimethyltetrahydro-2H-pyran-2-yl)-1-methyl-1H-pyrazol-4-yl)-2-(2,6-difluorophenyl)thiazole-4-carboxamide 342

Following the procedure of Example 341 also provided 342 (absolute stereochemistry is arbitrary). 1H NMR (500 MHz, CDCl3) δ 9.76 (s, 1H), 8.36 (s, 1H), 8.15 (s, 1H), 7.46-7.43 (m, 1H), 7.07-7.04 (m, 2H), 4.82-4.79 (d, 1H), 3.80 (s, 3H), 3.47-3.45 (d, 1H), 2.96-2.95 (s, 1H), 2.08-2.05 (m, 1H), 1.81-1.74 (m, 4H), 1.54-1.52 (m, 3H), 1.02 (s, 3H). LCMS (ES+) m/z 464 (M+1).

Example 343

N-(5-((2R,4R,5S,6R)-4-amino-5-hydroxy-5,6-dimethyltetrahydro-2H-pyran-2-yl)-1-methyl-1H-pyrazol-4-yl)-6-(2,6-difluorophenyl)-5-fluoropicolinamide 343

Following the procedure for Example 341, replacing 2-(2,6-difluorophenyl)thiazole-4-carboxylic acid with 6-(2,6-difluorophenyl)-5-fluoropicolinic acid (see US2012/225061), and separation of the enantiomers prior to Boc deprotection (SFC; Chiralpak IC) provided 343. Note: absolute stereochemistry is arbitrary. 1H NMR (500 MHz, CDCl3) δ 10.10 (s, 1H), 8.43-8.40 (m, 1H), 8.27 (s, 1H), 7.72-7.69 (m, 1H), 7.51-7.47 (m, 1H), 7.07-7.04 (m, 2H), 4.78-4.75 (m, 1H), 3.79-3.78 (m, 3H), 3.37-3.34 (m, 1H), 2.81-2.79 (m, 1H), 2.00-1.94 (m, 1H), 1.64-1.55 (m, 4H), 0.94-0.93 (m, 3H), 0.79 (s, 3H). LCMS (ES+) m/z 476 (M+1).

Example 344

N-(5-((2S,4S,5R,6S)-4-amino-5-hydroxy-5,6-dimethyltetrahydro-2H-pyran-2-yl)-1-methyl-1H-pyrazol-4-yl)-6-(2,6-difluorophenyl)-5-fluoropicolinamide 344

Following the procedure of Example 343 also provided 344 (absolute stereochemistry is arbitrary). 1H NMR (500 MHz, CDCl3) δ 10.09 (s, 1H), 8.42-8.40 (m, 1H), 8.26 (s, 1H), 7.72-7.69 (m, 1H), 7.49-7.47 (m, 1H), 7.07-7.04 (m, 2H), 4.78-4.76 (m, 1H), 3.79 (s, 3H), 3.37-3.36 (m, 1H), 2.83-2.81 (m, 1H), 1.98-1.95 (m, 1H), 1.65-1.57 (m, 4H), 0.94-0.93 (m, 3H), 0.80 (s, 3H). LCMS (ES+) m/z 476 (M+1).

Example 345

5-amino-N-(5-((2R,4R,5S,6R)-4-amino-5-hydroxy-5,6-dimethyltetrahydro-2H-pyran-2-yl)-1-methyl-1H-pyrazol-4-yl)-2-(2,6-difluorophenyl)thiazole-4-carboxamide 345

Following the procedure for Example 341, replacing 2-(2,6-difluorophenyl)thiazole-4-carboxylic acid with 5-(tert-butoxycarbonylamino)-2-(2,6-difluorophenyl)thiazole-4-carboxylic acid (Example 8) and separation of the enantiomers prior to Boc deprotection (SFC; Chiralpak AD-H) provided 345. Note: absolute stereochemistry is arbitrary. 1H NMR (500 MHz, DMSO-d6) δ 9.39 (s, 1H), 7.90-7.89 (m, 1H), 7.60-7.55 (m, 1H), 7.47 (s, 2H), 7.27-7.24 (m, 2H), 4.89-4.86 (m, 1H), 4.37 (s, 1H), 3.76 (s, 3H), 2.74-2.72 (m, 1H), 1.86-1.83 (m, 1H), 1.46-1.44 (m, 1H), 1.36-1.28 (m, 1H), 1.02 (d, J=7 Hz, 3H), 0.80 (s, 3H). LCMS (ES+) m/z 479 (M+1).

Example 346

5-amino-N-(5-((2S,4S,5R,6S)-4-amino-5-hydroxy-5,6-dimethyltetrahydro-2H-pyran-2-yl)-1-methyl-1H-pyrazol-4-yl)-2-(2,6-difluorophenyl)thiazole-4-carboxamide 346

Following the procedure of Example 345 also provided 346 (absolute stereochemistry is arbitrary). 1H NMR (500 MHz, DMSO-d6) δ 9.39 (s, 1H), 7.90-7.89 (m, 1H), 7.60-7.55 (m, 1H), 7.47 (s, 2H), 7.27-7.24 (m, 2H), 4.89-4.86 (m, 1H), 4.37 (s, 1H), 3.76 (s, 3H), 2.74-2.72 (m, 1H), 1.86-1.83 (m, 1H), 1.46-1.44 (m, 1H), 1.36-1.28 (m, 1H), 1.02 (d, J=7 Hz, 3H), 0.80 (s, 3H). LCMS (ES+) m/z 479 (M+1).

Example 347

N-(5-((2S,5R,6S)-5-amino-6-methoxyoxepan-2-yl)-1-methyl-1H-pyrazol-4-yl)-2-(2,6-difluorophenyl)thiazole-4-carboxamide 347

Following the procedure for Example 101 starting from tert-butyl ((3S,4R,7S)-7-(4-(2-bromothiazole-4-carboxamido)-1-methyl-1H-pyrazol-5-yl)-3-methoxyoxepan-4-yl)carbamate (Intermediate 102), and replacing 3,6-dihydro-2H-pyran-4-boronic acid pinacol ester with (2,6-difluorophenyl)boronic acid gave 347. 1H NMR (500 MHz, DMSO-d6) δ 10.13 (s, 1H), 8.65 (s, 1H), 7.94 (s, 1H), 7.69-7.65 (m, 1H), 7.40-7.36 (m, 2H), 5.11-5.09 (m, 1H), 3.85-3.79 (m, 2H), 3.72 (s, 3H), 3.57 (s, 2H), 3.46-3.43 (m, 1H), 3.30 (s, 1H), 3.01 (s, 3H), 2.43-2.37 (m, 1H), 1.74-1.58 (m, 3H). LCMS (ES+) m/z 464 (M+1).

Example 348

N-(5-((2S,5R,6S)-5-amino-6-methoxyoxepan-2-yl)-1-methyl-1H-pyrazol-4-yl)-2-(3-methylpyridin-2-yl)thiazole-4-carboxamide 348

Following the procedure for Example 101 starting from tert-butyl ((3S,4R,7S)-7-(4-(2-bromothiazole-4-carboxamido)-1-methyl-1H-pyrazol-5-yl)-3-methoxyoxepan-4-yl)carbamate (Intermediate 102), and replacing 3,6-dihydro-2H-pyran-4-boronic acid pinacol ester with (3-methylpyridin-2-yl)boronic acid gave 348. 1H NMR (500 MHz, DMSO-d6) δ 9.67 (s, 1H), 8.52-8.51 (m, 1H), 8.27 (s, 1H), 8.23 (s, 1H), 7.67-7.65 (m, 1H), 7.29-7.26 (m, 1H), 5.03-5.00 (m, 1H), 4.04-3.93 (m, 2H), 3.78 (s, 3H), 3.56-3.54 (m, 1H), 3.38-3.36 (m, 1H), 3.33 (s, 3H), 2.88 (s, 3H), 2.61 (s, 2H), 2.13-2.09 (m, 1H), 1.98-1.70 (m, 2H), 1.68-1.56 (m, 1H). LCMS (ES+) m/z 443 (M+1).

Example 349

N-(5-((2S,5R,6S)-5-amino-6-fluorooxepan-2-yl)-1-methyl-1H-pyrazol-4-yl)-2-(3-chloro-5-fluoropyridin-4-yl)thiazole-4-carboxamide 349

Following the procedure for Example 101, 349 was prepared. $^1$H NMR (500 MHz, CDCl$_3$) δ 9.83 (s, 1H), 8.63 (s, 1H), 8.56 (s, 1H), 8.14 (s, 1H), 4.57 (m, 1H), 4.26 (m, 2H), 3.88 (m, 1H), 3.85 (s, 3H), 3.42 (m, 1H), 1.99 (m, 2H), 1.79 (m, 1H), 1.69 (m, 1H), 1.56 (s, 2H). LCMS (ES+) m/z 469.1 (M+1).

Example 350

N-(5-((2S,5R,6R)-5-amino-6-hydroxyoxepan-2-yl)-1-methyl-1H-pyrazol-4-yl)-2-(2,6-difluorophenyl)thiazole-4-carboxamide 350

Following the procedure for Example 101, 350 was prepared. $^1$H NMR (500 MHz, DMSO-d$_6$) δ 10.05 (s, 1H), 8.63 (s, 1H), 7.90 (s, 1H), 7.68-7.65 (m, 1H), 7.38-7.35 (m, 2H), 5.03-5.00 (m, 1H), 4.79 (bs, 1H), 3.96-3.93 (m, 1H), 3.88-3.87 (m, 1H), 3.73 (s, 3H), 3.63-3.59 (m, 1H), 3.13-3.11 (m, 1H), 2.22-2.18 (m, 1H), 1.83-1.81 (m, 1H), 1.64-1.58 (m, 2H). LCMS (ES+) m/z 450.1 (M+1)

Example 351

N-(5-((2R,5S,6S)-5-amino-6-hydroxyoxepan-2-yl)-1-methyl-1H-pyrazol-4-yl)-2-(2,6-difluorophenyl)thiazole-4-carboxamide 351

Following the procedure for Example 101, 351 was prepared. $^1$H NMR (500 MHz, DMSO-d$_6$) δ 10.07 (s, 1H), 8.63 (s, 1H), 7.90 (s, 1H), 7.68-7.65 (m, 1H), 7.38-7.35 (m, 2H), 5.04-5.01 (m, 1H), 4.71 (bs, 1H), 3.94-3.90 (m, 1H), 3.85-3.84 (m, 1H), 3.73 (s, 3H), 3.63-3.59 (m, 1H), 3.10-3.08 (m, 1H), 2.24-2.20 (m, 1H), 1.80-1.58 (m, 5H). LCMS (ES+) m/z 450.1 (M+1)

Example 352

N-(5-((2S,5R,6S)-5-amino-6-hydroxyoxepan-2-yl)-1-methyl-1H-pyrazol-4-yl)-2-(2,6-difluorophenyl)thiazole-4-carboxamide 352

Following the procedure for Example 101, 352 was prepared. $^1$H NMR (500 MHz, DMSO-d$_6$) δ 9.88 (s, 1H), 8.64 (s, 1H), 7.73-7.34 (m, 4H), 4.82-4.79 (d, 2H), 3.84-3.75 (m, 6H), 2.81-2.77 (s, 1H), 2.05-1.51 (m, 6H). LCMS (ES+) m/z 450.1 (M+1)

Example 353

N-(5-((2R,5S,6R)-5-amino-6-hydroxyoxepan-2-yl)-1-methyl-1H-pyrazol-4-yl)-2-(2,6-difluorophenyl)thiazole-4-carboxamide 353

Following the procedure for Example 101, 353 was prepared. $^1$H NMR (500 MHz, DMSO-d$_6$) δ 9.88 (s, 1H), 8.64 (s, 1H), 7.74-7.34 (m, 4H), 4.82-4.74 (m, 2H), 3.84-3.76 (m, 6H), 2.80-2.76 (s, 1H), 2.05-1.48 (m, 6H). LCMS (ES+) m/z 450.1 (M+1)

Example 354

N-(5-((2S,5R,6S)-5-amino-6-fluorooxepan-2-yl)-1-methyl-1H-pyrazol-4-yl)-2-(4-(dimethylcarbamoyl)-2,6-difluorophenyl)thiazole-4-carboxamide 354

Following the procedure for Example 101, 354 was prepared. $^1$H NMR (500 MHz, CDCl$_3$) δ 9.81 (s, 1H), 8.36 (s, 1H), 8.14 (s, 1H), 7.14 (d, J=8.5 Hz, 2H), 4.59-4.55 (m, 1H), 4.49-4.32 (m, 2H), 4.02-3.92 (m, 1H), 3.82 (s, 3H), 3.53-3.46 (m, 1H), 2.11-1.99 (m, 2H), 1.89-1.81 (m, 1H), 1.32-1.26 (m, 1H). LCMS (ES+) m/z 523.2 (M+1)

Example 355

N-(5-((2S,5R,6S)-5-amino-6-methoxyoxepan-2-yl)-1-methyl-1H-pyrazol-4-yl)-2-(2,6-difluoro-4-methylphenyl)thiazole-4-carboxamide 355

Following the procedure for Example 101, 355 was prepared. $^1$H NMR (400 MHz, CDCl$_3$) δ 10.04 (s, 1H), 8.30 (s, 1H), 8.22 (s, 1H), 6.92 (d, J=8 Hz, 2H), 4.99-4.97 (m, 1H), 4.15 (dd, J=3.2 Hz, 10.4 Hz, 1H), 3.94 (dd, J=6.4 Hz, 4 Hz, 1H), 3.76 (s, 3H), 3.74-3.72 (m, 1H), 3.62-3.54 (m, 1H), 3.32 (s, 3H), 2.39 (s, 3H), 1.90-1.87 (m, 1H), 1.87-1.85 (m, 1H), 1.75-1.67 (m, 2H), 1.65-1.57 (m, 2H). LCMS (ES+) m/z 478.1 (M+1)

Example 356

N-(5-((2S,5R,6S)-5-amino-6-fluorooxepan-2-yl)-1-methyl-1H-pyrazol-4-yl)-2-(2-fluoro-5-methoxyphenyl)thiazole-4-carboxamide 356

Following the procedure for Example 101, 356 was prepared. $^1$H NMR (400 MHz, DMSO-d$_6$) δ 9.88 (s, 1H), 8.54 (s, 1H), 7.97-7.95 (m, 1H), 7.72 (s, 1H), 7.43-7.39 (m, 1H), 7.18-7.15 (m, 1H) 4.83-4.81 (dd, J=8.0, 2.8 Hz, 1H), 4.44-4.33 (dm, J=38.8 Hz, 1H), 4.22-3.95 (m, 2H), 3.87 (s, 3H), 3.83 (s, 3H), 3.25-3.19 (m, 1H), 2.13-2.10 (m, 1H), 1.94-1.66 (m, 5H). LCMS (ES+) m/z 464.1 (M+1)

Example 357

N-(5-((2S,5R,6S)-5-amino-6-fluorooxepan-2-yl)-1-methyl-1H-pyrazol-4-yl)-2-(3-methoxyphenyl)thiazole-4-carboxamide 357

Following the procedure for Example 101, 357 was prepared. $^1$H NMR (500 MHz, CDCl$_3$) δ 9.65 (s, 1H), 8.16 (s, 2H), 7.68 (d, J=9.0 Hz, 1H), 7.50 (t, J=2.2 Hz, 1H), 7.39 (t, J=7.5 Hz, 1H), 7.02-7.00 (m, 1H), 4.63-4.41 (m, 3H), 4.05-3.95 (m, 1H), 3.89 (s, 3H), 3.83 (s, 3H), 3.65-3.58 (m, 1H), 2.10-2.07 (m, 2H), 1.88-1.72 (m, 2H), 1.32-1.26 (m, 1H). LCMS (ES+) m/z 446.2 (M+1)

Example 358

N-(5-((2S,5R,6S)-5-amino-6-fluorooxepan-2-yl)-1-methyl-1H-pyrazol-4-yl)-2-(4-cyclopropyl-2,6-difluorophenyl)thiazole-4-carboxamide 358

Following the procedure for Example 101, 358 was prepared. $^1$H NMR (500 MHz, CDCl$_3$) δ 9.68 (s, 1H), 8.29 (s, 1H), 8.09 (s, 1H), 6.75 (d, J=10.1 Hz, 2H), 4.70-4.52 (m, 1H), 4.50-4.28 (m, 2H), 3.97 (ddd, J=33.0, 14.6, 4.2 Hz, 1H), 3.83 (s, 3H), 3.49 (dt, J=17.0, 8.6 Hz, 1H), 2.07 (dd, J=10.9, 6.4 Hz, 3H), 1.99-1.64 (m, 4H), 1.35-0.98 (m, 2H), 0.92-0.68 (m, 2H). LCMS (ES+) m/z 492.2 (M+1)

Example 359

N-(5-((2S,5R,6S)-5-amino-6-fluorooxepan-2-yl)-1-methyl-1H-pyrazol-4-yl)-6-(4-chloro-2-fluorophenyl)-5-fluoropicolinamide 359

Following the procedure for Example 101, 359 was prepared. $^1$H NMR (500 MHz, DMSO-d$_6$) δ 10.16 (s, 1H), 8.26-8.23 (m, 1H), 8.12-8.08 (m, 1H), 7.89 (s, 1H), 7.80-7.77 (m, 1H), 7.66-7.64 (m, 1H), 7.52-7.50 (m, 1H), 4.84-4.82 (m, 1H), 4.34-3.93 (m, 3H), 3.76 (s, 3H), 3.10-3.07 (m, 1H), 2.08-2.05 (m, 1H), 1.79-1.63 (m, 5H). LCMS (ES+) m/z 480.1 (M+1)

Example 360

N-[5-[(2S,5R,6S)-5-amino-6-fluoro-oxepan-2-yl]-1-methyl-pyrazol-4-yl]-2-(2,6-difluoro-3-methylsulfonyl-phenyl)thiazole-4-carboxamide 360

Following the procedure for Example 101, 360 was prepared. $^1$H NMR (400 MHz, DMSO-d$_6$) δ 9.95 (s, 1H), 8.71 (s, 1H), 8.09 (ddd, J=9.2, 8.0, 5.9 Hz, 1H), 7.80 (s, 1H), 7.60 (t, J=9.3 Hz, 1H), 4.83 (dd, J=10.5, 3.8 Hz, 1H), 4.39-4.24 (m, 1H), 4.22-4.10 (m, 1H), 4.05-3.89 (m, 1H), 3.77 (s, 3H), 3.40 (s, 3H), 2.12-2.02 (m, 1H), 1.86-1.74 (m, 2H), 1.72-1.64 (m, 2H). LCMS (ES+) m/z 530.11 (M+1)

Example 361

N-[5-[(2S,5R,6S)-5-amino-6-fluoro-oxepan-2-yl]-1-methyl-pyrazol-4-yl]-2-(2-fluoro-3-methyl-phenyl)thiazole-4-carboxamide 361

Following the procedure for Example 101, 361 was prepared. $^1$H NMR (400 MHz, DMSO-d$_6$) δ 9.88 (s, 1H), 8.52 (s, 1H), 8.29 (t, J=7.7 Hz, 1H), 7.89 (s, 1H), 7.46 (t, J=7.4 Hz, 1H), 7.28 (t, J=7.7 Hz, 1H), 4.87 (dd, J=10.7, 3.6 Hz, 1H), 4.60-4.37 (m, 1H), 4.31 (dd, J=22.4, 14.9 Hz, 1H), 4.20-3.95 (m, 1H), 3.78 (s, 3H), 3.39-3.29 (m, 1H), 2.36 (d, J=2.2 Hz, 3H), 2.14-2.03 (m, 1H), 1.91-1.68 (m, 5H). LCMS (ES+) m/z 448.2 (M+1)

Example 362

N-(5-((2S,5R,6S)-5-amino-6-fluorooxepan-2-yl)-1-methyl-1H-pyrazol-4-yl)-2-(2-fluoro-3-methoxyphenyl)thiazole-4-carboxamide 362

Following the procedure for Example 101, 362 was prepared. $^1$H NMR (500 MHz, CDCl$_3$) δ 9.79 (s, 1H), 8.28 (s, 1H), 8.22 (s, 1H), 8.01-7.99 (m, 1H), 7.22-7.19 (m, 1H), 7.08-7.04 (m, 1H), 4.64-4.55 (m, 3H), 4.20-3.97 (m, 1H), 3.95 (s, 3H), 3.82 (s, 3H), 3.64-3.60 (m, 1H), 2.09-2.05 (m, 2H), 1.83-1.77 (m, 2H), 1.55 (s, 2H). LCMS (ES+) m/z 464.1 (M+1)

Example 363

N-(5-((2S,5R,6S)-5-amino-6-fluorooxepan-2-yl)-1-methyl-1H-pyrazol-4-yl)-2-(3-cyclopropyl-2,6-difluorophenyl)thiazole-4-carboxamide 363

Following the procedure for Example 101, 363 was prepared. $^1$H NMR (500 MHz, CDCl$_3$) δ 9.69 (s, 1H), 8.31 (s, 1H), 8.10 (s, 1H), 7.07-6.86 (m, 2H), 4.66-4.53 (m, 1H), 4.42 (dd, J=13.6, 6.7 Hz, 1H), 3.97 (ddd, J=32.6, 14.6, 4.1 Hz, 1H), 3.83 (s, 3H), 3.50 (dt, J=18.0, 9.0 Hz, 1H), 2.19-2.00 (m, 3H), 1.84 (m, 1H), 1.78-1.63 (m, 1H), 1.07-0.96 (m, 2H), 0.73 (q, J=5.2 Hz, 2H). LCMS (ES+) m/z 492.2 (M+1)

Example 364

N-(5-((2S,5R,6S)-5-amino-6-fluorooxepan-2-yl)-1-methyl-1H-pyrazol-4-yl)-2-(2,4,6-trifluorophenyl)thiazole-4-carboxamide 364

Following the procedure for Example 101, 364 was prepared. $^1$H NMR (400 MHz, DMSO-d$_6$) δ 9.92 (s, 1H), 8.63 (s, 1H), 7.81 (s, 1H), 7.48-7.45 (t, J=7.2 Hz, 2H), 4.82-4.79 (m, 1H), 4.37-4.27 (m, 1H), 4.20-4.12 (m, 1H), 4.03-3.92 (m, 1H), 3.77 (s, 3H), 3.21-3.19 (m, 1H), 2.07-2.03 (m, 1H), 1.80-1.67 (m, 5H). LCMS (ES+) m/z 470.1 (M+1)

Example 365

N-(5-((2S,5R,6S)-5-amino-6-fluorooxepan-2-yl)-1-methyl-1H-pyrazol-4-yl)-2-(2,3-difluoro-4-((S)-1-hydroxyethyl)phenyl)thiazole-4-carboxamide 365

Following the procedure for Example 101, 365 was prepared. $^1$H NMR (400 MHz, DMSO-d$_6$) δ 9.89 (s, 1H), 8.56 (s, 1H), 8.28-8.18 (m, 1H), 7.90 (s, 1H), 7.52-7.46 (m, 1H), 5.63-5.50 (m, 1H), 5.10-5.00 (m, 1H), 4.89 (dd, J=10.4, 3.7 Hz, 1H), 4.58-4.41 (m, 1H), 4.39-4.26 (m, 1H), 4.18-4.00 (m, 1H), 3.78 (s, 3H), 2.13-2.04 (m, 1H), 1.89-1.68 (m, 5H), 1.39 (d, J=6.5 Hz, 3H). LCMS (ES+) m/z 496.2 (M+1). Note: benzylic hydroxyl stereochemistry assigned arbitrarily.

Example 366

N-(5-((2S,5R,6S)-5-amino-6-fluorooxepan-2-yl)-1-methyl-1H-pyrazol-4-yl)-2-(2,3-difluoro-4-((R)-1-hydroxyethyl)phenyl)thiazole-4-carboxamide 366

Following the procedure for Example 101, 366 was prepared. $^1$H NMR (400 MHz, DMSO-d$_6$) δ 9.88 (s, 1H), 8.56 (s, 1H), 8.23 (t, J=7.7 Hz, 1H), 7.90 (s, 1H), 7.54-7.45 (m, 1H), 5.58 (d, J=4.6 Hz, 1H), 5.10-5.00 (m, 1H), 4.89 (dd, J=10.5, 3.7 Hz, 1H), 4.60-4.41 (m, 1H), 4.39-4.24 (m, 1H), 4.19-3.99 (m, 1H), 3.78 (s, 3H), 2.14-2.03 (m, 1H), 1.89-1.67 (m, 5H), 1.39 (d, J=6.5 Hz, 3H). LCMS (ES+) m/z 496.2 (M+1). Note: benzylic hydroxyl stereochemistry assigned arbitrarily.

Example 367

N-(5-((2S,5R,6S)-5-amino-6-fluorooxepan-2-yl)-1-methyl-1H-pyrazol-4-yl)-2-(2,6-difluoro-4-isobutyrylphenyl)thiazole-4-carboxamide 367

Following the procedure for Example 101, 367 was prepared. $^1$H NMR (500 MHz, CDCl$_3$) δ 9.81 (s, 1H), 8.39 (s, 1H), 8.15 (s, 1H), 7.62 (d, J=9.0 Hz, 2H), 4.61-4.33 (m, 3H), 4.06-3.93 (m, 1H), 3.82 (s, 3H), 3.51-3.44 (m, 2H), 2.10-1.99 (m, 2H), 1.85-1.85 (m, 1H), 1.76-1.70 (m, 1H), 1.26 (d, J=7.0 Hz, 6H). LCMS (ES+) m/z 522.2 (M+1)

Example 368

N-(5-((2S,5R,6S)-5-amino-6-methoxyoxepan-2-yl)-1-methyl-1H-pyrazol-4-yl)-2-(2,6-difluoro-3-methoxyphenyl)thiazole-4-carboxamide 368

Following the procedure for Example 101, 368 was prepared. $^1$H NMR (500 MHz, DMSO-d$_6$) δ: 10.13 (s, 1H), 8.65 (s, 1H), 7.95 (s, 1H), 7.44-7.41 (m, 1H), 7.33-7.30 (m, 1H), 5.11 (t, 1H), 3.91 (s, 3H), 3.86-3.83 (m, 1H), 3.78-3.74 (m, 1H), 3.21 (s, 3H), 3.43-3.41 (m, 1H), 3.30-3.29 (m, 1H), 3.02 (s, 3H), 2.46-2.41 (m, 1H), 1.71-1.52 (m, 5H). LCMS (ES+) m/z 494.2 (M+1)

Example 369

N-[5-[(2S,5R,6S)-5-amino-6-fluoro-oxepan-2-yl]-1-methyl-pyrazol-4-yl]-2-(2-fluoro-6-methyl-phenyl)-5-methyl-thiazole-4-carboxamide 369

Following the procedure for Example 101, 369 was prepared. $^1$H NMR (400 MHz, DMSO) δ 9.75-9.64 (s, 1H), 7.80-7.75 (s, 1H), 7.49-7.38 (m, 1H), 7.26-7.16 (m, 2H), 4.82-4.74 (dd, J=10.9, 3.5 Hz, 1H), 4.41-4.23 (m, 1H), 4.17-4.04 (m, 1H), 4.03-3.86 (ddd, J=37.7, 15.0, 3.4 Hz, 1H), 3.79-3.74 (s, 3H), 3.23-3.07 (m, 1H), 2.88-2.83 (s, 3H), 2.43-2.39 (s, 3H), 2.10-1.96 (m, 1H), 1.91-1.75 (d, J=11.7 Hz, 1H), 1.73-1.62 (s, 2H). LCMS (ES+) m/z 462.2 (M+1)

Example 370

N-[5-[(2S,5R,6S)-5-amino-6-fluoro-oxepan-2-yl]-1-methyl-pyrazol-4-yl]-2-(2,6-difluorophenyl)-5-methyl-thiazole-4-carboxamide 370

Following the procedure for Example 101, 370 was prepared. $^1$H NMR (400 MHz, DMSO) δ 9.91-9.85 (s, 1H), 7.88-7.83 (s, 1H), 7.67-7.57 (tt, J=8.4, 6.4 Hz, 1H), 7.36-7.25 (m, 2H), 4.85-4.78 (dd, J=10.7, 3.5 Hz, 1H), 4.51-4.31 (m, 1H), 4.25-4.11 (m, 1H), 4.10-3.93 (ddd, J=37.0, 14.9, 3.6 Hz, 1H), 3.79-3.72 (s, 3H), 3.35-3.23 (m, 1H), 2.88-2.83 (s, 3H), 2.11-2.00 (m, 1H), 1.87-1.66 (m, 3H). LCMS (ES+) m/z 466.2 (M+1)

Example 371

N-(5-((2S,5R,6S)-5-amino-6-fluorooxepan-2-yl)-1-methyl-1H-pyrazol-4-yl)-2-(2,6-difluoro-4-((S)-tetrahydrofuran-2-yl)phenyl)thiazole-4-carboxamide 371

Following the procedure for Example 101, 371 was prepared. $^1$H NMR (500 MHz, CDCl$_3$) δ 9.71 (s, 1H), 8.33 (s, 1H), 8.11 (s, 1H), 7.08 (d, J=3.0 Hz, 2H), 4.97-4.95 (m, 1H), 4.61-4.44 (m, 3H), 4.14-3.98 (m, 3H), 3.88 (s, 3H), 3.52-3.50 (m, 1H), 2.43-2.40 (m, 1H), 2.12-1.80 (m, 7H), 1.27-1.23 (m, 2H). LCMS (ES+) m/z 522.2 (M+1). Note: benzylic THF stereochemistry assigned arbitrarily.

Example 372

N-(5-((2S,5R,6S)-5-amino-6-fluorooxepan-2-yl)-1-methyl-1H-pyrazol-4-yl)-2-(4,5-dimethyl-1H-pyrazol-3-yl)thiazole-4-carboxamide 372

Following the procedure for Example 101, 372 was prepared. $^1$H NMR (400 MHz, DMSO-d$_6$) δ 12.87 (s, 1H), 9.48

(s, 1H), 8.27 (s, 1H), 7.81 (s, 1H), 4.84-4.81 (dd, J=8.4, 3.2, 1H), 4.46-4.33 (dm, J=44.0 Hz, 1H), 4.19-3.99 (m, 2H), 3.79 (s, 3H), 3.25-3.14 (m, 1H), 2.33 (s, 3H), 2.23 (s, 3H), 2.10-2.06 (m, 1H), 1.91-1.62 (m, 5H). LCMS (ES+) m/z 434.2 (M+1)

Example 373

N-(5-((2S,5R,6S)-5-amino-6-fluorooxepan-2-yl)-1-methyl-1H-pyrazol-4-yl)-2-(6,6-dimethyl-4,5,6,7-tetrahydro-1H-indazol-3-yl)thiazole-4-carboxamide 373

Following the procedure for Example 101, 373 was prepared. $^1$H NMR (500 MHz, DMSO-d$_6$) δ: 12.84 (s, 1H), 9.46 (s, 1H), 8.26 (s, 1H), 7.80 (s, 1H), 4.83 (dd, J=4.0, 11.0 Hz, 1H), 4.44-4.18 (m, 1H), 4.11-4.00 (m, 2H), 3.79 (s, 3H), 3.23-3.15 (m, 1H), 2.94-2.78 (m, 2H), 2.43 (s, 2H), 2.11-2.06 (m, 1H), 1.90-1.82 (m, 1H), 1.77-1.73 (m, 4H), 1.58-1.57 (m, 2H), 1.01 (s, 6H). LCMS (ES+) m/z 488.2 (M+1)

Example 374

N-(5-((2S,5R,6S)-5-amino-6-fluorooxepan-2-yl)-1-methyl-1H-pyrazol-4-yl)-2-(4,5,6,7-tetrahydro-1H-indazol-3-yl)thiazole-4-carboxamide 374

Following the procedure for Example 101, 374 was prepared. $^1$H NMR (500 MHz, DMSO-d$_6$) δ 12.89 (s, 1H), 9.45 (s, 1H), 8.25 (s, 1H), 7.77 (s, 1H), 4.82-4.77 (m, 1H), 4.44-4.01 (m, 4H), 3.78 (s, 3H), 3.19-3.16 (m, 1H), 2.92-2.78 (m, 2H), 2.63 (s, 2H), 2.08-1.88 (m, 4H), 1.87-1.76 (m, 4H), 1.30 (s, 1H). LCMS (ES+) m/z 460.2 (M+1)

Example 375

N-(5-((2S,5R,6S)-5-amino-6-fluorooxepan-2-yl)-1-methyl-1H-pyrazol-4-yl)-6-(4-chloro-2,6-difluorophenyl)-5-fluoropicolinamide 375

Following the procedure for Example 101, 375 was prepared. $^1$H NMR (500 MHz, CDCl$_3$) δ 10.24 (s, 1H), 8.34-8.31 (m, 1H), 8.20-8.17 (m, 1H), 7.95 (s, 1H), 7.62 (d, J=7.5 Hz, 2H), 4.86-4.84 (m, 1H), 4.29-4.16 (m, 1H), 4.05-3.88 (m, 2H), 3.76 (s, 3H), 3.08-3.02 (m, 1H), 2.09-2.05 (m, 1H), 1.75-1.64 (m, 5H). LCMS (ES+) m/z 498.1 (M+1)

Example 376

N-[5-[(2S,5R,6S)-5-amino-6-fluoro-oxepan-2-yl]-1-methyl-pyrazol-4-yl]-2-[3-(dimethylcarbamoyl)-2,6-difluoro-phenyl]thiazole-4-carboxamide 376

Following the procedure for Example 101, 376 was prepared. $^1$H NMR (400 MHz, DMSO-d$_6$) δ 9.92-9.84 (s, 1H), 8.69-8.63 (s, 1H), 7.81-7.77 (s, 1H), 7.70-7.60 (td, J=8.1, 6.3 Hz, 1H), 7.46-7.37 (t, J=9.2 Hz, 1H), 4.87-4.78 (dd, J=10.8, 3.4 Hz, 1H), 4.59-4.37 (dd, J=51.8, 6.8 Hz, 1H), 4.28-4.13 (m, 1H), 4.13-3.94 (ddd, J=37.2, 15.0, 3.5 Hz, 1H), 3.85-3.74 (s, 3H), 3.06-2.99 (s, 3H), 2.94-2.86 (s, 3H), 2.14-2.02 (m, 1H), 1.95-1.67 (m, 5H). LCMS (ES+) m/z 523.2 (M+1)

Example 377

N-[5-[(2S,5R,6S)-5-amino-6-fluoro-oxepan-2-yl]-1-methyl-pyrazol-4-yl]-2-[3-(difluoromethyl)-2,6-difluoro-phenyl]thiazole-4-carboxamide 377

Following the procedure for Example 101, 377 was prepared. $^1$H NMR (400 MHz, DMSO-d$_6$) δ 9.98-9.92 (s, 1H), 8.69-8.66 (s, 1H), 7.95-7.85 (q, J=7.6 Hz, 1H), 7.84-7.80 (s, 1H), 7.55-7.43 (dd, J=17.7, 8.6 Hz, 1H), 7.41-7.13 (m, 1H), 4.89-4.79 (d, J=9.3 Hz, 1H), 4.54-4.34 (d, J=49.6 Hz, 1H), 4.32-3.92 (m, 2H), 3.82-3.76 (s, 3H), 2.15-2.01 (d, J=13.0 Hz, 1H), 1.93-1.65 (m, 5H). LCMS (ES+) m/z 502.1 (M+1)

Example 378

N-[5-[(2S,5R,6S)-5-amino-6-fluoro-oxepan-2-yl]-1-methyl-pyrazol-4-yl]-2-[3-(difluoromethyl)-2-fluoro-6-methoxy-phenyl]thiazole-4-carboxamide 378

Following the procedure for Example 101, 378 was prepared. $^1$H NMR (400 MHz, DMSO-d$_6$) δ 9.93-9.88 (s, 1H), 8.61-8.57 (d, J=1.5 Hz, 1H), 7.83-7.75 (t, J=8.5 Hz, 1H), 7.75-7.70 (s, 1H), 7.37-6.90 (m, 4H), 4.90-4.66 (m, 2H), 4.42-4.27 (dd, J=23.5, 14.9 Hz, 1H), 4.22-4.03 (dd, J=37.7, 15.6 Hz, 1H), 4.02-3.96 (s, 3H), 3.83-3.78 (s, 3H), 3.64-3.49 (s, 1H), 2.22-2.09 (d, J=11.9 Hz, 1H), 2.00-1.75 (m, 4H). LCMS (ES+) m/z 514.1 (M+1)

Example 379

N-[5-[(2S,5R,6S)-5-amino-6-fluoro-oxepan-2-yl]-1-methyl-pyrazol-4-yl]-2-(1H-pyrazol-3-yl)thiazole-4-carboxamide 379

Following the procedure for Example 101, 379 was prepared. $^1$H NMR (400 MHz, DMSO-d$_6$) δ 9.78 (s, 1H), 8.29 (s, 1H), 7.95-7.87 (m, 2H), 6.96 (d, J=2.4 Hz, 1H), 4.88 (dd, J=10.4, 3.8 Hz, 1H), 4.59-4.38 (m, 1H), 4.37-4.23 (m, 1H), 4.19-3.95 (m, 1H), 3.77 (s, 3H), 3.39-3.25 (m, 1H), 2.50 (ddd, J=23.7, 3.8, 1.9 Hz, 1H), 2.13-2.03 (m, 1H), 1.89-1.69 (m, 4H). LCMS (ES+) m/z 406.2 (M+1)

Example 380

N-(5-((2S,5R,6S)-5-amino-6-fluorooxepan-2-yl)-1-methyl-1H-pyrazol-4-yl)-2-(2,6-difluoro-4-((R)-tetrahydrofuran-2-yl)phenyl)thiazole-4-carboxamide 380

Following the procedure for Example 101, 380 was prepared. $^1$H NMR (500 MHz, CDCl$_3$) δ 9.71 (s, 1H), 8.33 (s, 1H), 8.12 (s, 1H), 7.08 (d, J=9.5 Hz, 2H), 4.98-4.95 (m, 1H), 4.61-4.44 (m, 3H), 4.14-3.98 (m, 3H), 3.85 (s, 3H), 3.55-3.48 (m, 1H), 2.44-2.40 (m, 1H), 2.11-1.73 (m, 8H), 1.28-1.26 (m, 1H). LCMS (ES+) m/z 522.2 (M+1). Note: benzylic THF stereochemistry assigned arbitrarily.

Example 381

N-(5-((2S,5R,6S)-5-amino-6-fluorooxepan-2-yl)-1-methyl-1H-pyrazol-4-yl)-2-(1H-indazol-3-yl)thiazole-4-carboxamide 381

Following the procedure for Example 101, 381 was prepared. $^1$H NMR (500 MHz, CDCl$_3$) δ 10.64 (s, 1H), 9.38 (s, 1H), 8.47-8.45 (m, 1H), 8.22 (s, 1H), 8.06 (s, 1H), 7.56-7.54 (m, 1H), 7.50-7.47 (m, 1H), 7.38-7.26 (m, 1H), 4.68-4.65 (m, 1H), 4.47-4.40 (m, 2H), 4.09-4.02 (m, 1H), 3.88 (s, 3H), 3.48-3.47 (m, 1H), 2.17-2.13 (m, 2H), 1.90-1.89 (m, 1H), 1.72-1.70 (m, 1H), 1.59 (s, 2H). LCMS (ES+) m/z 456.1 (M+1)

Example 382

N-[5-[(2S,5R,6S)-5-amino-6-fluoro-oxepan-2-yl]-1-methyl-pyrazol-4-yl]-2-[2-fluoro-6-(hydroxymethyl)phenyl]thiazole-4-carboxamide 382

Following the procedure for Example 101, 382 was prepared. $^1$H NMR (400 MHz, DMSO-d$_6$) δ 9.77 (s, 1H), 8.60 (s, 1H), 7.71 (s, 1H), 7.63-7.52 (m, 2H), 7.36-7.27 (m, 1H), 4.79 (dd, J=11.0, 3.6 Hz, 1H), 4.71 (d, J=3.3 Hz, 2H), 4.40 (dd, J=49.4, 6.9 Hz, 1H), 4.23-4.11 (m, 1H), 4.05-3.89 (m, 1H), 3.80 (s, 3H), 3.26-3.19 (m, 1H), 2.11-2.03 (m, 1H), 1.96-1.84 (m, 1H), 1.76-1.66 (m, 2H). LCMS (ES+) m/z 464.2 (M+1)

Example 383

N-[5-[(2S,5R,6S)-5-amino-6-fluoro-oxepan-2-yl]-1-methyl-pyrazol-4-yl]-2-(3-pyridyl)thiazole-4-carboxamide 383

Following the procedure for Example 101, 383 was prepared. LCMS (ES+) m/z 417.1 (M+1)

Example 384

N-[5-[(2S,5R,6S)-5-amino-6-fluoro-oxepan-2-yl]-1-methyl-pyrazol-4-yl]-2-(2-isopropoxy-3-pyridyl)thiazole-4-carboxamide 384

Following the procedure for Example 101, 384 was prepared. $^1$H NMR (400 MHz, DMSO) δ 9.91-9.87 (s, 1H), 8.85-8.77 (dd, J=7.6, 2.0 Hz, 1H), 8.48-8.45 (s, 1H), 8.36-8.30 (dd, J=4.8, 1.9 Hz, 1H), 7.91-7.87 (s, 1H), 7.20-7.13 (dd, J=7.7, 4.8 Hz, 1H), 5.57-5.49 (m, 1H), 4.91-4.83 (dd, J=10.5, 3.6 Hz, 1H), 4.58-4.39 (m, 1H), 4.39-4.25 (dd, J=22.6, 15.0 Hz, 1H), 4.19-4.00 (ddd, J=39.7, 15.1, 3.4 Hz, 1H), 3.80-3.76 (s, 3H), 3.35-3.27 (m, 1H), 2.13-2.03 (m, 1H), 1.92-1.67 (m, 3H), 1.51-1.42 (d, J=6.2 Hz, 6H). LCMS (ES+) m/z 475.2 (M+1)

Example 385

N-[5-[(2S,5R,6S)-5-amino-6-fluoro-oxepan-2-yl]-1-methyl-pyrazol-4-yl]-2-[6-(dimethylamino)-3-pyridyl]thiazole-4-carboxamide 385

Following the procedure for Example 101, 385 was prepared. LCMS (ES+) m/z 460.2 (M+1)

Example 386

2-(6-acetamido-3-pyridyl)-N-[5-[(2S,5R,6S)-5-amino-6-fluoro-oxepan-2-yl]-1-methyl-pyrazol-4-yl]thiazole-4-carboxamide 386

Following the procedure for Example 101, 386 was prepared. LCMS (ES+) m/z 474.2 (M+1)

Example 387

N-(5-((2S,5R,6S)-5-amino-6-fluorooxepan-2-yl)-1-methyl-1H-pyrazol-4-yl)-2-(5-fluoro-1-methyl-2-oxo-1,2-dihydropyridin-4-yl)thiazole-4-carboxamide 387

Following the procedure for Example 101, 387 was prepared. $^1$H NMR (400 MHz, CDCl$_3$-d) δ 9.73 (s, 1H), 8.41 (s, 1H), 8.26 (s, 1H), 7.51 (d, J=5.6 Hz, 1H), 7.38 (d, J=4.8 Hz, 1H), 4.48-4.67 (m, 3H), 3.90-4.01 (m, 1H), 3.83 (s, 3H), 3.66-3.74 (m, 1H), 3.55 (s, 3H), 2.10-2.14 (m, 2H), 1.83-1.89. LCMS (ES+) m/z 465.1 (M+1)

Example 388

N-(5-((2S,5R,6S)-5-amino-6-fluorooxepan-2-yl)-1-methyl-1H-pyrazol-4-yl)-2-(1H-pyrazol-1-yl)thiazole-4-carboxamide 388

Following the procedure for Example 101, 388 was prepared. $^1$H NMR (500 MHz, DMSO-d$_6$) δ 9.72 (s, 1H), 8.56 (s, 1H), 8.17 (s, 1H) 7.89-7.93 (d, 2H), 6.71-6.72 (t, 1H), 4.89-4.91 (m, 1H), 4.00-4.56 (m, 3H), 3.78 (s, 3H), 2.36-2.36 (s, 1H), 2.08-2.12 (m, 1H), 1.68-1.82 (m, 5H). LCMS (ES+) m/z 406.1 (M+1)

Example 389

N-(5-((2S,5R,6S)-5-amino-6-fluorooxepan-2-yl)-1-methyl-1H-pyrazol-4-yl)-2-(4,5,6,7-tetrahydro-1H-indazol-1-yl)thiazole-4-carboxamide 389

Following the procedure for Example 101, 389 was prepared. $^1$H NMR (500 MHz, DMSO-d$_6$) δ 9.36 (s, 1H), 8.10 (s, 1H), 7.76 (s, 1H), 7.64 (s, 1H), 4.82 (dd, J=10.5, 6.5 Hz, 1H), 4.45-4.34 (m, 1H), 4.15-4.00 (m, 2H), 3.78 (s, 3H), 3.24-3.09 (m, 3H), 2.09-2.05 (m, 1H), 1.88-1.80 (m, 3H), 1.72-1.65 (m, 6H). LCMS (ES+) m/z 460.2 (M+1)

Example 390

N-(5-((2S,5R,6S)-5-amino-6-fluorooxepan-2-yl)-1-methyl-1H-pyrazol-4-yl)-2-(4,5,6,7-tetrahydro-2H-indazol-2-yl)thiazole-4-carboxamide 390

Following the procedure for Example 101, 390 was prepared. $^1$H NMR (500 MHz, DMSO-d$_6$) δ 9.69 (s, 1H), 8.22 (s, 1H), 8.07 (s, 1H), 7.88 (s, 1H), 4.8 (dd, J=10.0, 6.5 Hz, 1H), 4.56-4.44 (m, 1H), 4.33 (dd, J=22.5, 7.0 Hz, 1H), 4.13-4.01 (m, 1), 3.77 (s, 3H), 3.28-3.27 (m, 2H), 2.67-2.65 (m, 2H), 2.57 (s, 2H), 2.10-2.05 (m, 1H), 1.89-1.70 (m, 8H). LCMS (ES+) m/z 460.2 (M+1)

Example 391

N-(5-((2S,5R,6S)-5-amino-6-fluorooxepan-2-yl)-1-methyl-1H-pyrazol-4-yl)-2-(5,7-difluoro-2,3-dihydrobenzofuran-6-yl)thiazole-4-carboxamide 391

Following the procedure for Example 101, 391 was prepared. $^1$H NMR (400 MHz, DMSO-d$_6$) δ 9.87 (s, 1H), 8.63 (s, 1H), 7.76 (s, 1H), 7.31-7.29 (d, J=7.2 Hz, 1H), 4.87-4.71 (m, 4H), 4.33-4.11 (m, 2H), 3.81 (s, 3H), 3.58-3.55 (m, 1H), 3.04-3.01 (m, 2H), 2.16-2.14 (m, 1H), 1.96-1.73 (m, 5H). LCMS (ES+) m/z 494.1 (M+1)

Example 901

Pim Kinase Binding Activity

PIM-1, -2, and -3 enzymes were generated as fusion proteins expressed in bacteria and purified by IMAC column chromatography (Sun, X., Chiu, J. F., and He, Q. Y. (2005) Expert Rev. Proteomics, 2:649-657). A fluorescent-labeled Pim-specific peptide substrate, was custom synthesized by American Peptide Company (Sunnyvale, Calif.). Reaction Buffer contained 10 mM HEPES, pH 7.2, 10 mM $MgCl_2$, 0.01% Tween 20, 2 mM DTT. Termination Buffer contained 190 mM HEPES, pH 7.2, 0.015% Brij-35, 0.2% Coating Reagent 3 (Caliper Life Sciences, Hopkinton, Mass.), 20 mM EDTA. Separation Buffer contained 100 mM HEPES, pH 7.2, 0.015% Brij-35, 0.1% Coating Reagent 3, 1:200 Coating Reagent 8 (Caliper Life Sciences, Hopkinton, Mass.), 10 mM EDTA and 5% DMSO.

PIM reactions were carried out in a final volume of 10 µL per well in a 384-well plate. A standard enzymatic reaction, initiated by the addition of 5 µL 2×ATP and test compound to 5 µL of 2× enzyme and FAM-peptide, contained 20 pM PIM1, 50 pM PIM2, or 55 pM PIM3, 1 µM FAM-peptide, and 10 µM ATP, in Reaction Buffer. After 90 minutes of incubation at room temperature, the phosphorylation reaction was stopped by the addition of 10 µL Termination Buffer. The product and substrate in each independent reaction were separated on a 12-sipper microfluidic chip (Caliper Life Sciences, Hopkinton, Mass.) run on a Caliper LC3000® (Caliper Life Sciences, Hopkinton, Mass.). The separation of product and substrate was optimized by choosing voltages and pressure using Caliper's Optimizer software (Hopkinton, Mass.). The separation conditions used a downstream voltage of −500V, an upstream voltage of −2150V, and a screening pressure of −1.2 psi. The product and substrate fluorophore were excited at 488 nm and detected at 530 nm. Substrate conversion was calculated from the electropherogram using HTS Well Analyzer software (Caliper Life Sciences, Hopkinton, Mass.). Ki values for the test compound were calculated. See Table 1 for representative PIM1 LC3K Ki in micromolar values of exemplary compounds.

Example 902

In Vitro Cell Proliferation Potency Assays

BaF3 parental line was obtained from the DSMZ repository. BaF3 lines transfected with PIM1 or PIM2 were generated. Mouse IL-3 was purchased from R&D Systems. G418 was purchased from Clontech. Media for BaF3 parental line contained RPMI, 10% FBS, 2 mM L-Glutamine, 2 ng/mL mIL-3. Media for BaF3 PIM1 & 2 lines contained RPMI, 10% FBS, 2 mM L-Glutamine, 250 µg/mL. Media for MM1.S (multiple myeloma cells) line contained RPMI, 10% FBS, 2 mM L-Glutamine.

BaF3, a murine interleukin-3 dependent pro-B cell line, parental cells, BaF3 PIM1 cells, BaF3 PIM2 cells, and MM1.S (multiple myeloma) cells were seeded at 2 k/well, 5 k/well, 5 k/well, and 10 k/well respectively, in a 384-well plate, at 45 µL/well. Test compound was added at 5 µL/well. BaF3 cells (parental and transfected) were incubated overnight, while MM1.S cells were incubated for 72 hours at 37° C., 5% $CO_2$. CELL TITER GLO® Reagent (Promega) was added at 50 µL/well, the plates were incubated for 30 minutes, and their luminescence read on an HT Analyst. $IC_{50}/EC_{50}$ values for the test compound were calculated.

Representative compounds of the present invention were tested as described above and found to exhibit a $Ki/IC_{50}/EC_{50}$ in µM (micromolar) as shown below in Tables 2a, 2b, and 2c.

TABLE 2a

| No. | Prolif BaF3 IL3 (IC50) µM (micromolar) | Prolif BaF3 PIM1 (IC50) µM (micromolar) | Prolif MM1S ATP (EC50) µM (micromolar) |
| --- | --- | --- | --- |
| 109 | 8.3 | 0.115 | 9.2 |
| 110 | 9.4 | 0.0448 | 2.4 |
| 112 | 6.9 | 2.1 | 8.5 |
| 115 | 3.4 | 0.0192 | 0.0718 |
| 117 | 3 | 0.0307 | 0.122 |
| 121 | 3.5 | 0.0136 | 0.0119 |
| 126 | 25 | 0.0252 | 0.0217 |
| 129 | 6.9 | 0.0247 | 0.109 |
| 131 | 6.8 | 1.5 | 10 |
| 135 | 12.7 | 2.5 | 4.3 |
| 148 | 25 | 1.6 | 7.7 |

TABLE 2b

| No. | Prolif BaF3 IL3 (IC50) µM (micromolar) | Prolif BaF3 PIM1 (IC50) µM (micromolar) | Prolif MM1S ATP (EC50) µM (micromolar) |
| --- | --- | --- | --- |
| 286 | 11.3 | 0.947 | 12.6 |
| 316 | 9.3 | 0.126 | 0.686 |
| 317 | 7.9 | 0.0152 | 0.0345 |
| 319 | 7.8 | 0.129 | 0.875 |
| 320 | >25 | 0.0244 | 0.187 |
| 321 | 4.4+ | 0.0506 | 0.385 |
| 322 | 6.3+ | 0.113 | 1.5 |
| 323 | >25 | 0.186 | 10 |
| 324 | >25 | 0.0453 | 0.116 |
| 325 | 6.3 | 0.142 | 0.735 |
| 326 | 12.4 | 0.132 | 0.436 |
| 327 | 16.8 | 0.176 | 0.648 |
| 328 | 12.5 | 0.0214 | 1.5 |
| 329 | 2.4 | 0.348 | 1.7 |
| 339 | >25 | 0.0522 | 1.9 |
| 340 | 20.7 | 0.0517 | >6.2 |
| 341 | >25 | 0.0968 | 6.9 |
| 342 | 10.0 | 12.7 | 21.6 |
| 343 | 12.8 | 0.342 | 0.781 |
| 344 | 14 | 9 | 9.8 |
| 345 | >25 | 6.8 | >25 |
| 346 | >25 | 0.517 | 4.3 |
| 347 | 5 | 0.157 | 3.3 |
| 348 | 10.5 | 0.359 | 1 |

TABLE 2c

| No. | Prolif BaF3 + IL3 (IC50) µM (micromolar) | Prolif BaF3_PIM1 (IC50) µM (micromolar) | Prolif MM1S ATP (EC50) µM (micromolar) |
| --- | --- | --- | --- |
| 351 | 9.9 | 0.621 | 0.52 |
| 354 | 7.3 | 3.4 | 5.1 |
| 355 | 3.9 | 0.0535 | 1.6 |
| 356 | 6.5 | 0.108 | 1.4 |
| 358 | 4.1 | 0.0682 | 0.938 |
| 359 | 11.6 | 0.262 | 5.8 |
| 360 | 16.5 | 15.2 | 9.4 |
| 361 | 2.8 | 0.25 | 0.452 |
| 362 | 3.1 | 0.0507 | 0.336 |
| 363 | 4.5 | 0.294 | 0.937 |
| 364 | 20.2 | 0.208 | 1.1 |
| 365 | 15.9 | 0.408 | 0.348 |
| 366 | 10.3 | 0.302 | 1.7 |
| 367 | 24 | 0.245 | 5.4 |
| 368 | 1.9 | 0.1 | 2.4 |
| 370 | 6.4 | 0.675 | 1.8 |
| 371 | >25 | 0.151 | 4.4 |
| 372 | 20.5 | 0.602 | 1.6 |
| 373 | 8.6 | 0.101 | 3.4 |
| 374 | 13.1 | 0.246 | 1.4 |
| 374 | 10.9 | 0.0709 | 4.1 |
| 377 | 9.9 | 0.0686 | 4.2 |

TABLE 2c-continued

| No. | Prolif BaF3 + IL3 (IC50) µM (micromolar) | Prolif BaF3_PIM1 (IC50) µM (micromolar) | Prolif MM1S ATP (EC50) µM (micromolar) |
|---|---|---|---|
| 379 | >25 | 0.98 | 2.9 |
| 380 | 12.2 | 0.0372 | 1.7 |
| 381 | 5.8 | 0.0794 | 0.64 |
| 383 | 20.8 | 0.823 | 5.7 |
| 384 | 7.2 | 5.6 | 4.4 |
| 385 | 12 | 0.118 | 1.2 |
| 387 | 8.2 | 3.2 | 2 |

Example 903 hERG Assays hERG Assays (2-pt) were Carried Out as Follows:

The in vitro potential for hERG (the human Ether-à-go-go-Related Gene) potassium channel current inhibition by a selection of the compounds of the invention was assessed according to the study site standard procedures (ChanTest, Cleveland, Ohio). In brief, hERG-expressing HEK-293 cells (n=2/concentration) were evaluated at 1 and 10 mM in the automated PatchXpress 7000A system (Molecular Devices, Sunnyvale, Calif.) for 5 minutes after adding the test article. hERG assays (2-pt) data were expressed as percent of maximal current.

hERG Assays ($IC_{50}$) were Carried Out as Follows:

The in vitro potential for hERG potassium channel current inhibition was assessed according to the study site standard procedures (ChanTest, Cleveland, Ohio). In brief, hERG inhibition (% max) was determined in hERG-expressing HEK-293 cells (n=2/concentration) using the automated PatchXpress 7000A system (Molecular Devices, Sunnyvale, Calif.) for 5 minutes after adding the test article. $IC_{50}$ values were calculated based on hERG inhibition at test article concentrations of 0.01, 0.1, 1, 10, 30, and 100 µM.

hERG $IC_{50}$ and $IC_{20}$ values of certain compounds of the invention were measured and compared with a compound, 5-amino-N-(5-((4R,5R)-4-amino-5-fluoroazepan-1-yl)-1-methyl-1H-pyrazol-4-yl)-2-(2,6-difluorophenyl)thiazole-4-carboxamide, No. 139, from a series of PIM inhibitors where corresponding $R^2$ is an N-linked heterocyclyl or C-linked carbocyclyl moiety (US 2013/0079321). The $IC_{50/20}$ values for this compound No. 139 of US 2013/0079321 were 2.7 and 0.7 micromolar (µM), respectively. In contrast, the $IC_{50/20}$ values for compound No. 154, 5-Amino-N-[5-[(2S,5R,6R)-5-amino-6-methoxy-oxepan-2-yl]-1-methyl-pyrazol-4-yl]-2-(2,6-difluorophenyl)thiazole-4-carboxamide, from Table 1b of the present invention were 9.1 and 1.6 micromolar, respectively. The $IC_{50/20}$ values for compound No. 177, 5-Amino-N-[5-[(2S,5R,6S)-5-amino-6-fluoro-oxepan-2-yl]-1-methyl-pyrazol-4-yl]-2-(2,6-difluorophenyl)thiazole-4-carboxamide from Table 1b of the present invention were 16 and 3.9 micromolar, respectively. This hERG data indicates the compounds of the invention present diminished susceptibility to QTc prolongation. An excessively prolonged QTc-interval may lead to serious ventricular arrhythmia and sudden death (De Bruin, M. L et al (2005) European Heart Journal, 26:590-597; Redfern, W. S. et al (2003) Cardiovascular Research, 58:32-45).

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

We claim:

1. A compound selected from Formula 1:

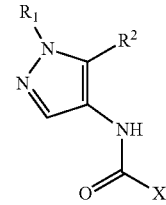

and stereoisomers, geometric isomers, tautomers, or pharmaceutically acceptable salts thereof, wherein:

$R^1$ is selected from H, $C_1$-$C_{12}$ alkyl, $C_2$-$C_{12}$ alkenyl, $C_2$-$C_{12}$ alkynyl, $C_6$-$C_{20}$ aryl, $C_3$-$C_{12}$ carbocyclyl, $C_2$-$C_{20}$ heterocyclyl, $C_1$-$C_{20}$ heteroaryl, and —($C_1$-$C_{12}$ alkylene)-($C_2$-$C_{20}$ heterocyclyl);

$R^2$ is selected from the structures:

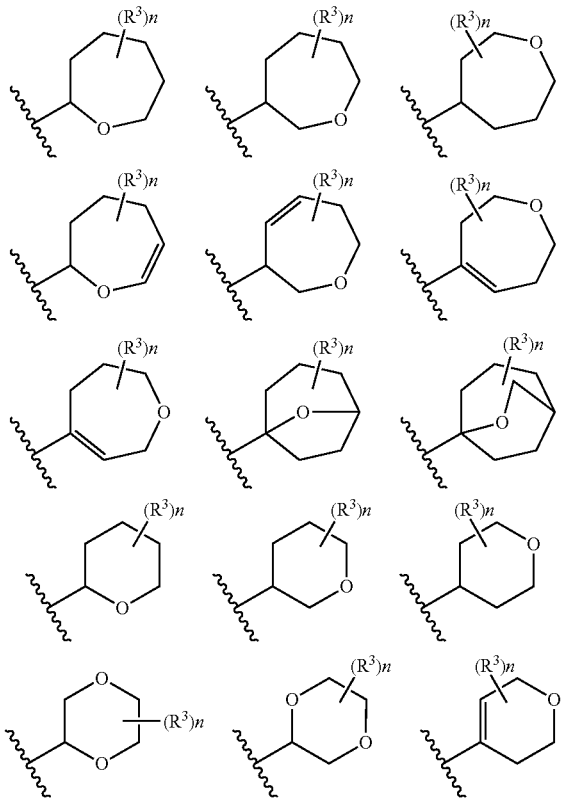

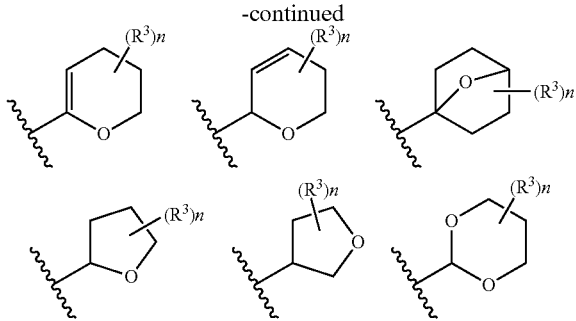

where the wavy line indicates the site of attachment;
R³ is independently selected from F, Cl, Br, I, —CH₃, —CH₂CH₃, —CH(CH₃)₂, —C(CH₃)₃, —CH₂CH(CH₃)₂, —CH=CH₂, —CH=C(CH₃)₂, =CH₂, —CH₂F, —CHF₂, —CF₃, —CH₂OH, —CH₂OCH₃, —CH₂NH₂, —CH₂NHCH₃, —CH₂CH₂NH₂, —CH₂CHCH₂NH₂, —CH₂CH(CH₃)NH₂, —CH₂OH, —CH₂CH₂OH, —C(CH₃)₂OH, —CH(OH)CH(CH₃)₂, —C(CH₃)₂CH₂OH, —CH₂CH₂SO₂CH₃, —CN, —CO₂H, —COCH₃, —COCH₂NH₂, —CO₂CH₃, —CO₂C(CH₃)₃, —COCH(OH)CH₃, —CONH₂, —CONHCH₃, —CON(CH₃)₂, —C(CH₃)₂CONH₂, —NO₂, —NH₂, —NHCH₃, —N(CH₃)₂, —NHCH₂CHF₂, —NHCH₂CF₃, —NHCH₂CH₂OH, —NHCOCH₃, —N(CH₃)COCH₃, —NHC(O)OCH₂CH₃, —NHC(O)OCH₂Cl₃, —NHC(O)OC₆H₅, —NHS(O)₂CH₃, —N(CH₃)C(CH₃)₂CONH₂, —N(CH₃)CH₂CH₂S(O)₂CH₃, =O, —OH, —OCH₃, —OCHF₂, —OCH₂F, —OCH₂CH₃, —OCH(CH₃)₂, —OCH₂CH(CH₃)₂, —OC(CH₃)₃, —S(O)₂N(CH₃)₂, —SCH₃, —CH₂OCH₃, —S(O)₂CH₃, cyclopropyl, cyclobutyl, cyclopentyl, cyclohexyl, cycloheptyl, azetidinyl, azepanyl, oxetanyl, oxetan-3-ylmethylamino, (3-methyloxetan-3-yl)methylamino, pyrrolidinyl, piperazinyl, piperidinyl, (piperidin-4-yl)ethyl), pyranyl, (piperidin-4-ylmethyl), morpholinomethyl, and morpholino;
or where two geminal R³ groups form a spiro ring selected from a cyclopropyl, cyclobutyl, cyclopentyl, cyclohexyl, pyrrolidinyl, azetidinyl, azepanyl, oxetanyl, pyrrolidinyl, piperazinyl, or piperidinyl ring, where the spiro ring is optionally substituted with one or more groups independently selected from —F, —OH, =O, —CH₃, —NH₂, —CH₂F, —CH₂OH, —CH₂OCH₃, —CH₂NH₂, and —CF₃;
or where two vicinal R³ groups form a five-membered or six-membered heterocyclyl fused ring, where the heterocyclyl fused ring is optionally substituted with one or more groups independently selected from —F, —OH, =O, —CH₃, —NH₂, —CH₂F, —CH₂OH, —CH₂OCH₃, —CH₂NH₂, and —CF₃;
n is 0, 1, 2, 3, 4, 5, or 6;
X is selected from the structures:

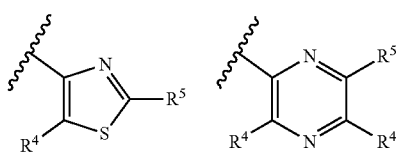

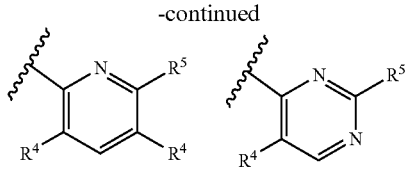

where the wavy line indicates the site of attachment;
R⁴ is independently H, F, —CH₃, or —NH₂; and
R⁵ is selected from H, Cl, Br, C₁-C₁₂ alkyl, —O—(C₁-C₁₂ alkyl), —(C₁-C₁₂ alkylene)-(C₃-C₁₂ carbocyclyl), —(C₁-C₁₂ alkylene)-(C₂-C₂₀ heterocyclyl), —(C₂-C₈ alkenylene)-(C₃-C₁₂ carbocyclyl), —(C₂-C₈ alkenylene)-(C₂-C₂₀ heterocyclyl), C₆-C₂₀ aryl, —(C₆-C₂₀ arylene)-(C₂-C₂₀ heterocyclyl), —(C₆-C₂₀ arylene)-(C₆-C₂₀ arylene), —(C₆-C₂₀ arylene)-(C₁-C₁₂ alkylene)-(C₂-C₂₀ heterocyclyl), —(C₆-C₂₀ arylene)-O—(C₂-C₂₀ heterocyclyl), —(C₆-C₂₀ arylene)-O—(C₁-C₁₂ alkyl), C₃-C₁₂ carbocyclyl, C₂-C₂₀ heterocyclyl, C₁-C₂₀ heteroaryl, —(C₁-C₂₀ heteroaryl)-(C₂-C₂₀ heterocyclyl), and —(C₁-C₂₀ heteroaryl)-(C₁-C₁₂ alkyl); where alkyl, alkenyl, alkynyl, alkylene, carbocyclyl, heterocyclyl, aryl, and heteroaryl are optionally substituted with one or more groups independently selected from F, Cl, Br, I, —CH₃, —CH₂CH₃, —CH(CH₃)₂, —CH₂CH(CH₃)₂, —CH₂NH₂, —CH₂CH₂NH₂, —CH₂CHCH₂NH₂, —CH₂CH(CH₃)NH₂, —CH₂OH, —CH₂CH₂OH, —CH(CH₂OH)₂, —C(CH₂OH)₃, —CH(CH₃)OH, —C(CH₃)₂OH, —CH(OH)CH(CH₃)₂, —C(CH₃)₂CH₂OH, —CH₂CH₂SO₂CH₃, —CN, —CF₃, —CHF₂, —CH₂F, —CO₂H, —COCH₃, —COCH(CH₃)₂, —CO₂CH₃, —CO₂C(CH₃)₃, —COCH(OH)CH₃, —CONH₂, —CONHCH₃, —CON(CH₃)₂, —C(CH₃)₂CONH₂, —NO₂, —NH₂, —NHCH₃, —N(CH₃)₂, —NHCOCH₃, —N(CH₃)COCH₃, —NHS(O)₂CH₃, —N(CH₃)C(CH₃)₂CONH₂, —N(CH₃)CH₂CH₂S(O)₂CH₃, =O, —OH, —OCH₃, —OCF₃, —OCH(CH₃)₂, —S(O)₂N(CH₃)₂, —SCH₃, —CH₂OCH₃, —S(O)₂CH₃, cyclopropyl, cyclobutyl, cyclopentyl, cyclohexyl, cycloheptyl, azetidinyl, azepanyl, oxetanyl, phenyl, pyrrolidinyl, piperazinyl, piperidinyl, (piperidin-4-yl)ethyl), pyranyl, (piperidin-4-ylmethyl), morpholinomethyl, and morpholino.

2. The compound of claim 1 wherein R¹ is H.

3. The compound of claim 1 wherein R¹ is C₁-C₁₂ alkyl or C₃-C₁₂ carbocyclyl.

4. The compound of claim 3 wherein R¹ is selected from —CH₃, —CH₂CH₃, —CH₂CHF₂, and —CH₂CF₃.

5. The compound of claim 1 wherein R¹ is —(C₁-C₁₂ alkylene)-(C₂-C₂₀ heterocyclyl).

6. The compound of claim 5 wherein R¹ is oxetan-3-ylmethyl.

7. The compound of claim 5 wherein R² has the structure:

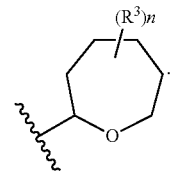

8. The compound of claim 1 wherein $R^3$ is independently selected from F, Cl, —OH, —$CH_3$, —$CH_2CH_3$, —$CF_3$, —$NH_2$, —$NHCH_3$, —$N(CH_3)_2$, —$NHCH_2CHF_2$, —$NHCH_2CF_3$, —$CH_2NHCH_3$, and —$OCH_3$; and n is 1, 2, or 3.

9. The compound of claim 1 wherein $R^4$ is —$NH_2$.

10. The compound of claim 1 wherein $R^4$ is H.

11. The compound of claim 1 wherein $R^5$ is $C_6$-$C_{20}$ aryl.

12. The compound of claim 11 wherein $R^5$ is phenyl substituted with one or more F.

13. The compound of claim 1 selected from Formula Ia-Id:

Ia
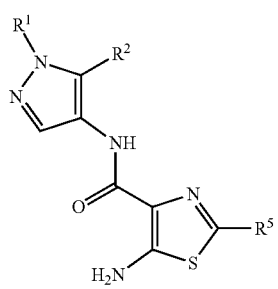

Ib
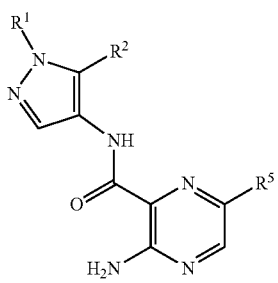

Ic
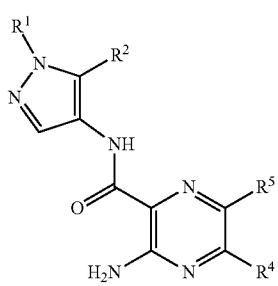

Id
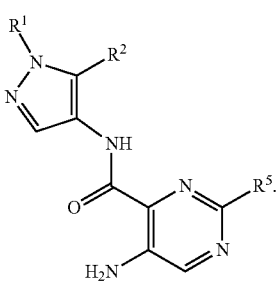

14. The compound of claim 1 selected from Formula Ie-Ih:

Ie
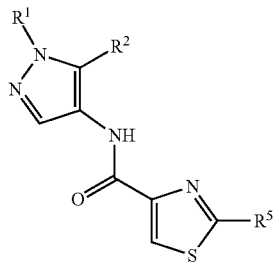

If
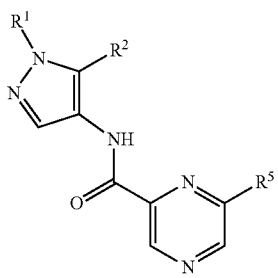

Ig
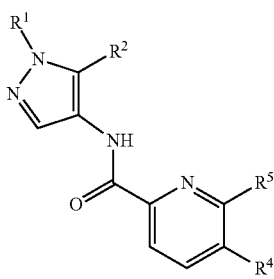

Ih
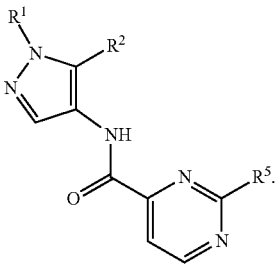

15. The compound of claim 1 selected from the group consisting of:
- 5-amino-2-(2,6-difluorophenyl)-N-[5-(3,6-dihydro-2H-pyran-4-yl)-1-methyl-pyrazol-4-yl]thiazole-4-carboxamide
- 5-amino-2-(2,6-difluorophenyl)-N-[5-(3,4-dihydro-2H-pyran-6-yl)-1-methyl-pyrazol-4-yl]thiazole-4-carboxamide
- 5-amino-2-(2,6-difluorophenyl)-N-[5-(2-methoxytetrahydropyran-2-yl)-1-methyl-pyrazol-4-yl]thiazole-4-carboxamide
- 5-amino-2-(2,6-difluorophenyl)-N-(1-methyl-5-tetrahydropyran-2-yl-pyrazol-4-yl)thiazole-4-carboxamide
- 5-amino-2-(3-fluoro-2-pyridyl)-N-[5-(2-methoxytetrahydropyran-2-yl)-1-methyl-pyrazol-4-yl]thiazole-4-carboxamide
- 5-amino-2-(2,6-difluorophenyl)-N-(5-((1S,4S,5S)-4-hydroxy-8-oxabicyclo[3.2.1]octan-1-yl)-1-methyl-1H-pyrazol-4-yl)thiazole-4-carboxamide 5-amino-N-[5-(2-amino-8-oxabicyclo[3.2.1]octan-5-yl)-1-methyl-pyrazol-4-yl]-2-(2,6-difluorophenyl)thiazole-4-carboxamide 5-amino-2-(2,6-difluorophenyl)-N-(5-((2R,7R)-5-hydroxy-7-methyloxepan-2-yl)-1-methyl-1H-pyrazol-4-yl)thiazole-4-carboxamide 5-amino-2-(2,6-difluorophenyl)-N-[5-(2-hydroxy-8-oxabicyclo[3.2.1]octan-5-yl)-1-methyl-pyrazol-4-yl]thiazole-4-carboxamide 5-amino-2-(2,6-difluorophenyl)-N-(5-((5R,6S)-5,6-dihydroxyoxepan-2-yl)-1-methyl-1H-pyrazol-4-yl)thiazole-4-carboxamide 5-amino-N-(5-((2R,7R)-5-amino-7-ethyloxepan-2-yl)-1-methyl-1H-pyrazol-4-yl)-2-(2,6-difluorophenyl)thiazole-4-carboxamide 5-amino-N-(5-((2R,7R)-5-amino-7-methyloxepan-2-yl)-1-methyl-1H-pyrazol-4-yl)-2-(2,6-difluorophenyl)thiazole-4-carboxamide 5-amino-N-[5-(6-amino-4,4-difluoro-oxepan-2-yl)-1-methyl-pyrazol-4-yl]-2-(2,6-difluorophenyl)thiazole-4-carboxamide 5-amino-N-(5-((1S,4S,5S)-4-amino-8-oxabicyclo[3.2.1]octan-1-yl)-1-methyl-1H-pyrazol-4-yl)-2-(2,6-difluorophenyl)thiazole-4-carboxamide 5-amino-N-(5-((1S,4R,5S)-4-amino-8-oxabicyclo[3.2.1]octan-1-yl)-1-methyl-1H-pyrazol-4-yl)-2-(2,6-difluorophenyl)thiazole-4-carboxamide 5-amino-N-(5-((1R,4S,5R)-4-amino-8-oxabicyclo[3.2.1]octan-1-yl)-1-methyl-1H-pyrazol-4-yl)-2-(2,6-difluorophenyl)thiazole-4-carboxamide 5-amino-N-(5-((1R,4R,5R)-4-amino-8-oxabicyclo[3.2.1]octan-1-yl)-1-methyl-1H-pyrazol-4-yl)-2-(2,6-difluorophenyl)thiazole-4-carboxamide 5-amino-N-(5-((5R,6R)-5-amino-6-fluorooxepan-2-yl)-1-methyl-1H-pyrazol-4-yl)-2-(2,6-difluorophenyl)thiazole-4-carboxamide 5-amino-N-(5-((2R,5R,7R)-5-amino-7-methyloxepan-2-yl)-1-methyl-1H-pyrazol-4-yl)-2-(2,6-difluorophenyl)thiazole-4-carboxamide 5-amino-N-(5-((2R,5S,7R)-5-amino-7-methyloxepan-2-yl)-1-methyl-1H-pyrazol-4-yl)-2-(2,6-difluorophenyl)thiazole-4-carboxamide 5-amino-N-[5-(6-amino-4,4-difluoro-oxepan-2-yl)-1-methyl-pyrazol-4-yl]-2-(2,6-difluorophenyl)thiazole-4-carboxamide 5-amino-N-(5-((5S,6S)-6-amino-5-methoxyoxepan-2-yl)-1-methyl-1H-pyrazol-4-yl)-2-(2,6-difluorophenyl)thiazole-4-carboxamide 5-amino-N-[5-(5-amino-6-fluoro-oxepan-2-yl)-1-methyl-pyrazol-4-yl]-2-(2,6-difluorophenyl)thiazole-4-carboxamide 5-amino-N-(5-((2R,7R)-5-amino-7-ethyloxepan-2-yl)-1-methyl-1H-pyrazol-4-yl)-2-(2,6-difluorophenyl)thiazole-4-carboxamide 5-amino-N-(5-((5R,6S)-5-amino-6-methoxyoxepan-2-yl)-1-methyl-1H-pyrazol-4-yl)-2-(2,6-difluorophenyl)thiazole-4-carboxamide 5-amino-N-(5-((4R,5R)-4-amino-5-fluorooxepan-2-yl)-1-methyl-1H-pyrazol-4-yl)-2-(2,6-difluorophenyl)thiazole-4-carboxamide 5-amino-N-(5-((5S,6S)-5-amino-6-methoxyoxepan-2-yl)-1-methyl-1H-pyrazol-4-yl)-2-(2,6-difluorophenyl)thiazole-4-carboxamide 5-amino-N-(5-((5R,6R)-5-amino-6-fluorooxepan-2-yl)-1-methyl-1H-pyrazol-4-yl)-2-(2,6-difluorophenyl)thiazole-4-carboxamide 5-amino-N-(5-((4S,5S)-4-amino-5-fluorooxepan-2-yl)-1-methyl-1H-pyrazol-4-yl)-2-(2,6-difluorophenyl)thiazole-4-carboxamide 5-amino-N-(5-((5S,6S)-5-amino-6-fluorooxepan-2-yl)-1-methyl-1H-pyrazol-4-yl)-2-(2,6-difluorophenyl)thiazole-4-carboxamide 5-amino-N-[5-(6-amino-4,4-difluoro-oxepan-2-yl)-1-methyl-pyrazol-4-yl]-2-(2,6-difluorophenyl)thiazole-4-carboxamide 5-amino-2-(2,6-difluorophenyl)-N-[5-(5-hydroxyoxepan-2-yl)-1-methyl-pyrazol-4-yl]thiazole-4-carboxamide 5-amino-N-[5-(5-amino-4-fluoro-oxepan-2-yl)-1-methyl-pyrazol-4-yl]-2-(2,6-difluorophenyl)thiazole-4-carboxamide 5-amino-N-(5-((2S,4R,5R)-5-amino-4-methoxyoxepan-2-yl)-1-methyl-1H-pyrazol-4-yl)-2-(2,6-difluorophenyl)thiazole-4-carboxamide 5-amino-N-(5-((2R,4S,5S)-5-amino-4-fluorooxepan-2-yl)-1-methyl-1H-pyrazol-4-yl)-2-(2,6-difluorophenyl)thiazole-4-carboxamide 5-amino-N-(5-((2R,4S,5S)-5-amino-4-methoxyoxepan-2-yl)-1-methyl-1H-pyrazol-4-yl)-2-(2,6-difluorophenyl)thiazole-4-carboxamide 5-amino-N-[5-[1-(aminomethyl)-7-oxabicyclo[2.2.1]heptan-4-yl]-1-methyl-pyrazol-4-yl]-2-(2-fluorophenyl)thiazole-4-carboxamide 5-amino-N-(5-(5-amino-fluorooxepan-2-yl)-1-methyl-1H-pyrazol-4-yl)-2-(2,6-difluorophenyl)thiazole-4-carboxamide 5-amino-N-(5-((4R,5R)-4-amino-5-fluorooxepan-2-yl)-1-methyl-1H-pyrazol-4-yl)-2-(2,6-difluorophenyl)thiazole-4-carboxamide 5-amino-N-[5-(4-amino-5-hydroxy-3,5-dimethyl-tetrahydropyran-2-yl)-1-methyl-pyrazol-4-yl]-2-(2,6-difluorophenyl)thiazole-4-carboxamide 5-amino-N-[5-(6-aminooxepan-3-yl)-1-methyl-pyrazol-4-yl]-2-(2,6-difluorophenyl)thiazole-4-carboxamide 5-amino-N-[5-(6-aminooxepan-3-yl)-1-methyl-pyrazol-4-yl]-2-(2,6-difluorophenyl)thiazole-4-carboxamide 5-Amino-N-[5-[6-amino-5-fluoro-oxepan-2-yl]-1-methyl-pyrazol-4-yl]-2-(2,6-difluorophenyl)thiazole-4-carboxamide 5-amino-2-(2,6-difluorophenyl)-N-(5-((2S,4R)-4-hydroxytetrahydro-2H-pyran-2-yl)-1-methyl-1H-pyrazol-4-yl)thiazole-4-carboxamide 5-amino-N-[5-(6-aminooxepan-3-yl)-1-methyl-pyrazol-4-yl]-2-(2,6-difluorophenyl)thiazole-4-carboxamide 5-Amino-N-[5-[5-amino-6-fluoro-oxepan-2-yl]-1-methyl-pyrazol-4-yl]-2-(2,6-difluorophenyl)thiazole-4-carboxamide 5-amino-2-(2,6-difluorophenyl)-N-(5-((2R,4S)-4-hydroxytetrahydro-2H-pyran-2-yl)-1-methyl-1H-pyrazol-4-yl)thiazole-4-carboxamide 5-Amino-N-[5-[(2S,5R)-5-amino-4-fluoro-oxepan-2-yl]-1-methyl-pyrazol-4-yl]-2-(2,6-difluorophenyl)thiazole-4-carboxamide 5-Amino-N-[5-[(2R,5S)-5-amino-4-fluoro-oxepan-2-yl]-1-methyl-pyrazol-4-yl]-2-(2,6-difluorophenyl)thiazole-4-carboxamide 5-Amino-N-[5-[(5-amino-6,6-difluoro-oxepan-2-yl]-1-methyl-pyrazol-4-yl]-2-(2,6-difluorophenyl)thiazole-4-carboxamide 5-Amino-N-[5-[(2R,5S,6S)-6-amino-5-fluoro-oxepan-2-yl]-1-methyl-pyrazol-4-yl]-2-(2,6-difluorophenyl)thiazole-4-carboxamide 5-Amino-N-[5-[(2S,5R,6R)-5-amino-6-methoxy-oxepan-2-yl]-1-methyl-pyrazol-4-yl]-2-(2,6-difluorophenyl)thiazole-4-carboxamide; and 5-Amino-N-[5-[5-(aminomethyl)tetrahydrofuran-2-yl]-1-methyl-pyrazol-4-yl]-2-(2,6-difluorophenyl)thiazole-4-carboxamide, or a pharmaceutically acceptable salt thereof.

16. The compound of claim 1 selected from the group consisting of:

5-amino-N-(5-((2S,5R,6S)-5-amino-6-fluorooxepan-2-yl)-1-methyl-1H-pyrazol-4-yl)-2-(2-fluoro-3-(trifluoromethyl)phenyl)thiazole-4-carboxamide 5-amino-N-(5-((2S,5R,6S)-5-amino-6-fluorooxepan-2-yl)-1-methyl-1H-pyrazol-4-yl)-2-(2-(trifluoromethoxy)phenyl)thiazole-4-carboxamide Amino-N-[5-[4-aminotetrahydropyran-2-yl]-1-methyl-pyrazol-4-yl]-2-(2,6-difluorophenyl)thiazole-4-carboxamide 5-Amino-N-[5-[(2R,4S)-4-aminotetrahydropyran-2-yl]-1-methyl-pyrazol-4-yl]-2-(2,6-difluorophenyl)thiazole-4-carboxamide 5-Amino-N-[5-[(2S,4R)-4-aminotetrahydropyran-2-yl]-1-methyl-pyrazol-4-yl]-2-(2,6-difluorophenyl)thiazole-4-carboxamide 5-Amino-N-[5-[2-amino-8-oxabicyclo[3.2.1]octan-5-yl]-1-methyl-pyrazol-4-yl]-2-(3-fluoro-4-pyridyl)thiazole-4-carboxamide 5-Amino-2-(2,6-difluorophenyl)-N-[5-[(2R,5R)5-ethyl-5-(hydroxymethyl)-1,3-dioxan-2-yl]-1-methyl-pyrazol-4-yl]thiazole-4-carboxamide 5-Amino-2-(2,6-difluorophenyl)-N-[5-[(2S,5S)5-ethyl-5-(hydroxymethyl)-1,3-dioxan-2-yl]-1-methyl-pyrazol-4-yl]thiazole-4-carboxamide 5-Amino-2-(2,6-difluorophenyl)-N-[5-[5-(hydroxymethyl)-1,3-dioxan-2-yl]-1-methyl-pyrazol-4-yl]thiazole-4-carboxamide 5-Amino-2-(2,6-difluorophenyl)-N-[5-[5-(hydroxymethyl)-5-methyl-1,3-dioxan-2-yl]-1-methyl-pyrazol-4-yl]thiazole-4-carboxamide 5-Amino-N-[5-[5-(aminomethyl)-1,3-dioxan-2-yl]-1-methyl-pyrazol-4-yl]-2-(2,6-difluorophenyl)thiazole-4-carboxamide 5-Amino-N-[5-[(2S,5R)-5-amino-6,6-difluoro-oxepan-2-yl]-1-methyl-pyrazol-4-yl]-2-(2,6-difluorophenyl)thiazole-4-carboxamide 5-Amino-N-[5-[(2R,5S)-5-amino-6,6-difluoro-oxepan-2-yl]-1-methyl-pyrazol-4-yl]-2-(2,6-difluorophenyl)thiazole-4-carboxamide 5-Amino-N-[5-[4-amino-5-fluoro-oxepan-2-yl]-1-methyl-pyrazol-4-yl]-2-(2,6-difluorophenyl)thiazole-4-carboxamide 5-Amino-N-[5-[(2R,5R)-5-(aminomethyl)tetrahydrofuran-2-yl]-1-methyl-pyrazol-4-yl]-2-(2,6-difluorophenyl)thiazole-4-carboxamide 5-Amino-N-[5-[(2S,5S)-5-(aminomethyl)tetrahydrofuran-2-yl]-1-methyl-pyrazol-4-yl]-2-(2,6-difluorophenyl)thiazole-4-carboxamide 5-Amino-N-[5-[5-(aminomethyl)-5-ethyl-1,3-dioxan-2-yl]-1-methyl-pyrazol-4-yl]-2-(2,6-difluorophenyl)thiazole-4-carboxamide 5-Amino-N-[5-[(2S,5R,6S)-5-amino-6-(trideuteriomethoxy)oxepan-2-yl]-1-methyl-pyrazol-4-yl]-2-(2,6-difluorophenyl)thiazole-4-carboxamide 5-Amino-N-[5-[5-(aminomethyl)-5-methyl-1,3-dioxan-2-yl]-1-methyl-pyrazol-4-yl]-2-(2,6-difluorophenyl)thiazole-4-carboxamide 5-Amino-N-[5-[(2R,5S,6R)-5-amino-6-fluoro-oxepan-2-yl]-1-methyl-pyrazol-4-yl]-2-(2,6-difluorophenyl)thiazole-4-carboxamide 5-Amino-N-[5-[(2S,5R,6S)-5-amino-6-fluoro-oxepan-2-yl]-1-methyl-pyrazol-4-yl]-2-(2,6-difluorophenyl)thiazole-4-carboxamide 5-Amino-N-[5-[5-(aminomethyl)-5-methyl-1,3-dioxan-2-yl]-1-methyl-pyrazol-4-yl]-2-(2,6-difluorophenyl)thiazole-4-carboxamide 5-Amino-N-[5-[5-amino-4,4-difluoro-5,6-dimethyl-tetrahydropyran-2-yl]-1-methyl-pyrazol-4-yl]-2-(2,6-difluorophenyl)thiazole-4-carboxamide 5-Amino-N-[5-[(2R,5S,6R)-5-amino-6-(trideuteriomethoxy)oxepan-2-yl]-1-methyl-pyrazol-4-yl]-2-(2,6-difluorophenyl)thiazole-4-carboxamide 5-Amino-N-[5-[(2S,5R,6R)-5-amino-6-fluoro-oxepan-2-yl]-1-methyl-pyrazol-4-yl]-2-(2,3-difluorophenyl)thiazole-4-carboxamide 5-Amino-N-[5-[(2S,5R,6R)-5-amino-6-fluoro-oxepan-2-yl]-1-methyl-pyrazol-4-yl]-2-(3-fluoro-4-pyridyl)thiazole-4-carboxamide 5-Amino-N-[5-[(2S,5R,6R)-5-amino-6-methoxy-oxepan-2-yl]-1-methyl-pyrazol-4-yl]-2-(2-fluorophenyl)thiazole-4-carboxamide 5-Amino-N-(5-((2R,5S,6R)-5-amino-4,4-difluoro-5,6-dimethyltetrahydro-2H-pyran-2-yl)-1-methyl-1H-pyrazol-4-yl)-2-(2,6-difluorophenyl)thiazole-4-carboxamide 5-Amino-N-(5-((2S,5R,6S)-5-amino-4,4-difluoro-5,6-dimethyltetrahydro-2H-pyran-2-yl)-1-methyl-1H-pyrazol-4-yl)-2-(2,6-difluorophenyl)thiazole-4-carboxamide 5-Amino-N-(5-((2S,5R,6R)-5-amino-6-fluorooxepan-2-yl)-1-methyl-1H-pyrazol-4-yl)-2-(2-fluorophenyl)thiazole-4-carboxamide N-(5-((2S,5R,6R)-5-Amino-6-fluorooxepan-2-yl)-1-methyl-1H-pyrazol-4-yl)-6-(2,6-difluoro-4-methoxyphenyl)-5-fluoropicolinamide N-(5-((2S,5R,6R)-5-Amino-6-fluorooxepan-2-yl)-1-methyl-1H-pyrazol-4-yl)-6-(2,6-difluoro-4-((tetrahydro-2H-pyran-4-yl)oxy)phenyl)-5-fluoropicolinamide N-(5-((2S,5R,6R)-5-Amino-6-fluorooxepan-2-yl)-1-methyl-1H-pyrazol-4-yl)-6-(2,6-difluoro-4-(2-methoxyethoxy)phenyl)-5-fluoropicolinamide N-(5-((2S,5R,6R)-5-Amino-6-fluorooxepan-2-yl)-1-methyl-1H-pyrazol-4-yl)-6-(2,6-difluoro-4-(2-hydroxyethoxy)phenyl)-5-fluoropicolinamide N-(5-((2S,5R,6S)-5-Amino-6-hydroxyoxepan-2-yl)-1-methyl-1H-pyrazol-4-yl)-6-(2,6-difluoro-4-(2-methoxyethoxy)phenyl)-5-fluoropicolinamide N-(5-((2S,5R,6S)-5-amino-6-fluorooxepan-2-yl)-1-methyl-1H-pyrazol-4-yl)-6-(2,6-difluoro-4-(2-methoxyethoxy)phenyl)-5-fluoropicolinamide N-(5-((2S,5R,6S)-5-amino-6-fluorooxepan-2-yl)-1-methyl-1H-pyrazol-4-yl)-6-(2,6-difluoro-4-(3-hydroxyoxetan-3-yl)phenyl)-5-fluoropicolinamide N-(5-((2S,5R,6S)-5-amino-6-fluorooxepan-2-yl)-1-methyl-1H-pyrazol-4-yl)-6-(2,6-difluoro-4-(3-fluorooxetan-3-yl)phenyl)-5 fluoropicolinamide N-(5-((2S,5R,6S)-5-amino-6-fluorooxepan-2-yl)-1-methyl-1H-pyrazol-4-yl)-6-(2,6-difluorophenyl)-5-fluoropicolinamide N-(5-((2S,5R,6S)-5-amino-6-fluorooxepan-2-yl)-1-methyl-1H-pyrazol-4-yl)-6-(2,6-difluoro-4-(4-hydroxytetrahydro-2H-pyran-4-yl)phenyl)-5-fluoropicolinamide N-(5-((2S,5R,6S)-5-Amino-6-fluorooxepan-2-yl)-1-methyl-1H-pyrazol-4-yl)-6-(2,6-difluoro-4-((tetrahydro-2H-pyran-4-yl)oxy)phenyl)-5-fluoropicolinamide
N-(5-((2S,5R,6S)-5-amino-6-fluorooxepan-2-yl)-1-methyl-1H-pyrazol-4-yl)-6-(2,6-difluoro-4-(1-hydroxycyclobutyl)phenyl)-5-fluoropicolinamide
N-(5-((2S,5R,6S)-5-amino-6-fluorooxepan-2-yl)-1-methyl-1H-pyrazol-4-yl)-6-(2,6-difluoro-4-(methoxymethyl)phenyl)-5-fluoropicolinamide
N-(5-((2S,5R,6S)-5-amino-6-fluorooxepan-2-yl)-1-methyl-1H-pyrazol-4-yl)-6-(2,6-difluoro-4-(2-hydroxypropan-2-yl)phenyl)-5-fluoropicolinamide
N-(5-((2S,5R,6S)-5-amino-6-fluorooxepan-2-yl)-1-methyl-1H-pyrazol-4-yl)-6-(2,6-difluoro-4-methoxyphenyl)-5-fluoropicolinamide
N-(5-((2S,5R,6S)-5-amino-6-fluorooxepan-2-yl)-1-methyl-1H-pyrazol-4-yl)-6-(2,6-difluoro-4-(3-methoxyoxetan-3-yl)phenyl)-5-fluoropicolinamide
N-(5-((2S,5R,6R)-5-amino-6-fluorooxepan-2-yl)-1-methyl-1H-pyrazol-4-yl)-6-(2,6-difluoro-4-(3-methoxyoxetan-3-yl)phenyl)-5-fluoropicolinamide
N-(5-((2S,5R,6S)-5-amino-6-fluorooxepan-2-yl)-1-methyl-1H-pyrazol-4-yl)-6-(2,6-difluoro-4-(1-hydroxycyclopropyl)phenyl)-5-fluoropicolinamide
N-(5-((2S,5R,6S)-5-amino-6-fluorooxepan-2-yl)-1-methyl-1H-pyrazol-4-yl)-6-(2,6-difluoro-4-propionylphenyl)-5-fluoropicolinamide
N-(5-((2S,5R,6S)-5-amino-6-fluorooxepan-2-yl)-1-methyl-1H-pyrazol-4-yl)-6-(2,6-difluoro-4-(4-fluorotetrahydro-2H-pyran-4-yl)phenyl)-5-fluoropicolinamide
N-(5-((2S,5R,6S)-5-amino-6-fluorooxepan-2-yl)-1-methyl-1H-pyrazol-4-yl)-6-(2,6-difluoro-4-(1-hydroxyethyl)phenyl)-5-fluoropicolinamide
N-(5-((2S,5R,6S)-5-amino-6-fluorooxepan-2-yl)-1-methyl-1H-pyrazol-4-yl)-6-(2,6-difluoro-4-hydroxyphenyl)-5-fluoropicolinamide
N-(5-((2S,5R,6S)-5-Amino-6-fluorooxepan-2-yl)-1-methyl-1H-pyrazol-4-yl)-6-(2,6-difluoro-4-(2-hydroxyethoxy)phenyl)-5-fluoropicolinamide
N-(5-((2S,5R,6R)-5-amino-6-fluorooxepan-2-yl)-1-methyl-1H-pyrazol-4-yl)-6-(2,6-difluoro-4-(1-hydroxyethyl)phenyl)-5-fluoropicolinamide
N-(5-((2S,5R,6R)-5-amino-6-fluorooxepan-2-yl)-1-methyl-1H-pyrazol-4-yl)-6-(2,6-difluoro-4-(1-methoxyethyl)phenyl)-5-fluoropicolinamide
N-(5-((2S,5R,6R)-5-amino-6-fluorooxepan-2-yl)-1-methyl-1H-pyrazol-4-yl)-6-(2,6-difluoro-4-(1,2,3-trihydroxypropan-2-yl)phenyl)-5-fluoropicolinamide
N-(5-((2S,5R,6S)-5-amino-6-fluorooxepan-2-yl)-1-methyl-1H-pyrazol-4-yl)-6-(4-(cyclopropyl(methoxy)methyl)-2,6-difluorophenyl)-5-fluoropicolinamide
N-(5-((2S,5R,6S)-5-amino-6-fluorooxepan-2-yl)-1-methyl-1H-pyrazol-4-yl)-6-(4-(1,3-dihydroxypropan-2-yl)-2,6-difluorophenyl)-5-fluoropicolinamide
N-(5-((2S,5R,6S)-5-amino-6-fluorooxepan-2-yl)-1-methyl-1H-pyrazol-4-yl)-2-(2,6-difluoro-4-(3-hydroxytetrahydrofuran-3-yl)phenyl)thiazole-4-carboxamide
N-(5-((2S,5R,6S)-5-amino-6-fluorooxepan-2-yl)-1-methyl-1H-pyrazol-4-yl)-2-(2,6-difluoro-4-(tetrahydrofuran-3-yl)phenyl)thiazole-4-carboxamide
N-(5-((2S,5R,6S)-5-amino-6-fluorooxepan-2-yl)-1-methyl-1H-pyrazol-4-yl)-2-(2,6-difluoro-4-(((R)-tetrahydrofuran-3-yl)oxy)phenyl)thiazole-4-carboxamide
N-(5-((2S,5R,6S)-5-amino-6-fluorooxepan-2-yl)-1-methyl-1H-pyrazol-4-yl)-2-(2,6-difluoro-4-(((S)-tetrahydrofuran-3-yl)oxy)phenyl)thiazole-4-carboxamide
5-amino-N-(5-((2S,5R,6R)-5-amino-6-methoxyoxepan-2-yl)-1-methyl-1H-pyrazol-4-yl)-2-(2,3-difluorophenyl)thiazole-4-carboxamide
5-amino-N-(5-((2S,5R,6R)-5-amino-6-methoxyoxepan-2-yl)-1-methyl-1H-pyrazol-4-yl)-2-(2-(trifluoromethyl)phenyl)thiazole-4-carboxamide
N-(5-((2S,5R,6R)-5-amino-6-methoxyoxepan-2-yl)-1-methyl-1H-pyrazol-4-yl)-2-(2,6-difluorophenyl)thiazole-4-carboxamide
N-(5-((2S,5R,6S)-5-amino-6-fluorooxepan-2-yl)-1-methyl-1H-pyrazol-4-yl)-6-(2,6-difluorophenyl)-5-fluoropicolinamide
N-(5-((2S,5R,6S)-5-amino-6-fluorooxepan-2-yl)-1-methyl-1H-pyrazol-4-yl)-6-(2,3-difluorophenyl)-5-fluoropicolinamide
N-(5-((2S,5R,6S)-5-amino-6-fluorooxepan-2-yl)-1-methyl-1H-pyrazol-4-yl)-2-(2,6-difluoro-4-(3-hydroxyoxetan-3-yl)phenyl)thiazole-4-carboxamide
N-(5-((2S,5R,6S)-5-amino-6-fluorooxepan-2-yl)-1-methyl-1H-pyrazol-4-yl)-2-(2,6-difluoro-4-(1-hydroxycyclopropyl)phenyl)thiazole-4-carboxamide
N-(5-((2S,5R,6S)-5-amino-6-fluorooxepan-2-yl)-1-methyl-1H-pyrazol-4-yl)-5-fluoro-6-(2-fluoro-4-methoxyphenyl)picolinamide
N-(5-((2S,5R,6S)-5-amino-6-fluorooxepan-2-yl)-1-methyl-1H-pyrazol-4-yl)-6-(2-chloro-3-fluorophenyl)-5-fluoropicolinamide
N-(5-((2S,5R,6S)-5-amino-6-fluorooxepan-2-yl)-1-methyl-1H-pyrazol-4-yl)-2-(1-(2-hydroxy-2-methylpropyl)-1H-pyrazol-4-yl)thiazole-4-carboxamide
N-(5-((2S,5R,6S)-5-amino-6-fluorooxepan-2-yl)-1-methyl-1H-pyrazol-4-yl)-2-(2,6-difluoro-3-methoxyphenyl)thiazole-4-carboxamide
N-(5-((2S,5R,6R)-5-amino-6-fluorooxepan-2-yl)-1-methyl-1H-pyrazol-4-yl)-2-(2,3,6-trifluorophenyl)thiazole-4-carboxamide
N-(5-((2S,5R,6S)-5-amino-6-fluorooxepan-2-yl)-1-methyl-1H-pyrazol-4-yl)-2-(3-methylpyridin-2-yl)thiazole-4-carboxamide
N-(5-((2S,5R,6S)-5-amino-6-fluorooxepan-2-yl)-1-methyl-1H-pyrazol-4-yl)-2-(2-methoxypyridin-3-yl)thiazole-4-carboxamide
N-(5-((2S,5R,6S)-5-amino-6-fluorooxepan-2-yl)-1-methyl-1H-pyrazol-4-yl)-2-(2-oxo-1,2-dihydropyridin-3-yl)thiazole-4-carboxamide
N-(5-((2S,5R,6S)-5-amino-6-fluorooxepan-2-yl)-1-methyl-1H-pyrazol-4-yl)-2-(3,5-dimethylisoxazol-4-yl)thiazole-4-carboxamide
N-(5-((2S,5R,6S)-5-amino-6-fluorooxepan-2-yl)-1-methyl-1H-pyrazol-4-yl)-2-(1-cyclopropyl-1H-pyrazol-4-yl)thiazole-4-carboxamide
N-(5-((2S,5R,6S)-5-amino-6-fluorooxepan-2-yl)-1-methyl-1H-pyrazol-4-yl)-2-(2,3,5-trifluorophenyl)thiazole-4-carboxamide
N-(5-((2S,5R,6S)-5-amino-6-fluorooxepan-2-yl)-1-methyl-1H-pyrazol-4-yl)-2-(3-fluoropyridin-2-yl)thiazole-4-carboxamide
N-(5-((2S,5R,6S)-5-amino-6-fluorooxepan-2-yl)-1-methyl-1H-pyrazol-4-yl)-2-(2-fluoro-5-methylphenyl)thiazole-4-carboxamide
N-(5-((2S,5R,6S)-5-amino-6-fluorooxepan-2-yl)-1-methyl-1H-pyrazol-4-yl)-2-(5-fluoropyridin-3-yl)thiazole-4-carboxamide
N-(5-((2S,5R,6S)-5-amino-6-fluorooxepan-2-yl)-1-methyl-1H-pyrazol-4-yl)-2-(3-fluoropyridin-4-yl)thiazole-4-carboxamide N-(5-((2S,5R,6S)-5-amino-6-fluorooxepan-2-yl)-1-methyl-1H-pyrazol-4-yl)-2-(1,3-dimethyl-1H-pyrazol-4-yl)thiazole-4-carboxamide N-(5-((2S,5R,6S)-5-amino-6-fluorooxepan-2-yl)-1-methyl-1H-pyrazol-4-yl)-2-(1,5-dimethyl-1H-pyrazol-4-yl)thiazole-4-carboxamide N-(5-((2S,5R,6S)-5-amino-6-fluorooxepan-2-yl)-1-methyl-1H-pyrazol-4-yl)-2-(2,3,6-trifluorophenyl)thiazole-4-carboxamide N-(5-((2S,5R,6R)-5-amino-6-fluorooxepan-2-yl)-1-methyl-1H-pyrazol-4-yl)-2-(3,5-dimethylisoxazol-4-yl)thiazole-4-carboxamide N-(5-((2S,5R,6R)-5-amino-6-fluorooxepan-2-yl)-1-methyl-1H-pyrazol-4-yl)-2-(2,3-difluorophenyl)thiazole-4-carboxamide N-(5-((2S,5R,6R)-5-amino-6-fluorooxepan-2-yl)-1-methyl-1H-pyrazol-4-yl)-2-(5-fluoropyridin-3-yl)thiazole-4-carboxamide N-(5-((2S,5R,6R)-5-amino-6-fluorooxepan-2-yl)-1-methyl-1H-pyrazol-4-yl)-2-(3,5-difluoropyridin-4-yl)thiazole-4-carboxamide N-(5-((2S,5R,6R)-5-amino-6-fluorooxepan-2-yl)-1-methyl-1H-pyrazol-4-yl)-2-(3-chloro-2-fluorophenyl)thiazole-4-carboxamide N-(5-((2S,5R,6R)-5-amino-6-fluorooxepan-2-yl)-1-methyl-1H-pyrazol-4-yl)-2-(3'-chloro-2,2'-difluoro-[1,1'-biphenyl]-3-yl)thiazole-4-carboxamide N-(5-((2S,5R,6R)-5-amino-6-fluorooxepan-2-yl)-1-methyl-1H-pyrazol-4-yl)-2-(2-chloro-3-fluorophenyl)thiazole-4-carboxamide N-(5-((2S,5R,6R)-5-amino-6-fluorooxepan-2-yl)-1-methyl-1H-pyrazol-4-yl)-2-(2'-chloro-3',6-difluoro-[1,1'-biphenyl]-2-yl)thiazole-4-carboxamide N-(5-((2S,5R,6R)-5-amino-6-fluorooxepan-2-yl)-1-methyl-1H-pyrazol-4-yl)-2-(1-methyl-3-(trifluoromethyl)-1H-pyrazol-4-yl)thiazole-4-carboxamide N-(5-((2S,5R,6R)-5-amino-6-fluorooxepan-2-yl)-1-methyl-1H-pyrazol-4-yl)-2-(3-cyclopropyl-1-methyl-1H-pyrazol-4-yl)thiazole-4-carboxamide 5-amino-N-(5-((2S,5R,6R)-5-amino-6-fluorooxepan-2-yl)-1-methyl-1H-pyrazol-4-yl)-2-(1,3-dimethyl-1H-pyrazol-4-yl)thiazole-4-carboxamide 5-amino-N-(5-((2S,5R,6R)-5-amino-6-fluorooxepan-2-yl)-1-methyl-1H-pyrazol-4-yl)-2-(1,5-dimethyl-1H-pyrazol-4-yl)thiazole-4-carboxamide 5-amino-N-(5-((2S,5R,6R)-5-amino-6-fluorooxepan-2-yl)-1-methyl-1H-pyrazol-4-yl)-2-(1-isopropyl-1H-pyrazol-4-yl)thiazole-4-carboxamide 5-amino-N-(5-((2S,5R,6S)-5-amino-6-fluorooxepan-2-yl)-1-methyl-1H-pyrazol-4-yl)-2-(1,5-dimethyl-1H-pyrazol-4-yl)thiazole-4-carboxamide N-(5-((2S,5R,6R)-5-amino-6-methoxyoxepan-2-yl)-1-methyl-1H-pyrazol-4-yl)-2-(2,3,6-trifluorophenyl)thiazole-4-carboxamide 5-amino-N-(5-((2S,5R,6R)-5-amino-6-fluorooxepan-2-yl)-1-methyl-1H-pyrazol-4-yl)-2-(2-fluoro-4-(trifluoromethyl)phenyl)thiazole-4-carboxamide 5-amino-N-(5-((2S,5R,6R)-5-amino-6-fluorooxepan-2-yl)-1-methyl-1H-pyrazol-4-yl)-2-(2,3,6-trifluorophenyl)thiazole-4-carboxamide 5-amino-N-(5-((2S,5R,6R)-5-amino-6-fluorooxepan-2-yl)-1-methyl-1H-pyrazol-4-yl)-2-(2,3,5-trifluorophenyl)thiazole-4-carboxamide 5-amino-N-(5-((2S,5R,6R)-5-amino-6-methoxyoxepan-2-yl)-1-methyl-1H-pyrazol-4-yl)-2-(2,3,6-trifluorophenyl)thiazole-4-carboxamide 5-amino-N-(5-((2S,5R,6R)-5-amino-6-methoxyoxepan-2-yl)-1-methyl-1H-pyrazol-4-yl)-2-(2,3,5-trifluorophenyl)thiazole-4-carboxamide 5-amino-N-(5-((2S,5R,6R)-5-amino-6-methoxyoxepan-2-yl)-1-methyl-1H-pyrazol-4-yl)-2-(2-fluoro-5-methylphenyl)thiazole-4-carboxamide N-(5-((2S,5R,6R)-5-amino-6-methoxyoxepan-2-yl)-1-methyl-1H-pyrazol-4-yl)-2-(2,6-difluoro-4-methoxyphenyl)thiazole-4-carboxamide 5-amino-N-(5-((2S,5R,6R)-5-amino-6-fluorooxepan-2-yl)-1-methyl-1H-pyrazol-4-yl)-2-(2-(trifluoromethoxy)phenyl)thiazole-4-carboxamide 5-amino-N-(5-((2S,5R,6R)-5-amino-6-fluorooxepan-2-yl)-1-methyl-1H-pyrazol-4-yl)-2-(3-fluoro-2-(trifluoromethyl)phenyl)thiazole-4-carboxamide 5-amino-N-(5-((2S,5R,6R)-5-amino-6-fluorooxepan-2-yl)-1-methyl-1H-pyrazol-4-yl)-2-(2-fluoro-3-(trifluoromethyl)phenyl)thiazole-4-carboxamide 5-amino-N-(5-((2S,5R,6R)-5-amino-6-methoxyoxepan-2-yl)-1-methyl-1H-pyrazol-4-yl)-2-(2-fluoro-6-methylphenyl)thiazole-4-carboxamide 5-amino-N-(5-((2S,5R,6R)-5-amino-6-fluorooxepan-2-yl)-1-methyl-1H-pyrazol-4-yl)-2-(2-(trifluoromethyl)phenyl)thiazole-4-carboxamide 5-amino-N-(5-((2S,5R,6R)-5-amino-6-fluorooxepan-2-yl)-1-methyl-1H-pyrazol-4-yl)-2-(cyclopent-1-en-1-yl)thiazole-4-carboxamide 5-amino-N-(5-((2S,5R,6R)-5-amino-6-fluorooxepan-2-yl)-1-methyl-1H-pyrazol-4-yl)-2-cyclopentylthiazole-4-carboxamide 5-amino-N-(5-((2S,5R,6R)-5-amino-6-fluorooxepan-2-yl)-1-methyl-1H-pyrazol-4-yl)-2-(2-fluoro-6-methylphenyl)thiazole-4-carboxamide 5-amino-N-(5-((2S,5R,6R)-5-amino-6-fluorooxepan-2-yl)-1-methyl-1H-pyrazol-4-yl)-2-(2-fluoro-5-methylphenyl)thiazole-4-carboxamide N-(5-((2S,5R,6S)-5-amino-6-fluorooxepan-2-yl)-1-methyl-1H-pyrazol-4-yl)-2-(4-(cyclopropyl(hydroxy)methyl)-2,6-difluorophenyl)thiazole-4-carboxamide N-(5-((2S,5R,6S)-5-amino-6-fluorooxepan-2-yl)-1-methyl-1H-pyrazol-4-yl)-2-(4-(cyclopropyl(methoxy)methyl)-2,6-difluorophenyl)thiazole-4-carboxamide 5-amino-N-(5-((2S,5R,6R)-5-amino-6-fluorooxepan-2-yl)-1-methyl-1H-pyrazol-4-yl)-2-(2,3-difluoro-6-methoxyphenyl)thiazole-4-carboxamide 5-amino-N-(5-((2S,5R,6R)-5-amino-6-fluorooxepan-2-yl)-1-methyl-1H-pyrazol-4-yl)-2-(2-fluoro-6-(trifluoromethyl)phenyl)thiazole-4-carboxamide 5-amino-N-(5-((2S,5R,6R)-5-amino-6-methoxyoxepan-2-yl)-1-methyl-1H-pyrazol-4-yl)-2-(2-fluoro-6-(trifluoromethyl)phenyl)thiazole-4-carboxamide 5-amino-N-(5-((2S,5R,6R)-5-amino-6-methoxyoxepan-2-yl)-1-methyl-1H-pyrazol-4-yl)-2-(2-chloro-6-fluorophenyl)thiazole-4-carboxamide 5-amino-N-(5-((2S,5R,6R)-5-amino-6-methoxyoxepan-2-yl)-1-methyl-1H-pyrazol-4-yl)-2-(5-chloro-2-fluorophenyl)thiazole-4-carboxamide 5-amino-N-(5-((2S,5R,6S)-5-amino-6-fluorooxepan-2-yl)-1-methyl-1H-pyrazol-4-yl)-2-(1-methyl-5-(trifluoromethyl)-1H-pyrazol-4-yl)thiazole-4-carboxamide N-(5-((2S,5R,6R)-5-amino-6-fluorooxepan-2-yl)-1-methyl-1H-pyrazol-4-yl)-2-(1-methyl-5-(trifluoromethyl)-1H-pyrazol-4-yl)thiazole-4-carboxamide N-(5-((2S,5R,6S)-5-amino-6-fluorooxepan-2-yl)-1-methyl-1H-pyrazol-4-yl)-2-(2-chloro-6-fluorophenyl)thiazole-4-carboxamide N-(5-((2S,5R,6S)-5-amino-6-fluorooxepan-2-yl)-1-methyl-1H-pyrazol-4-yl)-2-(3-ethoxy-2,6-difluorophenyl)thiazole-4-carboxamide N-(5-((2S,5R,6S)-5-amino-6-fluorooxepan-2-yl)-1-methyl-1H-pyrazol-4-yl)-2-(5-fluoro-1,3-dimethyl-1H-pyrazol-4-yl)thiazole-4-carboxamide N-(5-((2S,5R,6R)-5-amino-6-fluorooxepan-2-yl)-1-methyl-1H-pyrazol-4-yl)-2-(2-fluoro-4-methoxyphenyl)thiazole-4-carboxamide N-(5-((2S,5R,6R)-5-amino-6-fluorooxepan-2-yl)-1-methyl-1H-pyrazol-4-yl)-2-(2,6-difluoro-4-methoxyphenyl)thiazole-4-carboxamide N-(5-((2S,5R,6R)-5-amino-6-fluorooxepan-2-yl)-1-methyl-1H-pyrazol-4-yl)-6-(2,6-difluoro-4-(2-hydroxypropan-2-yl)phenyl)-5-fluoropicolinamide N-(5-((2S,5R,6R)-5-amino-6-fluorooxepan-2-yl)-1-methyl-1H-pyrazol-4-yl)-6-(2,6-difluoro-4-(1-hydroxycyclobutyl)phenyl)-5-fluoropicolinamide 5-amino-N-(5-((2S,5R,6S)-5-amino-6-fluorooxepan-2-yl)-1-methyl-1H-pyrazol-4-yl)-2-(5-chloro-2-fluorophenyl)thiazole-4-carboxamide 5-amino-N-(5-((2S,5R,6S)-5-amino-6-fluorooxepan-2-yl)-1-methyl-1H-pyrazol-4-yl)-2-(2-fluoro-5-methylphenyl)thiazole-4-carboxamide N-(5-((2S,5R,6S)-5-amino-6-fluorooxepan-2-yl)-1-methyl-1H-pyrazol-4-yl)-2-(2-fluoro-4-methoxyphenyl)thiazole-4-carboxamide N-(5-((2S,5R,6S)-5-amino-6-fluorooxepan-2-yl)-1-methyl-1H-pyrazol-4-yl)-2-(2,6-difluoro-4-(1-hydroxyethyl)phenyl)thiazole-4-carboxamide N-(5-((2S,5R,6S)-5-amino-6-fluorooxepan-2-yl)-1-methyl-1H-pyrazol-4-yl)-2-(2,6-difluoro-4-(1-hydroxycyclobutyl)phenyl)thiazole-4-carboxamide N-(5-((2S,5R,6S)-5-amino-6-fluorooxepan-2-yl)-1-methyl-1H-pyrazol-4-yl)-2-(2,6-difluoro-4-methoxyphenyl)thiazole-4-carboxamide N-(5-((2S,5R,6S)-5-amino-6-fluorooxepan-2-yl)-1-methyl-1H-pyrazol-4-yl)-2-(2,6-difluoro-4-(2-hydroxypropan-2-yl)phenyl)thiazole-4-carboxamide N-(5-((2S,5R,6S)-5-amino-6-fluorooxepan-2-yl)-1-methyl-1H-pyrazol-4-yl)-2-(2-(difluoromethyl)phenyl)thiazole-4-carboxamide N-(5-((2S,5R,6S)-5-amino-6-fluorooxepan-2-yl)-1-methyl-1H-pyrazol-4-yl)-2-(5-bromo-2-fluorophenyl)thiazole-4-carboxamide N-(5-((2S,5R,6S)-5-amino-6-fluorooxepan-2-yl)-1-methyl-1H-pyrazol-4-yl)-2-(3-fluoropyridin-4-yl)thiazole-4-carboxamide N-(5-((2S,5R,6S)-5-amino-6-fluorooxepan-2-yl)-1-methyl-1H-pyrazol-4-yl)-2-(2,5-difluorophenyl)thiazole-4-carboxamide N-(5-((2S,5R,6S)-5-amino-6-fluorooxepan-2-yl)-1-methyl-1H-pyrazol-4-yl)-2-(5-chloro-2-fluorophenyl)thiazole-4-carboxamide N-(5-((2S,5R,6S)-5-amino-6-fluorooxepan-2-yl)-1-methyl-1H-pyrazol-4-yl)-2-(2,6-difluoro-3-methylphenyl)thiazole-4-carboxamide N-(5-((2S,5R,6S)-5-amino-6-fluorooxepan-2-yl)-1-methyl-1H-pyrazol-4-yl)-2-(2,6-difluoro-4-((R)-1-hydroxyethyl)phenyl)thiazole-4-carboxamide N-(5-((2S,5R,6S)-5-amino-6-fluorooxepan-2-yl)-1-methyl-1H-pyrazol-4-yl)-2-(2,6-difluoro-4-((S)-1-hydroxyethyl)phenyl)thiazole-4-carboxamide N-(5-((2S,5R,6S)-5-amino-6-fluorooxepan-2-yl)-1-methyl-1H-pyrazol-4-yl)-2-(2,3-difluorophenyl)thiazole-4-carboxamide N-(5-((2S,5R,6S)-5-amino-6-fluorooxepan-2-yl)-1-methyl-1H-pyrazol-4-yl)-2-(5-ethyl-2-fluorophenyl)thiazole-4-carboxamide N-(5-((2S,56R,6S)-5-amino-6-fluorooxepan-2-yl)-1-methyl-1H-pyrazol-4-yl)-2-(3-chloro-2-fluorophenyl)thiazol-4-carboxamide N-(5-((2S,5R,6S)-5-amino-6-fluorooxepan-2-yl)-1-methyl-1H-pyrazol-4-yl)-2-(2-chloro-3-fluorophenyl)thiazole-4-carboxamide N-(5-((2S,5R,6S)-5-amino-6-fluorooxepan-2-yl)-1-methyl-1H-pyrazol-4-yl)-2-(5-cyclopropyl-2-fluorophenyl)thiazole-4-carboxamide N-(5-((2S,5R,6S)-5-amino-6-fluorooxepan-2-yl)-1-methyl-1H-pyrazol-4-yl)-2-(2-(trifluoromethyl)phenyl)thiazole-4-carboxamide N-(5-((2S,5R,6S)-5-amino-6-fluorooxepan-2-yl)-1-methyl-1H-pyrazol-4-yl)-2-(2,6-difluoro-4-methylphenyl)thiazole-4-carboxamide N-(5-((2S,5R,6S)-5-amino-6-fluorooxepan-2-yl)-1-methyl-1H-pyrazol-4-yl)-2-(4-chloro-2-fluorophenyl)thiazole-4-carboxamide N-(5-((2S,5R,6S)-5-amino-6-fluorooxepan-2-yl)-1-methyl-1H-pyrazol-4-yl)-2-(6-(trifluoromethyl)pyridin-2-yl)thiazole-4-carboxamide N-(5-((2S,5R,6S)-5-amino-6-fluorooxepan-2-yl)-1-methyl-1H-pyrazol-4-yl)-2-(2-fluoro-6-methylphenyl)thiazole-4-carboxamide N-(5-((2S,5R,6S)-5-amino-6-fluorooxepan-2-yl)-1-methyl-1H-pyrazol-4-yl)-2-(2-fluoro-4-methylphenyl)thiazole-4-carboxamide 5-amino-N-(5-((2S,5R,6S)-5-amino-6-fluorooxepan-2-yl)-1-methyl-1H-pyrazol-4-yl)-2-(2-fluorophenyl)thiazole-4-carboxamide N-(5-((2S,5R,6R)-5-amino-6-fluorooxepan-2-yl)-1-methyl-1H-pyrazol-4-yl)-2-(2-fluorophenyl)thiazole-4-carboxamide N-(5-((2S,5R,6R)-5-amino-6-fluorooxepan-2-yl)-1-methyl-1H-pyrazol-4-yl)-2-(2,6-difluorophenyl)thiazole-4-carboxamide 5-amino-N-(5-((2S,5R,6S)-5-amino-6-fluorooxepan-2-yl)-1-methyl-1H-pyrazol-4-yl)-2-phenylthiazole-4-carboxamide N-(5-((2S,5R,6S)-5-amino-6-fluorooxepan-2-yl)-1-methyl-1H-pyrazol-4-yl)-2-(2,6-difluorophenyl)thiazole-4-carboxamide N-(5-((2S,5R,6S)-5-amino-6-fluorooxepan-2-yl)-1-methyl-1H-pyrazol-4-yl)-2-(2-fluorophenyl)thiazole-4-carboxamide 5-amino-N-(5-((2S,5R,6S)-5-amino-6-fluorooxepan-2-yl)-1-methyl-1H-pyrazol-4-yl)-2-(2-(trifluoromethyl)phenyl)thiazole-4-carboxamide 5-amino-N-(5-((2S,5R,6S)-5-amino-6-fluorooxepan-2-yl)-1-methyl-1H-pyrazol-4-yl)-2-(2,3-difluorophenyl)thiazole-4-carboxamide N-(5-((2S,5R,6S)-5-amino-6-fluorooxepan-2-yl)-1-methyl-1H-pyrazol-4-yl)-2-(2,4-difluorophenyl)thiazole-4-carboxamide N-(5-((2S,5R,6S)-5-amino-6-fluorooxepan-2-yl)-1-methyl-1H-pyrazol-4-yl)-2-(pyridin-2-yl)thiazole-4-carboxamide N-(5-((2S,5R,6S)-5-amino-6-fluorooxepan-2-yl)-1-methyl-1H-pyrazol-4-yl)-2-phenylthiazole-4-carboxamide 5-amino-N-(5-((2S,5R,6S)-5-amino-6-fluorooxepan-2-yl)-1-methyl-1H-pyrazol-4-yl)-2-(2-chloro-6-fluorophenyl)thiazole-4-carboxamide 5-amino-N-(5-((2S,5R,6S)-5-amino-6-fluorooxepan-2-yl)-1-methyl-1H-pyrazol-4-yl)-2-(2-chloro-6-(trifluoromethyl)phenyl)thiazole-4-carboxamide 5-amino-N-(5-((2S,5R,6S)-5-amino-6-fluorooxepan-2-yl)-1-methyl-1H-pyrazol-4-yl)-2-(2-fluoro-6-methylphenyl)thiazole-4-carboxamide 5-amino-N-(5-((2S,5R,6S)-5-amino-6-fluorooxepan-2-yl)-1-methyl-1H-pyrazol-4-yl)-2-(2-fluoro-6-(trifluoromethyl)phenyl)thiazole-4-carboxamide 5-amino-N-(5-((2S,5R,6S)-5-amino-6-fluorooxepan-2-yl)-1-methyl-1H-pyrazol-4-yl)-2-(2,3,6-trifluorophenyl)thiazole-4-carboxamide 5-amino-N-(5-((2S,5R,6S)-5-amino-6-fluorooxepan-2-yl)-1-methyl-1H-pyrazol-4-yl)-2-(cyclopent-1-en-1-yl)thiazole-4-carboxamide 5-amino-N-(5-((2S,5R,6S)-5-amino-6-fluorooxepan-2-yl)-1-methyl-1H-pyrazol-4-yl)-2-cyclopentylthiazole-4-carboxamide 5-amino-N-(5-((2S,5R,6S)-5-amino-6-fluorooxepan-2-yl)-1-methyl-1H-pyrazol-4-yl)-2-(2-(difluoromethyl)phenyl)thiazole-4-carboxamide 5-amino-N-(5-((2S,5R,6S)-5-amino-6-fluorooxepan-2-yl)-1-methyl-1H-pyrazol-4-yl)-2-(3-fluoro-2-(trifluoromethyl)phenyl)thiazole-4-carboxamide 5-amino-N-(5-((2S,5R,6S)-5-amino-6-fluorooxepan-2-yl)-1-methyl-1H-pyrazol-4-yl)-2-(2-chloro-3-fluorophenyl)thiazole-4-carboxamide 5-amino-N-(5-((2S,5R,6S)-5-amino-6-fluorooxepan-2-yl)-1-methyl-1H-pyrazol-4-yl)-2-(3-chloro-2-fluorophenyl)thiazole-4-carboxamide N-(5-((2S,5R,6S)-5-amino-6-fluorooxepan-2-yl)-1-methyl-1H-pyrazol-4-yl)-2-(2,6-difluoro-4-(3-methoxyoxetan-3-yl)phenyl)thiazole-4-carboxamide N-(5-((2S,5R,6S)-5-amino-6-fluorooxepan-2-yl)-1-methyl-1H-pyrazol-4-yl)-2-(2,6-difluoro-4-(3-fluorooxetan-3-yl)phenyl)thiazole-4-carboxamide N-(5-((2R,4R,5S,6R)-4-amino-5-hydroxy-5,6-dimethyltetrahydro-2H-pyran-2-yl)-1-methyl-1H-pyrazol-4-yl)-2-(2,6-difluorophenyl)thiazole-4-carboxamide N-(5-((2S,4S,5R,6S)-4-amino-5-hydroxy-5,6-dimethyltetrahydro-2H-pyran-2-yl)-1-methyl-1H-pyrazol-4-yl)-2-(2,6-difluorophenyl)thiazole-4-carboxamide N-(5-((2R,4R,5S,6R)-4-amino-5-hydroxy-5,6-dimethyltetrahydro-2H-pyran-2-yl)-1-methyl-1H-pyrazol-4-yl)-6-(2,6-difluorophenyl)-5-fluoropicolinamide N-(5-((2S,4S,5R,6S)-4-amino-5-hydroxy-5,6-dimethyltetrahydro-2H-pyran-2-yl)-1-methyl-1H-pyrazol-4-yl)-6-(2,6-difluorophenyl)-5-fluoropicolinamide 5-amino-N-(5-((2R,4R,5S,6R)-4-amino-5-hydroxy-5,6-dimethyltetrahydro-2H-pyran-2-yl)-1-methyl-1H-pyrazol-4-yl)-2-(2,6-difluorophenyl)thiazole-4-carboxamide 5-amino-N-(5-((2S,4S,5R,6S)-4-amino-5-hydroxy-5,6-dimethyltetrahydro-2H-pyran-2-yl)-1-methyl-1H-pyrazol-4-yl)-2-(2,6-difluorophenyl)thiazole-4-carboxamide N-(5-((2S,5R,6S)-5-amino-6-methoxyoxepan-2-yl)-1-methyl-1H-pyrazol-4-yl)-2-(2,6-difluorophenyl)thiazole-4-carboxamide; and N-(5-((2S,5R,6S)-5-amino-6-methoxyoxepan-2-yl)-1-methyl-1H-pyrazol-4-yl)-2-(3-methylpyridin-2-yl)thiazole-4-carboxamide, or a pharmaceutically acceptable salt thereof.

17. The compound of claim 1 selected from the group consisting of:

N-(5-((2S,5R,6S)-5-amino-6-fluorooxepan-2-yl)-1-methyl-1H-pyrazol-4-yl)-2-(3-chloro-5-fluoropyridin-4-yl)thiazole-4-carboxamide N-(5-((2S,5R,6R)-5-amino-6-hydroxyoxepan-2-yl)-1-methyl-1H-pyrazol-4-yl)-2-(2,6-difluorophenyl)thiazole-4-carboxamide N-(5-((2R,5S,6S)-5-amino-6-hydroxyoxepan-2-yl)-1-methyl-1H-pyrazol-4-yl)-2-(2,6-difluorophenyl)thiazole-4-carboxamide N-(5-((2S,5R,6S)-5-amino-6-hydroxyoxepan-2-yl)-1-methyl-1H-pyrazol-4-yl)-2-(2,6-difluorophenyl)thiazole-4-carboxamide N-(5-((2R,5S,6R)-5-amino-6-hydroxyoxepan-2-yl)-1-methyl-1H-pyrazol-4-yl)-2-(2,6-difluorophenyl)thiazole-4-carboxamide N-(5-((2S,5R,6S)-5-amino-6-fluorooxepan-2-yl)-1-methyl-1H-pyrazol-4-yl)-2-(4-(dimethylcarbamoyl)-2,6-difluorophenyl)thiazole-4-carboxamide N-(5-((2S,5R,6S)-5-amino-6-methoxyoxepan-2-yl)-1-methyl-1H-pyrazol-4-yl)-2-(2,6-difluoro-4-methylphenyl)thiazole-4-carboxamide N-(5-((2S,5R,6S)-5-amino-6-fluorooxepan-2-yl)-1-methyl-1H-pyrazol-4-yl)-2-(2-fluoro-5-methoxyphenyl)thiazole-4-carboxamide N-(5-((2S,5R,6S)-5-amino-6-fluorooxepan-2-yl)-1-methyl-1H-pyrazol-4-yl)-2-(3-methoxyphenyl)thiazole-4-carboxamide N-(5-((2S,5R,6S)-5-amino-6-fluorooxepan-2-yl)-1-methyl-1H-pyrazol-4-yl)-2-(4-cyclopropyl-2,6-difluorophenyl)thiazole-4-carboxamide N-(5-((2S,5R,6S)-5-amino-6-fluorooxepan-2-yl)-1-methyl-1H-pyrazol-4-yl)-6-(4-chloro-2-fluorophenyl)-5-fluoropicolinamide N-[5-[(2S,5R,6S)-5-amino-6-fluoro-oxepan-2-yl]-1-methyl-pyrazol-4-yl]-2-(2,6-difluoro-3-methylsulfonyl-phenyl)thiazole-4-carboxamide N-[5-[(2S,5R,6S)-5-amino-6-fluoro-oxepan-2-yl]-1-methyl-pyrazol-4-yl]-2-(2-fluoro-3-methyl-phenyl)thiazole-4-carboxamide N-(5-((2S,5R,6S)-5-amino-6-fluorooxepan-2-yl)-1-methyl-1H-pyrazol-4-yl)-2-(2-fluoro-3-methoxyphenyl)thiazole-4-carboxamide N-(5-((2S,5R,6S)-5-amino-6-fluorooxepan-2-yl)-1-methyl-1H-pyrazol-4-yl)-2-(3-cyclopropyl-2,6-difluorophenyl)thiazole-4-carboxamide N-(5-((2S,5R,6S)-5-amino-6-fluorooxepan-2-yl)-1-methyl-1H-pyrazol-4-yl)-2-(2,4,6-trifluorophenyl)thiazole-4-carboxamide N-(5-((2S,5R,6S)-5-amino-6-fluorooxepan-2-yl)-1-methyl-1H-pyrazol-4-yl)-2-(2,3-difluoro-4-((S)-1-hydroxyethyl)phenyl)thiazole-4-carboxamide N-(5-((2S,5R,6S)-5-amino-6-fluorooxepan-2-yl)-1-methyl-1H-pyrazol-4-yl)-2-(2,3-difluoro-4-((R)-1-hydroxyethyl)phenyl)thiazole-4-carboxamide N-(5-((2S,5R,6S)-5-amino-6-fluorooxepan-2-yl)-1-methyl-1H-pyrazol-4-yl)-2-(2,6-difluoro-4-isobutyrylphenyl)thiazole-4-carboxamide N-(5-((2S,5R,6S)-5-amino-6-methoxyoxepan-2-yl)-1-methyl-1H-pyrazol-4-yl)-2-(2,6-difluoro-3-methoxyphenyl)thiazole-4-carboxamide N-[5-[(2S,5R,6S)-5-amino-6-fluoro-oxepan-2-yl]-1-methyl-pyrazol-4-yl]-2-(2-fluoro-6-methyl-phenyl)-5-methyl-thiazole-4-carboxamide N-[5-[(2S,5R,6S)-5-amino-6-fluoro-oxepan-2-yl]-1-methyl-pyrazol-4-yl]-2-(2,6-difluorophenyl)-5-methyl-thiazole-4-carboxamide N-(5-((2S,5R,6S)-5-amino-6-fluorooxepan-2-yl)-1-methyl-1H-pyrazol-4-yl)-2-(2,6-difluoro-4-((S)-tetrahydrofuran-2-yl)phenyl)thiazole-4-carboxamide N-(5-((2S,5R,6S)-5-amino-6-fluorooxepan-2-yl)-1-methyl-1H-pyrazol-4-yl)-2-(4,5-dimethyl-1H-pyrazol-3-yl)thiazole-4-carboxamide N-(5-((2S,5R,6S)-5-amino-6-fluorooxepan-2-yl)-1-methyl-1H-pyrazol-4-yl)-2-(6,6-dimethyl-4,5,6,7-tetrahydro-1H-indazol-3-yl)thiazole-4-carboxamide N-(5-((2S,5R,6S)-5-amino-6-fluorooxepan-2-yl)-1-methyl-1H-pyrazol-4-yl)-2-(4,5,6,7-tetrahydro-1H-indazol-3-yl)thiazole-4-carboxamide N-(5-((2S,5R,6S)-5-amino-6-fluorooxepan-2-yl)-1-methyl-1H-pyrazol-4-yl)-6-(4-chloro-2,6-difluorophenyl)-5-fluoropicolinamide N-[5-[(2S,5R,6S)-5-amino-6-fluoro-oxepan-2-yl]-1-methyl-pyrazol-4-yl]-2-[3-(dimethylcarbamoyl)-2,6-difluoro-phenyl]thiazole-4-carboxamide N-[5-[(2S,5R,6S)-5-amino-6-fluoro-oxepan-2-yl]-1-methyl-pyrazol-4-yl]-2-[3-(difluoromethyl)-2,6-difluoro-phenyl]thiazole-4-carboxamide N-[5-[(2S,5R,6S)-5-amino-6-fluoro-oxepan-2-yl]-1-methyl-pyrazol-4-yl]-2-[3-(difluoromethyl)-2-fluoro-6-methoxy-phenyl]thiazole-4-carboxamide N-[5-[(2S,5R,6S)-5-amino-6-fluoro-oxepan-2-yl]-1-methyl-pyrazol-4-yl]-2-(1H-pyrazol-3-yl)thiazole-4-carboxamide N-(5-((2S,5R,6S)-5-amino-6-fluorooxepan-2-yl)-1-methyl-1H-pyrazol-4-yl)-2-(2,6-difluoro-4-((R)-tetrahydrofuran-2-yl)phenyl)thiazole-4-carboxamide N-(5-((2S,5R,6S)-5-amino-6-fluorooxepan-2-yl)-1-methyl-1H-pyrazol-4-yl)-2-(1H-indazol-3-yl)thiazole-4-carboxamide N-[5-[(2S,5R,6S)-5-amino-6-fluoro-oxepan-2-yl]-1-methyl-pyrazol-4-yl]-2-[2-fluoro-6-(hydroxymethyl)phenyl]thiazole-4-carboxamide N-[5-[(2S,5R,6S)-5-amino-6-fluoro-oxepan-2-yl]-1-methyl-pyrazol-4-yl]-2-(3-pyridyl)thiazole-4-carboxamide N-[5-[(2S,5R,6S)-5-amino-6-fluoro-oxepan-2-yl]-1-methyl-pyrazol-4-yl]-2-(2-isopropoxy-3-pyridyl)thiazole-4-carboxamide N-[5-[(2S,5R,6S)-5-amino-6-fluoro-oxepan-2-yl]-1-methyl-pyrazol-4-yl]-2-[6-(dimethylamino)-3-pyridyl]thiazole-4-carboxamide 2-(6-acetamido-3-pyridyl)-N-[5-[(2S,5R,6S)-5-amino-6-fluoro-oxepan-2-yl]-1-methyl-pyrazol-4-yl]thiazole-4-carboxamide N-(5-((2S,5R,6S)-5-amino-6-fluorooxepan-2-yl)-1-methyl-1H-pyrazol-4-yl)-2-(5-fluoro-1-methyl-2-oxo-1,2-dihydropyridin-4-yl)thiazole-4-carboxamide N-(5-((2S,5R,6S)-5-amino-6-fluorooxepan-2-yl)-1-methyl-1H-pyrazol-4-yl)-2-(1H-pyrazol-1-yl)thiazole-4-carboxamide N-(5-((2S,5R,6S)-5-amino-6-fluorooxepan-2-yl)-1-methyl-1H-pyrazol-4-yl)-2-(4,5,6,7-tetrahydro-1H-indazol-1-yl)thiazole-4-carboxamide N-(5-((2S,5R,6S)-5-amino-6-fluorooxepan-2-yl)-1-methyl-1H-pyrazol-4-yl)-2-(4,5,6,7-tetrahydro-2H-indazol-2-yl)thiazole-4-carboxamide N-(5-((2S,5R,6S)-5-amino-6-fluorooxepan-2-yl)-1-methyl-1H-pyrazol-4-yl)-2-(5,7-difluoro-2,3-dihydrobenzofuran-6-yl)thiazole-4-carboxamide N-(5-((2S,5R,6S)-5-amino-6-fluorooxepan-2-yl)-1-methyl-1H-pyrazol-4-yl)-6-(2,6-difluoro-4-methylphenyl)-5-fluoropicolinamide N-(5-((2S,5R,6S)-5-amino-6-fluorooxepan-2-yl)-1-methyl-1H-pyrazol-4-yl)-2-(2-fluoro-4-(3-methyloxetan-3-yl)phenyl)thiazole-4-carboxamide N-(5-((2S,5R,6S)-5-amino-6-fluorooxepan-2-yl)-1-methyl-1H-pyrazol-4-yl)-2-(4-(1,1-difluoroethyl)-2,6-difluorophenyl)thiazole-4-carboxamide N-(5-((2S,5R,6S)-5-amino-6-fluorooxepan-2-yl)-1-methyl-1H-pyrazol-4-yl)-2-(1H-indazol-1-yl)thiazole-4-carboxamide N-(5-((2S,5R,6S)-5-amino-6-fluorooxepan-2-yl)-1-methyl-1H-pyrazol-4-yl)-2-(2H-indazol-2-yl)thiazole-4-carboxamide N-[5-[(2S,5R,6S)-5-amino-6-fluoro-oxepan-2-yl]-1-methyl-pyrazol-4-yl]-6-(2,6-difluorophenyl)-5-fluoro-pyridine-2-carboxamide N-[5-[(2S,5R,6S)-5-amino-6-fluoro-oxepan-2-yl]-1-methyl-pyrazol-4-yl]-2-(3-methyl-2-pyridyl)thiazole-4-carboxamide N-[5-[(2S,5R,6S)-5-amino-6-fluoro-oxepan-2-yl]-1-methyl-pyrazol-4-yl]-2-(1,5-naphthyridin-3-yl)thiazole-4-carboxamide N-[5-[(2S,5R,6S)-5-amino-6-fluoro-oxepan-2-yl]-1-methyl-pyrazol-4-yl]-2-(5-fluoro-1H-indol-4-yl)thiazole-4-carboxamide N-[5-[(2S,5R,6S)-5-amino-6-fluoro-oxepan-2-yl]-1-methyl-pyrazol-4-yl]-2-(3-benzyloxyphenyl)thiazole-4-carboxamide N-[5-[(2S,5R,6S)-5-amino-6-fluoro-oxepan-2-yl]-1-methyl-pyrazol-4-yl]-2-(1-methylindazol-4-yl)thiazole-4-carboxamide N-[5-[(2S,5R,6S)-5-amino-6-fluoro-oxepan-2-yl]-1-methyl-pyrazol-4-yl]-2-(1-methylindazol-7-yl)thiazole-4-carboxamide N-[5-[(2S,5R,6S)-5-amino-6-fluoro-oxepan-2-yl]-1-methyl-pyrazol-4-yl]-2-(1H-indazol-6-yl)thiazole-4-carboxamide N-[5-[(2S,5R,6S)-5-amino-6-fluoro-oxepan-2-yl]-1-methyl-pyrazol-4-yl]-2-(1H-indazol-7-yl)thiazole-4-carboxamide N-[5-[(2S,5R,6S)-5-amino-6-fluoro-oxepan-2-yl]-1-methyl-pyrazol-4-yl]-2-(1H-indazol-4-yl)thiazole-4-carboxamide N-(5-((3S,4R,5R)-5-amino-4-methoxy-3-methylazepan-1-yl)-1-methyl-1H-pyrazol-4-yl)-2-(2,6-difluorophenyl)thiazole-4-carboxamide N-(5-((3R,4S,5S)-5-amino-4-methoxy-3-methylazepan-1-yl)-1-methyl-1H-pyrazol-4-yl)-2-(2,6-difluorophenyl)thiazole-4-carboxamide N-(5-((3R,4R,5R)-5-amino-4-methoxy-3-methylazepan-1-yl)-1-methyl-1H-pyrazol-4-yl)-2-(2,6-difluorophenyl)thiazole-4-carboxamide; and N-(5-((3S,4S,5S)-5-amino-4-methoxy-3-methylazepan-1-yl)-1-methyl-1H-pyrazol-4-yl)-2-(2,6-difluorophenyl)thiazole-4-carboxamide or a pharmaceutically acceptable salt thereof.

18. A pharmaceutical composition comprised of a compound of claim 1 and a pharmaceutically acceptable carrier, glidant, diluent, or excipient.

19. The pharmaceutical composition according to claim 18, further comprising a chemotherapeutic agent.

20. The pharmaceutical composition of claim 18 for use in treating a disease or disorder selected from cancer, immune disorders, cardiovascular disease, viral infection, inflammation, metabolism/endocrine function disorders and neurological disorders, and mediated by Pim kinase.

21. The compound of claim 16, wherein said is compound is N-(5-((2S,5R,6S)-5-amino-6-fluorooxepan-2-yl)-1-methyl-1H-pyrazol-4-yl)-2-(2,6-difluorophenyl)thiazole-4-carboxamide, or a pharmaceutically acceptable salt thereof.

22. A pharmaceutical composition comprised of a compound having the structure:

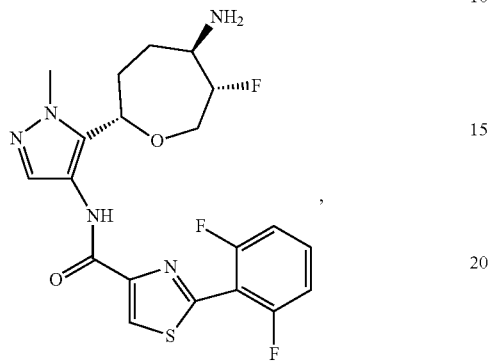

or a pharmaceutically acceptable salt thereof, and a pharmaceutically acceptable carrier, glidant, diluent, or excipient.

23. The pharmaceutical composition of claim 22, further comprising a chemotherapeutic agent.

* * * * *